(12) United States Patent
Abraham et al.

(10) Patent No.: US 11,878,976 B2
(45) Date of Patent: Jan. 23, 2024

(54) FGFR3 INHIBITOR COMPOUNDS

(71) Applicant: Eli Lilly and Company, Indianapolis, IN (US)

(72) Inventors: Adedoyin David Abraham, Thornton, CO (US); Desta Doro Bume, Broomfield, CO (US); Kevin Ronald Condroski, Lafayette, CO (US); Robert Alan Hazlitt, Broomfield, CO (US); Timothy Scott Kercher, Longmont, CO (US); Andrew Terrance Metcalf, Erie, CO (US); Kaveri Balan Urkalan, Longmont, CO (US); Shane Michael Walls, Lafayette, CO (US); Andrew Karl Dilger, Golden, CO (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 37 days.

(21) Appl. No.: 17/685,753

(22) Filed: Mar. 3, 2022

(65) Prior Publication Data

US 2023/0095122 A1    Mar. 30, 2023

Related U.S. Application Data

(60) Provisional application No. 63/156,527, filed on Mar. 4, 2021.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC .................................................. C07D 471/04
USPC .................................................... 514/210.21
See application file for complete search history.

(56) References Cited

U.S. PATENT DOCUMENTS

| | | | |
|---|---|---|---|
| 9,926,307 B2 * | 3/2018 | Jones | ............... C07D 417/14 |
| 2014/0228349 A1 | 8/2014 | Boys et al. | |
| 2019/0027074 A1 | 1/2019 | Zeng | |

FOREIGN PATENT DOCUMENTS

| | | |
|---|---|---|
| EP | 2545045 A1 | 1/2013 |
| EP | 3290418 A1 | 3/2018 |
| WO | 2010017047 A1 | 2/2010 |
| WO | 2011112662 A1 | 9/2011 |
| WO | 2011131046 A1 | 10/2011 |
| WO | 2015017610 A1 | 2/2015 |
| WO | 2016134320 A1 | 8/2016 |
| WO | 2016173484 A1 | 11/2016 |
| WO | 2016191172 A1 | 12/2016 |
| WO | 2019034973 A1 | 2/2019 |
| WO | 2020131627 A1 | 6/2020 |

OTHER PUBLICATIONS

Martin, James S., Claire J. MacKenzie, Daniel Fletcher, and Ian H. Gilbert. "Characterising covalent warhead reactivity." Bioorganic & medicinal chemistry 27, No. 10 (2019): 2066-2074.
Patent Cooperation Treaty International Search Report pertaining to International Application No. PCT/US2022/018644; dated Jun. 10, 2022, 6 pages.
Patent Cooperation Treaty Written Opinion of the International Searching Authority pertaining to International Application No. PCT/US2022/018644; dated Jun. 10, 2022, 9 pages.

* cited by examiner

*Primary Examiner* — Niloofar Rahmani
(74) *Attorney, Agent, or Firm* — Cedric A. D'Hue

(57) ABSTRACT

The present invention provides compounds of the formula:

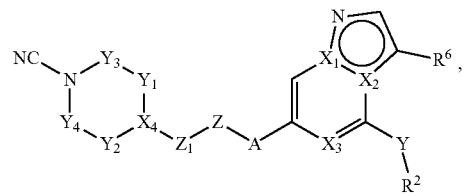

for use in the treatment of systemic sclerosis, fibrosis (e.g. pulmonary fibrosis), achondroplasia, thanatophoric dysplasia (e.g. type I), severe achondroplasia with developmental delay and acanthosis nigricans (SADDAN), muenke syndrome or cancer.

37 Claims, No Drawings

FGFR3 INHIBITOR COMPOUNDS

BACKGROUND

Fibroblast growth factor (FGF) has been recognized as an important mediator of many physiological processes, such as morphogenesis during development, fibrosis, and angiogenesis. The fibroblast growth factor receptor (FGFR) family consists of five members four of which (FGFR 1-4) are glycoproteins composed of extracellular immunoglobulin (Ig)-like domains, a hydrophobic transmembrane region and a cytoplasmic part containing a tyrosine kinase domain. FGF binding leads to FGFR dimerization, followed by receptor autophosphorylation and activation of downstream signaling pathways. Receptor activation is sufficient for the recruitment and activation of specific downstream signaling partners that participate in the regulation of diverse processes such as cell growth, cell metabolism and cell survival. Thus, the FGF/FGFR signaling pathway has pleiotropic effects on many biological processes critical to tumor cell proliferation, migration, invasion, and angiogenesis.

SUMMARY

Provided herein are compounds of the formula:

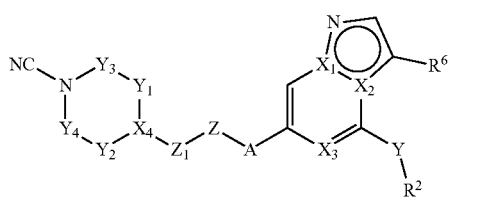

(I)

or a pharmaceutically acceptable salt thereof, wherein A, $X_1$, $X_2$, $X_3$, $X_4$, Y, $Y_1$, $Y_2$, $Y_3$, $Y_4$, Z, $Z_1$, $R^2$ and $R^6$ are as defined herein.

Provided herein are compounds of the formula:

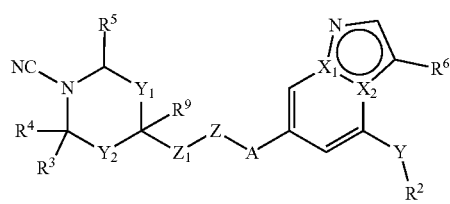

(II)

or a pharmaceutically acceptable salt thereof, wherein A, $X_1$, $X_2$, Y, $Y_1$, $Y_2$, Z, $Z_1$, $R^2$, $R^3$, $R^4$, $R^5$, $R^6$ and $R^9$ are as defined herein.

Provided herein are compounds of the formula:

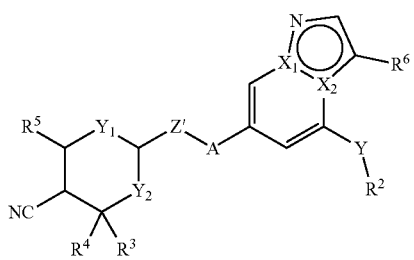

(III)

or a pharmaceutically acceptable salt thereof, wherein A, $X_1$, $X_2$, Y, $Y_1$, $Y_2$, Z', $R^2$, $R^3$, $R^4$, $R^5$ and $R^6$ are as defined herein.

Provided herein are pharmaceutical compositions comprising a compound of formula (I), (II), (IIA) or (III), or a pharmaceutically acceptable salt thereof, with one or more pharmaceutically acceptable carriers, diluents, or excipients.

Provided herein are methods of using the compounds of formula (I), (II), (IA) or (III), or a pharmaceutically acceptable salt thereof, and pharmaceutical compositions thereof, to treat systemic sclerosis, fibrosis, pulmonary fibrosis, achondroplasia, thanatophoric dysplasia, severe achondroplasia with developmental delay and acanthosis nigricans (SADDAN), muenke syndrome or proliferative disorders such as cancer, particularly to treat FGFR3-associated cancer. The methods include administering an effective amount of a compound of formula (I), (II), (IA) or (III), or a pharmaceutically acceptable salt thereof, to a patient in need.

DESCRIPTION

Provided herein are compounds believed to have clinical use for the treatment of systemic sclerosis, fibrosis, pulmonary fibrosis, achondroplasia, thanatophoric dysplasia, severe achondroplasia with developmental delay and acanthosis nigricans (SADDAN), muenke syndrome, proliferative disorders such as cancer and particularly for the treatment of FGFR3-associated cancer.

Certain compounds provided herein have superior FGFR3 potency compared to certain previously known FGFR inhibitors. Certain compounds provided herein have superior selectivity for FGFR3 over FGFR1 compared to certain previously known FGFR inhibitors, reducing potential dose limiting toxicity caused by inhibition of FGFR1 (e.g. hyperphosphatemia).

The compounds provided herein are of formula:

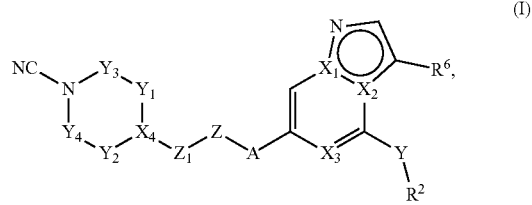

(I)

wherein

A is pyrazole, triazole, thiadiazole or oxadiazole, substituted with $R^1$ and $R^{1A}$;

$R^1$ is hydrogen or $C_1$-$C_3$ alkyl;

$R^{1A}$ is hydrogen, halo, CN, or $C_1$-$C_3$ alkyl optionally substituted with one or more substituents independently selected from halo, OH, and $OCH_3$;

$X_1$ and $X_2$ are independently selected from N and C, wherein when one of $X_1$ or $X_2$ is N the other is C;

$X_3$ is N or CH;

$X_4$ is N or C—$R^9$;

Y is NH, O, S or a bond;

$Y_1$ is a bond, $CHR^7$, $CH_2$—$CHR^7$, $CHR^7$—$CH_2$, $CF_2$, $CH_2$—$CF_2$ or $CF_2$—$CH_2$;

$Y_2$ is a bond, $CHR^3$, $CH_2$—$CHR^3$, $CHR^3$—$CH_2$, $CF_2$, $CH_2$—$CF_2$ or $CF_2$—$CH_2$;

$Y_3$ is $CR^4R^5$ or $CF_2$;

$Y_4$ is $CR^3R^4$, or $CF_2$;

Z is a bond, $CHR^{9A}$, $CR^4R^{4A}$, $CR^4R^{4A}$—$CH_2$, $CH_2$—$CR^4R^{4A}$, cyclobutyl, cyclopentyl, cyclohexyl, bicyclo(1.1.1)pentane, bicyclo(2.1.1)hexane, azetidine, pyrrolidine or piperidine;

$Z_1$ is a bond when Z is a bond, $CR^4R^{4A}$, $CR^4R^{4A}$—$CH_2$, $CH_2$—$CR^4R^{4A}$, cyclobutyl, cyclopentyl, cyclohexyl, bicyclo(1.1.1)pentane, bicyclo(2.1.1)hexane, azetidine, pyrrolidine or piperidine, or $Z_1$ is $CH_2$ or $CH_2$—$CH_2$ when Z is $CHR^{9A}$;

$Z_2$ is a bond, C(O), $SO_2$ or —$NR^4C(O)$;

$Z_3$ is a bond, C(O), $SO_2$ or —$NR^4C(O)$;

$R^2$ is $C_1$-$C_5$ alkyl or $R^8$, wherein $C_1$-$C_5$ alkyl is optionally substituted with one or more substituents independently selected from halo, OH, CN, oxo, —$OC_1$-$C_4$ alkyl, —$OC_3$-$C_5$ cycloalkyl, —$Z_2$—$R^{11}$ and $R^{10}$, wherein $C_1$-$C_4$ alky and $C_3$-$C_5$ cycloalkyl are optionally substituted with one or more substituents independently selected from halo, OH, $OCH_3$, methylamine, N,N-dimethylamine and CN;

$R^3$ is hydrogen, F, OH, $OCH_3$, $C_1$-$C_3$ alkyl, cyclopropyl, or one $R^3$ is fused with $R^5$ or $R^7$ to form $CH_2$, $CH_2$—$CH_2$ or $CH_2OCH_2$;

$R^4$ is hydrogen or $C_1$-$C_3$ alkyl;

$R^{4A}$ is hydrogen, halo, OH, or $C_1$-$C_3$ alkyl;

$R^5$ is hydrogen, F, OH, $OCH_3$, $C_1$-$C_3$ alkyl, cyclopropyl, or is fused with one $R^3$ to form $CH_2$, $CH_2$—$CH_2$ or $CH_2OCH_2$;

$R^6$ is hydrogen, halo, $C_1$-$C_5$ alkyl, CN, 3-6 membered cycloalkyl, 4-6 membered heterocycloalkyl, 5-6 membered aryl or 5-6 membered heteroaryl, wherein 3-6 membered cycloalkyl, 4-6 membered heterocycloalkyl, 5-6 membered aryl and 5-6 membered heteroaryl are optionally substituted with one or more substituents independently selected from halo, methyl, halomethyl, OH or $OCH_3$ and wherein $C_1$-$C_5$ alkyl is optionally substituted with one or more substituents independently selected from halo, OH and $OCH_3$;

$R^7$ is hydrogen, F, OH, $OCH_3$, $C_1$-$C_3$ alkyl or is fused with one $R^3$ to form $CH_2$, $CH_2$—$CH_2$ or $CH_2OCH_2$;

$R^7$ is 3-6 membered cycloalkyl, 4-6 membered heterocycloalkyl, 5-6 membered aryl or 5-6 membered heteroaryl, optionally fused or substituted with $R^{8A}$;

$R^{8A}$ is 3-6 membered cycloalkyl, 4-6 membered heterocycloalkyl, 5-6 membered aryl or 5-6 membered heteroaryl;

$R^9$ is hydrogen, $C_1$-$C_3$ alkyl, or is fused with $R^{9A}$ to form $CH_2$ or $CH_2$—$CH_2$;

$R^{10}$ is 3-6 membered cycloalkyl, 4-6 membered heterocycloalkyl, 5-6 membered aryl or 5-6 membered heteroaryl, optionally fused or substituted with $R^{8A}$;

$R_{11}$ is $C_1$-$C_4$ alkyl, $NH_2$, $NHC_1$-$C_3$ alkyl, $NHC_3$-$C_5$ cycloalkyl or $N(C_1$-$C_3$ alkyl$)_2$, wherein $C_1$-$C_4$ alkyl, $C_1$-$C_3$ alkyl and $C_3$-$C_5$ cycloalkyl are optionally substituted with one or more substituents independently selected from halo, OH, $OCH_3$, methylamine, N,N-dimethylamine and CN;

$R^{12}$ is $C_1$-$C_4$ alkyl, $C_3$-$C_5$ cycloalkyl, $NH_2$, $NHC_1$-$C_3$ alkyl, $NHC_3$-$C_5$ cycloalkyl or $N(C_1$-$C_3$ alkyl$)_2$, wherein $C_1$-$C_4$ alky, $C_1$-$C_3$ alkyl and $C_3$-$C_5$ cycloalkyl are optionally substituted with one or more substituents independently selected from halo, OH, $OCH_3$, methylamine, N,N-dimethylamine and CN; and $R^8$, $R^{10}$ and $R^{8A}$ are optionally substituted with one or more substituents independently selected from halo, OH, CN, —$OC_1$-$C_4$ alkyl, —$OC_3$-$C_5$ cycloalkyl and —$Z_3$—$R^{12}$ wherein $C_1$-$C_4$ alky and $C_3$-$C_5$ cycloalkyl are optionally substituted with one or more substituents independently selected from halo, OH, $OCH_3$, methylamine, N,N-dimethylamine and CN;

or a pharmaceutically acceptable salt thereof, and of formula:

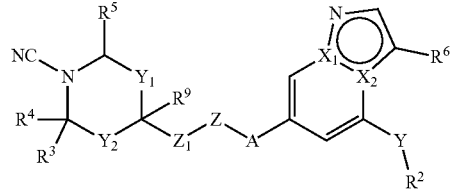

(II)

or a pharmaceutically acceptable salt thereof, and of formula:

(III)

or a pharmaceutically acceptable salt thereof. In formula (II), $X_1$ and $X_2$ are independently selected from N and C, wherein when one of $X_1$ or $X_2$ is N the other is C;

Z is a bond, $CHR^{9A}$, azetidine, pyrrolidine or piperidine;

$Z_1$ is a bond when Z is a bond, azetidine, pyrrolidine or piperidine, or $Z_1$ is $CH_2$ or $CH_2$—$CH_2$ when Z is $CHR^{9A}$; and $R^9$ is hydrogen or is fused with $R^{9A}$ to form $CH_2$ or $CH_2$—$CH_2$.

In formula (III), $X_1$ and $X_2$ are independently selected from N and C, wherein when one of $X_1$ or $X_2$ is N the other is C; and Z' is a bond, azetidine, pyrrolidine or piperidine.

In formula (II) and (III),

A is pyrazole, triazole, thiadiazole or oxadiazole, optionally substituted with $R^1$;

$R^1$ is $C_1$-$C_3$ alkyl;

Y is NH, O, or a bond;

$Y_1$ is a bond, $CHR^7$, $CH_2$—$CHR^7$ or $CHR^7$—$CH_2$;

$Y_2$ is a bond, $CH_2$, $CF_2$, $CHR^3$, $CH_2$—$CHR^3$ or $CHR^3$—$CH_2$;

$R^2$ is $C_1$-$C_5$ alkyl or $R^8$, wherein $C_1$-$C_5$ alkyl is optionally substituted with one or more substituents independently selected from OH, methoxy, halomethyl and $R^{10}$;

$R^3$ is hydrogen, $C_1$-$C_3$ alkyl, or one $R^3$ is fused with $R^5$ or $R^7$ to form $CH_2$ or $CH_2$—$CH_2$;

$R^4$ is hydrogen, or $C_1$-$C_3$ alkyl;

$R^5$ is hydrogen, or is fused with one $R^3$ to form $CH_2$ or $CH_2$—$CH_2$;

$R^6$ is hydrogen, $CH_3$, CN, Cl or F;

$R^7$ is hydrogen, or is fused with one $R^3$ to form $CH_2$ or $CH_2$—$CH_2$;

$R^7$ is 3-6 membered cycloalkyl, 5-6 membered heterocycloalkyl, 5-6 membered aryl or 5-6 membered heteroaryl, optionally fused with $R^{8A}$;

$R^{8A}$ is 3-6 membered cycloalkyl, 5-6 membered heterocycloalkyl, 5-6 membered aryl or 5-6 membered heteroaryl;

$R^{10}$ is 3-6 membered cycloalkyl, 5-6 membered heterocycloalkyl, 5-6 membered aryl or 5-6 membered heteroaryl, optionally fused or substituted with $R^{8A}$; and $R^8$, $R^{10}$ and $R^{8A}$ are optionally substituted with one or more substituents independently selected from halogen, CN, methyl, halomethyl, methoxy, ethyl, ethoxy, methylamine, $S(O)_2CH_3$, $C(O)NH_2$, N,N-dimethylamine and C(O)N,N-dimethylamine.

In the compounds of formula (I), (II) or (III), $X_1$ can be C, and $X_2$ can be N; or $X_1$ can be N, and $X_2$ can be C.

In the compounds of formula (I), (II) or (III), $X_1$ can be C, and $X_2$ can be N, forming:

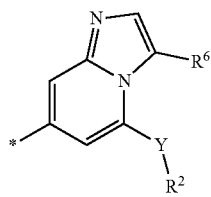

wherein * indicates the connection point to A in formula (I), (II) or (III).

In the compounds of formula (I), (II) or (III), $X_1$ can be N, and $X_2$ can be C, forming:

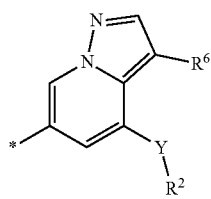

wherein * indicates the connection point to A in formula (II. (III or (III).

The specific chemical naming conventions used herein are intended to be familiar to one of skill in the chemical arts. Some terms are defined specifically for additional clarity.

As used herein, the term "alkyl" refers to a hydrocarbon chain that may be a straight chain or branched chain, containing the indicated number of carbon atoms. For example, the term "$C_1$-$C_5$ alkyl" as used herein refers to saturated linear or branched-chain monovalent hydrocarbon radicals of one, two, three, four or five carbon atoms. Examples of $C_1$-$C_5$ alkyl include, but are not limited to, methyl, ethyl, 1-propyl, isopropyl, 1-butyl, isobutyl, sec-butyl, tert-butyl, 2-methyl-2-propyl, pentyl, and neopentyl. Examples of $C_1$-$C_4$ alkyl include, but are not limited to, methyl, ethyl, 1-propyl, isopropyl, 1-butyl, isobutyl, sec-butyl, tert-butyl, and 2-methyl-2-propyl. Examples of $C_1$-$C_3$ alkyl include, but are not limited to, methyl, ethyl, 1-propyl or isopropyl.

As used herein, the term "cycloalkyl" means a saturated cyclic hydrocarbon group containing the indicated number of carbon atoms. For example, the term "3-6 membered cycloalkyl" as used herein refers to a saturated cyclic hydrocarbon group having three, four, five or six carbon atoms. Examples of 3-6 membered cycloalkyl include, cyclopropyl, cyclobutyl, cyclopentyl and cyclohexyl.

As used herein, the term "heterocycloalkyl" means a saturated cyclic group containing the indicated number of atoms selected from $C(O)_{0-1}$, N, O and $S(O)_{0-2}$. For example, the term "5-6 membered heterocycloalkyl" as used herein refers to a saturated cyclic ring system having five or six ring atoms, one, two or three of which are selected from N, O and $S(O)_{0-2}$, the remainder being $C(O)_{0-1}$. Examples of 4-6 membered heterocycloalkyl groups include, but are not limited to, azetidinyl, pyrrolidinyl, piperidinyl, piperazinyl, pyrrolidinyl, pyrrolidin-2-onyl, dioxanyl, morpholinyl, oxetanyl, tetrahydrofuranyl, tetrahydrothiophenyl, tetrahydropyranyl, oxazolidinyl, isothiazolidinyl oxozolid-2-onyl and isothiazolid-2-onyl. Examples of 5-6 membered heterocycloalkyl groups include, but are not limited to, piperidinyl, piperazinyl, pyrrolidinyl, pyrrolidin-2-onyl, dioxanyl, morpholinyl, tetrahydrofuranyl, tetrahydrothiophenyl, tetrahydropyranyl, oxazolidinyl, isothiazolidinyl oxozolid-2-onyl and isothiazolid-2-onyl.

As used herein, the term "aryl" refers to an aromatic cyclic hydrocarbon group having the indicated number of carbon atoms. For example, the term "5-6 membered aryl" as used herein refers to an aromatic cyclic hydrocarbon group having five or six carbon atoms. Examples of 5-6 membered aryls include cyclopentadienyl and phenyl.

As used herein, the term "heteroaryl" refers to an aromatic cyclic group having the indicated number of atoms selected from C, N, O and S. For example, the term "5-6 membered heteroaryl" as used herein refers to an aromatic cyclic group having five or six ring atoms, one, two or three of which are selected from N, O and S, the remainder being C. Examples of 5-6 membered heteroaryls include, but are not limited to, pyridinyl, pyrazinyl, pyrimidinyl, pyridazinyl, furanyl, pyrrolyl, thiophenyl, imidazolyl, pyrazolyl, triazolyl, oxazolyl, isoxazolyl, thiazolyl, isothiazolyl, oxadiazolyl and thiadiazolyl. Examples of 6 membered heteroaryls include, but are not limited to, pyridinyl, pyrazinyl, pyrimidinyl and pyridazinyl.

As used herein the term "halogen" or "halo" refers to F (fluoro), Cl (chloro), Br (bromo) and I (iodo).

As used herein the term "halomethyl" refers to —$CH_3$, in which one or more hydrogen atoms is/are replaced with an independently selected halo.

As used herein the term "oxo" refers to the substitution of $CH_2$ with O to form C(O).

As used herein the term "$N(C_1$-$C_3$ alkyl)$_2$" allows the independent selection of each $C_1$-$C_3$ alkyl substituent, for example, N may be substituted by methyl and ethyl.

As used herein the substituent —$NR^4C(O)$ is connected to $R^2$ through N.

Also provided is a compound of the formula:

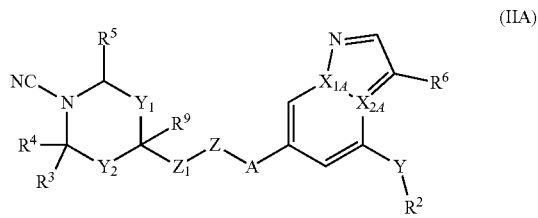

(IIA)

wherein

A is pyrazole, triazole, thiadiazole or oxadiazole, optionally substituted with $R_1$;

$R^1$ is $C_1$-$C_3$ alkyl;

$X_{1A}$ and $X_{2A}$ are independently selected from N and CH, wherein when one of $X_{1A}$ or $X_{2A}$ is N the other is CH;

Y is NH, O, or a bond;

$Y_1$ is a bond, $CHR^7$, $CH_2$—$CHR^7$ or $CHR^7$—$CH_2$;

$Y_2$ is a bond, $CH_2$, $CF_2$, $CHR^3$, $CH_2$—$CHR^3$ or $CHR^3$—$CH_2$;

Z is a bond, $CHR^{9A}$, azetidine, pyrrolidine or piperidine;

$Z_1$ is a bond when Z is a bond, azetidine, pyrrolidine or piperidine, or $Z_1$ is $CH_2$ or $CH_2$—$CH_2$ when Z is $CHR^{9A}$;

$R^2$ is $C_1$-$C_5$ alkyl or $R^8$, wherein $C_1$-$C_5$ alkyl is optionally substituted with one or more substituents independently selected from OH, methoxy, halomethyl and $R^{10}$;

$R^3$ is hydrogen, $C_1$-$C_3$ alkyl, or one $R^3$ is fused with $R^5$ or $R^7$ to form $CH_2$ or $CH_2$—$CH_2$;

$R^4$ is hydrogen, or $C_1$-$C_3$ alkyl;

$R^5$ is hydrogen, or is fused with one $R^3$ to form $CH_2$ or $CH_2$—$CH_2$;

$R^6$ is hydrogen, $CH_3$, CN, Cl or F;

$R^7$ is hydrogen, or is fused with one $R^3$ to form $CH_2$ or $CH_2$—$CH_2$;

$R^7$ is 3-6 membered cycloalkyl, 5-6 membered heterocycloalkyl, 5-6 membered aryl or 5-6 membered heteroaryl, optionally fused or substituted with $R^{8A}$;

$R^{8A}$ is 3-6 membered cycloalkyl, 5-6 membered heterocycloalkyl, 5-6 membered aryl or 5-6 membered heteroaryl;

$R^9$ is hydrogen or is fused with $R^{9A}$ to form $CH_2$ or $CH_2$—$CH_2$;

$R^{10}$ is 3-6 membered cycloalkyl, 5-6 membered heterocycloalkyl, 5-6 membered aryl or 5-6 membered heteroaryl, optionally fused or substituted with $R^{8A}$; and $R^8$, $R^{10}$ and $R^{8A}$ are optionally substituted with one or more substituents independently selected from halogen, CN, methyl, halomethyl, methoxy, ethyl, ethoxy, methylamine, $S(O)_2CH_3$, $C(O)NH_2$, N,N-dimethylamine and C(O)N,N-dimethylamine;

or a pharmaceutically acceptable salt thereof.

In the compound of formula (IIA), $X_{1A}$ can be CH, and $X_{2A}$ can be N, forming:

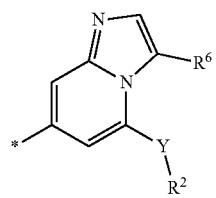

wherein * indicates the connection point to A in formula (IIA), forming a compound of the formula:

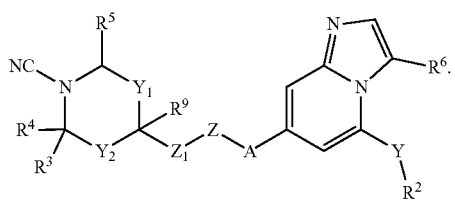

In the compound of formula (IIA), $X_{1A}$ can be N, and $X_{2A}$ can be CH, forming:

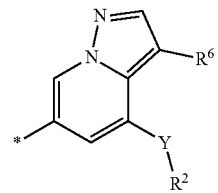

wherein * indicates the connection point to A in formula (IIA), forming a compound of the formula:

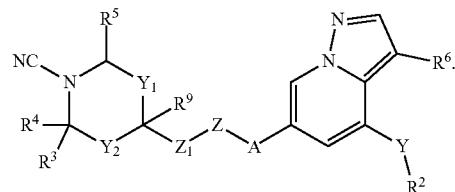

In the compounds of formula (I), A can be pyrazole, 1,2,3 triazole, 1,2,4 triazole, 1,2,3 thiadiazole, 1,2,4 thiadiazole, 1,2,5 thiadiazole, 1,3,4 thiadiazole, 1,2,3 oxadiazole, 1,2,4 oxadiazole, 1,2,5 oxadiazole, or 1,3,4 oxadiazole, substituted with $R^1$ and $R^{1A}$.

In the compounds of formula (I), A can be pyrazole, 1,2,3 triazole, or 1,2,4 triazole, substituted with $R^1$ and $R^{1A}$.

In the compounds of formula (I), A can be pyrazole, 1,2,3 triazole, or 1,2,4 triazole, substituted with $R^1$ and $R^{1A}$, wherein $R^{1A}$ is hydrogen and $R^1$ is $C_1$-$C_3$ alkyl.

In the compounds of formula (I), A can be pyrazole, 1,2,3 triazole, or 1,2,4 triazole, substituted with $R^1$ and $R^{1A}$, wherein $R^{1A}$ is hydrogen and $R^1$ is $CH_3$.

In the compounds of formula (II), (IIA) or (III), A can be pyrazole, 1,2,3 triazole, 1,2,4 triazole, 1,2,3 thiadiazole, 1,2,4 thiadiazole, 1,2,5 thiadiazole, 1,3,4 thiadiazole, 1,2,3 oxadiazole, 1,2,4 oxadiazole, 1,2,5 oxadiazole, or 1,3,4 oxadiazole, optionally substituted with $R^1$.

In the compounds of formula (II), (IIA) or (III), A can be pyrazole, 1,2,3 triazole, or 1,2,4 triazole, optionally substituted with $R^1$.

In the compounds of formula (II), (IIA) or (III), A can be pyrazole, 1,2,3 triazole, or 1,2,4 triazole, substituted with $R^1$.

In the compounds of formula (II), (IIA) or (III), A can be pyrazole, 1,2,3 triazole, or 1,2,4 triazole, substituted with $CH_3$.

In the compounds of formula (I), (II), (IIA) or (III), A can be:

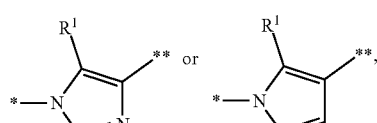

wherein * indicates the connection point to Z or Z' and ** indicates the other connection point from A in formula (I), (II), (IIA) or (III); and $R^1$ can be $C_1$-$C_3$ alkyl.

In the compounds of formula (I), Z can be $CHR^{9A}$, cyclobutyl, azetidine, pyrrolidine or piperidine.

In the compounds of formula (I), Z can be a bond,

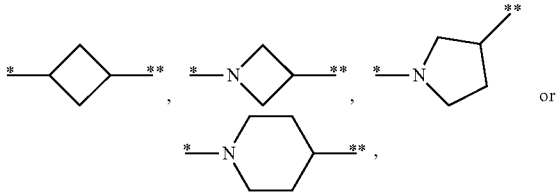

wherein * indicates the connection point to $Z_1$ and ** indicates the connection point to A in formula (I).

In the compounds of formula (I), Z can be a bond,

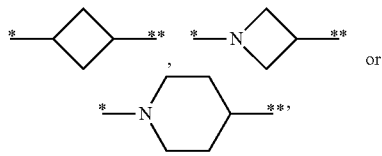

wherein * indicates the connection point to $Z_1$ and ** indicates the connection point to A in formula (I).

In the compounds of formula (II) or (IIA), Z can be $CHR^{9A}$, azetidine, pyrrolidine or piperidine.

In the compounds of formula (II) or (IIA), Z can be a bond,

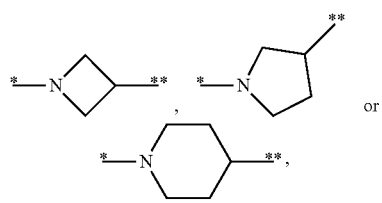

wherein * indicates the connection point to $Z_1$ and ** indicates the connection point to A in formula (II) or (IIA).

In the compounds of formula (II) or (IIA), Z can be:

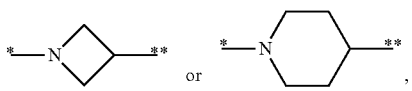

wherein * indicates the connection point to $Z_1$ and ** indicates the connection point to A in formula (II) or (IIA).

In the compounds of formula (I), (II) or (IIA), Z can be $CHR^{9A}$, $Z_1$ can be selected from $CH_2$ or $CH_2$—$CH_2$, and $R^9$ can be fused with $R^{9A}$ to form $CH_2$ or $CH_2$—$CH_2$.

In the compounds of formula (I), (II) or (IIA), Z can be $CHR^{9A}$, $Z_1$ can be $CH_2$, and $R^9$ can be fused with $R^{9A}$ to form $CH_2$ or $CH_2$—$CH_2$.

In the compounds of formula (I), (II) or (IIA), Z can be $CHR^{9A}$, $Z_1$ can be $CH_2$—$CH_2$, and $R^9$ can be fused with $R^{9A}$ to form $CH_2$ or $CH_2$—$CH_2$.

In the compounds of formula (I), (II) or (IIA), Z can be $CHR^{9A}$, $Z_1$ can be selected from $CH_2$ or $CH_2$—$CH_2$, and $R^9$ can be fused with $R^{9A}$ to form $CH_2$.

In the compounds of formula (I), (II) or (IIA), Z can be $CHR^{9A}$, $Z_1$ can be selected from $CH_2$ or $CH_2$—$CH_2$, and $R^9$ can be fused with $R^{9A}$ to form $CH_2$—$CH_2$.

In the compounds of formula (I), (II) or (IIA), Z can be $CHR^{9A}$, $Z_1$ can be $CH_2$, and $R^9$ can be fused with $R^{9A}$ to form $CH_2$.

In the compounds of formula (I), (II) or (IIA), Z can be $CHR^{9A}$, $Z_1$ can be $CH_2$—$CH_2$, and $R^9$ can be fused with $R^{9A}$ to form $CH_2$—$CH_2$.

In the compounds of formula (III), Z' can be:

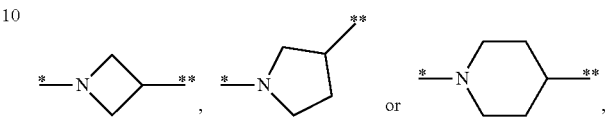

wherein ** indicates the connection point to A and * indicates the other connection point from Z' in formula (III).

In the compounds of formula (III), Z' can be:

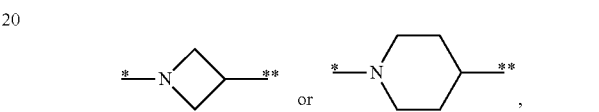

wherein ** indicates the connection point to A and * indicates the other connection point from Z' in formula (III).

In the compounds of formula (I), (II) or (IIA), Z can be a bond.

In the compounds of formula (III), Z' can be a bond.

In the compounds of formula (I), (II) or (IIA), $Z_1$ can be a bond.

In the compounds of formula (I), (II), (IIA) or (III), Y can be NH or O.

In the compounds of formula (I), (II), (IIA) or (III), Y can be O.

In the compounds of formula (I), $Y_1$ can be a bond, $CHR^7$, $CH_2$—$CHR^7$ or $CHR^7$—$CH_2$, wherein $R^7$ is selected from hydrogen, F, OH and $CH_3$; and $Y_2$ can a bond, $CHR^3$, $CH_2$—$CHR^3$ or $CHR^3$—$CH_2$, wherein $R^3$ is selected from hydrogen, F, OH and $CH_3$.

In the compounds of formula (I), $Y_1$ can be a bond or $CHR^7$, wherein $R^7$ is hydrogen, F, OH or $CH_3$; and $Y_2$ can a bond or $CHR^3$, wherein $R^3$ is hydrogen, F, OH or $CH_3$.

In the compounds of formula (I), $Y_1$ can be a bond, $CHR^7$, $CH_2$—$CHR^7$ or $CHR^7$—$CH_2$, wherein $R^7$ is hydrogen, F, OH or $CH_3$; and $Y_2$ can a bond, $CHR^3$, $CH_2$—$CHR^3$ or $CHR^3$—$CH_2$, wherein $R^3$ is hydrogen, F, OH or $CH_3$, forming:

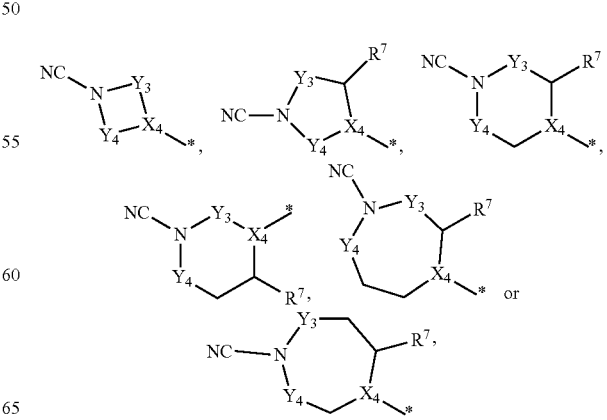

wherein * indicates the connection point to $Z_1$ in formula (I).

In the compounds of formula (I), $Y_1$ can be a bond or $CHR^7$, wherein $R^7$ is hydrogen, F, OH or $CH_3$; and $Y_2$ can a bond or $CHR^3$, wherein $R^3$ is hydrogen, F, OH or $CH_3$, forming:

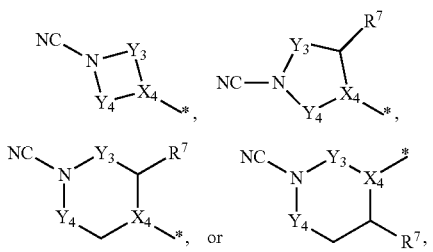

wherein * indicates the connection point to $Z_1$ in formula (I).

In the compounds of formula (II), (IIA) or (III), $Y_1$ can be a bond, $CH_2$, or $CH_2$—$CH_2$, and $Y_2$ can be a bond, $CH_2$, $CF_2$ or $CH_2$—$CH_2$, forming:

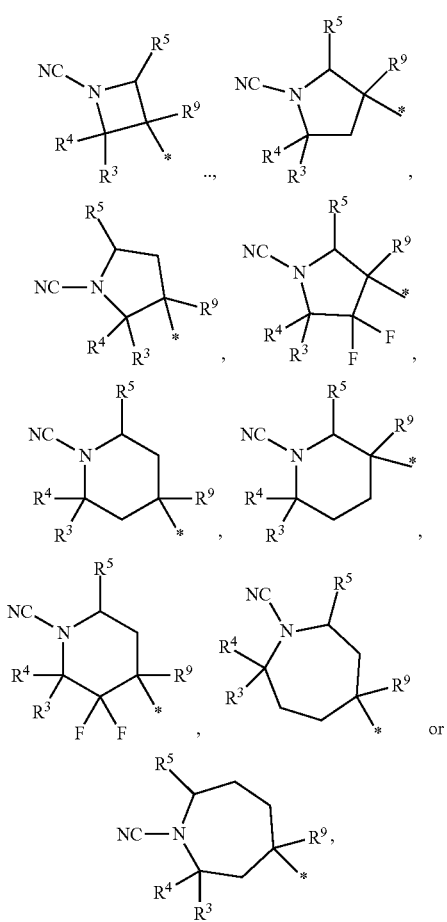

wherein * indicates the connection point to $Z_1$ in formula (II) or (IIA), or Z' in formula (III).

In the compounds of formula (II), (IIA) or (III), $Y_1$ can be a bond, $CH_2$, or $CH_2$—$CH_2$; and $Y_2$ can be a bond, $CH_2$, or $CF_2$, forming:

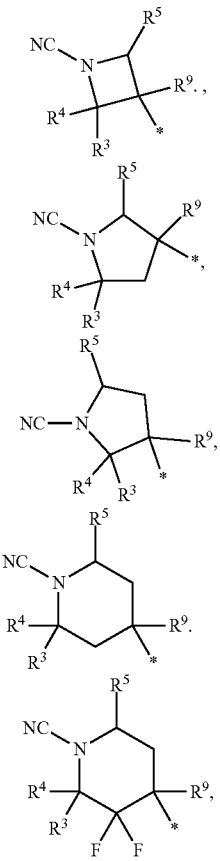

wherein * indicates the connection point to $Z_1$ in formula (II) or (IIA), or Z' in formula (III).

In the compounds of formula (I), $R^{1A}$ can be hydrogen, or $C_1$-$C_3$ alkyl optionally substituted with one or more substituents independently selected from halo, OH, and $OCH_3$.

In the compounds of formula (I), $R^{1A}$ can be hydrogen or $CH_3$.

In the compounds of formula (I), $R^{1A}$ can be hydrogen.

In the compounds of formula (I), (II), (IIA) or (III), $R^1$ can be methyl, ethyl or propyl.

In the compounds of formula (I), (II), (IIA) or (III), $R^1$ can be methyl.

In the compounds of formula (I), $R^2$ can be $C_1$-$C_3$ alkyl optionally substituted with one, two, three or four substituents independently selected from halo, OH, CN, oxo, —$OC_1$-$C_4$ alkyl, —$OC_3$-$C_5$ cycloalkyl, —$Z_2$—$R^{11}$ and $R^{10}$, wherein $C_1$-$C_4$ alkyl and $C_3$-$C_5$ cycloalkyl are optionally substituted with one or more substituents independently selected from halo, OH, $OCH_3$, methylamine, N,N-dimethylamine and CN.

In the compounds of formula (I), $R^2$ can be $C_1$-$C_4$ alkyl optionally substituted with one or more substituents independently selected from F, OH, CN, oxo, —$OCH_3$, —$OC_3$ cycloalkyl and $R^{10}$.

In the compounds of formula (I), $R^2$ can be:

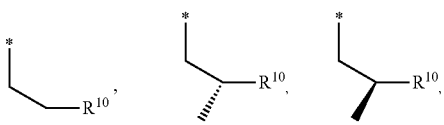

-continued

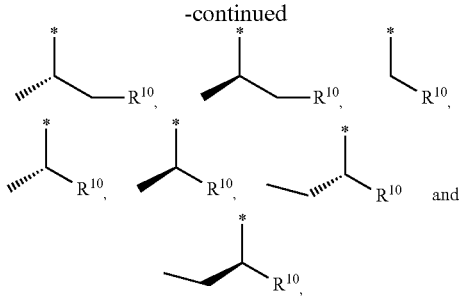

optionally substituted with one, two, three or four substituents independently selected from halo, OH, CN, oxo, —OC$_1$-C$_4$ alkyl, —OC$_3$-C$_5$ cycloalkyl, —Z$_2$—R$^{11}$ and R$^{10}$, wherein C$_1$-C$_4$ alkyl and C$_3$-C$_5$ cycloalkyl are optionally substituted with one or more substituents independently selected from halo, OH, OCH$_3$, methylamine, N,N-dimethylamine and CN, wherein * indicates the connection point to Y in formula (I).

In the compounds of formula (I), R$^2$ can be:

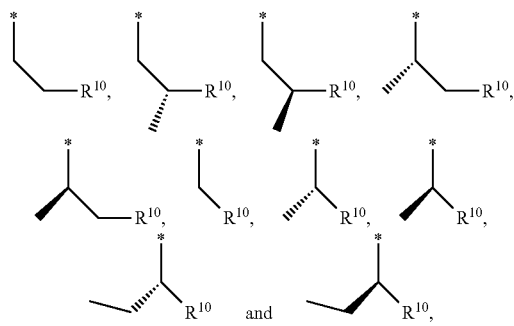

optionally substituted with one, two, three or four substituents independently selected from F, OH, CN, oxo, —OCH$_3$, —OC$_3$ cycloalkyl and R$^{10}$, wherein * indicates the connection point to Y in formula (I).

In the compounds of formula (I), R$^2$ can be:

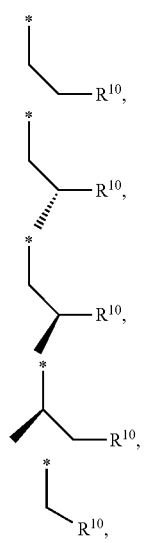

-continued

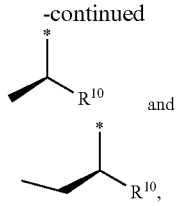

optionally substituted with one, two, three or four substituents independently selected from halo, OH, CN, oxo, —OC$_1$-C$_4$ alkyl, —OC$_3$-C$_5$ cycloalkyl, —Z$_2$—R$^{11}$ and R$^{10}$, wherein C$_1$-C$_4$ alkyl and C$_3$-C$_5$ cycloalkyl are optionally substituted with one or more substituents independently selected from halo, OH, OCH$_3$, methylamine, N,N-dimethylamine and CN, wherein * indicates the connection point to Y in formula (I).

In the compounds of formula (I), R$^2$ can be:

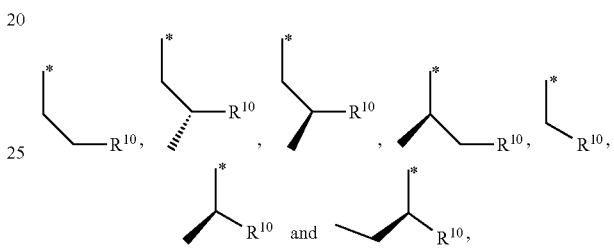

optionally substituted with one, two, three or four substituents independently selected from F, OH, CN, oxo, —OCH$_3$ and —OC$_3$ cycloalkyl and R$^{10}$, wherein * indicates the connection point to Y in formula (I).

In the compounds of formula (II), (IIA) or (III), R$^2$ can be C$_1$-C$_4$ alkyl optionally substituted with one or more substituents independently selected from OH, methoxy, halomethyl and R$^{10}$.

In the compounds of formula (II), (IIA) or (III), R$^2$ can be C$_1$-C$_3$ alkyl optionally substituted with one or two substituents independently selected from OH, methoxy, halomethyl and R$^{10}$.

In the compounds of formula (II), (IIA) or (III), R$^2$ can be C$_1$-C$_3$ alkyl optionally substituted with one or more substituents independently selected from OH, methoxy, halomethyl and R$^{10}$.

In the compounds of formula (II), (IIA) or (III), R$^2$ can be C$_1$-C$_3$ alkyl optionally substituted with one, two or three substituents independently selected from OH, methoxy, halomethyl and R$^{10}$.

In the compounds of formula (II), (IIA) or (III), R$^2$ can be C$_1$-C$_2$ alkyl optionally substituted with one or two substituents independently selected from OH, methoxy, halomethyl and R$^{10}$.

In the compounds of formula (II), (IIA) or (III), R$^2$ can be:

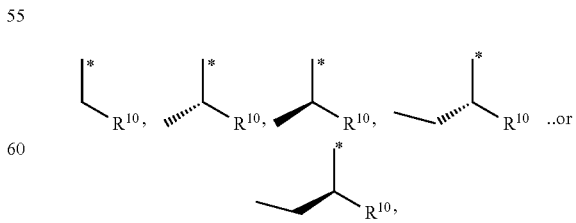

optionally substituted with one or two substituents independently selected from OH, CF$_3$ and methoxy, wherein * indicates the connection point to Y in formula (II), (IIA) or (III).

In the compounds of formula (II), (IIA) or (III), $R^2$ can be:

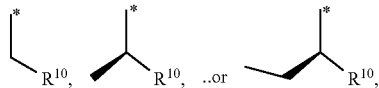

optionally substituted with one or two substituents independently selected from OH, $CF_3$ and methoxy, wherein * indicates the connection point to Y in formula (II), (IIA) or (III).

In the compounds of formula (II) (IIA) or (III), $R^Z$ can be:

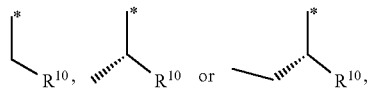

optionally substituted with one or two substituents independently selected from OH, $CF_3$ and methoxy, wherein * indicates the connection point to Y in formula (II), (IIA) or (III).

In the compounds of formula (I), $Y_3$ can be $CR^4R^5$ or $CF_2$, wherein $R^4$ is hydrogen or $CH_3$ and $R^5$ is hydrogen, F, OH or $CH_3$; and $Y_4$ is $CR^3R^4$ or $CF_2$ wherein $R^4$ is hydrogen or $CH_3$, and $R^3$ is hydrogen, F, OH or $CH_3$.

In the compounds of formula (I), $Y_3$ can be $CR^4R^5$, wherein $R^4$ is hydrogen and $R^5$ is fused with one $R^3$ to form $CH_2$, $CH_2$—$CH_2$ or $CH_2OCH_2$; and $Y_4$ is $CR^3R^4$ wherein $R^4$ is hydrogen, and $R^3$ is fused with $R^5$ to form $CH_2$, $CH_2$—$CH_2$ or $CH_2OCH_2$.

In the compounds of formula (I), $Y_3$ can be $CR^4R^5$, wherein $R^4$ is hydrogen and $R^5$ is fused with one $R^3$ to form $CH_2$, $CH_2$—$CH_2$ or $CH_2OCH_2$; and $Y_4$ is $CR^3R^4$ wherein $R^4$ is hydrogen, and $R^3$ is fused with $R^5$ to form $CH_2$, $CH_2$—$CH_2$ or $CH_2OCH_2$, forming:

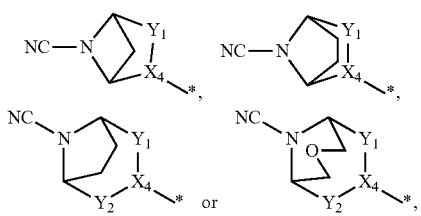

wherein * indicates the connection point to $Z_1$ in formula (I).

In the compounds of formula (I), $X_4$ can be N or C—$R^9$ wherein $R^9$ is hydrogen or $CH_3$.

In the compounds of formula (I), $X_4$ can be C—$R^9$ wherein $R^9$ is fused with $R^{9A}$ to form $CH_2$ or $CH_2$—$CH_2$; and $Z_1$ is $CH_2$ or $CH_2$—$CH_2$.

In the compounds of formula (I), $X_4$ can be N or CH.

In the compounds of formula (II), (IIA) or (III), $R^3$ can be hydrogen, $C_1$-$C_3$ alkyl, or fused with $R^5$ to form $CH_2$ or $CH_2$—$CH_2$.

In the compounds of formula (II), (IIA) or (III), $R^3$ can be hydrogen, $C_1$-$C_2$ alkyl, or fused with $R^5$ to form $CH_2$ or $CH_2$—$CH_2$.

In the compounds of formula (II), (IIA) or (III), $R^3$ can be hydrogen or methyl.

In the compounds of formula (II), (IIA) or (III), $R^4$ can be hydrogen or $C_1$-$C_2$ alkyl.

In the compounds of formula (II), (IIA) or (III), $R^4$ can be hydrogen or methyl.

In the compounds of formula (II), (IIA) or (III), $R^3$ and $R^4$ can be hydrogen.

In the compounds of formula (II), (IIA) or (III), $R^5$ can be hydrogen.

In the compounds of formula (II), (IIA) or (III), $R^5$ can fuse with one $R^3$ to form $CH_2$—$CH_2$.

In the compounds of formula (I), $R^6$ can be CN, F, Cl, $CH_3$, $CF_3$ or cyclopropyl.

In the compounds of formula (I), $R^6$ can be CN, F or Cl.

In the compounds of formula (I), (II), (IIA) or (III), $R^6$ can be CN or Cl.

In the compounds of formula (I), (II), (IIA) or (III), $R^6$ can be CN.

In the compounds of formula (II), (IIA) or (III), $R^7$ can be hydrogen.

In the compounds of formula (II), (IIA) or (III), $R^7$ can fuse with one $R^3$ to form $CH_2$.

In the compounds of formula (I), (II), (IIA) or (III), $R^8$ can be 5-6 membered cycloalkyl, 5-6 membered heterocycloalkyl, 5-6 membered aryl or 5-6 membered heteroaryl, optionally fused or substituted with $R^{8A}$.

In the compounds of formula (I), (II), (IIA) or (III), $R^8$ can be 5-6 membered cycloalkyl, or 5-6 membered heterocycloalkyl, optionally fused with $R^{8A}$.

In the compounds of formula (I), (II), (IIA) or (III), $R^8$ can be cyclopentyl, cyclohexyl, piperidinyl, pyrrolidinyl, tetrahydrofuranyl, tetrahydropyranyl, phenyl or pyridinyl, optionally fused with $R^{8A}$.

In the compounds of formula (I), (II), (IIA) or (III), $R^8$ can be cyclopentyl, cyclohexyl, piperidinyl, pyrrolidinyl, tetrahydrofuranyl or tetrahydropyranyl, fused with $R^{8A}$.

In the compounds of formula (I), (II), (IIA) or (III), $R^8$ can be cyclopentyl, cyclohexyl, piperidinyl, pyrrolidinyl, tetrahydrofuranyl or tetrahydropyranyl, fused with $R^{8A}$, wherein $R^{8A}$ can be phenyl or 6 membered heteroaryl.

In the compounds of formula (I), (II), (IIA) or (III), $R^9$ can be hydrogen.

In the compounds of formula (I), (II), (IIA) or (III), $R^{10}$ can be 3-6 membered cycloalkyl, 5-6 membered heterocycloalkyl, 5-6 membered aryl or 5-6 membered heteroaryl, optionally fused with $R^{8A}$.

In the compounds of formula (I), (II), (IIA) or (III), $R^{10}$ can be 3-6 membered cycloalkyl, 5-6 membered heterocycloalkyl, phenyl or 5-6 membered heteroaryl, optionally fused with $R^{8A}$.

In the compounds of formula (I), (II), (IIA) or (III), $R^{10}$ can be cyclopropyl, cyclobutyl, cyclopentyl, cyclohexyl, piperidinyl, piperazinyl, pyrrolidinyl, pyrrolidin-2-onyl, dioxanyl, morpholinyl, tetrahydrofuranyl, tetrahydrothiophenyl, tetrahydropyranyl, oxazolidinyl, isothiazolidinyl, oxozolid-2-onyl, isothiazolid-2-onyl, phenyl, pyridinyl, pyrazinyl, pyrimidinyl, pyridazinyl, furanyl, pyrrolyl, thiophenyl, imidazolyl, pyrazolyl, triazolyl, oxazolyl, isoxazolyl, thiazolyl, isothiazolyl, oxadiazolyl or thiadiazolyl, optionally fused with $R^{8A}$.

In the compounds of formula (I), (II), (IIA) or (III), $R^{10}$ can be cyclopropyl, cyclobutyl, cyclopentyl, cyclohexyl, tetrahydrofuranyl, tetrahydropyranyl, phenyl, pyridinyl, pyrazinyl, pyrimidinyl, pyridazinyl, pyrazolyl, triazolyl, oxazolyl, isoxazolyl, thiazolyl, isothiazolyl, oxadiazolyl or thiadiazolyl, optionally fused with $R^{8A}$.

In the compounds of formula (I), (II), (IIA) or (III), $R^{10}$ can be cyclopropyl, cyclobutyl, cyclopentyl, cyclohexyl, tetrahydrofuranyl, tetrahydropyranyl, phenyl, pyridinyl, pyrazinyl, pyrimidinyl, pyridazinyl, oxazolyl, isoxazolyl, thiazolyl, isothiazolyl, oxadiazolyl or thiadiazolyl, optionally fused with $R^{8A}$.

In the compounds of formula (I), (II), (IIA) or (III), $R^{10}$ can be cyclopropyl, cyclobutyl, phenyl, pyridinyl, oxazolyl, isoxazolyl, thiazolyl or isothiazolyl, optionally fused with $R^{8A}$.

In the compounds of formula (I), (II), (IIA) or (III), $R^{10}$ can be cyclopropyl, cyclobutyl, cyclopentyl, cyclohexyl, piperidinyl, piperazinyl, pyrrolidinyl, pyrrolidin-2-onyl, dioxanyl, morpholinyl, tetrahydrofuranyl, tetrahydrothiophenyl, tetrahydropyranyl, oxazolidinyl, isothiazolidinyl, oxozolid-2-onyl, isothiazolid-2-onyl, phenyl, pyridinyl, pyrazinyl, pyrimidinyl, pyridazinyl, furanyl, pyrrolyl, thiophenyl, imidazolyl, pyrazolyl, triazolyl, oxazolyl, isoxazolyl, thiazolyl, isothiazolyl, oxadiazolyl or thiadiazolyl.

In the compounds of formula (I), (II), (IIA) or (III), $R^{10}$ can be cyclopropyl, cyclobutyl, cyclopentyl, cyclohexyl, tetrahydrofuranyl, tetrahydropyranyl, phenyl, pyridinyl, pyrazinyl, pyrimidinyl, pyridazinyl, pyrazolyl, triazolyl, oxazolyl, isoxazolyl, thiazolyl, isothiazolyl, oxadiazolyl or thiadiazolyl.

In the compounds of formula (I), (II), (IIA) or (III), $R^{10}$ can be cyclopropyl, cyclobutyl, cyclopentyl, cyclohexyl, tetrahydrofuranyl, tetrahydropyranyl, phenyl, pyridinyl, pyrazinyl, pyrimidinyl, pyridazinyl, oxazolyl, isoxazolyl, thiazolyl, isothiazolyl, oxadiazolyl or thiadiazolyl.

In the compounds of formula (I), (II), (IIA) or (III), $R^{10}$ can be cyclopropyl, cyclobutyl, phenyl, pyridinyl, oxazolyl, isoxazolyl, thiazolyl or isothiazolyl.

In the compounds of formula (II), (IIA) or (III), $R^{10}$ can be 5-6 membered cycloalkyl, 5-6 membered heterocycloalkyl, phenyl or 5-6 membered heteroaryl, fused with $R^{8A}$.

In the compounds of formula (I), (II), (IIA) or (III), $R^{10}$ can be cyclopentyl, cyclohexyl, tetrahydrofuranyl, tetrahydropyranyl, phenyl, pyridinyl, pyrazinyl, pyrimidinyl, pyridazinyl, pyrazolyl, triazolyl, oxazolyl, isoxazolyl, thiazolyl, isothiazolyl, oxadiazolyl or thiadiazolyl, fused with $R^{8A}$.

In the compounds of formula (I), (II), (IIA) or (III), $R^{10}$ can be cyclopentyl, cyclohexyl, piperidinyl, pyrrolidinyl, tetrahydrofuranyl, tetrahydropyranyl, phenyl or pyridinyl, fused with $R^{8A}$.

In the compounds of formula (I), (II), (IIA) or (III), $R^{10}$ can be cyclopentyl, cyclohexyl, piperidinyl, pyrrolidinyl, tetrahydrofuranyl, tetrahydropyranyl, phenyl or pyridinyl, fused with $R^{8A}$.

In the compounds of formula (I, (II), (IIA) or (III), $R^{10}$ can be cyclopentyl, cyclohexyl, piperidinyl, pyrrolidinyl, tetrahydrofuranyl, tetrahydropyranyl, phenyl or pyridinyl, fused with $R^{8A}$.

In the compounds of formula (I), (II), (IIA) or (III), $R^{10}$ can be cyclopentyl, cyclohexyl, phenyl or pyridinyl, fused with $R^{8A}$.

In the compounds of formula (I), (II), (IIA) or (III), $R^{10}$ can be phenyl or pyridinyl, fused with $R^{8A}$ wherein $R^{8A}$ can be 5-6 membered heterocycloalkyl or 5-6 membered heteroaryl.

In the compounds of formula (I), (II), (IIA) or (III), $R^{10}$ can be phenyl or pyridinyl, fused with $R^{8A}$ wherein $R^{8A}$ can be pyrrolidinyl, pyrrolidin-2-onyl, dioxanyl, tetrahydrofuranyl, tetrahydrothiophenyl, tetrahydropyranyl, oxazolidinyl, isothiazolidinyl, oxozolid-2-onyl, isothiazolid-2-onyl furanyl, pyrrolyl, thiophenyl, imidazolyl, pyrazolyl, triazolyl, oxazolyl, isoxazolyl, thiazolyl, isothiazolyl, oxadiazolyl or thiadiazolyl.

In the compounds of formula (I), (II), (IIA) or (III), $R^{10}$ can be phenyl or pyridinyl, fused with $R^{8A}$ wherein $R^{8A}$ can be tetrahydrofuranyl, tetrahydrothiophenyl, tetrahydropyranyl, oxazolidinyl, isothiazolidinyl, oxozolid-2-onyl, isothiazolid-2-onyl, furanyl, pyrrolyl, thiophenyl, imidazolyl, pyrazolyl, triazolyl, oxazolyl, isoxazolyl, thiazolyl, isothiazolyl, oxadiazolyl or thiadiazolyl.

In the compounds of formula (I), (II), (IIA) or (III), $R^{10}$ can be phenyl or pyridinyl, fused with $R^{8A}$ wherein $R^{8A}$ can be tetrahydrofuranyl, tetrahydrothiophenyl, tetrahydropyranyl, oxazolidinyl, isothiazolidinyl, oxozolid-2-only or isothiazolid-2-onyl.

In the compounds of formula (I), (II) or (IIA), where both Z and $Z_1$ are a bond, together they form a single bond.

In the compounds of formula (I), Z can be $CHR^{9A}$, $Z_1$ can be $CH_2$, $X_4$ can be $C-R^9$, and $R^9$ can be fused with $R^{9A}$ to form $CH_2$, forming:

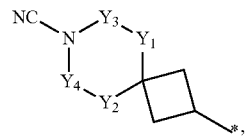

wherein * indicates the connection point to A.

In the compounds of formula (II) or (IIA), Z can be $CHR^{9A}$, $Z_1$ can be $CH_2$, and $R^9$ can be fused with $R^{9A}$ to form $CH_2$, forming:

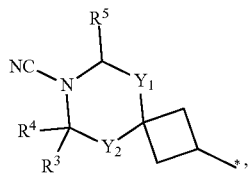

wherein * indicates the connection point to A.

In the compounds of formula (I), (II), (IIA) or (III), $R^5$ can be fused with one $R^3$ to form $CH_2-CH_2$, for example forming:

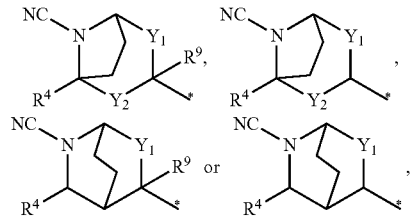

wherein * indicates the connection point to $Z_1$ in formula (I) or Z' in formula (II), (IIA) or (III).

In the compounds of formula (I), (II), (IIA) or (III), $R^7$ can be cyclopentyl, fused with $R^{8A}$, wherein $R^{8A}$ can be pyridinyl, for example forming:

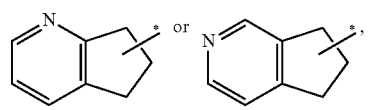

wherein * indicates the connection point to Y.

In the compounds of formula (I), A can be pyrazole, 1,2,3 triazole, or 1,2,4 triazole, substituted with $R^1$ and $R^{1A}$; and Y can be NH or O.

In the compounds of formula (I), A can be pyrazole, 1,2,3 triazole, or 1,2,4 triazole, substituted with $R^1$ and $R^{1A}$, wherein $R^{1A}$ is hydrogen and $R^1$ is $C_1$-$C_3$ alkyl; and Y can be NH or O.

In the compounds of formula (II), (IIA) or (III), A can be pyrazole, 1,2,3 triazole, or 1,2,4 triazole, substituted with $R^1$; and Y can be NH or O.

In the compounds of formula (I), (II), (IIA) or (III), A can be:

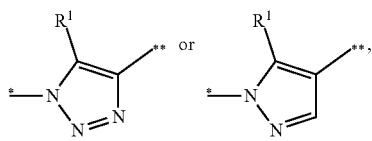

wherein * indicates the connection point to Z or Z' and ** indicates the other connection point from A in formula (I), (II), (IIA) or (III); $R^1$ can be $C_1$-$C_3$ alkyl; and Y can be NH or O.

In the compounds of formula (I), A can be pyrazole, 1,2,3 triazole, or 1,2,4 triazole, substituted with $R^1$ and $R^{1A}$; and Y can be O.

In the compounds of formula (I), A can be pyrazole, 1,2,3 triazole, or 1,2,4 triazole, substituted with $R^1$ and $R^{1A}$, wherein $R^{1A}$ is hydrogen and $R^1$ is $C_1$-$C_3$ alkyl; and Y can be O.

In the compounds of formula (II), (IIA) or (III), A can be pyrazole, 1,2,3 triazole, or 1,2,4 triazole, substituted with $R^1$; and Y can be O.

In the compounds of formula (I), (II), (IIA) or (III), A can be:

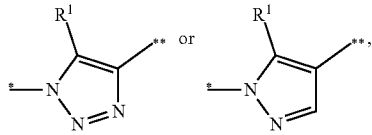

wherein * indicates the connection point to Z or Z' and ** indicates the other connection point from A in formula (I), (II), (IIA) or (III); $R^1$ can be $C_1$-$C_3$ alkyl; and Y can be O.

In the compounds of formula (I), A can be pyrazole, 1,2,3 triazole, or 1,2,4 triazole, substituted with $R^1$ and $R^{1A}$; and $R^6$ can be CN, F, Cl, $CH_3$, $CF_3$ or cyclopropyl.

In the compounds of formula (I), A can be pyrazole, 1,2,3 triazole, or 1,2,4 triazole, substituted with $R^1$ and $R^{1A}$, wherein $R^{1A}$ is hydrogen and $R^1$ is $C_1$-$C_3$ alkyl; and $R^6$ can be CN, F, Cl or $CF_3$.

In the compounds of formula (I), A can be:

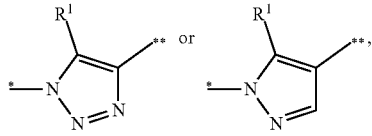

wherein * indicates the connection point to Z or Z' and ** indicates the other connection point from A in formula (I); and $R^6$ can be CN, F, Cl, $CH_3$, $CF_3$ or cyclopropyl.

In the compounds of formula (I), A can be:

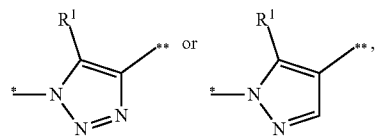

wherein * indicates the connection point to Z or Z' and ** indicates the other connection point from A in formula (I); and $R^6$ can be CN, F, Cl or $CF_3$.

In the compounds of formula (II), (IIA) or (III), A can be pyrazole, 1,2,3 triazole, or 1,2,4 triazole, substituted with $R^1$; and $R^6$ can be CN or Cl.

In the compounds of formula (I), (II), (IIA) or (III), A can be:

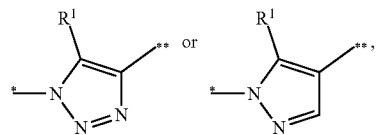

wherein * indicates the connection point to Z or Z' and ** indicates the other connection point from A in formula (I), (II), (IIA) or (III); $R^1$ can be $C_1$-$C_3$ alkyl; and $R^6$ can be CN or Cl.

In the compounds of formula (I), A can be pyrazole, 1,2,3 triazole, or 1,2,4 triazole, substituted with $R^1$ and $R^{1A}$; $R^6$ can be CN, F, Cl, $CH_3$, $CF_3$ or cyclopropyl; and Y can be NH or O.

In the compounds of formula (I), A can be pyrazole, 1,2,3 triazole, or 1,2,4 triazole, substituted with $R^1$ and $R^{1A}$, wherein $R^{1A}$ is hydrogen and $R^1$ is $C_1$-$C_3$ alkyl; $R^6$ can be CN, F, Cl or $CF_3$; and Y can be NH or O.

In the compounds of formula (I), A can be:

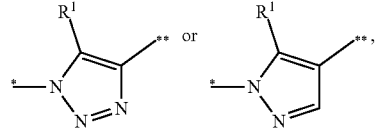

wherein * indicates the connection point to Z or Z' and ** indicates the other connection point from A in formula (I); $R^6$ can be CN, F, Cl, $CH_3$, $CF_3$ or cyclopropyl; and Y can be NH or O.

In the compounds of formula (I), A can be:

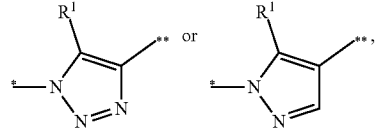

wherein * indicates the connection point to Z or Z' and ** indicates the other connection point from A in formula (I); $R^6$ can be CN, F, Cl or $CF_3$; and Y can be NH or O.

In the compounds of formula (II), (IIA) or (III), A can be pyrazole, 1,2,3 triazole, or 1,2,4 triazole, substituted with $R^1$; $R^6$ can be CN or Cl; and Y can be NH or O.

In the compounds of formula (I), (II), (IIA) or (III), A can be:

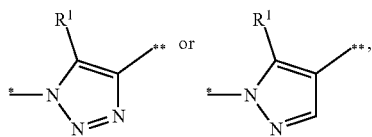

wherein * indicates the connection point to Z or Z' and ** indicates the other connection point from A in formula (I), (II), (IIA) or (III); $R^1$ can be $C_1$-$C_3$ alkyl; $R^6$ can be CN or Cl; and Y can be NH or O.

In the compounds of formula (I), A can be pyrazole, 1,2,3 triazole, or 1,2,4 triazole, substituted with $R^1$ and $R^{1A}$; $R^6$ can be CN, F, Cl, $CH_3$, $CF_3$ or cyclopropyl; and Y can be O.

In the compounds of formula (I), A can be pyrazole, 1,2,3 triazole, or 1,2,4 triazole, substituted with $R^1$ and $R^{1A}$, wherein $R^{1A}$ is hydrogen and $R^1$ is $C_1$-$C_3$ alkyl; $R^6$ can be CN, F, Cl or $CF_3$; and Y can be O.

In the compounds of formula (I), A can be:

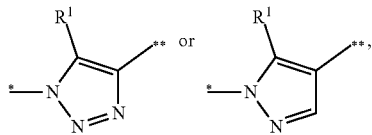

wherein * indicates the connection point to Z or Z' and ** indicates the other connection point from A in formula (I); $R^6$ can be CN, F, Cl, $CH_3$, $CF_3$ or cyclopropyl; and Y can be O.

In the compounds of formula (I), A can be:

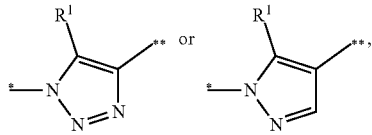

wherein * indicates the connection point to Z or Z' and ** indicates the other connection point from A in formula (I); $R^6$ can be CN, F, Cl or $CF_3$; and Y can be O.

In the compounds of formula (II), (IIA) or (III), A can be pyrazole, 1,2,3 triazole, or 1,2,4 triazole, substituted with $R^1$; $R^6$ can be CN or Cl; and Y can be O.

In the compounds of formula (I), (II), (IIA) or (III), A can be:

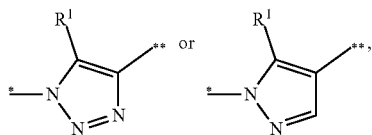

wherein * indicates the connection point to Z or Z' and ** indicates the other connection point from A in formula (I), (II), (IIA) or (III); $R^1$ can be $C_1$-$C_3$ alkyl; $R^6$ can be CN or Cl; and Y can be O.

In the compounds of formula (I), A can be pyrazole, 1,2,3 triazole, or 1,2,4 triazole, substituted with $R^1$ and $R^{1A}$; $R^6$ can be CN, F, Cl, $CH_3$, $CF_3$ or cyclopropyl; Y can be NH or O; and $R^2$ can be $C_1$-$C_3$ alkyl optionally substituted with one, two, three or four substituents independently selected from halo, OH, CN, oxo, —$OC_1$-$C_4$ alkyl, —$OC_3$-$C_5$ cycloalkyl, —$Z_2$—$R^{11}$ and $R^{10}$, wherein $C_1$-$C_4$ alkyl and $C_3$-$C_5$ cycloalkyl are optionally substituted with one or more substituents independently selected from halo, OH, $OCH_3$, methylamine, N,N-dimethylamine and CN.

In the compounds of formula (I), A can be pyrazole, 1,2,3 triazole, or 1,2,4 triazole, substituted with $R^1$ and $R^{1A}$; $R^6$ can be CN, F, Cl, $CH_3$, $CF_3$ or cyclopropyl; Y can be NH or O; and $R^2$ can be $C_1$-$C_4$ alkyl optionally substituted with one or more substituents independently selected from F, OH, CN, oxo, —$OCH_3$, —$OC_3$ cycloalkyl and $R^{10}$.

In the compounds of formula (I), A can be pyrazole, 1,2,3 triazole, or 1,2,4 triazole, substituted with $R^1$ and $R^{1A}$; $R^6$ can be CN, F, Cl or $CF_3$; Y can be NH or O; and $R^2$ can be:

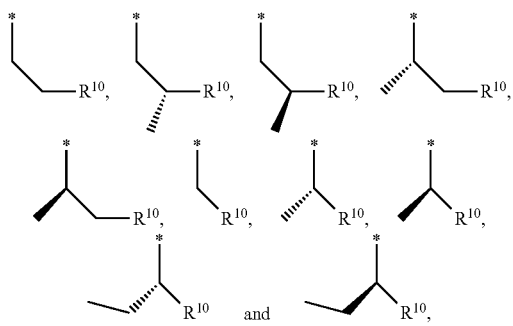

optionally substituted with one, two, three or four substituents independently selected from halo, OH, CN, oxo, —$OC_1$-$C_4$ alkyl, —$OC_3$-$C_5$ cycloalkyl, —$Z_2$—$R^{11}$ and $R^{10}$, wherein $C_1$-$C_4$ alkyl and $C_3$-$C_5$ cycloalkyl are optionally substituted with one or more substituents independently selected from halo, OH, $OCH_3$, methylamine, N,N-dimethylamine and CN, wherein * indicates the connection point to Y in formula (I).

In the compounds of formula (I), A can be pyrazole, 1,2,3 triazole, or 1,2,4 triazole, substituted with $R^1$ and $R^{1A}$; $R^6$ can CN, F, Cl or $CF_3$; Y can be NH or O; and $R^2$ can be:

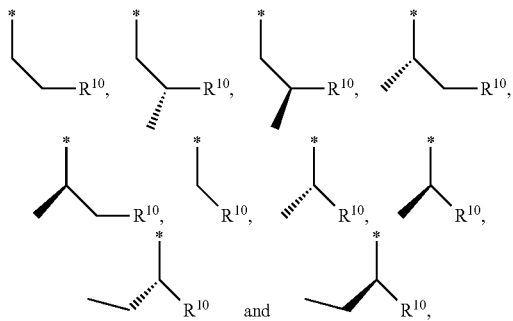

optionally substituted with one, two, three or four substituents independently selected from F, OH, CN, oxo, —$OCH_3$, —$OC_3$ cycloalkyl and $R^{10}$, wherein * indicates the connection point to Y in formula (I).

In the compounds of formula (I), A can be pyrazole, 1,2,3 triazole, or 1,2,4 triazole, substituted with $R^1$ and $R^{1A}$; $R^6$ can be CN, F, Cl or $CF_3$; Y can be NH or O; and $R^2$ can be:

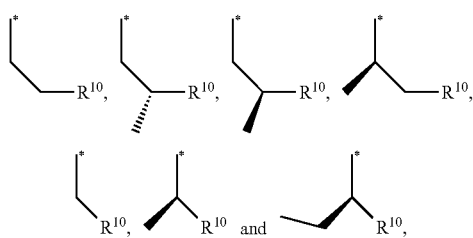

optionally substituted with one, two, three or four substituents independently selected from halo, OH, CN, oxo, —OC$_1$-C$_4$ alkyl, —OC$_3$-C$_5$ cycloalkyl, —Z$_2$—R$^{11}$ and R$^{10}$, wherein C$_1$-C$_4$ alkyl and C$_3$-C$_5$ cycloalkyl are optionally substituted with one or more substituents independently selected from halo, OH, OCH$_3$, methylamine, N,N-dimethylamine and CN, wherein * indicates the connection point to Y in formula (I).

In the compounds of formula (I), A can be pyrazole, 1,2,3 triazole, or 1,2,4 triazole, substituted with R$^1$ and R$^{1A}$; R$^6$ can CN, F, Cl or CF$_3$; Y can be NH or O; and R$^2$ can be:

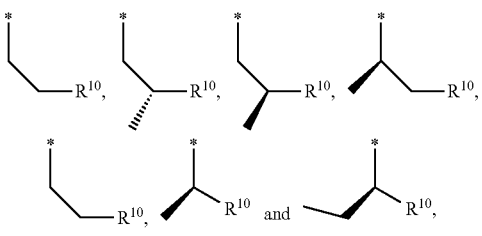

optionally substituted with one, two, three or four substituents independently selected from F, OH, CN, oxo, —OCH$_3$, —OC$_3$ cycloalkyl and R$^{10}$, wherein * indicates the connection point to Y in formula (I).

In the compounds of formula (I), A can be:

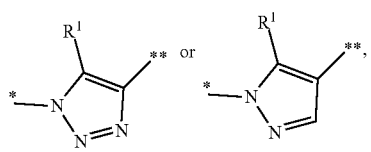

wherein * indicates the connection point to Z or Z' and ** indicates the other connection point from A in formula (I); R$^6$ can be CN, F, Cl, CH$_3$, CF$_3$ or cyclopropyl; Y can be NH or O; and R$^2$ can be C$_1$-C$_3$ alkyl optionally substituted with one, two, three or four substituents independently selected from halo, OH, CN, oxo, —OC$_1$-C$_4$ alkyl, —OC$_3$-C$_5$ cycloalkyl, —Z$_2$—R$^{11}$ and R$^{10}$, wherein C$_1$-C$_4$ alkyl and C$_3$-C$_5$ cycloalkyl are optionally substituted with one or more substituents independently selected from halo, OH, OCH$_3$, methylamine, N,N-dimethylamine and CN.

In the compounds of formula (I), A can be:

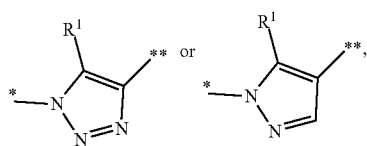

wherein * indicates the connection point to Z or Z' and ** indicates the other connection point from A in formula (I); R$^6$ can be CN, F, Cl, CH$_3$, CF$_3$ or cyclopropyl; Y can be NH or O; and R$^2$ can be C$_1$-C$_4$ alkyl optionally substituted with one or more substituents independently selected from F, OH, CN, oxo, —OCH$_3$, —OC$_3$ cycloalkyl and R$^{10}$.

In the compounds of formula (I), A can be:

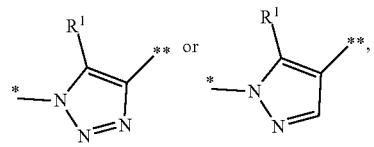

wherein * indicates the connection point to Z or Z' and ** indicates the other connection point from A in formula (I); R$^6$ can be CN, F, Cl or CF$_3$; Y can be NH or O; and R$^2$ can be:

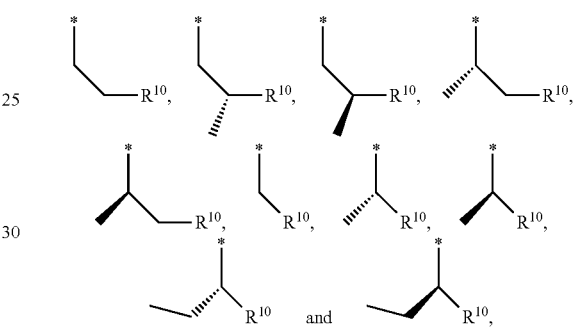

optionally substituted with one, two, three or four substituents independently selected from halo, OH, CN, oxo, —OC$_1$-C$_4$ alkyl, —OC$_3$-C$_5$ cycloalkyl, —Z$_2$—R$^{11}$ and R$^{10}$, wherein C$_1$-C$_4$ alkyl and C$_3$-C$_5$ cycloalkyl are optionally substituted with one or more substituents independently selected from halo, OH, OCH$_3$, methylamine, N,N-dimethylamine and CN, wherein * indicates the connection point to Y in formula (I).

In the compounds of formula (I), A can be:

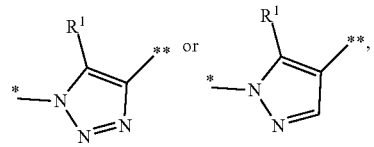

wherein * indicates the connection point to Z or Z' and ** indicates the other connection point from A in formula (I); R$^6$ can CN, F, Cl or CF$_3$; Y can be NH or O; and R$^2$ can be:

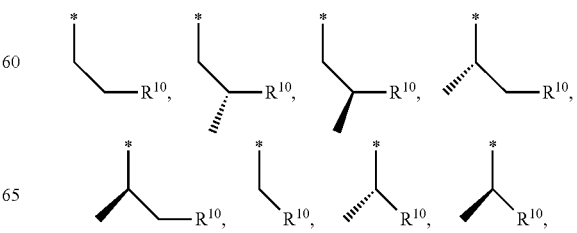

-continued

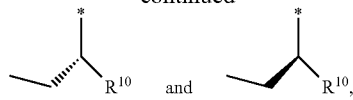

optionally substituted with one, two, three or four substituents independently selected from F, OH, CN, oxo, —OCH$_3$, —OC$_3$ cycloalkyl and R$^{10}$, wherein * indicates the connection point to Y in formula (I).

In the compounds of formula (I), A can be:

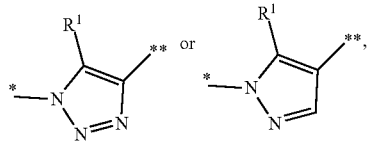

wherein * indicates the connection point to Z or Z' and ** indicates the other connection point from A in formula (I); R$^6$ can be CN, F, Cl or CF$_3$; Y can be NH or O; and R$^2$ can be:

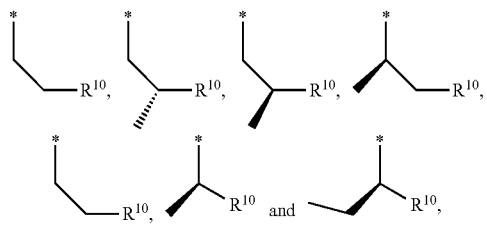

optionally substituted with one, two, three or four substituents independently selected from halo, OH, CN, oxo, —OC$_1$-C$_4$ alkyl, —OC$_3$-C$_5$ cycloalkyl, —Z$_2$—R$^{11}$ and R$^{10}$, wherein C$_1$-C$_4$ alkyl and C$_3$-C$_5$ cycloalkyl are optionally substituted with one or more substituents independently selected from halo, OH, OCH$_3$, methylamine, N,N-dimethylamine and CN, wherein * indicates the connection point to Y in formula (I).

In the compounds of formula (I), A can be:

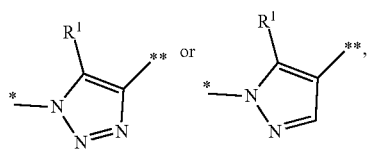

wherein * indicates the connection point to Z or Z' and ** indicates the other connection point from A in formula (I); R$^6$ can CN, F, Cl or CF$_3$; Y can be NH or O; and R$^2$ can be:

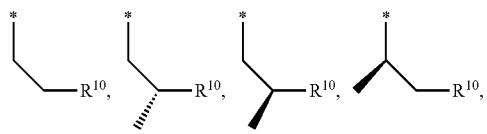

-continued

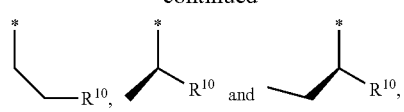

optionally substituted with one, two, three or four substituents independently selected from F, OH, CN, oxo, —OCH$_3$, —OC$_3$ cycloalkyl and R$^{10}$, wherein * indicates the connection point to Y in formula (I).

In the compounds of formula (II), (IIA) or (III), A can be pyrazole, 1,2,3 triazole, or 1,2,4 triazole, substituted with R$^1$; Y can be O; R$^6$ can be CN or Cl; and R$^2$ can be C$_1$-C$_3$ alkyl optionally substituted with one, two or three substituents independently selected from OH, methoxy, halomethyl and R$^{10}$.

In the compounds of formula (II), (IIA) or (III), A can be:

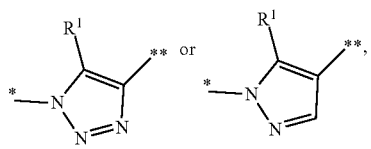

wherein * indicates the connection point to Z or Z' and ** indicates the other connection point from A in formula (II), (IIA) or (III); Y can be O; R$^6$ can be CN or Cl; and R$^2$ can be C$_1$-C$_3$ alkyl optionally substituted with one, two or three substituents independently selected from OH, methoxy, halomethyl and R$^{10}$.

In the compounds of formula (II), (IIA) or (III), A can be pyrazole, 1,2,3 triazole, or 1,2,4 triazole, substituted with R$^1$; Y can be O; R$^6$ can be CN or Cl; and R$^2$ can be:

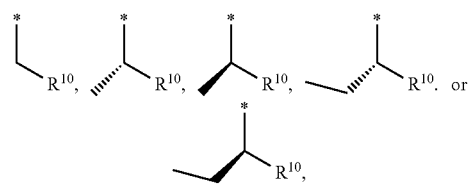

optionally substituted with one or two substituents independently selected from OH, CF$_3$ and methoxy, wherein * indicates the connection point to Y in formula (II), (IIA) or (III).

In the compounds of formula (II), (IIA) or (III), A can be:

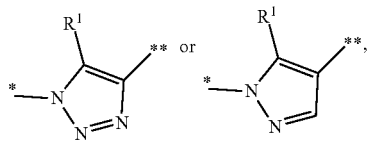

wherein * indicates the connection point to Z or Z' and ** indicates the other connection point from A in formula (II), (IIA) or (III); Y can be O; R$^6$ can be CN or Cl; and R$^2$ can be:

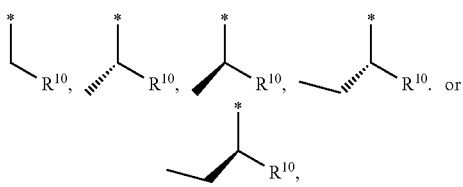

optionally substituted with one or two substituents independently selected from OH, $CF_3$ and methoxy, wherein * indicates the connection point to Y in formula (II), (IIA) or (III).

In the compounds of formula (I), A can be pyrazole, 1,2,3 triazole, or 1,2,4 triazole, substituted with $R^1$ and $R^{1A}$; $R^6$ can be CN, F, Cl, $CH_3$, $CF_3$ or cyclopropyl; Y can be NH or O; $R^2$ can be $C_1$-$C_3$ alkyl optionally substituted with one, two, three or four substituents independently selected from halo, OH, CN, oxo, $-OC_1$-$C_4$ alkyl, $-OC_3$-$C_5$ cycloalkyl, $-Z_2-R^{11}$ and $R^{10}$, wherein $C_1$-$C_4$ alkyl and $C_3$-$C_5$ cycloalkyl are optionally substituted with one or more substituents independently selected from halo, OH, $OCH_3$, methylamine, N,N-dimethylamine and CN; and Z can be a bond,

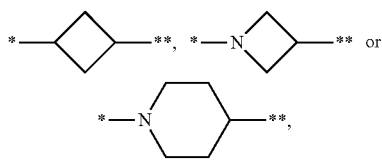

wherein * indicates the connection point to $Z_1$ and ** indicates the connection point to A in formula (I).

In the compounds of formula (I), A can be pyrazole, 1,2,3 triazole, or 1,2,4 triazole, substituted with $R^1$ and $R^{1A}$; $R^6$ can be CN, F, Cl, $CH_3$, $CF_3$ or cyclopropyl; Y can be NH or O; $R^2$ can be $C_1$-$C_4$ alkyl optionally substituted with one or more substituents independently selected from F, OH, CN, oxo, $-OCH_3$, $-OC_3$ cycloalkyl and $R^{10}$; and Z can be a bond,

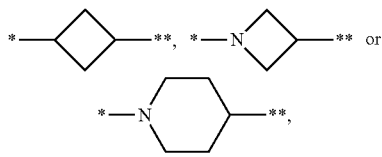

wherein * indicates the connection point to $Z_1$ and ** indicates the connection point to A in formula (I).

In the compounds of formula (I), A can be pyrazole, 1,2,3 triazole, or 1,2,4 triazole, substituted with $R^1$ and $R^{1A}$; $R^6$ can be CN, F, Cl or $CF_3$; Y can be NH or O; and $R^2$ can be:

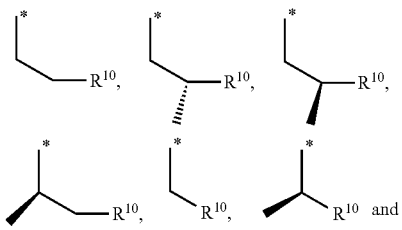

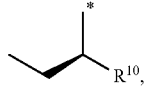

optionally substituted with one, two, three or four substituents independently selected from halo, OH, CN, oxo, $-OC_1$-$C_4$ alkyl, $-OC_3$-$C_5$ cycloalkyl, $-Z_2-R^{11}$ and $R^{10}$, wherein $C_1$-$C_4$ alkyl and $C_3$-$C_5$ cycloalkyl are optionally substituted with one or more substituents independently selected from halo, OH, $OCH_3$, methylamine, N,N-dimethylamine and CN, wherein * indicates the connection point to Y in formula (I); and Z can be a bond,

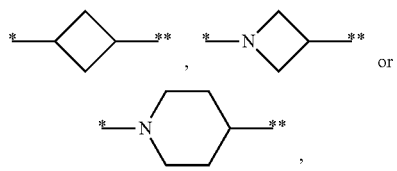

wherein * indicates the connection point to $Z_1$ and ** indicates the connection point to A in formula (I).

In the compounds of formula (I), A can be pyrazole, 1,2,3 triazole, or 1,2,4 triazole, substituted with $R^1$ and $R^{1A}$; $R^6$ can CN, F, Cl or $CF_3$; Y can be NH or O; and $R^2$ can be:

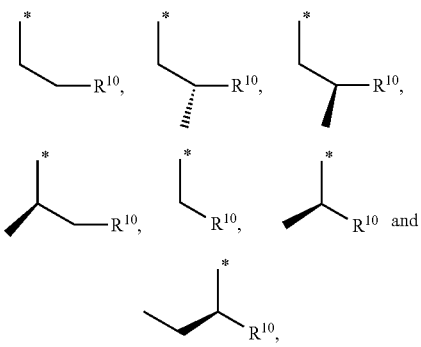

optionally substituted with one, two, three or four substituents independently selected from F, OH, CN, oxo, $-OCH_3$, $-OC_3$ cycloalkyl and $R^{10}$, wherein * indicates the connection point to Y in formula (I); and Z can be a bond,

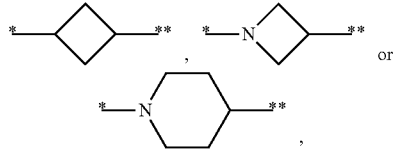

wherein * indicates the connection point to $Z_1$ and ** indicates the connection point to A in formula (I).

In the compounds of formula (I), A can be:

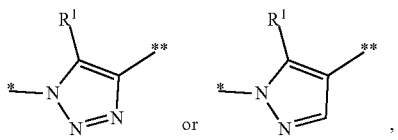

wherein * indicates the connection point to Z or Z' and ** indicates the other connection point from A in formula (I); $R^6$ can be CN, F, Cl, $CH_3$, $CF_3$ or cyclopropyl; Y can be NH or O; $R^2$ can be $C_1$-$C_3$ alkyl optionally substituted with one, two, three or four substituents independently selected from halo, OH, CN, oxo, —$OC_1$-$C_4$ alkyl, —$OC_3$-$C_5$ cycloalkyl, —$Z_2$—$R^{11}$ and $R^{10}$, wherein $C_1$-$C_4$ alkyl and $C_3$-$C_5$ cycloalkyl are optionally substituted with one or more substituents independently selected from halo, OH, $OCH_3$, methylamine, N,N-dimethylamine and CN; and Z can be a bond,

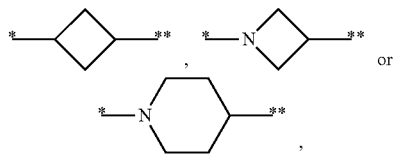

wherein * indicates the connection point to $Z_1$ and ** indicates the connection point to A in formula (I).

In the compounds of formula (I), A can be:

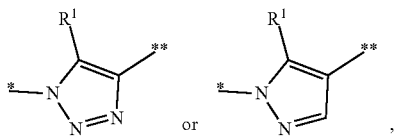

wherein * indicates the connection point to Z or Z' and ** indicates the other connection point from A in formula (I); $R^6$ can be CN, F, Cl, $CH_3$, $CF_3$ or cyclopropyl; Y can be NH or O; $R^2$ can be $C_1$-$C_4$ alkyl optionally substituted with one or more substituents independently selected from F, OH, CN, oxo, —$OCH_3$, —$OC_3$ cycloalkyl and $R^{10}$; and Z can be a bond,

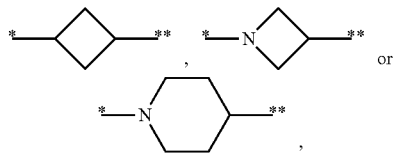

wherein * indicates the connection point to $Z_1$ and ** indicates the connection point to A in formula (I).

In the compounds of formula (I), A can be:

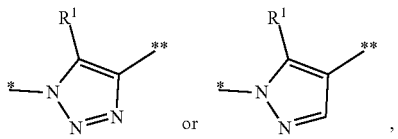

wherein * indicates the connection point to Z or Z' and ** indicates the other connection point from A in formula (I); $R^6$ can be CN, F, Cl or $CF_3$; Y can be NH or O; $R^2$ can be:

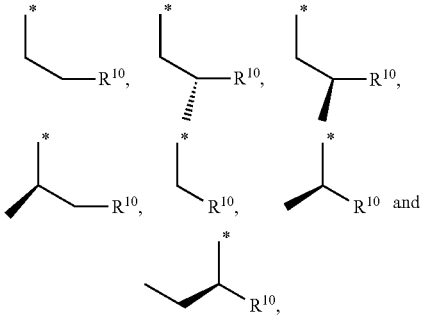

optionally substituted with one, two, three or four substituents independently selected from halo, OH, CN, oxo, —$OC_1$-$C_4$ alkyl, —$OC_3$-$C_5$ cycloalkyl, —$Z_2$—$R^{11}$ and $R^{10}$, wherein $C_1$-$C_4$ alkyl and $C_3$-$C_5$ cycloalkyl are optionally substituted with one or more substituents independently selected from halo, OH, $OCH_3$, methylamine, N,N-dimethylamine and CN, wherein * indicates the connection point to Y in formula (I); and
Z can be a bond,

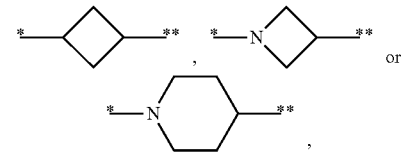

wherein * indicates the connection point to $Z_1$ and ** indicates the connection point to A in formula (I).

In the compounds of formula (I), A can be:

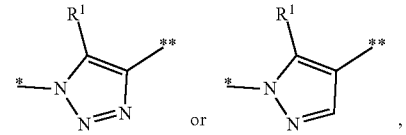

wherein * indicates the connection point to Z or Z' and ** indicates the other connection point from A in formula (I); $R^6$ can CN, F, Cl or $CF_3$; Y can be NH or O; and $R^2$ can be:

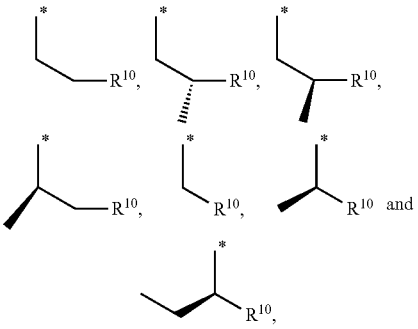

optionally substituted with one, two, three or four substituents independently selected from F, OH, CN, oxo, —OCH$_3$, —OC$_3$ cycloalkyl and R$^{10}$, wherein * indicates the connection point to Y in formula (I); and Z can be a bond,

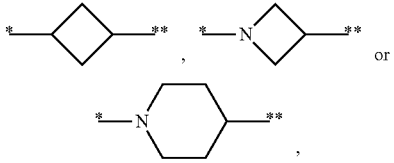

wherein * indicates the connection point to Z$_1$ and ** indicates the connection point to A in formula (I).

In the compounds of formula (I), A can be pyrazole, 1,2,3 triazole, or 1,2,4 triazole, substituted with R$^1$ and R$^{1A}$; R$^6$ can be CN, F, Cl, CH$_3$, CF$_3$ or cyclopropyl; Y can be NH or O; R$^2$ can be C$_1$-C$_3$ alkyl optionally substituted with one, two, three or four substituents independently selected from halo, OH, CN, oxo, —OC$_1$-C$_4$ alkyl, —OC$_3$-C$_5$ cycloalkyl, —Z$_2$—R$^{11}$ and R$^{10}$, wherein C$_1$-C$_4$ alkyl and C$_3$-C$_5$ cycloalkyl are optionally substituted with one or more substituents independently selected from halo, OH, OCH$_3$, methylamine, N,N-dimethylamine and CN; Z can be a bond,

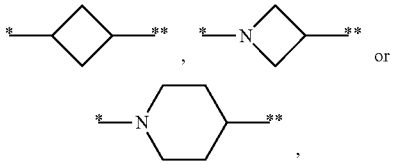

wherein * indicates the connection point to Z$_1$ and ** indicates the connection point to A in formula (I); Y$_1$ can be a bond or CHR$^7$, wherein R$^7$ is hydrogen, F, OH or CH$_3$; and Y$_2$ can a bond or CHR$^3$, wherein R$^3$ is hydrogen, F, OH or CH$_3$.

In the compounds of formula (I), A can be pyrazole, 1,2,3 triazole, or 1,2,4 triazole, substituted with R$^1$ and R$^{1A}$; R$^6$ can be CN, F, Cl, CH$_3$, CF$_3$ or cyclopropyl; Y can be NH or O; R$^2$ can be C$_1$-C$_4$ alkyl optionally substituted with one or more substituents independently selected from F, OH, CN, oxo, —OCH$_3$, —OC$_3$ cycloalkyl and R$^{10}$; Z can be a bond,

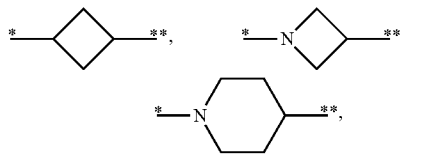

wherein * indicates the connection point to Z$_1$ and ** indicates the connection point to A in formula (I); Y$_1$ can be a bond or CHR$^7$, wherein R$^7$ is hydrogen, F, OH or CH$_3$; and Y$_2$ can a bond or CHR$^3$, wherein R$^3$ is hydrogen, F, OH or CH$_3$.

In the compounds of formula (I), A can be:

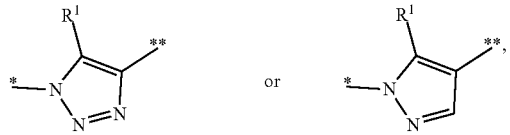

wherein * indicates the connection point to Z or Z' and ** indicates the other connection point from A in formula (I); R$^6$ can CN, F, Cl or CF$_3$; Y can be NH or O; and R$^2$ can be:

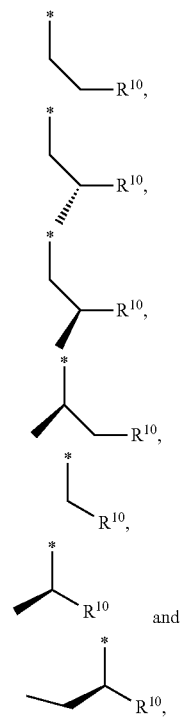

optionally substituted with one, two, three or four substituents independently selected from F, OH, CN, oxo, —OCH$_3$, —OC$_3$ cycloalkyl and R$^{10}$, wherein * indicates the connection point to Y in formula (I); Z can be a bond,

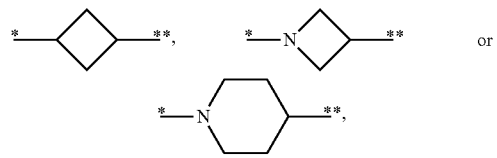

wherein * indicates the connection point to Z$_1$ and ** indicates the connection point to A in formula (I); Y$_1$ can be a bond or CHR$^7$, wherein R$^7$ is hydrogen, F, OH or CH$_3$; and Y$_2$ can a bond or CHR$^3$, wherein R$^3$ is hydrogen, F, OH or CH$_3$.

In the compounds of formula (II), (IIA) or (III), A can be pyrazole, 1,2,3 triazole, or 1,2,4 triazole, substituted with R$^1$; Y can be O; R$^6$ can be CN or Cl; R$^2$ can be C$_1$-C$_3$ alkyl optionally substituted with one, two or three substituents independently selected from OH, methoxy, halomethyl and R$^{10}$; Y$_1$ can be a bond, CH$_2$, or CH$_2$—CH$_2$; and Y$_2$ can be a bond, CH$_2$, CF$_2$ or CH$_2$—CH$_2$.

In the compounds of formula (II), (IIA) or (III), A can be:

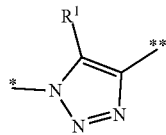 or 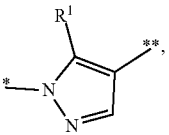, wherein * indicates the connection point to Z or Z' and ** indicates the other connection point from A in formula (II), (IIA) or (III); Y can be O; $R^6$ can be CN or Cl; $R^2$ can be $C_1$-$C_3$ alkyl optionally substituted with one, two or three substituents independently selected from OH, methoxy, halomethyl and $R^{10}$; $Y_1$ can be a bond, $CH_2$, or $CH_2$—$CH_2$; and $Y_2$ can be a bond, $CH_2$, $CF_2$ or $CH_2$—$CH_2$.

In the compounds of formula (II) or (IIA), A can be pyrazole, 1,2,3 triazole, or 1,2,4 triazole, substituted with $R^1$; Y can be O; $R^6$ can be CN or Cl; $R^2$ can be $C_1$-$C_3$ alkyl optionally substituted with one, two or three substituents independently selected from OH, methoxy, halomethyl and $R^{10}$; $Y_1$ can be a bond, $CH_2$, or $CH_2$—$CH_2$; $Y_2$ can be a bond, $CH_2$, $CF_2$ or $CH_2$—$CH_2$; Z can be $CHR^{9A}$; $Z_1$ can be $CH_2$; and $R^9$ can be fused with $R^{9A}$ to form $CH_2$.

In the compounds of formula (II) or (IIA), A can be:

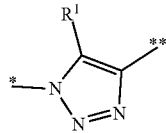 or 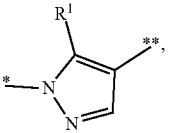, wherein * indicates the connection point to Z and ** indicates the other connection point from A in formula (II) or (IIA); Y can be O; $R^6$ can be CN or Cl; $R^2$ can be $C_1$-$C_3$ alkyl optionally substituted with one, two or three substituents independently selected from OH, methoxy, halomethyl and $R^{10}$; $Y_1$ can be a bond, $CH_2$, or $CH_2$—$CH_2$; and $Y_2$ can be a bond, $CH_2$, $CF_2$ or $CH_2$—$CH_2$; Z can be $CHR^{9A}$; $Z_1$ can be $CH_2$; and $R^9$ can be fused with $R^{9A}$ to form $CH_2$.

In the compounds of formula (III), A can be pyrazole, 1,2,3 triazole, or 1,2,4 triazole, substituted with $R_1$; Y can be O; $R^6$ can be CN or Cl; $R^2$ can be $C_1$-$C_3$ alkyl optionally substituted with one, two or three substituents independently selected from OH, methoxy, halomethyl and $R^{10}$; $Y_1$ can be a bond, $CH_2$, or $CH_2$—$CH_2$; $Y_2$ can be a bond, $CH_2$, $CF_2$ or $CH_2$—$CH_2$; and Z' can be:

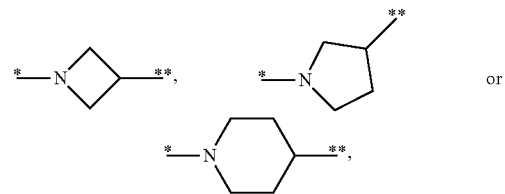

wherein ** indicates the connection point to A and * indicates the other connection point from Z'.

In the compounds of formula (III), A can be:

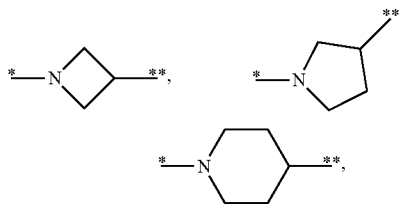

wherein * indicates the connection point to Z' and ** indicates the other connection point from A in formula (I); Y can be O; $R^6$ can be CN or Cl; $R^2$ can be $C_1$-$C_3$ alkyl optionally substituted with one, two or three substituents independently selected from OH, methoxy, halomethyl and $R^{10}$; $Y_1$ can be a bond, $CH_2$, or $CH_2$—$CH_2$; and $Y_2$ can be a bond, $CH_2$, $CF_2$ or $CH_2$—$CH_2$; and Z' can be:

wherein ** indicates the connection point to A and * indicates the other connection point from Z'.

In one embodiment, the compounds of Formula (I) are selected from the group consisting of:

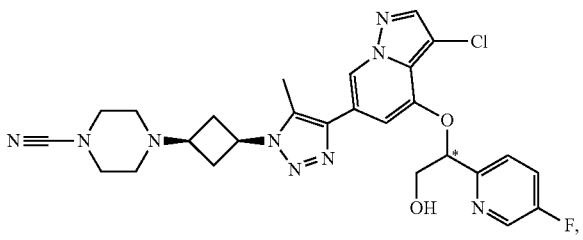

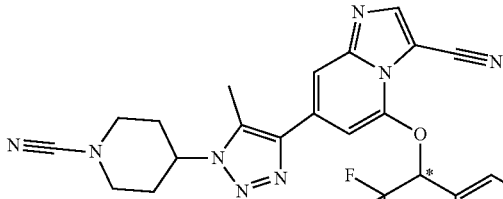

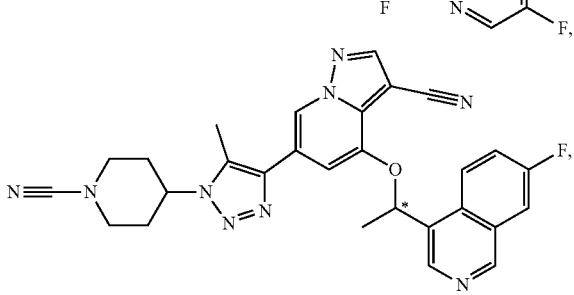

35
-continued
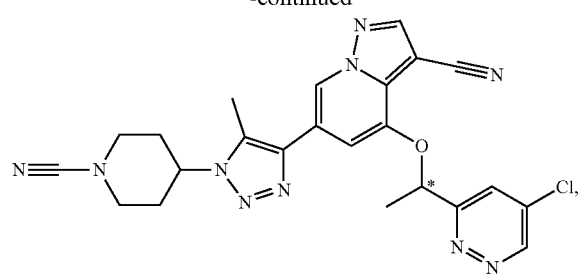
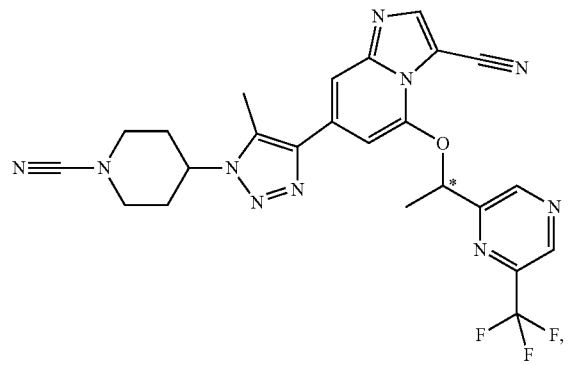
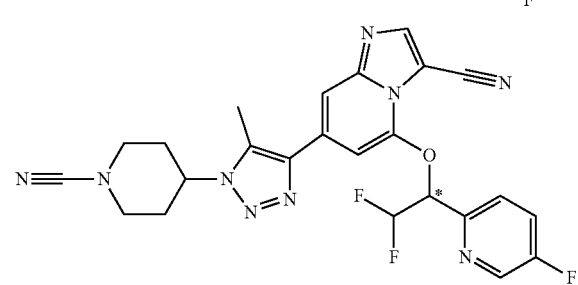
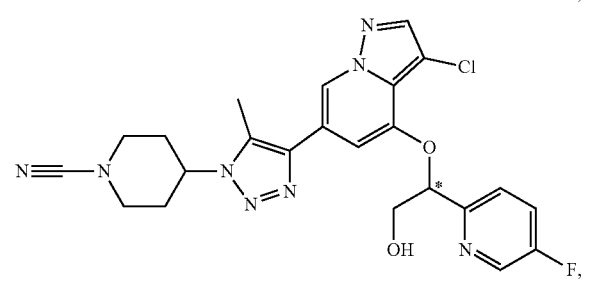
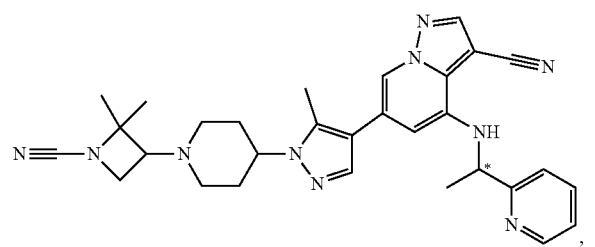
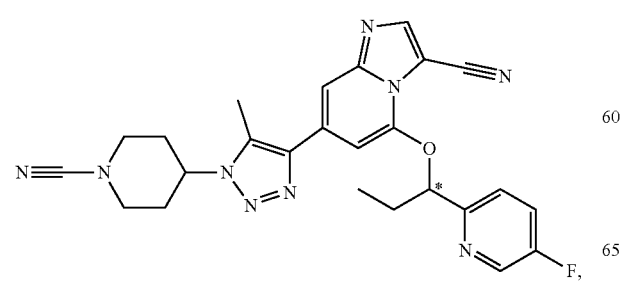
36
-continued
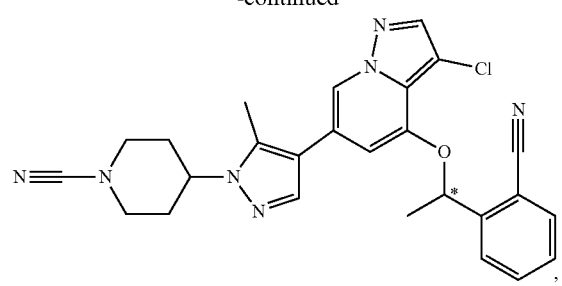
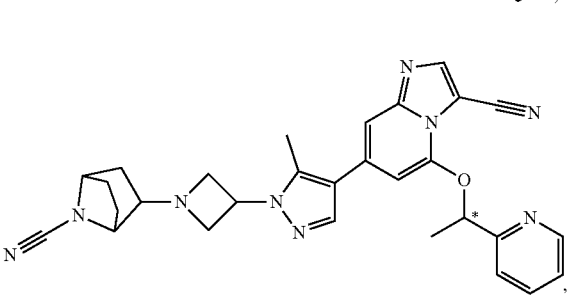
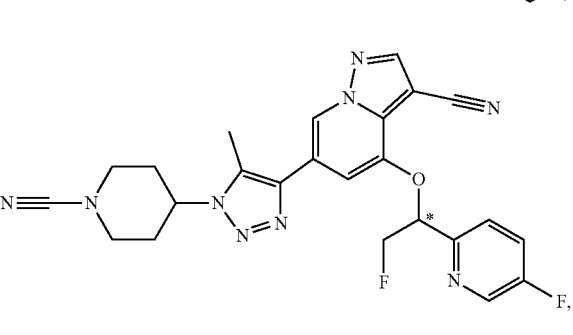
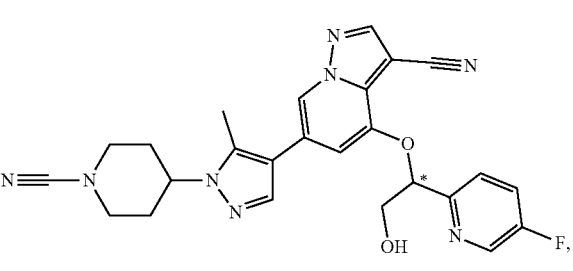
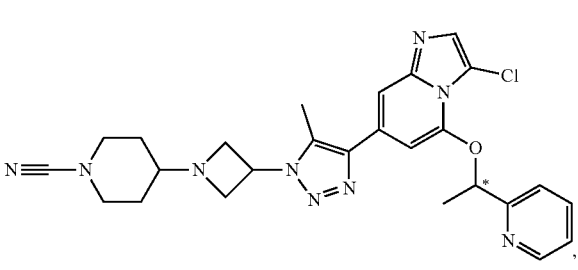
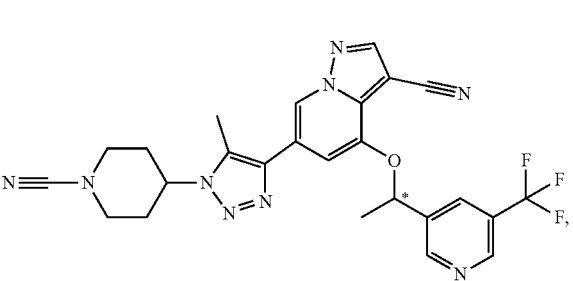

or a pharmaceutically acceptable salt thereof,
wherein the bond at the * position is as represented, For example, for the compound of formula:

where the bond at the * position is as represented,

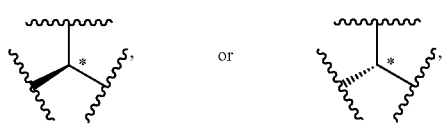
forms the compounds:
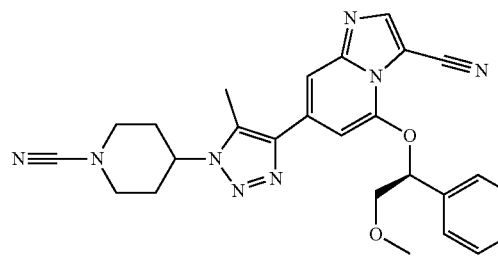
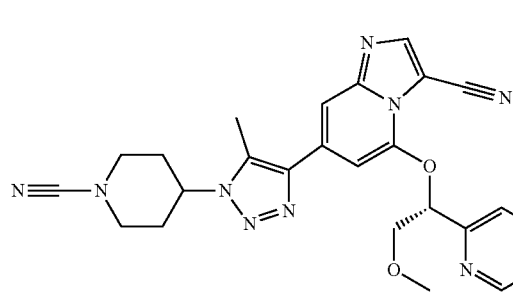
In a further embodiment, the compounds of Formula (I) are selected from the group consisting of:
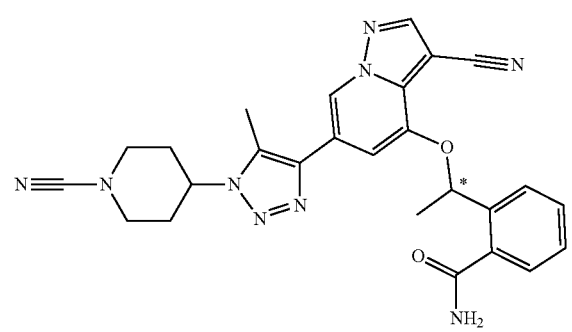
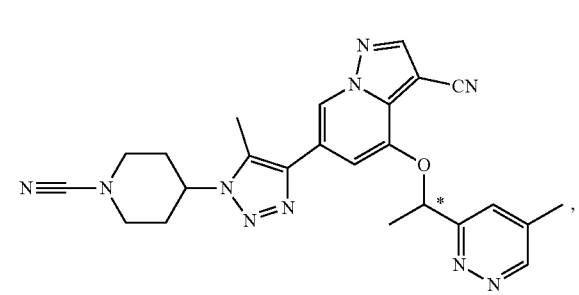
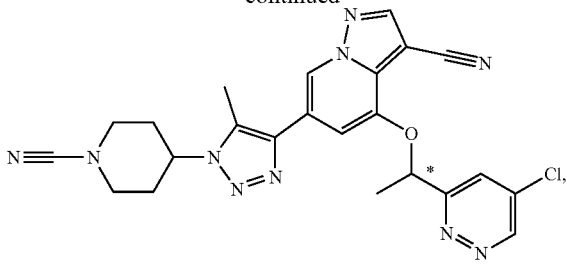
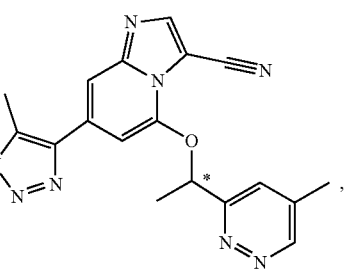
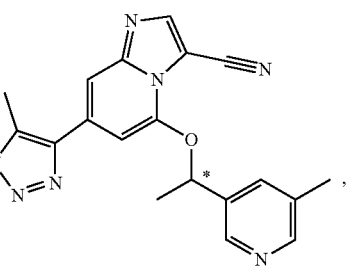
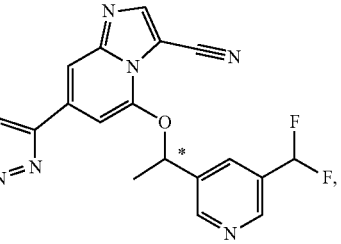
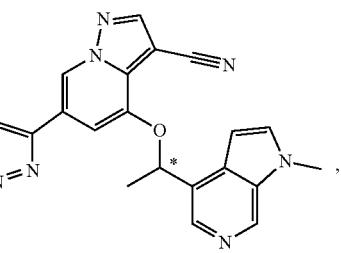
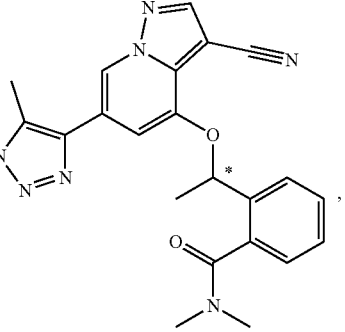

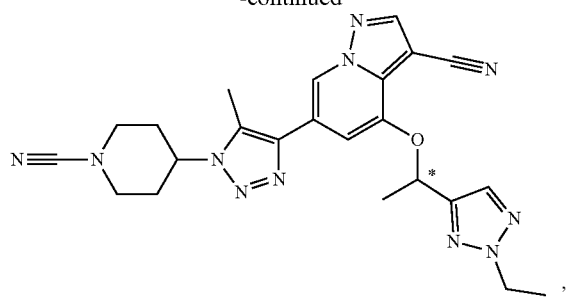
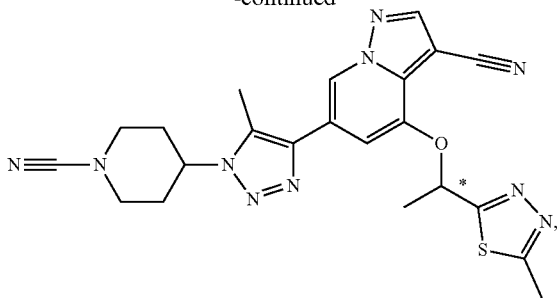

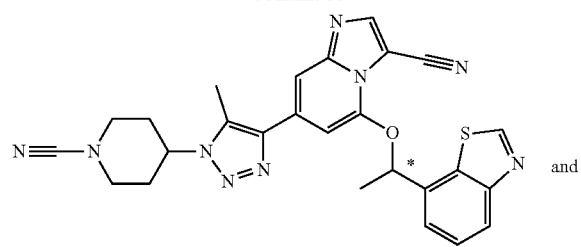
and
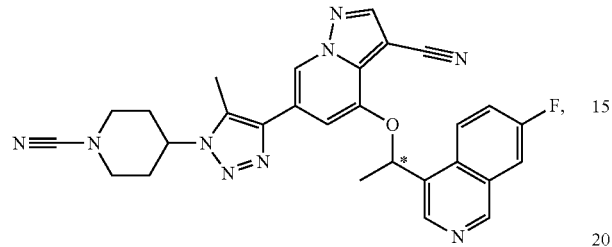
or a pharmaceutically acceptable salt thereof, where the bond at the * position is as represented,
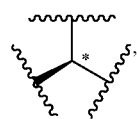 or 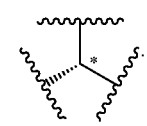.
In a further embodiment, the compounds of Formula (I) are selected from the group consisting of:
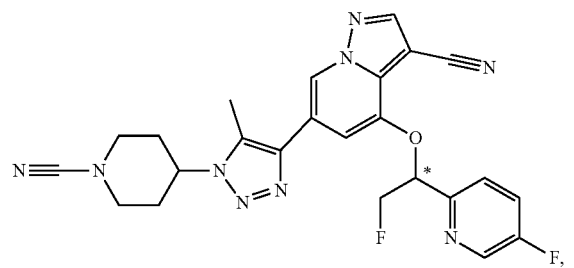
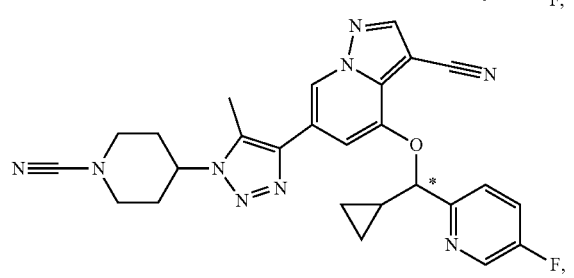
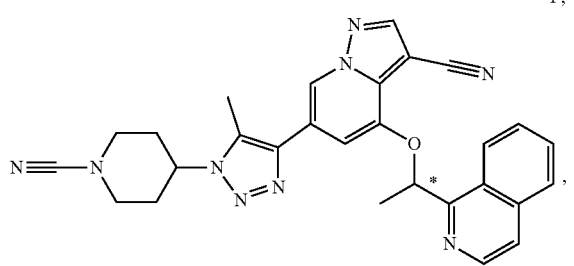
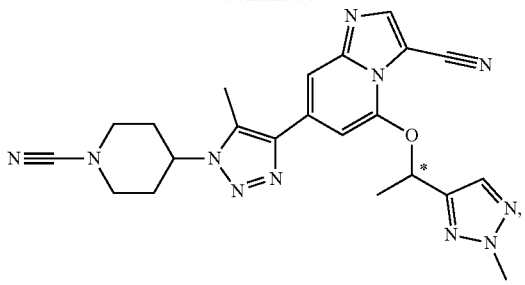
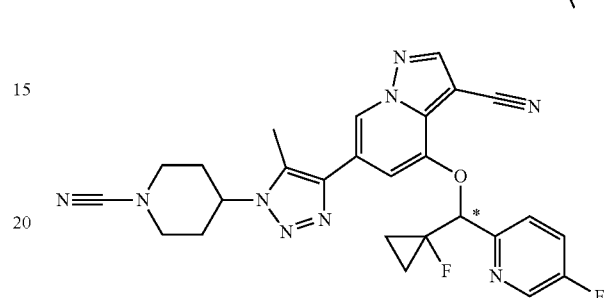
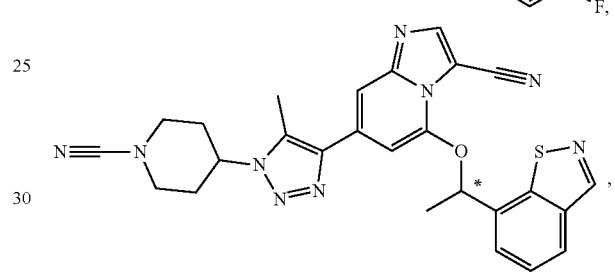
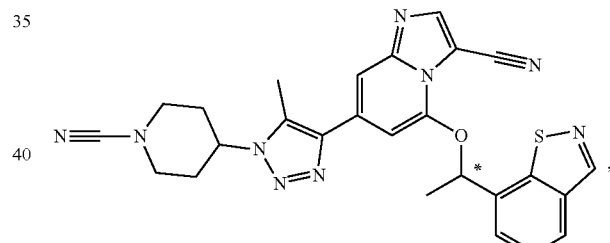
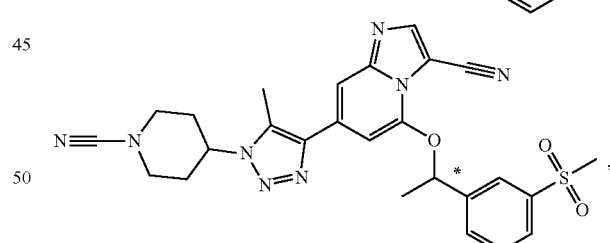
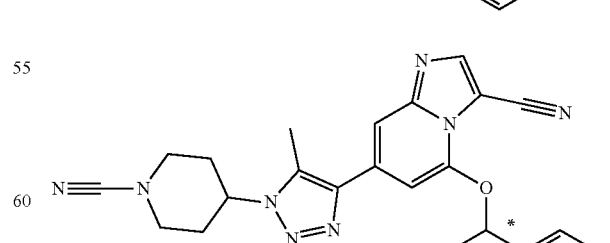

-continued
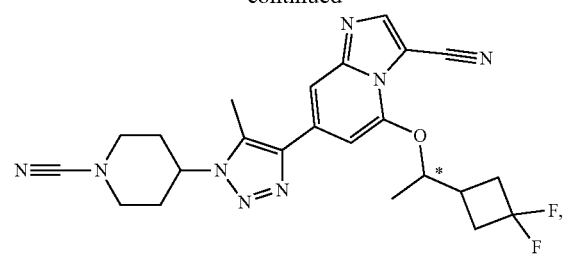
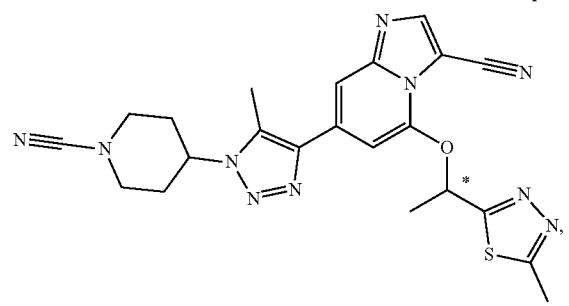
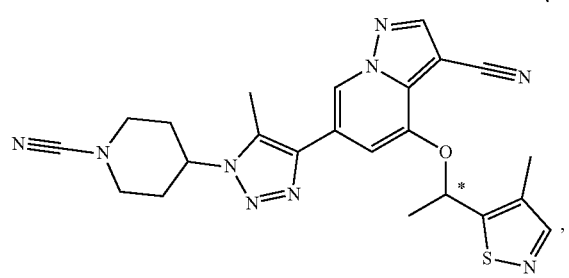
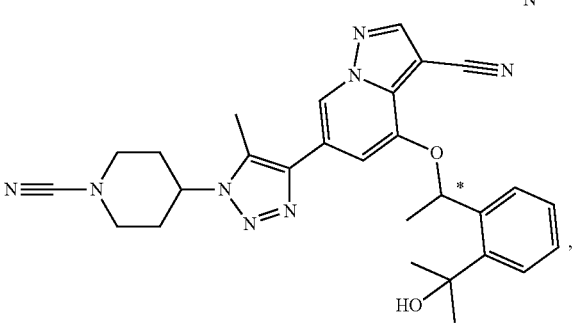
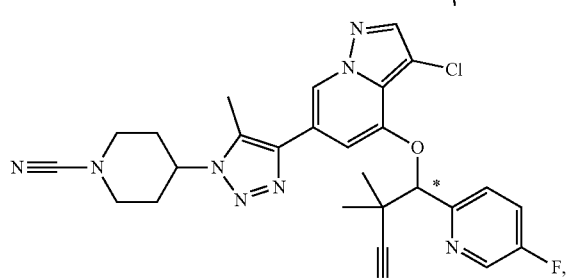
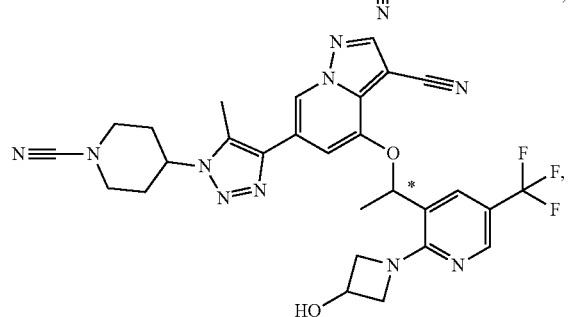
-continued
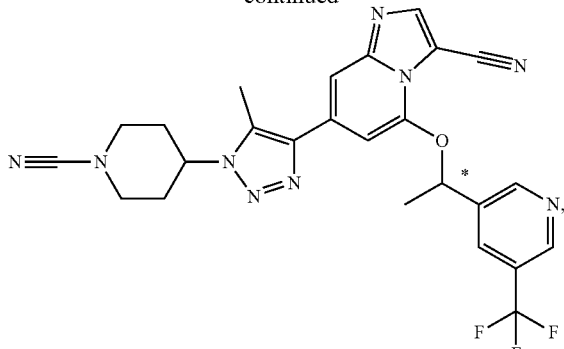
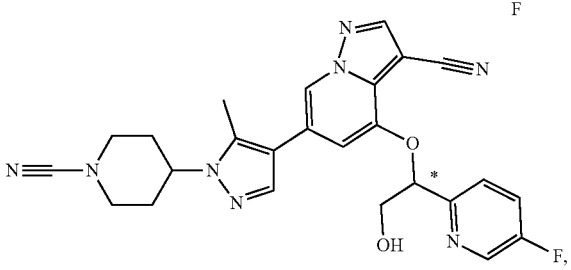
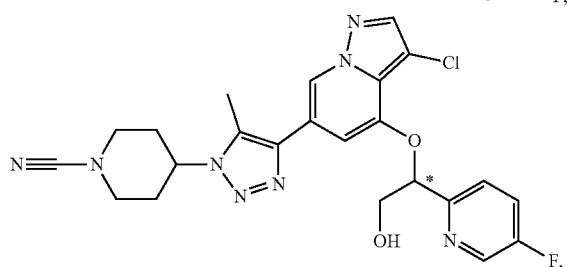
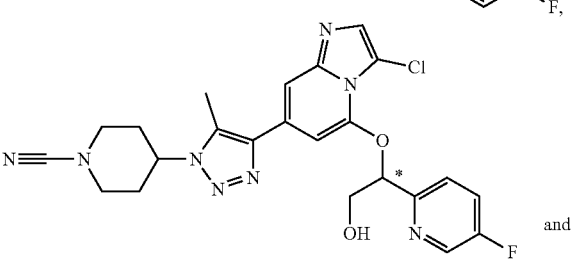
and
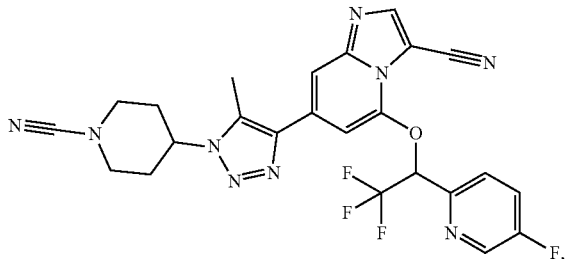
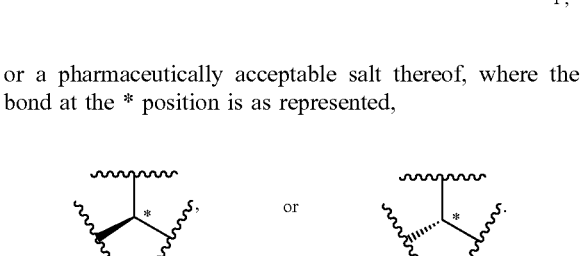
or a pharmaceutically acceptable salt thereof, where the bond at the * position is as represented,
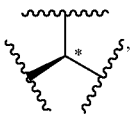 or 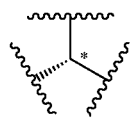
In a further embodiment, the compounds of Formula (I) are selected from the group consisting of:

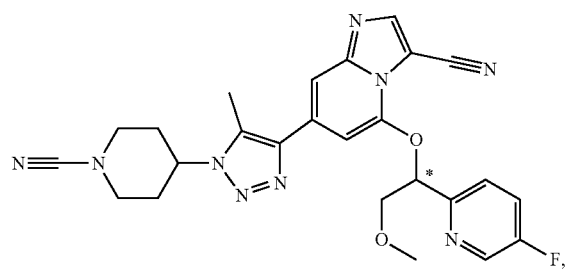
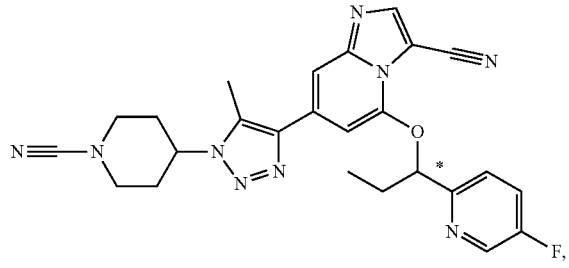
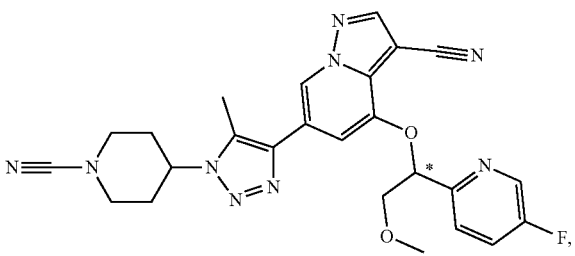
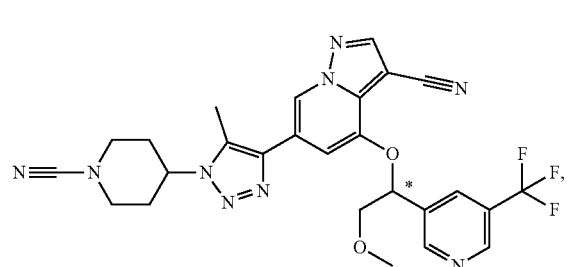
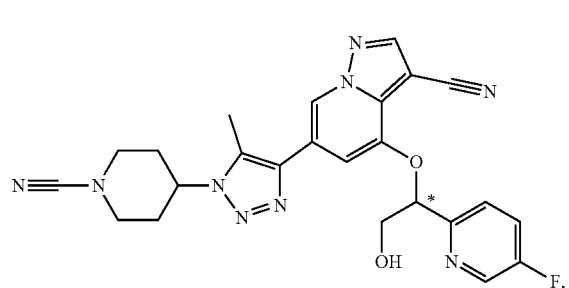
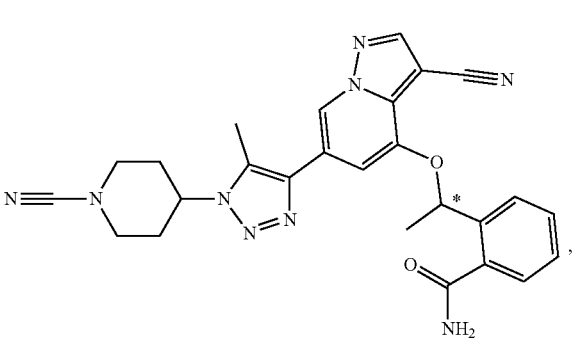
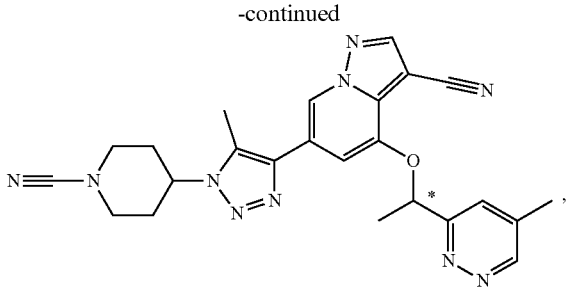
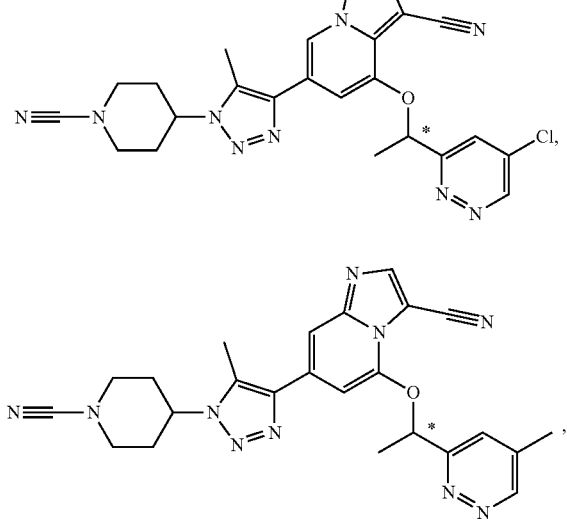
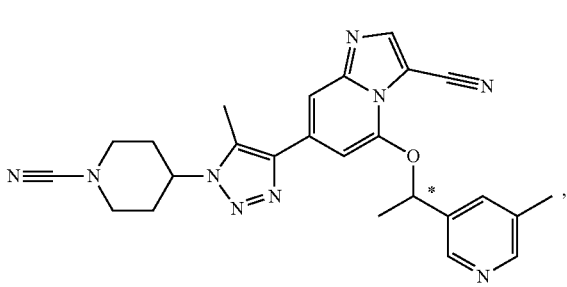
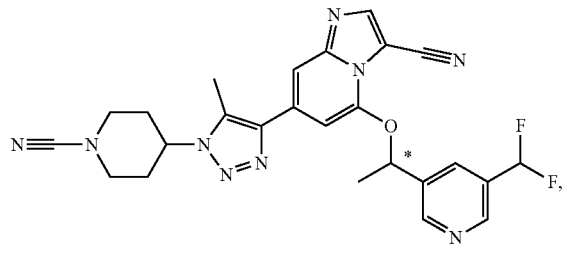
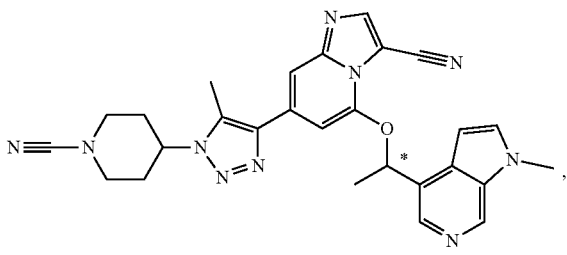

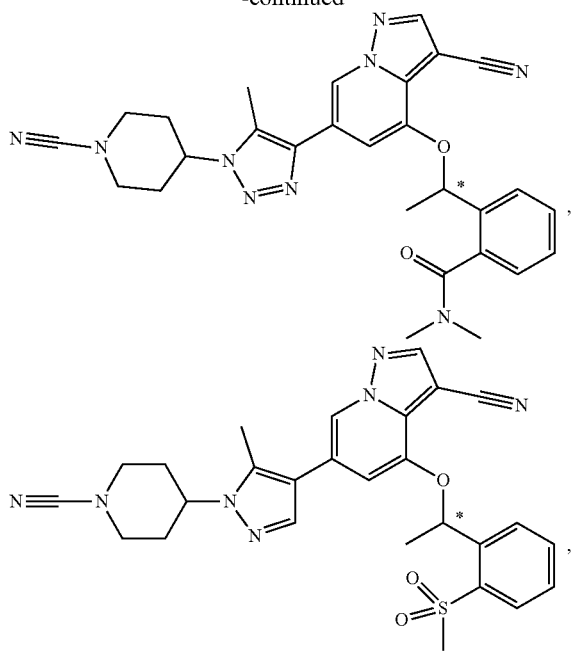
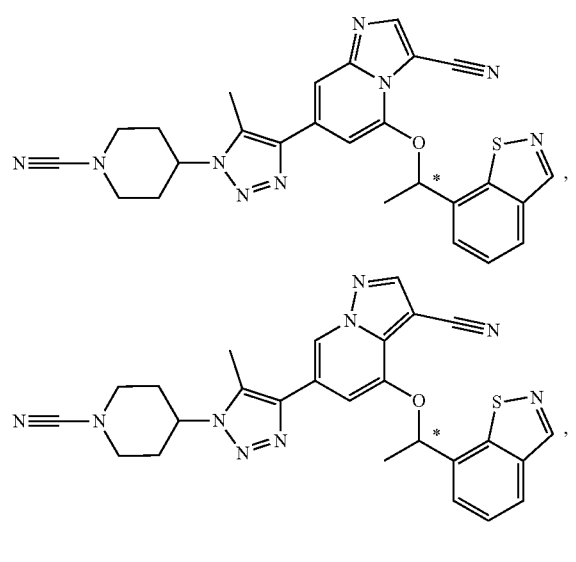
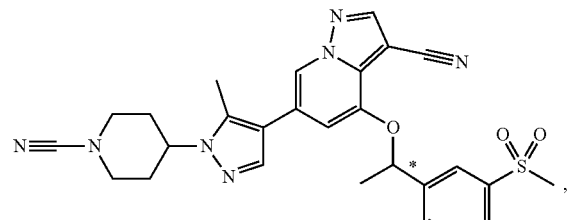
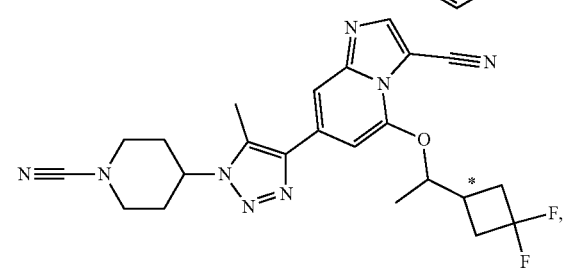
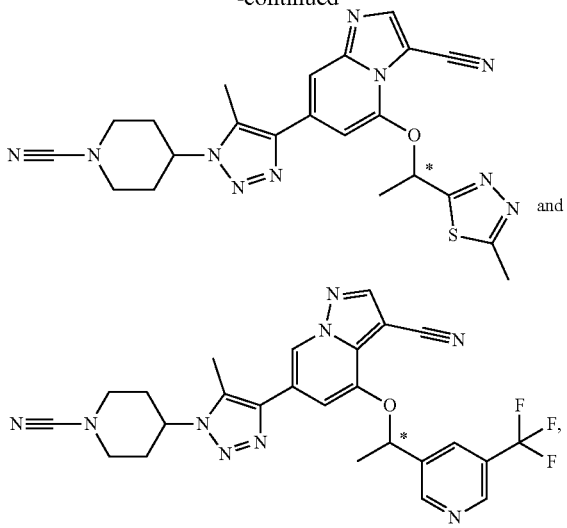
or a pharmaceutically acceptable salt thereof, where the bond at the * position is as represented,
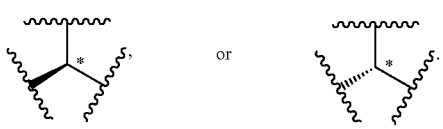
In a further embodiment, the compounds of Formula (I) are selected from the group consisting of:
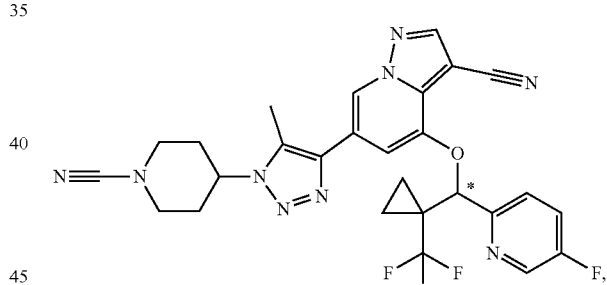
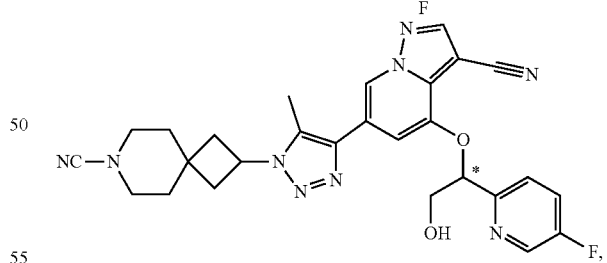
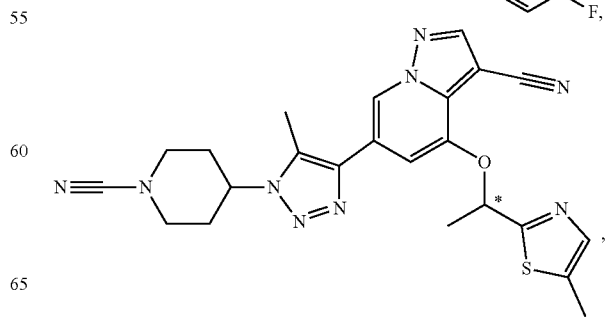

-continued
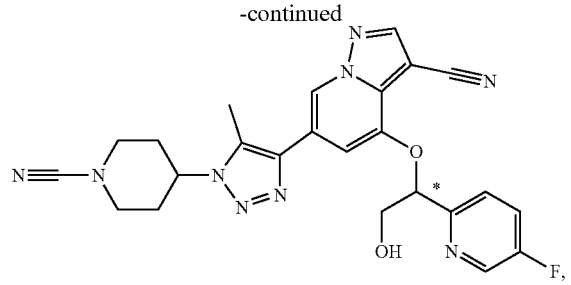
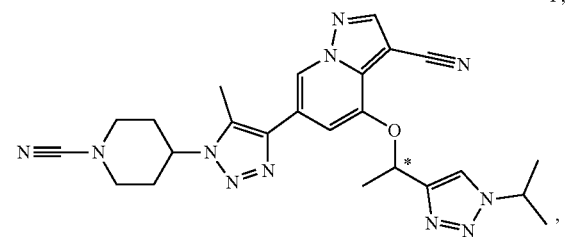
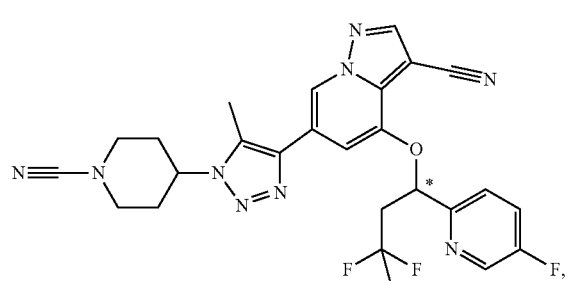
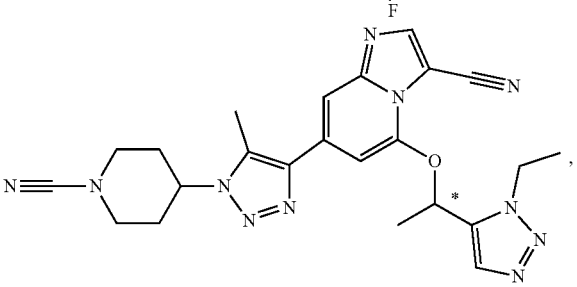
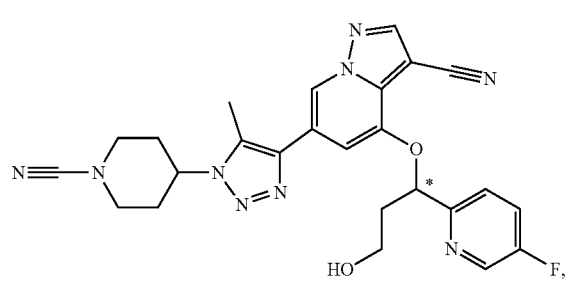
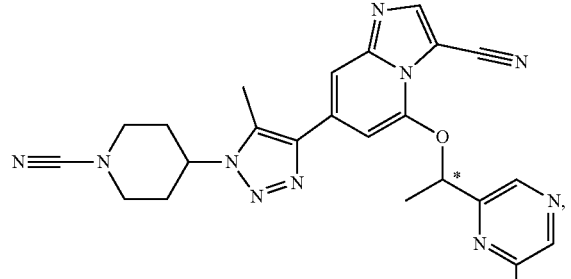
-continued
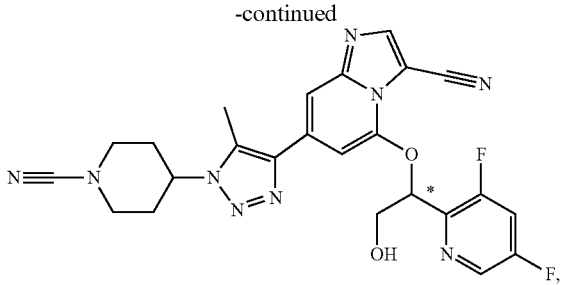
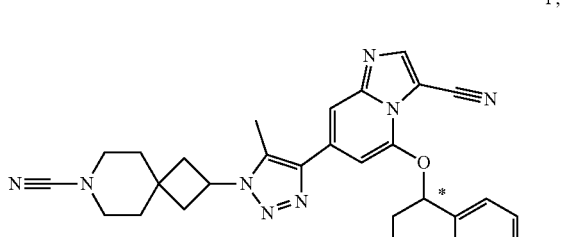
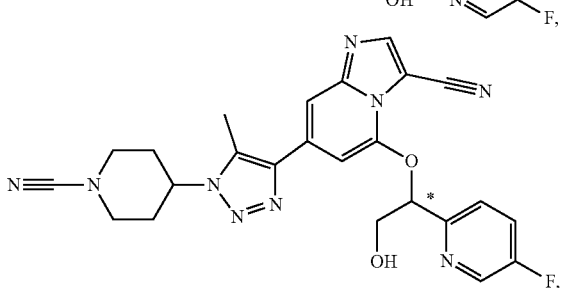
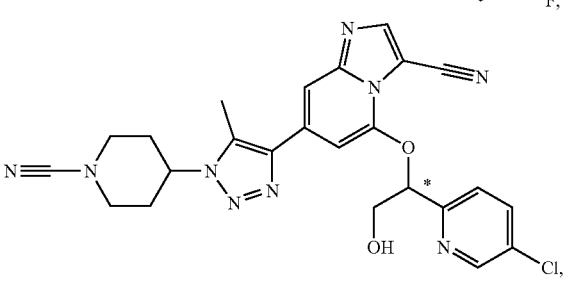
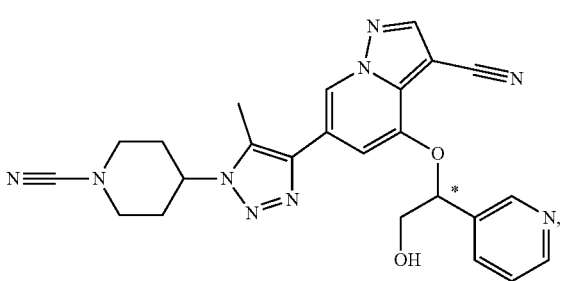
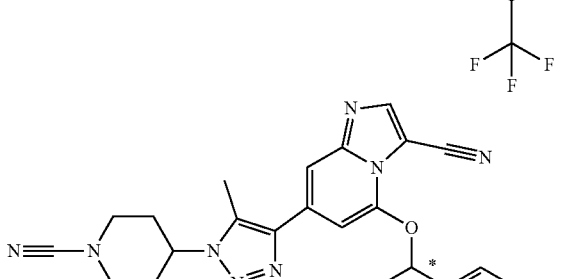

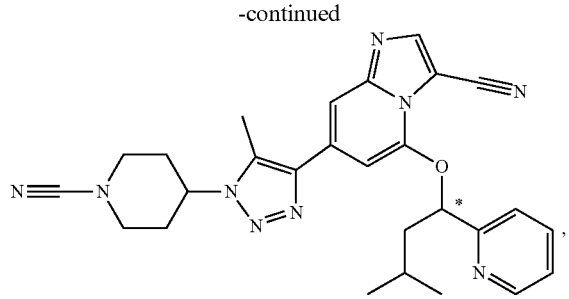
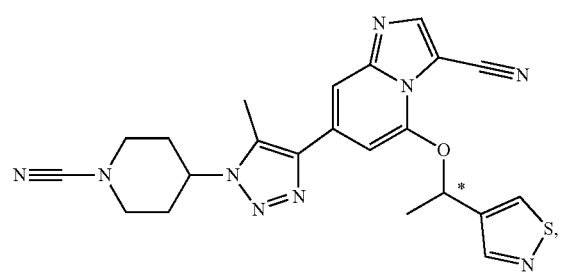
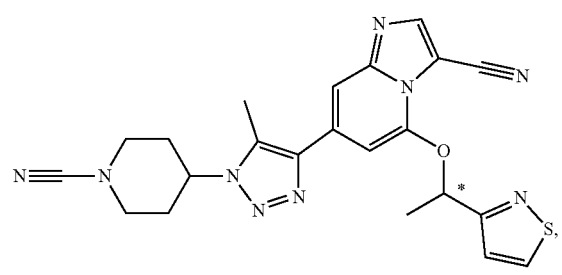
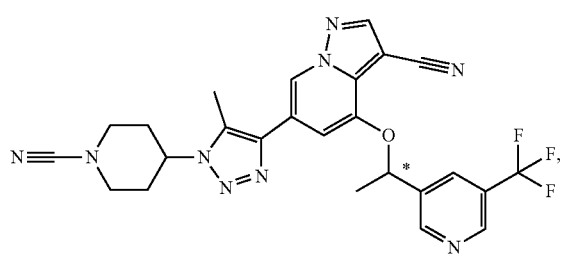
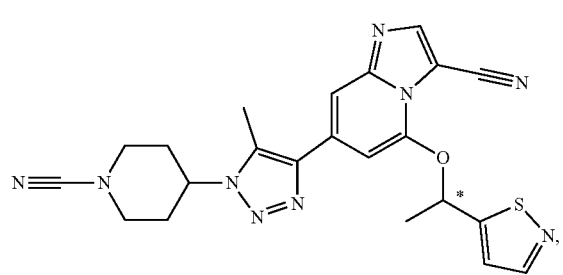
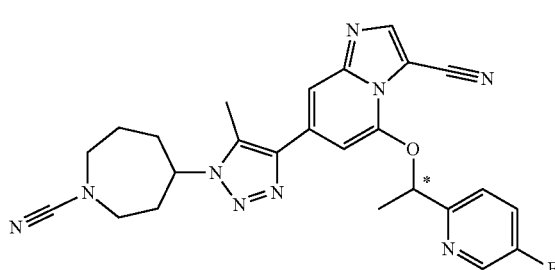
or a pharmaceutically acceptable salt thereof, where the bond at the * position is as represented,
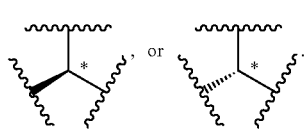
In a further embodiment, the compounds of Formula (I) are selected from the group consisting of:
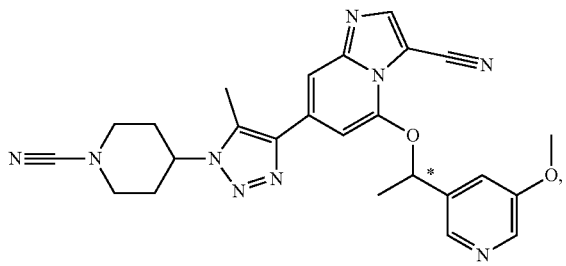

-continued
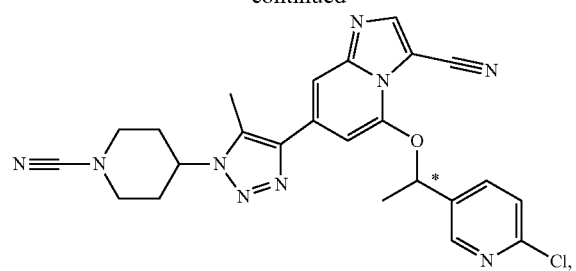
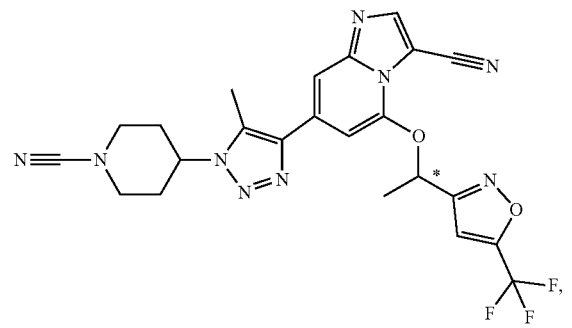
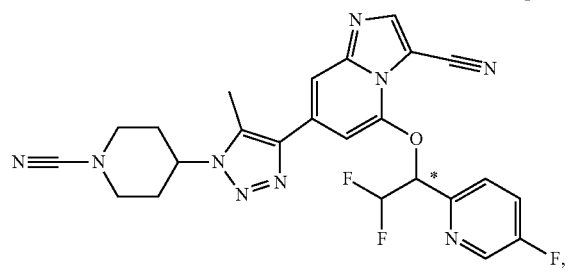
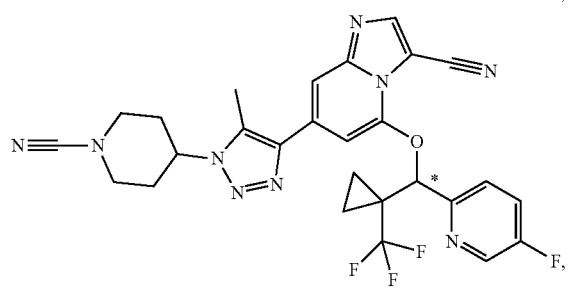
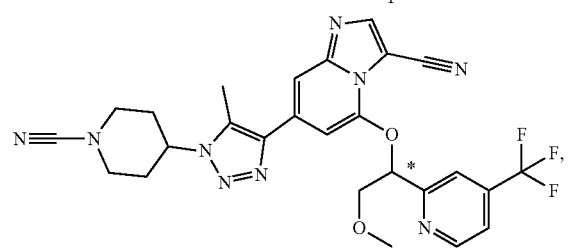
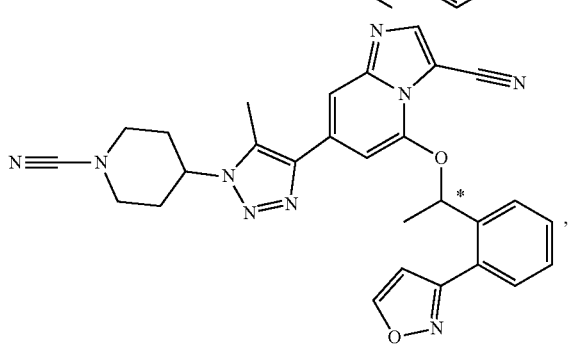
-continued
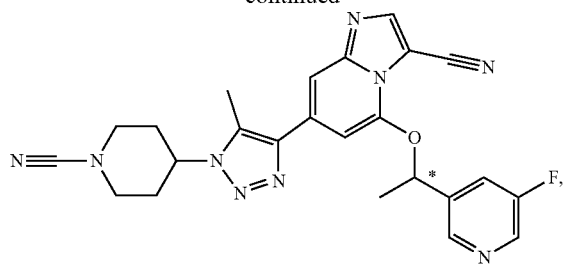
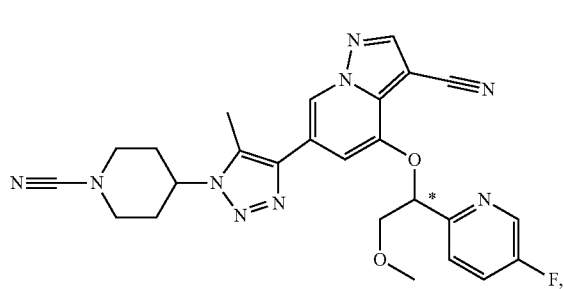
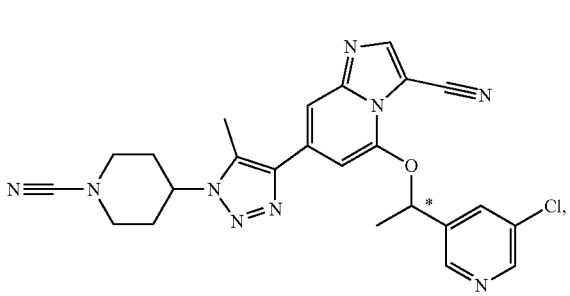
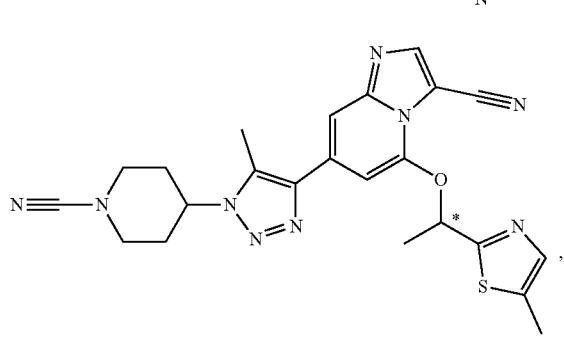
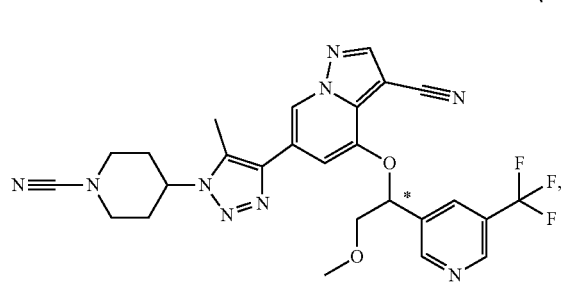
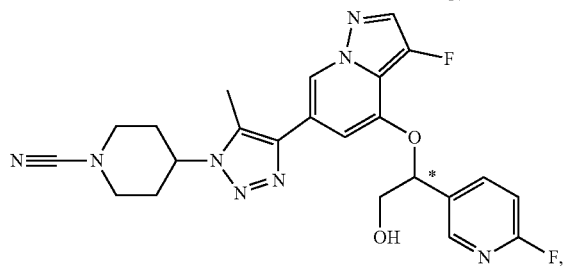

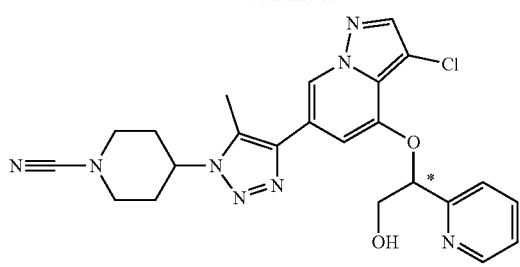
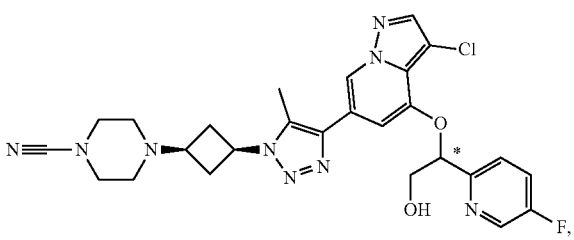
or a pharmaceutically acceptable salt thereof, where the bond at the * position is as represented,
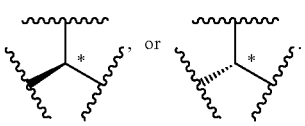
In a further embodiment, the compounds of Formula (I) are selected from the group consisting of:
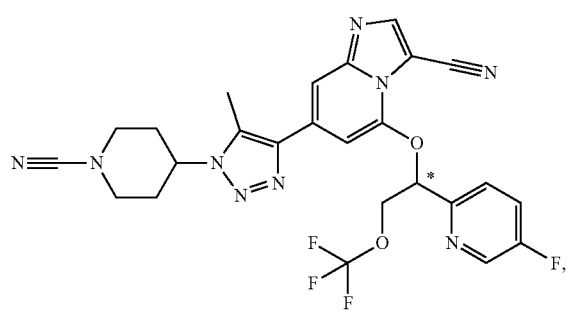
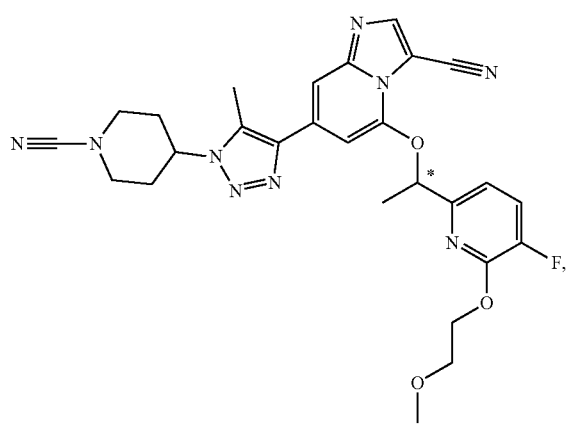
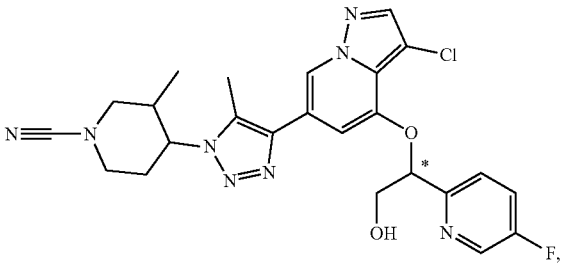
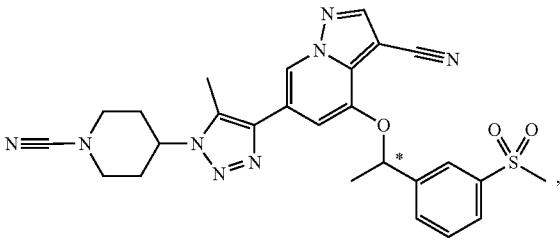
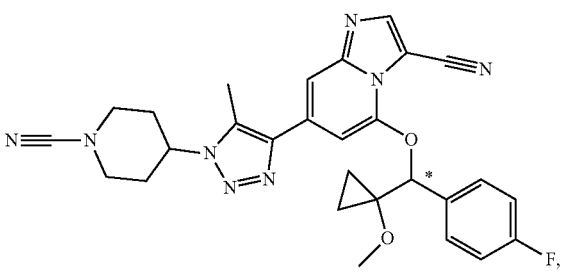
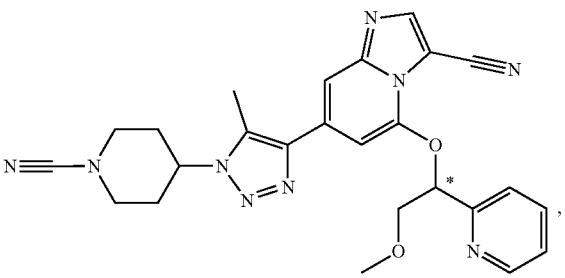
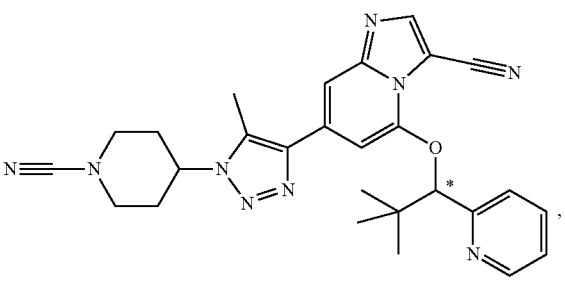

-continued
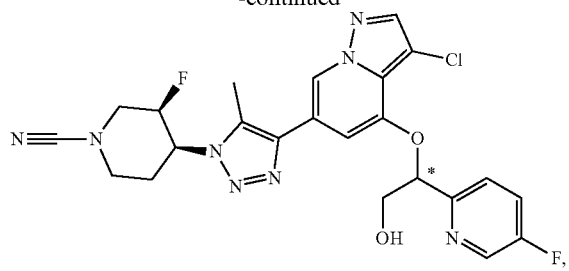
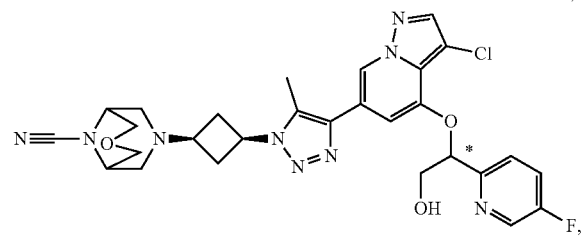
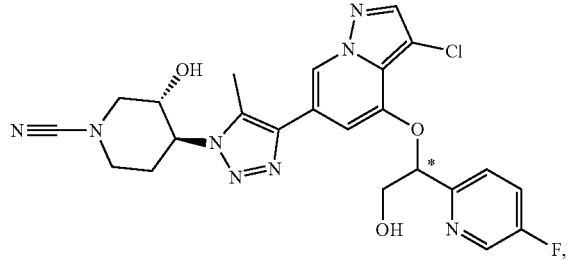
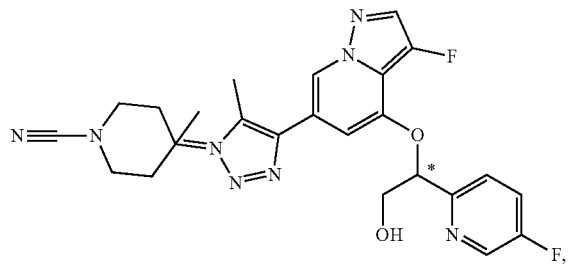
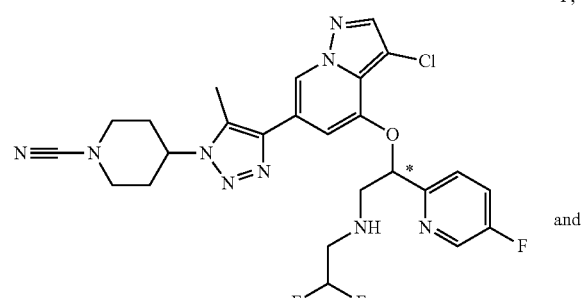
and
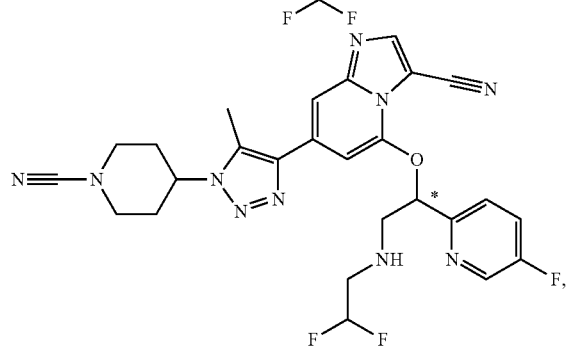
or a pharmaceutically acceptable salt thereof, where the bond at the * position is as represented,
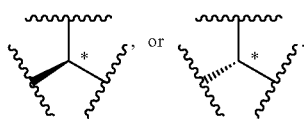
In a further embodiment, the compounds of Formula (I) are selected from the group consisting of:
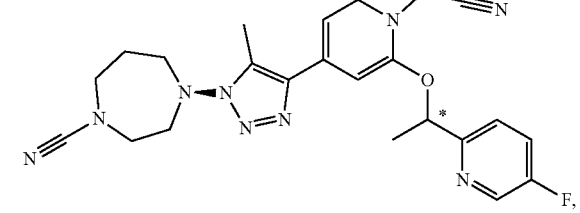
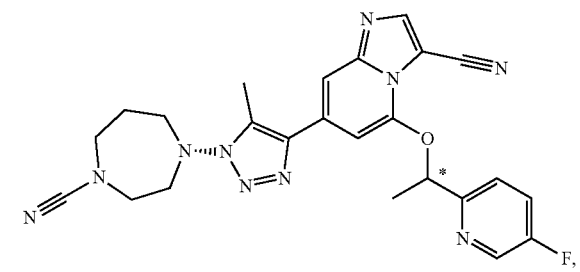
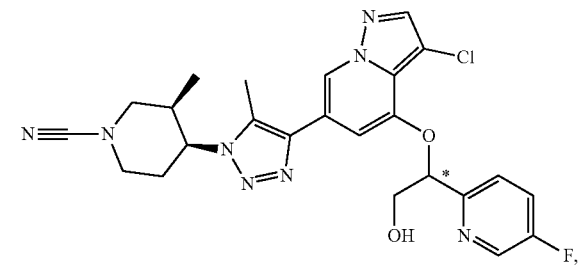
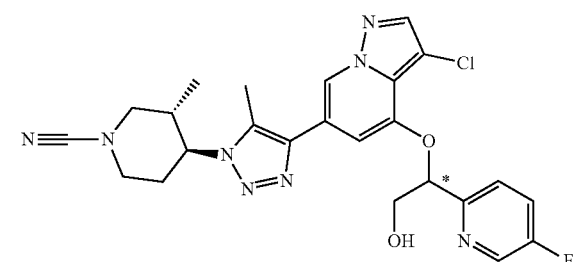
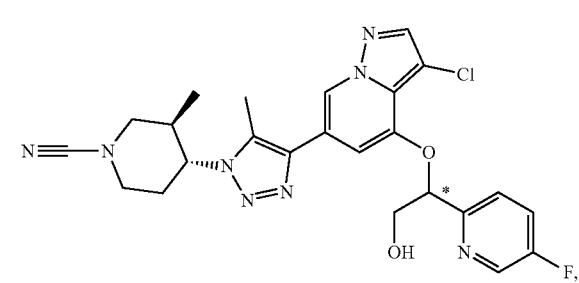

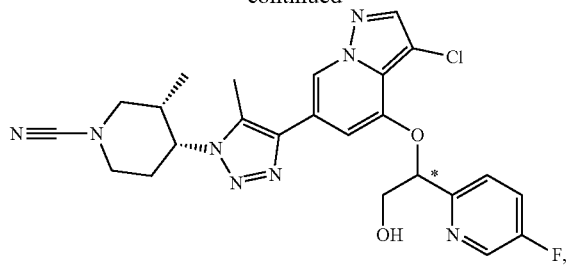
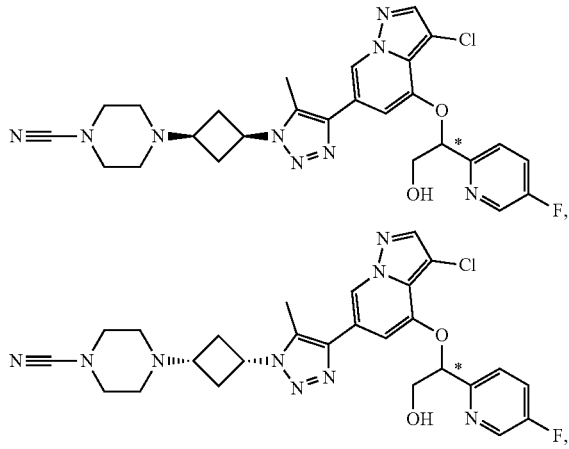
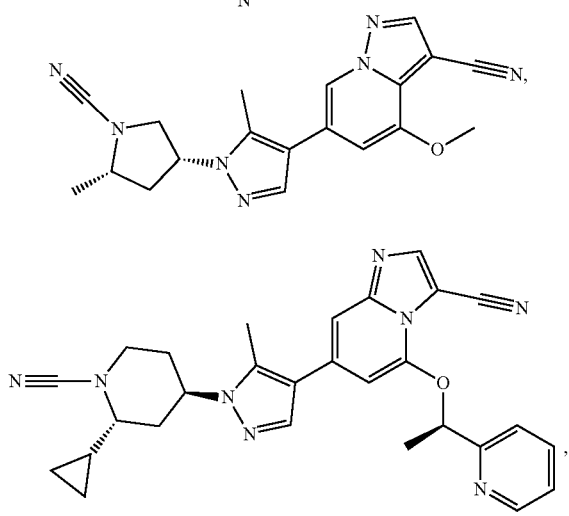
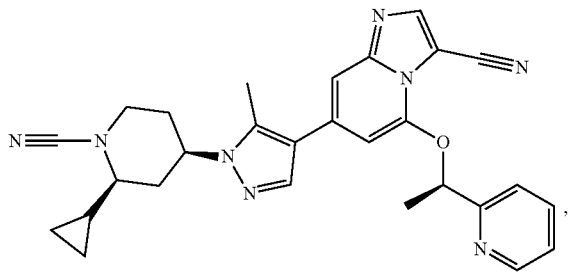
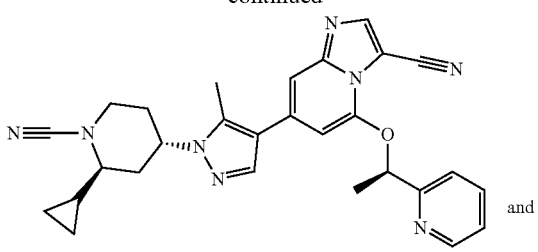
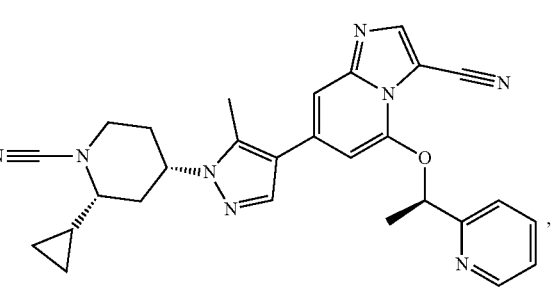
or a pharmaceutically acceptable salt thereof, where the bond at the * position is as represented,
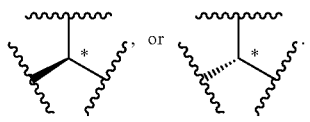
In a further embodiment, the compounds of Formula (I) are selected from the group consisting of:
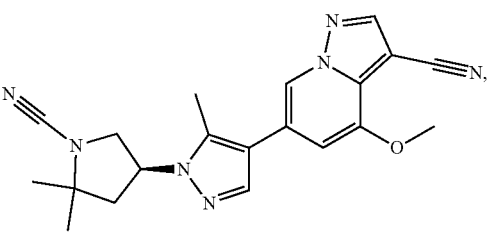

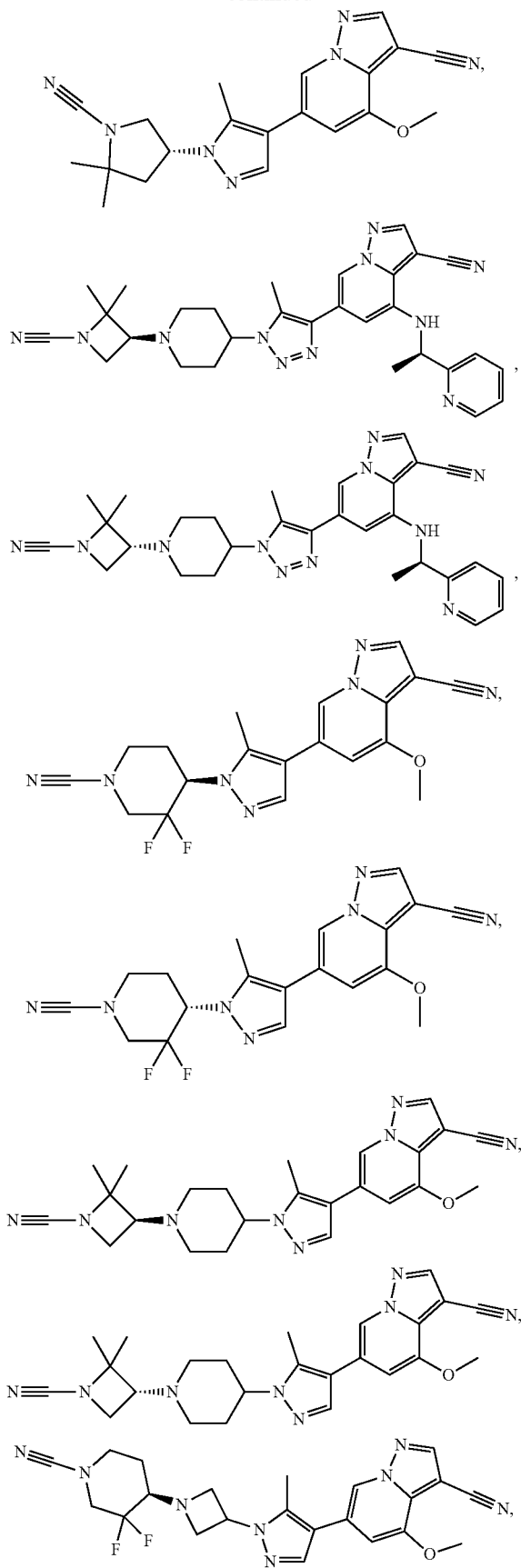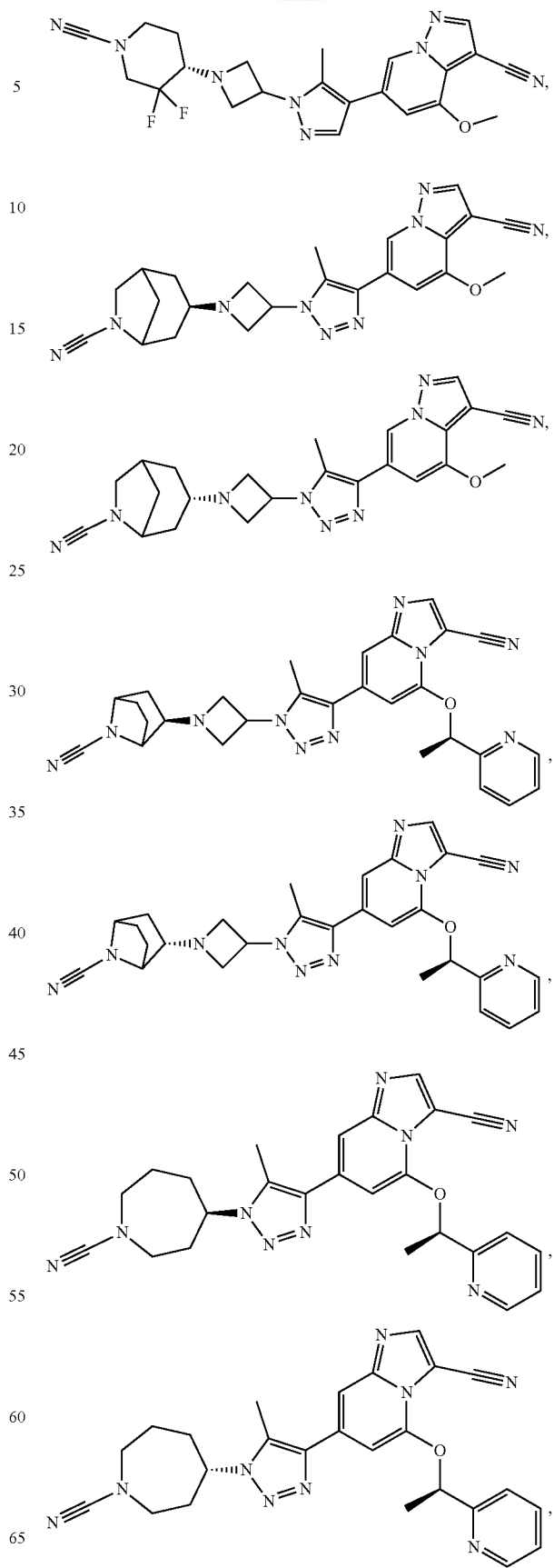

-continued
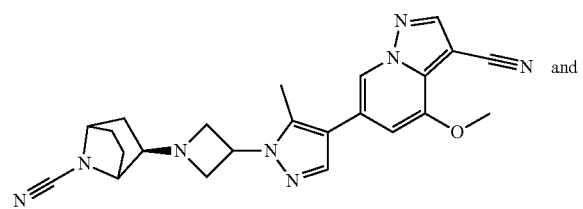 and
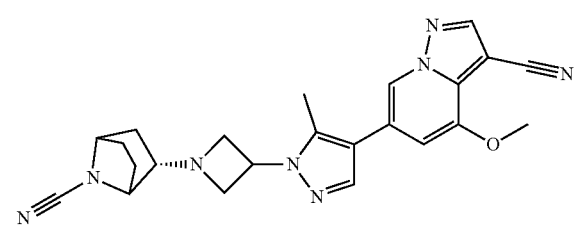
or a pharmaceutically acceptable salt thereof.
In a further embodiment, the compounds of Formula (I) are selected from the group consisting of:
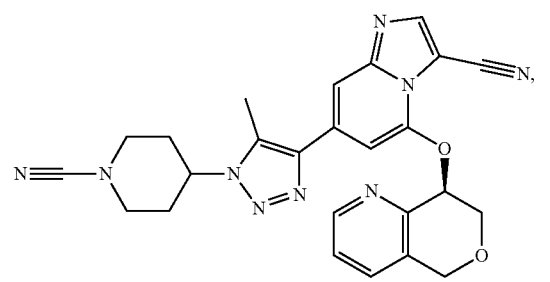
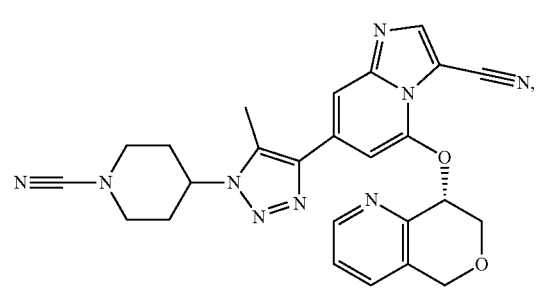
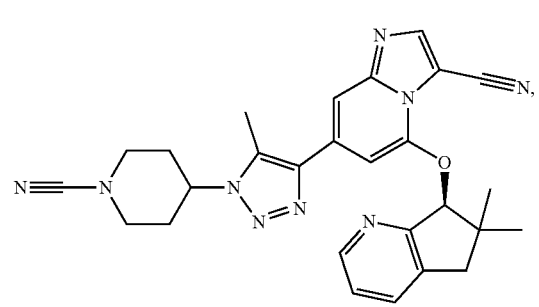
-continued
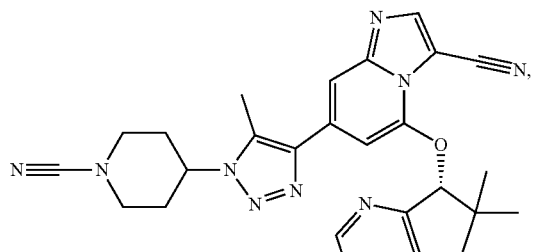
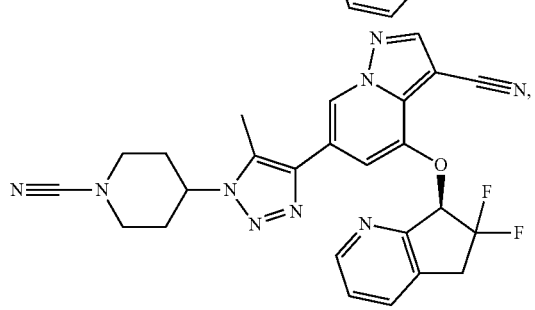
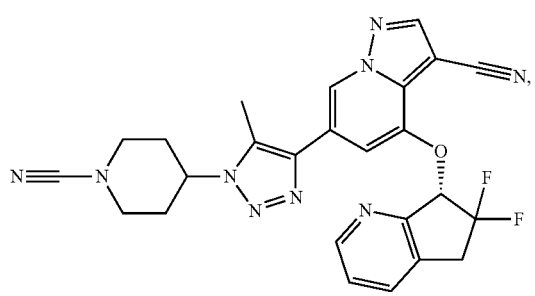
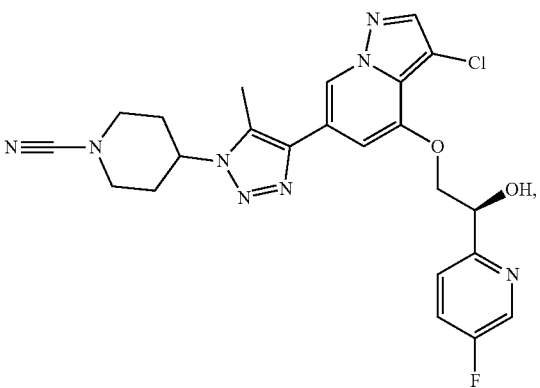
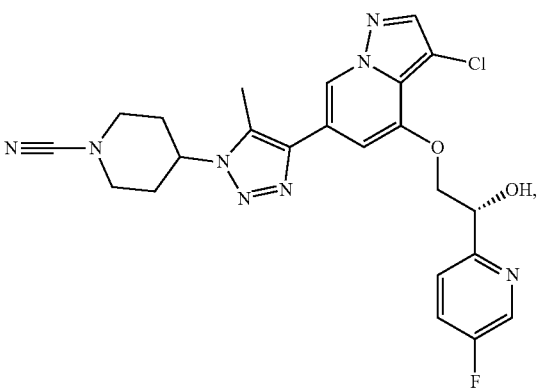

-continued

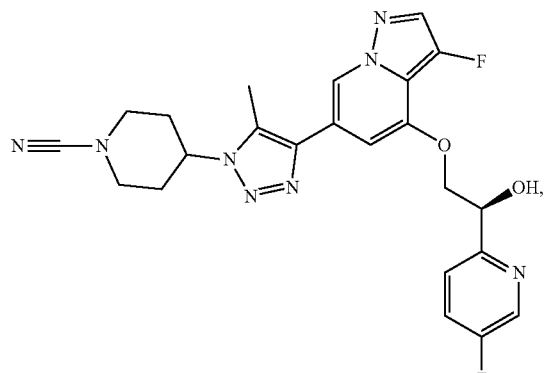

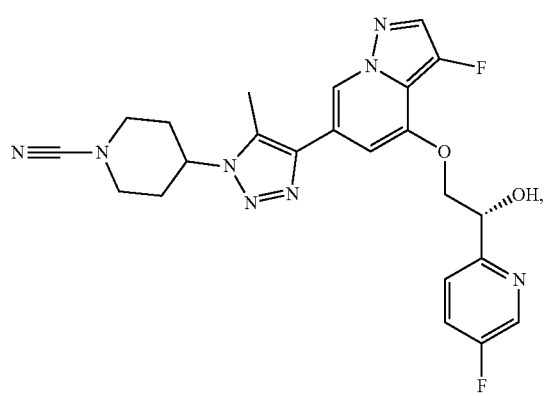

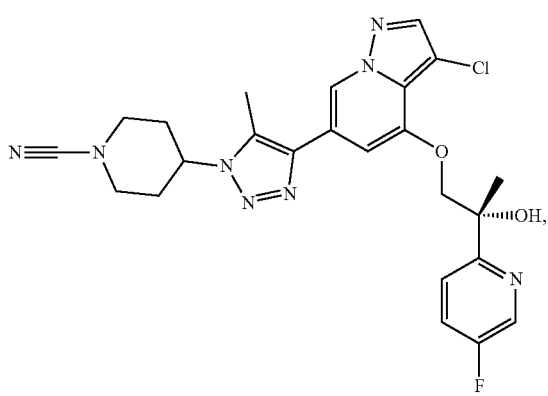

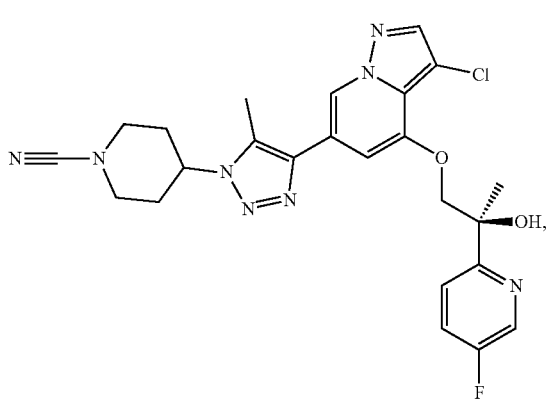

-continued

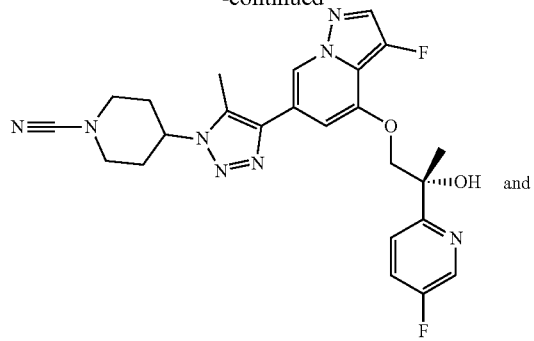

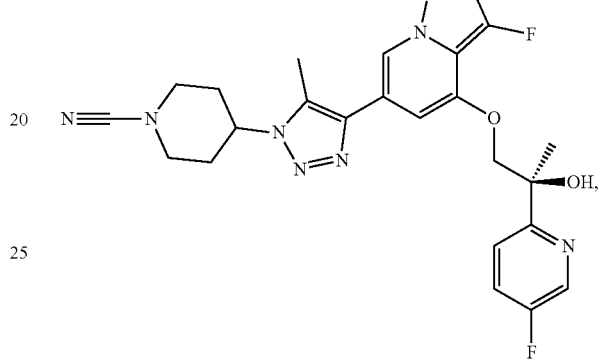

or a pharmaceutically acceptable salt thereof.

The compounds of formula (I), (II), (IIA) or (III), provided herein, or a pharmaceutically acceptable salt thereof, any or all hydrogens present in the compound, or in a particular group or moiety within the compound, may be replaced by a deuterium or a tritium. Thus, a recitation of alkyl includes deuterated alkyl, where from one to the maximum number of hydrogens present may be replaced by deuterium. For example, ethyl refers to both $C_2H_5$ or $C_2H_5$ where from 1 to 5 hydrogens are replaced by deuterium, such as in $C_2D_xH_{5-x}$.

The compounds of formula (I), (II), (IIA) or (III) provided herein may form pharmaceutically acceptable salts. The Examples provided herein may form pharmaceutically acceptable salts. Such pharmaceutically acceptable salts are intended to be included. Pharmaceutically acceptable salts and common methodology for preparing them are well known in the art (see, e.g., P. Stahl, et al. *Handbook of Pharmaceutical Salts: Properties, Selection and Use*, 2$^{nd}$ Revised Edition (Wiley-VCH, 2011); S. M. Berge, et al., "Pharmaceutical Salts," *Journal of Pharmaceutical Sciences*, Vol. 66, No. 1, January 1977).

The compounds of formula (I), (II), (IIA) or (III) provided herein, or a pharmaceutically acceptable salt thereof, can be mixed with one or more pharmaceutically acceptable carriers, diluents, or excipients. More particularly, the compounds of formula (I), (II), (IIA) or (III) provided herein, or a pharmaceutically acceptable salt thereof, can be formulated as pharmaceutical compositions. Such pharmaceutical compositions and processes for preparing the same are well known in the art (see, e.g., *Remington: The Science and Practice of Pharmacy* (A. Gennaro, et al., eds., 21st ed., Mack Publishing Co., 2005)).

The compounds of formula (I), (II), (IIA) or (III) provided herein, or a pharmaceutically acceptable salt thereof, and their pharmaceutical compositions can be administered by a variety of routes. Such routes of administration include oral and intravenous.

The compounds of formula (I), (II), (IIA) or (III) provided herein, or a pharmaceutically acceptable salt thereof, can be combined with one or more other therapeutic agents.

The compounds of formula (I), (II), (IIA) or (III) provided herein, or a pharmaceutically acceptable salt thereof, can be a component in a pharmaceutical composition for the treatment of systemic sclerosis, fibrosis, pulmonary fibrosis, achondroplasia, thanatophoric dysplasia, severe achondroplasia with developmental delay and acanthosis nigricans (SADDAN), muenke syndrome or cancer with one or more pharmaceutically acceptable carriers, diluents, or excipients, and optionally with one or more additional therapeutic agents.

The compounds of formula (I), (II), (IIA) or (III) provided herein, or a pharmaceutically acceptable salt thereof, can be a component in a pharmaceutical composition for the treatment of cancer with one or more pharmaceutically acceptable carriers, diluents, or excipients, and optionally with one or more additional therapeutic agents.

The compounds of formula (I), (II), (IIA) or (III) provided herein, or a pharmaceutically acceptable salt thereof, can be combined with one or more other therapeutic agents for simultaneous, separate or sequential administration.

The compounds of formula (I), (II), (IIA) or (III) provided herein, or a pharmaceutically acceptable salt thereof, and their pharmaceutical compositions can be used in the methods described herein.

The compounds of formula (I), (II), (IIA) or (III) provided herein, or a pharmaceutically acceptable salt thereof, are generally effective over a wide dosage range. For example, dosages per day normally fall within the range of about 0.5 to about 100 mg/kg of body weight. In some instances, dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

Certain compounds of formula (I), (II), (IIA) or (III), or a pharmaceutically acceptable salt thereof, selectively target FGFR3. For example, certain compounds of formula (I), (II), (IIA) or (III), or a pharmaceutically acceptable salt thereof, selectively target FGFR3 over another FGFR. For example, certain compounds of formula (I), (II), (IIA) or (III), or a pharmaceutically acceptable salt thereof, selectively target FGFR3 over FGFR1. For example, certain compounds of formula (I), (II), (IIA) or (III), or a pharmaceutically acceptable salt thereof, are at least about 3 fold (e.g. at least about 4-, 5-, 6-, 7-, 8-, 9-, 10-, 15-, 20-, 30-, 40-, 50-fold, or more) more selective for FGFR3 than for FGFR1.

As used herein, the term "selectivity" of a compound refers to the compound having more potent activity at the first target than the second target. A fold selectivity can be calculated by any method known in the art. For example, a fold selectivity can be calculated by dividing the $IC_{50}$ value of a compound for the second target (e.g., FGFR1) by the $IC_{50}$ value of the same compound for the first target (e.g., FGFR3). An $IC_{50}$ value can be determined by any method known in the art. For example, an $IC_{50}$ value can be determined as described in the assays below.

As used herein, the term "cancer" refers to or describes the physiological condition in patients that is typically characterized by unregulated cell proliferation. Included in this definition are benign and malignant cancers.

As used herein, the term "FGFR3-associated cancer" refers to cancers associated with or having a dysregulation of the FGFR3 gene, the FGFR3 kinase protein, or expression or activity, or level of any of the same. Non-limiting examples of FGFR3-associated cancer are described herein. As used herein an "FGFR3-associated cancer" includes but is not limited to breast cancer (e.g. invasive ductal cancer, invasive lobular cancer), lung cancer (e.g. non-small-cell lung cancer, lung adenocarcinoma, squamous cell lung cancer and small-cell lung cancer), urothelial cancer, bladder cancer (e.g. urothelial bladder cancer, non-muscle invasive bladder cancer, muscle invasive bladder cancer), upper tract cancer (e.g. urothelial upper tract cancer), urethral cancer, gastric cancer, pancreatic cancer, prostate cancer, colorectal cancer, multiple myeloma, liver cancer, melanoma (e.g. cutaneous melanoma), head and neck cancer (e.g. oral cancer), thyroid cancer, renal cancer (e.g. renal pelvis cancer), glioblastoma, endometrial cancer, cervical cancer, ovarian cancer, and testicular cancer.

As used herein, the term "treating" (or "treatment") refers to restraining, slowing, stopping, or reversing the progression or severity of an existing symptom, condition or disorder.

As used herein, the term "patient" refers to a mammal, particularly a human.

Provided herein are methods of treating systemic sclerosis, fibrosis, pulmonary fibrosis, achondroplasia, thanatophoric dysplasia, severe achondroplasia with developmental delay and acanthosis nigricans (SADDAN), muenke syndrome or cancer, comprising administering to a patient in need of such treatment an effective amount of the compounds of formula (I), (II), (IIA) or (III), or a pharmaceutically acceptable salt thereof.

Provided herein are methods of treating cancer, comprising administering to a patient in need of such treatment an effective amount of the compounds of formula (I), (II), (IIA) or (III), or a pharmaceutically acceptable salt thereof.

Provided in the methods herein, the cancer is selected from the group consisting of breast cancer (e.g. invasive ductal cancer, invasive lobular cancer), lung cancer (e.g. non-small-cell lung cancer, lung adenocarcinoma, squamous cell lung cancer and small-cell lung cancer), urothelial cancer, bladder cancer (e.g. urothelial bladder cancer, non-muscle invasive bladder cancer, muscle invasive bladder cancer), upper tract cancer (e.g. urothelial upper tract cancer), urethral cancer, gastric cancer, pancreatic cancer, prostate cancer, colorectal cancer, multiple myeloma, liver cancer, melanoma (e.g. cutaneous melanoma), head and neck cancer (e.g. oral cancer), thyroid cancer, renal cancer (e.g. renal pelvis cancer), glioblastoma, endometrial cancer, cervical cancer, ovarian cancer, and testicular cancer. Particularly, the cancer is selected from the group consisting of breast cancer (e.g. invasive ductal cancer, invasive lobular cancer), lung cancer (e.g. non-small-cell lung cancer, lung adenocarcinoma, squamous cell lung cancer and small-cell lung cancer), urothelial cancer, bladder cancer (e.g. urothelial bladder cancer, non-muscle invasive bladder cancer, muscle invasive bladder cancer), upper tract cancer (e.g. urothelial upper tract cancer), urethral cancer, pancreatic cancer, prostate cancer, colorectal cancer, melanoma (e.g. cutaneous melanoma), renal cancer (e.g. renal pelvis cancer), glioblastoma, endometrial cancer, and ovarian cancer. More particularly, the cancer is selected from the group consisting of breast cancer (e.g. invasive ductal cancer, invasive lobular cancer), lung cancer (e.g. non-small-cell lung cancer, lung adenocarcinoma, squamous cell lung cancer and small-cell lung cancer), urothelial cancer, bladder cancer (e.g. urothelial bladder cancer, non-muscle invasive bladder cancer, muscle invasive bladder cancer), upper tract cancer (e.g. urothelial upper tract cancer) and glioblastoma. Most particularly, the cancer is bladder cancer (e.g. urothelial bladder cancer, non-muscle invasive bladder cancer, muscle invasive bladder cancer).

The compounds provided herein can be prepared as illustrated in the preparations and examples below.

Certain abbreviations are defined as follows: "ACN" refers to acetonitrile; "AcOH" refers to acetic acid; "Ac2O" refers to acetic anhydride; "aq." refers to aqueous; "AIBN" refers to azobisisobutyronitrile; "BINAP" refers to 2,2'-bis(diphenylphosphino)-1,1'-binaphthyl; "Pd(DtBPF)Cl$_2$" refers to [1,1-Bis(di-tert-butylphosphino) ferrocene]dichloropalladium(II); NBS" refers to N-bromosuccinimide; "n-BuOH" refers to n-butyl alcohol or n-butanol; "BOC" refers to tert-butyloxycarbonyl; "Boc$_2$O" refers to di-tert-butyl dicarbonate; "BuLi" refers to butyl lithium; "CuSO$_4$ 5H$_2$O" refers to copper sulfate pentahydrate; 'CsF" refers to cesium fluoride; "F-TEDA" refers to 1-chloromethyl-4-fluoro-1,4-diazoniabicyclo[2.2.2]octane; "CuI" refers to copper iodide; "DMP" refers to Dess-Martin periodinane; "DCE" refers to 1,2-dichloroethane; "DCM" refers to dichloromethane or methylene chloride; "DMEA" refers to dimethylethylamine; "NDM" refers to 1-dodecanethiol; "DEA" refers to diethanolamine; "DEAD" refers to diethyl azodicarboxylate; "DIAD" refers to diisopropyl azodicarboxylate; "DIEA" or "DIPEA" refers to N,N-diisopropylethylamine; "DMA" refers to N,N-dimethylaniline; "DMAP" refers to 4-dimethylaminopyridine; "DMF" refers to N,N-dimethylformamide; "DPPA" refers to diphenylphosphoryl azide; "EAA" refers to ethyl acetoacetate; "EtOAc" refers to ethyl acetate; "FA" refers to formic acid "hr" refers to hour or hours; "i-PrMgCl" refers to isopropyl magnesium chloride; "IPA" refers to isopropyl amine; "T3P" refers to propylphosphonic anhydride; "KOAc" refers to potassium acetate; "LiBH$_4$" refers to lithium borohydride; "LDA" refers to lithium diisopropylamide; "MsCl" refers to methanesulfonyl chloride; "MTBE" refers to methyl tert-butyl ether; "NCS" refers to N-chlorosuccinimide; "NIS" refers to N-iodosuccinimide; 'MeMgBr" refers to methyl magnesium bromide; "NMP" refers to N-methyl-2-pyrrolidone; "—OAc" refers to acetate; "OMs" refers to methanesulfonate, also known as mesylate; "min" or "min." refers to minute or minutes; "N$_2$" refers to nitrogen; "sat." or "sat'd" refers to saturated; "soln." refers to solution; "—OTf" refers to trifluoromethanesulfonate, also known as triflate; "PCy$_3$" refers to tricyclohexylphosphine; "Pd (AcO)$_2$" refers to palladium(II) acetate; "Pd(dba)$_2$" refers to bis(dibenzylideneacetone)palladium(0); "Pd$_2$(dba)$_3$" refers to tris(dibenzylideneacetone) dipalladium(0); "Pd2 (dba)$_3$·CHCl$_3$" refers to tris(dibenzylideneacetone)dipalladium-chloroform adduct; "Pd(dppf)Cl$_2$" refers to [1,1'-bis(diphenylphosphino)ferrocene] dichloropalladium (II); "Pd (dppf)Cl$_2$·CH$_2$Cl$_2$" refers to 1,1'-bis(diphenylphosphino) ferrocene-palladium(II)dichloride dichloromethane complex; "PE" refers to petroleum ether; "K$_3$PO$_4$" refers to potassium phosphate; "RT" refers to room temperature; "PPh$_3$" refers to triphenylphosphine; "Pd(PPh$_3$)$_4$" refers to tetrakis(triphenylphosphine)palladium(0); "Ph" refers to phenyl; "NaH" refers to sodium hydride; "TBAF" refers to tetra-n-butylammonium fluoride; "TEA" refers to triethylamine; "TFA" refers to trifluoroacetic acid; "Tf$_2$O" refers to trifluoromethane sulfonic anhydride; "THF" refers to tetrahydrofuran; "TsCl" refers to 4-toluenesulfonyl chloride; "TMSCF$_3$" refers to (trifluoromethyl)trimethylsilane; "TMSOTf" refers to trimethylsilyltrifluoro methanesulfonate; "(CF$_3$SO$_2$)$_2$O" refers to trifluoromethanesulfonic anhydride; "t$_{(R)}$" refers to retention time; "Xantphos" refers to 4,5-bis(diphenylphosphino)-9,9-dimethylxanthene; "X-Phos" refers to 2-dicyclohexyl phosphino-2,4,6-triisopropylbiphenyl; "XPhos Pd G2" refers to chloro(2-dicyclohexylphosphino-2',4',6'-triisopropyl-1,1'-biphenyl)[2-(2'-amino-1,1'-biphenyl)]palladium(II); and "XPhos Pd G$_4$" refers to CAS #1599466-81-5; "ZnCl$_2$" refers to zinc chloride.

Certain stereochemical centers have been left unspecified and certain substituents have been eliminated in the following schemes for the sake of clarity and are not intended to limit the teaching of the schemes in any way. Furthermore, individual isomers, enantiomers, and diastereomers may be separated or resolved by one of ordinary skill in the art at any convenient point in the synthesis of compounds of the invention, by methods such as selective crystallization techniques or chiral chromatography (See for example, J. Jacques, et al., "Enantiomers, Racemates, and Resolutions", John Wiley and Sons, Inc., 1981, and E. L. Eliel and S. H. Wilen, "Stereochemistry of Organic Compounds", Wiley-Interscience, 1994). The designations "isomer 1" and "isomer 2" refer to the compounds that elute from chiral chromatography first and second, respectively, under the conditions described herein and if chiral chromatography is initiated early in the synthesis, the same designation is applied to subsequent intermediates and examples. Where more than one chiral chromatography is conducted in the preparation, a further designation of "A" and "B" is provided where "A" refers to the compounds that elute first and "B" for those that elute second. For example "isomer 2A" refer to the first eluting compounds from the chiral chromatography of a compound previously designated "isomer 2". Additionally, the intermediates described in the following schemes contain a number of nitrogen or oxygen protecting groups. The variable protecting group may be the same or different in each occurrence depending on the particular reaction conditions and the particular transformations to be performed. The protection and deprotection conditions are well known to the skilled artisan and are described in the literature (See for example "Greene's Protective Groups in Organic Synthesis", Fourth Edition, by Peter G. M. Wuts and Theodora W. Greene, John Wiley and Sons, Inc. 2007).

In the schemes below, all substituents, unless otherwise indicated, are as previously defined. "PG" refers to a protecting group developed for the amino group, such as carbamates and amides, an example being a BOC protecting group. Such protecting groups are well known and appreciated in the art. The reagents and starting materials are generally readily available to one of ordinary skill in the art. Others may be made by standard techniques of organic and heterocyclic chemistry which are analogous to the syntheses of known structurally similar compounds and the procedures described in the Preparations and Examples which follow including any novel procedures. Intermediates and processes useful for the synthesis of the compounds of formula (I), (II), (IIA) or (III) are intended to be included in this description.

Scheme 1

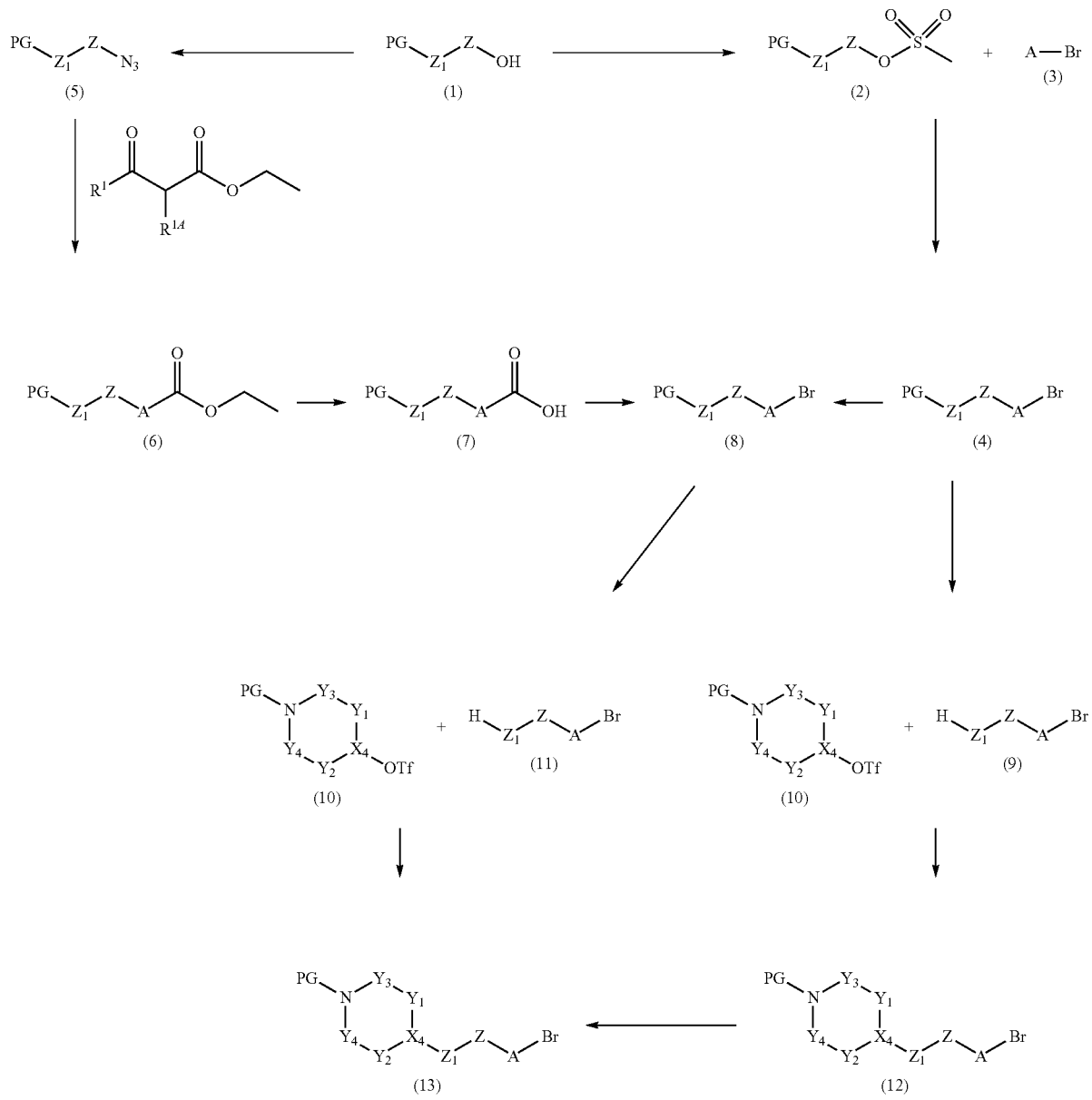

Scheme 1 depicts the preparation of compounds of (4) and (8) that lead to compound 13 through different routes and will be further elaborated to formula (I). A person of skill in the art will recognize that alcohol (1) may react with a mesyl chloride to afford mesylate (2) that can be further reacted with (3) to provide (4). Treatment of compound (4) with LDA and an appropriate alkylating agent may afford compound (8). Alternatively, one skilled in the art may start with compound (3) that is substituted bromide (3) that when reacted with mesylate (2) directly affords compounds of (8).

Compound (8) can also be synthesized through an alternative route as depicted in Scheme 1. Additionally, a skilled artisan will appreciate that alcohol (1) may react under Mitsunobu conditions to provide azide (5). Azide (5) may be condensed with a beta-keto ester to afford triazole ester (6) that can undergo saponification to provide carboxylic acid (7). Treatment of carboxylic acid (7) with bromine in the presence of base affords compounds of (8).

Scheme 1 further depicts the preparation of compounds of (12) and (13) that will be further elaborated to formula (I). A skilled artisan will recognize that compounds of (4) and (8) may be deprotected to give (9) and (11) that when reacted with triflate (10) result in bromide compounds of (12) and (13). Compound (12) may further be alkylated to give compounds of (13). A skilled artisan will appreciate that ketone compounds may be substituted for the triflate compounds of (10). Alternatively, reacting compound (9) or (11) with an appropriate ketone under reductive amination conditions may also afford compounds (12) or (13).

Scheme 2

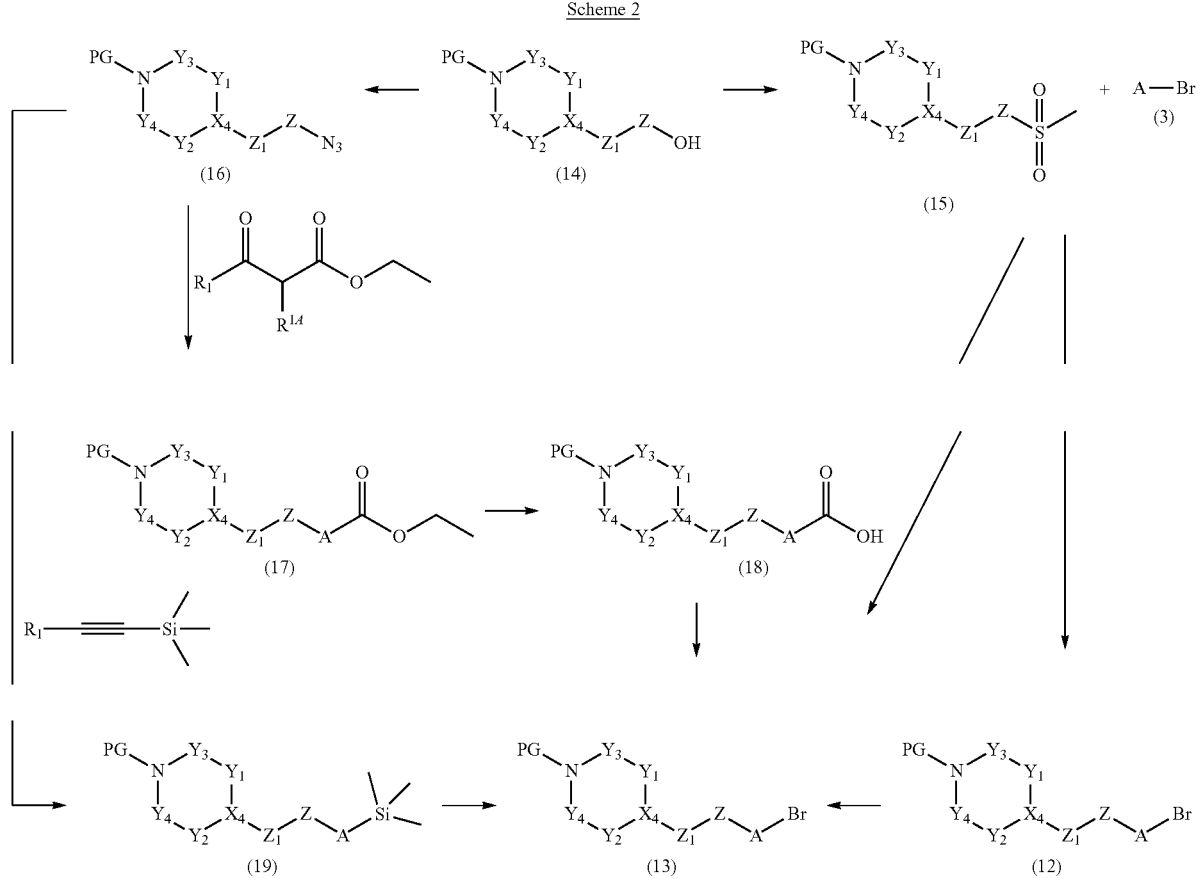

Scheme 2 depicts an alternative preparation of compounds of (12) and (13) that will be further elaborated to formula (I). A person of skill in the art will recognize that alcohol (14) may react with mesyl chloride to afford mesylate (15) that can be further reacted with a compound (3) to provide (12). Compounds of (12) may further be alkylated to furnish compounds of (13). Alternatively, compound (3) that is substituted may be reacted with (15) to directly give compounds of (13).

Additionally, compound (13) may also be synthesized from alternative routes as depicted in Scheme 2. Alcohol (14) may react under Mitsunobu conditions to provide azide (16). Azide (16) may be condensed with a beta-keto ester to afford triazole ester (17) that can undergo saponification to provide carboxylic acid (18). Treatment of carboxylic acid (18) with bromine in the presence of base affords bromide (13). Alternatively, azide (16) may be reacted with an appropriately substituted trimethylsilylalkyne to afford trimethylsilyl analog (19). Reaction of (19) with NBS in the presence of silicon dioxide provides compounds of (13).

Scheme 3

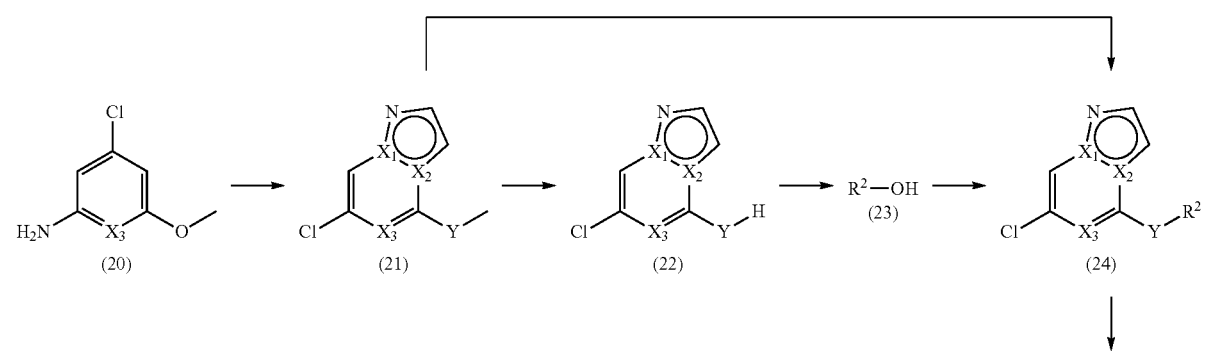

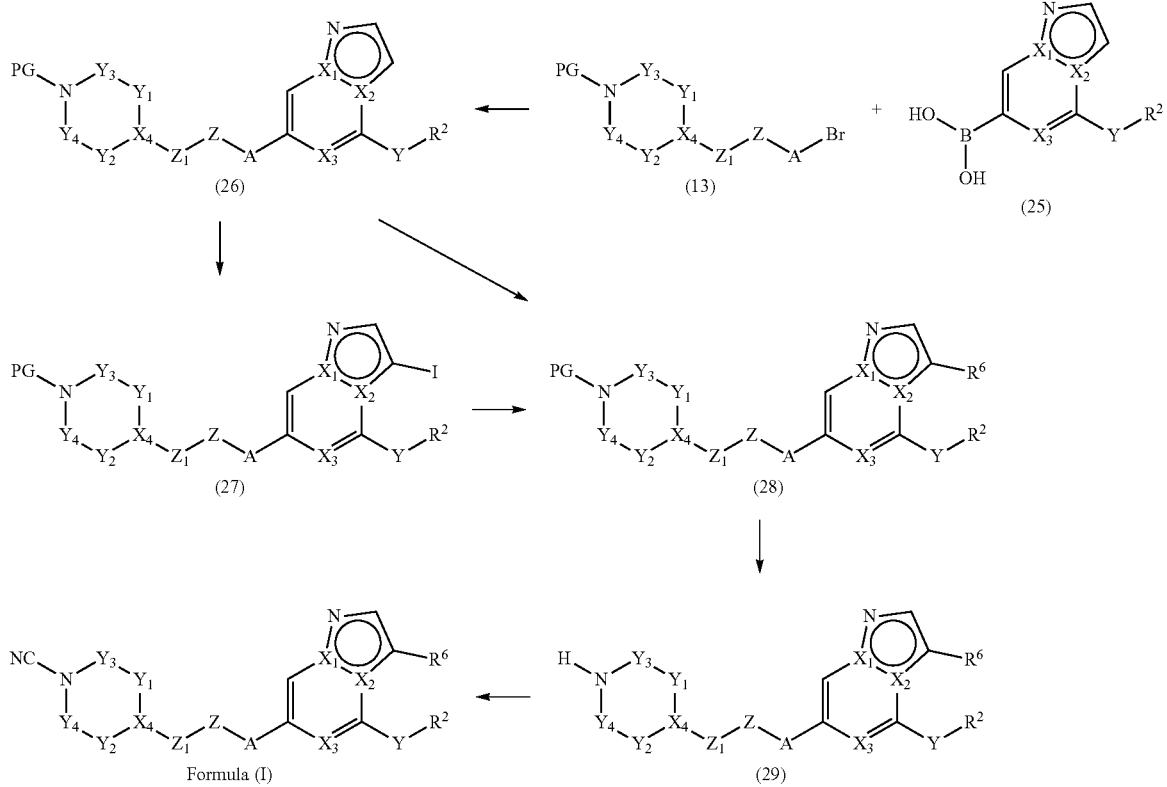

Scheme 3 depicts the preparation of compounds of formula (I). Reaction of (20) with chloroacetaldehyde provides heteroaryl chloride (21) that may be demethylated to give (22). Compound (22) may react with alcohol (23) via Mitsunobu conditions to provide a $R^2$ substituted heteroaryl chloride (24). A skilled artisan will recognize that when $R^2$ is methyl, it is unnecessary to demethylate (22) to arrive at a $R^2$ substituted (24). Conversion of heteroaryl chloride (24) to boronic acid (25) is achieved by treatment of (24) with bis(pinocolato)diboron under palladium catalyzed conditions. Boronic acid (25) may be reacted with bromide (13) to result in compounds of (26) through Suzuki coupling. Iodination of compounds of (26) in the presence of NIS provides (27) that may be further elaborated to provide $R^6$ substituted compounds of (28). Alternatively, as would be known to one skilled in the art, compounds of (26) may be reacted with reagents such as NCS or NBS to afford $R^6$ as chlorine or bromine directly without the intermediate iodination step to arrive at (28). Compounds of (28) are deprotected to provide compounds of (29). N-Cyanation of (29) results in N-cyanoamino compounds of formula (I).

Alternatively, a skilled artisan will appreciate that prior to conversion of (24) to boronic acid (25), compounds of (24) may first be iodinated then reacted with copper cyanide in DMF to afford a $R^6$ substituted heteroaryl chloride (24). Next, the $R^6$ substituted heteroaryl chloride (24) may be converted to a $R^6$ substituted boronic acid $R^6$ substituted (25) that can be reacted with bromide (13) to provide compounds of (28). Deprotection of (28) followed by N-cyanation results in N-cyanoamino compounds of formula (I).

Scheme 4

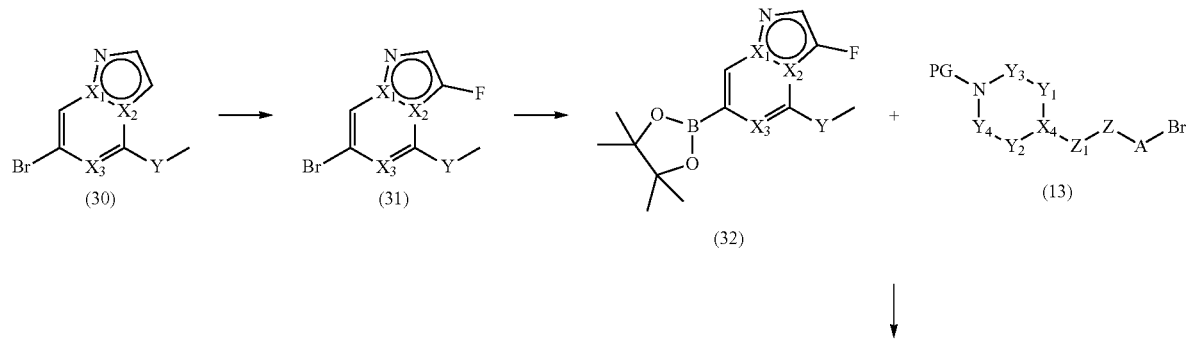

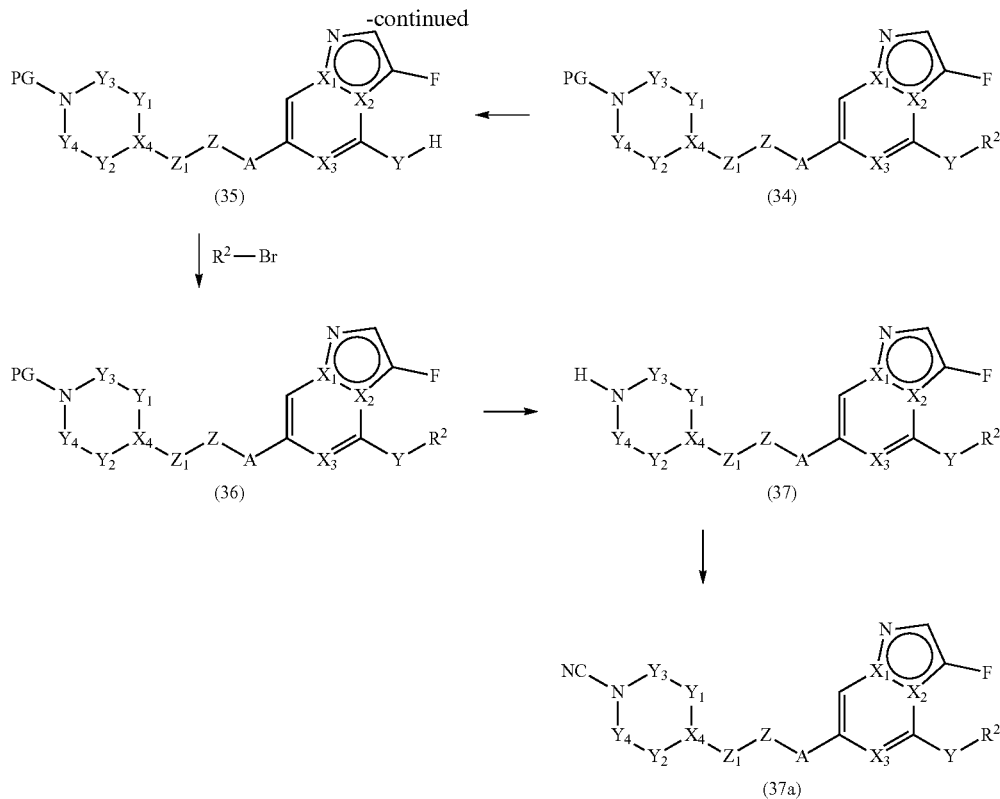

Scheme 4 depicts the preparation of compounds of (37a). Reaction of (30) in the presence of 1-(chloromethyl)-4-fluoro-1,4-diazabicyclo[2.2.2]octane-1,4-diium tetrafluoroborate affords the fluorinated bicyclic analog (31). Reaction of (31) with bis(pinocolato)diboron under palladium catalyzed conditions provides the boronate ester (32). Reaction of (32) with bromide (13) under palladium catalyzed conditions affords (34). Demethylation of (34) with aqueous sodium hydroxide and dodecane-1-thiol provides hydroxy bicyclic analog (35). Alkylation of (35) with the appropriate bromide gives compound (36). Deprotection of (36) followed by N-cyanation results in N-cyanoamino compounds of (37a).

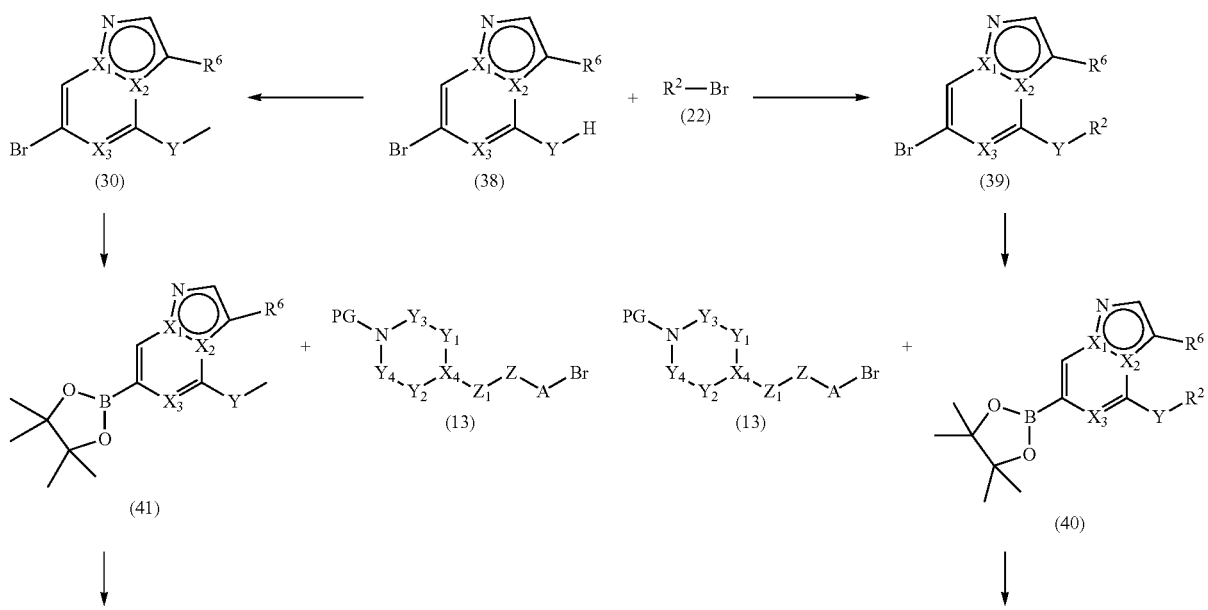

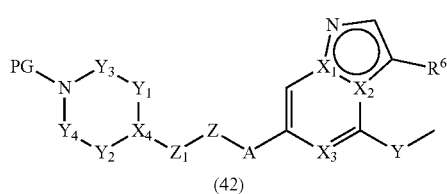

(42)

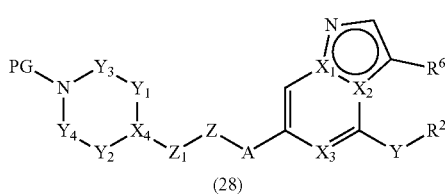

(28)

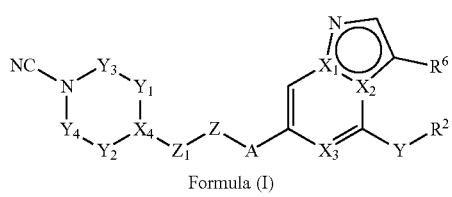

Formula (I)

Scheme 5 depicts an alternative preparation of cyano-amino compounds of Formula (I). One of ordinary skill will recognize that compounds of (30) may be demethylated to afford (38). Demethylated (38) may be reacted with alcohol (22) under Mitsunobu conditions to provide $R^2$ substituted bromide compounds (39). Alternatively, Compound (39) may be alkylated by substituting $R^2OH$ (22) with the corresponding iodo analog $R^2I$ of (22). Conversion of $R^2$ substituted bromide (39) to boronate ester (40) may be achieved by treating (39) with bis(pinocolato)diboron under palladium catalyzed conditions. Boronate ester (40) reacted with (13) results in compounds of (28) through Suzuki coupling. Alternatively, a skilled artisan will recognize that, as depicted in Scheme 5, methylated compounds of (30) may first be treated with bis(pinocolato)diboron under palladium catalyzed conditions to provide boronate ester (41). Boronate ester (41) may be reacted with (13) to give compounds of (42) through Suzuki coupling. A skilled artisan will recognize that compounds of (42) are also compounds of (28) where $R^2$ is methyl. Lastly, compounds of (28) may be deprotected to provide amine (29). N-Cyanation of amine (28) gives N-cyanoamino compounds of formula (I).

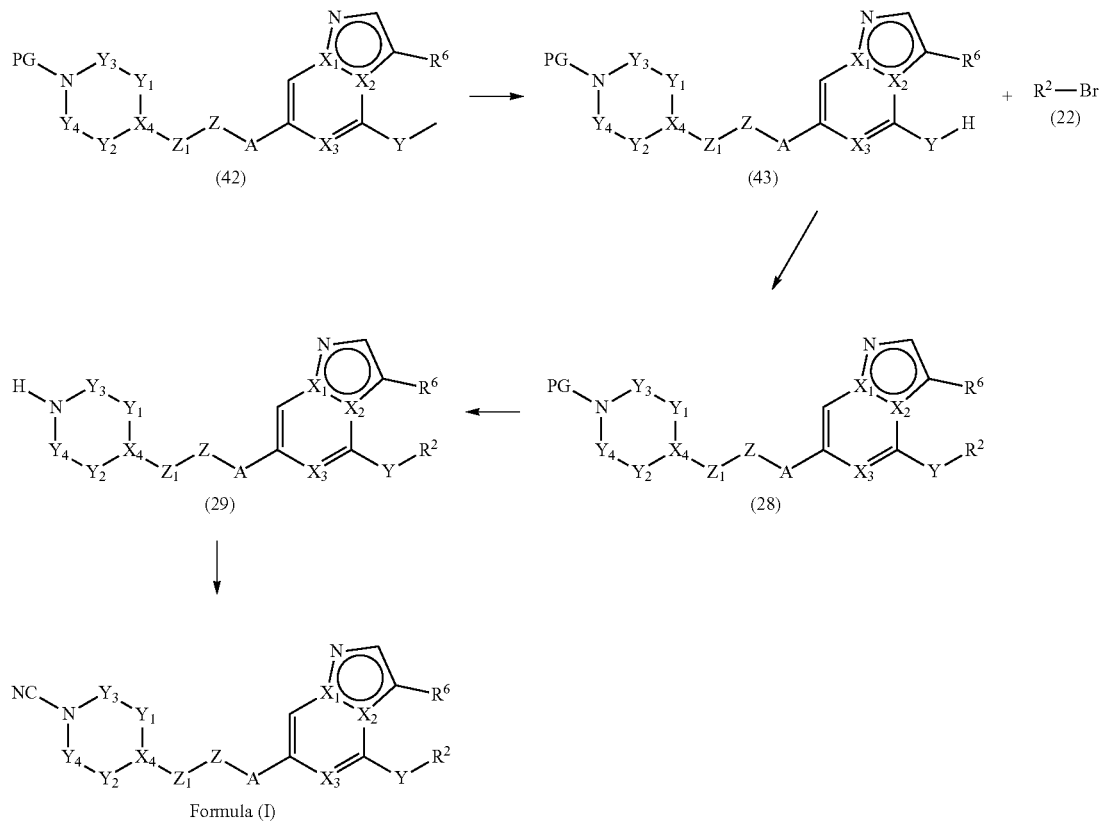

Scheme 6 depicts an alternative preparation of compounds of formula (I) starting with compounds (42) from Scheme 5 and compounds (28) from Schemes 3 and 5 where $R^2$ is methyl. Compounds (42) are demethylated to provide compounds of (43) that are reacted with alcohol (22) under Mitsunobu conditions to provide $R^2$ substituted compounds of (28) where the $R^2$ group is not methyl. $R^2$ substituted (28) may be deprotected to give compound (29) and then N-cyanated to give N-cyanoamino compounds of formula (I).

One skilled in the art will recognize alternative reactants may also result in compounds of (28). For instance, alcohol (22) may be converted to triflate analog ($R^2$—OTf) of (22) that may then be reacted with compounds of (43) to give compounds of (28). Additionally, alcohol compounds of (43) may first be converted to triflate compounds of (35) that may then be reacted with $R^2$—$NH_2$ analogs of (22) to afford an amine-$R^2$ substituted compounds of (28).

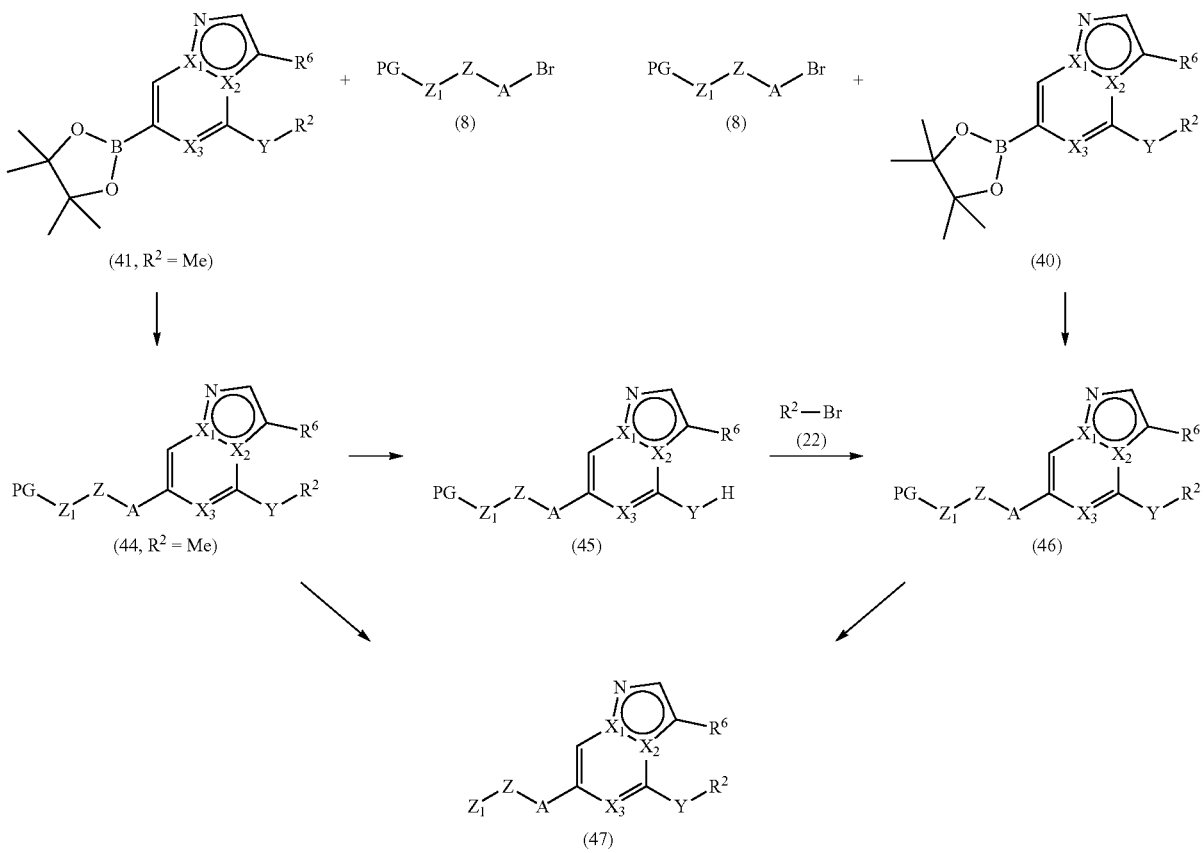

Scheme 7 depicts the preparation of compounds of (47) that are further elaborated to cyanoamino compounds of Formula (I) in Scheme 8. Boronate ester (40), as prepared in Scheme 5, may be reacted with (8) to result in compounds of (46) through Suzuki coupling. Alternatively, a skilled artisan will recognize that boronate ester (41), as prepared in Scheme 5, may be reacted with (8) to give compounds of (44) through Suzuki coupling. A skilled artisan will recognize that boronic acid $R^6$ substituted (25) as prepared in Scheme 3 may be substituted for boronic esters (40) and (41) in these reactions. Compounds of (44) may be demethylated to afford compounds of (45) that when reacted with alcohol (22) under Mitsunobu conditions afford compounds of (46). Lastly, compounds of (44) or (46) may be deprotected to provide amine (47).

A skilled artisan will recognize that amine (47) may also be prepared by replacing the $R^1$ substituted compounds (8) with unsubstituted compounds (4) to result in amine (47) where the A group is unsubstituted.

Scheme 8

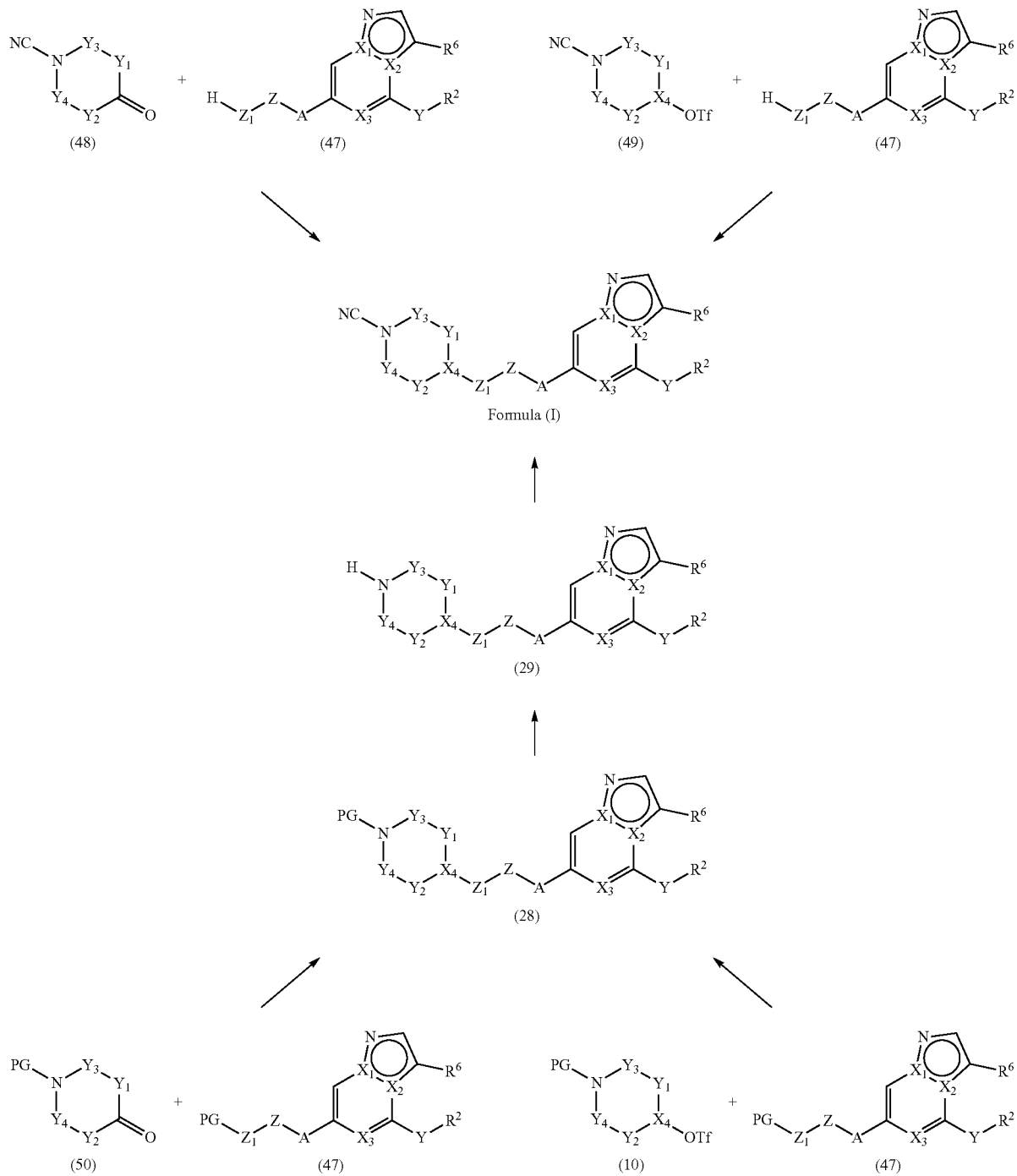

Scheme 8 depicts the preparation of compounds of Formula (I). Reductive amination of compounds of (47), as prepared in Scheme 7, with ketone (48) affords compounds of Formula (I). Alternatively, alkylation of (47) with triflate (49) gives compounds of Formula (I). A skilled artisan will also appreciate that mesylate (—OMs) compounds of (49) may be substituted for triflate (49).

Additionally, a skilled artisan will recognize that N-protected ketone compounds of (50) and triflate compounds of (10) may also be used instead of N-cyanoamino compounds (48) and (49). Reductive amination of compounds of (47), as prepared in Scheme 7, with N-protected ketone (50) affords N-protected (281. Alkylation of (47) with N-protected triflate (10) also affords N-protected (28). Protected (28) may be deprotected to give compounds of (29) that when reacted with cyanogen bromide result in N-cyanoamino compounds of formula (I).

Scheme 9

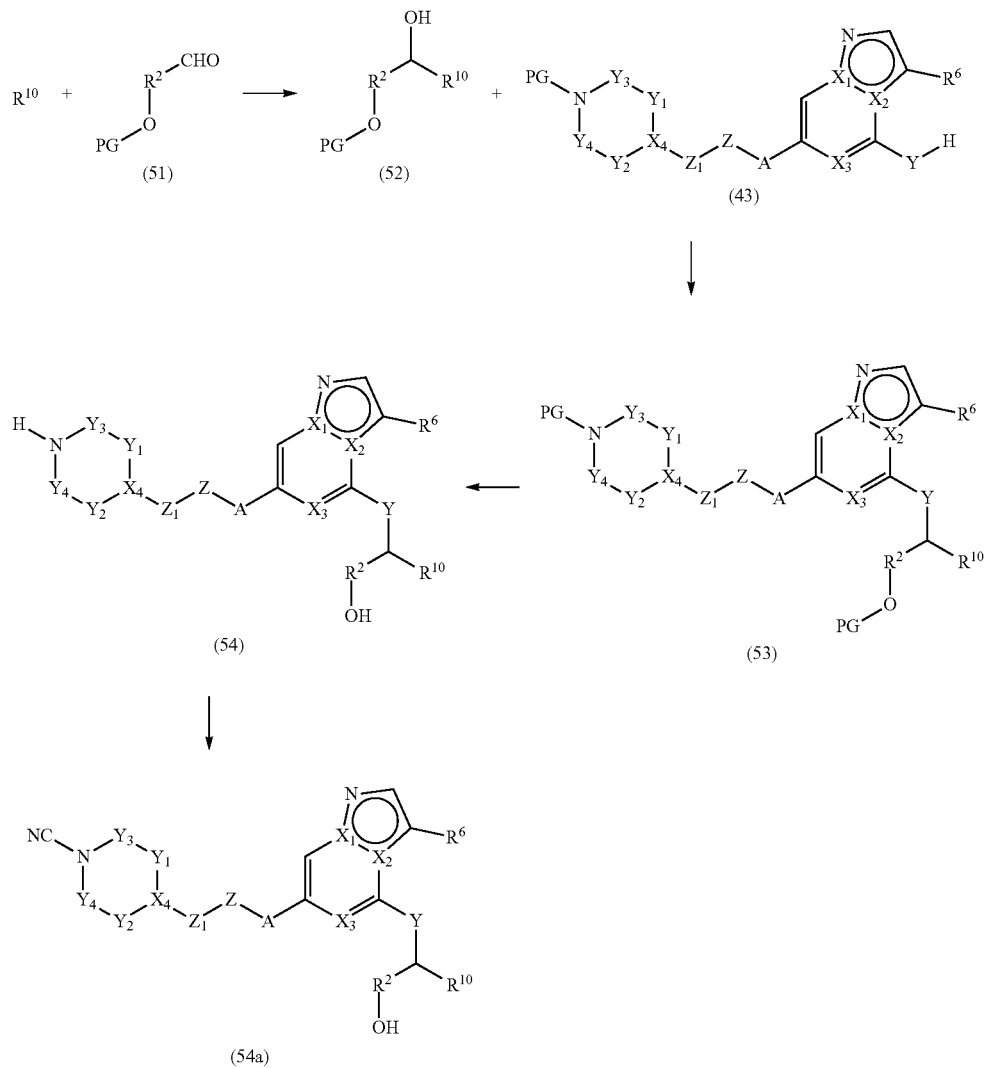

Scheme 9 depicts the preparation of compounds of (54a). Compounds of $R^{10}$, where $R^{10}$ is a 5-6 membered aryl or a 5-6-membered heteroaryl substituted with, but not limited to a halogen, may undergo a halogen-magnesium exchange with reagents such as iPrMgCl. The resultant Grignard reagent is reacted with the TBDMS protected alcohol $R^2$ aldehyde (51) to convert the aldehyde into the alcohol (52). Protecting groups other than TBDMS may be used to protect the $R^2$ alcohol in this step. Reacting the alcohol (52) under Mitsunobu conditions provides compounds (53). Treatment of (53) under acidic conditions affords the double deprotected compound (54). Reacting (54) with cyanogen bromide results in N-cyanoamino compounds of (54a).

Scheme 10

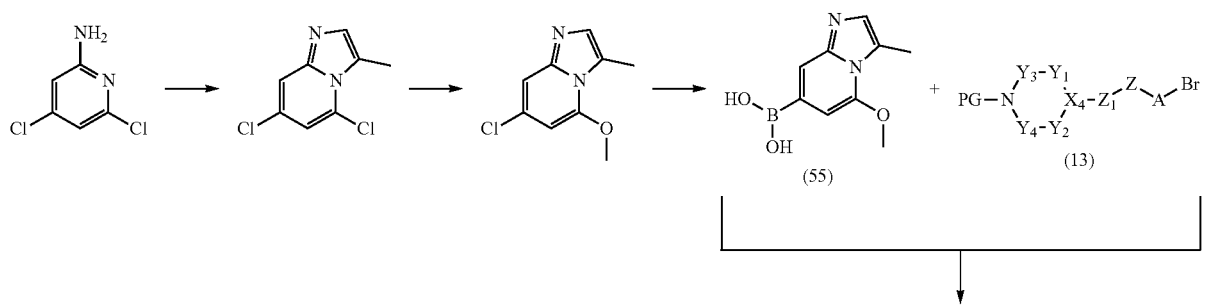

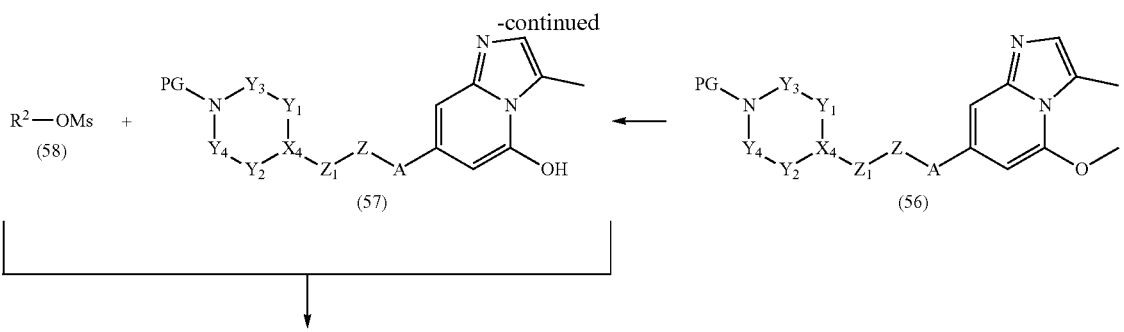

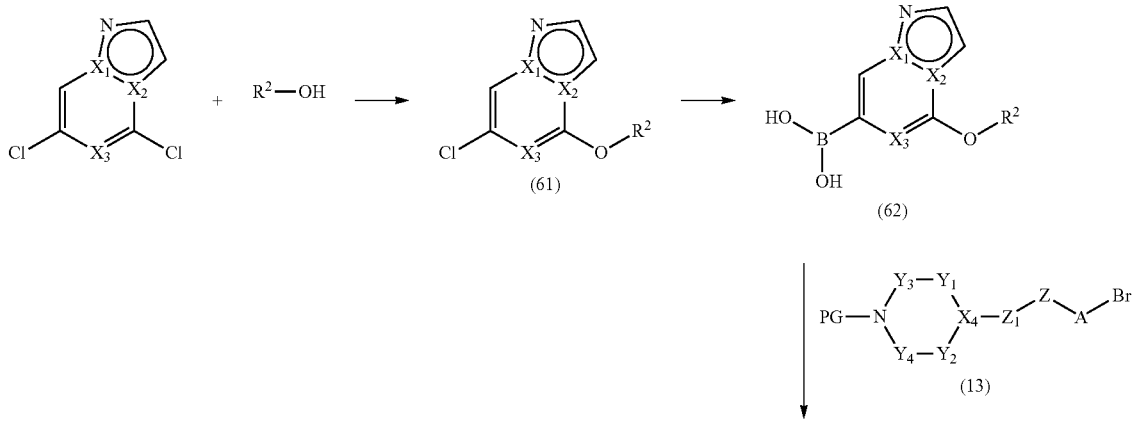

Scheme 10 depicts the preparation of compounds of (60a). 4,6-dichloropyridin-2-amine is reacted with a solution of 2-bromo-1,1-dimethoxypropane previously treated with aq. HCl in EtOH to afford 5,7-dichloro-3-methylimidazo[1,2-a]pyridine. The 5,7-dichloro intermediate is treated with sodium methoxide to yield 7-chloro-5-methoxy-3-methyl-imidazo[1,2-a]pyridine. The boronate ester (55) is formed by Pd catalyzed reaction of 7-chloro-5-methoxy-3-methyl-imidazo[1,2-a]pyridine with bis(pinacolato)diboron. Suzuki coupling of boronate ester (55) with bromide (56) affords compound (57). Hydrolysis of (57) with NaOH gives hydroxy compound (58). Alkylation of (58) with mesylate (59) provides compound (60). Deprotection of (60) affords (61) with is cyanogen bromide to afford the N-cyanoamino compounds of (60a).

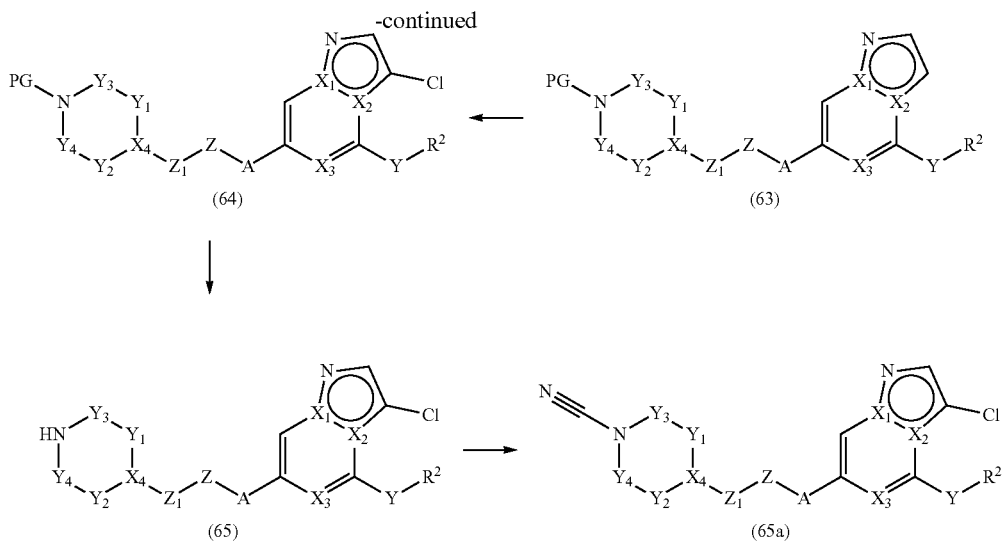

Scheme 11 depicts the preparation of (65a). Treatment of $R^2OH$ in the presence of base followed by the addition of 4,6-dichloropyridin-2-amine affords compound (61). The boronate ester (62) is formed by the Pd catalyzed reaction of compound (61) with bis(pinacolato)diboron. Suzuki coupling of boronate ester (62) and compound (13) provides compound (63). Chlorination of (63) with 1,3-dichloro-5,5-dimethyl-imidazolidine-2,4-dione affords compound (64) which is then deprotected under acidic conditions to give compound (65). Subsequent treatment of (65) with cyanogen bromide affords the N-cyanoamino compounds of (65a).

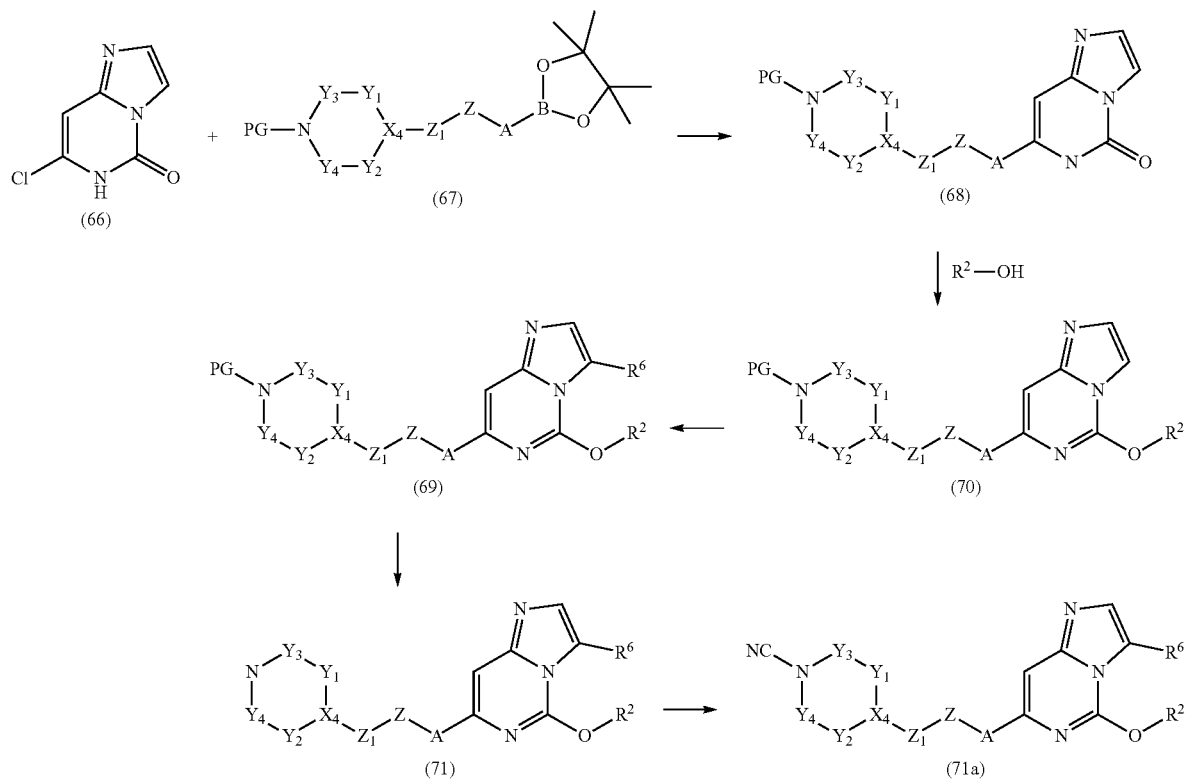

Scheme 12 depicts the preparation of (71a). Treatment of 7-chloro-6H-imidazo[1,2-c]pyrimidin-5-one with the boronate ester (67) under palladium catalyzed conditions provides (68). Reaction of (68) under Mitsunobu conditions affords (70). Halogenation of (70) in the presence of NCS yields (69). Deprotection of (69) affords (71). Subsequent treatment of (71) with cyanogen bromide affords compounds of (71a).

The compounds of the present invention, or pharmaceutically acceptable salts thereof, may be prepared according to the following Preparations and Examples by methods well known and appreciated in the art. Suitable reaction conditions for the steps of these Preparations and Examples are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. As an illustration, compounds of the preparations and examples can be isolated, for example, by silica gel purification, isolated directly by filtration, or crystallization. Furthermore, the skilled artisan will appreciate that in some circumstances, the order in which moieties are introduced is not critical. The particular order of steps required to produce the compounds of the present invention is dependent upon the particular compound being synthesized, the starting compound, and the relative liability of the substituted moieties, as is well appreciated by the skilled chemist. All substituents, unless otherwise indicated, are as previously defined, and all reagents are well known and appreciated in the art.

PREPARATIONS AND EXAMPLES

Preparation 1

3-Benzyloxycyclobutanol

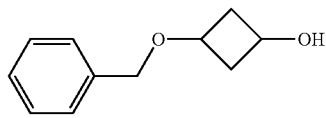 [SMILES: OC1CC(OCc2ccccc2)C1]

A mixture of 3-(benzyloxy)cyclobutan-1-one (20 g, 113.5 mmol) and NaBH$_4$ (4.29 g, 113.5 mmol) in MeOH (50 mL) is stirred for 2 hr at RT under N$_2$. The reaction is quenched with H$_2$O at 0° C., extracted with EtOAc (3×100 mL), washed with brine (2×100 mL), dried over Na$_2$SO$_4$, and filtered. The filtrate is concentrated under reduced pressure to afford the title compound (20 g, 98.9%) as a light-yellow oil. $^1$H NMR (400 MHz, DMSO-d6) δ 7.42-7.21 (m, 5H), 4.45 (s, 2H), 3.93-3.85 (m, 1H), 3.71-3.62 (m, 1H), 2.82-2.63 (m, 2H), 1.97-1.92 (m, 2H).

Preparation 2 tert-Butyl (2S,4S)-2-cyclopropyl-4-hydroxy-piperidine-1-carboxylate

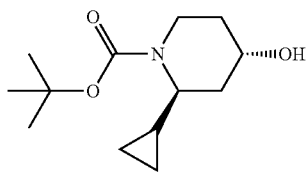 [SMILES: CC(C)(C)OC(=O)N1CC[C@H](O)C[C@H]1C1CC1]

To trans-2-cyclopropylpiperidin-4-ol hydrochloride (3.00 g, 16.9 mmol) in H$_2$O (15.00 mL) and DCM (15.00 mL) is added NaOH (2.03 g, 50.7 mmol) in portions at 0° C. under N$_2$. The mixture is stirred for 10 min at RT then Boc$_2$O (4.05 g, 18.6 mmol) is added in portions. The reaction is stirred for 2 hr at RT. The mixture is diluted with H$_2$O (100 mL) and extracted with DCM (2×120 mL). The combined organic layers are washed with brine (2×100 mL), dried over Na$_2$SO$_4$, and filtered. The filtrate is concentrated in vacuo to afford the title compound (5 g, crude) as a yellow solid, which is taken on to the next step without further purification. $^1$H NMR (400 MHz, DMSO-d6) δ 4.69 (d, 1H), 3.98-3.79 (m, 2H), 3.40-3.33 (m, 1H), 2.99-2.85 (m, 1H), 1.94-1.74 (m, 2H), 1.37 (s, 9H), 1.31-1.18 (m, 2H), 1.15-1.08 (m, 1H), 0.54-0.45 (m, 1H), 0.42-0.26 (m, 2H), 0.22-0.12 (m, 1H).

Preparation 3

N-diazo-1,1,1-trifluoro-methanesulfonamide

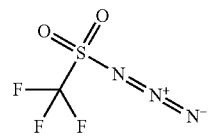

To a solution of NaN$_3$ (9.22 g, 142 mmol) and hydrogen tetra(but-1-yl)ammonium sulfate (481 mg, 1.42 mmol) in distilled H$_2$O (30 mL) to 0° C. is added slowly a solution of (CF$_3$SO$_2$)$_2$O (8.00 g, 28.4 mmol) in heptane (25 mL). The reaction is stirred 1-2 hr at 0° C. Heptane (25 ml) is added to the reaction and the layers are separated. The aqueous layer is extracted with heptane (3×10 ml). The combined organic layers are dried over NaOH pellets. The organic layer is decanted and the solution is used immediately in the subsequent reaction.

Preparation 4

(1r,3r)-3-Azidocyclobutanol

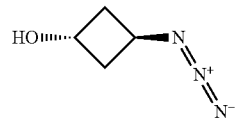

A solution of (1r,3r)-3-aminocyclobutan-1-ol (1.23 g, 14.2 mmol), NaHCO₃ (4.05 g, 48.2 mmol), and CuSO₄ 5H₂O (1.77 g, 7.08 mmol) in MeOH (15 mL) and H₂O (15 mL) (v/v) is treated with a freshly prepared stock solution of N-diazo-1,1,1-trifluoro-methanesulfonamide in heptane (4.96 g, 28.3 mmol). Additional MeOH is added to the reaction in 5 mL increments until a homogeneous mixture results (20 mL total added). The reaction is stirred overnight at RT. EtOAc is added and the layers are separated. The aqueous layer is extracted with EtOAc (3×). The combined organic layers are concentrated in vacuo to afford a dark green solution. Assumed quantitative yield. $^1$H NMR (400 MHz, DMSO-d6) δ 2.05-2.31 (m, 4H) 4.07-4.18 (m, 1H) 4.29 (br s, 1H) 5.14-5.32 (m, 1H).

Preparation 5 tert-Butyl 4-(2-azido-1,1-dimethyl-ethyl)piperazine-1-carboxylate

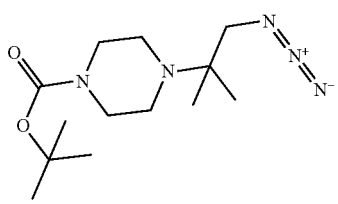 [SMILES: CC(C)(C)OC(=O)N1CCN(C(C)(C)CN=[N+]=[N-])CC1]

To a stirred solution of tert-butyl 4-(1-hydroxy-2-methylpropan-2-yl)piperazine-1-carboxylate (6.00 g, 23.22 mmol) and DBU (4.24 g, 27.87 mmol) in toluene (100 mL) is added DPPA (7.67 g, 27.89 mmol) dropwise at 0° C. under N₂. The mixture is stirred overnight at RT then concentrated in vacuo. The residue is purified by silica gel chromatography eluting with PE:EtOAc (20:1 to 10:1) to afford the title compound (6 g, 91.2%) as a light yellow oil. ES/MS m/z: 284.3 [M+H]⁺.

Preparation 6 tert-Butyl 2-azido-7-azaspiro[3.5]nonane-7-carboxylate

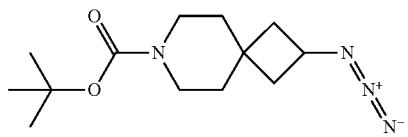 [SMILES: CC(C)(C)OC(=O)N1CCC2(CC1)CC(N=[N+]=[N-])C2]

To tert-butyl 2-hydroxy-7-azaspiro[3.5]nonane-7-carboxylate (10 g, 41.44 mmol) and PPh₃ (15.22 g, 58.01 mmol) in THF (150 ml) is added DEAD (10.10 g, 58.01 mmol) dropwise at 0° C. under N₂. The reaction is stirred 1 hr at 0° C. then DPPA (13.68 g, 49.72 mmol) is added dropwise. The reaction is stirred overnight at RT. The reaction is concentrated in vacuo then purified by silica gel chromatography, eluting with PE:EtOAc (30:1 to 20:1) to afford the title compound (14.5 g, crude) as a colorless oil which is carried forward without a further purification. $^1$H NMR (300 MHz, CDCl₃) δ 3.98-3.84 (m, 1H), 3.39-3.28 (m, 4H), 2.32-2.20 (m, 2H), 1.94-1.80 (m, 2H), 1.60-1.52 (m, 4H), 1.47 (s, 9H).

The following compounds are prepared essentially as described for tert-butyl 2-azido-7-azaspiro[3.5]nonane-7-carboxylate using the appropriate reagents and adjusting the reaction times to determine completion of the reactions. DIAD can be substituted for DEAD.

TABLE 1

| Prep No. | Chemical Name | Structure | $^1$NMR (400 MHz, CDCl₃), δ |
|---|---|---|---|
| 7[1] | tert-Butyl 4-azidoazepane-1-carboxylate | 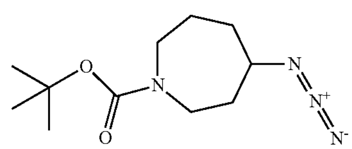 [SMILES: CC(C)(C)OC(=O)N1CCCC(N=[N+]=[N-])CC1] | 3.67-3.61 (m, 1H), 3.52-3.28 (m, 4H), 2.25-1.62 (m, 6H), 1.52 (s, 9H) |
| 8[2] | tert-Butyl (3R)-3-azidopiperidine-1-carboxylate | 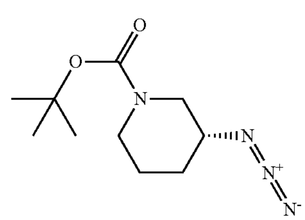 [SMILES: CC(C)(C)OC(=O)N1CCC[C@@H](N=[N+]=[N-])C1] | a |
| 9 | Cis-3-(Azidocyclobutoxy)methyl benzene | 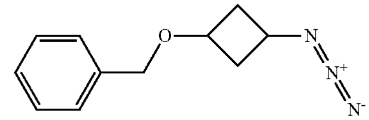 [SMILES: [N-]=[N+]=NC1CC(OCc2ccccc2)C1] | 2.44-2.27 (m, 4H), 4.16-4.08 (m, 1H), 4.28-4.21 (m, 1H), 4.41 (s, 2H), 7.39-7.28 (m, 5H) |

TABLE 1-continued

| Prep No. | Chemical Name | Structure | $^1$NMR (400 MHz, CDCl$_3$), δ |
|---|---|---|---|
| 10 | tert-butyl (2S,4R)-4-azido-2-cyclopropyl-piperidine-1-carboxylate | 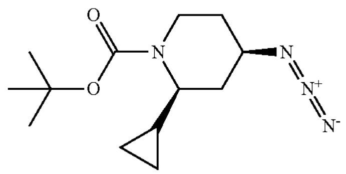 [SMILES: CC(C)(C)OC(=O)N1CC[C@@H](N=[N+]=[N-])C[C@H]1C1CC1] | a |
| 11[3,4] | tert-Butyl (3R,4S)-4-azido-3-fluoro-piperidine-1-carboxylate | 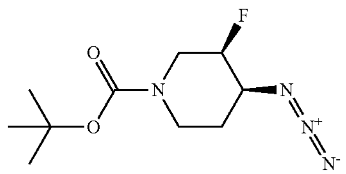 [SMILES: CC(C)(C)OC(=O)N1CC[C@H](N=[N+]=[N-])[C@H](F)C1] | 4.89-4.82 (m, 1H), 4.09-4.01 (m, 1H), 3.95-3.60 (m, 2H), 3.15 (dd, 2H), 1.90-1.64 (m, 2H), 1.40 (s, 9H) |
| 12[4,5] | tert-Butyl (3S,4S)-4-azido-3-fluoro-piperidine-1-carboxylate | 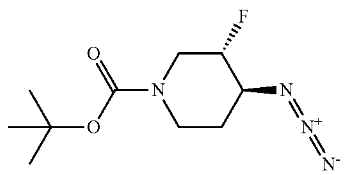 [SMILES: CC(C)(C)OC(=O)N1CC[C@H](N=[N+]=[N-])[C@@H](F)C1] | 4.41-4.36 (m, 1H), 4.06-3.85 (m, 2H), 3.68-3.57 (m, 1H), 3.06-2.97 (m, 2H), 1.93-1.83 (m, 1H), 1.40 (s, 10H) |
| 13[6,7] | tert-Butyl (3S,4R)-4-azido-3-fluoro-piperidine-1-carboxylate | 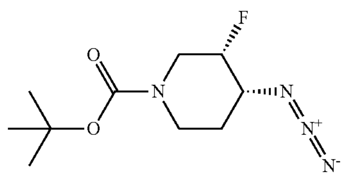 [SMILES: CC(C)(C)OC(=O)N1CC[C@@H](N=[N+]=[N-])[C@@H](F)C1] | 4.98-4.76 (m, 1H), 4.12-3.96 (m, 1H), 3.97-3.64 (m, 2H), 3.26-2.82 (m, 2H), 1.85-1.63 (m, 2H), 1.39 (s, 9 |
| 14[4] | tert-Butyl (3R,4R)-4-azido-3-fluoro-piperidine-1-carboxylate | 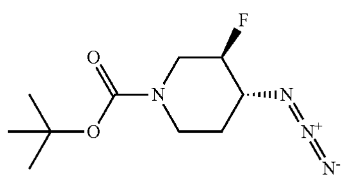 [SMILES: CC(C)(C)OC(=O)N1CC[C@@H](N=[N+]=[N-])[C@H](F)C1] | 4.63-4.24 (m, 1H), 4.09-3.83 (m, 2H), 3.80-3.55 (m, 1H), 3.20-2.84 (m, 2H), 2.06-1.78 (m, 1H), 1.42-1.36 (m, 10H) |
| 15[4] | tert-butyl (3RS,4RS)-4-azido-3-methyl-piperidine-1-carboxylate | 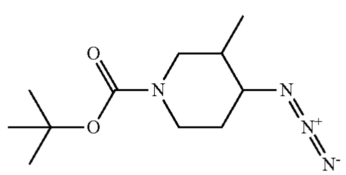 [SMILES: CC1CN(C(=O)OC(C)(C)C)CCC1N=[N+]=[N-]] | 4.02-3.84 (m, 2H), 3.38-3.27 (m, 1H), 3.02-2.87 (m, 1H), 2.03 (d, 1H), 1.55-1.37 (m, 12H), 1.06-0.97 (m, 3H) |
| 16[4,8] | tert-Butyl (3RS,4SR)-4-azido-3-methyl-piperidine-1-carboxylate | 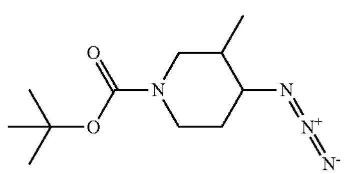 [SMILES: CC1CN(C(=O)OC(C)(C)C)CCC1N=[N+]=[N-]] | 3.97-3.89 (m, 1H), 3.47-3.38 (m, 2H), 3.37-3.29 (m, 1H), 3.28-3.16 (m, 1H), 1.90-1.79 (m, 1H), 1.67-1.55 (m, 2H), 1.43-1.33 (m, 9H), 0.87 (d, 3H) |

[1]Purified by Prep-TLC, PE:EtOAc (6:1 to 4:1)
[2]Purified by silica gel chromatography, eluting with PE:EtOAc (2:1).
[3]Purified by reverse phase chromatography; C18 column; eluting with 40% to 50% ACN in H$_2$O.
[4] $^1$H NMR (300 MHz, DMSO-d$_6$).
[5]Purified by silica gel chromatography, eluting with PE: EA (20:1).
[6]Purified by silica gel chromatography, eluting with PE: EA (15:1).
[7]$^1$H NMR (400 MHz, DMSO-d6).
[8]Purified by silica gel chromatography, eluting with PE/EA (30:1 to 20:1).
a Material is used without further purification.

Preparation 17 tert-Butyl (3S,4S)-4-azido-3-hydroxy-piperidine-1-carboxylate

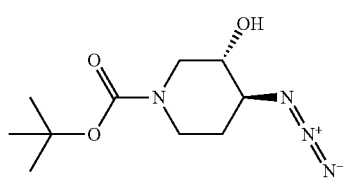 [SMILES: CC(C)(C)OC(=O)N1CC[C@H](N=[N+]=[N-])[C@@H](O)C1]

Imidazole-1-sulfonyl azide (3.75 g, 21.63 mmol) is added to a mixture of tert-butyl (3S,4S)-4-amino-3-hydroxypiperidine-1-carboxylate (3.9 g, 18.03 mmol), K$_2$CO$_3$ (1.25 g, 9.02 mmol) and CuSO$_4$.5H$_2$O (0.45 g, 1.80 mmol) in MeOH (25 mL) at RT under N$_2$. The reaction is stirred overnight at RT. The reaction is quenched with H$_2$O and the mixture is extracted with EA (2×500 mL). The combined organic layers are washed with brine (2×3 00 mL), dried over Na$_2$SO$_4$, filtered, and concentrated in vacuo to afford the title compound (4.3 g, crude) as a light-yellow oil. $^1$H NMR (400 MHz, DMSO-d6) δ 5.67 (d, 1H), 3.95-3.77 (m, 2H), 3.48-3.35 (m, 1H), 3.33-3.17 (m, 1H), 2.67 (d, 2H), 1.89-1.80 (m, 1H), 1.39 (s, 9H), 1.24-1.16 (m, 1H).

The following compounds are prepared essentially as described for tert-butyl (3S,4S)-4-azido-3-hydroxy-piperidine-1-carboxylate using the appropriate reagents and adjusting the reaction times to determine completion of the reactions. DIAD can be substituted for DEAD.

Preparation 21

(2S)-2-Hydroxypropanehydrazide

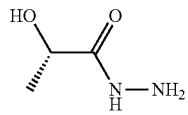

A mixture of ethyl lactate (3.00 g, 25.40 mmol), hydrazine hydrate (7.63 g, 152.37 mmol, 80% in H$_2$O) and EtOH (10.00 mL) is heated for 12 hr at 50° C. under N$_2$. Upon cooling to RT, the reaction is concentrated in vacuo to afford the title compound (3.0 g, crude). The title compound is taken on to the next step without further purification. ES/MS m/z: 105.2 [M+H]$^+$.

Preparation 22

(2S)—N-[(E)-dimethylaminomethyleneamino]-2-hydroxy-propanamide

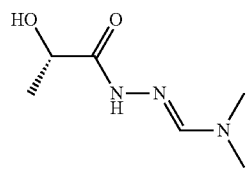

A mixture of (2S)-2-hydroxypropanehydrazide (3.0 g, crude), (dimethoxymethyl) dimethylamine (6.44 g, 43.22 mmol) and i-PrOH (15 mL) is heated at 50° C. for 5 hr under

TABLE 2

| Prep No. | Chemical Name | Structure | $^1$NMR (400 MHz, DMSO-d$_6$), δ |
|---|---|---|---|
| 18 | tert-Butyl (3R,4S)-4-azido-3-hydroxy-piperidine-1-carboxylate | 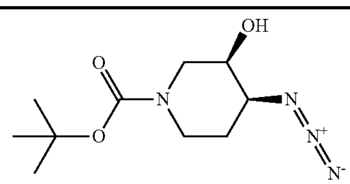 | 5.50-5.13 (m, 1H), 3.75-3.69 (m, 3H), 3.67-3.58 (m, 3H), 1.80-1.68 (m, 1H), 1.62-1.52 (m, 1H), 1.38 (s, 9H) |
| 19 | tert-Butyl (3S,4R)-4-azido-3-hydroxy-piperidine-1-carboxylate | 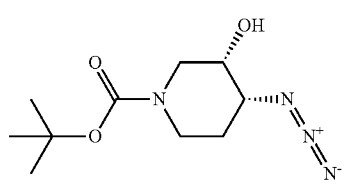 [SMILES: CC(C)(C)OC(=O)N1CC[C@@H](N=[N+]=[N-])[C@@H](O)C1] | 5.39 (s, 1H), 4.17-4.03 (m, 1H), 3.68-3.62 (m, 1H), 3.38-3.30 (m, 4H), 1.80-1.69 (m, 1H), 1.63-1.53 (m, 1H), 1.39 (s, 9H). |
| 20 | tert-Butyl (3R,4R)-4-azido-3-hydroxy-piperidine-1-carboxylate | 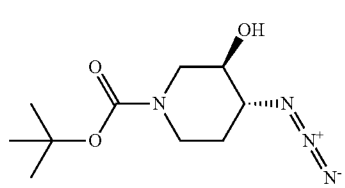 [SMILES: CC(C)(C)OC(=O)N1CC[C@@H](N=[N+]=[N-])[C@H](O)C1] | 5.58 (s, 1H), 3.98-3.86 (m, 1H), 3.85-3.75 (m, 1H), 3.43-3.34 (m, 1H), 3.33-3.19 (m, 1H), 2.66-2.57 (m, 1H), 1.89-1.76 (m, 1H), 1.39 (s, 9H), 1.28-1.11 (m, 2H). |

N₂. Upon cooling to RT, the reaction is concentrated in vacuo. The residue is purified by silica gel chromatography eluting with DCM:MeOH (10:1 to 8:1) to afford the title compound (3.0 g, 62.1%) as a white solid. ES/MS m/z: 160.2 [M+H]⁺.

Preparation 23 tert-Butyl 4-(4-methyl-1,2,4-triazol-3-yl)piperazine-1-carboxylate

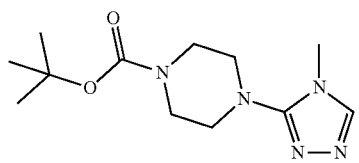 [SMILES: Cn1cnnc1N1CCN(C(=O)OC(C)(C)C)CC1]

A solution of 1-(4-methyl-4H-1,2,4-triazol-3-yl)piperazine (500 mg, 2.99 mmol) in THF (3 mL) and H₂O (0.25 mL) is added TEA (605 mg, 5.98 mmol). After stirring 15 minutes BOC₂O (783 mg, 3.59 mmol) is added. The reaction is stirred at 50° C. for 15 minutes. Upon cooling to RT pH is adjusted to ~14 by addition of 19N NaOH (aq.). The mixture is extracted with 3:1 CHCl₃:iPrOH. Organic layers are combined and washed with brine (ensuring pH remains near 12), dried over Na₂SO₄, filtered, and concentrated in vacuo to afford the title compound as a pale-yellow solid (647 mg, 2.42 mmol). ES/MS m/z: 168.1 [M+2H—BOC]⁺.

Preparation 24

2-(1-Bromoethyl)-N,N-dimethyl-benzamide

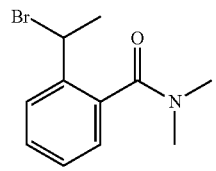

A reaction flask containing 2-ethyl-N,N-dimethylbenzamide (0.81 g, 4.6 mmol), AIBN (75 mg, 0.46 mmol) and NBS (0.89 g, 5.0 mmol) is evacuated and backfilled with N₂ (3×). CCl₄ (5 mL) is added, and the reaction is stirred 2 hr at 80° C. Upon cooling to RT, the reaction is filtered, insoluble material is washed with CCl₄ (2×10 mL), then concentrated in vacuo to obtain the title compound as a clear oil (0.8 g, 70%), which is carried forward without a further purification. ¹H NMR (400 MHz, CdCl₃), δ 7.67 (m, 1H), 7.40 (m, 1H), 7.30 (m, 1H), 7.25 (m, 1H), 5.45 (m, 1H), 3.18 (3H), 2.91 (3H), 2.08 (3H).

Preparation 25

2-Fluoro-N-methoxy-N-methyl-acetamide

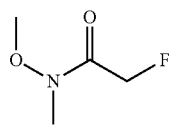

To N,O-dimethylhydroxylamine hydrochloride (3.68 g, 37.70 mmol) under N₂ is added DCM (40 mL) and the solution is cooled to −10° C. 2M Trimethylaluminum in hexanes (2.72 g, 37.70 mmol) is slowly added to the reaction. Once the addition is complete the reaction is allowed to warm to RT and stirred at RT for 1 hr. In a separate flask ethyl-2-fluoroacetate (2.00 g, 18.85 mmol) and DCM (20 mL) is added under N₂, and the reaction mixture is cooled −10° C. Next, the solution prepared from trimethylaluminium and N,O-dimethylhydroxylamine is slowly transferred to the reaction containing ethyl-2-fluoroacetate, warmed to RT, and is stirred for 18 hr. The reaction is quenched by slowly adding 1M Rochelle's salt (10 mL). The mixture is stirred for 1 hr, diluted with H₂O, layers separated, and the aq. layer is extracted with DCM (3×10 mL). The combined organics are washed with brine, dried over Na₂SO₄, and concentrated in vacuo to give the title compound as a light-brown oil (1.6 g, 13 mmol). ¹H NMR (400 MHz, CDCl₃) δ 3.15 (m, 3H), 3.63 (s, 3H), 5.01 (d, J=47.6 Hz, 2H).

Preparation 26

7-Fluoro-N-methoxy-N-methyl-isoquinoline-4-carboxamide

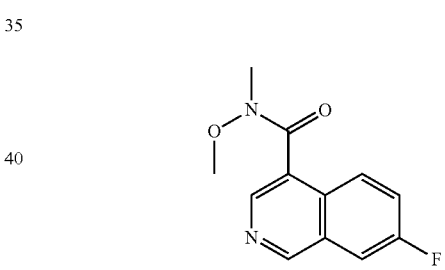

To a mixture of 7-fluoroisoquinoline-4-carboxylic acid (900 mg, 4.71 mmol), N,O-dimethylhydroxylamine hydrochloride (551 mg, 5.65 mmol) in DCM (5 mL) is added dropwise DIEA (2.43 g, 18.8 mmol). The solution is stirred for 5 min, followed by dropwise addition of 2,4,6-tripropyl-1,3,5,2,4,6-trioxatriphosphinane-2,4,6-trioxide (4.49 g, 14.1 mmol). The mixture is stirred for 3 hr at RT, diluted with H₂O and extracted with EtOAc. The combined organic layers are dried over Na₂SO₄, filtered, and concentrated in vacuo. The crude product is purified by silica gel column chromatography column with 0% to 100% EtOAc in heptane to afford the title compound (1.03 g, 93.4%). ¹H NMR (400 MHz, CDCl₃) δ 3.47 (br s, 6H), 7.50-7.61 (m, 1H), 7.65 (dd, J=8.44, 2.20 Hz, 1H), 7.97 (dd, J=9.11, 5.07 Hz, 1H), 8.60 (s, 1H), 9.26 (s, 1H). The following compounds are prepared essentially as described for 7-fluoro-N-methoxy-N-methyl-isoquinoline-4-carboxamide using the appropriate reagents and adjusting the reaction times to determine completion of the reactions.

TABLE 3

| Prep No. | Chemical Name | Structure | ES/MS m/z [M + H]+ |
|---|---|---|---|
| 27[1] | N-Methoxy-N-methyl-1-(trifluoromethyl)cyclopropanecarboxamide | 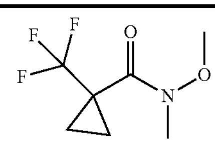 | 198.1 |
| 28 | N-Methoxy-N,5-dimethyl-pyridazine-3-carboxamide | 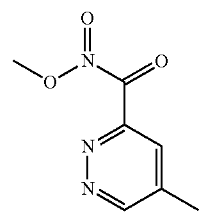 | a |
| 29 | 5-Chloro-N-methoxy-N-methyl-pyridazine-3-carboxamide | 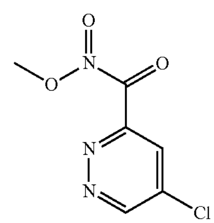 | b |
| 30[2] | N,1-Dimethoxy-N-methyl-cyclopropanecarboxamide | 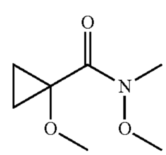 | 160.2 |
| 31 | N-Methoxy-N,4-dimethyl-isothiazole-5-carboxamide | 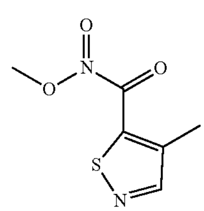 | c |
| 32[3] | N-Methoxy-N-methyl-2-(trifluoromethoxy)acetamide | 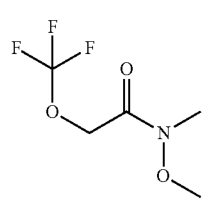 | 188.1 |
| 33[4] | N-methoxy-N-methyl-5-(trifluoromethoxy)pyridine-3-carboxamide | 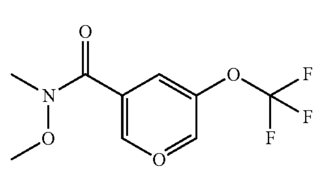 | 251.1 |

TABLE 3-continued

| Prep No. | Chemical Name | Structure | ES/MS m/z [M + H]+ |
|---|---|---|---|
| 34 | (4R)-N-methoxy-N,2,2-trimethyl-1,3-dioxolane-4-carboxamide | (structure) | e |

[1] O-Dimethylhydroxylamine is used instead of HCl salt. EtOAc is used as solvent.
[2] Purified by silica gel column chromatography, eluting with PE:EtOAc (10:1 to 4:1).
[3] Purified by silica gel column chromatography, eluting with PE:EtOAc (10:1 to 1:1).
[4] Purified by silica gel column chromatography, eluting with PE:EtOAc (10:1 to 5:1).
a Material carried forward to next step without being characterized.
b $^1$H NMR (400 MHz, CDCl$_3$) δ 3.43 (br s, 3H), 3.84 (br s, 3H), 7.78 (br s, 1H), 9.24 (br s, 1H).
c $^1$H NMR (400 MHz, CDCl$_3$) δ 2.59 (br s, 3H), 3.37 (br s, 3H), 3.79 (br s, 3H), 8.30 (br s, 1H).
d sodium 2-(trifluoromethoxy)acetate is used.
e $^1$H NMR (400 MHz, CdCl$_3$) δ 1.45 (s, 3H) 1.51 (s, 3H) 3.23 (s, 3H) 3.73 (s, 3H) 4.04-4.11 (m, 1H) 4.24-4.33 (m, 1H) 4.84-4.92 (m, 1H).

Preparation 35

4-Oxopiperidine-1-carbonitrile

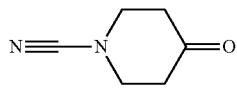

A solution of BrCN (256 mg, 2.42 mmol) in DCM (3.00 mL) is added dropwise to a stirred mixture of 4-piperidinone (200 mg, 2.02 mmol) and NaHCO$_3$ (509 mg, 6.05 mmol) in H$_2$O (4.50 mL) and DCM (1.50 mL) at 0° C. The mixture is stirred for 30 min at 0° C. then stirred at RT overnight. The mixture is quenched with H$_2$O (10 mL) and extracted with DCM (3×15 mL). The combined organic extracts are washed with sat. NaHCO$_3$ (3×5 mL) and brine (3×10 mL), dried over anhydrous Na$_2$SO$_4$, filtered, and the filtrate is concentrated under reduced pressure to give the title compound as a yellow oil (120 mg, 48%). $^1$H NMR (400 MHz, d$_6$-DMSO) δ 3.54 (t, 4H), 2.47 (t, 4H).

Preparation 36

Ethyl 1-methylpyrrolo[2,3-c]pyridine-4-carboxylate

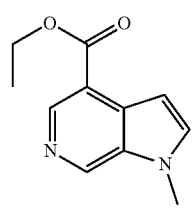

A mixture of 4-bromo-1-methyl-pyrrolo[2,3-c]pyridine (500 mg, 1 mmol), diethyl oxalate (415 mg, 2.84 mmol), PdCl$_2$(PPh$_3$)$_2$ (9.98 mg, 14.2 μmol), and N,N-dimethylpyridin-4-amine (347 mg, 2.84 mmol) in EtOH (327 mg, 7.11 mmol) is heated at 170° C. for 1 hr with microwave irradiation. The mixture is diluted with EtOAc (10 mL) and washed with sat. aq. NH$_4$Cl (10 mL). The aq. layer is extracted with EtOAc (3×10 mL) and the combined organic layers are concentrated in vacuo. The residue is purified by reverse phase chromatography eluting with a gradient of 0% to 100% ACN in water to afford the title compound (265 mg, 54.8%). ES/MS m/z: 205.1 [M+H]+.

Preparation 37

(1-Methylpyrrolo[2,3-c]pyridin-4-yl)methanol

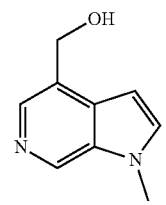

To a solution of ethyl 1-methylpyrrolo[2,3-c]pyridine-4-carboxylate (265 mg, 1.30 mmol) in THF (3 mL) at −78° C. is added a 1M solution of LiAlH$_4$ (73.9 mg, 1.95 mmol) in Et$_2$O. The reaction is stirred for 20 min then allowed to warm to RT and stirred for 1 hr. The mixture is diluted with Et$_2$O and after cooling to 0° C., H$_2$O (0.1 mL) is slowly added. Then a 15% aq. soln. of NaOH (0.07 mL) is added, followed by H$_2$O (0.2 mL), and the mixture is warmed to RT. After stirring for 15 min, MgSO$_4$ is added, and the mixture is stirred for an additional 15 min. The solids are removed by filtration and the filtrate is concentrated in vacuo to afford the title compound (190 mg, 90.3%). ES/MS m/z 163.1 [M+H]+.

Preparation 38

1-Methylpyrrolo[2,3-c]pyridine-4-carbaldehyde

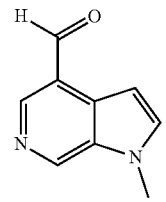

To a solution of (1-methylpyrrolo[2,3-c]pyridin-4-yl)methanol (190 mg, 1.17 mmol) in DCM (4 ml) at 0° C. is added DMP (646 mg, 1.52 mmol) and the reaction is stirred for 1 hr. The mixture is diluted with DCM (10 mL) and washed with sat. aq. NaHCO$_3$ (10 mL) and brine (10 mL). The volatiles are removed in vacuo and the residue is purified by reverse phase chromatography eluting with a gradient of 0% to 100% ACN in water to afford the title compound (70 mg, 37%). ES/MS m/z 161.1 [M+H]$^+$.

Preparation 39

2-Morpholino-5-(trifluoromethyl)pyridine-3-carbaldehyde

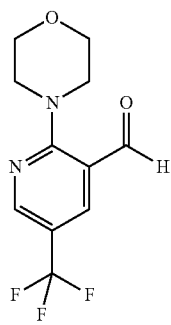 [SMILES: O=Cc1cc(C(F)(F)F)cnc1N1CCOCC1]

2-Chloro-5-(trifluoromethyl)nicotinaldehyde (700 mg, 3.34 mmol) and morpholine (291 mg, 3.34 mmol) are dissolved in EtOH (10 mL) and treated with TEA (338 mg, 3.34 mmol) at RT. The reaction is heated to 80° C. for 6 hr. The reaction is cooled to RT, concentrated in vacuo, and purified by flash silica gel chromatography eluting with a gradient of 0% to 20% MeOH in DCM to afford the title compound as a clear oil (0.7 g, 80%). ES/MS m/z 261.1 [M+H]$^+$.

Preparation 40

5,7-Dichloroimidazo[1,2-a]pyridine

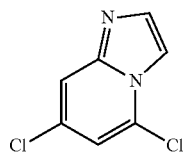 [SMILES: Clc1cc(Cl)n2ccnc2c1]

To a 1 L pressure tank is added 4,6-dichloropyridin-2-amine (100.00 g, 614 mmol), NaHCO$_3$ (154.6 g, 1840 mmol), chloroacetaldehyde (180.5 g, 920 mmol, 40% in water) and n-BuOH (500 mL) at RT under a N$_2$. The resulting mixture is stirred overnight at 80° C. Upon cooling to RT, the mixture is concentrated in vacuo. The residue is purified by silica gel column chromatography, eluting with a gradient of PE:EtOAc (8:1 to 5:1) to give the title compound as a yellow solid (88 g, 76.7%). ES/MS m/z 187.0 [M+H]$^+$.

Preparation 41

5,7-Dichloro-3-methylimidazo[1,2-a]pyridine

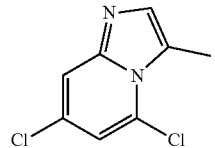

To a solution of 2-bromo-1,1-dimethoxypropane (16.84 g, 92 mmol) in EtOH (50 mL) at RT under N$_2$ is added 12M HCl (33.55 g, 920 mmol). The reaction is stirred overnight at 80° C. Upon cooling to RT, the pH of the mixture is adjusted to approximately pH 8 with NaHCO$_3$ (90.19 g, 1074 mmol). Next, 4,6-dichloropyridin-2-amine (5.0 g, 30.68 mmol) is added to the reaction and the mixture is stirred overnight at 80° C. Upon cooling to RT, the mixture is filtered, and the filter cake is washed with EtOAc (3×100 mL). The filtrate is concentrated in vacuo. The residue is purified by silica gel chromatography, eluting with PE:EtOAc (10:1), to give the title compound as a yellow solid (2.5 g, 40.5%). ES/MS m/z 201.1 [M+H]$^+$.

The following compound is prepared essentially as described for 5,7-dichloro-3-methylimidazo[1,2-a]pyridine using the appropriate reagents and adjusting the reaction temperature and time to determine completion of the reactions.

TABLE 4

| Prep No. | Chemical Name | Structure | ES/MS m/z [M + H]$^+$ |
|---|---|---|---|
| 42 | 7-Bromo-5-chloro-imidazo[1,2-a]pyridine | 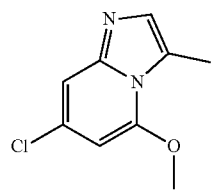 | ($^{79}$Br/$^{81}$Br) 231.0/233.0 |

Preparation 43

7-Chloro-5-methoxy-3-methylimidazo[1,2-a]pyridine

To 5,7-dichloro-3-methylimidazo[1,2-a]pyridine (1.5 g, 7.46 mmol) in MeOH (20 mL) at RT under N$_2$ is added NaOMe (4.03 g, 74.61 mmol). The reaction is stirred at 80° C. for 1 hr then concentrated in vacuo. The residue is diluted with H$_2$O (50 mL) and extracted with EtOAc (3×30 mL). The combined organic layers are washed with brine (2×30 mL), dried over Na$_2$SO$_4$, filtered, and concentrated in vacuo to give the title compound as a yellow solid (1.35 g, 92.0%). ES/MS m/z 197.1 [M+H]$^+$.

Preparation 44

5,7-Dichloro-3-iodo-imidazo[1,2-a]pyridine

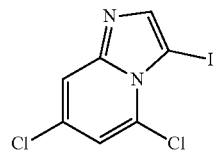 [SMILES: Clc1cc(Cl)n2c(I)cnc2c1]

To 5,7-dichloroimidazo[1,2-a]pyridine (5.00 g, 26.73 mmol) in DCM (50.00 mL) is added NIS (12.03 g, 53.47 mmol) in portions at RT under $N_2$. The reaction is stirred for 2 hr then quenched with $H_2O$ (100 mL). The mixture is extracted with DCM (3×50 mL), organic layers are washed with brine (3×50 mL), and dried over $Na_2SO_4$. After filtration, the filtrate is concentrated in vacuo to afford the title compound as a dark-yellow solid (12.0 g, crude). ES/MS m/z 312.9 [M+H]$^+$.

Preparation 45

6-Bromo-3-iodo-4-methoxy-pyrazolo[1,5-a]pyridine

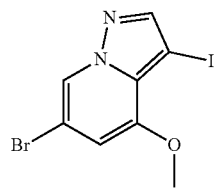

6-Bromo-4-methoxypyrazolo[1,5-a]pyridine (0.41 g, 1.81 mmol) and NIS (609 mg, 2.71 mmol) are dissolved in ACN (8 mL) and stirred at RT for 1 hr. The suspension is filtered, and the filtrate is concentrated in vacuo. The residue is purified by silica gel chromatography eluting with a linear gradient of 0% to 100% EtOAc in heptane. The fractions containing the title compound is concentrated in vacuo and combined with the filtered solid to afford the title compound (0.60 g, 94.1%). ES/MS m/z ($^{79}$Br/$^{81}$Br) 352.6/354.6 [M+H]$^+$.

Preparation 46

6-bromo-3-fluoro-4-methoxy-pyrazolo[1,5-a]pyridine

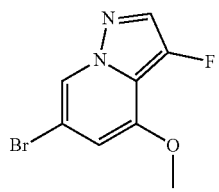

A solution of 6-bromo-4-methoxypyrazolo[1,5-a]pyridine (5 g, 22.02 mmol) and 1-Chloromethyl-4-fluoro-1,4-diazoniabicyclo[2.2.2]octane bis(tetrafluoroborate) (7.04 g, 22.021 mmol) in ACN (50 mL) is stirred overnight at RT under $N_2$. The mixture is diluted with $H_2O$ (50 mL) then extracted with EtOAc (3×100 mL). The combined organic layers are washed with brine (2×100 mL), dried over $Na_2SO_4$, and filtered. The filtrate is concentrated in vacuo. The residue is purified by reverse phase chromatography with the following conditions: Column, C18; mobile phase, 30% to 40% ACN in $H_2O$ (0.1% FA), over a 10 min. period to afford the title compound (810 mg, 15.01%) as a yellow solid. $^1$H NMR (300 MHz, DMSO-d$_6$) δ 8.56 (t, 1H), 8.04 (d, 1H), 6.77 (d, 1H), 3.97 (s, 3H).

Preparation 47

6-Bromo-4-methoxy-3-(trifluoromethyl)pyrazolo[1,5-a]pyridine

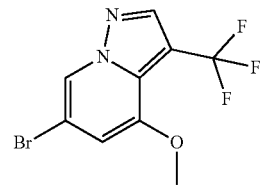 [SMILES: COc1cc(Br)cn2ncc(C(F)(F)F)c12]

A mixture of 6-bromo-3-iodo-4-methoxypyrazolo[1,5-a]pyridine (0.6 g, 1.7 mmol), methyl 2,2-difluoro-2-(fluorosulfonyl)acetate (0.5 g, 2.6 mmol), and CuI (0.4 g, 2.1 mmol) in DMF (6 mL) is heated for 6 hr. to 80° C. The suspension is filtered and the filtrate is concentrated in vacuo. The residue is purified by normal phase chromatography eluting with a linear gradient of 0% to 100% EtOAc in heptane to afford the title compound (0.125 g, 20%) as a white solid. ES/MS m/z 249.9 [M+H]$^+$.

Preparation 48

5,7-Dichloroimidazo[1,2-a]pyridine-3-carbonitrile

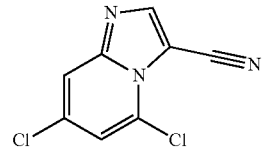 [SMILES: N#Cc1cnc2cc(Cl)cc(Cl)n12]

To of 5,7-dichloro-3-iodoimidazo[1,2-a]pyridine (11.00 g, 35.15 mmol) in DMF (50.00 mL) is added in portions CuCN (6.30 g, 70.31 mmol) at RT under $N_2$. The reaction is stirred for 2 hr at 100° C. Upon cooling to RT, NH$_4$OH (100 mL) is added dropwise over 5 minutes. The mixture is diluted with $H_2O$ (300 mL), stirred for 2 hr, then extracted with DCM (3×400 mL). The combined organic layers are washed with brine (3×300 mL), dried over $Na_2SO_4$, filtered, and concentrated in vacuo. The residue is purified by silica gel column chromatography, eluting with PE:EtOAc (5:1 to 1:2), to afford the title compound as a yellow solid (3.5 g, 47.0%). ES/MS m/z ($^{35}$Cl/$^{37}$Cl) 211.9/213.9 [M+H]$^+$.

Preparation 49

6-Bromo-4-hydroxypyrazolo[1,5-a]pyridine-3-carbonitrile

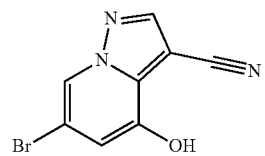 [SMILES: N#Cc1cnn2cc(Br)cc(O)c12]

A stirred solution of 6-bromo-4-methoxypyrazolo[1,5-a]pyridine-3-carbonitrile (5.60 g, 22.22 mmol) and NDM (5.39 g, 26.66 mmol) in DMA (20.0 mL) is treated with NaOH (5.33 g, 66.65 mmol, 50% in $H_2O$) at RT under $N_2$, and the mixture is stirred for 2 hrs at 50° C. under $N_2$. The mixture is diluted with $H_2O$ (200 mL), acidified to pH 4-5 with conc. HCl, and extracted with EtOAc (3×200 mL). The combined organic extracts are washed with brine (3×100 mL) and concentrated under reduced pressure. The residue is purified by silica gel column chromatography, eluting with a gradient of PE:EtOAc (3:1) to give the title compound as a yellow solid (4.6 g, 90.7%) ES/MS m/z 235.9/237.9 [M−H]⁻.

Preparation 50

6-Bromo-4-isopropoxy-pyrazolo[1,5-a]pyridine-3-carbonitrile

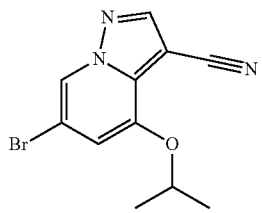 [SMILES: CC(C)Oc1cc(Br)cn2ncc(C#N)c12]

A mixture of 6-bromo-4-hydroxy-pyrazolo[1,5-a]pyridine-3-carbonitrile (200 mg, 0.84 mmol) and Cs$_2$CO$_3$ (410.63 mg, 1.26 mmol) in DMF (2 mL) is treated with 2-iodopropane (0.1 mL, 1 mmol) and stirred for 7.5 hrs. The reaction mixture is purified by silica gel chromatography, eluting with a gradient of hexanes:EtOAc (0-100%) to give the title compound as a light-yellow solid (174.2 mg, 0.62 mmol, 74.02%). ES/MS m/z 282.00 [M+H]⁺.

Preparation 51

2-[3-[tert-Butyl(dimethyl)silyl]oxyazetidin-1-yl]-5-(trifluoromethyl)pyridine-3-carbaldehyde

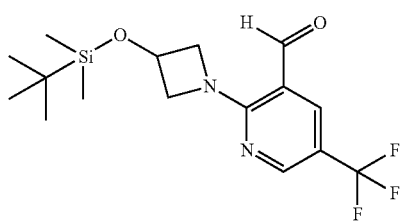 [SMILES: CC(C)(C)[Si](C)(C)OC1CN(c2ncc(C(F)(F)F)cc2C=O)C1]

2-Chloro-5-(trifluoromethyl)nicotinaldehyde (575 mg, 2.74 mmol) and 3-((tert-butyldimethylsilyl)oxy)azetidine (566 mg, 3.02 mmol) are dissolved in EtOH (8 mL) and treated with NEt$_3$ (305 mg, 3.02 mmol) at RT. The reaction is heated for 4 hr at 80° C. Upon cooling to RT, the reaction is concentrated and purified by silica gel chromatography eluting with 0% to 100% EtOAc in heptane to obtain the title compound (0.73 g, 2.03 mmol, 74%) as a clear oil. ¹H NMR (400 MHz, CDCl$_3$) δ 9.90 (s, 1H), 8.51 (s, 1H), 8.09 (s, 1H), 4.75 (m, 1H), 4.50 (m, 2H), 4.08 (m, 2H), 0.91 (s, 9H), 0.09 (s, 6H).

Preparation 52

1-(4-Isoquinolyl)ethanol

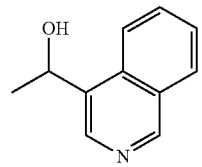

To a solution of isoquinoline-4-carbaldehyde (500 mg, 3.18 mmol) in anhydrous THF (7 mL) at 0° C. is added 3M methylmagnesium bromide (455 mg, 3.82 mmol). The reaction is stirred at 0° C. for 20 minutes, allowed to warm to RT, then stirred for 2 hr at RT. The reaction is quenched with sat. NH$_4$Cl, extracted with EtOAc (3×30 mL), dried over Na$_2$SO$_4$, filtered and concentrated in vacuo. The residue is purified by silica gel chromatography eluting with 0% to 100% in heptane to give the title compound. (540 mg, 98.0%). ¹H NMR (400 MHz, CDCl$_3$) δ 1.73 (d, J=6.48 Hz, 3H), 2.72 (br s, 1H), 5.59 (q, J=6.48 Hz, 1H), 7.63 (ddd, J=8.10, 7.00, 1.04 Hz, 1H), 7.75 (ddd, J=8.47, 6.94, 1.34 Hz, 1H), 7.99 (d, J=8.07 Hz, 1H), 8.18-8.22 (m, 1H), 8.61 (s, 1H), 9.15 (s, 1H).

The following compounds are prepared essentially as described for 1-(4-isoquinolyl)ethanol using the appropriate reagents and adjusting the reaction temperature and times to determine completion of the reactions.

TABLE 5

| Prep No. | Chemical Name | Structure | ES/MS m/z [M + H]⁺ |
|---|---|---|---|
| 53 | 1-(1-Isopropyltriazol-4-yl)ethanol | 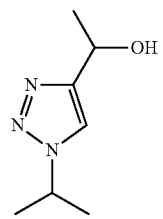 | a |
| 54 | 1-(2-Ethyltriazol-4-yl)ethanol | 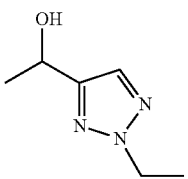 | b |

TABLE 5-continued

| Prep No. | Chemical Name | Structure | ES/MS m/z [M + H]+ |
|---|---|---|---|
| 55 | 1-(3-Ethyltriazol-4-yl)ethanol | 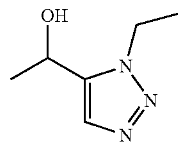 | c |
| 56 | 1-(6-Methylpyrazin-2-yl)ethanol | 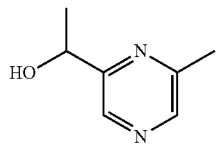 | d |
| 57 | 1-[2-Morpholino-5-(trifluoromethyl)-3-pyridyl]ethanol | 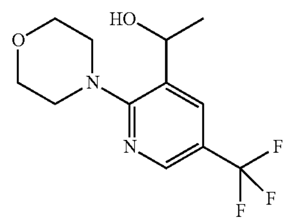 [SMILES: CC(O)c1cc(C(F)(F)F)cnc1N1CCOCC1] | e |
| 58 | 1-(5-Methyl-1,3,4-thiadiazol-2-yl)ethanol | 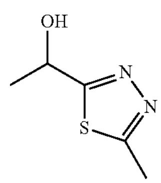 | f |
| 59 | 1-Isothiazol-5-ylethanol | 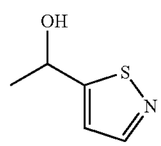 | g |
| 60 | 1-(3-Methylsulfonylphenyl)ethanol | 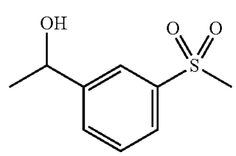 | h |
| 61 | 1-(5-Fluoro-3-pyridyl)ethanol | 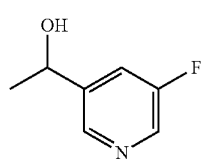 | i |
| 62 | 1-(5-Chloro-3-pyridyl)ethanol | 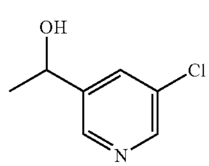 | 158.2 |
| 63 | 1-(1-Methylpyrrolo[2,3-c]pyridin-4-yl)ethanol | 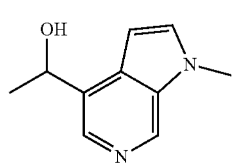 | 177.1 |

TABLE 5-continued

| Prep No. | Chemical Name | Structure | ES/MS m/z [M + H]+ |
|---|---|---|---|
| 64 | 1-[2-Chloro-5-(trifluoromethyl)-3-pyridyl]ethanol | 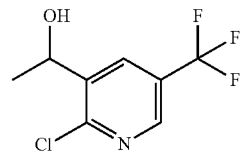 | j |
| 65 | 1-[2-[3-[tert-Butyl(dimethyl)silyl]oxyazetidin-1-yl]-5-(trifluoromethyl)-3-pyridyl]ethanol | | k | a¹H NMR (400 MHz, CDCl₃) δ 1.55-1.67 (m, 9H), 2.80 (br s, 1H), 4.14 (q, J = 6.77 Hz, 1H), 4.84 (dt, J = 12.96, 6.36 Hz, 1H), 5.11 (q, J = 5.91 Hz, 1H), 7.50 (s, 1H).
b¹H NMR (400 MHz, d₆-DMSO) δ 1.35-1.46 (m, 6H), 4.37 (m, 2H), 4.81 (m, 1H), 5.30 (br s, 1H), 7.61 (br s, 1H).
c¹H NMR (300 MHz, d₆-DMSO) δ 7.58 (s, 1H), 5.50 (d, 1H), 4.95-4.85 (m, 1H), 4.50-4.32 (m, 2H), 1.56-1.38 (m, 6H).
d¹H NMR (400 MHz, CDCl₃) δ 8.46 (s, 1H), 8.39 (s, 1H), 4.91-5.02 (m, 1H), 2.59 (s, 3H), 1.56 (br d, J = 6.36 Hz, 3H).
e¹H NMR (400 MHz, CDCl₃) δ 1.57 (br d, J = 6.11 Hz, 3H), 3.24 (br s, 4H), 3.48 (br s, 1H), 3.87 (br s, 4H), 5.08-5.19 (m, 1H), 7.92 (br s, 1H), 8.51 (br s, 1H).
f ¹H NMR (400 MHz, CDCl₃) δ 1.66 (br d, J = 6.11 Hz, 3H), 2.73-2.80 (m, 3H), 2.97-3.27 (m, 1H), 5.21-5.35 (m, 1H).
g¹H NMR (400 MHz, CDCl₃) δ 8.41-8.29 (m, 1H), 7.13-7.03 (m, 1H), 5.34-5.21 (m, 1H), 1.62 (t, 3H).
h¹H NMR (400 MHz, CDCl₃) δ 1.55 (d, J = 6.7 Hz, 3H), 3.08 (s, 3H), 4.96-5.07 (m, 1H), 7.52-7.61 (m, 1H), 7.68 (br t, J = 6.8 Hz, 1H), 7.78-7.91 (m, 1H), 7.96-8.01 (m, 1H).
i¹H NMR (400 MHz, CDCl₃) δ 8.36 (t, 1H), 8.32 (d, 1H), 7.62-7.39 (m, 1H), 4.99 (q, 1H), 2.82 (s, 1H), 1.53 (d, 3H).
j¹H NMR (400 MHz, CDCl₃) δ 8.56 (s, 1H), 8.32 (s, 1H), 5.28 (m, 1H), 1.54 (d, 3H).
k¹H NMR (400 MHz, CDCl₃) δ 8.34 (s, 1H), 7.84 (s, 1H), 4.95 (m, 1H), 4.73 (m, 1H), 4.39 (m, 2H), 4.04 (m, 2H), 1.50 (d, 3H), 0.90 (s, 9H), 0.09 (s, 6H).

Preparation 66

1-(5-Fluoro-3-methyl-2-pyridyl)ethanone

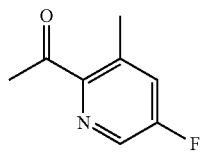

To 2-bromo-5-fluoro-3-methylpyridine (3 g, 15.8 mmol) in toluene (50 mL) is added i-PrMgCl (12 mL, 23.7 mmol, 2 M in THF) dropwise at RT under N₂. After stirring 3 hr at RT, N-methoxy-N-methylacetamide HCl (2.4 g, 23.7 mmol) is added. The reaction is stirred 2 hr then quenched with H₂O (100 mL). The mixture is extracted with EtOAc (3×100 mL). The organic layers are combined, washed with brine (100 mL), dried over Na₂SO₄, filtered, and concentrated in vacuo to give the title compound (2 g, 83%). ES/MS m/z 154.1 [M+H]⁺.

The following compounds are prepared essentially as described for 1-(5-fluoro-3-methyl-2-pyridyl)ethanone using the appropriate reagents and adjusting the reaction temperature and times to determine completion of the reactions.

TABLE 6

| Prep No. | Chemical Name | Structure | ES/MS m/z [M + H]+ |
|---|---|---|---|
| 67 | 2,2-Difluoro-1-(5-fluoro-2-pyridyl)ethanone | 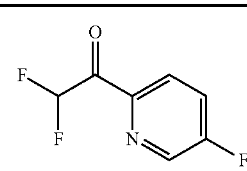 | 174.0 [M − H] |
| 68 | (5-Fluoro-2-pyridyl)-[1-(trifluoromethyl)cyclopropyl]methanone | 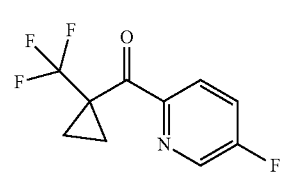 [SMILES: O=C(c1ccc(F)cn1)C1(C(F)(F)F)CC1] | 233.8 |

TABLE 6-continued

| Prep No. | Chemical Name | Structure | ES/MS m/z [M + H]+ |
|---|---|---|---|
| 69[1] | (5-Fluoro-2-pyridyl)-(1-methoxycyclopropyl)methanone | 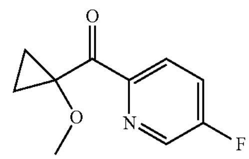 | 196.1 |
| 70[2] | 1-[5-(trifluoromethoxy)-3-pyridyl]ethanone | 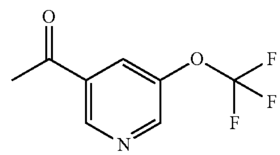 | 205.9 |

[1]Purified by silica gel column chromatography, eluting with PE:EA (12:1 to 10:1).
[2]Purified by silica gel column chromatography, eluting with PE:EA (20:1 to 4:1).

Preparation 71

1-(7-Fluoro-4-isoquinolyl)ethanone

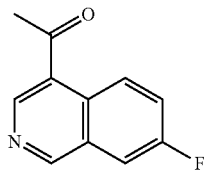

To a solution of 7-fluoro-N-methoxy-N-methylisoquinoline-4-carboxamide (500 mg, 2.13 mmol) in THF (10 mL) at 0° C. is added dropwise a solution of 3M MeMgBr in Et$_2$O (255 mg, 2.13 mmol, 0.71 ml). The reaction is stirred at 0° C. for 20 min, then allowed to warm to RT and stirred for an additional 2 hr. The reaction is quenched with sat. aq. NH$_4$Cl solution. Layers are separated and the aq. layer is extracted with EtOAc. Combined organics are dried over Na$_2$SO$_4$, filtered, and concentrated in vacuo. The residue is purified by silica gel chromatography eluting with a gradient of 0% to 10% MeOH in DCM to give the title compound (389 mg, 96.3%). $^1$H NMR (400 MHz, CDCl$_3$) δ 2.81 (s, 3H), 7.59-7.67 (m, 2H), 8.99 (dd, J=9.11, 5.32 Hz, 1H), 9.05 (s, 1H), 9.33 (s, 1H).

The following compounds are prepared essentially as described for 1-(7-Fluoro-4-isoquinolyl)ethanone using the appropriate reagents and adjusting the reaction temperature and times to determine completion of the reactions.

TABLE 7

| Prep No. | Chemical Name | Structure | ES/MS m/z [M + H]+ |
|---|---|---|---|
| 72[1] | 1-(5-Methylpyridazin-3-yl)ethanone | | a |
| 73 | 1-(5-Chloropyridazin-3-yl)ethenone | 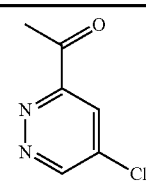 | b |
| 74[1] | 1-(4-Methylisothiazol-5-yl)ethanone | 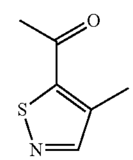 | c |

[1]Purified by flash chromatography eluting with 0% to 100% EtOAc in heptane.
a$^1$H NMR (400 MHz, d$_6$-DMSO) δ 2.42 (s, 3H), 2.77 (s, 3H), 7.96 (br s, 1H), 9.31 (br s, 1H).
b$^1$H NMR (300 MHz, d$_6$-DMSO) δ 9.63 (br s, 1H), 8.26 (br s, 1H), 2.79 (br s, 3H).
c$^1$H NMR (400 MHz, CDCl$_3$) δ 2.54 (br s, 3H), 2.60 (br s, 3H), 8.35 (br s, 1H).

Preparation 75

2-Fluoro-1-(5-fluoro-2-pyridyl)ethanone

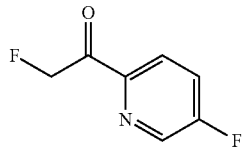 [SMILES: O=C(CF)c1ccc(F)cn1]

A solution of 2-bromo-5-fluoropyridine (1.1 g, 6.3 mmol) in toluene (6 mL) is cooled to −78° C. under N$_2$ then a soln of n-BuLi (0.44 g, 2.8 ml, 6.9 mmol, 2.5M in hexanes) is slowly added. The reaction mixture is then stirred at −78° C. for 30 min. 2-Fluoro-N-methoxy-N-methylacetamide (0.83 g, 6.9 mmol) in toluene (2.0 mL) is added to the reaction. After stirring at −78° C. for 30 min the cooling bath is removed, and the reaction is quenched with sat. aq NH$_4$Cl and extracted with DCM. The organic layer is washed with brine, dried over Na$_2$SO$_4$, filtered, and concentrated in vacuo to obtain the title compound (0.9 g, 90%) as a brown solid. $^1$H NMR (400 MHz, CDCl$_3$) δ 5.77 (d, J=47.6 Hz, 2H) 7.46-7.55 (m, 1H) 8.05-8.12 (m, 1H) 8.39-8.44 (m, 1H)

Preparation 76

1-[5-Fluoro-6-(2-methoxyethoxy)-2-pyridyl]ethanone

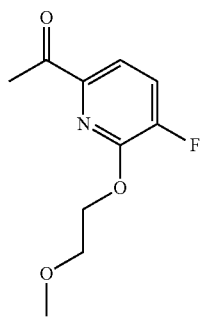

To 6-bromo-3-fluoro-2-(2-methoxyethoxy)pyridine (1.7 g, 6.80 mmol) in THF (50 mL, 617.2 mmol) is added n-BuLi (2.72 mL, 6.80 mmol, 2.5 M in hexane) dropwise at −78° C. under N$_2$. The reaction is stirred for 0.5 hr at −78° C. Next, N-methoxy-N-methylacetamide (2.10 g, 20.39 mmol) is added and stirring continues for an additional 1 hr at −78° C. The reaction is quenched by the addition of H$_2$O (50 mL) at −78° C. Upon warming to RT the reaction is extracted with EtOAc (3×50 mL). Organic layers are combined and washed with brine (3×50 mL), dried over Na$_2$SO$_4$, filtered and the filtrate is concentrated in vacuo. The residue is used in a subsequent step directly without further purification. ES/MS m/z 213.9 [M+H]$^+$.

The following compound is prepared essentially as described for 1-[5-Fluoro-6-(2-methoxyethoxy)-2-pyridyl]ethanone using the appropriate reagents and adjusting the reaction temperature and time to determine completion of the reaction.

Preparation 78

(1E)-2-Bromobenzaldehyde oxime

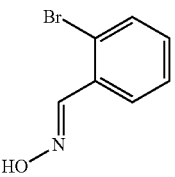

A mixture of 2-bromobenzaldehyde (10 g, 54.05 mmol) and NH$_2$OH·HCl (4.1 g, 59.45 mmol) in EtOH (100 mL) is stirred for 2 hr at 80° C. under N$_2$. The reaction is concentrated in vacuo. The residue is dissolved in EtOAc (100 mL) and washed with H$_2$O (3×50 mL). The combined organic layers are dried over Na$_2$SO$_4$, filtered, and concentrated in vacuo to afford the title compound as an off-white solid (12 g) which is carried forward without a further purification. ES/MS m/z ($^{79}$Br/$^{81}$Br) 200/202 [M+H]$^+$. $^1$H NMR (300 MHz, DMSO-d6) δ 11.69 (s, 1H), 8.32 (s, 1H), 7.80 (dd, 1H), 7.67 (dd, 1H), 7.45-7.38 (m, 1H), 7.34 (td, 1H).

Preparation 79

3-(2-Bromophenyl)isoxazole

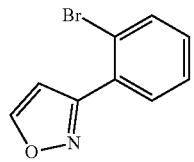 [SMILES: Brc1ccccc1-c1ccon1]

To a stirred solution of (E)-N-[(2-bromophenyl)methylidene]hydroxylamine (5 g, 25.00 mmol) and NCS (4.33 g, 32.49 mmol) in CCl$_4$ (50 mL) is added calcium carbide (11.19 g, 175.00 mmol) and H$_2$O (6.30 g, 349.93 mmol) dropwise at RT under N$_2$. The reaction is stirred overnight. The suspension is filtered, the filter cake is washed with DCM (3×30 mL). The filtrate is concentrated in vacuo. The residue is purified by silica gel column chromatography, eluting with PE:EtOAc (12:1) to afford the title compound as an off-white solid (3.5 g, 62.50%). ES/MS m/z ($^{79}$Br/$^{81}$Br) 224/226 [M+H]$^+$.

TABLE 8

| Prep No. | Chemical Name | Structure | ES/MS m/z [M + H]$^+$ |
|---|---|---|---|
| 77 | [(4R)-2,2-dimethyl-1,3-dioxolan-4-yl]-(5-fluoro-2-pyridyl)methanone | | a | a $^1$H NMR (400 MHz, CdCl$_3$) δ 1.43 (s, 3H) 1.47 (s, 3H) 3.92 (dd, J = 8.56, 6.48 Hz, 1H) 4.50-4.59 (m, 1H) 5.61-5.68 (m, 1H) 7.45-7.54 (m, 1H) 8.08-8.15 (m, 1H) 8.39-8.44 (m, 1H).

Preparation 80

2-(1-Ethoxyvinyl)-6-(trifluoromethyl)pyrazine

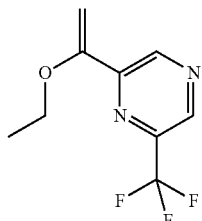

To a stirred solution of 2-chloro-6-(trifluoromethyl)pyrazine (2000 mg, 10.957 mmol) and tributyl(1-ethoxyethenyl)stannane (4748.68 mg, 13.148 mmol) in dioxane (25 mL) is added Pd(PPh$_3$)$_4$ (1266.16 mg, 1.096 mmol) at RT under N$_2$. The resulting mixture is stirred for 4 hr at 80° C. The mixture is allowed to cool down to RT and is concentrated under vacuum. The residue is purified by silica gel column chromatography, eluting with PE:EtOAc (8:1 to 4:1) to afford the title compound as a yellow oil (1.8 g, 75.29%). $^1$H NMR (300 MHz, d$_6$-DMSO) δ 9.18-9.16 (m, 2H), 5.47-5.41 (m, 1H), 4.75-4.69 (m, 1H), 4.03 (q, 2H), 1.40 (t, 3H).

The following compound is prepared essentially as described for 2-(1-Ethoxyvinyl)-6-(trifluoromethyl)pyrazine using the appropriate reagents and adjusting the reaction time to determine completion of the reaction.

TABLE 9

| Prep No. | Chemical Name | Structure | ES/MS m/z [M + H]$^+$ |
|---|---|---|---|
| 81[1] | 3-[2-(1-Ethoxyvinyl)phenyl]isoxazole | 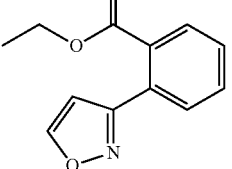 | 216.1 |

[1]Purified by silica gel column chromatography, eluting with PE:EtOAc (20:1 to 5:1).

Preparation 82

1-(2-Isoxazol-3-ylphenyl)ethanone

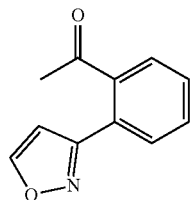

To 3-[2-(1-ethoxyethenyl)phenyl]-1,2-oxazole (2.20 g, 10.22 mmol) in MeOH (20 mL) is added 4M HCl in MeOH (20 mL) at RT. The reaction is stirred for 1 hr under N$_2$. The reaction is quenched with H$_2$O (100 mL). The mixture is extracted with EtOAc (3×100 mL). The combined organic layers are washed with brine (2×100 mL), dried over Na$_2$SO$_4$, filtered and concentrated in vacuo. The residue is purified by silica gel column chromatography, eluting with PE:EtOAc (3:1) to afford the title compound as a yellow oil (1.6 g, 83.6%). ES/MS m/z 188.1 [M+H]$^+$.

Preparation 83

1-[6-(Trifluoromethyl)pyrazin-2-yl]ethanone

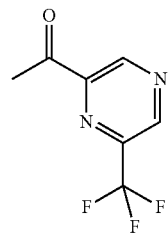

A mixture of 2-(1-ethoxyethenyl)-6-(trifluoromethyl)pyrazine (1.20 g, 5.50 mmol) and 12 M HCl (2.29 mL, 27.50 mmol) in THF (20 mL) is stirred for 2 hr at RT under N$_2$. The resulting mixture is concentrated in vacuo to afford the title compound which is carried forward without a further purification. $^1$H NMR (400 MHz, d$_6$-DMSO) δ 9.45 (s, 1H), 9.41 (s, 1H), 2.67 (s, 3H).

Preparation 84

2-Methoxy-1-[5-(trifluoromethyl)pyridin-3-yl]ethanone

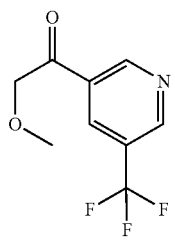

A solution of i-PrMgCl (3.3 mL, 6.61 mmol) is added dropwise under N$_2$ at 0° C. to a solution of 3-bromo-5-(trifluoromethyl)pyridine (1.00 g, 4.42 mmol) in dry THF (40 mL). The solution is stirred for 1 hr under N$_2$ at 50° C. To the above solution is added N-2-dimethoxy-N-methylacetamide (1.18 g, 8.86 mmol) in dry THF (1 mL) under N$_2$ at RT. The solution is stirred for 2 hr under N$_2$ at RT. The residue is acidified to pH 6 with conc. aq HCL. The mixture is diluted with H$_2$O (50 mL), the pH adjusted to 11 with solid Na$_2$CO$_3$, and extracted with EtOAc (3×50 mL). The organic layers are combined, washed with brine (3×50 mL), and dried over anhydrous Na$_2$SO$_4$. The mixture is filtered and the filtrate is concentrated under reduced pressure. The crude product (5.00 g) is used without further purification. $^1$H NMR (300 MHz, CDCl$_3$) δ 9.38-9.30 (d, 1H), 9.14-9.05 (m, 1H), 8.56-8.48 (m, 1H), 4.69 (s, 2H), 3.55-3.53 (in, 3H).

The following compounds are prepared essentially as described for 2-methoxy-1-[5-(trifluoromethyl)pyridin-3-yl]ethanone using the appropriate reagents and adjusting the reaction times to determine completion of the reactions.

TABLE 10

| Prep No. | Chemical Name | Structure | ES/MS m/z [M + H]+ |
|---|---|---|---|
| 85 | 3,3,3-Trifluoro-1-(5-fluoro-2-pyridyl)propan-1-one | 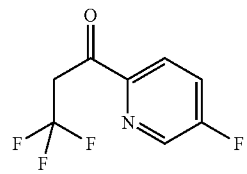 [SMILES: O=C(CC(F)(F)F)c1ccc(F)cn1] | a |
| 86[1] | 2-Pyridyl-[1-(trifluoromethyl)cyclopropyl]methanone | 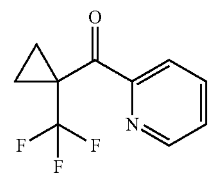 [SMILES: O=C(c1ccccn1)C1(C(F)(F)F)CC1] | 216.1 |
| 87[2] | 1-(5-Fluoro-2-pyridyl)-2-methoxyethanone | 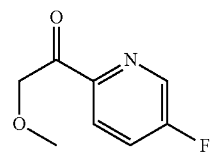 | 170.1 |
| 88 | 1-(5-Fluoro-2-pyridyl)-2-(trifluoromethoxy)ethanone | 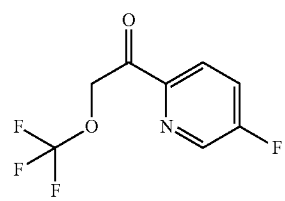 [SMILES: O=C(COC(F)(F)F)c1ccc(F)cn1] | b |

[1] 2.5M BuLi used instead of iPrMgCl. Reaction run in toluene at −78° C.
[2] Purification by silica gel column chromatography, eluting with PE:EtOAc (12:1).
a $^1$H NMR (400 MHz, CDCl$_3$) δ 5.83 (d, J = 47.6 Hz, 2H), 7.54-7.61 (m, 1H), 8.15 (dd, J = 8.68, 4.65 Hz, 1H), 8.47 (s, 1H).
b Material is used without further purification.

Preparation 89

2-Methoxy-1-[5-(trifluoromethyl)pyridin-3-yl]ethanol

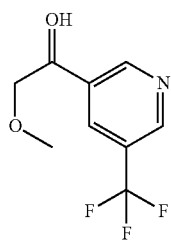

NaBH$_4$ (860 mg, 22.73 mmol) is added in portions at RT under N$_2$ to a stirred mixture of 2-methoxy-1-[5-(trifluoromethyl)pyridin-3-yl]ethanone (5.00 g) in MeOH (20 mL). The reaction is quenched with H$_2$O (5 mL) at RT and concentrated under reduced pressure. The residue is purified by silica gel column chromatography, eluting with PE:EtOAc (10:1 to 2:1) to give the title compound (500 mg, 9.91%) as a yellow liquid. ES/MS m/z 222.0 [M+H]+.

The following compounds are prepared essentially as described for 2-methoxy-1-[5-(trifluoromethyl)pyridin-3-yl]ethanol using the appropriate reagents and adjusting the reaction times to determine completion of the reactions.

TABLE 11

| Prep No. | Chemical Name | Structure | ES/MS m/z [M + H]+ |
|---|---|---|---|
| 90[1] | 1-(5-Methylpyridazin-3-yl)ethanol | 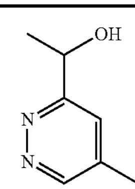 | a |

TABLE 11-continued

| Prep No. | Chemical Name | Structure | ES/MS m/z [M + H]+ |
|---|---|---|---|
| 91[1] | 2-Fluoro-1-(5-fluoro-2-pyridyl)ethanol | 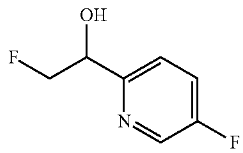 [SMILES: OC(CF)c1ccc(F)cn1] | b |
| 92[1] | 1-(7-Fluoro-4-isoquinolyl)ethanol | 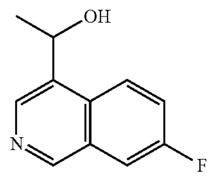 | c |
| 93 | 1-[6-(Trifluoromethyl)pyrazin-2-yl]ethanol | 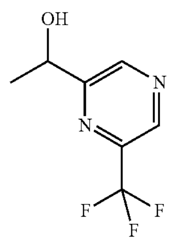 | d |
| 94 | 1-(2-Pyridyl)propan-1-ol | 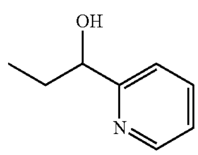 | 138.1 |
| 95 | 1-(5-Chloropyridazin-3-yl)ethanol | 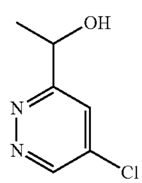 | e |
| 96 | 1-(5-Methyl-3-pyridyl)ethanol | 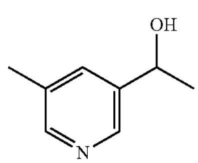 | f |
| 97 | 1-[5-(Difluoromethyl)-3-pyridyl]ethanol | 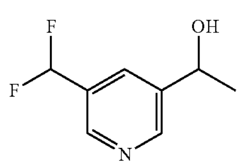 | g |
| 98 | 3,3,3-Trifluoro-1-(5-fluoro-2-pyridyl)propan-1-ol | 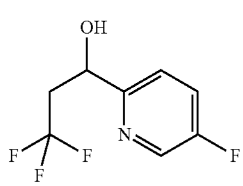 [SMILES: OC(CC(F)(F)F)c1ccc(F)cn1] | 210.1 |

TABLE 11-continued

| Prep No. | Chemical Name | Structure | ES/MS m/z [M + H]+ |
|---|---|---|---|
| 99 | (5-Fluoro-2-pyridyl)-(1-methoxycyclopropyl)methanol | 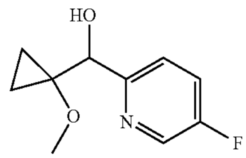 | 198.1 |
| 100[2] | 2-Pyridyl-[1-(trifluoromethyl)cyclopropyl]methanol | 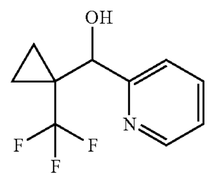 [SMILES: OC(c1ccccn1)C1(C(F)(F)F)CC1] | 218.0 |
| 101 | 1-(2-Methylsulfonylphenyl)ethanol | 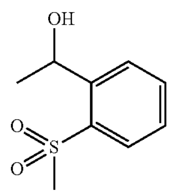 | 183.1 [M − OH]+ |
| 102 | 1-(5-Fluoro-3-methyl-2-pyridyl)ethanol | 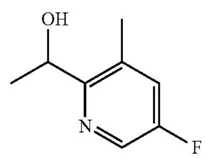 | 156.1 |
| 103[3] | 2,2-Difluoro-1-(5-fluoro-2-pyridyl)ethanol | 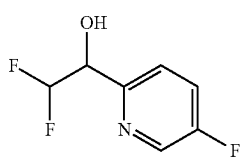 [SMILES: OC(c1ccc(F)cn1)C(F)F] | 178.3 |
| 104[4] | 1-(2-Isoxazol-3-ylphenyl)ethanol | 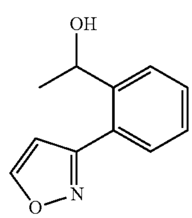 | 188.0 [M − H]− |
| 105 | 1-(5-Fluoro-2-pyridyl)-2-methoxy-ethanol | 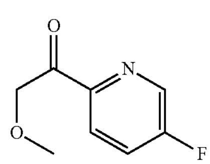 | 172.1 |
| 106 | 1-(2-Isothiazol-3-ylphenyl)ethanol | 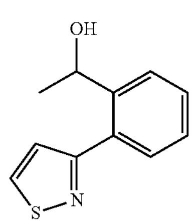 | h |

TABLE 11-continued

| Prep No. | Chemical Name | Structure | ES/MS m/z [M + H]+ |
|---|---|---|---|
| 107[1] | 1-(4-Methylisothiazol-5-yl)ethanol | 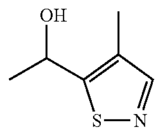 | i |
| 108 | 1-(5-Fluoro-2-pyridyl)-2-(trifluoromethoxy)ethanol | 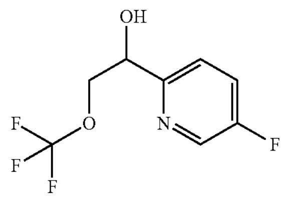 [SMILES: OC(COC(F)(F)F)c1ccc(F)cn1] | 226.1 |
| 109 | 1-[5-Fluoro-6-(2-methoxyethoxy)-2-pyridyl]ethanol | 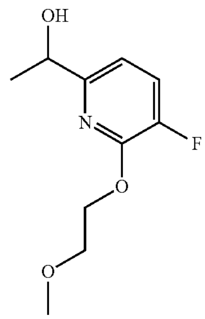 | 216.1 |
| 110 | 1-[5-(trifluoromethoxy)-3-pyridyl]ethanol | 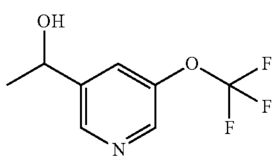 | 208.0 |
| 111 | [(4R)-2,2-dimethyl-1,3-dioxolan-4-yl]-(5-fluoro-2-pyridyl)methanol | 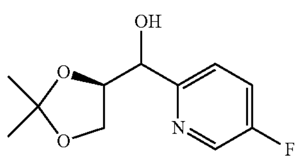 [SMILES: CC1(C)OC[C@H](C(O)c2ccc(F)cn2)O1] | j |
| 112 | (5-Fluoro-2-pyridyl)-[1-(trifluoromethyl)cyclopropyl]methanol | 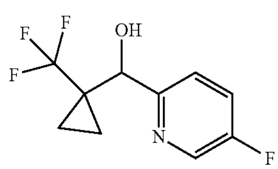 [SMILES: OC(c1ccc(F)cn1)C1(C(F)(F)F)CC1] | 236.0 |

[1] Purified by silica gel column chromatography, eluting with 0% to 100% EtOAc in heptane.
[2] Purified by silica gel column chromatography, eluting with PE:EtOAc (6:1 to 2:1).
[3] Purified by silica gel column chromatography, eluting with PE:EtOAc (9:1).
[4] Purified by silica gel column chromatography, eluting with PE:EtOAc (1:1).
[5] Purified by silica gel column chromatography, eluting with a gradient of 0% to 100% EtOAc in heptane.
a $^1$H NMR (400 MHz, d$_6$-DMSO) δ 1.41 (d, J = 6.60 Hz, 3H), 2.33 (s, 3H), 4.93 (qd, J = 6.56, 4.65 Hz, 1H), 5.59 (d, J = 4.65 Hz, 1H), 7.58 (d, J = 0.98 Hz, 1H), 8.97 (d, J = 2.08 Hz, 1H).
b $^1$H NMR (400 MHz, CdCl$_3$) δ ppm 4.61 (dd, J = 47.2, 5.3 Hz, 2H) 5.02 (dt, J = 16.1, 5.3 Hz, 1H) 7.46-7.53 (m, 2H) 8.46 (s, 1H).
c $^1$H NMR (400 MHz, CDCl$_3$) δ 1.73 (d, J = 6.48 Hz, 3H), 2.42 (br s, 1H), 5.56 (q, J = 6.56 Hz, 1H), 7.50-7.57 (m, 1H), 7.61 (br d, J = 8.68 Hz, 1H), 8.29 (dd, J = 9.23, 5.20 Hz, 1H), 8.59 (s, 1H), 9.13 (s, 1H).
d $^1$H NMR (400 MHz, d$_6$-DMSO) δ 9.11 (s, 1H), 9.07 (s, 1H), 5.82 (d, 1H), 4.95-4.88 (m, 1H), 1.44 (d, 3H).
e Material is used without further purification.
f $^1$H NMR (400 MHz, CDCl$_3$) δ 1.51 (br d, J = 6.11 Hz, 3H), 2.34 (s, 3H), 2.75-2.90 (m, 1H), 4.87-4.97 (m, 1H), 7.55 (br s, 1H), 8.31 (br s, 1H), 8.36 (br s, 1H).
g $^1$H NMR (400 MHz, CDCl$_3$) δ 1.56 (br d, J = 6.24 Hz, 3H), 2.54 (br s, 1H), 5.04 (q, J = 5.79 Hz, 1H), 6.72 (t, J = 55.8 Hz, 1H,) 7.91 (br s, 1H), 8.65 (br s, 1H), 8.72 (br s, 1H).
h $^1$H NMR (400 MHz, CDCl$_3$) δ 1.55 (d, J = 6.6 Hz, 3H) 4.95 (q, J = 6.6 Hz, 1H) 7.37-7.46 (m, 1H) 7.46-7.52 (m, 2H) 7.53-7.59 (m, 1H) 7.66 (br d, J = 7.58 Hz, 1H) 8.79 (d, J = 4.65 Hz, 1H).
i $^1$H NMR (400 MHz, CdCl$_3$) δ 2.54-2.58 (m, 3H), 2.61-2.64 (m, 3H), 3.39 (m, 1H), 3.80 (m, 1H), 8.37 (br s, 1H).
j $^1$H NMR (400 MHz, CdCl$_3$) δ 1.35 (s, 3H) 1.44 (s, 3H) 3.92-3.98 (m, 1H) 4.00-4.07 (m, 1H) 4.40-4.47 (m, 1H) 4.76-4.80 (m, 1H) 7.42-7.55 (m, 2H) 8.41-8.46 (m, 1H)

Preparation 113

Cis-3-Benzyloxycyclobutanol

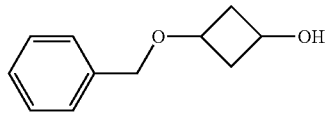

A mixture of 3-(benzyloxy)cyclobutan-1-one (20 g, 113.5 mmol) and NaBH$_4$ (4.29 g, 113.5 mmol) in MeOH (50 mL) is stirred for 2 hr at RT under N$_2$. The reaction is quenched with H$_2$O at 0° C., extracted with EtOAc (3×100 mL), washed with brine (2×100 mL), dried over Na$_2$SO$_4$, and filtered. The filtrate is concentrated under reduced pressure to afford the title compound (20 g, 98.9%) as a light-yellow oil. $^1$H NMR (400 MHz, DMSO-d6) δ 7.42-7.21 (m, 5H), 4.45 (s, 2H), 3.93-3.85 (m, 1H), 3.71-3.62 (m, 1H), 2.82-2.63 (m, 2H), 1.97-1.92 (m, 2H).

Preparation 114

3-(5-Fluoro-2-pyridyl)-3-hydroxy-2,2-dimethyl-propanenitrile

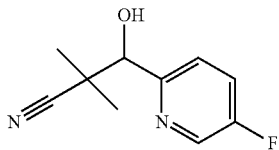

Lithiumdiisopropylamide in THF (2.57 g, 24.0 mmol, 2M in THF) is slowly added to a cooled solution of isobutyronitrile (1.66 g, 24.0 mmol) in THF (25 mL) at −78° C. under N$_2$. The reaction is stirred at −78° C. for 30 minutes. Next, 5-fluoro picolinaldehyde (2.00 g, 16.0 mmol) in THF (6 mL) is slowly added to the reaction. After stirring for an additional hour, the reaction is allowed to warm to RT. The reaction is quenched with sat. NH$_4$Cl, extracted in EtOAc, dried over Na$_2$SO$_4$, filtered and concentrated in vacuo. The residue is purified by phase silica gel flash chromatography eluting with a gradient of 0% to 100% EtOAc in Heptane to afford the title compound (1.60 g, 51.5%) as a white solid. $^1$H NMR (400 MHz, CdCl$_3$) δ 8.46 (s, 1H), 7.55-7.47 (m, 2H), 4.68 (s, 1H), 4.54 (brs, 1H), 1.44 (s, 3H), 1.21 (s, 3H).

Preparation 115

2,2,2-Trifluoro-1-(5-fluoropyridin-2-yl)ethanol

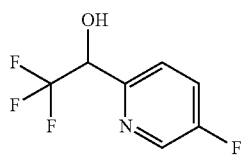 [SMILES: OC(c1ccc(F)cn1)C(F)(F)F]

To 5-fluoropyridine-2-carbaldehyde (2 g, 15.99 mmol) and TMSCF$_3$ (3.41 g, 23.98 mmol) in THF (5.00 mL) is added TBAF (3.20 mL, 3.200 mmol) dropwise at 0° C. under N$_2$. The resulting mixture is stirred at RT for 3 hr then concentrated in vacuo. The residue is purified by silica gel column chromatography, eluting with 50% EtOAc in PE to afford the title compound as a white solid (2 g, 64.12%). ES/MS m/z 196.1 [M+H]$^+$.

Preparation 116

2-[tert-Butyl(dimethyl)silyl]oxy-1-(4-isoquinolyl)ethanol

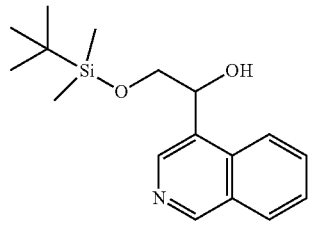 [SMILES: CC(C)(C)[Si](C)(C)OCC(O)c1cncc2ccccc12]

To 4-bromoisoquinoline (2.00 g, 9.61 mmol) dissolved in THF (8 mL) under N$_2$ is added dropwise 2M isopropylmagnesium chloride (1.48 g, 14.42 mmol) at RT. The reaction is stirred 30 minutes at RT, then 2-((tert-butyldimethylsilyl)oxy)acetaldehyde (3.35 g, 19.23 mmol) is added dropwise. The reaction is stirred at RT for 2 hr, then is quenched with aq. sat. NH$_4$Cl. The mixture is extracted with EtOAc (2×100 mL). The combined organic layers are dried over Na$_2$SO$_4$, filtered, and concentrated in vacuo. The residue is purified by silica gel chromatography eluting with 0% to 100% EtOAc in heptane. The isolated material is further purified by silica gel chromatography eluting with 20% DCM in EtOAc to afford the title compound which is contaminated with the isoquinoline biproduct (400 mg, 13.7%). $^1$H NMR (400 MHz, CDCl3) δ 0.07 (s, 6H), 0.93 (s, 9H), 3.72-3.91 (m, 1H), 3.99 (dd, J=10.27, 3.42 Hz, 1H), 5.47 (dd, J=8.38, 3.36 Hz, 1H), 7.58-7.78 (m, 7H), 7.84 (d, J=8.31 Hz, 2H), 7.96-8.04 (m, 2H), 8.12 (d, J=8.44 Hz, 1H), 8.54 (d, J=5.62 Hz, 1H), 8.70 (s, 1H), 9.22 (s, 1H), 9.27 (s, 1H).

Preparation 117

2-[(tert-Butyldimethylsilyl) oxy]-1-(5-fluoropyridin-2-yl) ethanol

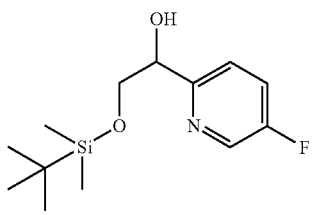 [SMILES: CC(C)(C)[Si](C)(C)OCC(O)c1ccc(F)cn1]

A solution of i-PrMgCl (5.11 mL, 10.23 mmol, 2 M in THF) is added dropwise at 0° C. under N$_2$ to a stirred solution of 2-bromo-5-fluoropyridine (1.2 g, 6.82 mmol) in toluene (10.00 mL). The mixture is stirred for 30 min at 0° C. under N$_2$. 2-[(tert-Butyldimethylsilyl)oxy] acetaldehyde (1.78 g, 10.23 mmol) is added dropwise over 10 min at 0° C. to the mixture. The mixture is stirred 2 hr at 0° C. The reaction is quenched with H₂O and extracted with EtOAc (3×20 mL). The combined organic layers are washed with brine (2×10 mL), dried over anhydrous Na₂SO₄, filtered, and the filtrate is concentrated under reduced pressure. The residue is purified by silica gel column chromatography, eluting with PE:EtOAc (10:1 to 5:1) to give the title compound (420 mg, 22.69%) as a colorless oil. ES/MS m/z 272.2 [M+H]⁺

The following compounds are prepared essentially as described for 2-[(tert-Butyldimethylsilyl) oxy]-1-(5-fluoro-pyridin-2-yl) ethanol using the appropriate reagents and adjusting the reaction times to determine completion of the reactions.

TABLE 12

| Prep No. | Chemical Name | Structure | ES/MS m/z [M + H]⁺ |
|---|---|---|---|
| 118 | 2-[tert-Butyl(dimethyl)silyl]oxy-1-[5-(trifluoromethyl)-3-pyridyl]ethanol | 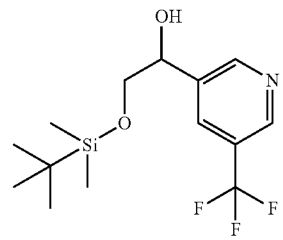 [SMILES: CC(C)(C)[Si](C)(C)OCC(O)c1cncc(C(F)(F)F)c1] | 322.1 |
| 119¹ | 2-[tert-Butyl(dimethyl)silyl]oxy-1-(3,5-difluoro-2-pyridyl)ethanol | | 290.1 |
| 120 | 3-[tert-Butyl(dimethyl)silyl]oxy-1-(5-fluoro-2-pyridyl)propan-1-ol | 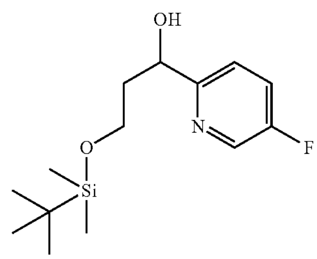 [SMILES: CC(C)(C)[Si](C)(C)OCCC(O)c1ccc(F)cn1] | 286.2 |
| 121² | 2-[tert-Butyl(dimethyl)silyl]oxy-1-(5-chloro-2-pyridyl)ethanol | | 288.1 |
| 122 | Cyclopropyl-(5-fluoro-2-pyridyl)methanol | 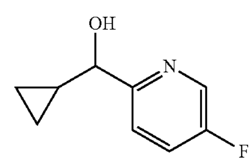 [SMILES: OC(c1ccc(F)cn1)C1CC1] | 150.0 [M − OH]⁺ |
| 123 | (1-Fluorocyclopropyl)-(5-fluoro-2-pyridyl)methanol | 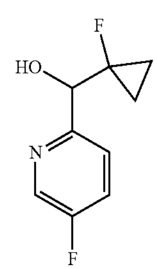 [SMILES: OC(c1ccc(F)cn1)C1(F)CC1] | a |

TABLE 12-continued

| Prep No. | Chemical Name | Structure | ES/MS m/z [M + H]⁺ |
|---|---|---|---|
| 124³ | 2-[tert-Butyl(dimethyl)silyl]oxy-1-(2-pyridyl)ethanol | | 254.0 |

¹Purified by silica gel column chromatography, eluting with PE:EtOAc (20:01 to 10:1).
²Purified by silica gel column chromatography, eluting with PE:EtOAc (5:1-3:1).
³Quenched with saturated NH₄Cl.
a¹H NMR (400 MHz, DMSO-d6) δ 0.78-1.04 (m, 4H), 4.56-4.64 (m, 1H), 6.00 (d, J = 5.01 Hz, 1H), 7.52-7.78 (m, 2H), 8.52 (d, J = 2.69 Hz, 1H.)

Preparation 125

2-[(tert-Butyldimethylsilyl) oxy]-1-(5-fluoropyridin-2-yl) ethanol, Isomer 1 and 2-[(tert-Butyldimethylsilyl) oxy]-1-(5-fluoropyridin-2-yl) ethanol, Isomer 2

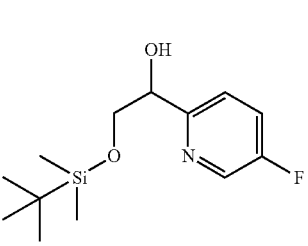 [SMILES: CC(C)(C)[Si](C)(C)OCC(O)c1ccc(F)cn1]

Separation of the 2-[(tert-Butyldimethylsilyl)oxy]-1-(5-fluoropyridin-2-yl)ethanol (70 g, 257.915 mmol) enantiomers is performed using the following conditions: Column: CHIRALPAK IG, 7*25 cm, 10 m; eluting with 60% ACN in H₂O (0.05% diethylamine); Flow rate: 200 mL/min; 266/204/208 nm; to afford 2-[(tert-Butyldimethylsilyl)oxy]-1-(5-fluoropyridin-2-yl)ethanol, Isomer 1, t₍R₎ is 7.5 min (20.0 g) and 2-[(tert-Butyldimethylsilyl)oxy]-1-(5-fluoropyridin-2-yl)ethanol, Isomer 2, t₍R₎ is 11.2 min (20.5 g).

2-[(tert-Butyldimethylsilyl)oxy]-1-(5-fluoropyridin-2-yl) ethanol, Isomer 1 is further purified by silica gel column chromatography, eluting with PE/EA (20:1 to 4:1) to afford 2-[(tert-Butyldimethylsilyl)oxy]-1-(5-fluoropyridin-2-yl) ethanol, Isomer 1 (15.0 g, 21% yield) with 98.6% ee, ES/MS m/z 272.1 [M+H]⁺.

2-[(tert-Butyldimethylsilyl)oxy]-1-(5-fluoropyridin-2-yl) ethanol, Isomer 2 is further purified by silica gel column chromatography, eluting with PE/EA (30:1 to 20:1) to afford 2-[(tert-Butyldimethylsilyl)oxy]-1-(5-fluoropyridin-2-yl) ethanol, Isomer 2 (14.0 g, 20% yield) with 93.1% ee, ES/MS m/z 272.1 [M+H]⁺.

Preparation 126

2-[tert-Butyl(dimethyl)silyl]oxy-1-(5-fluoro-2-pyridyl)ethyl] 4-methylbenzenesulfonate, Isomer 2

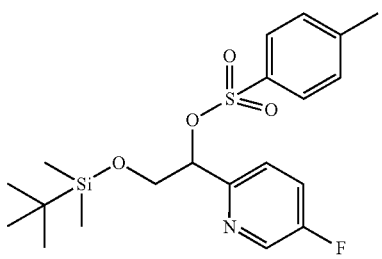 [SMILES: Cc1ccc(S(=O)(=O)OC(CO[Si](C)(C)C(C)(C)C)c2ccc(F)cn2)cc1]

To a solution of 2-[(tert-butyldimethylsilyl) oxy]-1-(5-fluoropyridin-2-yl) ethanol, Isomer 2 (30.4 g, 112 mmol), DMAP (1.37 g, 11.2 mmol), and Et₃N (22.7 g, 224 mmol) in DCM (0.2 L) cooled to 0° C. is added TsCl (27.8 g, 146 mmol). The reaction is stirred at 0° C. for 3 hours then stored overnight at 0° C. The resultant suspension is filtered and the insoluble material is rinsed with MTBE. H₂O (5 ml) is added to the filtrate. The filtrate is then concentrated in vacuo and the material is purified by silica gel chromatography eluting with 0% to 100% EA in heptane to afford the title compound (39.8 g, 93.5 mmol) as a white, waxy solid. ES/MS m/z 426.0 [M+H]⁺.

Preparation 127

2,2,2-Trifluoro-1-(oxan-4-yl)ethanol

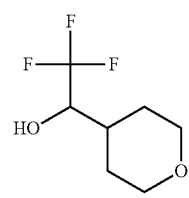

TMSCF₃ (3.74 g, 26.28 mmol) and TBAF (3.50 mL, 3.50 mmol, 1 mol/L) is added dropwise at 0° C. under N₂ to a stirred solution of oxane-4-carbaldehyde (2.00 g, 17.52 mmol) in THF (20.00 mL) and the mixture is stirred for 4 hrs at RT under $N_2$. The reaction is quenched by the addition of MeOH (5 mL), and the mixture is dried under reduced pressure. The residue is purified by silica gel column chromatography, eluting with a gradient of PE:EtOAc (4:1) to give the title compound as a yellow solid (3.1 g, 96.07%). $^1$H NMR (300 MHz, $d_6$-DMSO) δ 6.16 (d, 1H), 3.93-3.81 (m, 2H), 3.81-3.68 (m, 1H), 3.39-3.20 (m, 2H), 1.92-1.72 (m, 1H), 1.60 (d, 1H), 1.56-1.35 (m, 3H).

Preparation 128

2,2-Dimethyl-1-(pyridin-2-yl)propan-1-ol, Isomer 1 and 2,2-Dimethyl-1-(pyridin-2-yl)propan-1-ol, Isomer 2

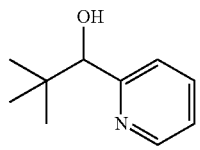

To a stirred solution of 2-iodopyridine (10.0 g, 48.78 mmol) in THF (150.0 mL) is added a soln of n-BuLi (21.4 mL, 53.65 mmol, 2.5M) in hexanes dropwise at −75° C. under $N_2$. The resulting mixture is stirred at −75° C. for 1 hr. To the above mixture is added pivaldehyde (5.0 g, 58.51 mmol) dropwise over a 10-minute period. After being stirred at −75° C. for 1 hr, the reaction is allowed to warm to RT then is quenched with $H_2O$ (100.0 mL). The mixture is extracted with EtOAc (3×200 mL). The combined organic layers are dried over $Na_2SO_4$, filtered, and concentrated in vacuo. The residue is purified by silica gel column chromatography, eluting with PE:EtOAc (20:1 to 15:1) to afford the title compound as a white solid (2.6 g, 32%). ES/MS m/z 166.3 [M+H]$^+$.

Separation of the 2,2-Dimethyl-1-(pyridin-2-yl)propan-1-ol (1.1 g, 6.7 mmol) enantiomers is performed using the following conditions: Column: CHIRALCEL AY-H, 2*25 cm, Sum; eluting with 5% EtOH in Hex (10 mM $NH_3$ in MeOH); 260/216 nm; to afford 2,2-dimethyl-1-(pyridin-2-yl)propan-1-ol, Isomer 1 as a light-yellow solid (400 mg, 36%). $t_{(R)}$=5.3 min. and 2,2-dimethyl-1-(pyridin-2-yl)propan-1-ol, Isomer 2 as a white solid (440 mg, 40%). $t_{(R)}$=6.2 min. Analytical column used for Rt: CHIRALCEL AY-3, 4.6*50 cm; eluting with 5% EtOH in hexanes; 254 nm.

Preparation 129

1-(2-Pyridyl)propyl acetate, Isomer 2

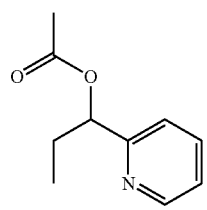

To a stirred solution of 1-(pyridin-2-yl)propan-1-ol (2.00 g, 14.58 mmol) and $Ac_2O$ (2.98 g, 29.16 mmol) in DCM (10.00 mL) is added TEA (4.43 g, 43.74 mmol) at RT under a $N_2$. The reaction is stirred overnight, quenched with $H_2O$ (20 mL), and extracted with DCM (2×20 mL). The combined organic layers are washed with brine (2×10 mL), dried over $Na_2SO_4$, filtered, and concentrated in vacuo. The residue is purified by reverse phase chromatography with the following conditions: Column, C18; eluting with a gradient of 40% to 50% ACN in water; UV 254 nm to afford a brown oil (2.50 g, 95.7%). ES/MS m/z 180.3.

The brown oil (1.00 g, 5.58 mmol) is subjected to the following conditions: Column: CHIRALPAK IG, 20*250 mm, 5 μm; eluting with 15% EtOH in $CO_2$; 203 nm; to afford and 1-(pyridin-2-yl)propyl acetate, Isomer 2 (400 mg), $t_{(R)}$ is 3.86 min with ee=100%; ES/MS m/z 180.3 [M+H]$^+$.

The following compound is prepared essentially as described for 1-(2-pyridyl)propyl acetate, Isomer 1 using the appropriate reagents and adjusting the reaction time to determine completion of the reaction.

TABLE 13

| Prep No. | Chemical Name | Structure | ES/MS m/z [M + H]$^+$ | $t_{(R)}$ min |
|---|---|---|---|---|
| 130[1] | [2-Methoxy-1-(2-pyridyl)ethyl] acetate, Isomer 1 | 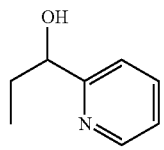 | 196.2 | 3.27 |

[1]Column: CHIRALPAK IG, 2 * 25 cm, 5 μm; eluting with 15% EtOH in $CO_2$, 254 nm.

Preparation 131

1-(2-Pyridyl)propan-1-ol, Isomer 2

To 1-(pyridin-2-yl)propyl acetate, Isomer 2 (380 mg, 2.12 mmol) in MeOH (3.00 mL) and $H_2O$ (3.00 mL) is added LiOH (101.55 mg, 4.24 mmol) in portions at RT under $N_2$. The reaction is stirred for 1 hr. The reaction is diluted with $H_2O$ (20 mL), then extracted with EtOAc (2×20 mL). The combined organic layers are washed with brine (2×10 mL), dried over $Na_2SO_4$, filtered and concentrated in vacuo to afford the title compound as a light-yellow oil (260 mg, 90%). ES/MS m/z 138.1 [M+H]$^+$.

The following compound is prepared essentially as described for 1-(2-pyridyl)propan-1-ol, Isomer 2 using the appropriate reagents and adjusting the reaction time to determine completion of the reaction.

TABLE 14

| Prep No. | Chemical Name | Structure | ES/MS m/z [M + H]+ |
|---|---|---|---|
| 132 | 2-Methoxy-1-(2-pyridyl)ethanol, Isomer 1 | 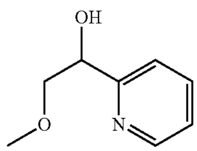 | 154.1 |

Preparation 133

1-[2-(2-Methoxyethylamino)-5-(trifluoromethyl)-3-pyridyl]ethanol

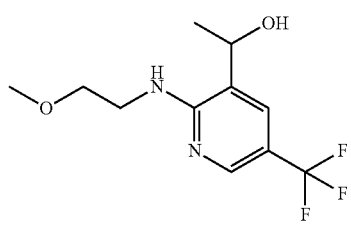 [SMILES: COCCNc1ncc(C(F)(F)F)cc1C(C)O]

A solution of 1-(2-chloro-5-(trifluoromethyl)pyridin-3-yl)ethan-1-ol (0.200 g, 0.89 mmol), 2-methoxyethan-1-amine (200 mg, 2.66 mmol), and DIPEA (573 mg, 4.43 mmol) in i-PrOH (4 mL) is stirred for 18 hr at 100° C. Upon cooling to RT, the reaction is concentrated in vacuo. The residue is purified by silica gel chromatography eluting with a linear gradient of 0% to 30% MeOH in DCM to afford the title compound (30 mg, 13%) as a brown oil. ES/MS m/z 265.1 [M+H]+.

Preparation 134

(1S)-1-[4-(2,2,2-Trifluoroethyl)-1,2,4-triazol-3-yl]ethanol

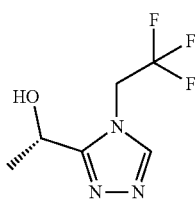

A mixture of (2S)—N'-[(1E)-(dimethylamino)methylidene]-2-hydroxypropane hydrazide (3.0 g, 18.8 mmol), ACN (10.0 mL) and HOAc (2.26 g, 37.7 mmol) is heated at 90° C. under N₂. Upon cooling to RT, the reaction is concentrated in vacuo. The residue is taken on to the next step without further purification. ES/MS m/z 196.1 [M+H]+.

Preparation 135

(1S)-1-(5-Fluoropyridin-2-yl)ethyl methanesulfonate

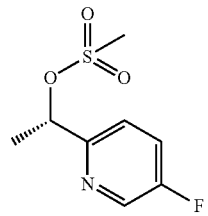

To a stirred solution of (1S)-1-(5-fluoropyridin-2-yl)ethanol (500.0 mg, 3.54 mmol) and TEA (1.07 g, 10.63 mmol) in DCM (10.0 mL) is added dropwise MsCl (608.69 mg, 5.313 mmol) at RT under N₂. The reaction is stirred for 1 hr at RT, diluted with water (20 mL) and extracted with EtOAc (2×20 mL). The combined organic layers are washed with brine (2×20 mL), dried over Na₂SO₄, filtered, and concentrated in vacuo to afford the title compound as a light-yellow oil (740 mg, 95.2%). ES/MS m/z 220.0 [M+H]+.

Preparation 136

[2,2,2-Trifluoro-1-(5-fluoro-2-pyridyl)ethyl] trifluoromethanesulfonate

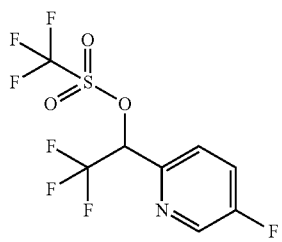 [SMILES: O=S(=O)(OC(c1ccc(F)cn1)C(F)(F)F)C(F)(F)F]

To 2,2,2-trifluoro-1-(5-fluoropyridin-2-yl)ethanol (700.00 mg, 3.59 mmol) and TEA (1.09 g, 10.76 mmol) in DCM (5.00 mL) is added Tf₂O (2.02 g, 7.17 mmol) dropwise at 0° C. under N₂. The resulting mixture is stirred for 3 hr at RT, diluted with water (5 mL) and separated. The aq. layer is extracted with EtOAc (3×5 mL). The combined organic layers are concentrated in vacuo to give the title compound as a crude product (1 g) which is carried forward without a further purification. ES/MS m/z 328.0 [M+H]+.

Preparation 137

2,2,2-Trifluoro-1-(oxan-4-yl)ethyl trifluoromethanesulfonate

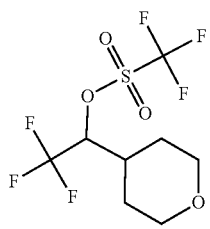 [SMILES: O=S(=O)(OC(C1CCOCC1)C(F)(F)F)C(F)(F)F]

Tf$_2$O (766.02 mg, 2.715 mmol) is added dropwise to stirred solution of 2,2,2-trifluoro-1-(oxan-4-yl)ethanol (500.00 mg, 2.72 mmol) and DIEA (1052.71 mg, 8.14 mmol) in DCM (10.00 mL) at 0° C. under N$_2$. The mixture is stirred for 1 hr at RT under N$_2$ and then used directly without further purification.

The following compounds are prepared essentially as described for 2,2,2-trifluoro-1-(oxan-4-yl)ethyl trifluoromethanesulfonate using the appropriate reagents and adjusting the reaction times to determine completion of the reactions. Temperature is varied from −70° C. to 0° C.

TABLE 15

| Prep No. | Chemical Name | Structure |
|---|---|---|
| 138 | tert-Butyl (3S)-3-(trifluoromethanesulfonyloxy)pyrrolidine-1-carboxylate | 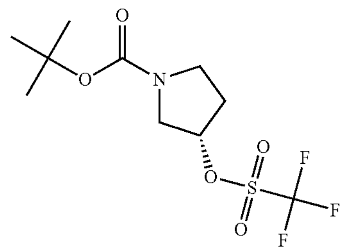 [SMILES: CC(C)(C)OC(=O)N1CC[C@H](OS(=O)(=O)C(F)(F)F)C1] |
| 139 | tert-Butyl (2S,4S)-2-methyl-4-(trifluoromethanesulfonyloxy)pyrrolidine-1-carboxylate | 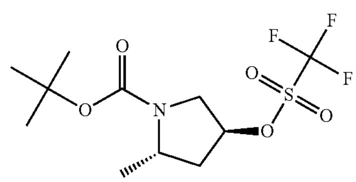 [SMILES: C[C@H]1C[C@H](OS(=O)(=O)C(F)(F)F)CN1C(=O)OC(C)(C)C] |
| 140 | tert-Butyl (2R,4S)-2-methyl-4-(trifluoromethanesulfonyloxy)pyrrolidine-1-carboxylate | 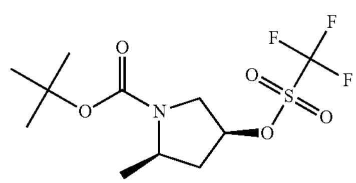 [SMILES: C[C@@H]1C[C@H](OS(=O)(=O)C(F)(F)F)CN1C(=O)OC(C)(C)C] |
| 141 | tert-Butyl (3R)-3-(trifluoromethylsulfonyloxy)pyrrolidine-1-carboxylate | 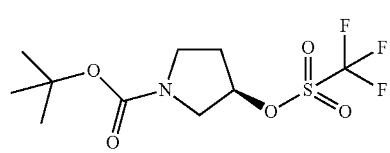 [SMILES: CC(C)(C)OC(=O)N1CC[C@@H](OS(=O)(=O)C(F)(F)F)C1] |

Preparation 142 tert-Butyl 4-(methane sulfonyl oxy)-2,2-dimethylpyrrolidine-1-carboxylate

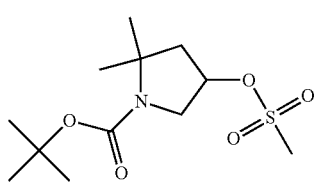 [SMILES: CC(C)(C)OC(=O)N1CC(OS(C)(=O)=O)CC1(C)C]

TEA (940.02 mg, 9.29 mmol) is added dropwise to a stirred mixture of tert-butyl 4-hydroxy-2,2-dimethylpyrrolidine-1-carboxylate (800.00 mg, 3.72 mmol) in DCM (10.00 mL) at RT under N$_2$. MsCl (553.35 mg, 4.83 mmol) is added dropwise to the solution over 2 min at 0° C., and the mixture is stirred for 2 hrs at RT. The reaction is quenched with H$_2$O (150 mL) and the mixture is extracted with DCM (2×200 mL). The combined organic extracts are washed with brine (2×150 mL), dried over anhydrous Na$_2$SO$_4$, filtered, and the filtrate is concentrated under reduced pressure to give the title compound as a brown-yellow solid (1.1 g, crude), which is used directly without further purification. $^1$H NM/R (400 MHz, d$_6$-DMSO) δ 5.23-5.18 (m, 1H), 3.66-3.60 (m, 1H), 3.51-3.45 (m, 1H), 3.22 (s, 3H), 2.40-2.14 (m, 2H), 1.41 (s, 9H), 1.23 (d, 3H).

The following compounds are prepared essentially as described for tert-butyl 4-(methanesulfonyl oxy)-2,2-dimethylpyrrolidine-1-carboxylate using the appropriate reagents and adjusting the reaction times to determine completion of the reactions.

TABLE 16

| Prep No. | Chemical Name | Structure | ES/MS m/z [M + H]+ |
|---|---|---|---|
| 143 | tert-Butyl (2S,4S)-4-(methanesulfonyloxy)-2-methylpyrrolidine-1-carboxylate | 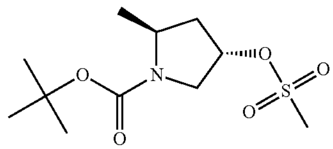 [SMILES: C[C@H]1C[C@H](OS(C)(=O)=O)CN1C(=O)OC(C)(C)C] | a |
| 144 | tert-Butyl (2R,4R)-4-(methanesulfonyloxy)-2-methylpyrrolidine-1-carboxylate | 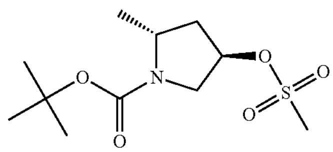 [SMILES: C[C@@H]1C[C@@H](OS(C)(=O)=O)CN1C(=O)OC(C)(C)C] | 280.3 |
| 145 | tert-Butyl (2S,4R)-4-(methanesulfonyloxy)-2-methylpyrrolidine-1-carboxylate | 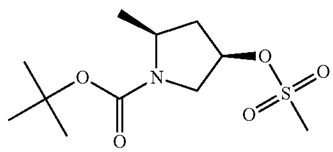 [SMILES: C[C@H]1C[C@@H](OS(C)(=O)=O)CN1C(=O)OC(C)(C)C] | b |
| 146 | tert-Butyl (2R,4S)-4-(methanesulfonyloxy)-2-methylpyrrolidine-1-carboxylate | 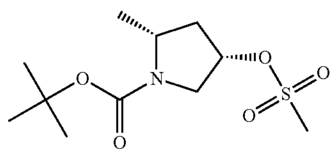 [SMILES: C[C@@H]1C[C@H](OS(C)(=O)=O)CN1C(=O)OC(C)(C)C] | c |
| 147 | [(1S)-1-[4-(2,2,2-Trifluoroethyl)-1,2,4-triazol-3-yl]ethyl] methanesulfonate | | 274.0 | a[1]H NMR (400 MHz, CDCl3) δ 5.21-5.15 (m, 1H), 4.05-3.80 (m, 2H), 3.56 (dd, 1H), 3.03 (s, 3H), 2.51-2.40 (m, 1H), 1.90-1.81 (m, 1H), 1.47 (s, 9H), 1.28 (d, 3H).
b[1]H NMR (400 MHz, d6-DMSO) δ 5.23-5.18 (m, 1H), 3.94-3.84 (m, 1H), 3.66-3.60 (m, 1H), 3.51-3.45 (m, 1H), 3.22 (s, 3H), 2.46-2.34 (m, 1H), 1.93-1.83 (m, 1H), 1.41 (s, 9H), 1.23 (d, 3H).
c[1]H NMR (300 MHz, d6-DMSO) δ 5.23-5.19 (m, 1H), 3.5-3.80 (m, 1H), 3.63 (dd, 1H), 3.48 (dt, 1H), 3.24 (s, 3H), 2.49-2.34 (m, 1H), 1.87 (d, 1H), 1.41 (s, 9H), 1.23 (d, 3H).

Preparation 148

2-(1-Bromoethyl)-N,N-dimethyl-benzamide

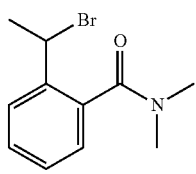

2-ethyl-N,N-dimethylbenzamide (0.81 g, 4.6 mmol), AIBN (75 mg, 0.46 mmol) and NBS (0.89 g, 5.0 mmol) are added into a vial that is evacuated and backfilled with N2 (3×). CCl4 (5 mL) is added and the reaction mixture is stirred at 80° C. for 2 hr. Upon cooling to RT, the reaction is filtered, and the solids are rinsed with CCl4 (2×10 mL). The filtrate is concentrated to obtain the title compound as a clear oil (0.8 g, 70%), which is carried forward without further purification.

Preparation 149 tert-Butyl 4-(2-tert-butoxycarbonylhydrazino)-3,3-difluoro-piperidine-1-carboxylate

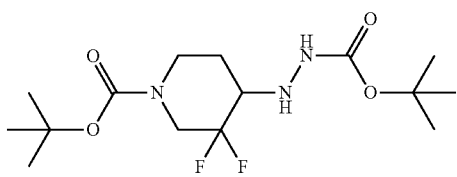 [SMILES: CC(C)(C)OC(=O)NNC1CCN(C(=O)OC(C)(C)C)CC1(F)F]

A mixture of tert-butyl 3,3-difluoro-4-oxopiperidine-1-carboxylate (10.00 g, 42.51 mmol), tert-butoxycarbohydrazide (3.09 g, 23.38 mmol) and AcOH (2.55 g, 42.51 mmol) in MeOH (40 mL) is stirred for 30 min at 50° C. under $N_2$. Upon cooling to RT $NaBH_3CN$ (8.01 g, 127.53 mmol) is added in portions. The reaction is stirred for 2 hr at 50° C. The mixture is basified to pH 8 with sat. aq. $NaHCO_3$. The mixture is extracted with EtOAc (3×150 mL), organic layers combined and washed with brine (3×50 mL), dried over $Na_2SO_4$, filtered, and concentrated in vacuo. The residue is purified by silica gel column chromatography, eluting with PE:EtOAc (10:1 to 5:1) to afford the title compound as an off-white oil (5 g, 67%). ES/MS m/z 240.2 [M+H—C8H16]$^+$.

Preparation 150

3,3-Difluoro-4-(5-methylpyrazol-1-yl)piperidine

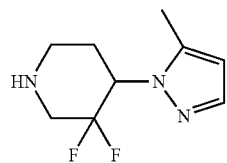

A mixture tert-butyl 4-[[(tert-butoxycarbonyl)amino]amino]-3,3-difluoropiperidine-1-carboxylate (5.50 g, 15.7 mmol) and 4,4-dimethoxybutan-2-one (3.10 g, 23.5 mmol) in AcOH (100 mL) is stirred overnight at 50° C. under $N_2$. To the above mixture is added HBr (25 mL) at RT. The reaction is stirred overnight. No brominated product is detected by LCMS. The mixture is concentrated in vacuo. The residue is carried forward to the next step without a further purification. ES/MS m/z 202.3 [M+H]$^+$.

Preparation 151 tert-Butyl 3,3-difluoro-4-(5-methylpyrazol-1-yl)piperidine-1-carboxylate

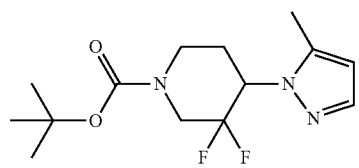 [SMILES: Cc1ccnn1C1CCN(C(=O)OC(C)(C)C)CC1(F)F]

To 3,3-difluoro-4-(5-methyl-1H-pyrazol-1-yl)piperidine (5.50 g, 27.33 mmol) and TEA (27.66 g, 273.3 mmol) in DCM (100 mL) is added $Boc_2O$ (29.83 g, 136.67 mmol) at RT under $N_2$. The reaction is stirred 2 hr then concentrated in vacuo. The residue is purified by silica gel column chromatography, eluting with PE:EtOAc (20:1 to 10:1) to give crude product. The crude product is purified by reverse phase chromatography with the following conditions: column, C18; mobile phase, eluting with 40% to 60% ACN in water (0.1% FA) to afford the title compound as a yellow oil (3 g, 36.4%). ES/MS m/z 302.3 [M+H]$^+$.

Preparation 152 tert-Butyl 4-[3-(2-methoxy-2-oxo-ethyl)-5-methyl-pyrazol-1-yl]piperidine-1-carboxylate

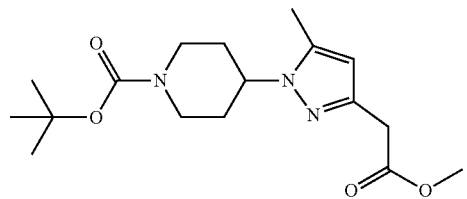 [SMILES: COC(=O)Cc1cc(C)n(C2CCN(C(=O)OC(C)(C)C)CC2)n1]

To methyl 2-(5-methyl-1H-pyrazol-3-yl)acetate (6 g, 38.92 mmol) and $Cs_2CO_3$ (25.36 g, 77.83 mmol) in DMF (80 mL) at RT is added tert-butyl 4-(methanesulfonyloxy)piperidine-1-carboxylate (16.31 g, 58.39 mmol). The reaction is stirred for 3 hr at 60° C. under $N_2$. Upon cooling to RT, the reaction is poured into $H_2O$ (400 mL), extracted with EtOAc (3×500 mL), organic layers are combined and washed with brine (3×200 mL), dried over $Na_2SO_4$, filtered, and rinsed with EtOAc (3×80 mL). The filtrate is concentrated in vacuo and the residue is purified by Prep-HPLC using the following conditions: Column: HEXI SpringXB-C18, 50*250, 10 um; eluting with a gradient of 30% to 55% ACN in $H_2O$ (0.05% TFA), flow rate: 100 mL/min; to afford the title compound (420 mg, 3.20%) as a yellow oil. ES/MS m/z 338.3 [M+H]$^+$.

Preparation 153 tert-Butyl 4-(5-bromo-4-methyl-1,2,4-triazol-3-yl)piperazine-1-carboxylate

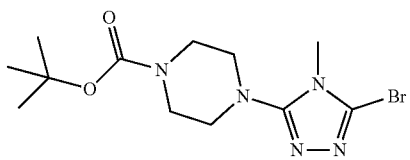 [SMILES: Cn1c(Br)nnc1N1CCN(C(=O)OC(C)(C)C)CC1]

A solution of tert-butyl 4-(4-methyl-4H-1,2,4-triazol-3-yl)piperazine-1-carboxylate (538 mg, 2.01 mmol) and NBS (430 mg, 2.41 mmol) in MeOH (5 mL) is heated to 40° C. for 20 minutes. Upon cooling to RT the reaction is extracted with 3:1 (v/v) chloroform:iPrOH. Organic phase is washed with 10% $Na_2S_2O_3$, $H_2O$, brine, dried over $Na_2SO_4$, filtered, and concentrated in vacuo to a yellow oil. The oil is purified by silica gel chromatography eluting with 5 to 20% MeOH in DCM to afford the title compound as a colorless oil (620 mg, 89.0%). ES/MS m/z 246.1, 248.8 ($^{79}$Br/$^{81}$Br) [M+2H-Boc]$^+$.

The following compounds are prepared essentially as described for tert-butyl 4-(5-bromo-4-methyl-1,2,4-triazol-3-yl)piperazine-1-carboxylate using the appropriate reagents and solvents and adjusting the reaction times to determine completion of the reactions.

TABLE 17

| Prep No. | Chemical Name | Structure | ES/MS m/z [M + H]+ |
|---|---|---|---|
| 154[1,2] | tert-Butyl 4-(4-bromo-5-methyl-pyrazol-1-yl)-3,3-difluoro-piperidine-1-carboxylate | 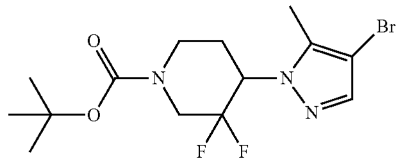 [SMILES: Cc1c(Br)cnn1C1CCN(C(=O)OC(C)(C)C)CC1(F)F] | ($^{79}$Br/$^{81}$Br) 379.7/381.7 |
| 155 | tert-Butyl 4-[4-bromo-3-(2-methoxy-2-oxo-ethyl)-5-methyl-pyrazol-1-yl]piperidine-1-carboxylate | 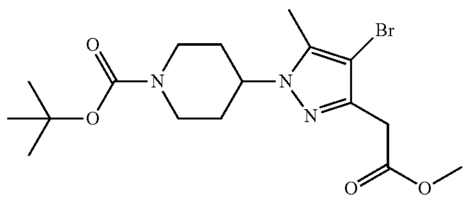 [SMILES: COC(=O)Cc1nn(C2CCN(C(=O)OC(C)(C)C)CC2)c(C)c1Br] | ($^{79}$Br/$^{81}$Br) 416.1/418.1 |

[1]DCM used as solvent
[2]Purified by silica gel column chromatography, eluting with DCM:MeOH (30:1 to 15:1).

Preparation 156

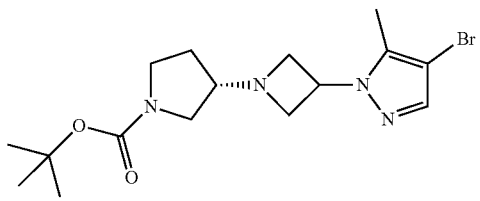 [SMILES: Cc1c(Br)cnn1C1CN([C@H]2CCN(C(=O)OC(C)(C)C)C2)C1]

A solution of 1-(azetidin-3-yl)-4-bromo-5-methylpyrazole (4.00 g) in DCM (20 mL) is basified to pH-10 with DIEA (3 mL) then cooled to −60° C. under N$_2$. tert-Butyl (3R)-3-(trifluoromethylsulfonyloxy)pyrrolidine-1-carboxylate is added dropwise and the reaction is stirred for 4 hr at −60° C. The mixture is concentrated in vacuo. The residue is purified by reverse phase chromatography with the following conditions: column, C18; eluting with 20% to 30% ACN in H$_2$O (0.1% FA), 220 nm. To afford the title compound as a light-yellow solid (7.00 g). ES/MS m/z ($^{79}$Br/$^{81}$Br) 385.1/387.1 [M+H]+.

Preparation 157 tert-Butyl (1R,3r,5S)-3-(4-bromo-1H-pyrazol-1-yl)-8-azabicyclo[3.2.1]octane-8-carboxylate Cs$_2$CO$_3$ (19.20 g, 58.941 mmol) is added in portions to a stirred RT mixture of 4-bromopyrazole (2.89 g, 19.65 mmol) and tert-butyl (1R,3s,5S)-3-((methylsulfonyl)oxy)-8-azabicyclo[3.2.1]octane-8-carboxylate (6.00 g, 19.65 mmol) in DMF (50 ml) and the mixture is stirred overnight at 70° C. under N$_2$. The mixture is concentrated under reduced pressure. The residue is purified by silica gel column chromatography, eluting with a gradient of PE:EtOAc (10:1-5:1) to give a crude product (5.2 g). The crude product is repurified by reverse Combi-flash chromatography with the following conditions: Column, C18; eluting with a gradient of 40% to 80% ACN in H$_2$O (0.1% FA), 220 nm to give the title compound as an off-white solid (3.5 g, 47.5%). ES/MS m/z 341.1/343.1 [M+H-tBu+ACN]+.

The following compounds are prepared essentially as described for tert-butyl (1R,3r,5S)-3-(4-bromo-1H-pyrazol-1-yl)-8-azabicyclo[3.2.1]octane-8-carboxylate using the appropriate reagents and adjusting the reaction times to determine completion of the reactions. K$_2$CO$_3$ can also be used as the base. Temperature is varied from 70° C. to 80° C.

TABLE 18

| Prep No. | Chemical Name | Structure | ES/MS m/z [M + H]+ |
|---|---|---|---|
| 158[1] | tert-Butyl (3R)-3-(4-bromopyrazol-1-yl)pyrrolidine-1-carboxylate | 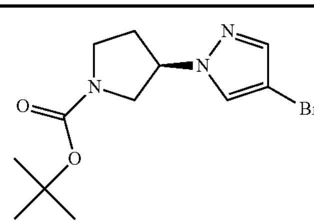 | a |

TABLE 18-continued

| Prep No. | Chemical Name | Structure | ES/MS m/z [M + H]+ |
|---|---|---|---|
| 159[2] | tert-Butyl (3S)-3-(4-bromopyrazol-1-yl)pyrrolidine-1-carboxylate | 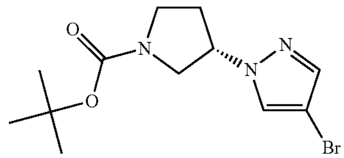 [SMILES: CC(C)(C)OC(=O)N1CC[C@H](n2cc(Br)cn2)C1] | b |
| 160[3] | tert-Butyl (2S,4R)-4-(4-bromopyrazol-1-yl)-2-methylpyrrolidine-1-carboxylate | 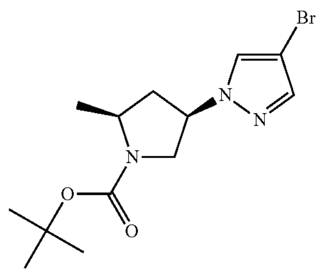 [SMILES: C[C@H]1C[C@@H](n2cc(Br)cn2)CN1C(=O)OC(C)(C)C] | c |
| 161[4] | tert-Butyl (2R,4S)-4-(4-bromopyrazol-1-yl)-2-methylpyrrolidine-1-carboxylate | 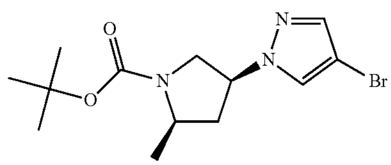 [SMILES: C[C@@H]1C[C@H](n2cc(Br)cn2)CN1C(=O)OC(C)(C)C] | 330.1/ 332.1 |
| 162[4] | tert-Butyl (2S,4S)-4-(4-bromopyrazol-1-yl)-2-methylpyrrolidine-1-carboxylate | 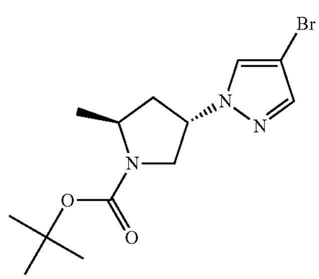 [SMILES: C[C@H]1C[C@H](n2cc(Br)cn2)CN1C(=O)OC(C)(C)C] | 330.1/ 332.1 |
| 163[5] | tert-Butyl 4-(4-bromopyrazol-1-yl)-2,2-dimethylpyrrolidine-1-carboxylate | 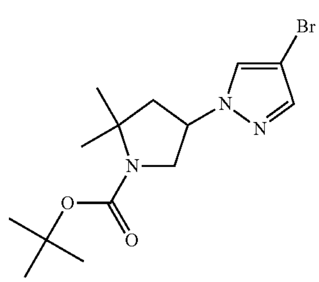 [SMILES: CC(C)(C)OC(=O)N1CC(n2cc(Br)cn2)CC1(C)C] | 344.1/ 346.1 |

TABLE 18-continued

| Prep No. | Chemical Name | Structure | ES/MS m/z [M + H]+ |
|---|---|---|---|
| 164[4] | tert-Butyl (2R,4R)-4-(4-bromopyrazol-1-yl)-2-methylpyrrolidine-1-carboxylate | 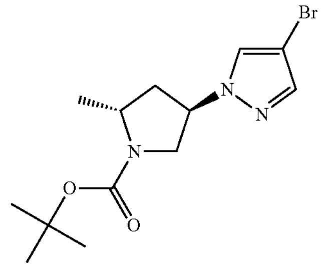 [SMILES: C[C@@H]1C[C@@H](n2cc(Br)cn2)CN1C(=O)OC(C)(C)C] | d |

[1]The mixture is filtered, the filter cake is washed with EtOAc (3 × 20 mL), and the filtrate is concentrated under reduced pressure. The residue is purified by silica gel column chromatography, eluting with PE:EtOAc.
[2]Crude product is not repurified.
[3]The residue is purified by reverse Combi-flash chromatography with the following conditions: Column, C18; mobile phase, ACN in H$_2$O (0.1% NH$_4$HCO$_3$). Not repurified.
[4]The mixture is filtered, the filter cake is washed with DCM (2 × 10 mL), and the filtrate is concentrated under reduced pressure prior to purification by reverse Combi-flash chromatography.
[5]Purified with only reverse Combi-flash chromatography.
a[1]H NMR (300 MHz, d$_6$-DMSO) δ 8.08 (s, 1H), 7.59 (s, 1H), 4.97-4.89 (m, 1H), 3.73-3.65 (m, 1H), 3.57-3.51 (m, 1H), 3.46-3.37 (m, 2H), 2.36-2.24 (m, 2H), 1.40 (d, 9H).
b[1]H NMR (400 MHz, CDCl$_3$) δ 7.55-7.50 (m, 2H), 4.89-4.83 (m, 1H), 3.77-3.51 (m, 4H), 2.38-2.33 (m, 2H), 1.48 (s, 9H).
c[1]H NMR (300 MHz, CDCl$_3$) δ 7.61 (d, 1H), 7.49 (d, 1H), 4.77-4.61 (m, 1H), 4.15-4.01 (m, 1H), 4.05-3.94 (m, 1H), 3.63 (dd, 1H), 2.71-2.55 (m, 1H), 2.25-2.10 (m, 1H), 1.49 (s, 9H), 1.31 (d, 3H).
d[1]H NMR (300 MHz, d$_6$-DMSO) δ 8.04 (s, 1H), 7.58 (s, 1H), 5.03-4.93 (m, 1H), 3.72-3.57 (m, 1H), 3.68-6.58 (m, 2H), 2.55-2.44 (m, 1H), 2.15-1.85 (m, 1H), 1.39 (s, 9H), 1.20 (d, 3H).

Preparation 165 tert-Butyl 2-(4-bromopyrazol-1-yl)-7-azaspiro[3.5]nonane-7-carboxylate

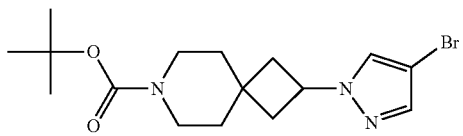 [SMILES: CC(C)(C)OC(=O)N1CCC2(CC1)CC(n1cc(Br)cn1)C2]

Cs$_2$CO$_3$ (18.36 g, 56.35 mmol) is added in portions at RT under N$_2$ to a stirred mixture of tert-butyl 2-(methanesulfonyloxy)-7-azaspiro[3.5]nonane-7-carboxylate (6.00 g, 18.78 mmol) and 4-bromopyrazole (2.76 g, 18.78 mmol) in DMF (50.00 mL) and the mixture is stirred for 2 hrs at 100° C. under N$_2$. The mixture is cooled to RT, diluted with H$_2$O (100 mL), and extracted with EtOAc (3×150 mL). The combined organic layers are washed with brine (2×200 mL), dried over anhydrous Na$_2$SO$_4$, filtered, and the filtrate is concentrated under reduced pressure. The residue is purified by reverse Combi-flash chromatography with the following conditions: Column, C18 eluting with a gradient of 40% to 50% ACN in H$_2$O (0.1% FA), 220 nm, to give the title compound (5 g). The product is dissolved in DCM (100 mL), washed with brine (2×150 mL), dried over anhydrous Na$_2$SO$_4$, filtered, and the filtrate is concentrated under reduced pressure to give the title compound as an off-white solid (4.5 g, 64.7%). $^1$H NMR (300 MHz, CDCl$_3$) δ 7.50 (s, 1H), 7.45 (s, 1H), 4.80-4.69 (m, 1H), 3.47-3.38 (m, 2H), 3.38-3.29 (m, 2H), 2.51-2.38 (m, 2H), 2.38-2.25 (m, 2H), 1.69-1.61 (m, 4H), 1.47 (s, 9H).

The following compounds are prepared essentially as described for tert-butyl 2-(4-bromopyrazol-1-yl)-7-azaspiro[3.5]nonane-7-carboxylate using the appropriate reagents, adjusting the reaction times to determine completion of the reactions, and adjusting the purification system as appropriate. Temperature is varied from 70° C. to 100° C.

TABLE 19

| Prep No. | Chemical Name | Structure | ES/MS m/z [M + H]+ |
|---|---|---|---|
| 166 | tert-Butyl (1R,3s,5S)-3-(4-bromo-1H-pyrazol-1-yl)-8-azabicyclo[3.2.1]octane-8-carboxylate | 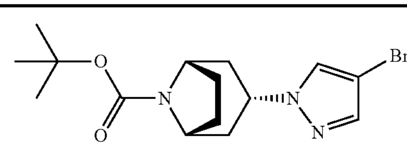 | b |
| 167[1] | tert-Butyl (4R)-4-(4-bromopyrazol-1-yl)azepane-1-carboxylate | 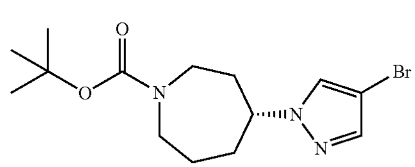 [SMILES: CC(C)(C)OC(=O)N1CCC[C@@H](n2cc(Br)cn2)CC1] | c |

TABLE 19-continued

| Prep No. | Chemical Name | Structure | ES/MS m/z [M + H]+ |
|---|---|---|---|
| 168 | tert-Butyl (4S)-4-(4-bromopyrazol-1-yl)azepane-1-carboxylate | 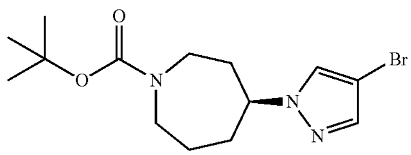 [SMILES: CC(C)(C)OC(=O)N1CCC[C@H](n2cc(Br)cn2)CC1] | 344.1/346.1 |
| 169[2] | tert-Butyl 3-(4-bromo-3-methylpyrazol-1-yl)azetidine-1-carboxylate | 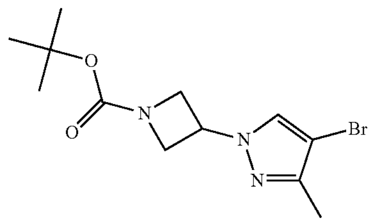 [SMILES: Cc1nn(C2CN(C(=O)OC(C)(C)C)C2)cc1Br] | 301.1/303.1 |
| 170[3] | tert-Butyl 4-(4-bromo-3-methylpyrazol-1-yl)piperidine-1-carboxylate | 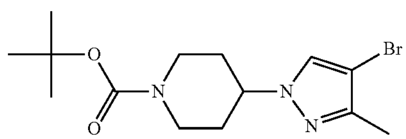 [SMILES: Cc1nn(C2CCN(C(=O)OC(C)(C)C)CC2)cc1Br] | 344.1/346.1 |

[1]The mixture is filtered, the filter cake is washed with DCM (3 × 20 mL) the filtrate is concentrated under reduced pressure, and the residue is purified by reverse Combi-flash chromatography with the following conditions: Column, C18; 40-60% ACN in H₂O.
[2]The crude product is used directly without further purification.
[3]The mixture is concentrated under reduced pressure, and the residue is purified by silica gel column chromatography eluting with (6:1-1:1 PE/EtOAc.
[a] $^1$H NMR (300 MHz, CDCl₃) δ 7.51 (d, 2H), 4.28-4.18 (m, 2H), 4.00-3.89 (m, 1H), 3.35-3.25 (m, 1H), 3.05-2.95 (m, 1H), 2.35-1.93 (m, 2H), 1.67-1.56 (m, 2H), 1.48 (s, 9H).
[b] $^1$H NMR (400 MHz, d₆-DMSO) δ 7.98 (s, 1H), 7.54 (s, 1H), 4.82-4.64 (m, 1H), 4.23-4.09 (m, 2H), 2.04-1.82 (m, 6H), 1.81-1.72 (m, 2H), 1.42 (s, 9H)
[c] $^1$H NMR (300 MHz, CDCl₃) δ 7.46 (d, 1H), 7.43 (d, 1H), 4.25 (ddt, 1H), 3.75-3.20 (m, 4H), 2.35-1.84 (m, 6H), 1.50 (s, 9H)

Preparation 171 tert-Butyl 3-(4-bromo-5-methylpyrazol-1-yl)azetidine-1-carboxylate

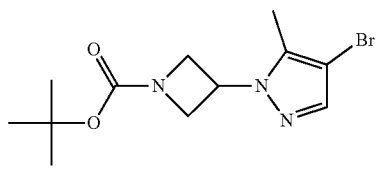 [SMILES: Cc1c(Br)cnn1C1CN(C(=O)OC(C)(C)C)C1]

A stirred solution of tert-butyl 3-(4-bromopyrazol-1-yl)azetidine-1-carboxylate (7.50 g, 24.82 mmol) in THF (160 mL) at 0° C. under N₂ is treated with LDA (2 mmol/L in THF) (37 mL, 74.46 mmol) and the mixture is stirred for 30 min. CH₃I (10.57 g, 74.46 mmol) is added and the mixture is stirred for 2 hrs at RT under N₂. The reaction is quenched with H₂O (100 mL) and extracted with EtOAc (3×100 mL). The combined organic extracts are washed with brine (1×100 mL), dried over anhydrous Na₂SO₄, filtered, and the filtrate is concentrated under reduced pressure. The residue is purified by silica gel column chromatography, eluting with a gradient of PE:EtOAc (9:1-5:1) to give the title compound as a yellow solid (4.13 g, 52.62%), which is used directly without further purification. $^1$H NMR (300 MHz, CDCl₃) δ 7.53 (s, 1H), 5.04-4.93 (m, 1H), 4.48-4.40 (m, 2H), 4.36-4.28 (m, 2H), 2.27 (s, 3H), 1.48 (s, 9H).

The following compounds are prepared essentially as described for tert-butyl 3-(4-bromo-5-methylpyrazol-1-yl)azetidine-1-carboxylate using the appropriate reagents, adjusting the reaction times to determine completion of the reactions and adjusting the purification system as appropriate. Temperature is varied from −78° C. to RT. The reaction can also be quenched with NH₄Cl.

TABLE 20

| Prep No. | Chemical Name | Structure | ES/MS m/z [M + H]+ |
|---|---|---|---|
| 172[1] | tert-Butyl (3R)-3-(4-Bromo-5-methylpyrazol-1-yl)pyrrolidine-1-carboxylate | 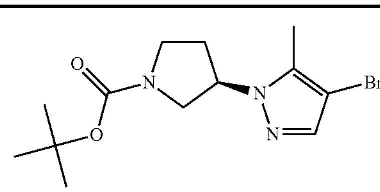 | a |

TABLE 20-continued

| Prep No. | Chemical Name | Structure | ES/MS m/z [M + H]+ |
|---|---|---|---|
| 173[1] | tert-Butyl (3S)-3-(4-bromo-5-methylpyrazol-1-yl)pyrrolidine-1-carboxylate | 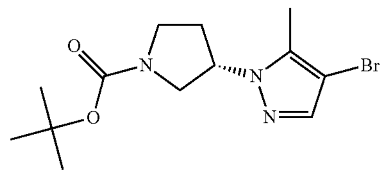 [SMILES: Cc1c(Br)cnn1[C@H]1CCN(C(=O)OC(C)(C)C)C1] | b |
| 174 | tert-Butyl 2-(4-bromo-5-methylpyrazol-1-yl)-7-azaspiro[3.5]nonane-7-carboxylate | 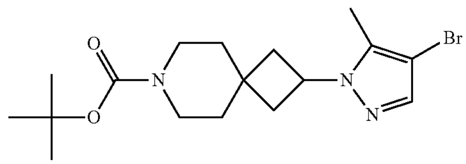 [SMILES: Cc1c(Br)cnn1C1CC2(CCN(C(=O)OC(C)(C)C)CC2)C1] | c |
| 175 | tert-Butyl (3R)-3-(4-bromo-5-methylpyrazol-1-yl)piperidine-1-carboxylate | 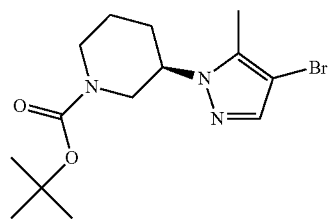 [SMILES: Cc1c(Br)cnn1[C@@H]1CCCN(C(=O)OC(C)(C)C)C1] | 344.1/346.1 |
| 176 | tert-Butyl (3S)-3-(4-bromo-5-methylpyrazol-1-yl)piperidine-1-carboxylate | 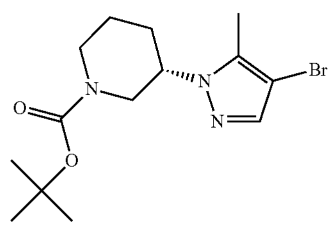 [SMILES: Cc1c(Br)cnn1[C@H]1CCCN(C(=O)OC(C)(C)C)C1] | d |
| 177 | tert-Butyl (1R,3r,5S)-3-(4-bromo-5-methyl-1H-pyrazol-1-yl)-8-azabicyclo[3.2.1]octane-8-carboxylate | 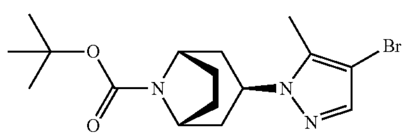 | 370.2/372.2 |
| 178 | tert-Butyl (1R,3s,5S)-3-(4-bromo-5-methyl-1H-pyrazol-1-yl)-8-azabicyclo[3.2.1]octane-8-carboxylate | 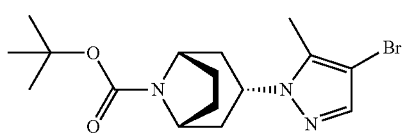 | 370.2/372.2 |
| 179[1] | tert-Butyl (4R)-4-(4-bromo-5-methylpyrazol-1-yl)azepane-1-carboxylate | 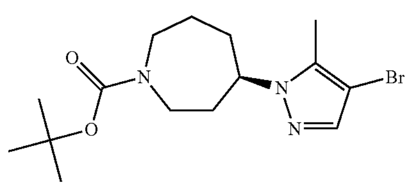 [SMILES: Cc1c(Br)cnn1[C@@H]1CCCN(C(=O)OC(C)(C)C)CC1] | e |
| 180 | tert-Butyl (4S)-4-(4-bromo-5-methylpyrazol-1-yl)azepane-1-carboxylate | 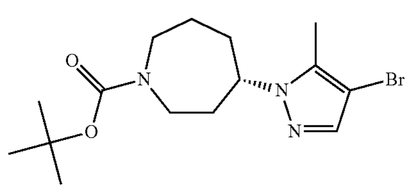 [SMILES: Cc1c(Br)cnn1[C@H]1CCCN(C(=O)OC(C)(C)C)CC1] | 358.1/360.1 |

TABLE 20-continued

| Prep No. | Chemical Name | Structure | ES/MS m/z [M + H]+ |
|---|---|---|---|
| 181 | tert-Butyl (2S,4R)-4-(4-bromo-5-methylpyrazol-1-yl)-2-methylpyrrolidine-1-carboxylate | 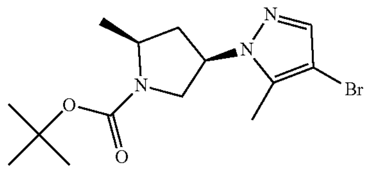 [SMILES: Cc1c(Br)cnn1[C@@H]1C[C@H](C)N(C(=O)OC(C)(C)C)C1] | f |
| 182[1] | tert-Butyl (2R,4S)-4-(4-bromo-5-methylpyrazol-1-yl)-2-methylpyrrolidine-1-carboxylate | 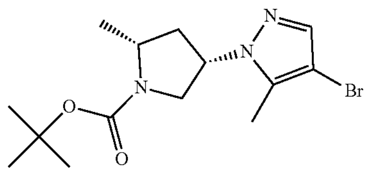 [SMILES: Cc1c(Br)cnn1[C@H]1C[C@@H](C)N(C(=O)OC(C)(C)C)C1] | 344.09/346.09 |
| 183[1] | tert-Butyl (2S,4S)-4-(4-bromo-5-methylpyrazol-1-yl)-2-methylpyrrolidine-1-carboxylate | 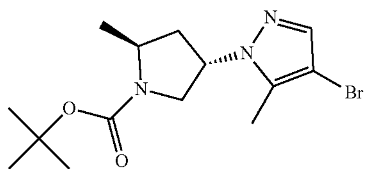 [SMILES: Cc1c(Br)cnn1[C@H]1C[C@H](C)N(C(=O)OC(C)(C)C)C1] | 344.1/346.1 |
| 184[1] | tert-Butyl 4-(4-bromo-5-methylpyrazol-1-yl)-2,2-dimethylpyrrolidine-1-carboxylate | 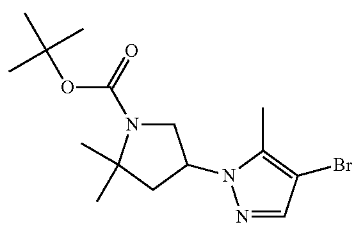 [SMILES: Cc1c(Br)cnn1C1CN(C(=O)OC(C)(C)C)C(C)(C)C1] | 358.1/360.1 |
| 185[2] | tert-Butyl (2R,4R)-4-(4-bromo-5-methylpyrazol-1-yl)-2-methylpyrrolidine-1-carboxylate | 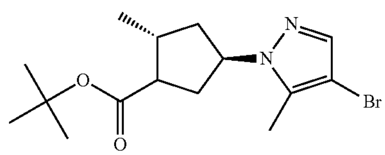 [SMILES: Cc1c(Br)cnn1[C@H]1CC(C(=O)OC(C)(C)C)[C@H](C)C1] | g |

[1] Crude product used directly without further purification.
[2] Dried extract is filtered and the filtrate is concentrated under reduced pressure.
[a] 1H NMR (300 MHz, d6-DMSO) δ 7.53 (s, 1H), 5.00 (d, 1H), 3.67 (d, 1H), 3.50-3.42 (m, 2H), 2.27 (s, 3H), 2.24-2.10 (m, 2H), 1.40 (d, 9H).
[b] 1H NMR (400 MHz, d6-DMSO) δ 7.53 (d, 1H), 5.00 (s, 1H), 3.71-3.65 (m, 1H), 3.54-3.42 (m, 3H), 2.27 (s, 3H), 2.19-2.06 (m, 2H), 1.41-1.39 (m, 9H).
[c] 1H NMR (300 MHz, d6-DMSO) δ 7.53 (s, 1H), 4.91-4.86 (m, 1H), 3.33-3.18 (m, 4H), 2.40-2.14 (m, 7H), 1.64-1.59 (m, 2H), 1.52-1.47 (m, 2H), 1.40 (s, 9H).
[d] 1H NMR (300 MHz, CDCl3) δ 7.42 (d, 1H), 4.05-3.95 (m, 1H), 3.20-3.00 (m, 1H), 2.77-2.68 (m, 1H), 2.29 (s, 3H), 2.20-2.10 (m, 3H), 2.07-2.04 (m, 1H), 1.89-1.82 (m, 1H), 1.67-1.57 (m, 1H), 1.45 (s, 9H).
[e] 1H NMR (400 MHz, CDCl3) δ 7.35 (s, 1H), 4.05-3.99 (m, 1H), 3.75-3.10 (m, 4H), 2.19 (s, 3H), 2.18-1.81 (m, 6H), 1.41 (s, 9H).
[f] 1H NMR (400 MHz, CDCl3) δ 7.44 (s, 1H), 4.64-4.54 (m, 1H), 3.98-3.90 (m, 2H), 3.62-3.45 (m, 1H), 2.54-2.45 (m, 1H), 2.35-2.21 (m, 4H), 1.48 (s, 9H), 1.37 (d, 3H).
[g] 1H NMR (300 MHz, d6-DMSO) δ 7.51 (s, 1H), 5.09-4.94 (m, 1H), 4.11-3.95 (m, 1H), 3.70-3.60 (m, 1H), 3.52 (dd, 1H), 2.50-2.40 (m, 1H), 2.28 (s, 3H), 2.02-1.91 (m, 1H), 1.39 (s, 9H), 1.22 (d, 3H).

Preparation 186

1-(Azetidin-3-yl)-4-bromo-5-methylpyrazole

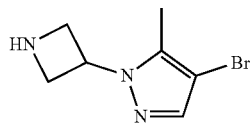

A solution of tert-butyl 3-(4-bromo-5-methylpyrazol-1-yl)azetidine-1-carboxylate (3.00 g, 9.488 mmol) in TFA (10 mL) and DCM (20 mL) is stirred for 2 hrs at RT. The solution is concentrated under reduced pressure to give the title compound as a brown oil (4 g, crude, TFA salt), which is used directly without further purification. 1H NMR (300 MHz, CDCl3) δ 7.50 (s, 1H), 5.16-5.06 (m, 1H), 4.30 (t, 2H), 3.88 (t, 2H), 2.25 (s, 3H). The compound is used directly without further purification.

The following compound is prepared essentially as described for 1-(Azetidin-3-yl)-4-bromo-5-methylpyrazole using the appropriate reagents, and adjusting the reaction time to determine completion of the reaction.

TABLE 21

| Prep No. | Chemical Name | Structure | ES/MS m/z [M + H]+ |
|---|---|---|---|
| 187 | 4-(4-Bromo-5-methyl-triazol-1-yl)piperidine HCl | 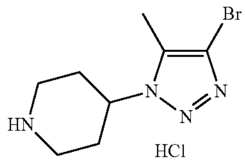 | ($^{79}$Br/$^{81}$Br) 245.1/ 247.1 |

Preparation 188 tert-Butyl (3S)-3-[3-(4-bromo-5-methylpyrazol-1-yl)azetidin-1-yl]pyrrolidine-1-carboxylate

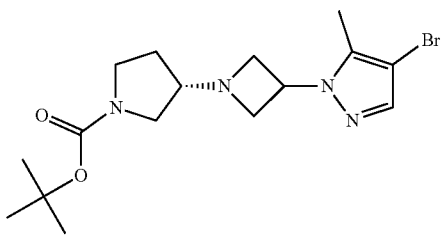 [SMILES: Cc1c(Br)cnn1C1CN([C@H]2CCN(C(=O)OC(C)(C)C)C2)C1]

Tf$_2$O (3.62 g, 12.82 mmol) is added dropwise to a stirred mixture of tert-butyl (3R)-3-hydroxypyrrolidine-1-carboxylate (2.00 g, 10.68 mmol) and DIEA (4.14 g, 32.05 mmol) in DCM (30 mL) at −40° C. under N$_2$. The mixture is added dropwise to a stirred solution of 1-(azetidin-3-yl)-4-bromo-5-methylpyrazole (4 g, crude) in DCM (30 mL). The mixture is made basic to pH-10 with DIEA (3 mL) at −40° C. under N$_2$. The mixture is stirred for an additional 4 hrs at −40° C. and then concentrated under vacuum. The solution is purified by reverse Combi-flash chromatography with the following conditions: Column, C18; eluting with a gradient of 20% to 30% ACN in H$_2$O (0.1% FA); 220 nm to give the title compound as a light-yellow solid (500 mg, 12%). ES/MS m/z ($^{79}$Br/$^{81}$Br) 385.1/387.1 [M+H]+.

Preparation 189 tert-Butyl (3R)-3-[3-(4-bromo-5-methylpyrazol-1-yl)azetidin-1-yl]pyrrolidine-1-carboxylate

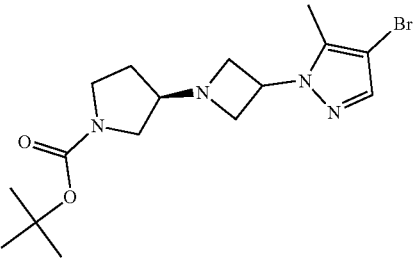 [SMILES: Cc1c(Br)cnn1C1CN([C@@H]2CCN(C(=O)OC(C)(C)C)C2)C1]

tert-Butyl (3S)-3-(trifluoromethanesulfonyloxy)pyrrolidine-1-carboxylate (2.05 g, 6.41 mmol, crude) is added dropwise to a stirred solution of 1-(azetidin-3-yl)-4-bromo-5-methylpyrazole (3 g, 13.88 mmol, crude) in DCM (30 mL). The solution is made basic to pH-10 with DIEA (3 mL) at −40° C. under N$_2$ and the mixture is stirred for 4 hrs at −40° C. The solution is quenched by H$_2$O (30 mL) and extracted with DCM (2×100 mL). The combined organic extracts are washed with brine (2×80 mL), dried over anhydrous Na$_2$SO$_4$, filtered, and the filtrate is concentrated under reduced pressure. The residue is purified by reverse Combi-flash chromatography with the following conditions: Column, C18; eluting with a gradient of 30% to 50% ACN in H$_2$O (0.1% FA) to give the title compound as a light-yellow oil (520 mg, 38.5%). ES/MS m/z ($^{79}$Br/$^{81}$Br) 385.0/387.0 [M+H]+.

The following compound is prepared essentially as described for tert-butyl (3R)-3-[3-(4-bromo-5-methylpyrazol-1-yl)azetidin-1-yl]pyrrolidine-1-carboxylate using the appropriate reagents and adjusting the reaction times to determine completion of the reactions. Temperature is varied from −70° C. to −40° C.

TABLE 22

| Prep No. | Chemical Name | Structure | ES/MS m/z [M + H]+ |
|---|---|---|---|
| 190[1] | tert-Butyl (2R,4R)-4-[3-(4-[3-cyano-4-methoxypyrazolo[1,5-a]pyridin-6-yl]-5-methylpyrazol-1-yl)azetidin-1-yl]-2-methylpyrrolidine-1-carboxylate | 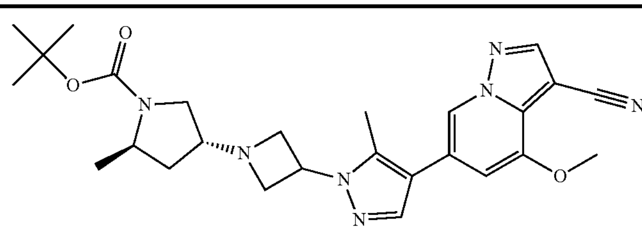 | 492.3 |

[1]Prep TLC (EtOAc).

Preparation 191 tert-Butyl 3-[3-(4-bromo-5-methylpyrazol-1-yl)azetidin-1-yl]piperidine-1-carboxylate

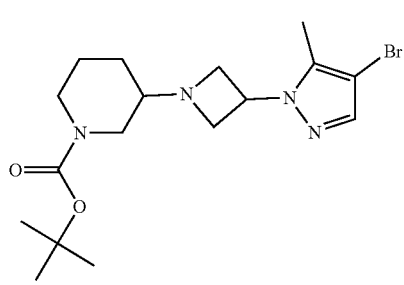 [SMILES: Cc1c(Br)cnn1C1CN(C2CCCN(C(=O)OC(C)(C)C)C2)C1]

NaBH$_3$CN (2.18 g, 34.709 mmol) is added in portions to a stirred mixture of 1-(azetidin-3-yl)-4-bromo-5-methylpyrazole (5.00 g, 23.14 mmol) and tert-butyl 3-oxopiperidine-1-carboxylate (5.53 g, 27.77 mmol) in MeOH (50 mL) at RT and the mixture is stirred for 2 hrs. The reaction is quenched with H$_2$O (50 mL) and extracted with EtOAc (3×100 mL). The combined organic extracts are washed with brine (50 mL), dried over anhydrous Na$_2$SO$_4$, filtered, and the filtrate is concentrated under reduced pressure. The residue is purified by silica gel column chromatography, eluting with a gradient of PE:EtOAc (5:1~1:1) to give the title compound as a brown solid (4.0 g, 43.2%). ES/MS m/z ($^{79}$Br/$^{81}$Br) 399.1/401.1 [M+H]$^+$.

The following compounds are prepared essentially as described for tert-butyl 3-[3-(4-bromo-5-methylpyrazol-1-yl)azetidin-1-yl]piperidine-1-carboxylate using the appropriate reagents, adjusting the reaction times to determine completion of the reactions, and adjusting the purification system as appropriate. Temperature is varied from RT to 50° C.

Preparation 194 tert-Butyl (3S)-3-[3-(4-bromo-5-methylpyrazol-1-yl)azetidin-1-yl]piperidine-1-carboxylate

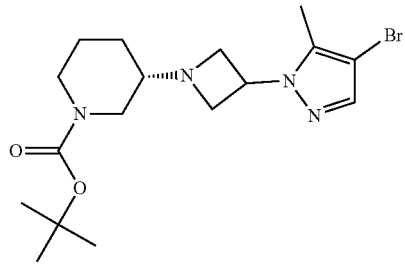 [SMILES: Cc1c(Br)cnn1C1CN([C@H]2CCCN(C(=O)OC(C)(C)C)C2)C1]

Preparation 195 tert-Butyl (3R)-3-[3-(4-bromo-5-methylpyrazol-1-yl)azetidin-1-yl]piperidine-1-carboxylate

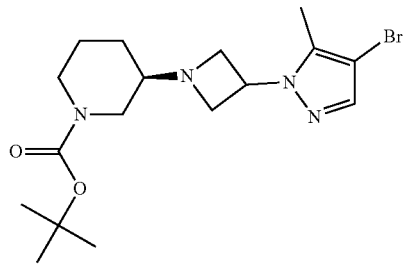 [SMILES: Cc1c(Br)cnn1C1CN([C@@H]2CCCN(C(=O)OC(C)(C)C)C2)C1]

tert-Butyl-3-[3-(4-bromo-5-methylpyrazol-1-yl)azetidin-1-yl]piperidine-1-carboxylate (1.0 g) is separated by Prep-chiral with the following conditions: Column, Phenomenex Lux 5μ Cellulose-4, AXIA Packed, 2.12*25 cm, 5 μm; eluting with 20% MeOH in CO$_2$, flow rate 40 mL/min; 210 nm; Analytical LC conditions are: Column Lux Cellulose-4, 0.46*10 cm, 3.0 μm eluting with 10% to 50% MeOH (0.1% DEA) in CO$_2$, flow rate of 2 mL/min to give t$_{(R)}$ tert-butyl (3S)-3-[3-(4-bromo-5-methylpyrazol-1-yl)azetidine-1-yl]

TABLE 23

| Prep No. | Chemical Name | Structure | ES/MS m/z [M + H]$^+$ |
|---|---|---|---|
| 192[1] | tert-Butyl 4-[3-(4-bromo-5-methylpyrazol-1-yl)azetidin-1-yl]-3,3-difluoropiperidine-1-carboxylate | 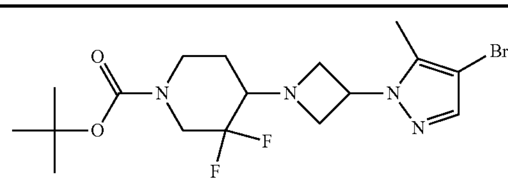 | ($^{79}$Br/$^{81}$Br) 435.1/437.1 |
| 193[2] | tert-Butyl 3-[3-[4-(3-cyano-4-methoxy-pyrazolo[1,5-a]pyridin-6-yl)-5-methyl-pyrazol-1-yl]azetidin-1-yl]-6-azabicyclo[3.2.1]octane-6-carboxylate | 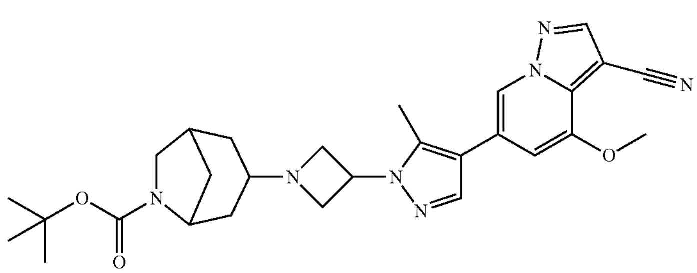 | 518.4 |

[1]TFA and catalytic AcOH is added to the initial solution before NaBH$_3$CN is added.
[2]Purified by silica gel column chromatography, eluting with PE:EtOAc (2:1 to 1:1)

piperidine-1-carboxylate, t$_{(R)}$ is 1.85 min with 100% ee as a light-yellow solid (460 mg); t$_{(R)}$ tert-butyl (3R)-3-[3-(4-bromo-5-methylpyrazol-1-yl)azetidine-1-yl]piperidine-1-carboxylate is 2.18 min with 100% ee as a light-yellow solid (450 mg). ES/MS m/z 399.1/401.1 [M+H]$^+$.

Preparation 196 tert-Butyl (3R,4S)-3-fluoro-4-(5-methyl-4-trimethylsilyl-triazol-1-yl)piperidine-1-carboxylate

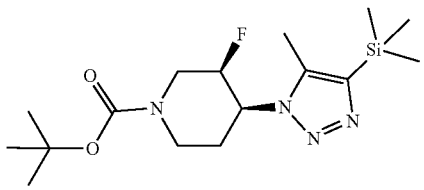 [SMILES: Cc1c([Si](C)(C)C)nnn1[C@H]1CCN(C(=O)OC(C)(C)C)C[C@H]1F]

A mixture of tert-butyl (3R,4S)-4-azido-3-fluoro-piperidine-1-carboxylate (1.00 g, 4.09 mmol) and trimethyl(prop-1-yn-1-yl)silane (1.38 g, 12.28 mmol) is irradiated with microwave radiation for 1 hr at 150° C. The reaction is concentrated in vacuo to afford the title compound (1.5 g) as a white solid, which is used in the next step without further purification. ES/MS m/z 357.1 [M+H]$^+$ The following compounds are prepared essentially as described for tert-butyl (3R,4S)-3-fluoro-4-(5-methyl-4-trimethylsilyl-triazol-1-yl)piperidine-1-carboxylate using the appropriate reagents, adjusting the reaction times to determine completion of the reactions, and adjusting the purification system as appropriate.

TABLE 24

| Prep No. | Chemical Name | Structure | ES/MS m/z [M + H]$^+$ |
|---|---|---|---|
| 197 | tert-Butyl (3S,4S)-3-fluoro-4-(5-methyl-4-trimethylsilyl-triazol-1-yl)piperidine-1-carboxylate | 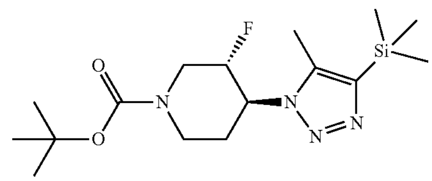 [SMILES: Cc1c([Si](C)(C)C)nnn1[C@H]1CCN(C(=O)OC(C)(C)C)C[C@@H]1F] | 357.2 |
| 198 | tert-Butyl (3S,4R)-3-fluoro-4-(5-methyl-4-trimethylsilyl-triazol-1-yl)piperidine-1-carboxylate | 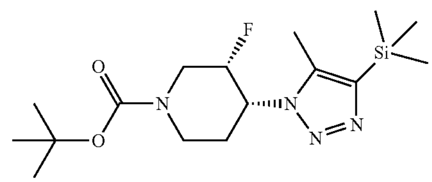 | 357.2 |
| 199 | tert-Butyl (3R,4R)-3-fluoro-4-(5-methyl-4-trimethylsilyl-triazol-1-yl)piperidine-1-carboxylate | 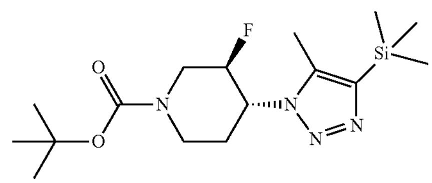 [SMILES: Cc1c([Si](C)(C)C)nnn1[C@@H]1CCN(C(=O)OC(C)(C)C)C[C@H]1F] | 357.2 |
| 200[1,2] | (1r,3r)-3-(5-methyl-4-(trimethylsilyl)-1H-1,2,3-triazol-1-yl)cyclobutan-1-ol | 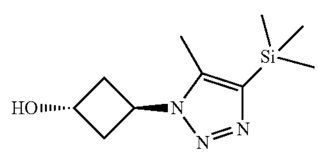 | a |
| 201[2,3] | tert-Butyl (3S,4S)-3-hydroxy-4-(5-methyl-4-trimethylsilyl-triazol-1-yl)piperidine-1-carboxylate | 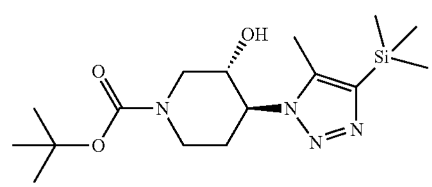 [SMILES: Cc1c([Si](C)(C)C)nnn1[C@H]1CCN(C(=O)OC(C)(C)C)C[C@@H]1O] | 355.3 [M − H]$^+$ |
| 202[2] | tert-Butyl (3R,4S)-3-hydroxy-4-(5-methyl-4-trimethylsilyl-triazol-1-yl)piperidine-1-carboxylate | 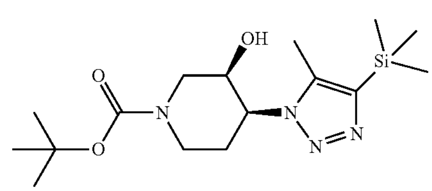 [SMILES: Cc1c([Si](C)(C)C)nnn1[C@H]1CCN(C(=O)OC(C)(C)C)C[C@H]1O] | 355.2 |

TABLE 24-continued

| Prep No. | Chemical Name | Structure | ES/MS m/z [M + H]⁺ |
|---|---|---|---|
| 203[3] | tert-Butyl (3S,4R)-3-hydroxy-4-(5-methyl-4-trimethylsilyl-triazol-1-yl)piperidine-1-carboxylate | 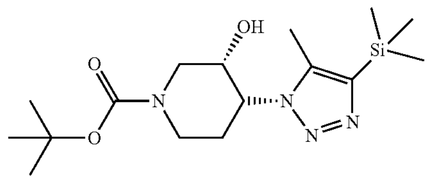 | 355.2 |
| 204[4] | tert-Butyl (3R,4R)-3-hydroxy-4-(5-methyl-4-trimethylsilyl-triazol-1-yl)piperidine-1-carboxylate | 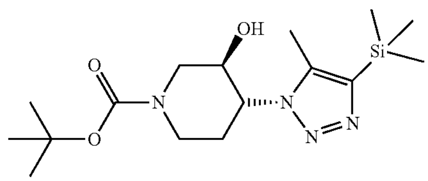 | 355.3 |
| 205[5] | tert-butyl (3RS,4RS)-3-methyl-4-(5-methyl-4-trimethylsilyl-triazol-1-yl)piperidine-1-carboxylate | 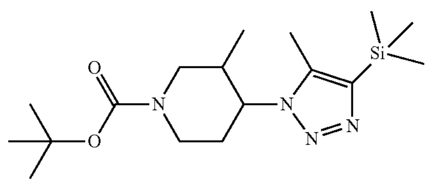 [SMILES: Cc1c([Si](C)(C)C)nnn1C1CCN(C(=O)OC(C)(C)C)CC1C] | 353.15 |
| 206[6] | tert-butyl (3RS,4SR)-3-methyl-4-(5-methyl-4-trimethylsilyl-triazol-1-yl)piperidine-1-carboxylate | 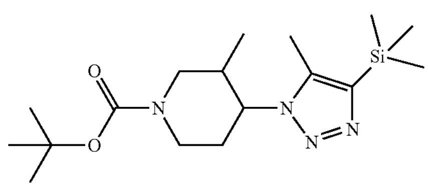 [SMILES: Cc1c([Si](C)(C)C)nnn1C1CCN(C(=O)OC(C)(C)C)CC1C] | 353.2 |

[1]Purified by silica gel chromatography eluting with 0% to 100% EtOAc in heptane.
[2]Reaction was run in toluene
[3]Purified by silica gel chromatography, eluting with PE:EA (4:1).
[4]Purified by silica gel chromatography, eluting with PE:EA (2:1).
[5]Purified by silica gel chromatography, eluting with PE:EA (5:1).
[6]Purified by silica gel chromatography, eluting with PE:EA (6:1 to 5:1).
[a]¹H NMR (400 MHz, DMSO-d6) δ 0.26 (s, 9H) 2.24 (s, 3H) 2.36-2.47 (m, 2H) 2.65-2.75 (m, 2H) 4.42-4.59 (m, 1H) 4.97 (ttd, J = 8.38, 8.38, 5.14, 5.14, 0.73 Hz, 1H) 5.31 (d, J = 4.89 Hz, 1H).

Preparation 207 tert-Butyl 4-[4-(ethoxycarbonyl)-5-methyl-1,2,3-triazol-1-yl]piperidine-1-carboxylate

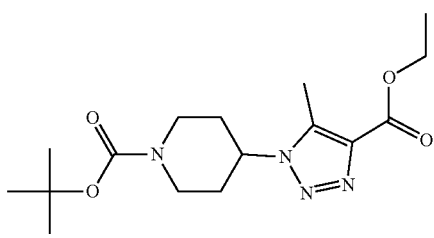 [SMILES: CCOC(=O)c1nnn(C2CCN(C(=O)OC(C)(C)C)CC2)c1C]

$K_2CO_3$ (414.00 mg, 3.00 mmol) is added in portions to a stirred solution of tert-butyl 4-azidopiperidine-1-carboxylate (226.00 mg, 1.00 mmol) and EAA (130.00 mg, 1.20 mmol) in DMSO (5.00 mL) at RT under $N_2$. The mixture is stirred for 6 hrs at 80° C. under $N_2$. The mixture is cooled to RT, $H_2O$ (10 mL) is added, and the mixture is extracted with EtOAc (3×30 mL). The combined organic extracts are washed with brine (2×20 mL), dried over anhydrous $Na_2SO_4$, filtered, and the filtrate is concentrated under reduced pressure. The residue is purified by silica gel column chromatography, eluting with a gradient of PE:EtOAc (10:1 to 0:1) to give the title compound as a yellow oil (330 mg, 66.80). ES/MS m/z 339.3 [M+H]⁺.

The following compounds are prepared essentially as described for tert-butyl 4-[4-(ethoxycarbonyl)-5-methyl-1,2,3-triazol-1-yl]piperidine-1-carboxylate using the appropriate reagents and adjusting the reaction times to determine completion of the reactions. DMF can also be used as the solvent. Temperature is varied from RT to 80° C.

TABLE 25

| Prep No. | Chemical Name | Structure | ES/MS m/z [M + H]+ |
|---|---|---|---|
| 208 | Ethyl 1-[1-(tert-butoxycarbonyl)azetidin-3-yl]-5-methyl-1,2,3-triazole-4-carboxylate | 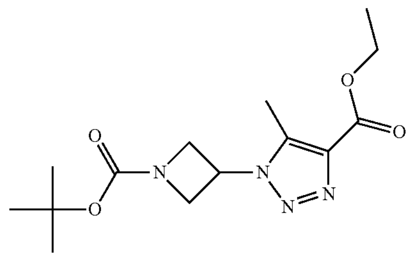 [SMILES: CCOC(=O)c1nnn(C2CN(C(=O)OC(C)(C)C)C2)c1C] | 311.2 |
| 209[1] | Ethyl 1-[(3R)-1-(tert-butoxycarbonyl)pyrrolidin-3-yl]-5-methyl-1,2,3-triazole-4-carboxylate | 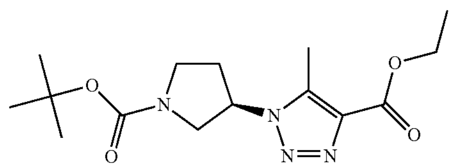 [SMILES: CCOC(=O)c1nnn([C@@H]2CCN(C(=O)OC(C)(C)C)C2)c1C] | 325.3 |
| 210[1] | Ethyl 1-[(3S)-1-(tert-butoxycarbonyl)pyrrolidin-3-yl]-5-methyl-1,2,3-triazole-4-carboxylate | 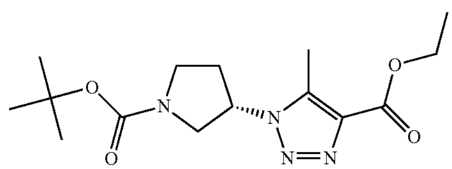 [SMILES: CCOC(=O)c1nnn([C@H]2CCN(C(=O)OC(C)(C)C)C2)c1C] | 325.1 |
| 211 | tert-Butyl 2-(4-ethoxycarbonyl-5-methyl-triazol-1-yl)-7-azaspiro[3.5]nonane-7-carboxylate | 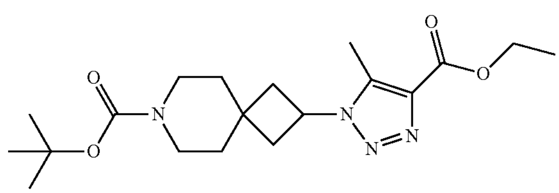 [SMILES: CCOC(=O)c1nnn(C2CC3(CCN(C(=O)OC(C)(C)C)CC3)C2)c1C] | a |
| 212 | tert-Butyl 4-(4-ethoxycarbonyl-5-methyl-triazol-1-yl)azepane-1-carboxylate | 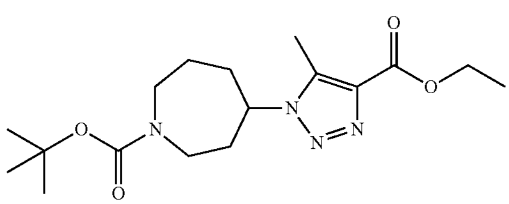 [SMILES: CCOC(=O)c1nnn(C2CCCN(C(=O)OC(C)(C)C)CC2)c1C] | 353.2 |
| 213[2] | tert-Butyl (3S)-3-(4-ethoxycarbonyl-5-methyl-triazol-1-yl)piperidine-1-carboxylate | 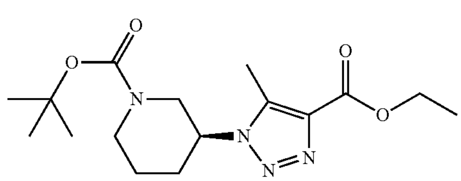 [SMILES: CCOC(=O)c1nnn([C@H]2CCCN(C(=O)OC(C)(C)C)C2)c1C] | 339.3 |
| 214 | tert-Butyl 4-(4-ethoxycarbonyl-5-methyl-triazol-1-yl)azepane-1-carboxylate | 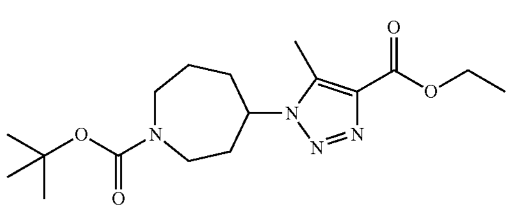 [SMILES: CCOC(=O)c1nnn(C2CCCN(C(=O)OC(C)(C)C)CC2)c1C] | 353.2 |

TABLE 25-continued

| Prep No. | Chemical Name | Structure | ES/MS m/z [M + H]+ |
|---|---|---|---|
| 215[3] | tert-Butyl (3R)-3-(4-ethoxycarbonyl-5-methyl-triazol-1-yl)piperidine-1-carboxylate | 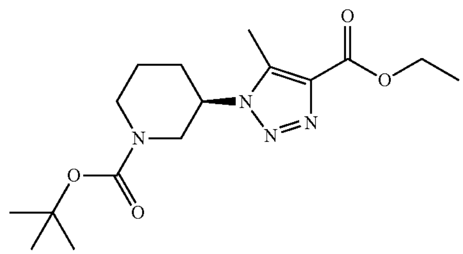 [SMILES: CCOC(=O)c1nnn([C@@H]2CCCN(C(=O)OC(C)(C)C)C2)c1C] | 339.1 |
| 216[4,2] | Cis-Ethyl 1-(3-benzyloxycyclobutyl)-5-methyl-triazole-4-carboxylate | 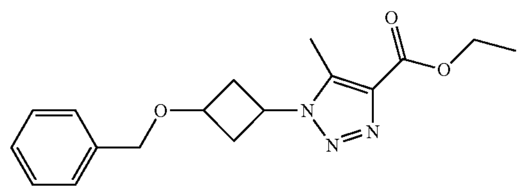 [SMILES: CCOC(=O)c1nnn(C2CC(OCc3ccccc3)C2)c1C] | b |
| 217 | tert-Butyl 4-[2-(4-ethoxycarbonyl-5-methyl-triazol-1-yl)-1,1-dimethyl-ethyl]piperazine-1-carboxylate | 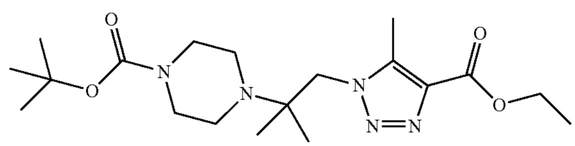 [SMILES: CCOC(=O)c1nnn(CC(C)(C)N2CCN(C(=O)OC(C)(C)C)CC2)c1C] | 396.4 |
| 218[6] | tert-Butyl (2SR,4RS)-2-cyclopropyl-4-(4-ethoxycarbonyl-5-methyl-triazol-1-yl)piperidine-1-carboxylate | 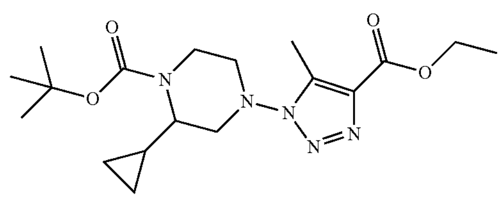 [SMILES: CCOC(=O)c1nnn(N2CCN(C(=O)OC(C)(C)C)C(C3CC3)C2)c1C] | 379.3 |

[1] The mixture is filtered, the filter cake is washed with DCM (3 × 50 mL), and the filtrate is concentrated under reduced pressure.
[2] Purified by silica gel column chromatography, eluting with PE:EtOAc (1:1).
[3] Purified by silica gel column chromatography, eluting with PE:EtOAc (10:1 to 2:1).
[4] DMF used as solvent.
[5] Purified by silica gel column chromatography, eluting with PE:EtOAc (2:1 to 1:1).
[6] Reverse flash chromatography: Column, C18, 55% to 60% ACN in H$_2$O (0.1% NH$_4$HCO$_3$).
a[1]H NMR (400 MHz, CDCl$_3$) δ 4.86-4.73 (m, 1H), 4.49-4.38 (m, 2H), 3.47-3.40 (m, 2H), 3.38-3.30 (m, 2H), 2.67-2.58 (m, 2H), 2.57-2.47 (m, 5H), 1.76-1.64 (m, 4H), 1.46 (s, 9H), 1.44-1.39 (m, 3H).
b[1]H NMR (300 MHz, DMSO-d6) δ 7.43-7.25 (m, 5H), 5.22-4.99 (m, 1H), 4.50-4.37 (m, 3H), 4.30 (q, 2H), 2.88-2.75 (m, 2H), 2.70-2.58 (m, 2H), 2.47 (s, 3H), 1.30 (t, 3H).

Preparation 219

1-[1-(tert-Butoxycarbonyl)piperidin-4-yl]-5-methyl-1,2,3-triazole-4-carboxylic Acid

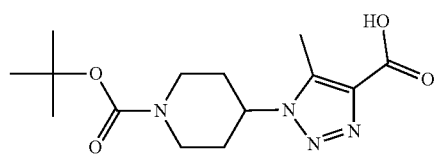

A solution of tert-butyl 4-[4-(ethoxycarbonyl)-5-methyl-1,2,3-triazol-1-yl]piperidine-1-carboxylate (300.00 mg, 0.890 mmol) and KOH (100.00 mg, 1.780 mmol) in H$_2$O (5.00 mL) is stirred for 2 hrs at 50° C. under N$_2$. The mixture is acidified to a pH of 4 with HCl (aq.) (1N) at 0° C. and extracted with EtOAc (3×30 mL). The combined organic extracts are washed with brine (2×15 mL), dried over anhydrous Na$_2$SO$_4$, filtered, and the filtrate is concentrated under reduced pressure to give the title compound as a yellow oil (250 mg, 900%). ES/MS m/z 311.3 [M+H]+.

The following compounds are prepared essentially as described for 1-[1-(tert-butoxycarbonyl)piperidin-4-yl]-5-methyl-1,2,3-triazole-4-carboxylic acid using the appropriate reagents and adjusting the reaction times to determine completion of the reactions. The solvent can be DMSO and the base can be NaOH.

TABLE 26

| Prep No. | Chemical Name | Structure | ES/MS m/z [M + H]+ |
|---|---|---|---|
| 220 | 1-[1-(tert-Butoxycarbonyl)azetidin-3-yl]-5-methyl-1,2,3-triazole-4-carboxylic acid | 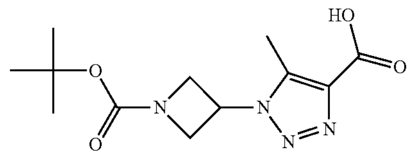 [SMILES: Cc1c(C(=O)O)nnn1C1CN(C(=O)OC(C)(C)C)C1] | 283.1 |
| 221 | 1-[(3R)-1-(tert-Butoxycarbonyl)pyrrolidin-3-yl]-5-methyl-1,2,3-triazole-4-carboxylic acid | 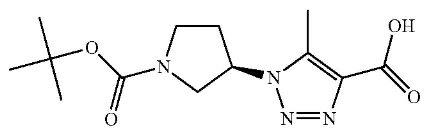 [SMILES: Cc1c(C(=O)O)nnn1[C@@H]1CCN(C(=O)OC(C)(C)C)C1] | 297.2 |
| 222[1] | 1-[(3S)-1-(tert-Butoxycarbonyl)pyrrolidin-3-yl]-5-methyl-1,2,3-triazole-4-carboxylic acid | 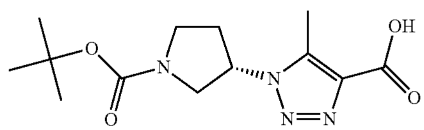 [SMILES: Cc1c(C(=O)O)nnn1[C@H]1CCN(C(=O)OC(C)(C)C)C1] | 241.0 |
| 223 | 1-(1-tert-Butoxycarbonylazepan-4-yl)-5-methyl-triazole-4-carboxylic acid | 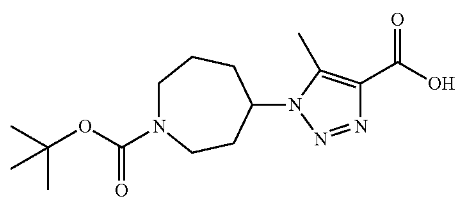 [SMILES: Cc1c(C(=O)O)nnn1C1CCCN(C(=O)OC(C)(C)C)CC1] | 325.2 |
| 224 | 1-[(3S)-1-tert-Butoxycarbonyl-3-piperidyl]-5-methyl-triazole-4-carboxylic acid | 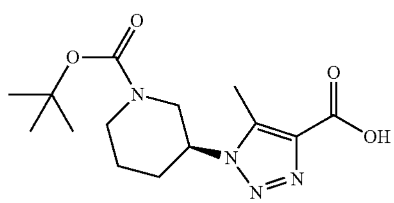 [SMILES: Cc1c(C(=O)O)nnn1[C@H]1CCCN(C(=O)OC(C)(C)C)C1] | 311.3 |
| 225 | 1-[(3R)-1-tert-Butoxycarbonyl-3-piperidyl]-5-methyl-triazole-4-carboxylic acid | 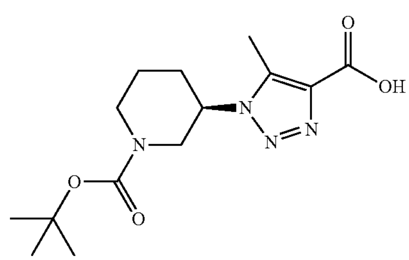 [SMILES: Cc1c(C(=O)O)nnn1[C@@H]1CCCN(C(=O)OC(C)(C)C)C1] | 311.2 |
| 226 | Cis-1-(3-Benzyloxy cyclobutyl)-5-methyl-triazole-4-carboxylic acid | 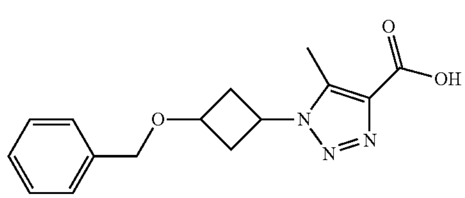 [SMILES: Cc1c(C(=O)O)nnn1C1CC(OCc2ccccc2)C1] | 288.3 |
| 227 | 1-[2-(4-tert-Butoxycarbonylpiperazin-1-yl)-2-methyl-propyl]-5-methyl-triazole-4-carboxylic acid | 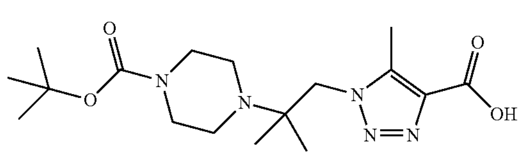 [SMILES: Cc1c(C(=O)O)nnn1CC(C)(C)N1CCN(C(=O)OC(C)(C)C)CC1] | 368.3 |

TABLE 26-continued

| Prep No. | Chemical Name | Structure | ES/MS m/z [M + H]+ |
|---|---|---|---|
| 228 | 1-[(2SR,4RS)-1-tert-butoxycarbonyl-2-cyclopropyl-4-piperidyl]-5-methyl-triazole-4-carboxylic acid | 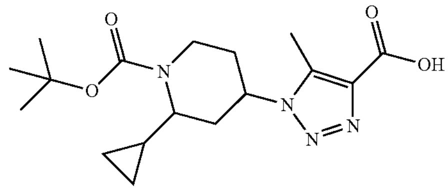 [SMILES: Cc1c(C(=O)O)nnn1C1CCN(C(=O)OC(C)(C)C)C(C2CC2)C1] | 351.2 |

[1] Precipitated solids are collected by filtration, washed with H₂O (3 × 20 mL), and dried in vacuo.

Preparation 229 tert-Butyl 4-[4-bromo-3-(2-hydroxyethyl)-5-methyl-pyrazol-1-yl]piperidine-1-carboxylate

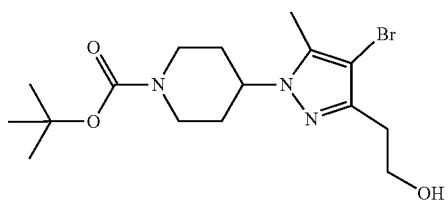 [SMILES: Cc1c(Br)c(CCO)nn1C1CCN(C(=O)OC(C)(C)C)CC1]

To a solution of tert-butyl 4-[4-bromo-3-(2-methoxy-2-oxo-ethyl)-5-methyl-pyrazol-1-yl]piperidine-1-carboxylate (390 mg, 0.94 mmol) in MeOH (5 mL) is added LiBH₄ (24.49 mg, 1.12 mmol) at 0° C. under N₂. The reaction is stirred 1 hr at RT, cooled to 0° C. and quenched with H₂O (10 mL). The mixture is extracted with EtOAc (3×20 mL). The organic layers are combined, washed with brine (2×10 mL), dried over Na₂SO₄, and filtered. The filtrate is concentrated in vacuo to afford the title compound (350 mg, 96.22%) as a yellow oil. ES/MS m/z (⁷⁹Br/⁸¹Br) 388.1/390.1 [M+H]⁺.

Preparation 230

7-Chloro-5-[[(1R)-1-(5-fluoro-2-pyridyl)ethyl]amino]imidazo[1,2-a]pyridine-3-carbonitrile

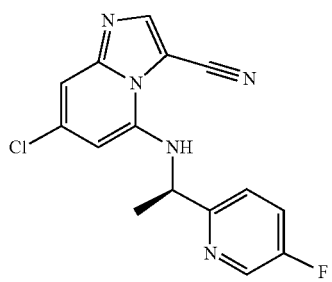 [SMILES: C[C@@H](Nc1cc(Cl)cc2ncc(C#N)n12)c1ccc(F)cn1]

To 5,7-dichloroimidazo[1,2-a]pyridine-3-carbonitrile (600 mg, 2.83 mmol) and (1R)-1-(5-fluoropyridin-2-yl)ethanamine hydrochloride (749.7 mg, 4.25 mmol) in toluene (10 mL) is added Cs₂CO₃ (5532 mg, 16.98 mmol), BINAP (176.2 mg, 0.28 mmol) and Pd(AcO)₂ (4.33 mg, 0.005 mmol) at RT under N₂. The reaction is stirred for 2 hr at 100° C. Upon cooling to RT, the reaction is concentrated in vacuo. The residue is purified by silica gel column chromatography, eluting with PE/EtOAc (5:1 to 1:3), to afford the title compound as a yellow solid (250 mg, 28%). ES/MS m/z 316.1 [M+H]⁺.

Preparation 231

7-Chloro-5-methoxyimidazo[1,2-a]pyridine

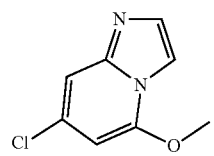

A solution of 4-chloro-6-methoxypyridin-2-amine (7.00 g, 44.14 mmol), chloroacetaldehyde (8.32 g, 52.99 mmol, 50%) and NaHCO₃ (11.12 g, 132.42 mmol) in n-butanol (140.00 mL) is divided into fourteen batches and stirred overnight at 65° C. in sealed tubes. The solution is cooled to RT, diluted with H₂O (200 mL) and extracted with EtOAc (3×200 mL). The organic extracts are dried over anhydrous Na₂SO₄ and concentrated under reduced pressure. The crude product is purified by silica gel chromatography (PE:EtOAc 1:1) to give the title compound as a light-brown solid (6.1 g, 75.68%). ES/MS m/z 183.10 [M+H]⁺.

The following compound is prepared essentially as described for 7-Chloro-5-methoxyimidazo[1,2-a]pyridine using the appropriate reagents and adjusting the reaction time to determine completion of the reactions.

TABLE 27

| Prep No. | Chemical Name | Structure | ES/MS m/z [M + H]+ |
|---|---|---|---|
| 232 | 6-Bromo-3-fluoro-pyrazolo[1,5-a]pyridin-4-ol | 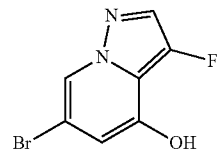 [SMILES: Oc1cc(Br)cn2ncc(F)c12] | (79Br/81Br) 231.0/233.0 |

Preparation 233

7-Chloroimidazo[1,2-a]pyridin-5-ol

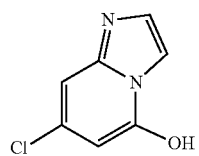 [SMILES: Oc1cc(Cl)cc2nccn12]

A mixture of 7-chloro-5-methoxyimidazo[1,2-a]pyridine (2.00 g, 10.95 mmol), NaOH (50% in H₂O) (1.31 g, 16.43 mmol) and NDM (3.33 g, 16.43 mmol) in DMA (10.00 mL) is stirred for 2 hrs at 50° C. under N₂. The mixture is diluted with H₂O (100 mL), acidified to pH 4-5 with 1 M HCl to give precipitated solids that are collected by filtration and washed with PE (3×100 mL), H₂O (3×10 mL), and dried in vacuo to give the title compound as a light-yellow solid (1.5 g, 81.24%). ES/MS m/z 169.2 [M+H]+.

Preparation 234 tert-Butyl-[2-(7-chloroimidazo[1,2-a]pyridin-5-yl)oxy-2-(5-fluoro-2-pyridyl)ethoxy]-dimethyl-silane

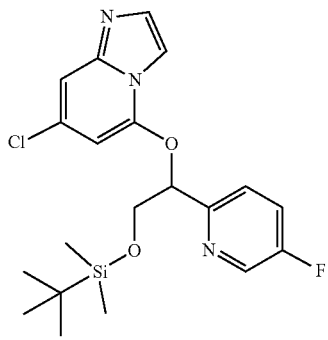 [SMILES: CC(C)(C)[Si](C)(C)OCC(Oc1cc(Cl)cc2nccn12)c1ccc(F)cn1]

To 2-[(tert-butyldimethylsilyl)oxy]-1-(5-fluoropyridin-2-yl)ethanol (6.53 g, 24.06 mmol) in THF (50.00 mL) is added 60% NaH (0.96 g, 24.06 mmol) at 0° C. under N₂. After being stirred at 0° C. for 0.5 hr, 5,7-dichloroimidazo[1,2-a]pyridine (3 g, 16.04 mmol) is added to the mixture. The reaction is stirred at RT for 2 hr under N₂. The reaction is quenched with H₂O (50 mL) then extracted with EtOAc (2×50 mL). The combined organic layers are washed with brine (2×50 mL), dried over Na₂SO₄, filtered, and concentrated in vacuo. The residue is purified by silica gel column chromatography, eluting with PE/EtOAc (5:1 to 4:1) to afford the title compound as a brown solid (2.5 g, 36.93%). ES/MS m/z 422.2. [M+H]+.

The following compounds are prepared essentially as described for tert-butyl-[2-(7-chloroimidazo[1,2-a]pyridin-5-yl)oxy-2-(5-fluoro-2-pyridyl)ethoxy]-dimethyl-silane using the appropriate reagents and adjusting the reaction time to determine completion of the reactions.

TABLE 28

| Prep No. | Chemical Name | Structure | ES/MS m/z [M + H]+ |
|---|---|---|---|
| 235[1] | 7-Chloro-5-[(5-fluoro-2-pyridyl)-(1-methoxycyclopropyl)methoxy]imidazo[1,2-a]pyridine-3-carbonitrile | 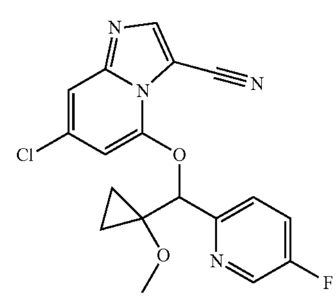 [SMILES: COC1(C(Oc2cc(Cl)cc3ncc(C#N)n23)c2ccc(F)cn2)CC1] | 373.1 |

TABLE 28-continued

| Prep No. | Chemical Name | Structure | ES/MS m/z [M + H]+ |
|---|---|---|---|
| 236[2] | [2-(6-Bromo-3-fluoro-pyrazolo[1,5-a]pyridin-4-yl)oxy-2-(5-fluoro-2-pyridyl)ethoxy]-tert-butyl-dimethyl-silane | 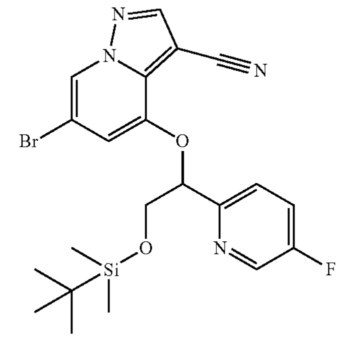 [SMILES: CC(C)(C)[Si](C)(C)OCC(Oc1cc(Br)cn2ncc(C#N)c12)c1ccc(F)cn1] | ([79]Br/[81]Br) 484.1/486.1 |

[1]Purified by silica gel column chromatography, eluting with PE:EtOAc (10:1 to 5:1).
[2]Purified by reverse phase chromatography: Column, C18; eluting with 0% to 100% ACN in H2O (0.1% NH3•H2O).

Preparation 237

6-Bromo-4-[(1R)-1-(pyridin-2-yl)ethoxy]pyrazolo[1,5-a]pyridine-3-carbonitrile

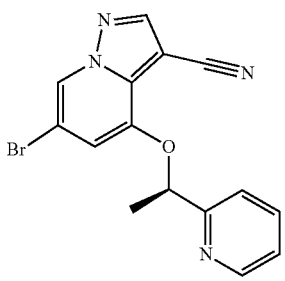 [SMILES: C[C@@H](Oc1cc(Br)cn2ncc(C#N)c12)c1ccccn1]

A solution of 6-bromo-4-hydroxypyrazolo[1,5-a]pyridine-3-carbonitrile (2.00 g, 8.40 mmol), (1S)-1-(pyridin-2-yl)ethanol (1.14 g, 9.24 mmol) and PPh₃ (2.64 g, 10.08 mmol) in THF (20.0 mL) is stirred for 10 min at RT under N₂. DEAD (1.76 g, 10.08 mmol) is added dropwise to the mixture over 10 min at RT. After the mixture is stirred for an additional 2 hrs at RT, it is concentrated under reduced pressure. The residue is purified by silica gel column chromatography, eluting with a gradient of PE:EtOAc (PE-3:1) to give the title compound as a green oil (1.48 g, 51.3%). ES/MS m/z 343.0/345.0 [M+H]+.

The following compounds are prepared essentially as described for 6-bromo-4-[(1R)-1-(pyridin-2-yl)ethoxy]pyrazolo[1,5-a]pyridine-3-carbonitrile using the appropriate reagents and adjusting the reaction times to determine completion of the reactions. Temperature is varied from 0° C. to RT.

TABLE 29

| Prep No. | Chemical Name | Structure | ES/MS m/z [M + H]+ |
|---|---|---|---|
| 238 | 6-Bromo-4-[(1S)-1-(pyridin-2-yl)ethoxy]pyrazolo[1,5-a]pyridine-3-carbonitrile | 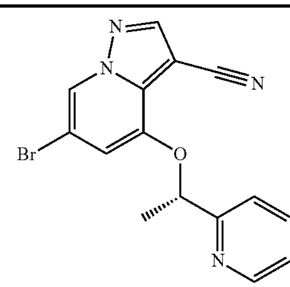 | 343.0/345.0 |
| 239 | 7-Chloro-5-[(1R)-1-(pyridin-2-yl)ethoxy]imidazo[1,2-a]pyridine | 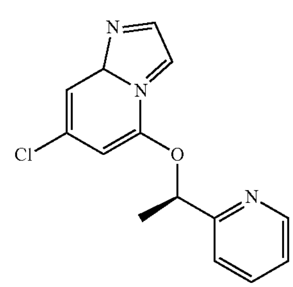 | 274.0 |

TABLE 29-continued

| Prep No. | Chemical Name | Structure | ES/MS m/z [M + H]+ |
|---|---|---|---|
| 240 | 6-Bromo-4-[(1R)-1-cyclobutylethoxy]pyrazolo[1,5-a]pyridine-3-carbonitrile | 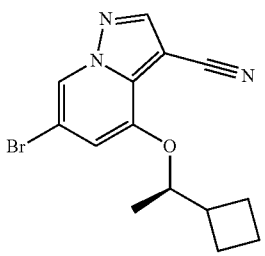 [SMILES: C[C@@H](Oc1cc(Br)cn2ncc(C#N)c12)C1CCC1] | 320.1/322.1 |
| 241 | 6-Bromo-4-[(1R)-1-cyclopropylethoxy]pyrazolo[1,5-a]pyridine-3-carbonitrile | 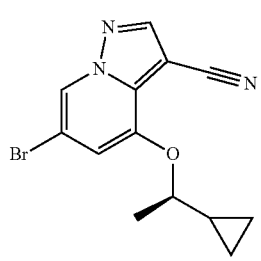 [SMILES: C[C@@H](Oc1cc(Br)cn2ncc(C#N)c12)C1CC1] | a |
| 242 | 6-Bromo-4-[(1R)-1-phenylethoxy]pyrazolo[1,5-a]pyridine-3-carbonitrile | 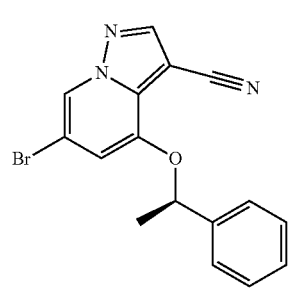 [SMILES: C[C@@H](Oc1cc(Br)cn2ncc(C#N)c12)c1ccccc1] | 341.8/343.8 |
| 243 | 7-Chloro-5-[(1R)-1-(5-fluoro-2-pyridyl)ethoxy]imidazo[1,2-a]pyridine | 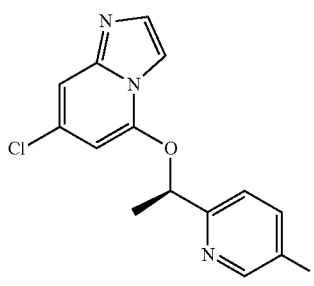 | 292.0 |
| 244[1] | [2-(6-Bromopyrazolo[1,5-a]pyridin-4-yl)oxy-2-(5-fluoro-2-pyridyl)ethoxy]-tert-butyl-dimethyl-silane, Isomer 2 | 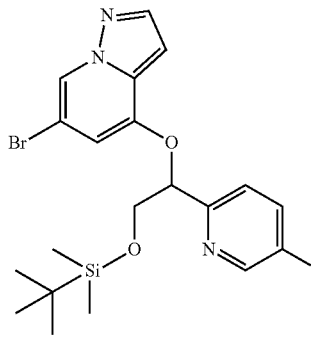 | 468.0 |

[1]Purified by silica gel chromatography, eluting with PE:EtOAc (15:1 to 10:1).

a$^1$H NMR (300 MHz, CDCl$_3$) δ 8.32 (d, 1H), 8.15 (s, 1H), 6.75 (d, 1H), 4.22-4.12 (m, 1H), 1.53 (d, 3H), 1.35-1.27 (m, 1H), 0.75-0.60 (m, 2H), 0.60-0.36 (m, 2H).

Preparation 245 tert-Butyl (3R,4S)-4-(4-bromo-5-methyl-triazol-1-yl)-3-fluoro-piperidine-1-carboxylate

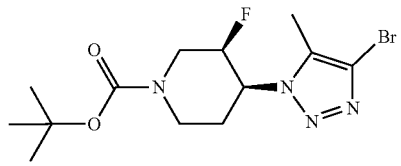 [SMILES: Cc1c(Br)nnn1[C@H]1CCN(C(=O)OC(C)(C)C)C[C@H]1F]

To tert-butyl (3R,4S)-3-fluoro-4-(5-methyl-4-trimethylsilyl-triazol-1-yl)piperidine-1-carboxylate (1.5 g) and $SiO_2$ (505.58 mg, 8.41 mmol) in ACN (15 mL) is added NBS (2.00 g, 11.22 mmol) at RT under $N_2$. The reaction is stirred for 2 hr at 80° C. Upon cooling to RT, the reaction is quenched with $H_2O$. The suspension is filtered and washed with EtOAc (2×5 mL). The filtrate is extracted with EtOAc (2×100 mL). The combined organic layers are washed with brine (2×100 mL), dried over $Na_2SO_4$, filtered, and concentrated in vacuo. The residue is purified by silica gel chromatography eluting with PE:EA (3:1) to afford the title compound (1.3 g, 85.1%) as a white solid. ES/MS m/z ($^{79}Br/^{81}Br$) 363.0/365.0 $[M+H]^+$.

The following compounds are prepared essentially as described for tert-butyl (3R,4S)-4-(4-bromo-5-methyl-triazol-1-yl)-3-fluoro-piperidine-1-carboxylate using the appropriate reagents, adjusting the reaction times to determine completion of the reactions, and adjusting the purification system as appropriate.

TABLE 30

| Prep No. | Chemical Name | Structure | ES/MS m/z $[M + H]^+$ |
|---|---|---|---|
| 246[1] | tert-Butyl (3S,4S)-4-(4-bromo-5-methyl-triazol-1-yl)-3-fluoro-piperidine-1-carboxylate | 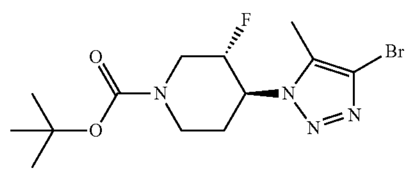 | ($^{79}Br/^{81}Br$) 363.0/365.0 |
| 247[2] | tert-Butyl (3S,4R)-4-(4-bromo-5-methyl-triazol-1-yl)-3-fluoro-piperidine-1-carboxylate | 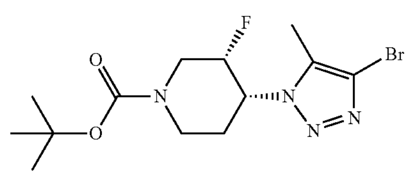 | ($^{79}Br/^{81}Br$) 404.0/406.0 $[M + H + ACN]^+$ |
| 248[1] | tert-Butyl (3R,4R)-4-(4-bromo-5-methyl-triazol-1-yl)-3-fluoro-piperidine-1-carboxylate | 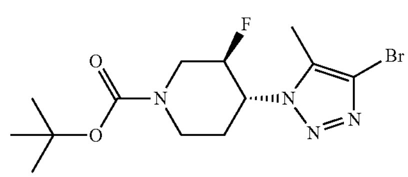 [SMILES: Cc1c(Br)nnn1[C@@H]1CCN(C(=O)OC(C)(C)C)C[C@H]1F] | ($^{79}Br/^{81}Br$) 363.1/364.9 |
| 249[3] | (1r,3r)-3-(4,5-dimethyl-1H-1,2,3-triazol-1-yl)cyclobutan-1-ol | 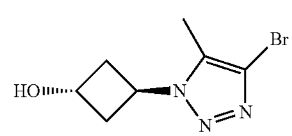 | a |
| 250[1] | tert-Butyl (3S,4S)-4-(4-bromo-5-methyl-triazol-1-yl)-3-hydroxy-piperidine-1-carboxylate | 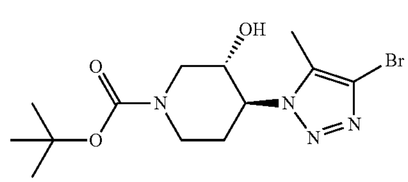 [SMILES: Cc1c(Br)nnn1[C@H]1CCN(C(=O)OC(C)(C)C)C[C@@H]1O] | ($^{79}Br/^{81}Br$) 361.08/363.0 |
| 251[1] | tert-Butyl (3R,4S)-4-(4-bromo-5-methyl-triazol-1-yl)-3-hydroxy-piperidine-1-carboxylate | 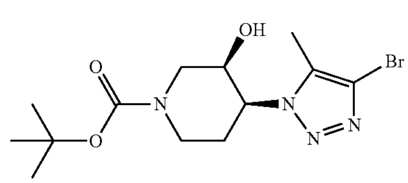 [SMILES: Cc1c(Br)nnn1[C@H]1CCN(C(=O)OC(C)(C)C)C[C@H]1O] | ($^{79}Br/^{81}Br$) 361.08/363.0 |

TABLE 30-continued

| Prep No. | Chemical Name | Structure | ES/MS m/z [M + H]+ |
|---|---|---|---|
| 252[1] | tert-Butyl (3S,4R)-4-(4-bromo-5-methyl-triazol-1-yl)-3-hydroxy-piperidine-1-carboxylate | 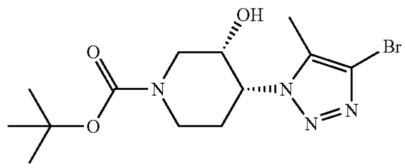 | ($^{79}$Br/$^{81}$Br) 361.1/363.1 |
| 253[4] | tert-butyl (3R,4R)-4-(4-bromo-5-methyl-triazol-1-yl)-3-hydroxy-piperidine-1-carboxylate | 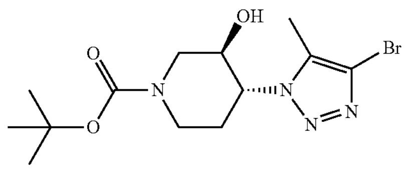 | ($^{79}$Br/$^{81}$Br) 361.1/363.1 |
| 254[4] | tert-butyl (3RS,4RS)-4-(4-bromo-5-methyl-triazol-1-yl)-3-methyl-piperidine-1-carboxylate | 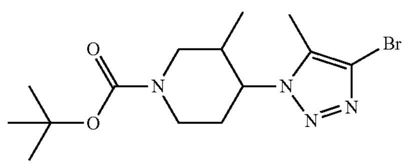 [SMILES: Cc1c(Br)nnn1C1CCN(C(=O)OC(C)(C)C)CC1C] | ($^{79}$Br/$^{81}$Br) 359.1/361.1 |
| 255[5] | tert-butyl (3RS,4SR)-4-(4-bromo-5-methyl-trazol-1-yl)-3-methyl-piperidine-1-carboxylate | 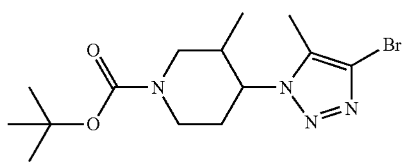 [SMILES: Cc1c(Br)nnn1C1CCN(C(=O)OC(C)(C)C)CC1C] | ($^{79}$Br/$^{81}$Br) 359.1, 361.1 |

[1]Purified by silica gel chromatography, eluting with PE:EA (4:1).
[2]Purified by silica gel chromatography, eluting with PE:EA (3:1).
[3]Purified by silica gel chromatography eluting with 0% to 100% EA in heptane.
[4]Purified by silica gel chromatography, eluting with PE:EA (5:1).
[5]Purified by silica gel chromatography, eluting with PE:EA (5:1 to 4:1).
a[1]H NMR (400 MHz, DMSO-d6) δ 2.20 (s, 3H) 2.37-2.47 (m, 2H) 2.69-2.77 (m, 2H) 4.41-4.49 (m, 1H) 4.99-5.09 (m, 1H) 5.09-5.67 (m, 1H).

Preparation 256 tert-Butyl 2-(4-bromo-5-methyl-triazol-1-yl)-7-azaspiro[3.5]nonane-7-carboxylate

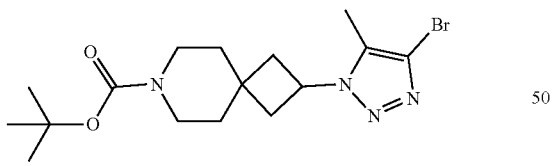

To tert-butyl 2-[4-(ethoxycarbonyl)-5-methyl-1,2,3-triazol-1-yl]-7-azaspiro[3.5]nonane-7-carboxylate (11.1 g, 29.3 mmol.) in H$_2$O (100 mL) is added KOH (6.59 g, 117.3 mmol) at RT under N$_2$. The reaction is stirred for 2 hr at 50° C. The reaction mixture is used in the next step directly without further purification.

To 1-(7-tert-butoxycarbonyl-7-azaspiro[3.5]nonan-2-yl)-5-methyl-triazole-4-carboxylic acid is added Br$_2$ (6.95 g, 43.99 mmol) dropwise at RT under N$_2$. The reaction is stirred for 1 hr at RT then extracted with EtOAc (2×100 mL). The combined organic layers are washed with sat. Na$_2$S$_2$O$_3$ (100 mL), brine (100 mL), dried over Na$_2$SO$_4$, filtered and concentrated to afford the title compound as a white solid (8.7 g, 75.35%). $^1$H NMR (400 MHz, CDCl$_3$) δ 4.84-4.69 (m, 1H), 3.50-3.40 (m, 2H), 3.38-3.30 (m, 2H), 2.62-2.54 (m, 2H), 2.53-2.44 (m, 2H), 2.24 (s, 3H), 1.77-1.62 (m, 4H), 1.46 (s, 9H).

Preparation 257 tert-Butyl 4-(4-bromo-5-methyl-1,2,3-triazol-1-yl)piperidine-1-carboxylate

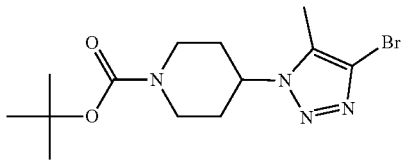 [SMILES: Cc1c(Br)nnn1C1CCN(C(=O)OC(C)(C)C)CC1]

Br$_2$ (154.00 mg, 0.96 mmol) is added in portions to a stirred solution of 1-[1-(tert-butoxycarbonyl)piperidin-4-yl]-5-methyl-1,2,3-triazole-4-carboxylic acid (248 mg, 0.80 mmol) and KOH (54.00 mg, 0.96 mmol) in H$_2$O (6 mL) and the mixture is stirred for 3 hrs at RT under N$_2$. A precipitate results, and the mixture is extracted with EtOAc (3×30 mL).

The combined organic extracts are washed with brine (2×15 mL), dried over anhydrous Na$_2$SO$_4$, filtered, and the filtrate is concentrated under reduced pressure to give the title compound as a yellow solid (190 mg, 690%). ES/MS m/z ($^{79}$Br/$^{81}$Br) 345.2/347.2 [M+H]$^+$, which is used directly without further purification.

The following compounds are prepared essentially as described for tert-butyl 4-(4-bromo-5-methyl-1,2,3-triazol-1-yl)piperidine-1-carboxylate using the appropriate reagents and adjusting the reaction times to determine completion of the reactions. Temperature is varied from 0° C. to RT. HBr/AcOH can be used as the solvent.

TABLE 31

| Prep No. | Chemical Name | Structure | ES/MS m/z ($^{79}$Br/$^{81}$Br) [M + H]$^+$ |
|---|---|---|---|
| 258 | tert-Butyl 3-(4-bromo-5-methyl-1,2,3-triazol-1-yl)azetidine-1-carboxylate | 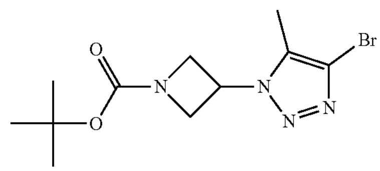 [SMILES: Cc1c(Br)nnn1C1CN(C(=O)OC(C)(C)C)C1] | 317.1/ 319.1 |
| 259 | tert-Butyl (3R)-3-(4-bromo-5-methyl-1,2,3-triazol-1-yl)pyrrolidine-1-carboxylate | 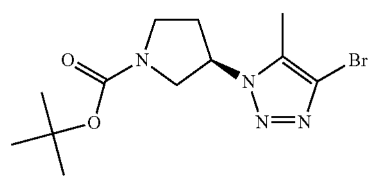 [SMILES: Cc1c(Br)nnn1[C@@H]1CCN(C(=O)OC(C)(C)C)C1] | 331.0/ 333.0 |
| 260 | tert-Butyl (3S)-3-(4-bromo-5-methyl-1,2,3-triazol-1-yl)pyrrolidine-1-carboxylate | 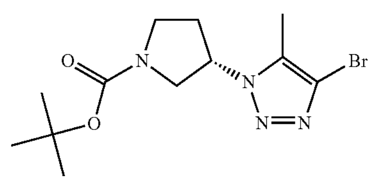 [SMILES: Cc1c(Br)nnn1[C@H]1CCN(C(=O)OC(C)(C)C)C1] | 331.1/ 333.1 |
| 261[1] | tert-Butyl 4-(4-bromo-5-methyl-triazol-1-yl)azepane-1-carboxylate | 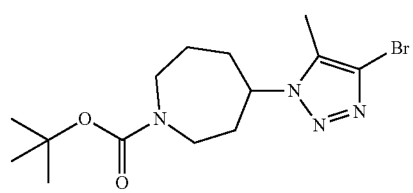 [SMILES: Cc1c(Br)nnn1C1CCCN(C(=O)OC(C)(C)C)CC1] | 359.1/ 361.1 |
| 262 | tert-Butyl (3S)-3-(4-bromo-5-methyl-triazol-1-yl)piperidine-1-carboxylate | 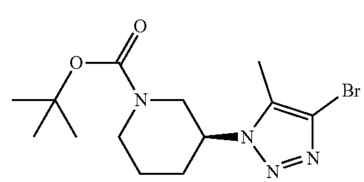 [SMILES: Cc1c(Br)nnn1[C@H]1CCCN(C(=O)OC(C)(C)C)C1] | 345.2/ 347.2 |
| 263 | tert-Butyl (3R)-3-(4-bromo-5-methyl-triazol-1-yl)piperidine-1-carboxylate | 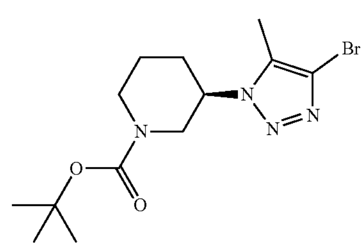 [SMILES: Cc1c(Br)nnn1[C@@H]1CCCN(C(=O)OC(C)(C)C)C1] | 345.0/ 347.0 |
| 264[3] | Cis-1-(3-Benzyloxycyclobutyl)-4-bromo-5-methyl-triazole | 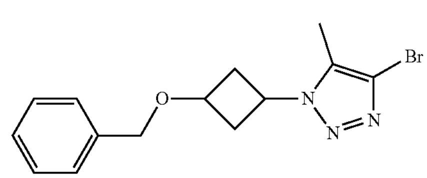 [SMILES: Cc1c(Br)nnn1C1CC(OCc2ccccc2)C1] | a |

TABLE 31-continued

| Prep No. | Chemical Name | Structure | ES/MS m/z ($^{79}$Br/$^{81}$Br) [M + H]$^+$ |
|---|---|---|---|
| 265[4] | tert-Butyl 4-[2-(4-bromo-5-methyl-triazol-1-yl)-1,1-dimethyl-ethyl]-3-oxo-piperazine-1-carboxylate | 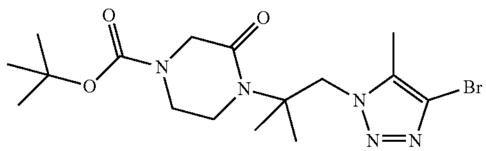 [SMILES: Cc1c(Br)nnn1CC(C)(C)N1CCN(C(=O)OC(C)(C)C)CC1=O] | 415.8/ 417.8 |
| 266[5] | tert-Butyl (2SR,4RS)-4-(4-bromo-5-methyl-triazol-1-yl)-2-cyclopropyl-piperidine-1-carboxylate | 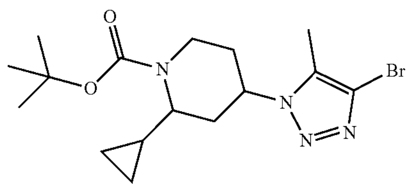 [SMILES: Cc1c(Br)nnn1C1CCN(C(=O)OC(C)(C)C)C(C2CC2)C1] | 385.1/ 387.1 |

[1]Reverse flash chromatography: Column, C18, 10% to 50% ACN in H$_2$O (0.1% NH$_4$HCO$_3$).
[2]Silica gel column chromatography eluting with PE:EtOAc (5:1).
[3]Reverse flash chromatography: Column, C18, 50% to 80% ACN in H$_2$O (0.1% FA).
[4]Reverse flash chromatography: Column, C18, 40% to 70% ACN in H$_2$O (0.1% FA).
[5]Reverse flash chromatography: Column, C18, 50% to 55% ACN in H$_2$O (0.1% NH$_4$HCO$_3$).
a[1]H NMR (400 MHz, DMSO-d6) δ 7.40-7.34 (m, 4H), 7.33-7.27 (m, 1H), 5.14-5.06 (m, 1H), 4.45 (s, 2H), 4.42-4.34 (m, 1H), 2.81-2.72 (m, 2H), 2.66-2.56 (m, 2H), 2.22 (s, 3H).

Preparation 267 tert-Butyl 4-[2-(4-bromo-5-methyl-triazol-1-yl)-1,1-dimethyl-ethyl]piperazine-1-carboxylate

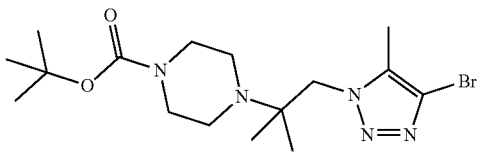 [SMILES: Cc1c(Br)nnn1CC(C)(C)N1CCN(C(=O)OC(C)(C)C)CC1]

To tert-butyl 4-[2-(4-bromo-5-methyl-triazol-1-yl)-1,1-dimethyl-ethyl]-3-oxo-piperazine-1-carboxylate (1 g, 2.40 mmol) in THF (10.00 mL) is added BH$_3$ (12.01 mL, 12.01 mol, 1M in THF) dropwise at 0° C. under N$_2$. The reaction is stirred for 2 hr at RT, cooled to 0° C. and quenched with MeOH (10 mL). The mixture is concentrated in vacuo. The residue is purified by silica gel chromatography eluting with PE:EtOAc (4:1 to 2:1) to afford the title compound (0.53 g, 54.8%) as a light yellow oil. ES/MS m/z ($^{79}$Br/$^{81}$Br) 401.8/ 403.8 [M+H]$^+$.

Preparation 268

Cis-3-(4-Bromo-5-methyl-triazol-1-yl)cyclobutanol

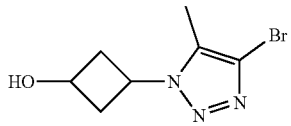

A mixture of 1-(3-benzyloxycyclobutyl)-4-bromo-5-methyl-triazole (8.5 g, 26.38 mmol) and FeCl$_3$ (8.56 g, 52.76 mmol) in DCM (100 mL) is stirred for 2 hr at 50° C. under N$_2$. Upon cooling to RT the reaction is diluted with H$_2$O (50 mL). The mixture is extracted with EtOAc (3×100 mL). The combined organic layers are washed with brine (2×100 mL), dried over Na$_2$SO$_4$ and filtered. The filtrate is concentrated in vacuo to afford the title compound (8.00 g, crude) as a brown solid. $^1$H NMR (400 MHz, DMSO-d6) δ 5.09-4.99 (m, 1H), 4.55-4.42 (m, 1H), 2.80-2.71 (m, 2H), 2.48-2.37 (m, 2H), 2.21 (s, 3H).

Preparation 269

3-(4-Bromo-5-methyl-triazol-1-yl)cyclobutanone

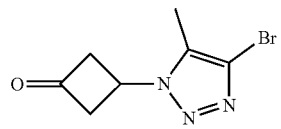

A mixture of 3-(4-bromo-5-methyl-triazol-1-yl)cyclobutanol (4.00 g, 17.23 mmol) and Dess-Martin (10.97 g, 25.85 mmol) in DCM (40 mL) is stirred for 2 hr RT under N$_2$. The mixture is diluted with H$_2$O (100 mL), extracted with EtOAc (3×100 mL), washed with brine (2×100 mL), dried over Na$_2$SO$_4$ and filtered. The filtrate is concentrated in vacuo. The residue is purified by reverse phase chromatography with the following conditions: column, C18; mobile phase, 20% to 40% ACN in H$_2$O (0.1% FA) to afford the title compound (2.10 g, 52.96%) as a white solid. ES/MS m/z ($^{79}$Br/$^{81}$Br) 229.9/231.9 [M+H]$^+$.

Preparation 270

1-Bromo-3-[(diphenylmethyl)amino]-3-methylbutan-2-one

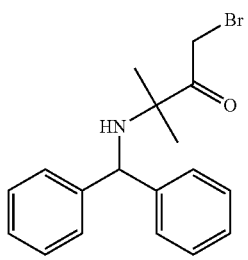 [SMILES: CC(C)(NC(c1ccccc1)c1ccccc1)C(=O)CBr]

A mixture of 3-[(diphenylmethyl)amino]-3-methylbutan-2-one (700.00 mg, 2.62 mmol) and Br$_2$ (418.39 mg, 2.62 mmol) in HBr in AcOH (40%, 6.00 mL) is stirred for 2 hrs at RT under N$_2$. The reaction is quenched with NaHCO$_3$/ice (300 mL) at 0° C. The mixture is extracted with DCM (2×300 mL). The combined organic extracts are washed with brine (1×300 mL), dried over anhydrous Na$_2$SO$_4$, filtered and the filtrate is concentrated under reduced pressure to give the title compound (800 mg) as yellow solid which is used without further purification. ES/MS m/z ($^{79}$Br/$^{81}$Br) 346.0/348.0 [M+H]$^+$.

Preparation 271

1-(Diphenylmethyl)-2,2-dimethylazetidin-3-one

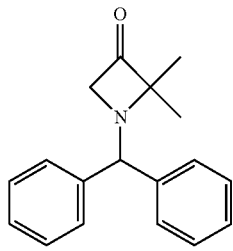 [SMILES: CC1(C)C(=O)CN1C(c1ccccc1)c1ccccc1]

A mixture of 1-bromo-3-[(diphenylmethyl)amino]-3-methylbutan-2-one (2.10 g, 6.07 mmol) and NaHCO$_3$ (764.21 mg, 9.10 mmol) in DMF (6.00 mL) and H$_2$O (1.50 mL) is stirred for 12 hours at RT under N$_2$. The mixture is diluted with EtOAc (100 mL) and washed with H$_2$O (3×80 mL). The organic layer is washed with brine (2×80 mL), dried over anhydrous Na$_2$SO$_4$, filtered, and the filtrate is concentrated under reduced pressure. The residue is purified by reverse Combi-flash chromatography with the following conditions: Column, C18; eluting with a gradient of 24% to 27% ACN in H$_2$O to give the title compound as a yellow solid (1.30 g, 75.4%). ES/MS m/z 284.3 [M+H$_2$O+H]$^+$.

Preparation 272

6-(1-[1-[1-(Diphenylmethyl)-2,2-dimethylazetidin-3-yl]piperidin-4-yl]-5-methylpyrazol-4-yl)-4-methoxypyrazolo[1,5-a]pyridine-3-carbonitrile

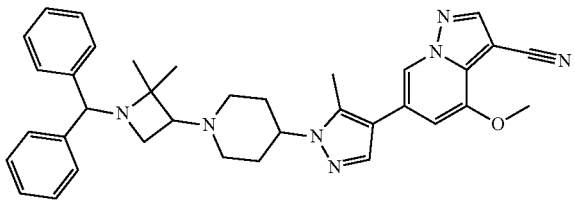 [SMILES: COc1cc(-c2cnn(C3CCN(C4CN(C(c5ccccc5)c5ccccc5)C4(C)C)CC3)c2C)cn2ncc(C#N)c12]

A mixture of 4-methoxy-6-[5-methyl-1-(piperidin-4-yl)pyrazol-4-yl]pyrazolo[1,5-a]pyridine-3-carbonitrile (300.00 mg, 0.89 mmol), 1-(phenylmethyl)-2,2-dimethylazetidin-3-one (473.29 mg, 1.78 mmol), AcOH (5.36 mg, 0.089 mmol) and NaBH$_3$CN (140.11 mg, 2.23 mmol) in MeOH (4.00 mL) is stirred for 12 hours at 50° C. under N$_2$. The reaction is quenched with NaHCO$_3$ (50 mL) at RT and the aqueous layer is extracted with EtOAc (2×80 mL). The combined organic extracts are washed with brine (50 mL), dried over anhydrous Na$_2$SO$_4$, filtered, and the filtrate is concentrated under reduced pressure. The residue is purified by reverse Combi-flash chromatography with the following conditions: Column, C18; eluting with a gradient of 38% to 40% ACN in H$_2$O (0.1% FA) to give the title compound as a yellow solid (400 mg, 76.57%). ES/MS m/z 586.3 [M+H]$^+$.

The following compounds are prepared essentially as described for 6-(1-[1-[1-(diphenylmethyl)-2,2-dimethylazetidin-3-yl]piperidin-4-yl]-5-methylpyrazol-4-yl)-4-methoxypyrazolo[1,5-a]pyridine-3-carbonitrile using the appropriate reagents, adjusting the reaction times to determine completion of the reactions, and adjusting the purification system as appropriate. The reaction can also be quenched with H$_2$O, and the filtrate can be washed with EtOAc.

TABLE 32

| Prep No. | Chemical Name | Structure | ES/MS m/z [M + H]$^+$ |
|---|---|---|---|
| 273 | tert-Butyl 4-[3-(4-[3-cyano-4-methoxypyrazolo[1,5-a]pyridin-6-yl]-5-methylpyrazol-1-yl]azetidin-1-yl]-2,2-dimethylpyrrolidine-1-carboxylate | 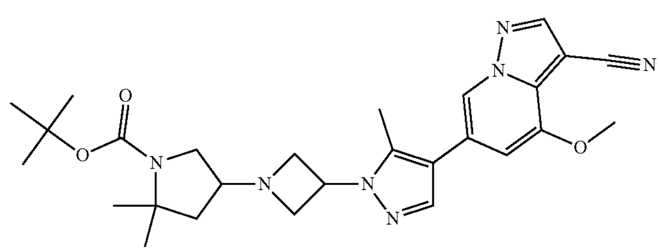 [SMILES: COc1cc(-c2cnn(C3CN(C4CN(C(=O)OC(C)(C)C)C(C)(C)C4)C3)c2C)cn2ncc(C#N)c12] | 506.4 |

TABLE 32-continued

| Prep No. | Chemical Name | Structure | ES/MS m/z [M + H]+ |
|---|---|---|---|
| 274[1] | Cis-tert-Butyl 4-[3-(4-bromo-5-methyl-triazol-1-yl)cyclobutyl]piperazine-1-carboxylate | 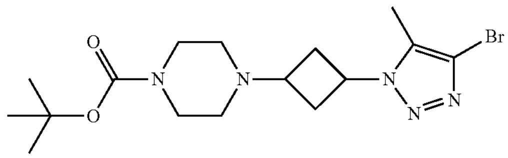 [SMILES: Cc1c(Br)nnn1C1CC(N2CCN(C(=O)OC(C)(C)C)CC2)C1] | ([79]Br/[81]Br) 400.0/402.0 |

[1]Purified by silica gel column chromatography, eluting with 1% to 50% EA in PE.

Preparation 275 tert-Butyl 4-[3-(4-bromo-5-methylpyrazol-1-yl)azetidin-1-yl]-3,3-difluoropiperidine-1-carboxylate, Isomer 1 and

Preparation 276 tert-Butyl 4-[3-(4-bromo-5-methylpyrazol-1-yl)azetidin-1-yl]-3,3-difluoropiperidine-1-carboxylate, Isomer 2

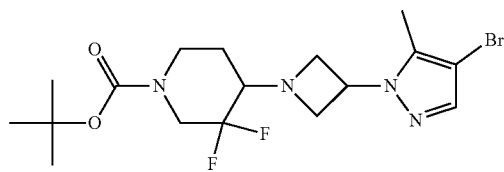 [SMILES: Cc1c(Br)cnn1C1CN(C2CCN(C(=O)OC(C)(C)C)CC2(F)F)C1]

The isomers of tert-Butyl 4-[3-(4-bromo-5-methylpyrazol-1-yl)azetidin-1-yl]-3,3-difluoropiperidine-1-carboxylate (1.9 g) are isolated by Chiral Prep-HPLC with the following conditions: Column, N-CHIRALPAK IG (Lot No. IG30CS-VL001), 4.6*100 mm, 3.0 μm; eluting with a gradient of 10%-50% MeOH (20 mM $NH_3$); flow rate: 2 mL/min; 210 nm; $t_{(R)}$ Isomer 1 is 2.30 min with 100% ee as a white solid (810 mg, 42.63%); $t_{(R)}$ Isomer 2 is 2.52 min with 100% ee as a white solid (788 mg, 41.47%).

Preparation 277

6,6-Difluoro-5,6-dihydro-7H-cyclopenta[b]pyridin-7-one

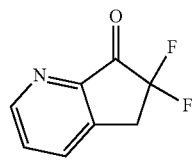

F-TEDA (23.95 g, 67.61 mmol) is added in portions to a stirred solution of 5H,6H-cyclopenta[b]pyridin-7-one (3.00 g, 22.53 mmol) and $Na_2SO_4$ (16.00 g, 112.64 mmol) in ACN (30 mL) at RT under $N_2$, and the mixture is stirred for 3 hrs at 80° C. under $N_2$. The mixture is concentrated under reduced pressure. The residue is purified by silica gel column chromatography, eluting with a gradient of PE/EtOAc (3:1) to give the title compound as a light-yellow solid (2.2 g, 57.73%). $^1$H NMR (400 MHz, $d_6$-DMSO) δ 8.88 (dd, 1H), 8.14 (dd, 1H), 7.78 (dd, 1H), 3.75 (t, 2H).

Preparation 278

6,6-Difluoro-6,7-dihydro-5H-cyclopenta[b]pyridin-7-ol

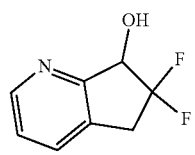 [SMILES: OC1c2ncccc2CC1(F)F]

A stirred solution of 6,6-difluoro-3H,4H,5H-cyclopenta[b]pyridin-7-one (1 g, 5.84 mmol) in MeOH (10 mL) is treated with $NaBH_4$ (220 mg, 5.82 mmol) and stirred for 2 hrs at RT under $N_2$. The mixture is concentrated in vacuo. The residue is purified by silica gel column chromatography, eluting with a gradient of PE/EtOAc (3:1) to give the title compound as a white solid (800 mg, 80%). ES/MS m/z 172.0 [M+H]+.

Preparation 279

(R)-2,2,2-Trifluoro-1-(pyridin-2-yl)ethyl trifluoromethanesulfonate

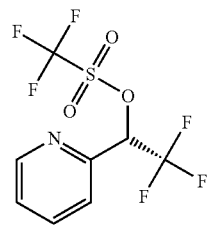

Tf$_2$O (597.33 mg, 2.12 mmol) is added dropwise at 0° C. to a stirred solution of (R)-2,2,2-trifluoro-1-(pyridin-2-yl)ethanol (250 mg, 1.41 mmol) and TEA (428.47 mg, 4.23 mmol) in DCM (10 mL) and the mixture is stirred for 4 hrs at RT under N$_2$. The mixture is diluted with H$_2$O (20 mL) and extracted with EtOAc (3×20 mL). The combined organic extracts are washed with brine (1×20 mL), dried over anhydrous Na$_2$SO$_4$, filtered, and the filtrate is concentrated under reduced pressure to give the title compound as a yellow oil (280 mg, crude). The product is used directly without further purification. ES/MS m/z 309.8 [M+H]$^+$.

The following compound is prepared essentially as described for (R)-2,2,2-trifluoro-1-(pyridin-2-yl)ethyl trifluoromethanesulfonate using the appropriate reagents, adjusting the reaction times to determine completion of the reactions, and adjusting the purification system as appropriate.

TABLE 33

| Prep No. | Chemical Name | Structure | ES/MS m/z [M + H]$^+$ |
|---|---|---|---|
| 280[1] | 6,6-Difluoro-6,7-dihydro-5H-cyclopenta[b]pyridin-7-yl trifluoromethanesulfonate | 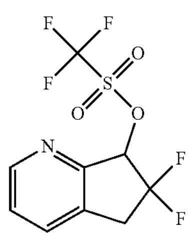 [SMILES: O=S(=O)(OC1c2ncccc2CC1(F)F)C(F)(F)F] | 304.0 |

[1]The extracts are concentrated under vacuum, and are not washed with brine, dried over anhydrous Na$_2$SO$_4$, or filtered.

Preparation 281

4-Methoxy-6-(4,4,5,5-tetramethyl-1,3,2-dioxaborolan-2-yl)pyrazolo[1,5-a]pyridine

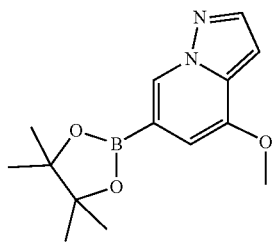

To 6-bromo-4-methoxypyrazolo[1,5-a]pyridine (5.00 g, 22.02 mmol) and bis(pinacolato)diboron (6710.27 mg, 26.43 mmol) in dioxane (10 mL) are added KOAc (6.48 g, 66.06 mmol) and Pd(dppf)Cl$_2$ (322.25 mg, 0.44 mmol, 0.02 equiv.) at RT under N$_2$. The resulting mixture is stirred for 2 hr at 80° C. under N$_2$. The mixture is carried forward without a further purification. ES/MS m/z 275.1 [M+H]$^+$.

Preparation 282

[5-[2-[tert-Butyl(dimethyl)silyl]oxy-1-(5-fluoro-2-pyridyl)ethoxy]imidazo[1,2-a]pyridin-7-yl]boronic Acid

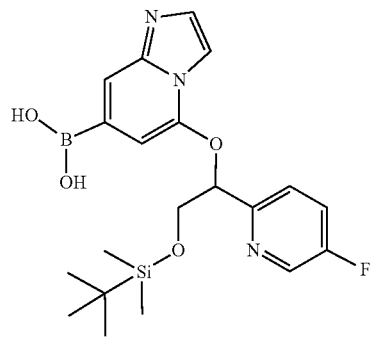 [SMILES: CC(C)(C)[Si](C)(C)OCC(Oc1cc(B(O)O)cc2nccn12)c1ccc(F)cn1]

A mixture of tert-Butyl-[2-(7-chloroimidazo[1,2-a]pyridin-5-yl)oxy-2-(5-fluoro-2-pyridyl)ethoxy]-dimethyl-silane (1.8 g, 4.27 mmol), bis(pinacolato)diboron (1.62 g, 6.40 mmol), KOAc (1.05 g, 10.67 mmol) and XPhos (0.24 g, 0.51 mmol), Pd$_2$(dba)$_3$ (0.39 g, 0.427 mmol) in dioxane (20 mL) is stirred at 80° C. for 2 hr under N$_2$. Upon cooling to RT, the reaction is carried forward to the next step without a further purification. ES/MS m/z 432.1 [M+H]$^+$.

Preparation 283

5-Methoxyimidazo[1,2-a]pyridin-7-ylboronic Acid

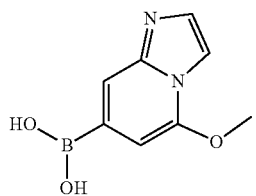

A stirred mixture of 7-chloro-5-methoxyimidazo[1,2-a]pyridine (1.00 g, 5.48 mmol) and bis(pinacolato)diboron (1.67 g, 6.57 mmol) in 1,4-dioxane is treated with KOAc (1.61 g, 16.43 mmol) and Xphos Pd G4 (0.05 g, 0.06 mmol) at RT under N$_2$ and stirred for 8 hrs at 80° C. The mixture is diluted with H$_2$O (100 mL), acidified to pH 4 with HCl aq. (1 N), and extracted with i-PrOH:CHCl$_3$ (3:1)(3×200 mL). The combined organic extracts are dried over anhydrous Na$_2$SO$_4$ and concentrated under vacuum to give the title compound as a light-pink solid (1.4 g, crude). ES/MS m/z 193.0 [M+H]$^+$.

The following compounds are prepared essentially as described for 5-methoxyimidazo[1,2-a]pyridin-7-ylboronic acid using the appropriate reagents and adjusting the reaction times to determine completion of the reactions. The catalyst can also be XPhos Pd G4.

TABLE 34

| Prep No. | Chemical Name | Structure | ES/MS m/z [M + H]+ |
|---|---|---|---|
| 284 | 3-Cyano-5-[(1R)-1-(pyridin-2-yl)ethoxy]imidazo[1,2-a]pyridin-7-ylboronic acid | 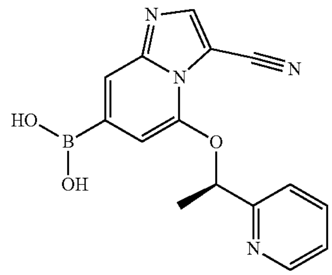 [SMILES: C[C@@H](Oc1cc(B(O)O)cc2ncc(C#N)n12)c1ccccn1] | 308.9 |
| 285 | [5-[(1R)-1-(5-Fluoro-2-pyridyl)ethoxy]imidazo[1,2-a]pyridin-7-yl]boronic acid | 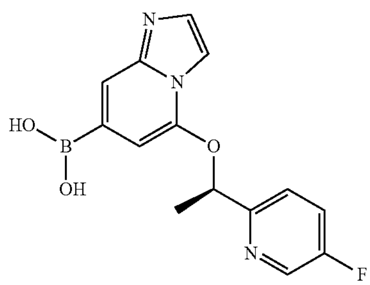 [SMILES: C[C@@H](Oc1cc(B(O)O)cc2nccn12)c1ccc(F)cn1] | 302.0 |
| 286[1] | (5-Methoxy-3-methyl-imidazo[1,2-a]pyridin-7-yl)boronic acid | 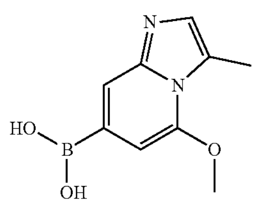 | 207.1 |

[1] 0.1 eq Xantphos Pd G4 and 0.2 eq X-Phos used

Preparation 287

4-[(1R)-1-(Pyridin-2-yl)ethoxy]-6-(4,4,5,5-tetramethyl-1,3,2-dioxaborolan-2-yl)pyrazolo[1,5-a]pyridine-3-carbonitrile

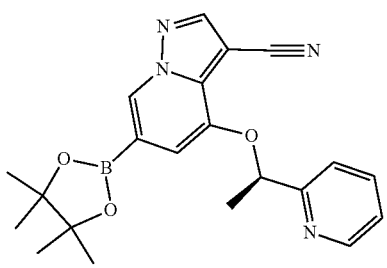 [SMILES: C[C@@H](Oc1cc(B2OC(C)(C)C(C)(C)O2)cn2ncc(C#N)c12)c1ccccn1]

A stirred RT solution of 6-bromo-4-[(1R)-1-(pyridin-2-yl)ethoxy]pyrazolo[1,5-a]pyridine-3-carbonitrile (1.40 g, 4.08 mmol), KOAc (1.20 g, 12.24 mmol) and bis(pinacolato)diboron (1.24 g, 4.90 mmol) in dioxane (20.00 mL) under $N_2$ is treated with Pd(dppf)Cl$_2$—CH$_2$Cl$_2$ (0.17 g, 0.20 mmol), and the mixture is stirred for 2 hrs at 100° C. under $N_2$. The mixture is filtered, the filter cake is washed with EtOAc (3×20 mL), and the filtrate is concentrated under reduced pressure to give the title compound as a black solid (2.5 g, crude), which is used directly without further purification. ES/MS m/z 391.3 [M+H]+.

The following compounds are prepared essentially as described for 4-[(1R)-1-(pyridin-2-yl)ethoxy]-6-(4,4,5,5-tetramethyl-1,3,2-dioxaborolan-2-yl)pyrazolo[1,5-a]pyridine-3-carbonitrile using the appropriate reagents and adjusting the reaction times to determine completion of the reactions. Temperature is varied from 80° C. to 100° C. The base can also be KF. The catalyst can also be Pd(PPh$_3$)$_4$, Pd$_2$(dba)$_3$ or Pd(dppf)Cl$_2$ and can be used alone or in combination with XPhos Pd G4.

TABLE 35

| Prep No. | Chemical Name | Structure | ES/MS m/z [M + H]+ |
|---|---|---|---|
| 288 | 4-[(1S)-1-(Pyridin-2-yl)ethoxy]-6-(4,4,5,5-tetramethyl-1,3,2-dioxaborolan-2-yl)pyrazolo[1,5-a]pyridine-3-carbonitrile | 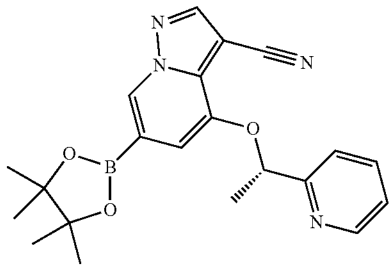 [SMILES: C[C@H](Oc1cc(B2OC(C)(C)C(C)(C)O2)cn2ncc(C#N)c12)c1ccccn1] | 309.1 |
| 289[1] | 5-[(1R)-1-(Pyridin-2-yl)ethoxy]imidazo[1,2-a]pyridin-7-ylboronic acid | 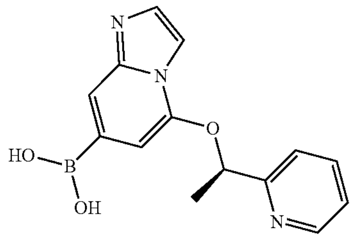 [SMILES: C[C@@H](Oc1cc(B(O)O)cc2nccn12)c1ccccn1] | 284.3 |
| 290[2] | 4-[(1R)-1-Cyclobutylethoxy]-6-(4,4,5,5-tetramethyl-1,3,2-dioxaborolan-2-yl)pyrazolo[1,5-a]pyridine-3-carbonitrile | 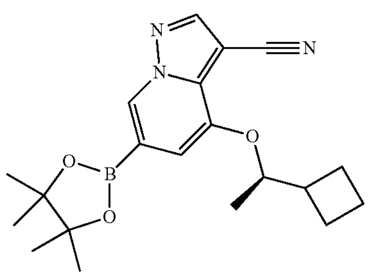 [SMILES: C[C@@H](Oc1cc(B2OC(C)(C)C(C)(C)O2)cn2ncc(C#N)c12)C1CCC1] | 368.2 |
| 291[1] | 4-[(1R)-1-Cyclopropylethoxy]-6-(4,4,5,5-tetramethyl-1,3,2-dioxaborolan-2-yl)pyrazolo[1,5-a]pyridine-3-carbonitrile | 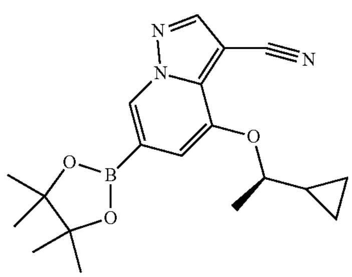 [SMILES: C[C@@H](Oc1cc(B2OC(C)(C)C(C)(C)O2)cn2ncc(C#N)c12)C1CC1] | 354.2 |
| 292[1] | 4-[(1R)-1-Phenylethoxy]-6-(4,4,5,5-tetramethyl-1,3,2-dioxaborolan-2-yl)pyrazolo[1,5-a]pyridine-3-carbonitrile | 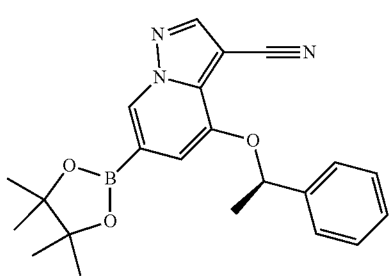 [SMILES: C[C@@H](Oc1cc(B2OC(C)(C)C(C)(C)O2)cn2ncc(C#N)c12)c1ccccc1] | 390.2 |
| 293[3] | 4-Isopropoxy-6-(4,4,5,5-tetramethyl-1,3,2-dioxaborolan-2-yl)pyrazolo[1,5-a]pyridine-3-carbonitrile | 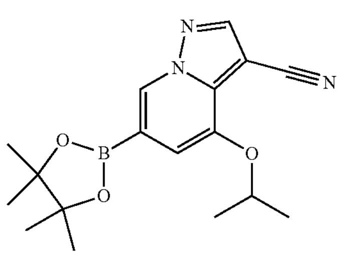 [SMILES: CC(C)Oc1cc(B2OC(C)(C)C(C)(C)O2)cn2ncc(C#N)c12] | 246.0 |

TABLE 35-continued

| Prep No. | Chemical Name | Structure | ES/MS m/z [M + H]+ |
|---|---|---|---|
| 294[4] | (3-Cyano-5-methoxy-imidazo[1,2-a]pyridin-7-yl)boronic acid | 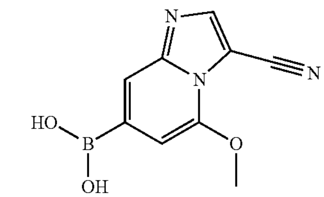 [SMILES: COc1cc(B(O)O)cc2ncc(C#N)n12] | 218.0 |
| 295[5] | 4-Methoxy-6-(4,4,5,5-tetramethyl-1,3,2-dioxaborolan-2-yl)pyrazolo[1,5-a]pyridine-3-carbonitrile | 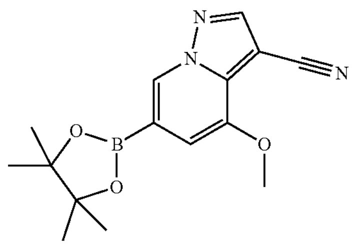 [SMILES: COc1cc(B2OC(C)(C)C(C)(C)O2)cn2ncc(C#N)c12] | 300.2 |
| 296[1] | [3-Cyano-5-[(5-fluoro-2-pyridyl)-(1-methoxycyclopropyl)methoxy]imidazo[1,2-a]pyridin-7-yl]boronic acid | 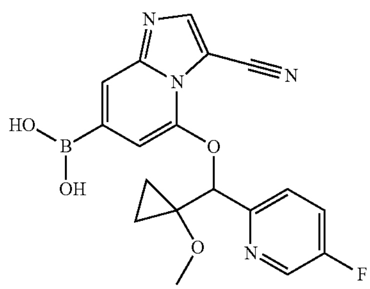 [SMILES: COC1(C(Oc2cc(B(O)O)cc3ncc(C#N)n23)c2ccc(F)cn2)CC1] | 383.0 |
| 297 | [3-Cyano-5-[[(1R)-1-(5-fluoro-2-pyridyl)ethyl]amino]imidazo[1,2-a]pyridin-7-yl]boronic acid | 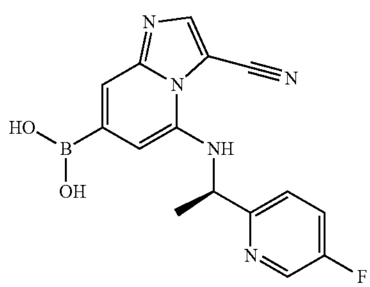 [SMILES: C[C@@H](Nc1cc(B(O)O)cc2ncc(C#N)n12)c1ccc(F)cn1] | 326.1 |
| 298 | 3-Fluoro-4-methoxy-6-(4,4,5,5-tetramethyl-1,3,2-dioxaborolan-2-yl)pyrazolo[1,5-a]pyridine | 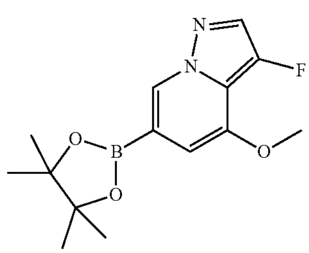 | 293.2 |
| 299 | 4-Methoxy-6-(4,4,5,5-tetramethyl-1,3,2-dioxaborolan-2-yl)pyrazolo[1,5-a]pyridine | 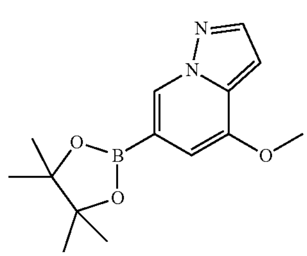 | 275.2 |

TABLE 35-continued

| Prep No. | Chemical Name | Structure | ES/MS m/z [M + H]⁺ |
|---|---|---|---|
| 300 | tert-Butyl-[2-(5-fluoro-2-pyridyl)-2-[6-(4,4,5,5-tetramethyl-1,3,2-dioxaborolan-2-yl)pyrazolo[1,5-a]pyridin-4-yl]oxy-ethoxy]-dimethyl-silane, Isomer 2 | 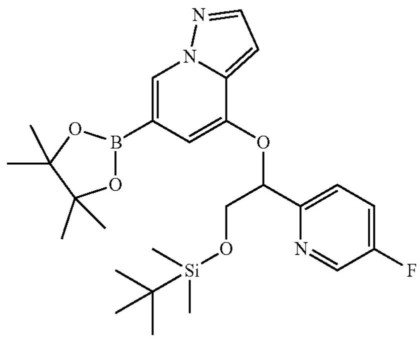 [SMILES: CC1(C)OB(c2cc(OC(CO[Si](C)(C)C(C)(C)C)c3ccc(F)cn3)c3ccnn3c2)OC1(C)C] | 514.3 |
| 301 | tert-Butyl-[2-(5-fluoro-2-pyridyl)-2-[3-fluoro-6-(4,4,5,5-tetramethyl-1,3,2-dioxaborolan-2-yl)pyrazolo[1,5-a]pyridin-4-yl]oxy-ethoxy]-dimethyl-silane, Isomer 2 | 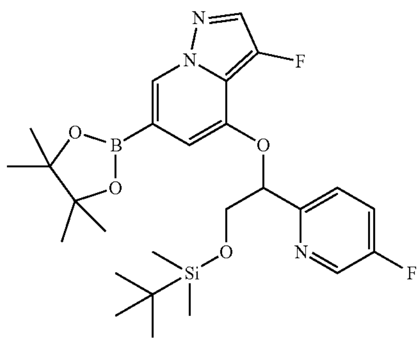 [SMILES: CC1(C)OB(c2cc(OC(CO[Si](C)(C)C(C)(C)C)c3ccc(F)cn3)c3c(F)cnn3c2)OC1(C)C] | 532.4 |

¹Mixture is used directly without further purification.
²Mixture is filtered, washed with 1,4-dioxane, concentrated under reduced pressure, and used directly without further purification.
³The reaction mixture is filtered and purified with reverse phase C18 chromatography.
⁴Upon workup the organic layers are combined, washed with H₂O. The aqueous layer is acidified to pH 3-4 with conc. HCl. The precipitate is collected by filtration, washed with water, and dried in vacuo.
⁵Purified by silica gel column chromatography, eluting with PE/EtOAc (20:1 to 3:1).
ᵃMaterial is used without further purification.

Preparation 302

3-Chloro-4-methoxy-6-(4,4,5,5-tetramethyl-1,3,2-dioxaborolan-2-yl)pyrazolo[1,5-a]pyridine

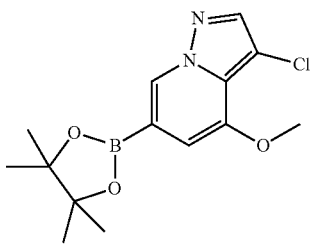

A mixture of 4-methoxy-6-(4,4,5,5-tetramethyl-1,3,2-dioxaborolan-2-yl)pyrazolo[1,5-a]pyridine (5.06 g, 18.46 mmol) and NCS (2.47 g, 18.46 mmol) in CHCl₃ (5 mL) is heated at 50° C. for 1 hr. Upon cooling to RT, the reaction is washed with H₂O, sat. aq. NaHCO₃, brine, dried over Na₂SO₄ and filtered. The filtrate is concentrated to afford the title compound (5.79 g, 18 mmol) as a light brown solid. ES/MS m/z 227.0 [M+H-C6H12]⁺.

Preparation 303 tert-Butyl 4-[4-(5-chloroimidazo[1,2-a]pyridin-7-yl)-5-methyl-pyrazol-1-yl]piperidine-1-carboxylate

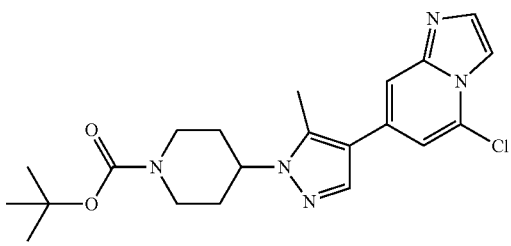 [SMILES: Cc1c(-c2cc(Cl)n3ccnc3c2)cnn1C1CCN(C(=O)OC(C)(C)C)CC1]

To 7-bromo-5-chloroimidazo[1,2-a]pyridine (700.0 mg, 3.02 mmol) and tert-butyl 4-[5-methyl-4-(4,4,5,5-tetramethyl-1,3,2-dioxaborolan-2-yl)pyrazol-1-yl]piperidine-1-carboxylate (946.7 mg, 2.41 mmol) in dioxane/H₂O (4:1, 10.0 mL) is added Pd(PPh₃)₄ (349.4 mg, 0.30 mmol) and KF (527.0 mg, 9.07 mmol) at RT under N₂. The reaction is stirred for 2 hr at 100° C. under N₂. The resulting mixture is filtered, the filter cake is washed with EtOAc (3×100 mL). The filtrate is concentrated in vacuo. The residue is purified by silica gel column chromatography, eluting with PE:EtOAc (1:2) to afford the title compound as a yellow solid (700 mg, 55.6%). ES/MS m/z 416.2 [M+H]⁺.

Preparation 304 tert-Butyl 4-[5-methyl-4-(5-oxo-6H-imidazo[1,2-c]pyrimidin-7-yl)pyrazol-1-yl]piperidine-1-carboxylate

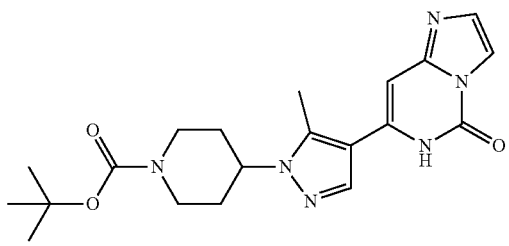 [SMILES: Cc1c(-c2cc3nccn3c(=O)[nH]2)cnn1C1CCN(C(=O)OC(C)(C)C)CC1]

7-chloroimidazo[1,2-c]pyrimidin-5(6H)-one (300 mg, 1.77 mmol), tert-butyl 4-(5-methyl-4-(4,4,5,5-tetramethyl-1,3,2-dioxaborolan-2-yl)-1H-pyrazol-1-yl)piperidine-1-carboxylate (1.04 g, 2.65 mmol), dicyclohexyl(2',4',6'-triisopropyl-[1,1'-biphenyl]-2-yl)phosphane (127 mg, 0.27 mmol), and K₃PO₄ (1.13 g, 5.31 mmol) in 1,4-dioxane (4 mL) is treated with Pd₂(dba)₃ (243 mg, 0.27 mmol) and sparged with N₂ for 5 min. The reaction is sealed and refluxed overnight. Upon cooling to RT, the reaction is diluted with H₂O and extracted with EtOAc (3×). The combined organic layers are washed with H₂O, followed by brine, dried over Na₂SO₄, filtered, and concentrated to a yellow oil. The oil is dissolved into DCM and purified by silica gel chromatography eluting with 0% to 10% MeOH in DCM to afford the title compound (470 mg, 1.18 mmol, 66.7%) as a solid. ES/MS m/z 399.2 [M+H]⁺.

Preparation 305 tert-Butyl 4-(4-[5-methoxyimidazo[1,2-a]pyridin-7-yl]-5-methyl-1,2,3-triazol-1-yl)piperidine-1-carboxylate

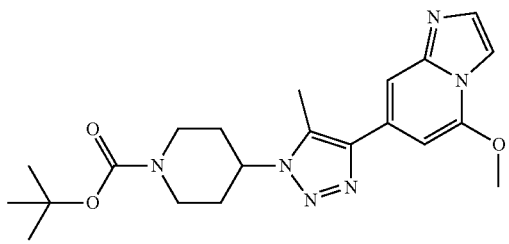 [SMILES: COc1cc(-c2nnn(C3CCN(C(=O)OC(C)(C)C)CC3)c2C)cc2nccn12]

A mixture of tert-butyl 4-(4-bromo-5-methyl-1,2,3-triazol-1-yl)piperidine-1-carboxylate (1.60 g, 4.63 mmol), 5-methoxyimidazo[1,2-a]pyridin-7-ylboronic acid (1.33 g, crude), K₂CO₃ (1.92 g, 13.90 mmol), Pd(PPh₃)₄ (0.27 g, 0.23 mmol), dioxane (8 mL) and H₂O (2.00 mL) is stirred for 8 hrs at 90° C. under N₂. The mixture is cooled to RT, diluted with EtOAc (100 mL), washed with H₂O (50 mL), and then brine (80 mL). The combined organic layers are dried over anhydrous Na₂SO₄, filtered, and the filtrate is concentrated under reduced pressure. The residue is purified by silica gel column chromatography, eluting with a gradient of PE:EtOAc (3:1 to 1:1) to give the title compound as a brown solid (520 mg, 18.2%). ES/MS m/z 413.3 [M+H]⁺.

Preparation 306 tert-Butyl 4-[4-(4-methoxypyrazolo[1,5-a]pyridin-6-yl)-5-methyl-triazol-1-yl]piperidine-1-carboxylate

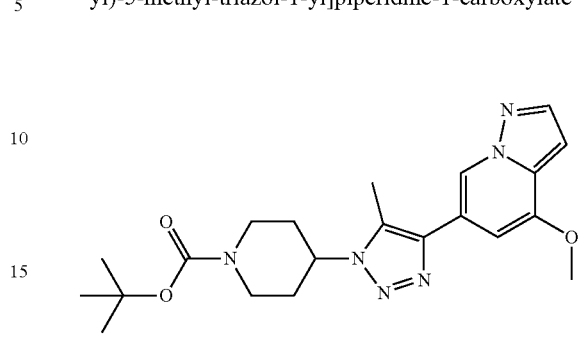

To 4-Methoxy-6-(4,4,5,5-tetramethyl-1,3,2-dioxaborolan-2-yl)pyrazolo[1,5-a]pyridine (5 g, 18.24 mmol) and tert-butyl 4-(4-bromo-5-methyl-1,2,3-triazol-1-yl)piperidine-1-carboxylate (6.93 g, 20.06 mmol) in dioxane (80 mL) and water (20 mL) is added K₂CO₃ (7.56 g, 54.72 mmol) and Pd(DtBPF)Cl₂ (0.24 g, 0.36 mmol) RT under N₂. The reaction is stirred overnight at 80° C. Upon cooling to RT, the resultant mixture is diluted with water (50 mL) and extracted with EtOAc (3×100 mL). The combined organic layers are washed with brine (2×80 mL), dried over Na₂SO₄, filtered, and concentrated in vacuo. The residue is purified by silica gel column chromatography eluting with a gradient of 30% to 60% EtOAc in PE to afford the title compound as a light-brown solid (4.5 g, 59.8%). ES/MS m/z 413.2 [M+H]⁺.

Preparation 307 tert-butyl 4-[4-(3-chloro-4-methoxy-pyrazolo[1,5-a]pyridin-6-yl)-5-methyl-triazol-1-yl]piperidine-1-carboxylate

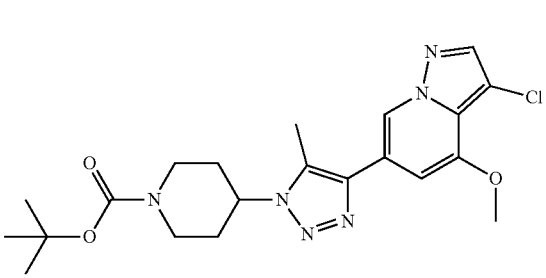 [SMILES: COc1cc(-c2nnn(C3CCN(C(=O)OC(C)(C)C)CC3)c2C)cn2ncc(Cl)c12]

A solution of tert-butyl 4-(4-(4-methoxypyrazolo[1,5-a]pyridin-6-yl)-5-methyl-1H-1,2,3-triazol-1-yl)piperidine-1-carboxylate (16.1 g, 39.02 mmol) in CHCl₃ (50 mL) is treated with PPTS (981 mg, 3.90 mmol) followed by NCS (5.21 g, 39.02 mmol). The reaction is stirred at 40° C. for 95 min. Upon cooling to RT, the reaction is concentrated in vacuo. The residue is purified by phase silica gel chromatography eluting with 0% to 100% EtOAc in heptane to afford the title compound (17.7 g, 101%) as a colorless solid. ES/MS m/z 391.2 [M+2H-tBu]⁺.

Preparation 308 tert-Butyl 3-[5-methyl-4-[5-[(1R)-1-(2-pyridyl)ethoxy]imidazo[1,2-a]pyridin-7-yl]triazol-1-yl]azetidine-1-carboxylate

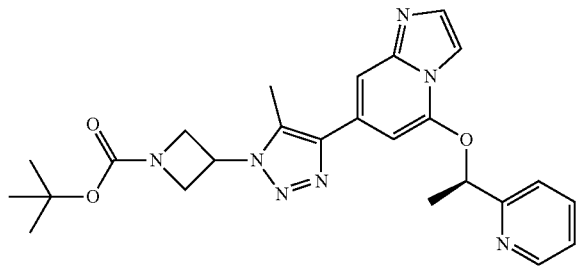 [SMILES: Cc1c(-c2cc(O[C@H](C)c3ccccn3)n3ccnc3c2)nnn1C1CN(C(=O)OC(C)(C)C)C1]

To 5-[(1R)-1-(pyridin-2-yl)ethoxy]imidazo[1,2-a]pyridin-7-ylboronic acid (1.00 g, 3.53 mmol), tert-butyl 3-(4-bromo-5-methyl-1,2,3-triazol-1-yl)azetidine-1-carboxylate (1.23 g, 3.89 mmol) and $K_2CO_3$ (1.46 g, 10.60 mmol) in dioxane (8.00 mL) and $H_2O$ (2.00 mL) is added Pd(PPh$_3$)$_4$ (0.41 g, 0.35 mmol) at RT under $N_2$. The resulting mixture is stirred at 100° C. for 2 hr under $N_2$. Upon cooling to RT, the reaction is concentrated in vacuo. The residue is purified by silica gel column chromatography, eluting with a gradient of 5% to 10% MeOH in DCM to afford the title compound as a yellow solid (550 mg, 32.74%). ES/MS m/z 476.1 [M+H]$^+$.

Preparation 309 tert-Butyl 4-[4-[5-[2-[tert-butyl(dimethyl)silyl]oxy-1-(5-fluoro-2-pyridyl)ethoxy]imidazo[1,2-a]pyridin-7-yl]-5-methyl-triazol-1-yl]piperidine-1-carboxylate

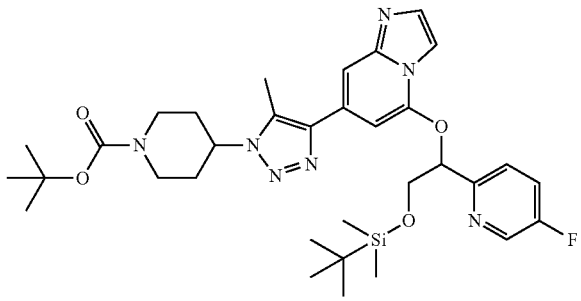 [SMILES: Cc1c(-c2cc(OC(CO[Si](C)(C)C(C)(C)C)c3ccc(F)cn3)n3ccnc3c2)nnn1C1CCN(C(=O)OC(C)(C)C)CC1]

A mixture of 5-[2-[(tert-butyldimethylsilyl)oxy]-1-(5-fluoropyridin-2-yl)ethoxy]imidazo[1,2-a]pyridin-7-ylboronic acid (1.6 g, 3.71 mmol), tert-butyl 4-(4-bromo-5-methyl-1,2,3-triazol-1-yl)piperidine-1-carboxylate (1.41 g, 4.08 mmol), $K_2CO_3$ (1.54 g, 11.13 mmol), Pd(DtBPF)Cl$_2$ (242 mg, 0.37 mmol) in dioxane (20 mL) and $H_2O$ (5 mL) is stirred at 80° C. for 2 hr under $N_2$. Upon cooling to RT, the reaction is concentrated in vacuo. The residue is purified by silica gel column chromatography, eluting with PE:EtOAc (1:2 to 1:1) to afford the title compound as a brown solid (1.2 g, 49.63%). ES/MS m/z 652.4 [M+H]$^+$.

Preparation 310 tert-Butyl 3-(4-[3-cyano-4-methoxypyrazolo[1,5-a]yridine-6-yl]-5-methylpyrazol-1-yl)azetidine-1-carboxylate

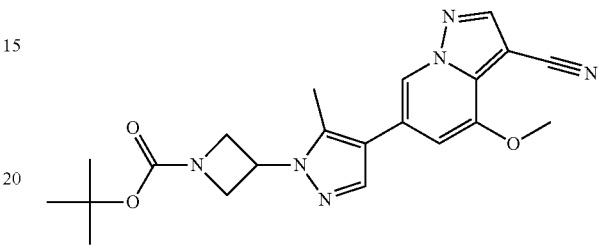

A stirred solution of tert-butyl 3-(4-bromo-5-methylpyrazol-1-yl)azetidine-1-carboxylate (2.50 g, 7.91 mmol) and 4-methoxy-6-(4,4,5,5-tetramethyl-1,3,2-dioxaborolan-2-yl)pyrazolo[1,5-a]pyridine-3-carbonitrile (2.37 g, 7.91 mmol) in dioxane:$H_2O$ (80 mL:20 mL) is treated with $K_2CO_3$ (3.28 g, 23.72 mmol) and Pd(PPh$_3$)$_4$ (0.09 g, 0.08 mmol) at RT under $N_2$, and the mixture is stirred overnight at 100° C. under $N_2$. The mixture is cooled to RT, the reaction is quenched with $H_2O$ (100 mL) and extracted with EtOAc (3×150 mL). The combined organic extracts are washed with brine (1×150 mL), dried over anhydrous $Na_2SO_4$, filtered, and the filtrate is concentrated under reduced pressure. The residue is purified by silica gel column chromatography, eluting with a gradient of PE:EtOAc (10:1-1:1) to give the title compound as a white solid (1.88 g, 58.21%). $^1$H NMR (300 MHz, d$_6$-DMSO) δ 8.61-8.51 (m, 2H), 7.95 (s, 1H), 7.09 (d, 1H), 5.41-5.26 (m, 1H), 4.37-4.26 (m, 2H), 4.18 (d, 2H), 4.06 (s, 3H), 2.41 (s, 3H), 1.43 (s, 9H).

The following compounds are prepared essentially as described for tert-butyl 3-(4-[3-cyano-4-methoxypyrazolo[1,5-a] yridine-6-yl]-5-methylpyrazol-1-yl)azetidine-1-carboxylate using the appropriate reagents and adjusting the reaction times to determine completion of the reactions. Temperature is varied from 80° C. to 100'C. The solvent can also be toluene:$H_2O$. The base can also be KOAc, $K_3PO_4$, or KF. The catalyst can also be CsF, Pd(AcO)$_2$, PCy$_3$, Pd(dppf)Cl$_2$ DCM, Pd$_2$(dba)$_3$·CHCl$_3$ or Pd(dppf)Cl$_2$, alone or in combination with X-Phos or Xphos Pd G4. Alternatively, the reaction can be carried out without a catalyst. The mixture can also be extracted with PE and CHCl$_3$:i-PrOH.

TABLE 36

| Prep No. | Chemical Name | Structure | ES/MS m/z [M + H]$^+$ |
|---|---|---|---|
| 311 | tert-Butyl (3R)-3-(4-[3-cyano-4-methoxypyrazolo[1,5-a]pyridin-6-yl]-5-methylpyrazol-1-yl)pyrrolidine-1-carboxylate | 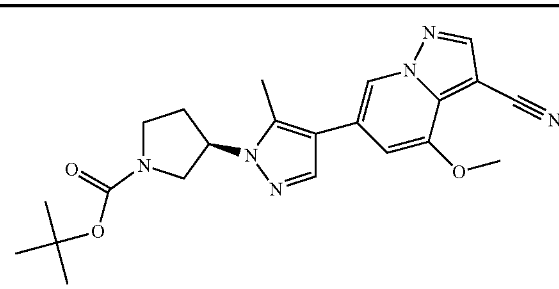 | 423.2 |

TABLE 36-continued

| Prep No. | Chemical Name | Structure | ES/MS m/z [M + H]+ |
|---|---|---|---|
| 312 | tert-Butyl (3S)-3-(4-[3-cyano-4-methoxypyrazolo[1,5-a]pyridin-6-yl]-5-methylpyrazol-1-yl)pyrrolidine-1-carboxylate | 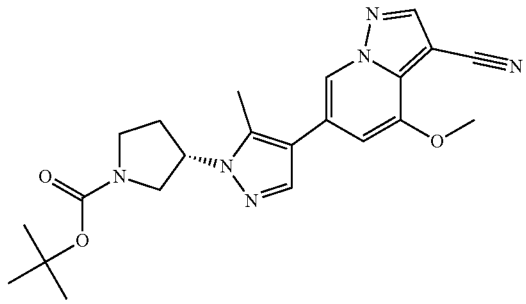 [SMILES: COc1cc(-c2cnn([C@H]3CCN(C(=O)OC(C)(C)C)C3)c2C)cn2ncc(C#N)c12] | 423.1 |
| 313 | tert-Butyl 3-(4-[3-cyano-4-methoxypyrazolo[1,5-a]pyridin-6-yl]-5-methyl-1,2,3-triazol-1-yl)azetidine-1-carboxylate | 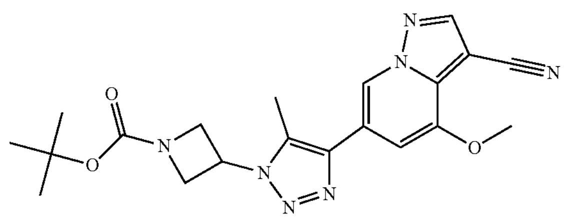 [SMILES: COc1cc(-c2nnn(C3CN(C(=O)OC(C)(C)C)C3)c2C)cn2ncc(C#N)c12] | 410.3 |
| 314[1] | tert-Butyl 4-(4-[3-cyano-4-methoxypyrazolo[1,5-a]pyridin-6-yl]-5-methyl-1,2,3-triazol-1-yl)piperidine-1-carboxylate | 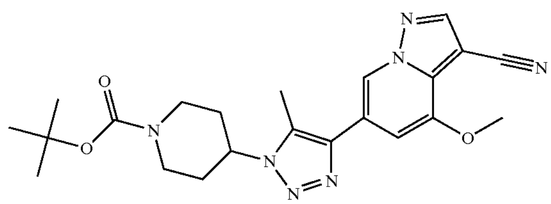 [SMILES: COc1cc(-c2nnn(C3CCN(C(=O)OC(C)(C)C)CC3)c2C)cn2ncc(C#N)c12] | 438.2 |
| 315 | tert-Butyl 4-(4-[3-cyano-4-isopropoxypyrazolo[1,5-a]pyridin-6-yl]-5-methyl-1,2,3-triazol-1-yl)piperidine-1-carboxylate | 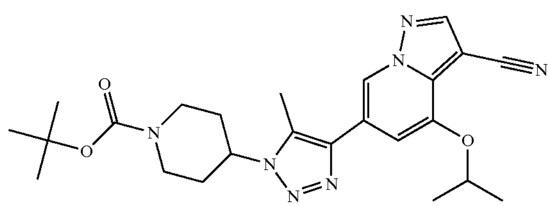 [SMILES: Cc1c(-c2cc(OC(C)C)c3c(C#N)cnn3c2)nnn1C1CCN(C(=O)OC(C)(C)C)CC1] | 466.3 |
| 316 | tert-Butyl (3R)-3-(4-[3-cyano-4-methoxypyrazolo[1,5-a]pyridin-6-yl]-5-methylpyrazol-1-yl)piperidine-1-carboxylate | 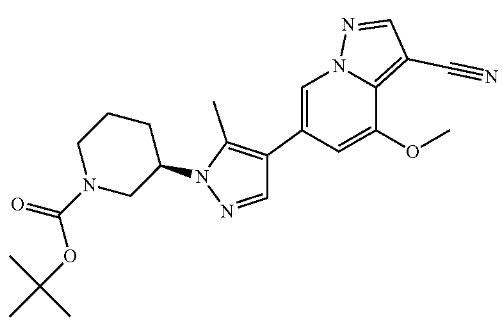 [SMILES: COc1cc(-c2cnn([C@@H]3CCCN(C(=O)OC(C)(C)C)C3)c2C)cn2ncc(C#N)c12] | 437.3 |
| 317[2] | tert-Butyl 3-(4-[3-cyano-4-isopropoxypyrazolo[1,5-a]pyridin-6-yl]-5-methyl-1,2,3-triazol-1-yl)azetidine-1-carboxylate | 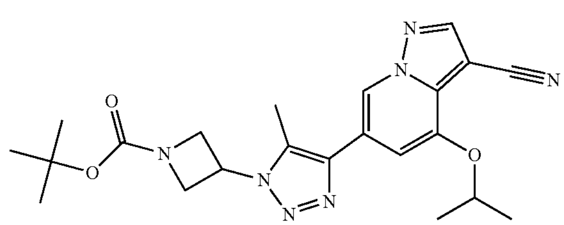 [SMILES: Cc1c(-c2cc(OC(C)C)c3c(C#N)cnn3c2)nnn1C1CN(C(=O)OC(C)(C)C)C1] | |

TABLE 36-continued

| Prep No. | Chemical Name | Structure | ES/MS m/z [M + H]+ |
|---|---|---|---|
| 318 | tert-Butyl (3S)-3-(4-[3-cyano-4-methoxypyrazolo[1,5-a]pyridin-6-yl]-5-methylpyrazol-1-yl)piperidine-1-carboxylate | 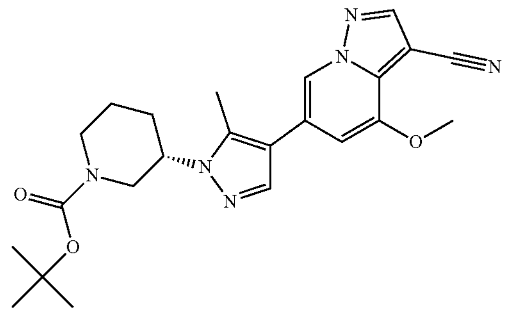 [SMILES: COc1cc(-c2cnn([C@H]3CCCN(C(=O)OC(C)(C)C)C3)c2C)cn2ncc(C#N)c12] | 437.1 |
| 319[3] | tert-Butyl (3R)-3-(4-(3-cyano-4-methoxypyrazolo[1,5-a]pyridin-6-yl)-5-methyl-1H-1,2,3-triazol-1-yl)pyrrolidine-1-carboxylate | 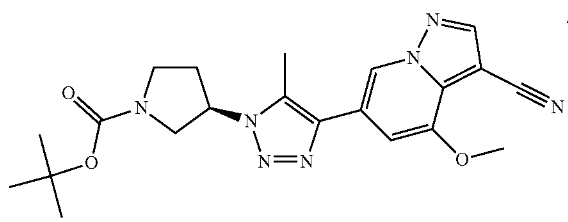 [SMILES: COc1cc(-c2nnn([C@@H]3CCN(C(=O)OC(C)(C)C)C3)c2C)cn2ncc(C#N)c12] | 424.3 |
| 320[4] | tert-Butyl (3S)-3-[3-(4-[3-cyano-4-methoxypyrazolo[1,5-a]pyridin-6-yl]-5-methylpyrazol-1-yl)azetidin-1-yl]pyrrolidine-1-carboxylate | 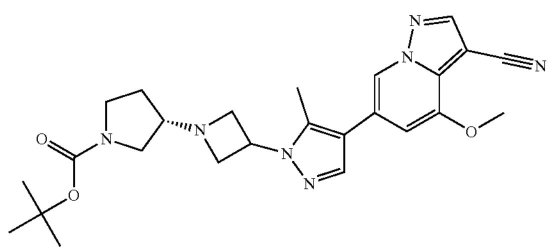 [SMILES: COc1cc(-c2cnn(C3CN([C@H]4CCN(C(=O)OC(C)(C)C)C4)C3)c2C)cn2ncc(C#N)c12] | 478.4 |
| 321 | tert-Butyl (1R,3s,5S)-3-(4-(3-cyano-4-methoxypyrazolo[1,5-a]pyridin-6-yl)-5-methyl-1H-pyrazol-1-yl)-8-azabicyclo[3.2.1]octane-8-carboxylate | 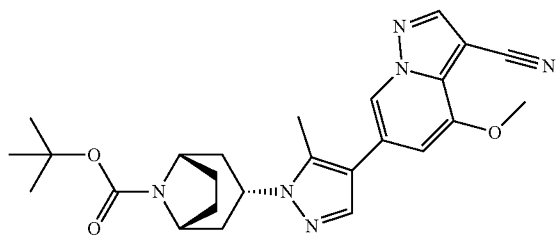 [SMILES: COc1cc(-c2cnn([C@@H]3C[C@H]4CC[C@@H](C3)N4C(=O)OC(C)(C)C)c2C)cn2ncc(C#N)c12] | |
| 322 | tert-Butyl 3-(4-[3-cyano-4-[(1R)-1-(pyridin-2-yl)ethoxy]pyrazolo[1,5-a]pyridin-6-yl]-5-methyl-1,2,3-triazol-1-yl)azetidine-1-carboxylate | 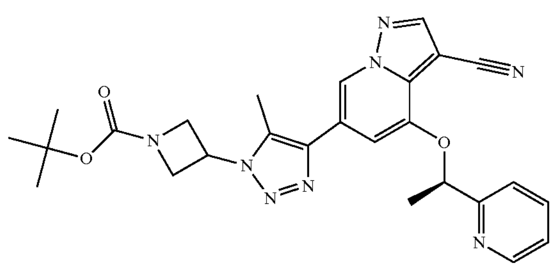 [SMILES: Cc1c(-c2cc(O[C@H](C)c3ccccn3)c3c(C#N)cnn3c2)nnn1C1CN(C(=O)OC(C)(C)C)C1] | 501.4 |
| 323[5] | tert-Butyl 4-(4-[3-cyano-4-[(1R)-1-(pyridin-2-yl)ethoxy]pyrazolo[1,5-a]pyridin-6-yl]-5-methylpyrazol-1-yl)piperidine-1-carboxylate | 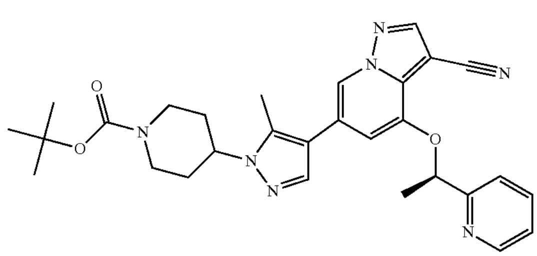 | 528.4 |

TABLE 36-continued

| Prep No. | Chemical Name | Structure | ES/MS m/z [M + H]+ |
|---|---|---|---|
| 324[5] | tert-Butyl 3-(4-[3-cyano-4-[(1R)-1-(pyridin-2-yl)ethoxy]pyrazolo[1,5-a]pyridin-6-yl]-5-methylpyrazol-1-yl)azetidine-1-carboxylate | 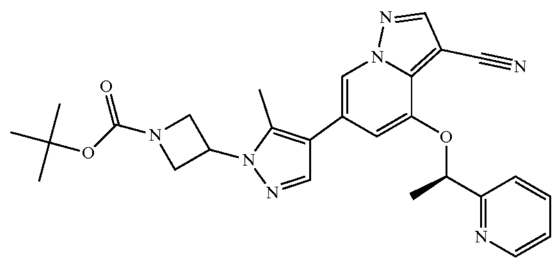 [SMILES: Cc1c(-c2cc(O[C@H](C)c3ccccn3)c3c(C#N)cnn3c2)cnn1C1CN(C(=O)OC(C)(C)C)C1] | 500.3 |
| 325 | tert-Butyl (4R)-4-(4-[3-cyano-4-methoxypyrazolo[1,5-a]pyridin-6-yl]-5-methylpyrazol-1-yl)azepane-1-carboxylate | 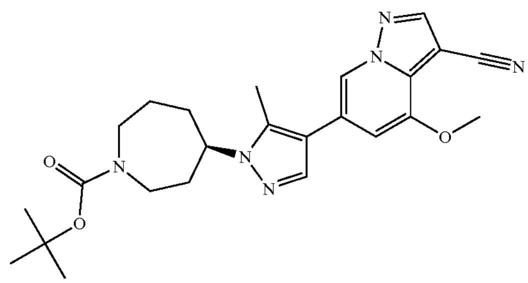 [SMILES: COc1cc(-c2cnn([C@@H]3CCCN(C(=O)OC(C)(C)C)CC3)c2C)cn2ncc(C#N)c12] | 451.1 |
| 326[6] | tert-Butyl 4-(4-[3-cyano-4-[(1S)-1-(pyridin-2-yl)ethoxy]pyrazolo[1,5-a]pyridin-6-yl]-5-methylpyrazol-1-yl)piperidine-1-carboxylate | 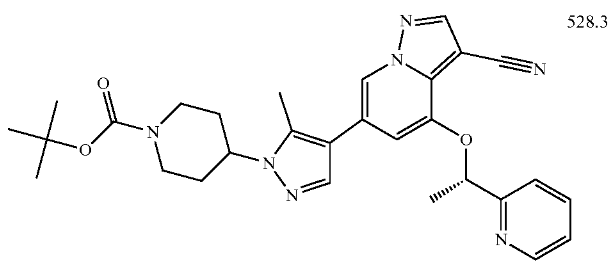 | 528.3 |
| 327 | tert-Butyl (3S)-3-[3-(4-[3-cyano-4-[(1R)-1-(pyridin-2-yl)ethoxy]pyrazolo[1,5-a]pyridin-6-yl]-5-methylpyrazol-1-yl)azetidin-1-yl]pyrrolidine-1-carboxylate | 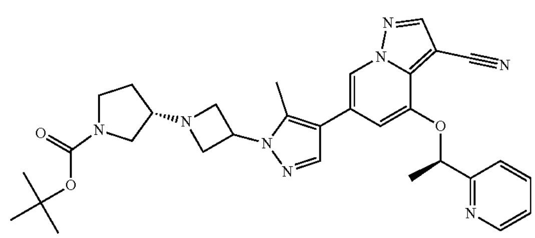 [SMILES: Cc1c(-c2cc(O[C@H](C)c3ccccn3)c3c(C#N)cnn3c2)cnn1C1CN([C@H]2CCN(C(=O)OC(C)(C)C)C2)C1] | 569.4 |
| 328 | tert-Butyl 4-(4-[3-cyano-4-methoxypyrazolo[1,5-a]pyridin-6-yl]pyrazol-1-yl)piperidine-1-carboxylate | 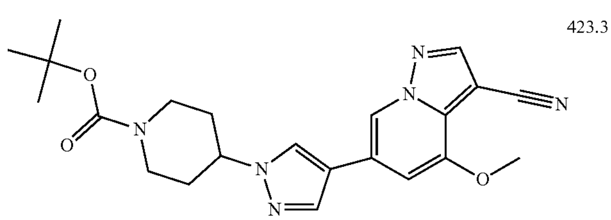 | 423.3 |
| 329 | tert-Butyl (4S)-4-(4-[3-cyano-4-methoxypyrazolo[1,5-a]pyridin-6-yl]-5-methylpyrazol-1-yl)azepane-1-carboxylate | 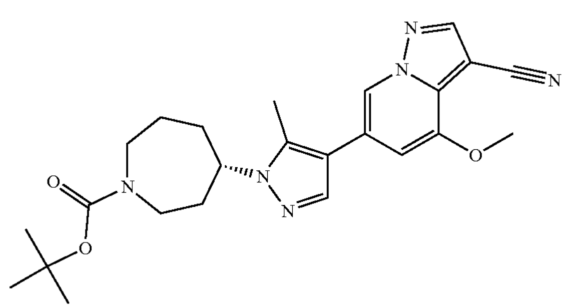 [SMILES: COc1cc(-c2cnn([C@H]3CCCN(C(=O)OC(C)(C)C)CC3)c2C)cn2ncc(C#N)c12] | 451.2 |

TABLE 36-continued

| Prep No. | Chemical Name | Structure | ES/MS m/z [M + H]+ |
|---|---|---|---|
| 330 | tert-Butyl 3-(4-[3-cyano-4-methoxypyrazolo[1,5-a]pyridin-6-yl]pyrazol-1-yl)azetidine-1-carboxylate | 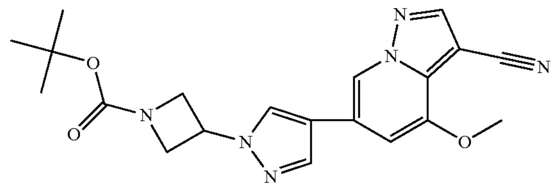 [SMILES: COc1cc(-c2cnn(C3CN(C(=O)OC(C)(C)C)C3)c2)cn2ncc(C#N)c12] | 339.3 |
| 331 | tert-Butyl 3-(4-[3-cyano-4-methoxypyrazolo[1,5-a]pyridin-6-yl]-3-methylpyrazol-1-yl)azetidine-1-carboxylate | 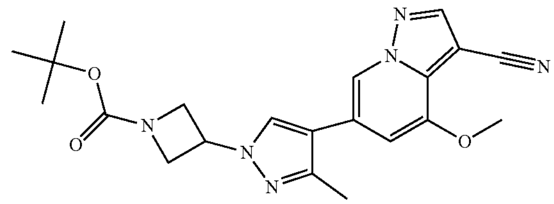 [SMILES: COc1cc(-c2cn(C3CN(C(=O)OC(C)(C)C)C3)nc2C)cn2ncc(C#N)c12] | a |
| 332 | tert-Butyl 4-(4-[5-[(1R)-1-(pyridin-2-yl)ethoxy]imidazo[1,2-a]pyridin-7-yl]-5-methyl-pyrazol-1-yl)piperidine-1-carboxylate | 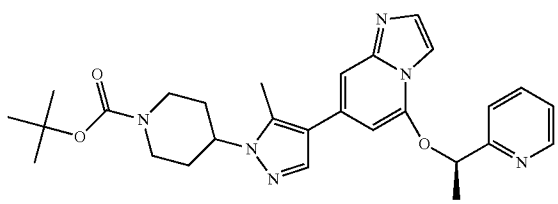 [SMILES: Cc1c(-c2cc(O[C@H](C)c3ccccn3)n3ccnc3c2)cnn1C1CCN(C(=O)OC(C)(C)C)CC1] | 503.2 |
| 333 | tert-Butyl 4-(4-[3-cyano-4-[(1R)-1-cyclobutylethoxy]pyrazolo[1,5-a]pyridin-6-yl]-5-methyl-1,2,3-triazol-1-yl)piperidine-1-carboxylate | 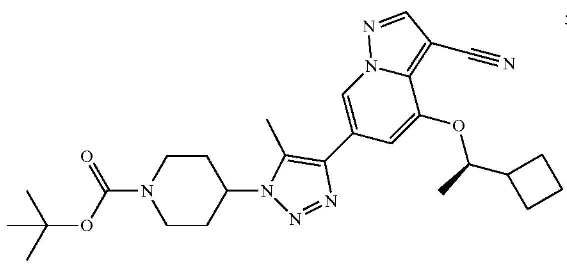 [SMILES: Cc1c(-c2cc(O[C@H](C)C3CCC3)c3c(C#N)cnn3c2)nnn1C1CCN(C(=O)OC(C)(C)C)CC1] | 506.3 |
| 334 | tert-Butyl (2S,4R)-methoxypyrazolo[1,4-(4-[3-cyano-4-5-a]pyridin-6-yl]-5-methylpyrazol-1-yl)-2-methylpyrrolidine-1-carboxylate | 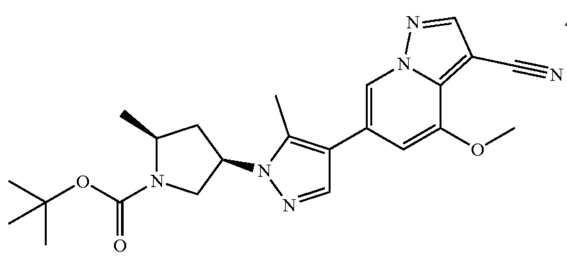 [SMILES: COc1cc(-c2cnn([C@@H]3C[C@H](C)N(C(=O)OC(C)(C)C)C3)c2C)cn2ncc(C#N)c12] | 437.3 |
| 335 | tert-Butyl 4-(4-[3-cyano-4-methoxypyrazolo[1,5-a]pyridin-6-yl]-5-methylpyrazol-1-yl)-2,2-dimethylpyrrolidine-1-carboxylate | 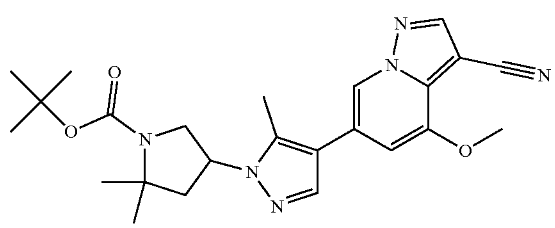 [SMILES: COc1cc(-c2cnn(C3CN(C(=O)OC(C)(C)C)C(C)(C)C3)c2C)cn2ncc(C#N)c12] | 451.2 |
| 336[2] | tert-Butyl (2R,4R)-4-(4-[3-cyano-4-methoxypyrazolo[1,5-a]pyridin-6-yl]-5-methylpyrazol-1-yl)-2-methylpyrrolidine-1-carboxylate | 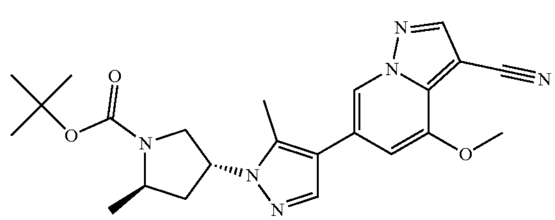 [SMILES: COc1cc(-c2cnn([C@@H]3C[C@@H](C)N(C(=O)OC(C)(C)C)C3)c2C)cn2ncc(C#N)c12] | 437.20 |

TABLE 36-continued

| Prep No. | Chemical Name | Structure | ES/MS m/z [M + H]+ |
|---|---|---|---|
| 337[7] | tert-Butyl 4-[4-[3-cyano-5-[(1R)-1-(2-pyridyl)ethoxy]imidazo[1,2-a]pyridin-7-yl]-5-methyl-triazol-1-yl]piperidine-1-carboxylate | 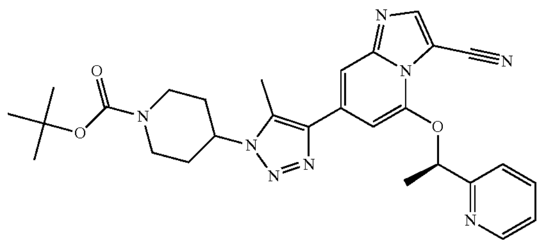 [SMILES: Cc1c(-c2cc(O[C@H](C)c3ccccn3)n3c(C#N)cnc3c2)nnn1C1CCN(C(=O)OC(C)(C)C)CC1] | 504.3 |
| 338 | tert-Butyl 4-[3-(4-[3-cyano-4-methoxypyrazolo[1,5-a]pyridin-6-yl]-5-methylpyrazol-1-yl)azetidin-1-yl]-3,3-difluoropiperidine-1-carboxylate, Isomer 1 | 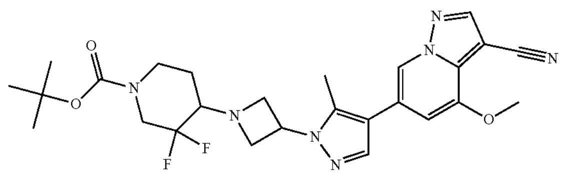 [SMILES: COc1cc(-c2cnn(C3CN(C4CCN(C(=O)OC(C)(C)C)CC4(F)F)C3)c2C)cn2ncc(C#N)c12] | 528.2 |
| 339 | tert-Butyl 4-[3-(4-[3-cyano-4-methoxypyrazolo[1,5-a]pyridin-6-yl]-5-methylpyrazol-1-yl)azetidin-1-yl]-3,3-difluoropiperidine-1-carboxylate, Isomer 2 | 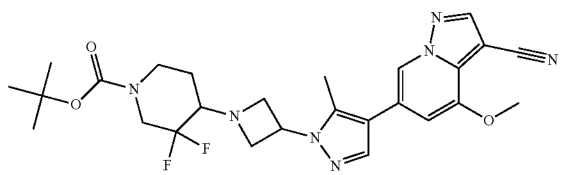 [SMILES: COc1cc(-c2cnn(C3CN(C4CCN(C(=O)OC(C)(C)C)CC4(F)F)C3)c2C)cn2ncc(C#N)c12] | 528.3 |
| 340 | tert-Butyl 4-(4-[3-cyano-4-[(1R)-1-cyclobutylethoxy]pyrazolo[1,5-a]pyridin-6-yl]-5-methylpyrazol-1-yl)piperidine-1-carboxylate | 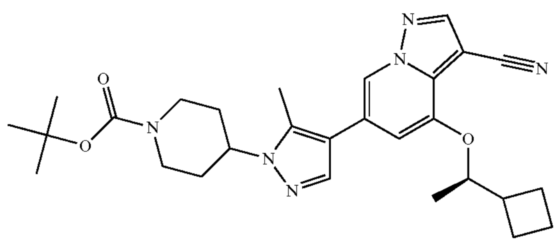 [SMILES: Cc1c(-c2cc(O[C@H](C)C3CCC3)c3c(C#N)cnn3c2)cnn1C1CCN(C(=O)OC(C)(C)C)CC1] | 449.2[b] |
| 341[8] | tert-Butyl 4-[4-(5-chloroimidazo[1,2-a]pyridin-7-yl)-5-methyl-pyrazol-1-yl]piperidine-1-carboxylate | 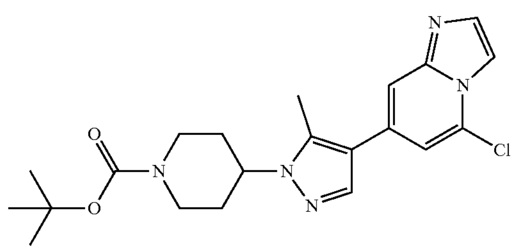 [SMILES: Cc1c(-c2cc(Cl)n3ccnc3c2)cnn1C1CCN(C(=O)OC(C)(C)C)CC1] | 416.2 |
| 342[2] | tert-butyl 2-[4-[3-cyano-5-[(1R)-1-(5-fluoro-2-pyridyl)ethoxy]imidazo[1,2-a]pyridin-7-yl]-5-methyl-triazol-1-yl]-7-azaspiro[3.5]nonane-7-carboxylate | 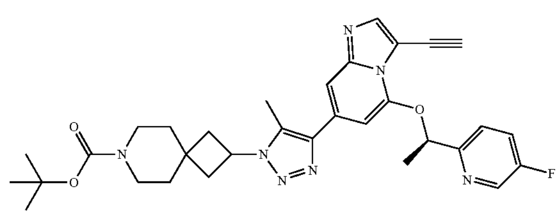 [SMILES: C#Cc1cnc2cc(-c3nnn(C4CC5(CCN(C(=O)OC(C)(C)C)CC5)C4)c3C)cc(O[C@H](C)c3ccc(F)cn3)n12] | 587.2 |
| 343[9] | tert-Butyl 4-[4-(5-methoxy-3-methyl-imidazo[1,2-a]pyridin-7-yl)-5-methyl-triazol-1-yl]piperidine-1-carboxylate | 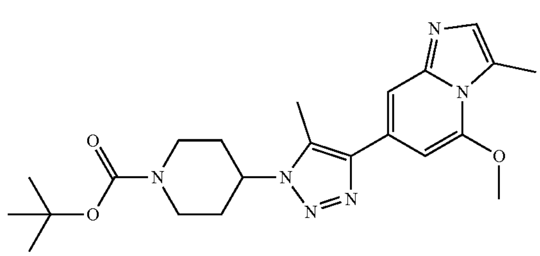 [SMILES: COc1cc(-c2nnn(C3CCN(C(=O)OC(C)(C)C)CC3)c2C)cc2ncc(C)n12] | 427.2 |

TABLE 36-continued

| Prep No. | Chemical Name | Structure | ES/MS m/z [M + H]+ |
|---|---|---|---|
| 344[10,11] | tert-butyl 2-[4-(3-cyano-5-methoxy-imidazo[1,2-a]pyridin-7-yl)-5-methyl-triazol-1-yl]-7-azaspiro[3.5]nonane-7-carboxylate | 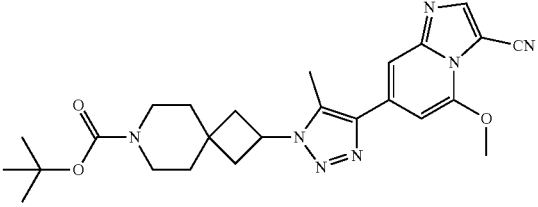 [SMILES: COc1cc(-c2nnn(C3CC4(CCN(C(=O)OC(C)(C)C)CC4)C3)c2C)cc2ncc(C#N)n12] | 478.2 |
| 345[13] | tert-Butyl 4-[4-(3-cyano-4-methoxy-pyrazolo[1,5-a]pyridin-6-yl)-5-methyl-pyrazol-1-yl]-3,3-difluoro-piperidine-1-carboxylate | 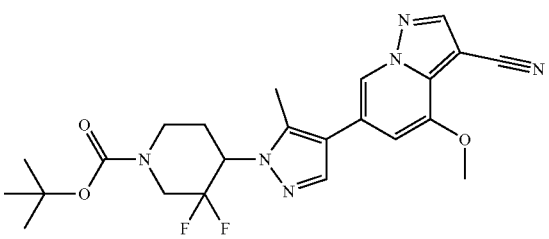 [SMILES: COc1cc(-c2cnn(C3CCN(C(=O)OC(C)(C)C)CC3(F)F)c2C)cn2ncc(C#N)c12] | 473.3 |
| 346[14] | tert-Butyl 4-[4-(4-methoxypyrazolo[1,5-a]pyridin-6-yl)-5-methyl-pyrazol-1-yl]piperidine-1-carboxylate | 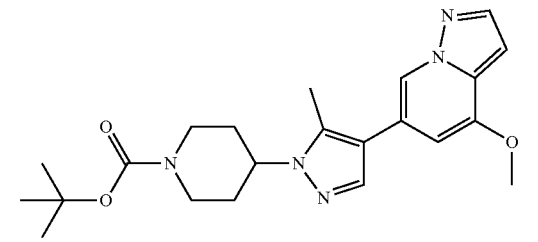 [SMILES: COc1cc(-c2cnn(C3CCN(C(=O)OC(C)(C)C)CC3)c2C)cn2nccc12] | 412.2 |
| 347[15] | tert-Butyl 2-[4-[3-cyano-5-[(1R)-1-(2-pyridyl)ethoxy]imidazo[1,2-a]pyridin-7-yl]-5-methyl-triazol-azaspiro[3.5]nonane-7-carboxylate | 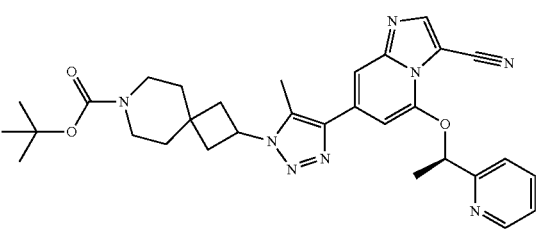 [SMILES: Cc1c(-c2cc(O[C@H](C)c3ccccn3)n3c(C#N)cnc3c2)nnn1C1CC2(CCN(C(=O)OC(C)(C)C)CC2)C1] | 569.0 |
| 348[13] | tert-butyl 4-(4-(3-cyano-4-methoxypyrazolo[1,5-a]pyridin-6-yl)-5-methyl-1H-pyrazol-1-yl)-3,3-difluoropiperidine-1-carboxylate | 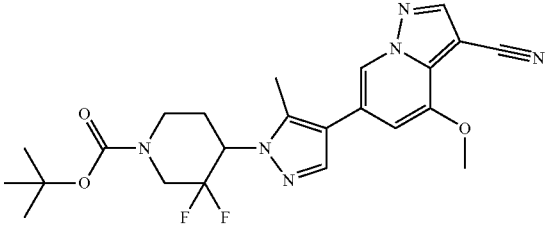 [SMILES: COc1cc(-c2cnn(C3CCN(C(=O)OC(C)(C)C)CC3(F)F)c2C)cn2ncc(C#N)c12] | 473.3 |
| 349[16] | tert-Butyl (3S)-3-[3-[4-(3-cyano-4-methoxy-pyrazolo[1,5-a]pyridin-6-yl)-5-methyl-pyrazol-1-yl]azetidin-1-yl]pyrrolidine-1-carboxylate | 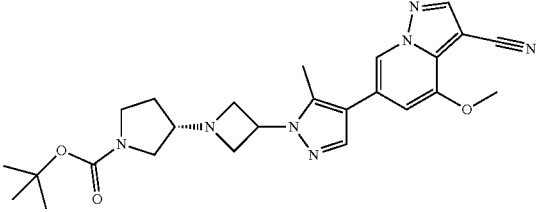 [SMILES: COc1cc(-c2cnn(C3CN([C@H]4CCN(C(=O)OC(C)(C)C)C4)C3)c2C)cn2ncc(C#N)c12] | 478.3 |

TABLE 36-continued

| Prep No. | Chemical Name | Structure | ES/MS m/z [M + H]+ |
|---|---|---|---|
| 350[1] | tert-Butyl 3-[4-[3-cyano-5-[(1R)-1-(2-pyridyl)ethoxy]imidazo[1,2-a]pyridin-7-yl]-5-methyl-pyrazol-1-yl]azetidine-1-carboxylate | 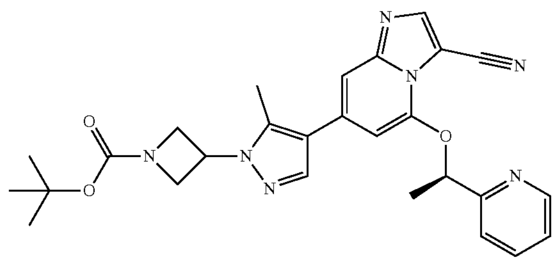 [SMILES: Cc1c(-c2cc(O[C@H](C)c3ccccn3)n3c(C#N)cnc3c2)cnn1C1CN(C(=O)OC(C)(C)C)C1] | 500.1 |
| 351[17] | tert-Butyl 4-[4-(5-methoxyimidazo[1,2-a]pyridin-7-yl)-5-methyl-triazol-1-yl]azepane-1-carboxylate | 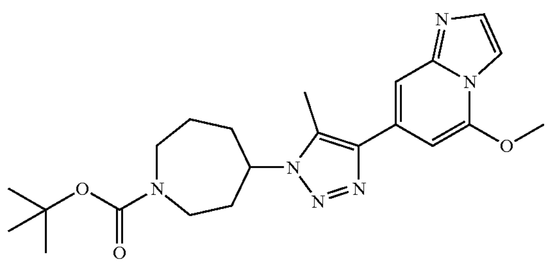 [SMILES: COc1cc(-c2nnn(C3CCCN(C(=O)OC(C)(C)C)CC3)c2C)cc2nccn12] | c |
| 352[18] | tert-Butyl (3S)-3-[4-(3-cyano-5-methoxy-imidazo[1,2-a]pyridin-7-yl)-5-methyl-triazol-1-yl]piperidine-1-carboxylate | 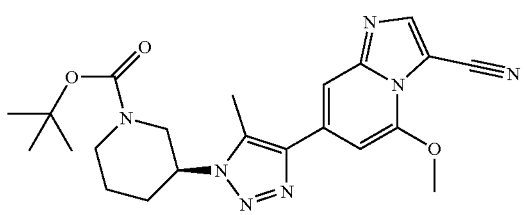 [SMILES: COc1cc(-c2nnn([C@H]3CCCN(C(=O)OC(C)(C)C)C3)c2C)cc2ncc(C#N)n12] | 438.1 |
| 353[10,21] | tert-Butyl 4-[4-(3-cyano-5-methoxy-imidazo[1,2-a]pyridin-7-yl)-5-methyl-triazol-1-yl]azepane-1-carboxylate | 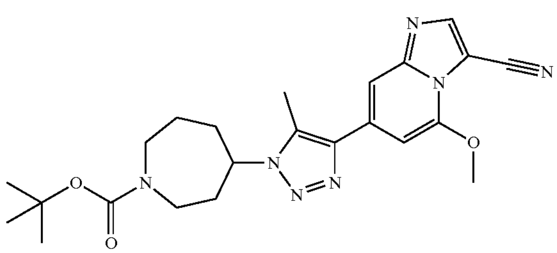 [SMILES: COc1cc(-c2nnn(C3CCCN(C(=O)OC(C)(C)C)CC3)c2C)cc2ncc(C#N)n12] | 452.3 |
| 354[10,19,20] | tert-Butyl 4-[4-[3-cyano-5-[[(1R)-1-(5-fluoro-2-pyridyl)ethyl]amino]imidazo[1,2-a]pyridin-7-yl]-5-methyl-triazol-1-yl]piperidine-1-carboxylate | 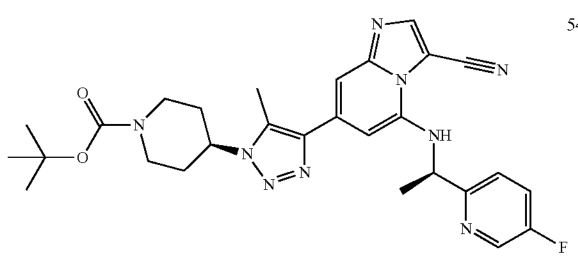 | 546.3 |
| 355[10,21,18] | tert-Butyl (3R)-3-[4-(3-cyano-5-methoxy-imidazo[1,2-a]pyridin-7-yl)-5-methyl-triazol-1-yl]piperidine-1-carboxylate | 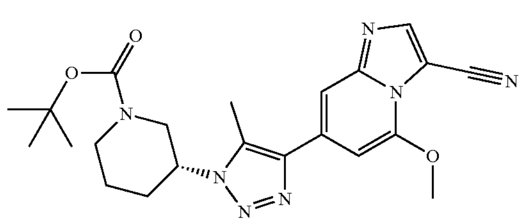 [SMILES: COc1cc(-c2nnn([C@@H]3CCCN(C(=O)OC(C)(C)C)C3)c2C)cc2ncc(C#N)n12] | 438.3 |

TABLE 36-continued

| Prep No. | Chemical Name | Structure | ES/MS m/z [M + H]+ |
|---|---|---|---|
| 356[22,23] | tert-Butyl 4-[4-(3-fluoro-4-methoxy-pyrazolo[1,5-a]pyridin-6-yl)-5-methyl-triazol-1-yl]piperidine-1-carboxylate | 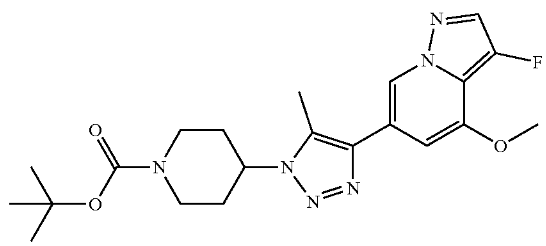 [SMILES: COc1cc(-c2nnn(C3CCN(C(=O)OC(C)(C)C)CC3)c2C)cn2ncc(F)c12] | 431.2 |
| 357[23] | Cis-tert-Butyl 4-[3-[4-(4-methoxy pyrazolo[1,5-a]pyridin-6-yl)-5-methyl-triazol-1-yl]cyclobutyl]piperazine-1-carboxylate | 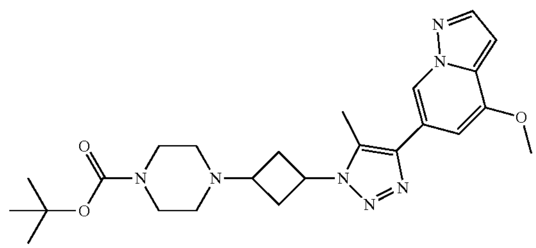 [SMILES: COc1cc(-c2nnn(C3CC(N4CCN(C(=O)OC(C)(C)C)CC4)C3)c2C)cn2nccc12] | 468.3 |
| 358[24] | tert-Butyl 4-[4-(3-cyano-5-methoxy-imidazo[1,2-a]pyridin-7-yl)-3-(2-hydroxyethyl)-5-methyl-pyrazol-1-yl]piperidine-1-carboxylate | 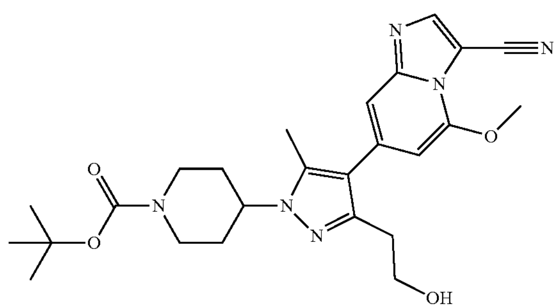 [SMILES: COc1cc(-c2c(CCO)nn(C3CCN(C(=O)OC(C)(C)C)CC3)c2C)cc2ncc(C#N)n12] | 481.3 |
| 359[25] | tert-Butyl 4-[4-[4-methoxy-3-(trifluoromethyl)pyrazolo[1,5-a]pyridin-6-yl]-5-methyl-pyrazol-1-yl]piperidine-1-carboxylate | 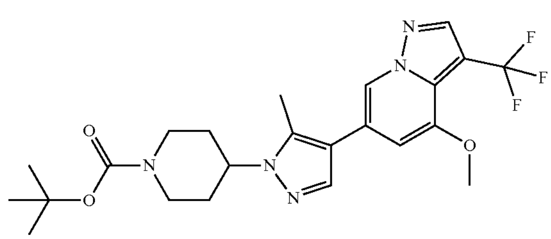 [SMILES: COc1cc(-c2cnn(C3CCN(C(=O)OC(C)(C)C)CC3)c2C)cn2ncc(C(F)(F)F)c12] | 424.8 [M + H − C4H8]+ |

TABLE 36-continued

| Prep No. | Chemical Name | Structure | ES/MS m/z [M + H]⁺ |
|---|---|---|---|
| 360[26] | tert-Butyl (2SR,4RS)-2-cyclopropyl-4-[4-(5-methoxyimidazo[1,2-a]pyridin-7-yl)-5-methyl-triazol-1-yl]piperidine-1-carboxylate | 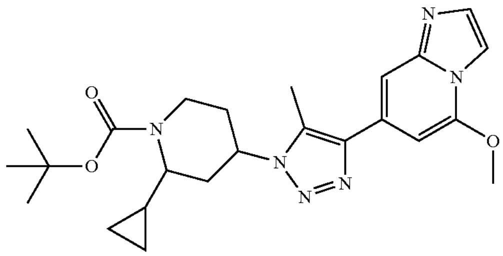 [SMILES: COc1cc(-c2nnn(C3CCN(C(=O)OC(C)(C)C)C(C4CC4)C3)c2C)cc2nccn12] | 453.2 |

[1]Prep-TLC (EtOAc:PE = 1:1).
[2]Reverse flash chromatography with the following conditions: column, C18; ACN in H₂O (0.1% NH₄HCO₃).
[3]Reverse flash chromatography with the following conditions: Column, C18, ACN in H₂O (0.1% FA).
[4]Reverse flash chromatography with the following conditions: Column, C18; ACN in H₂O (0.1% NH₃H₂O).
[5]Reverse flash chromatography with the following conditions: Column, C18; ACN in H₂O.
[6]Reverse flash chromatography with the following conditions: Column, C18, H₂O (0.1% FA).
[7]Silica gel column chromatography, eluting with a gradient of DCM:MeOH.
[8]Silica gel column chromatography, eluting with PE:EtOAc (1:2)
[9]Reverse flash chromatography: Column, C18, 40% to 70% ACN in H₂O (0.1% FA).
[10]Catalyst: Pd(DtBPF)Cl₂.
[11]Silica gel column chromatography, eluting with PE:EtOAc (1:1).
[13]Silica gel column chromatography, eluting with PE:EtOAc (4:1 to 1:2).
[14]Silica gel flash column chromatography, eluting 10% to 60% EtOAc in PE.
[15]Prep-TLC (EtOAc).
[16]Silica gel column chromatography, eluting with a gradient of DCM:MeOH (20:1).
[17]Reverse flash chromatography with the following conditions: column, C18; 10% to 50% ACN in H₂O (0.1% NH₄HCO₃).
[18]Reverse flash chromatography with the following conditions: Column, C18; 50% to 60% ACN in H₂O (0.1% NH₄HCO₃).
[19]Silica gel column chromatography, eluting with 50% to 100% EtOAc in PE.
[20]Silica gel column chromatography, eluting with a gradient of DCM:MeOH (20:1 to 12:1).
[21]Cs₂CO₃ used as base.
[22]Pd(DtBPF)Cl₂ used as catalyst
[23]Silica gel column chromatography, eluting with PE:EtOAc (2:1 to 1:1).
[24]Silica gel column chromatography, eluting with PE:EtOAc (2:1 to 1:1).
[25]Silica gel column chromatography, eluting with 0% to 100% EtOAc in heptane.
[26]Reverse flash chromatography with the following conditions: column, C18; 10% to 50% ACN in H₂O.
a ¹H NMR (300 MHz, Methanol-d₄) δ 7.82 (s, 1H), 7.60 (s, 1H), 7.41 (s, 1H), 6.77 (s, 1H), 4.24 (s, 3H), 3.86 – 3.73(m, 1H), 3.65-3.37 (m, 4H), 2.62 (s, 3H), 2.09-2.01 (m, 1H), 1.94 – 1.81(m, 1H), 1.54 (s, 9H), 1.49 – 1.14 (m, 4H).
b ES/MS m/z [M + 2H – tBu]⁺.
c ¹H NMR (300 MHz, d₆-DMSO) δ 8.59-8.49 (m, 2H), 8.35 (s, 1H), 7.12 (d, 1H), 5.24-5.11(m, 1H), 4.38-4.28(m, 2H), 4.22-4.12 (m, 2H), 4.06 (s, 3H), 2.41 (s, 3H), 1.42 (s, 9H).

Preparation 361 tert-Butyl 4-(4-[3-cyano-4-[(1R)-1-(pyridin-2-yl)ethoxy]pyrazolo[1,5-a]pyridin-6-yl]-5-methyl-1,2,3-triazol-1-yl)piperidine-1-carboxylate

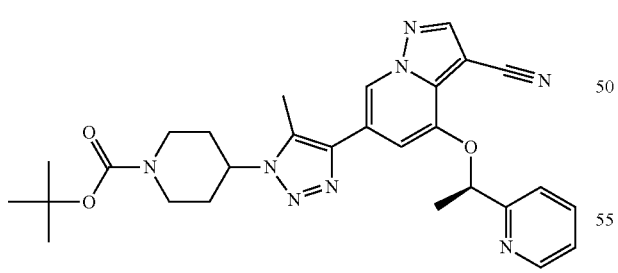

A solution of 4-[(1R)-1-(pyridin-2-yl)ethoxy]-6-(4,4,5,5-tetramethyl-1,3,2-dioxaborolan-2-yl)pyrazolo[1,5-a]pyridine-3-carbonitrile (500 mg, 1.28 mmol), tert-butyl 4-(4-bromo-5-methyl-1,2,3-triazol-1-yl)piperidine-1-carboxylate (487 mg, 1.41 mmol), K₂CO₃ (531 mg, 3.84 mmol), Pd(PPh₃)₄ (148 mg, 0.13 mmol), H₂O (2 mL) and dioxane (8 mL) is stirred overnight at 100° C. under N₂. The mixture is diluted with H₂O (20 mL) and extracted with EtOAc (2×20 mL). The combined organic extracts are washed with brine (2×20 mL), dried over anhydrous Na₂SO₄, filtered, and the filtrate is concentrated under reduced pressure. The residue is purified by reverse Combi-flash chromatography with the following conditions: Column, C18; eluting with a gradient of 50% to 60% ACN in H₂O (0.1% NH₄HCO₃) to give the title compound as a brown solid (354 mg, 52.27%). ES/MS m/z 529.3 [M+H]⁺.

Preparation 362 tert-Butyl 2-(4-[3-cyano-4-methoxypyrazolo[1,5-a]pyridin-6-yl]-5-methylpyrazol-1-yl)-7-azaspiro[3.5]nonane-7-carboxylate

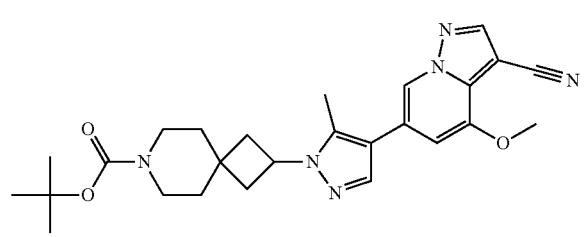 [SMILES: COc1cc(-c2cnn(C3CC4(CCN(C(=O)OC(C)(C)C)CC4)C3)c2C)cn2ncc(C#N)c12]

A stirred mixture of tert-butyl 2-(4-bromo-5-methylpyrazol-1-yl)-7-azaspiro[3.5]nonane-7-carboxylate (200.00 mg, 0.52 mmol) and 4-methoxy-6-(4,4,5,5-tetramethyl-1,3,2-dioxaborolan-2-yl)pyrazolo[1,5-a]pyridine-3-carbonitrile (171.24 mg, 0.57 mmol) in dioxane (4.00 mL) and H₂O (1 mL) is treated with K₂CO₃ (215.77 mg, 1.56 mmol) and Pd(PPh₃)₄ (120.27 mg, 0.10 mmol) in portions at RT under N₂. The mixture is stirred for 2 hrs at 80° C. under N₂. The mixture is cooled to RT and concentrated under reduced pressure. The residue is purified by silica gel column chromatography, eluting with a gradient of PE:EtOAc (3:1 to 2:1), to give the title compound as a yellow solid (110 mg, 44.3%). ES/MS m/z 462.3 [M-tBu+ACN+H]⁺.

The following compounds are prepared essentially as described for tert-butyl 2-(4-[3-cyano-4-methoxypyrazolo[1,5-a]pyridin-6-yl]-5-methylpyrazol-1-yl)-7-azaspiro[3.5]nonane-7-carboxylate using the appropriate reagents and adjusting the reaction times to determine completion of the reactions. Temperature is varied from 80° C. to 100° C. Toluene:H₂O can also be used as the solvent. Pd(AcO)₂, PCy₃, XPhos Pd G2, XPhos Pd G4, or Pd(dppf)Cl₂ can also be used as the catalyst or no catalyst can be used. K₃PO₄, KF or CsF can also be used as the base. Pd(DtBPF)Cl₂ may also be used as a catalyst.

TABLE 37

| Prep No. | Chemical Name | Structure | ES/MS m/z [M + H]⁺ |
|---|---|---|---|
| 363¹ | tert-Butyl 4-[4-(3-cyano-4-isopropoxy-pyrazolo[1,5-a]pyridin-6-yl)-5-methyl-pyrazol-1-yl]piperidine-1-carboxylate | 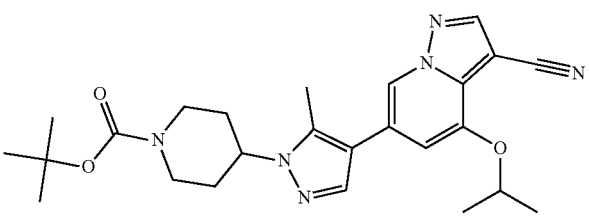 [SMILES: Cc1c(-c2cc(OC(C)C)c3c(C#N)cnn3c2)cnn1C1CCN(C(=O)OC(C)(C)C)CC1] | 465.3 |
| 364 | tert-Butyl (1R,3r,5S)-3-(4-(3-cyano-4-methoxypyrazolo[1,5-a]pyridin-6-yl)-5-methyl-1H-pyrazol-1-yl)-8-azabicyclo[3.2.1]octane-8-carboxylate | 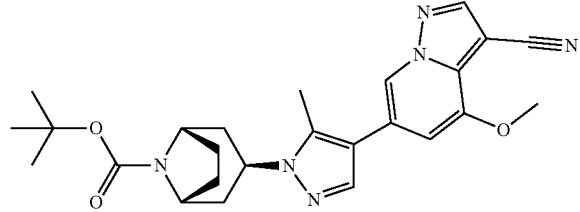 [SMILES: COc1cc(-c2cnn([C@H]3C[C@H]4CC[C@@H](C3)N4C(=O)OC(C)(C)C)c2C)cn2ncc(C#N)c12] | 463.1 |
| 365 | tert-Butyl (3S)-3-[3-(4-[3-cyano-4-methoxypyrazolo[1,5-a]pyridin-6-yl]-5-methylpyrazol-1-yl)azetidin-1-yl]piperidine-1-carboxylate | 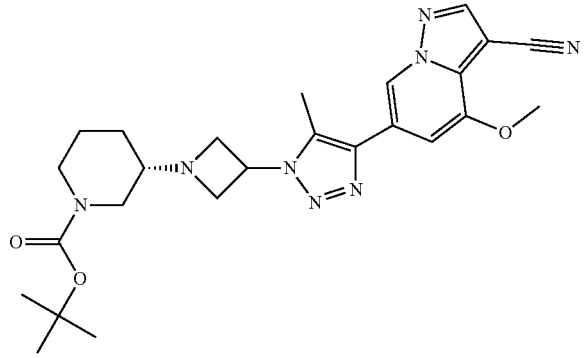 [SMILES: COc1cc(-c2nnn(C3CN([C@H]4CCCN(C(=O)OC(C)(C)C)C4)C3)c2C)cn2ncc(C#N)c12] | 492.3 |
| 366 | tert-Butyl (3R)-3-[3-(4-[3-cyano-4-methoxypyrazolo[1,5-a]pyridin-6-yl]-5-methylpyrazol-1-yl)azetidin-1-yl]piperidine-1-carboxylate | 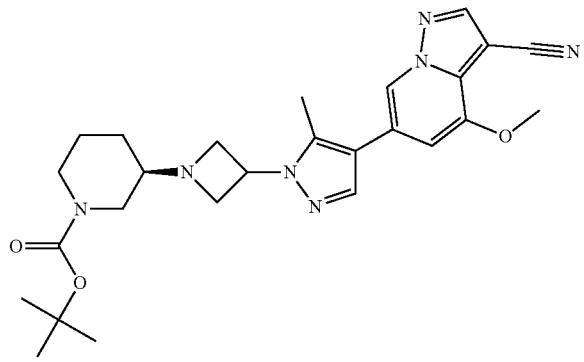 | 392.20 |

TABLE 37-continued

| Prep No. | Chemical Name | Structure | ES/MS m/z [M + H]⁺ |
|---|---|---|---|
| 367 | tert-Butyl (3R)-3-[3-[4-[3-cyano-4-[(1R)-1-(pyridin-2-yl)ethoxy]pyrazolo[1,5-a]pyridin-6-yl]-5-methylpyrazol-1-yl]azetidin-1-yl]pyrrolidine-1-carboxylate | 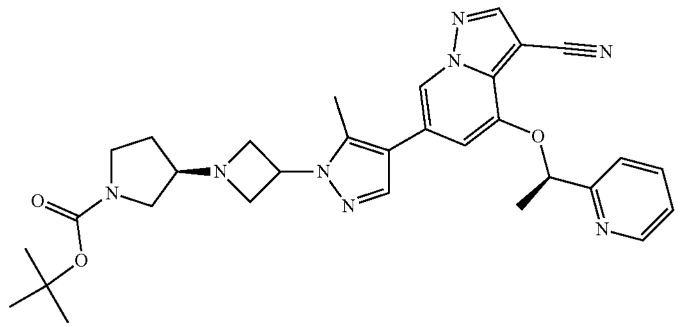 [SMILES: Cc1c(-c2cc(O[C@H](C)c3ccccn3)c3c(C#N)cnn3c2)cnn1C1CN([C@@H]2CCN(C(=O)OC(C)(C)C)C2)C1] | 569.3 |
| 368 | tert-Butyl 4-(4-[3-cyano-4-methoxypyrazolo[1,5-a]pyridin-6-yl]-3-methylpyrazol-1-yl)piperidine-1-carboxylate | 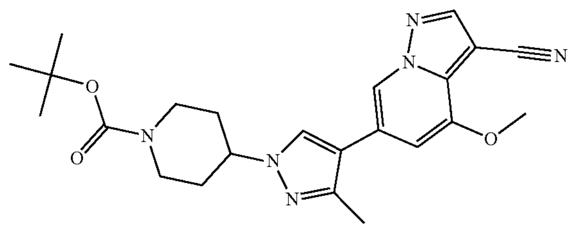 [SMILES: COc1cc(-c2cn(C3CCN(C(=O)OC(C)(C)C)CC3)nc2C)cn2ncc(C#N)c12] | 381.1 [M − tBu + H]⁺ |
| 369 | tert-Butyl (2R,4S)-4-(4-[3-cyano-4-methoxypyrazolo[1,5-a]pyridin-6-yl]-5-methylpyrazol-1-yl)-2-methylpyrrolidine-1-carboxylate | 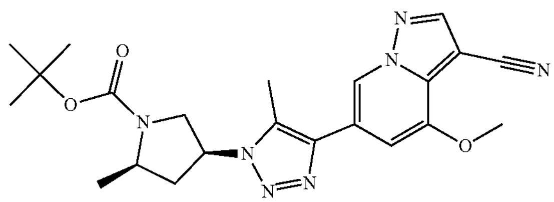 [SMILES: COc1cc(-c2nnn([C@H]3C[C@@H](C)N(C(=O)OC(C)(C)C)C3)c2C)cn2ncc(C#N)c12] | 437.3 |
| 370 | tert-Butyl (2S,4S)-4-(4-[3-cyano-4-methoxypyrazolo[1,5-a]pyridin-6-yl]-5-methylpyrazol-1-yl)-2-methylpyrrolidine-1-carboxylate | 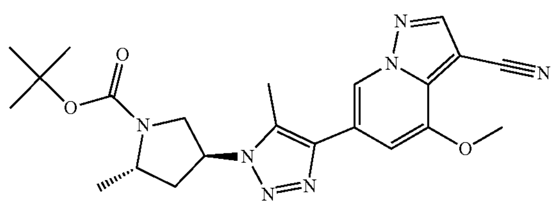 [SMILES: COc1cc(-c2nnn([C@H]3C[C@H](C)N(C(=O)OC(C)(C)C)C3)c2C)cn2ncc(C#N)c12] | 437.3 |
| 371 | tert-Butyl 4-(4-[3-cyano-4-[(1R)-1-cyclopropylethoxy]pyrazolo[1,5-a]pyridin-6-yl]-5-methyl-1,2,3-triazol-1-yl)piperidine-1-carboxylate | 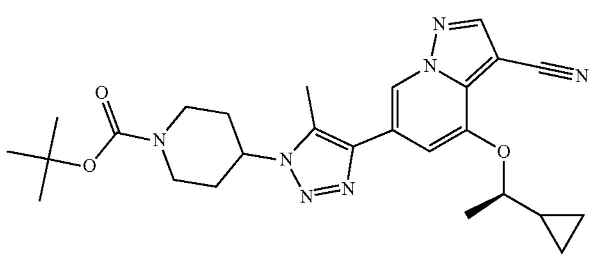 [SMILES: Cc1c(-c2cc(O[C@H](C)C3CC3)c3c(C#N)cnn3c2)nnn1C1CCN(C(=O)OC(C)(C)C)CC1] | 492.3 |
| 372 | tert-Butyl 4-(4-[3-cyano-4-[(1R)-1-cyclopropylethoxy]pyrazolo[1,5-a]pyridin-6-yl]-5-methylpyrazol-1-yl)piperidine-1-carboxylate | 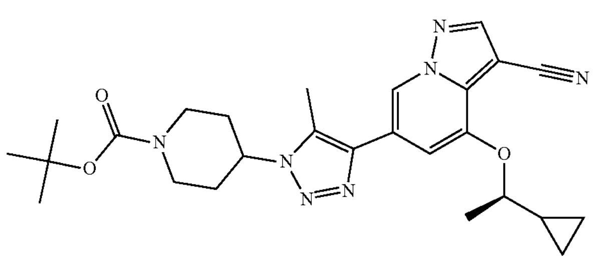 [SMILES: Cc1c(-c2cc(O[C@H](C)C3CC3)c3c(C#N)cnn3c2)nnn1C1CCN(C(=O)OC(C)(C)C)CC1] | 491.3 |

TABLE 37-continued

| Prep No. | Chemical Name | Structure | ES/MS m/z [M + H]+ |
|---|---|---|---|
| 373 | tert-Butyl 4-(4-[3-cyano-4-[(1R)-1-phenylethoxy]pyrazolo[1,5-a]pyridin-6-yl]-5-methyl-1,2,3-triazol-1-yl)piperidine-1-carboxylate | 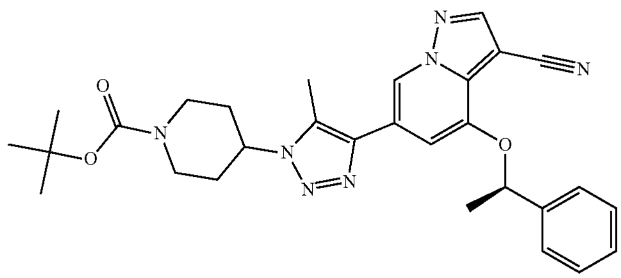 [SMILES: Cc1c(-c2cc(O[C@H](C)c3ccccc3)c3c(C#N)cnn3c2)nnn1C1CCN(C(=O)OC(C)(C)C)CC1] | 528.3 |
| 374[2] | tert-Butyl (3R)-3-(3-(4-(3-cyano-4-methoxypyrazolo[1,5-a]pyridin-6-yl)-5-methyl-1H-pyrazol-1-yl)azetidin-1-yl)pyrrolidine-1-carboxylate | 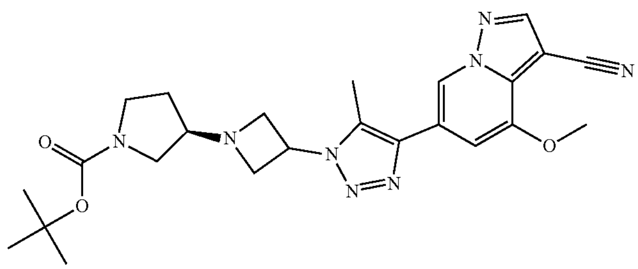 [SMILES: COc1cc(-c2nnn(C3CN([C@@H]4CCN(C(=O)OC(C)(C)C)C4)C3)c2C)cn2ncc(C#N)c12] | 478.3 |
| 375 | tert-Butyl 3-(4-[3-cyano-5-[(1R)-1-(pyridin-2-yl)ethoxy]imidazo[1,2-a]pyridin-7-yl]-5-methyl-1,2,3-triazol-1-yl)azetidine-1-carboxylate | 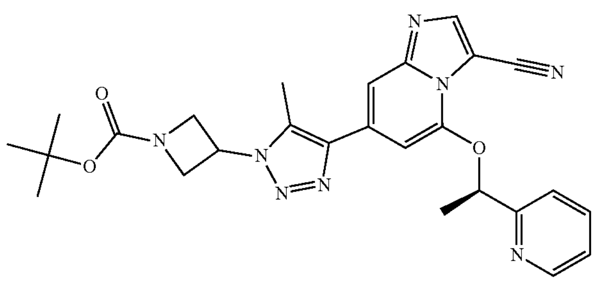 [SMILES: Cc1c(-c2cc(O[C@H](C)c3ccccn3)n3c(C#N)cnc3c2)nnn1C1CN(C(=O)OC(C)(C)C)C1] | 501.3 |
| 376[3] | tert-Butyl (3S)-3-(4-[3-cyano-4-methoxypyrazolo[1,5-a]pyridin-6-yl]-5-methyl-1,2,3-triazol-1-yl)pyrrolidine-1-carboxylate | 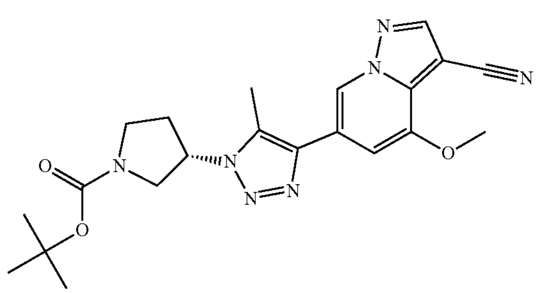 [SMILES: COc1cc(-c2nnn([C@H]3CCN(C(=O)OC(C)(C)C)C3)c2C)cn2ncc(C#N)c12] | 424.2 |
| 377 | tert-Butyl 4-[4-[5-[(1R)-1-(5-fluoro-2-pyridyl)ethoxy]imidazo[1,2-a]pyridin-7-yl]-5-methyl-triazol-1-yl]piperidine-1-carboxylate | 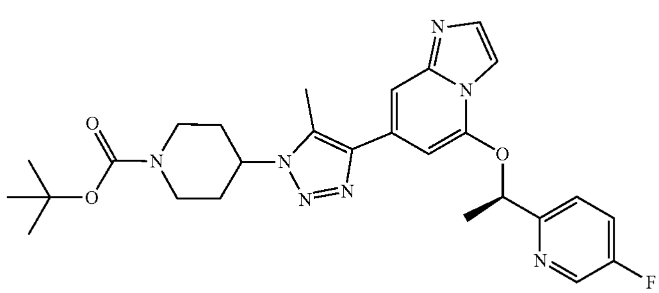 [SMILES: Cc1c(-c2cc(O[C@H](C)c3ccc(F)cn3)n3ccnc3c2)nnn1C1CCN(C(=O)OC(C)(C)C)CC1] | |

TABLE 37-continued

| Prep No. | Chemical Name | Structure | ES/MS m/z [M + H]+ |
|---|---|---|---|
| 378[4] | tert-Butyl 4-[4-[3-cyano-5-[(1R)-1-(3-pyridyl)ethoxy]imidazo[1,2-a]pyridin-7-yl]-5-methyl-triazol-1-yl]piperidine-1-carboxylate | 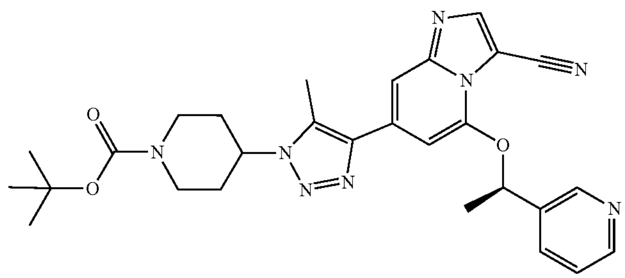 [SMILES: Cc1c(-c2cc(O[C@H](C)c3cccnc3)n3c(C#N)cnc3c2)nnn1C1CCN(C(=O)OC(C)(C)C)CC1] | 529.2 |
| 379[5] | tert-Butyl 4-[5-(3-cyano-4-methoxy-pyrazolo[1,5-a]pyridin-6-yl)-4-methyl-1,2,4-triazol-3-yl]piperazine-1-carboxylate | 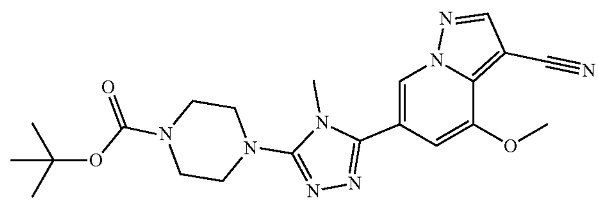 [SMILES: COc1cc(-c2nnc(N3CCN(C(=O)OC(C)(C)C)CC3)n2C)cn2ncc(C#N)c12] | 439.2 |
| 380[5] | tert-Butyl 4-[2-[4-[3-cyano-5-[(1R)-1-(2-pyridyl)ethoxy]imidazo[1,2-a]pyridin-7-yl]-5-methyl-triazol-1-yl]-1,1-dimethyl-ethyl]piperazine-1-carboxylate | 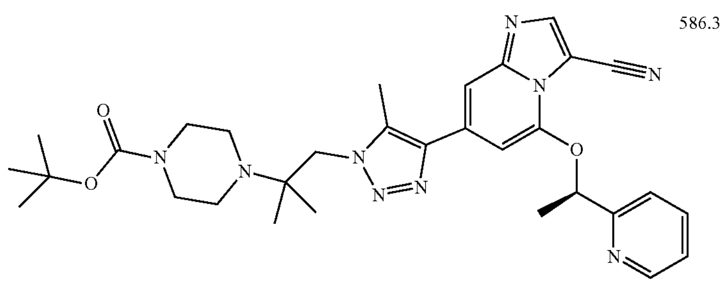 | 586.3 |
| 381[6] | tert-butyl (3R,4S)-4-[4-[4-[2-[tert-butyl(dimethyl)silyl]oxy-1-(5-fluoro-2-pyridyl)ethoxy]pyrazolo[1,5-a]pyridin-6-yl]-5-methyl-triazol-1-yl]-3-fluoro-piperidine-1-carboxylate, Isomer 2 | 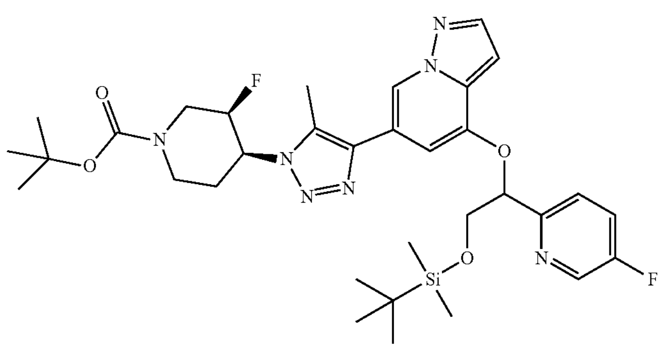 [SMILES: Cc1c(-c2cc(OC(CO[Si](C)(C)C(C)(C)C)c3ccc(F)cn3)c3ccnn3c2)nnn1[C@H]1CCN(C(=O)OC(C)(C)C)C[C@H]1F] | 670.3 |
| 382[7] | tert-Butyl (3S,4S)-4-[4-[4-[2-[tert-butyl(dimethyl)silyl]oxy-1-(5-fluoro-2-pyridyl)ethoxy]pyrazolo[1,5-a]pyridin-6-yl]-5-methyl-triazol-1-yl]-3-fluoro-piperidine-1-carboxylate, Isomer 2 | 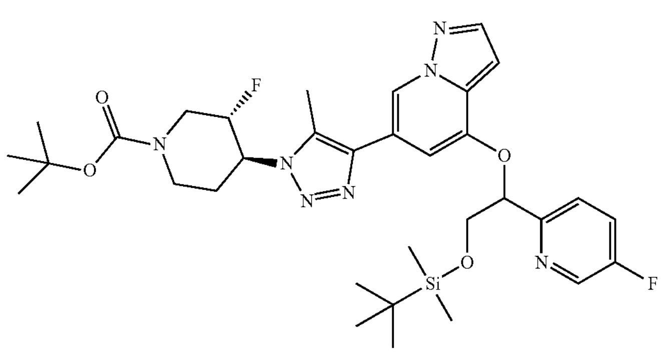 [SMILES: Cc1c(-c2cc(OC(CO[Si](C)(C)C(C)(C)C)c3ccc(F)cn3)c3ccnn3c2)nnn1[C@H]1CCN(C(=O)OC(C)(C)C)C[C@@H]1F] | 670.3 |

TABLE 37-continued

| Prep No. | Chemical Name | Structure | ES/MS m/z [M + H]+ |
|---|---|---|---|
| 383[8] | tert-Butyl (3S,4R)-4-[4-[4-[2-[tert-butyl (dimethyl)silyl]oxy-1-(5-fluoro-2-pyridyl)ethoxy] pyrazolo[1,5-a]pyridin-6-yl]-5-methyl-triazol-1-yl]-3-fluoro-piperidine-1-carboxylate, Isomer 2 | 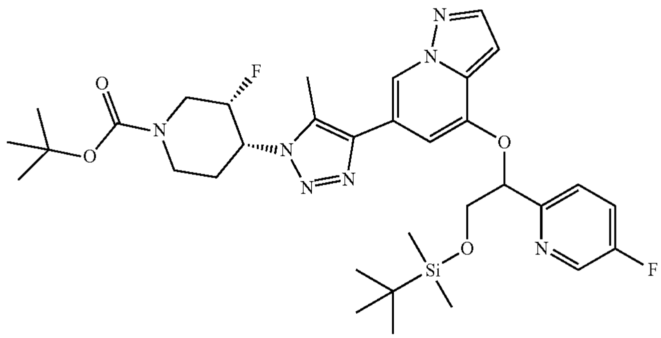 | 670.4 |
| 384[9] | tert-Butyl (3R,4R)-4-[4-[4-[2-[tert-butyl (dimethyl)silyl]oxy-1-(5-fluoro-2-pyridyl)ethoxy] pyrazolo[1,5-a]pyridin-6-yl]-5-methyl-triazol-1-yl]-3-fluoro-piperidine-1-carboxylate, Isomer 2 | 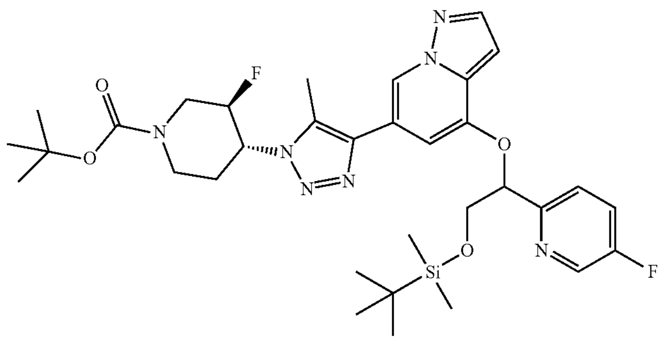 [SMILES: Cc1c(-c2cc(OC(CO[Si](C)(C)C(C)(C)C)c3ccc(F)cn3)c3ccnn3c2)nnn1[C@@H]1CCN(C(=O)OC(C)(C)C)C[C@H]1F] | 670.4 |
| 385[10] | (1r,3r)-3-(4-(3-Chloro-4-methoxypyrazolo[1,5-a]pyridin-6-yl)-5-methyl-1H-1,2,3-triazol-1-yl)cyclobutan-1-ol | 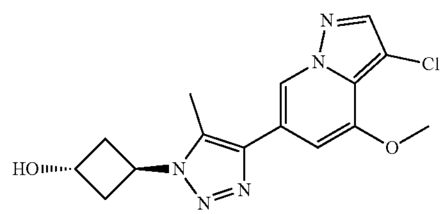 [SMILES: COc1cc(-c2nnn([C@H]3C[C@H](O)C3)c2C)cn2ncc(Cl)c12] | 334.2 |
| 386[11] | tert-Butyl (3S,4S)-4-[4-[4-[2-[tert-butyl (dimethyl) silyl]oxy-1-(5-fluoro-2-pyridyl)ethoxy] pyrazolo [1,5-a]pyridin-6-yl]-5-methyl-triazol-1-yl]-3-hydroxy-piperidine-1-carboxylate, Isomer 2 | 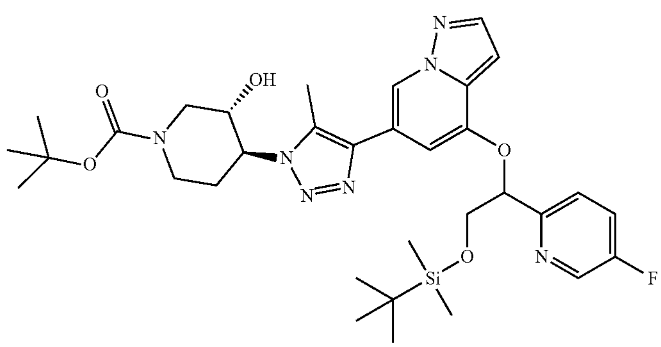 [SMILES: Cc1c(-c2cc(OC(CO[Si](C)(C)C(C)(C)C)c3ccc(F)cn3)c3ccnn3c2)nnn1[C@H]1CCN(C(=O)OC(C)(C)C)C[C@@H]1O] | 668.3 |
| 387[12] | tert-Butyl (3R,4S)-4-[4-[4-[2-[tert-butyl (dimethyl)silyl]oxy-1-(5-fluoro-2-pyridyl) ethoxy] pyrazolo[1,5-a]pyridin-6-yl]-5-methyl-triazol-1-yl]-3-hydroxy-piperidine-1-carboxylate, Isomer 2 | 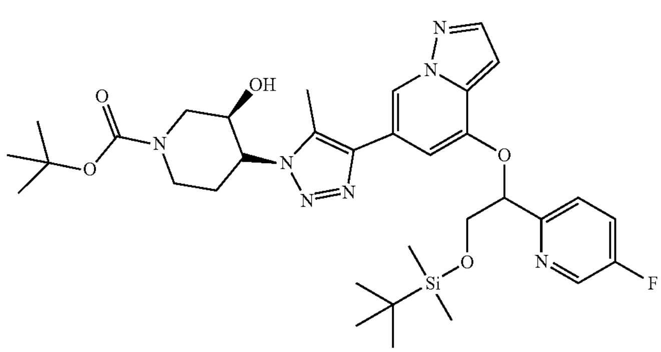 | 668.4 |

TABLE 37-continued

| Prep No. | Chemical Name | Structure | ES/MS m/z [M + H]+ |
|---|---|---|---|
| 388[12] | tert-Butyl (3S,4R)-4-[4-[4-[2-[tert-butyl(dimethyl)silyl]oxy-1-(5-fluoro-2-pyridyl)ethoxy]pyrazolo[1,5-a]pyridin-6-yl]-5-methyl-triazol-1-yl]-3-hydroxy-piperidine-1-carboxylate, Isomer 2 | 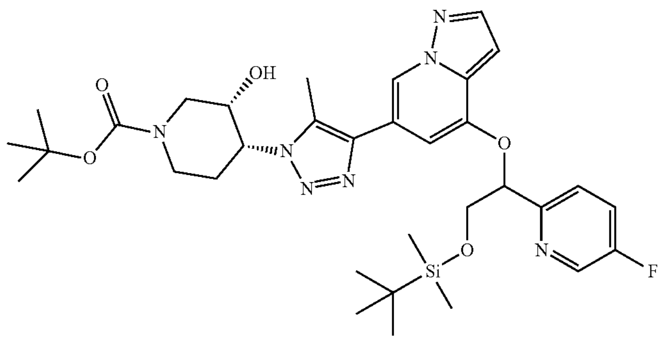 [SMILES: Cc1c(-c2cc(OC(CO[Si](C)(C)C(C)(C)C)c3ccc(F)cn3)c3ccnn3c2)nnn1[C@@H]1CCN(C(=O)OC(C)(C)C)C[C@@H]1O] | 668.3 |
| 389[13] | tert-Butyl (3R,4R)-4-[4-[4-[2-[tert-butyl(dimethyl)silyl]oxy-1-(5-fluoro-2-pyridyl)ethoxy]pyrazolo[1,5-a]pyridin-6-yl]-5-methyl-triazol-1-yl]-3-hydroxy-piperidine-1-carboxylate, Isomer 2 | 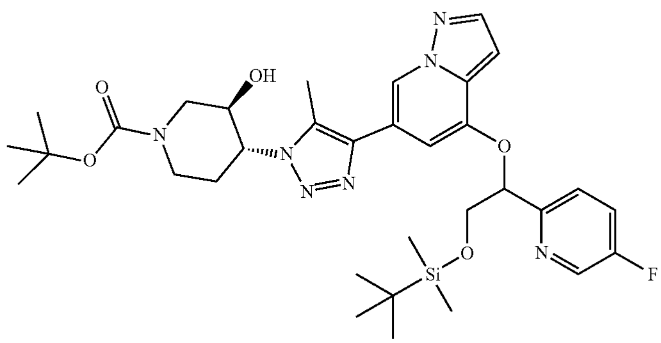 [SMILES: Cc1c(-c2cc(OC(CO[Si](C)(C)C(C)(C)C)c3ccc(F)cn3)c3ccnn3c2)nnn1[C@@H]1CCN(C(=O)OC(C)(C)C)C[C@H]1O] | 668.4 |
| 390[14] | tert-Butyl (3RS,4RS)-4-[4-[4-[2-[tert-butyl(dimethyl)silyl]oxy-1-(5-fluoro-2-pyridyl) ethoxy]pyrazolo[1,5-a]pyridin-6-yl]-5-methyl-triazol-1-yl]-3-methyl-piperidine-1-carboxylate, Isomer 2 | 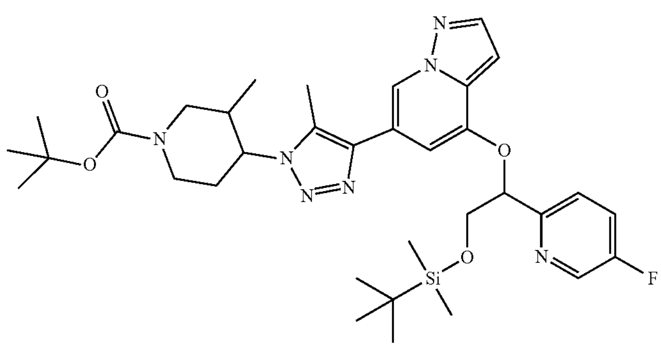 [SMILES: Cc1c(-c2cc(OC(CO[Si](C)(C)C(C)(C)C)c3ccc(F)cn3)c3ccnn3c2)nnn1C1CCN(C(=O)OC(C)(C)C)CC1C] | 666.3 |
| 391[6] | tert-butyl (3RS,4SR)-4-[4-[4-[2-[tert-butyl(dimethyl)silyl]oxy-1-(5-fluoro-2-pyridyl)ethoxy]pyrazolo[1,5-a]pyridin-6-yl]-5-methyl-triazol-1-yl]-3-methyl-piperidine-1-carboxylate, Isomer 2 | 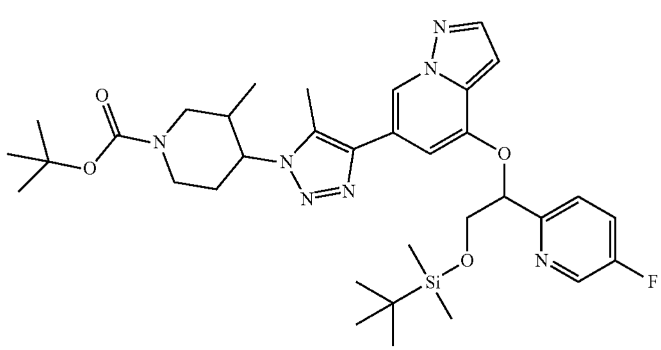 [SMILES: Cc1c(-c2cc(OC(CO[Si](C)(C)C(C)(C)C)c3ccc(F)cn3)c3ccnn3c2)nnn1C1CCN(C(=O)OC(C)(C)C)CC1C] | 666.2 |

TABLE 37-continued

| Prep No. | Chemical Name | Structure | ES/MS m/z [M + H]+ |
|---|---|---|---|
| 392[15] | tert-Butyl 4-[4-[4-[2-[tert-butyl(dimethyl)silyl]oxy-1-(5-fluoro-2-pyridyl)ethoxy]-3-fluoro-pyrazolo[1,5-a]pyridin-6-yl]-5-methyl-triazol-1-yl]-4-methyl-piperidine-1-carboxylate, Isomer 2 | 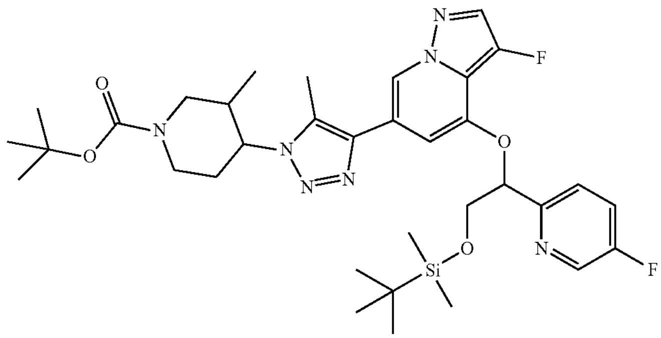 [SMILES: Cc1c(-c2cc(OC(CO[Si](C)(C)C(C)(C)C)c3ccc(F)cn3)c3c(F)cnn3c2)nnn1C1CCN(C(=O)OC(C)(C)C)CC1C] | 684.5 |

[1]ISCO Column, eluting with hexanes:EtOAc (10-100%).
[2]Purified by silica gel column chromatography, eluting with a gradient of DCM:MeOH (20:1).
[3]Purified by silica gel column chromatography, eluting with a gradient of 0% to 10% MeOH in DCM.
[4]Purified by Prep-TLC (EA)
[5]Purified by reverse Combi-flash chromatography with the following conditions: Column, C18; ACN in H2O (0.1% NH4HCO3).
[6]Purified by Prep-TLC PE:EtOAc (1:1).
[7]Purified by Prep-TLC (EA).
[8]Purified by silica gel column chromatography, eluting with PE:EtOAc (1:3).
[9]Purified by silica gel column chromatography, eluting with PE:EtOAc (2:3).
[10]Purified by silica gel column chromatography, eluting with a gradient of 0% to 10% MeOH in DCM.
[11]Purified by silica gel column chromatography, eluting with PE:EA (2:3).
[12]Purified by silica gel chromatography, eluting with PE:EA (1:1 to 1:2).
[13]Purified by reverse phase chromatography: column, C18; eluting with 40% to 50% ACN in H2O (0.1% NH4OH).
[14]Purified by silica gel column chromatography, eluting with PE:EtOAc (3:1).
[15]Purified by silica gel column chromatography, eluting with PE:EA (2:1 to 1:1).

Preparation 393 tert-Butyl (3R)-3-[4-(4-[3-cyano-4-methoxypyrazolo[1,5-a]pyridin-6-yl]-5-methylpyrazol-1-yl)piperidin-1-yl]pyrrolidine-1-carboxylate

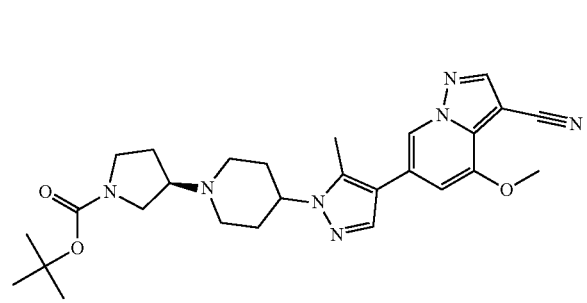 [SMILES: COc1cc(-c2cnn(C3CCN([C@@H]4CCN(C(=O)OC(C)(C)C)C4)CC3)c2C)cn2ncc(C#N)c12]

(Trifluoromethanesulfonyloxy)pyrrolidine-1-carboxylate (10 mL, 8.32 mmol) is added dropwise over 5 min to a stirred solution of 4-methoxy-6-[5-methyl-1-(piperidin-4-yl)pyrazol-4-yl]pyrazolo[1,5-a]pyridine-3-carbonitrile (400.00 mg, 1.18 mmol) and DIEA (307.36 mg, 2.37 mmol) in DCM (5.00 mL) at −60° C. under N2. The mixture is stirred for 1 hr at RT under N2, washed with H2O (3×20 mL), and concentrated under reduced pressure. The residue is purified by silica gel column chromatography, eluting with a gradient of DCM:MeOH (9:1) to give the title compound as a brown solid (411 mg, 68.36%). ES/MS m/z 506.3 [M+H]+.

Preparation 394 tert-Butyl (2S,4R)-4-[3-(4-[3-cyano-4-methoxypyrazolo[1,5-a]pyridin-6-yl]-5-methylpyrazol-1-yl)azetidin-1-yl]-2-methylpyrrolidine-1-carboxylate

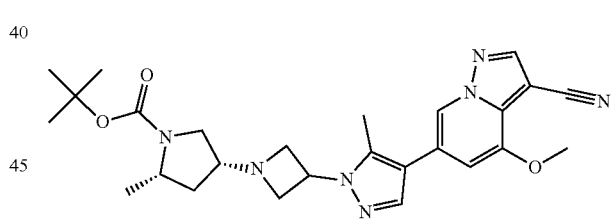

Tf2O (420.55 mg, 1.491 mmol) is added dropwise to a stirred solution of tert-butyl (2S,4S)-4-hydroxy-2-methylpyrrolidine-1-carboxylate (300.00 mg, 1.491 mmol) and DIEA (577.94 mg, 4.472 mmol) in DCM (5.00 mL) at −70° C. under N2 for 1 hr. The solution of tert-butyl (2S,4S)-2-methyl-4-(trifluoromethanesulfonyloxy)pyrrolidine-1-carboxylate is then added dropwise to a stirred solution of 6-[1-(azetidin-3-yl)-5-methylpyrazol-4-yl]-4-methoxypyrazolo[1,5-a]pyridine-3-carbonitrile.TFA (400.00 mg, 0.95 mmol) and DIEA (367.20 mg, 2.84 mmol) in DCM (20.00 mL) at −70° C. under N2. The solution is stirred overnight at RT, quenched by H2O (50 mL), and extracted with DCM (2×50 mL). The combined organic extracts are washed with brine (2×50 mL), dried over anhydrous Na2SO4, filtered, and the filtrate is concentrated under reduced pressure. The residue is purified by Prep-TLC (EtOAc) give the title compound as a light-yellow solid (80 mg, 17.18%). ES/MS m/z 492.2 [M+H]+.

Preparation 395 tert-Butyl (3S)-3-(4-(4-(3-cyano-4-methoxypyrazolo[1,5-a]pyridin-6-yl)-5-methyl-1H-pyrazol-1-yl)piperidin-1-yl)pyrrolidine-1-carboxylate

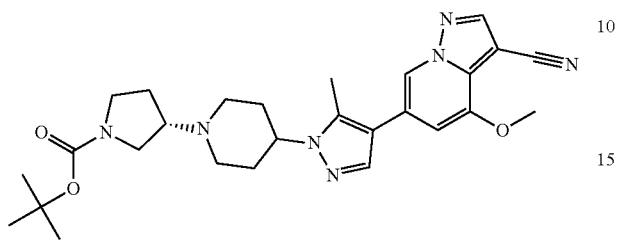

A mixture of 4-methoxy-6-(5-methyl-1-(piperidin-4-yl)-1H-pyrazol-4-yl)pyrazolo[1,5-a]pyridine-3-carbonitrile (300.00 mg, 0.89 mmol), tert-butyl (3R)-3-(methanesulfonyloxy)pyrrolidine-1-carboxylate (2.37 g, 8.92 mmol) and K₂CO₃ (369.75 mg, 2.68 mmol) in toluene (3.00 mL) is stirred for 4 hrs at 150° C. under N₂. The mixture is cooled to RT, poured into H₂O (20 mL), and extracted with DCM (2×20 mL). The combined organic extracts are washed with saturated NaCl aq. (50 mL), dried over anhydrous Na₂SO₄, filtered, and the filtrate is concentrated under reduced pressure. The residue is purified by silica gel column chromatography, eluting with a gradient of DCM:MeOH (95:5-90:10) to give the title compound as a light-yellow solid (260 mg, 57.66%). ES/MS m/z 506.4 [M+H]⁺.

Preparation 396 tert-Butyl 3-[4-(4-[3-cyano-4-methoxypyrazolo[1,5-a]pyridin-6-yl]-5-methylpyrazol-1-yl)piperidin-1-yl]-2,2-dimethylazetidine-1-carboxylate

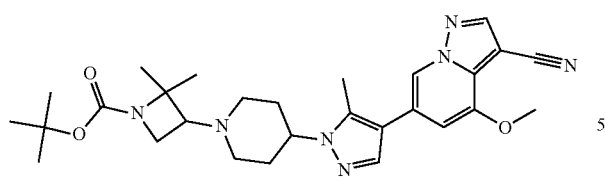

A mixture of 6-(1-[1-[1-(diphenylmethyl)-2,2-dimethylazetidin-3-yl]piperidin-4-yl]-5-methylpyrazol-4-yl)-4-methoxypyrazolo[1,5-a]pyridine-3-carbonitrile (400.00 mg, 0.68 mmol), Boc₂O (447.11 mg, 2.05 mmol) and Pd(OH)₂/C (287.69 mg) in MeOH (10.00 mL) is stirred for 12 hours at RT under H₂. The mixture is filtered, the filter cake is washed with MeOH (2×30 mL), and the filtrate is concentrated under reduced pressure. The residue is purified by reverse Combi-flash chromatography with the following conditions: Column, C18; eluting with a gradient of 30% to 33% ACN in H₂O (0.1% FA) to give the title compound as a yellow solid (260 mg, 73.27%). ES/MS m/z 520.4 [M+H]⁺.

Preparation 397 tert-Butyl 3-[4-(4-[3-cyano-4-methoxypyrazolo[1,5-a]pyridin-6-yl]-5-methylpyrazol-1-yl)piperidin-1-yl]-2,2-dimethylazetidine-1-carboxylate, Isomer 1 and

Preparation 398 tert-Butyl 3-[4-(4-[3-cyano-4-methoxypyrazolo[1,5-a]pyridin-6-yl]-5-methylpyrazol-1-yl)piperidin-1-yl]-2,2-dimethylazetidine-1-carboxylate, Isomer 2

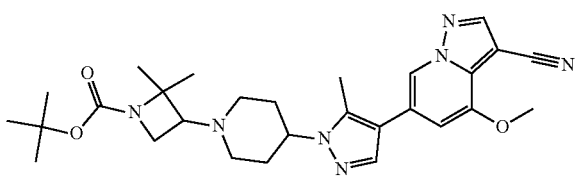 [SMILES: COc1cc(-c2cnn(C3CCN(C4CN(C(=O)OC(C)(C)C)C4(C)C)CC3)c2C)cn2ncc(C#N)c12]

Isomers of tert-butyl 3-[4-(4-[3-cyano-4-methoxypyrazolo[1,5-a]pyridin-6-yl]-5-methylpyrazol-1-yl)piperidin-1-yl]-2,2-dimethylazetidine-1-carboxylate (390.00 mg) are separated by Prep-chiral chromatography with the following conditions: Column, CHIRAL ART Cellulose-SB, 2*25 cm, 5 μm; eluting with a gradient of 30% iPrOH in hexanes (10 mM NH₃MeOH); flow rate 20 mL/min; 254/220 nm; t$_{(R)}$ Isomer 1 is 10.2 min (110 mg, 28.21%) as a yellow solid with 100% ee; t$_{(R)}$ Isomer 2 is 12.7 min (120 mg, 30.77%) as a yellow solid with 99.6% ee. ES/MS m/z 520.4 [M+H]⁺.

Preparation 399 tert-Butyl 3-[4-(4-[3-cyano-4-methoxypyrazolo[1,5-a]pyridin-6-yl]-5-methylpyrazol-1-yl)piperidin-1-yl]azetidine-1-carboxylate

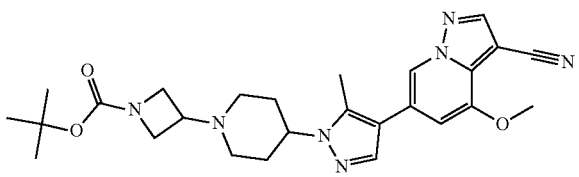 [SMILES: COc1cc(-c2cnn(C3CCN(C4CN(C(=O)OC(C)(C)C)C4)CC3)c2C)cn2ncc(C#N)c12]

tert-Butyl 3-oxoazetidine-1-carboxylate (101.18 mg, 0.59 mmol) in MeOH (4.00 mL) is added to 4-methoxy-6-(5-methyl-1-(piperidin-4-yl)-1H-pyrazol-4-yl)pyrazolo[1,5-a]pyridine-3-carbonitrile (100.00 mg, 0.30 mmol) at RT. The solution is stirred for 1 hr at 40° C. After the solution is cooled to RT, NaBH₃CN (37.14 mg, 0.591 mmol) is added and the mixture is stirred for 15 hrs at RT. The mixture is diluted with EtOAc (50 mL) and washed with H₂O (2×50 mL). The organic extract is dried over anhydrous Na₂SO₄, filtered, and the filtrate is concentrated under reduced pressure. The residue is purified by reverse Combi-flash chromatography with the following conditions: Column, C18;

eluting with a gradient of 50% to 60% ACN in H₂O (0.1% FA) to give the title compound as a light-yellow solid (130 mg, 89.5%). ES/MS m/z 492.2 [M+H]⁺.

Preparation 400 tert-Butyl (3R)-3-[3-(4-[3-cyano-4-methoxypyrazolo[1,5-a]pyridin-6-yl]-5-methylpyrazol-1-yl)azetidin-1-yl]pyrrolidine-1-carboxylate

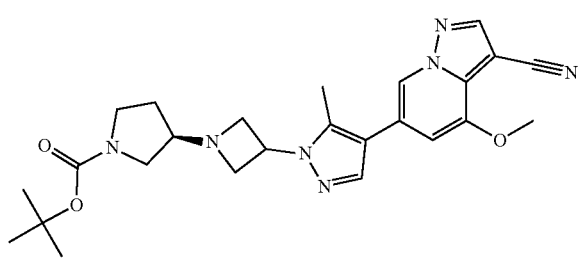 [SMILES: COc1cc(-c2cnn(C3CN([C@@H]4CCN(C(=O)OC(C)(C)C)C4)C3)c2C)cn2ncc(C#N)c12]

6-[1-(Azetidin-3-yl)-5-methylpyrazol-4-yl]-4-methoxy-pyrazolo[1,5-a]pyridine-3-carbonitrile (241 mg, 0.78 mmol) is added to a stirred solution of tert-butyl (3S)-3-(trifluoromethanesulfonyloxy) pyrrolidine-1-carboxylate (2.3 mL, 0.78 mmol, 3.4 M in DCM) in DCM (5 mL) at −50° C. under $N_2$. After the solution is stirred for 1 hr at −50° C., additional tert-butyl (3S)-3-(trifluoromethanesulfonyloxy)pyrrolidine-1-carboxylate (2.3 mL, 0.78. mmol, 3.4 M in DCM) is added and stirring is continued at −50° C. for an additional hr. The mixture is diluted with EtOAc (100 mL) and washed with $H_2O$ (2×20 mL) and brine (20 mL). The combined organic extracts are dried over anhydrous $Na_2SO_4$, filtered, and the filtrate is concentrated under reduced pressure. The residue is purified by reverse Combi-flash chromatography with the following conditions: C18; eluting with a gradient of 35% to 60% ACN in $H_2O$ (0.1% $NH_4HCO_3$) to give the title compound as a light-yellow solid (80 mg, 20.6%). ES/MS m/z 478.4 [M+H]⁺.

Preparation 401 tert-Butyl 4-(4-[3-iodo-5-methoxyimidazo[1,2-a]pyridin-7-yl]-5-methyl-1,2,3-triazol-1-yl)piperidine-1-carboxylate

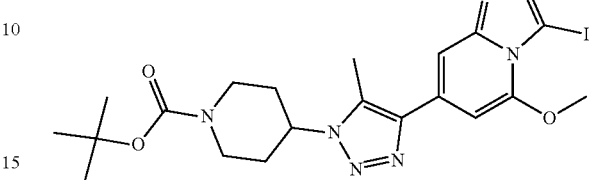

A stirred RT solution of tert-butyl 4-(4-[5-methoxyimidazo[1,2-a]pyridin-7-yl]-5-methyl-1,2,3-triazol-1-yl)piperidine-1-carboxylate (500 mg, 1.21 mmol) in DCM (6 mL) is treated with NIS (300 mg, 1.33 mmol) and stirred for 8 hrs at RT. The mixture is diluted with EtOAc (100 mL), washed with $H_2O$ (20 mL), and then brine (20 mL). The combined organic extracts are dried over anhydrous $Na_2SO_4$, filtered, and the filtrate is concentrated under reduced pressure to give the title compound (820 mg, crude), which is used directly without further purification. ES/MS m/z 539.2 [M+H]⁺.

The following compounds are prepared essentially as described for tert-butyl 4-(4-[3-iodo-5-methoxyimidazo[1,2-a]pyridin-7-yl]-5-methyl-1,2,3-triazol-1-yl)piperidine-1-carboxylate using the appropriate reagents, adjusting the reaction times to determine completion of the reactions, and adjusting the purification system as appropriate. The compound can also be chlorinated with NCS, or with 1,3-dichloro-5,5-dimethylimidazolidine-2,4-dione. The reaction can be quenched with $Na_2SO_3$, and the mixture can also be extracted with DCM. Temperature is varied from −60° C. to RT.

TABLE 38

| Prep No. | Chemical Name | Structure | ES/MS m/z [M + H]⁺ |
|---|---|---|---|
| 402 | tert-Butyl 4-(4-[3-iodo-5-[(1R)-1-(pyridin-2-yl)ethoxy]imidazo[1,2-a]pyridin-7-yl]-5-methylpyrazol-1-yl)piperidine-1-carboxylate | 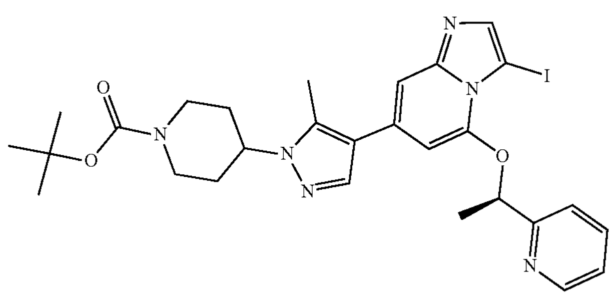 [SMILES: Cc1c(-c2cc(O[C@H](C)c3ccccn3)n3c(I)cnc3c2)cnn1C1CCN(C(=O)OC(C)(C)C)CC1] | 629.2 |
| 403 | tert-Butyl 4-(4-[3-iodo-5-[(1R)-1-(pyridin-2-yl)ethoxy]imidazo[1,2-a]pyridin-7-yl]-5-methyl-1,2,3-triazol-1-yl)piperidine-1-carboxylate | 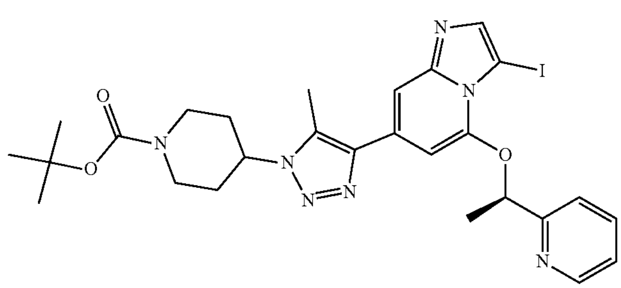 [SMILES: Cc1c(-c2cc(O[C@H](C)c3ccccn3)n3c(I)cnc3c2)nnn1C1CCN(C(=O)OC(C)(C)C)CC1] | 630.2 |

TABLE 38-continued

| Prep No. | Chemical Name | Structure | ES/MS m/z [M + H]+ |
|---|---|---|---|
| 404 | tert-Butyl 4-(4-[3-chloro-5-[(1R)-1-(pyridin-2-yl)ethoxy]imidazo[1,2-a]pyridin-7-yl]-5-methyl-1,2,3-triazol-1-yl)piperidine-1-carboxylate | 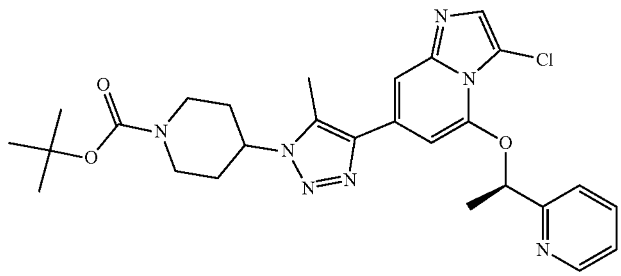 [SMILES: Cc1c(-c2cc(O[C@H](C)c3ccccn3)n3c(Cl)cnc3c2)nnn1C1CCN(C(=O)OC(C)(C)C)CC1] | 538.3 |
| 405 | tert-Butyl 4-[4-[3-chloro-5-[(1R)-1-(5-fluoro-2-pyridyl)ethoxy]imidazo[1,2-a]pyridin-7-yl]-5-methyl-triazol-1-yl]piperidine-1-carboxylate | 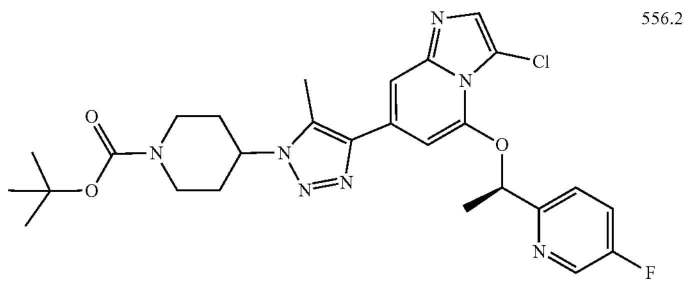 | 556.2 |
| 406 | 2-[(1R)-1-([7-Chloro-3-iodoimidazo[1,2-a]pyridin-5-yl]oxy)ethyl]pyridine | 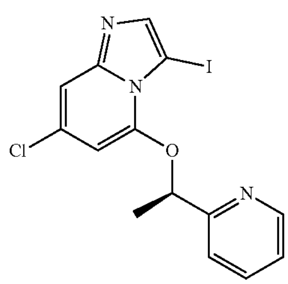 [SMILES: C[C@@H](Oc1cc(Cl)cc2ncc(I)n12)c1ccccn1] | 400.0 |
| 407 | tert-Butyl 4-[4-(5-chloro-3-iodo-imidazo[1,2-a]pyridin-7-yl)-5-methyl-pyrazol-1-yl]piperidine-1-carboxylate | 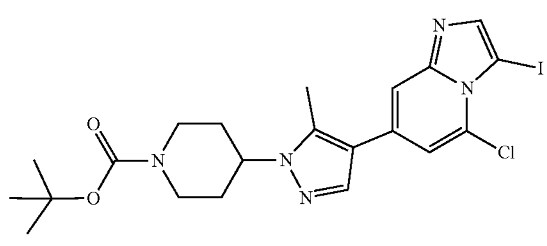 [SMILES: Cc1c(-c2cc(Cl)n3c(I)cnc3c2)cnn1C1CCN(C(=O)OC(C)(C)C)CC1] | 542.1 |
| 408 | tert-Butyl 4-[4-(3-iodo-5-methoxy-imidazo[1,2-a]pyridin-7-yl)-5-methyl-triazol-1-yl]azepane-1-carboxylate | 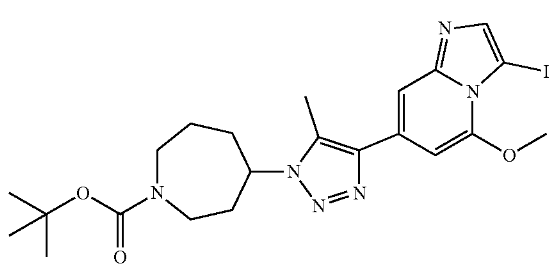 [SMILES: COc1cc(-c2nnn(C3CCCN(C(=O)OC(C)(C)C)CC3)c2C)cc2ncc(I)n12] | 553.0 |

TABLE 38-continued

| Prep No. | Chemical Name | Structure | ES/MS m/z [M + H]+ |
|---|---|---|---|
| 409[1] | tert-Butyl 4-[4-(3-iodo-4-methoxy-pyrazolo[1,5-a]pyridin-6-yl)-5-methyl-triazol-1-yl]piperidine-1-carboxylate | 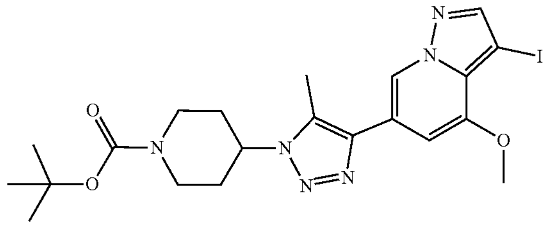 [SMILES: COc1cc(-c2nnn(C3CCN(C(=O)OC(C)(C)C)CC3)c2C)cn2ncc(I)c12] | 538.7 |
| 500 | tert-Butyl (2SR,4RS)-2-cyclopropyl-4-[4-(3-iodo-5-methoxy-imidazo[1,2-a]pyridin-7-yl)-5-methyl-triazol-1-yl]piperidine-1-carboxylate | 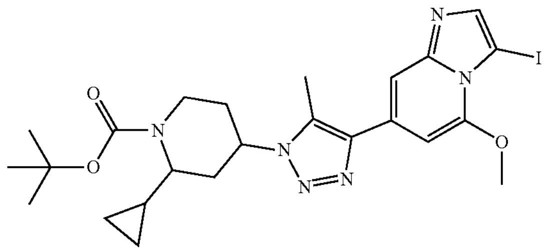 [SMILES: COc1cc(-c2nnn(C3CCN(C(=O)OC(C)(C)C)C(C4CC4)C3)c2C)cc2ncc(I)n12] | 579.0 |

[1]Purified by flash silica gel chromatography eluting with 0% to 100% EtOAc in heptane.

Preparation 501 tert-Butyl 4-[4-(3-cyclopropyl-4-methoxy-pyrazolo[1,5-a]pyridin-6-yl)-5-methyl-triazol-1-yl]piperidine-1-carboxylate

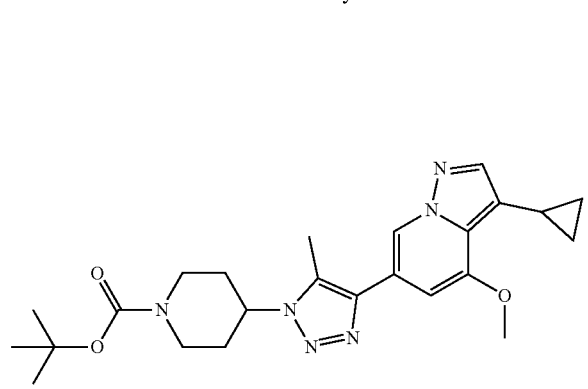

To a solution of tert-butyl 4-[4-(3-iodo-4-methoxy-pyrazolo[1,5-a]pyridin-6-yl)-5-methyl-triazol-1-yl]piperidine-1-carboxylate (500 mg, 0.929 mmol) in toluene:$H_2O$ 10:1 (6.6 mL) is added cyclopropylboronic acid (160 mg, 1.86 mmol), $K_3PO_4$ (986 mg, 4.64 mmol), tricyclohexylphosphane (57.3 mg, 0.204 mmol), and $PdOAc_2$ (22.9 mg, 0.102 mmol) and the mixture is heated at 100° C. for 16 hr. Upon cooling to RT, the reaction is diluted with EtOAc (20 mL) and $H_2O$ (20 mL), layers are separated, and the aqueous layer is extracted with EtOAc (3×10 mL). The combined organic layers are concentrated in vacuo and the residue is purified by reverse phase chromatography eluting with a gradient of 0% to 100% ACN in $H_2O$ to afford the title compound (79 mg, 19%). ES/MS m/z 452.9 [M+H]+.

Preparation 502 tert-Butyl 4-(4-[3-cyano-5-methoxyimidazo[1,2-a]pyridin-7-yl]-5-methyl-1,2,3-triazol-1-yl)piperidine-1-carboxylate

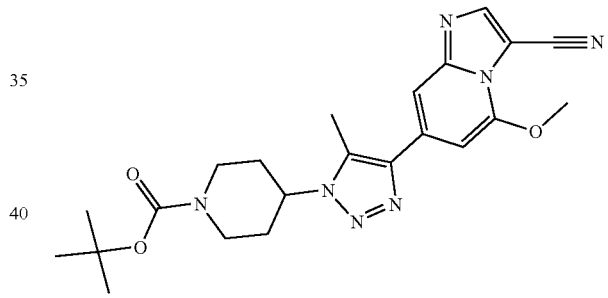

A solution of tert-butyl 4-(4-[3-iodo-5-methoxyimidazo[1,2-a]pyridin-7-yl]-5-methyl-1,2,3-triazol-1-yl)piperidine-1-carboxylate (800 mg, crude), DMF (8.00 mL), and CuCN (173.01 mg, 1.93 mmol) is stirred for 2 hrs at 100° C. under $N_2$. The mixture is diluted with DCM (100 mL), washed first with $H_2O$ (20 mL), and next washed with brine (20 mL). The combined organic layers are dried over anhydrous $Na_2SO_4$, filtered, and the filtrate is concentrated under reduced pressure. The residue is purified by reverse Combi-flash chromatography with the following conditions: Column, C18; eluting with a gradient of 50% to 70% ACN in $H_2O$ (0.1% FA) to give the title compound (450 mg, 46%%). ES/MS m/z 438.3 [M+H]+.

The following compounds are prepared essentially as described for tert-butyl 4-(4-[3-cyano-5-methoxyimidazo[1,2-a]pyridin-7-yl]-5-methyl-1,2,3-triazol-1-yl)piperidine-1-carboxylate using the appropriate reagents, adjusting the reaction times to determine completion of the reactions, and adjusting the purification system as appropriate. The temperature is varied from 80° C. to 100° C. The reaction can also be quenched with $H_2O$ or $NH_4OH$ aq., and the mixture can be extracted with EtOAc or DCM.

TABLE 39

| Prep No. | Chemical Name | Structure | ES/MS m/z [M + H]+ |
|---|---|---|---|
| 503 | tert-Butyl 4-(4-[3-cyano-5-[(1R)-1-(pyridin-2-yl)ethoxy]imidazo[1,2-a]pyridin-7-yl]-5-methylpyrazol-1-yl)piperidine-1-carboxylate | 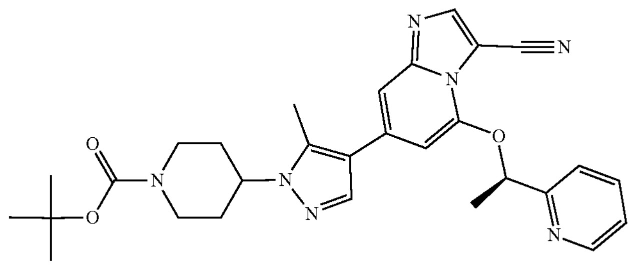 [SMILES: Cc1c(-c2cc(O[C@H](C)c3ccccn3)n3c(C#N)cnc3c2)cnn1C1CCN(C(=O)OC(C)(C)C)CC1] | 528.4 |
| 504 | tert-Butyl 4-(4-[3-cyano-5-[(1R)-1-(pyridin-2-yl)ethoxy]imidazo[1,2-a]pyridin-7-yl]-5-methyl-1,2,3-triazol-1-yl)piperidine-1-carboxylate | 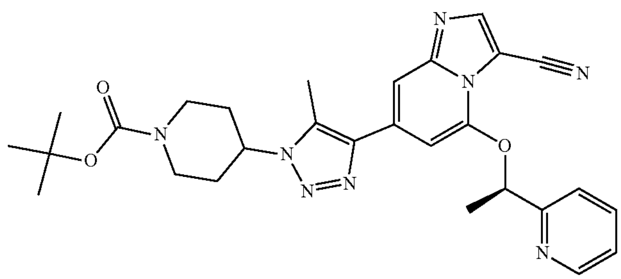 [SMILES: Cc1c(-c2cc(O[C@H](C)c3ccccn3)n3c(C#N)cnc3c2)nnn1C1CCN(C(=O)OC(C)(C)C)CC1] | 529.3 |
| 505 | 7-Chloro-5-[(1R)-1-(pyridin-2-yl)ethoxy]imidazo[1,2-a]pyridine-3-carbonitrile | 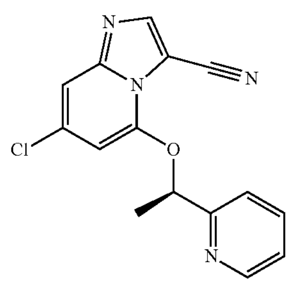 [SMILES: C[C@@H](Oc1cc(Cl)cc2ncc(C#N)n12)c1ccccn1] | 299.1 |
| 506 | tert-Butyl 4-[4-(5-chloro-3-cyano-imidazo[1,2-a]pyridin-7-yl)-5-methyl-pyrazol-1-yl]piperidine-1-carboxylate | 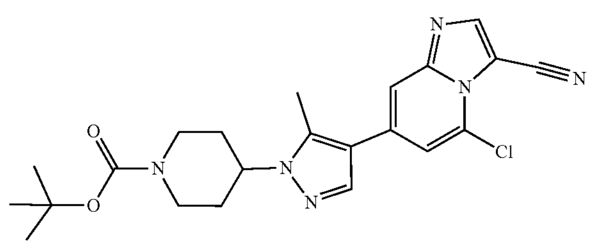 [SMILES: Cc1c(-c2cc(Cl)n3c(C#N)cnc3c2)cnn1C1CCN(C(=O)OC(C)(C)C)CC1] | 441.1 |
| 507 | tert-Butyl 4-[4-(3-cyano-5-methoxy-imidazo[1,2-a]pyridin-7-yl)-5-methyl-triazol-1-yl]azepane-1-carboxylate | 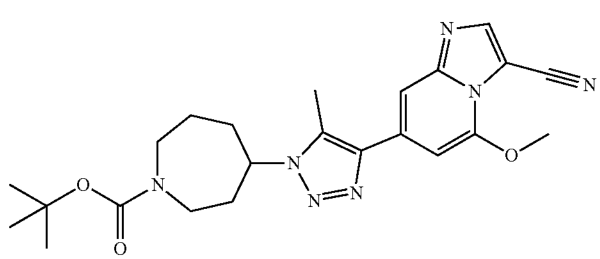 [SMILES: COc1cc(-c2nnn(C3CCCN(C(=O)OC(C)(C)C)CC3)c2C)cc2ncc(C#N)n12] | 452.0 |

TABLE 39-continued

| Prep No. | Chemical Name | Structure | ES/MS m/z [M + H]+ |
|---|---|---|---|
| 508[1] | tert-Butyl 4-[4-[3-cyano-5-[(1R)-1-(5-fluoro-2-pyridyl)ethoxy]imidazo[1,2-c]pyrimidin-7-yl]-5-methyl-pyrazol-1-yl]piperidine-1-carboxylate | 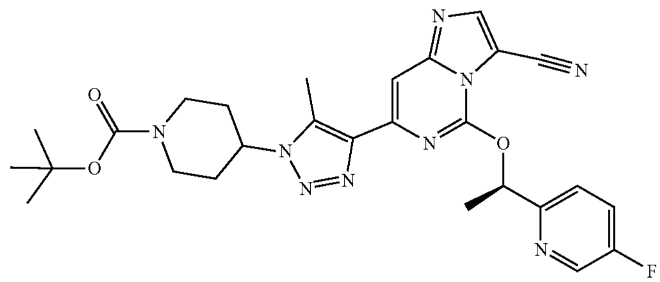 [SMILES: Cc1c(-c2cc3ncc(C#N)n3c(O[C@H](C)c3ccc(F)cn3)n2)nnn1C1CCN(C(=O)OC(C)(C)C)CC1] | 547.2 |
| 509 | tert-Butyl (2SR,4RS)-4-[4-(3-cyano-5-methoxy-imidazo[1,2-a]pyridin-7-yl)-5-methyl-triazol-1-yl]-2-cyclopropyl-piperidine-1-carboxylate | 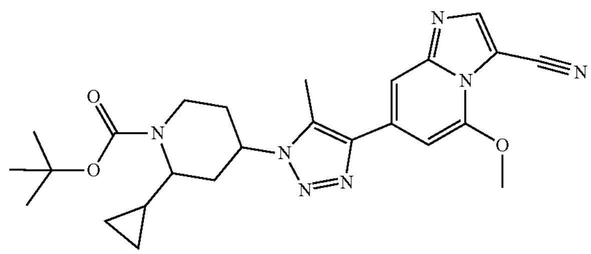 [SMILES: COc1cc(-c2nnn(C3CCN(C(=O)OC(C)(C)C)C(C4CC4)C3)c2C)cc2ncc(C#N)n12] | 478.2 |

[1]Purified by silica gel chromatography, eluting with 0% to 100% EtOAc in DCM.

Preparation 510

6-(1-((1r,3r)-3-((tert-Butyldimethylsilyl)oxy)cyclobutyl)-5-methyl-1H-1,2,3-triazol-4-yl)-3-chloro-4-methoxypyrazolo[1,5-a]pyridine

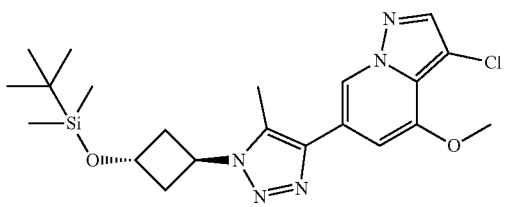 [SMILES: COc1cc(-c2nnn([C@H]3C[C@H](O[Si](C)(C)C(C)(C)C)C3)c2C)cn2ncc(Cl)c12]

A solution of (1r,3r)-3-(4-(3-Chloro-4-methoxypyrazolo[1,5-a]pyridin-6-yl)-5-methyl-1H-1,2,3-triazol-1-yl)cyclobutan-1-ol (1.03 g, 3.09 mmol), tert-butyldimethylchlorosilane (930 mg, 6.17 mmol) in DCM (15 mL) and imidazole (420 mg, 6.17 mmol) is stirred at RT for 30 min. The reaction is directly loaded onto a silica gel column which is eluting with 0% to 100% EtOAc in heptane to afford the title compound (700 mg, 1.56 mmol) as solid. ES/MS m/z 448.2 [M+H]+.

Preparation 511 tert-Butyl 4-(4-[3-cyano-5-hydroxyimidazo[1,2-a]pyridin-7-yl]-5-methyl-1,2,3-triazol-1-yl)piperidine-1-carboxylate

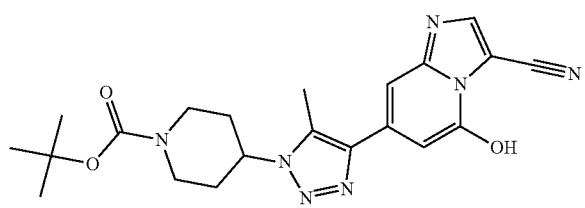 [SMILES: Cc1c(-c2cc(O)n3c(C#N)cnc3c2)nnn1C1CCN(C(=O)OC(C)(C)C)CC1]

NaOH (50% aq.) (8.23 g, 102.856 mmol) is added dropwise to a stirred solution of tert-butyl 4-(4-[3-cyano-5-methoxyimidazo[1,2-a]pyridin-7-yl]-5-methyl-1,2,3-triazol-1-yl)piperidine-1-carboxylate (15.00 g, 34.29 mmol) and NDM (10.41 g, 51.43 mmol) in DMA (200.00 mL) at RT under N₂. The mixture is stirred for 2 hrs at 50° C. under N₂. The mixture is diluted with H₂O (1500 mL) and PE (500 mL) and acidified to pH 4 with FA. The precipitated solids are collected by filtration, washed with H₂O (2×50 mL), PE (2×100 mL), and dried under reduced pressure to give the title compound as a white solid (13 g, 89.54%). ES/MS m/z 424.2 [M+H]+.

Preparation 512 tert-Butyl 4-[4-(4-hydroxypyrazolo[1,5-a]pyridin-6-yl)-5-methyl-triazol-1-yl]piperidine-1-carboxylate

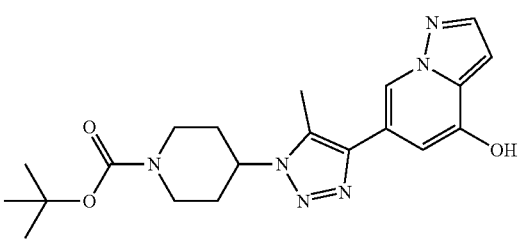 [SMILES: Cc1c(-c2cc(O)c3ccnn3c2)nnn1C1CCN(C(=O)OC(C)(C)C)CC1]

To tert-butyl 4-[4-(4-methoxypyrazolo[1,5-a]pyridin-6-yl)-5-methyl-triazol-1-yl]piperidine-1-carboxylate (900 mg, 2.18 mmol) and NaOH in water (523.60 mg, 6.55 mmol, 50% in water) in DMA (10 mL) is added dodecane-1-thiol (883 mg, 4.36 mmol) at RT under N₂. The reaction is stirred at 50° C. for 2 hr. Upon cooling to RT, the reaction is diluted with water (150 mL) and PE (50 mL). The pH of the mixture is acidified to pH 4 with FA. The mixture is stirred for 3 hr at RT under N₂. The resultant precipitate is filtered then washed with water (3×10 mL) and PE (3×10 mL). The solids are concentrated under vacuum to afford the title compound as a light-yellow solid (740 mg, 85.12%). ES/MS m/z 399.2 [M+H]⁺.

The following compounds are prepared essentially as described for tert-butyl 4-[4-(4-hydroxypyrazolo[1,5-a]pyridine-6-yl)-5-methyl-triazol-1-yl]piperidine-1-carboxylate using the appropriate reagents, adjusting the reaction times to determine completion of the reactions, and adjusting the purification system as appropriate.

TABLE 40

| Prep No. | Chemical Name | Structure | ES/MS m/z [M + H]⁺ |
|---|---|---|---|
| 513[1] | tert-Butyl 4-[4-(5-hydroxy-3-imidazo[1,2-a]pyridin-7-yl)-5-methyl-triazol-1-yl]piperidine-1-carboxylate | 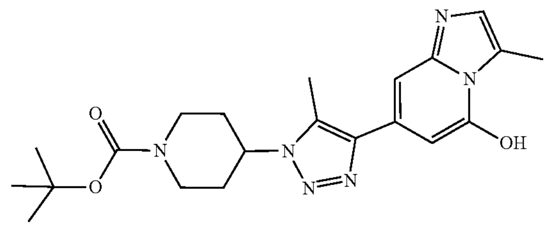 [SMILES: Cc1c(-c2cc(O)n3c(C)cnc3c2)nnn1C1CCN(C(=O)OC(C)(C)C)CC1] | 413.3 |
| 514[2] | tert-Butyl 4-[4-(4-hydroxypyrazolo[1,5-a]pyridin-6-yl)-5-methyl-pyrazol-1-yl]piperidine-1-carboxylate | 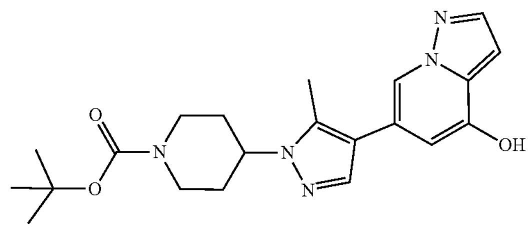 [SMILES: Cc1c(-c2cc(O)c3ccnn3c2)cnn1C1CCN(C(=O)OC(C)(C)C)CC1] | 398.0 |
| 515 | tert-Butyl (3S)-3-[4-(3-cyano-5-hydroxy-imidazo[1,2-a]pyridin-7-yl)-5-methyl-triazol-1-yl]piperidine-1-carboxylate | 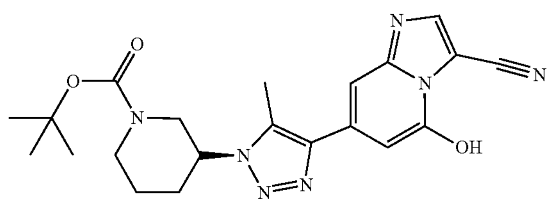 | 424.2 |
| 516[3] | tert-Butyl 4-[4-(3-cyano-5-hydroxy-imidazo[1,2-a]pyridin-7-yl)-5-methyl-triazol-1-yl]azepane-1-carboxylate | 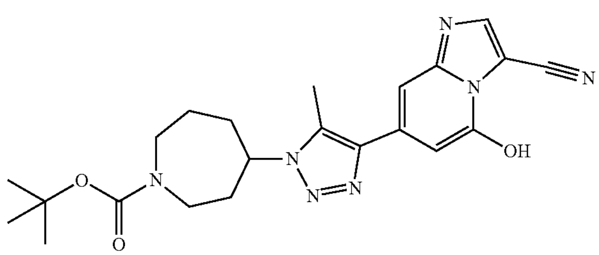 [SMILES: Cc1c(-c2cc(O)n3c(C#N)cnc3c2)nnn1C1CCCN(C(=O)OC(C)(C)C)CC1] | 438.4 |
| 517[4] | tert-Butyl (3R)-3-[4-(3-cyano-5-hydroxy-imidazo[1,2-a]pyridin-7-yl)-5-methyl-triazol-1-yl]piperidine-1-carboxylate | 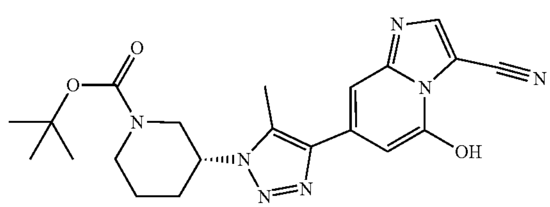 [SMILES: Cc1c(-c2cc(O)n3c(C#N)cnc3c2)nnn1[C@@H]1CCCN(C(=O)OC(C)(C)C)C1] | 424.2 |
| 518 | tert-Butyl 4-[4-(3-fluoro-4-hydroxy-pyrazolo[1,5-a]pyridin-6-yl)-5-methyl-triazol-1-yl]piperidine-1-carboxylate | 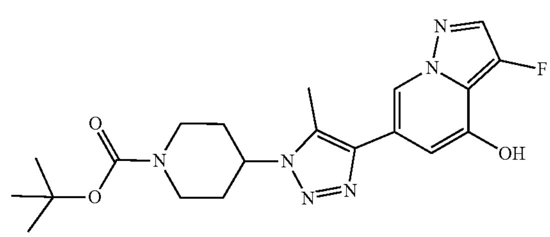 [SMILES: Cc1c(-c2cc(O)c3c(F)cnn3c2)nnn1C1CCN(C(=O)OC(C)(C)C)CC1] | 417.2 |

TABLE 40-continued

| Prep No. | Chemical Name | Structure | ES/MS m/z [M + H]+ |
|---|---|---|---|
| 519 | Cis-tert-butyl 4-[3-[4-(4-hydroxypyrazolo[1,5-a]pyridin-6-yl)-5-methyl-triazol-1-yl]cyclobutyl]piperazine-1-carboxylate | 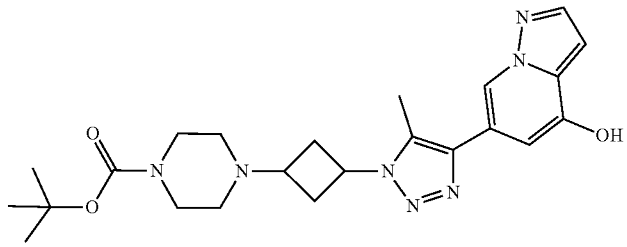 [SMILES: Cc1c(-c2cc(O)c3ccnn3c2)nnn1C1CC(N2CCN(C(=O)OC(C)(C)C)CC2)C1] | 454.2 |
| 520[5] | tert-Butyl 4-[4-(3-chloro-4-hydroxy-pyrazolo[1,5-a]pyridin-6-yl)-5-methyl-triazol-1-yl]piperidine-1-carboxylate | 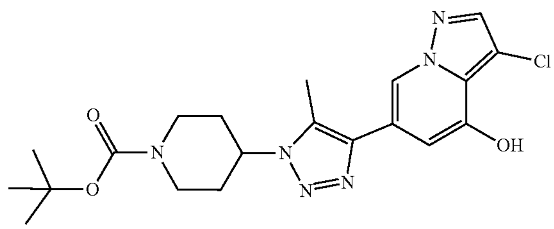 [SMILES: Cc1c(-c2cc(O)c3c(Cl)cnn3c2)nnn1C1CCN(C(=O)OC(C)(C)C)CC1] | 377.2 [M + 2H − tBu]+ |
| 521[6] | tert-Butyl 4-[4-(3-cyclopropyl-4-hydroxy-pyrazolo[1,5-a]pyridin-6-yl)-5-methyl-triazol-1-yl]piperidine-1-carboxylate | 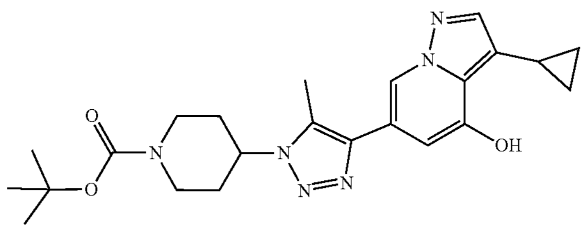 [SMILES: Cc1c(-c2cc(O)c3c(C4CC4)cnn3c2)nnn1C1CCN(C(=O)OC(C)(C)C)CC1] | 438.8 |
| 522[9] | tert-Butyl 4-[4-(3-cyano-5-hydroxy-imidazo[1,2-a]pyridin-7-yl)-3-(2-hydroxyethyl)-5-methyl-pyrazol-1-yl]piperidine-1-carboxylate | 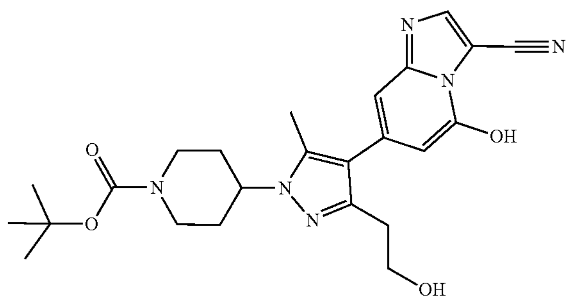 [SMILES: Cc1c(-c2cc(O)n3c(C#N)cnc3c2)c(CCO)nn1C1CCN(C(=O)OC(C)(C)C)CC1] | 467.1 |
| 523[7] | tert-Butyl (2SR,4RS)-4-[4-(3-cyano-5-hydroxy-imidazo[1,2-a]pyridin-7-yl)-5-methyl-triazol-1-yl]-2-cyclopropyl-piperidine-1-carboxylate | 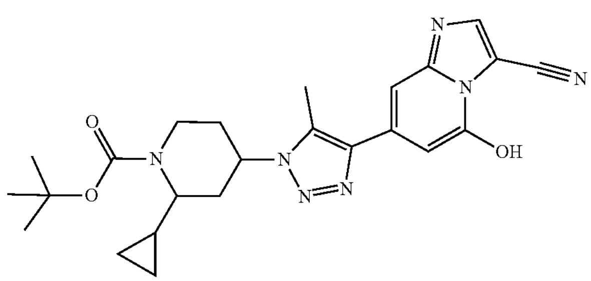 [SMILES: Cc1c(-c2cc(O)n3c(C#N)cnc3c2)nnn1C1CCN(C(=O)OC(C)(C)C)C(C2CC2)C1] | 464.3 |
| 524 | 3-chloro-6-(1-((1r,3r)-3-hydroxycyclobutyl)-5-methyl-1H-1,2,3-triazol-4-yl)pyrazolo[1,5-a]pyridin-4-ol | 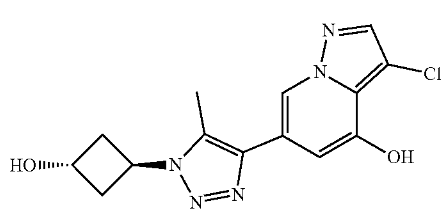 [SMILES: Cc1c(-c2cc(O)c3c(Cl)cnn3c2)nnn1[C@H]1C[C@H](O)C1] | 320.0 |

TABLE 40-continued

| Prep No. | Chemical Name | Structure | ES/MS m/z [M + H]+ |
|---|---|---|---|
| 525 | tert-Butyl 2-[4-(3-cyano-4-hydroxy-pyrazolo[1,5-a]pyridin-6-yl)-5-methyl-pyrazol-1-yl]-7-azaspiro[3.5]nonane-7-carboxylate | 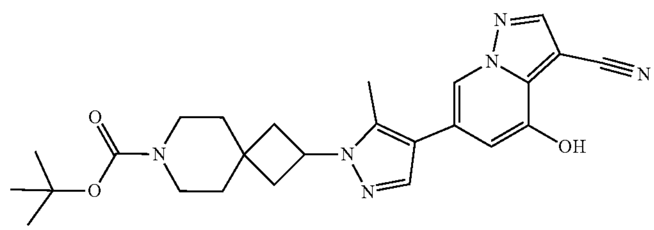 [SMILES: Cc1c(-c2cc(O)c3c(C#N)cnn3c2)cnn1C1CC2(CCN(C(=O)OC(C)(C)C)CC2)C1] | 407.2[a] |
| 526 | tert-Butyl 2-[4-(3-cyano-5-hydroxy-imidazo[1,2-a]pyridin-7-yl)-5-methyl-triazol-1-yl]-7-azaspiro[3.5]nonane-7-carboxylate | 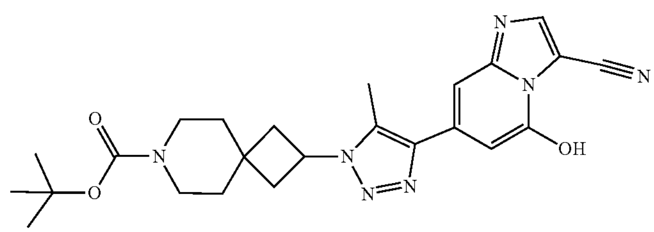 [SMILES: Cc1c(-c2cc(O)n3c(C#N)cnc3c2)nnn1C1CC2(CCN(C(=O)OC(C)(C)C)CC2)C1] | 464.2 |
| 527 | tert-Butyl (3S)-3-[3-[4-(3-cyano-4-hydroxy-pyrazolo[1,5-a]pyridin-6-yl)-5-methyl-pyrazol-1-yl]azetidin-1-yl]pyrrolidine-1-carboxylate | 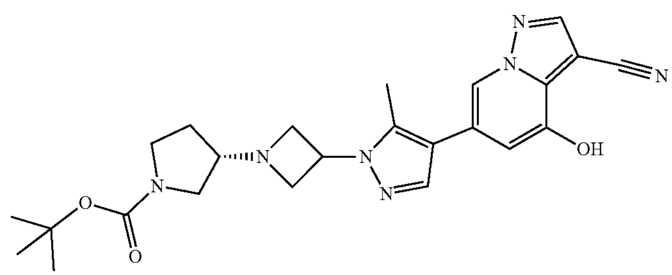 [SMILES: Cc1c(-c2cc(O)c3c(C#N)cnn3c2)cnn1C1CN([C@H]2CCN(C(=O)OC(C)(C)C)C2)C1] | 464.2 |
| 528[8] | tert-Butyl 4-[4-(3-cyano-5-hydroxy-imidazo[1,2-a]pyridin-7-yl)-5-methyl-triazol-1-yl]azepane-1-carboxylate | 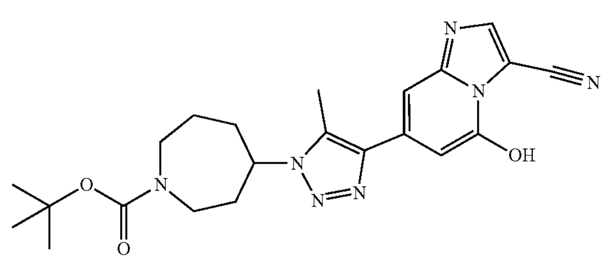 [SMILES: Cc1c(-c2cc(O)n3c(C#N)cnc3c2)nnn1C1CCCN(C(=O)OC(C)(C)C)CC1] | 483.2 |

[1] Purified by silica gel chromatography eluting with PE: EtOAc (1:2).

[2] Purified by flash silica gel chromatography eluting with 10% to 70% EtOAc in PE.

[3] Purified by flash reverse phase chromatography: Column, C18; eluting with 10% to 70% ACN in $H_2O$ (0.1% $NH_4CO_3$).

[4] Work up: Mixture acidified to pH 6 with FA. Insoluble material collected by filtration.

[5] Purified by silica gel chromatography eluting with 0% to 10% MeOH in DCM.

[6] Purified by flash reverse phase chromatography: Column, C18; eluting with 0% to 100% ACN in $H_2O$.

[7] Purified by reverse phase chromatography: Column, C18; eluting with 10% to 50% ACN in $H_2O$.

[8] Purified by reverse phase chromatography: Column, C18; eluting with 30% to 70% ACN in $H_2O$ (0.1% FA).

[a] $[M + H - C_4H_8]^+$

[9] Upon adjusting pH to 4 with FA, the resultant insoluble material is collected by filtration.

Preparation 529 tert-Butyl 4-(4-[3-cyano-4-hydroxypyrazolo[1,5-a]pyridin-6-yl]-5-methyl-1,2,3-triazol-1-yl)piperidine-1-carboxylate

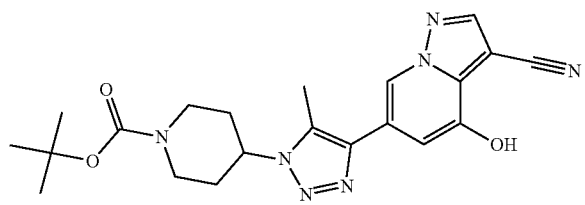 [SMILES: Cc1c(-c2cc(O)c3c(C#N)cnn3c2)nnn1C1CCN(C(=O)OC(C)(C)C)CC1]

NaOH (50% aq.) (36.57 g, 457.14 mmol) is added dropwise to a stirred mixture of tert-butyl 4-(4-[3-cyano-4-methoxypyrazolo[1,5-a]pyridin-6-yl]-5-methyl-1,2,3-triazol-1-yl)piperidine-1-carboxylate (40.00 g, 91.43 mmol) and NDM (55.51 g, 274.28 mmol) in DMA (400 mL) at 0° C. The mixture is stirred for 8 hrs at 50° C. The mixture is diluted with H$_2$O (400 mL), acidified to pH 6 with FA, filtered, and the filter cake is washed with H$_2$O, and dried under vacuum. The solid is triturated with a mixture of hexanes (200 mL) and Et$_2$O (200 mL), filtered, and stirred in MeOH (400 mL) for 2 hrs at 60° C. The mixture is filtered, and the filtered cake is concentrated under vacuum to give the title compound as a light-yellow solid (32 g, 82.6%). ES/MS m/z 424.3 [M+H]$^+$.

Preparation 530 tert-Butyl 4-(4-[3-cyano-4-hydroxypyrazolo[1,5-a]pyridin-6-yl]-5-methylpyrazol-1-yl)piperidine-1-carboxylate

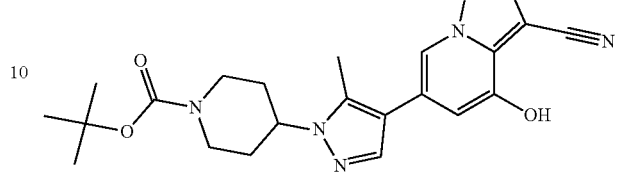

NaOH (50% aq.) (10.44 g, 130.58 mmol) is added to a stirred mixture of tert-butyl 4-(4-[3-cyano-4-methoxypyrazolo[1,5-a]pyridin-6-yl]-5-methylpyrazol-1-yl)piperidine-1-carboxylate (19.00 g, 43.53 mmol) and NDM (26.43 g, 130.58 mmol) in DMA (150 mL) under N$_2$ and the mixture is stirred for 3 hrs at 60° C. under N$_2$. The mixture is diluted with H$_2$O (1 L), acidified to pH~4 with FA, and extracted with EtOAc (3×1 L). The combined organic extracts are washed with brine (3×800 mL), dried over anhydrous Na$_2$SO$_4$, filtered, and the filtrate is concentrated under reduced pressure. The residue is crystallized with MTBE:DCM:MeOH (1000 mL:100 mL:10 mL). The precipitated solids are collected by filtration and washed with hexanes (3×50 mL) to give the title compound as a grey solid (15.03 g, 81.70). ES/MS m/z 421.30 [M–H]$^-$.

The following compounds are prepared essentially as described for tert-butyl 4-(4-[3-cyano-4-hydroxypyrazolo[1,5-a]pyridin-6-yl]-5-methylpyrazol-1-yl)piperidine-1-carboxylate using the appropriate reagents, adjusting the reaction times to determine completion of the reactions, and adjusting the purification system as appropriate. The extraction/washing/drying/crystallization steps can be omitted. The solids can also be washed with H$_2$O, hexanes, and PE. The solvent can also be 1,4-dioxane. Temperature is varied from 50° C. to 60° C.

TABLE 41

| Prep No. | Chemical Name | Structure | ES/MS m/z [M + H]$^+$ |
|---|---|---|---|
| 531 | tert-Butyl (3R)-3-(4-[3-cyano-4-hydroxypyrazolo[1,5-a]pyridin-6-yl]-5-methylpyrazol-1-yl)pyrrolidine-1-carboxylate | 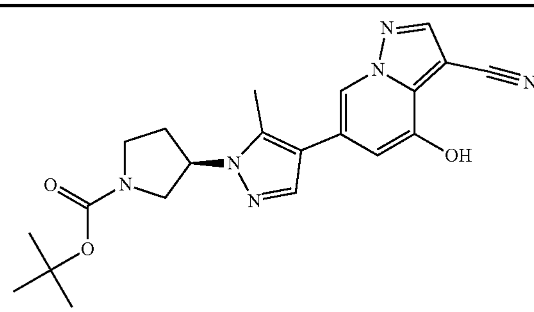 | 409.3 |
| 532 | tert-Butyl (3R)-3-(3-(4-(3-cyano-4-hydroxypyrazolo[1,5-a]pyridin-6-yl)-5-methyl-1H-pyrazol-1-yl)azetidin-1-yl)pyrrolidine-1-carboxylate | 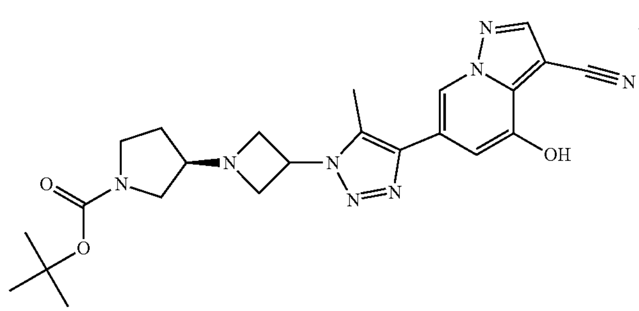 [SMILES: Cc1c(-c2cc(O)c3c(C#N)cnn3c2)nnn1C1CN([C@@H]2CCN(C(=O)OC(C)(C)C)C2)C1] | 464.3 |

TABLE 41-continued

| Prep No. | Chemical Name | Structure | ES/MS m/z [M + H]+ |
|---|---|---|---|
| 533 | tert-Butyl (3S)-3-(4-[3-cyano-4-hydroxypyrazolo[1,5-a]pyridin-6-yl]-5-methylpyrazol-1-yl)pyrrolidine-1-carboxylate | 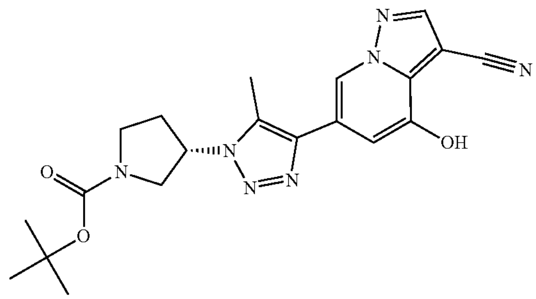 [SMILES: Cc1c(-c2cc(O)c3c(C#N)cnn3c2)nnn1[C@H]1CCN(C(=O)OC(C)(C)C)C1] | 409.2 |

Preparation 534 tert-Butyl (3S)-3-[3-[4-[3-cyano-4-(trifluoromethyl-sulfonyloxy)pyrazolo[1,5-a]pyridin-6-yl]-5-methyl-pyrazol-1-yl] azetidin-1-yl]pyrrolidine-1-carboxylate

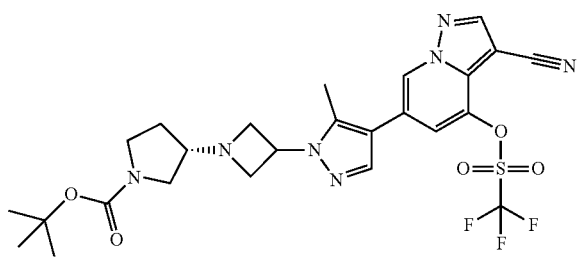 [SMILES: Cc1c(-c2cc(OS(=O)(=O)C(F)(F)F)c3c(C#N)cnn3c2)cnn1C1CN([C@H]2CCN(C(=O)OC(C)(C)C)C2)C1]

To tert-butyl (S)-3-(3-(4-(3-cyano-4-hydroxypyrazolo[1,5-a]pyridin-6-yl)-5-methyl-1H-pyrazol-1-yl)azetidin-1-yl)pyrrolidine-1-carboxylate (300 mg, 0.64 mmol) and 1,1,1-trifluoro-N-phenyl-N-trifluoromethanesulfonylmethane sulfonamide (346 mg, 0.97 mmol) in DCM (10.00 mL) is added TEA (196 mg, 1.94 mmol) and DMAP (7 mg, 0.06 mmol) at RT under N₂. The reaction is stirred for 1 hr at RT under N₂ then is concentrated in vacuo. The residue is purified by Prep-TLC 10% MeOH in DCM to afford the title compound as a light-yellow solid (350 mg, 90%). ES/MS m/z 596.2 [M+H]⁺.

Preparation 535 tert-Butyl 4-[4-(3-cyano-4-[[(2S)-1,1,1-trifluoropropan-2-yl]oxy]pyrazolo[1,5-a]pyridine-6-yl)-5-methylpyrazol-1-yl]piperidine-1-carboxylate

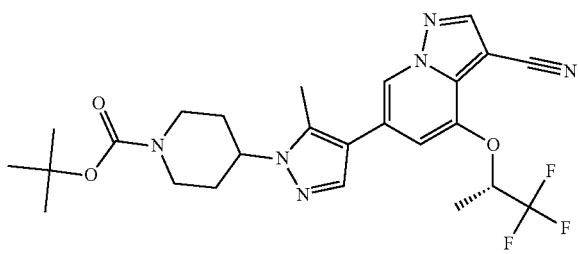 [SMILES: Cc1c(-c2cc(O[C@@H](C)C(F)(F)F)c3c(C#N)cnn3c2)cnn1C1CCN(C(=O)OC(C)(C)C)CC1]

A stirred solution of (2R)-1,1,1-trifluoropropan-2-ol (150.00 mg, 1.32 mmol) and DIEA (509.87 mg, 3.95 mmol) in DCM (5.00 mL) is treated with Tf₂O (371.02 mg, 1.32 mmol) at 0° C. under N₂, and the mixture is stirred for 1 hr at RT under N₂. The mixture is added directly to a stirred mixture of tert-butyl 4-(4-[3-cyano-4-hydroxypyrazolo[1,5-a]pyridine-6-yl]-5-methylpyrazol-1-yl)piperidine-1-carboxylate (100 mg, 0.41 mmol) and K₂CO₃ (168.46 mg, 1.22 mmol) in CAN (8.00 mL). The mixture is stirred for 5 hrs at 80° C. under N₂. The mixture is cooled to RT, the reaction quenched with H₂O (50 mL), and extracted with EtOAc (3×50 mL). The combined organic extracts are washed with brine (50 mL), dried over anhydrous Na₂SO₄, filtered, and the filtrate is concentrated under reduced pressure. The residue is purified by Prep-TLC (PE:EtOAc 2:1) to give the title compound as a light-yellow solid (60 mg, 48.89%). ES/MS m/z 504.3 [M-tBu+H]⁺.

The following compound is prepared essentially as described for tert-butyl 4-[4-(3-cyano-4-[[(2S)-1,1,1-trifluoropropan-2-yl]oxy]pyrazolo[1,5-a]215yridine-6-yl)-5-methylpyrazol-1-yl]piperidine-1-carboxylate using the appropriate reagents, adjusting the reaction times to determine completion of the reactions, and adjusting the purification system as appropriate.

TABLE 42

| Prep No. | Chemical Name | Structure | ES/MS m/z [M + H]+ |
|---|---|---|---|
| 536 | tert-Butyl 4-[4-(3-cyano-4-[[(2R)-1,1,1-trifluoropropan-2-yl]oxy]pyrazolo[1,5-a]215yridine-6-yl)-5-methylpyrazol-1-yl]piperidine-1-carboxylate | 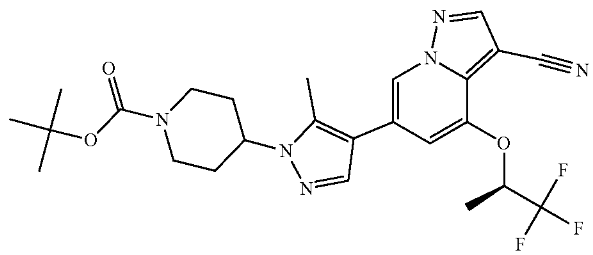 [SMILES: Cc1c(-c2cc(O[C@H](C)C(F)(F)F)c3c(C#N)cnn3c2)cnn1C1CCN(C(=O)OC(C)(C)C)CC1] | 519.1 |

Preparation 537 tert-Butyl (3S)-3-[3-[4-[3-cyano-4-[[(1R)-1-(2-pyridyl)ethyl]amino]pyrazolo[1,5-a]pyridin-6-yl]-5-methyl-pyrazol-1-yl]azetidin-1-yl]pyrrolidine-1-carboxylate

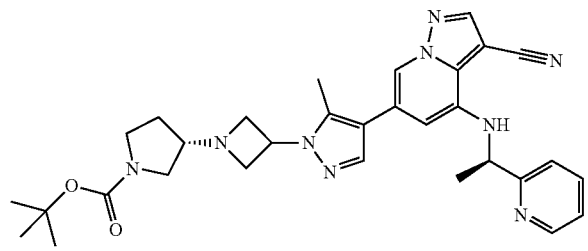 [SMILES: Cc1c(-c2cc(N[C@H](C)c3ccccn3)c3c(C#N)cnn3c2)cnn1C1CN([C@H]2CCN(C(=O)OC(C)(C)C)C2)C1]

To tert-butyl (3S)-3-[3-[4-[3-cyano-4-(trifluoromethylsulfonyloxy)pyrazolo[1,5-a]pyridin-6-yl]-5-methyl-pyrazol-1-yl]azetidin-1-yl]pyrrolidine-1-carboxylate (350 mg, 0.58 mmol) and (1R)-1-(pyridin-2-yl)ethanamine (358 mg, 2.93 mmol) in toluene (10 mL) at RT is added $Cs_2CO_3$ (765 mg, 2.35 mmol), XantPhos (68 mg, 0.11 mmol) and $Pd_2(dba)_3$ (53 mg, 0.05 mmol). The reaction is stirred overnight at 100° C. under $N_2$. Upon cooling to RT, the reaction is concentrated in vacuo. The residue is purified by silica gel column chromatography, eluting with DCM;MeOH (20:1 to 10:1) to afford the title compound as a green solid (60 mg, 17%). ES/MS m/z 568.4 [M+H]+.

Preparation 538 tert-Butyl 4-[4-[5-[(1R)-1-(5-fluoro-2-pyridyl)ethoxy]-3-methyl-imidazo[1,2-a]pyridin-7-yl]-5-methyl-triazol-1-yl]piperidine-1-carboxylate

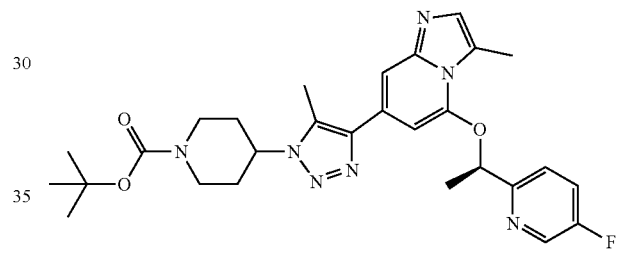

To tert-Butyl 4-(4-{5-hydroxy-3-methylimidazo[1,2-a]pyridin-7-yl}-5-methyl-1,2,3-triazol-1-yl)piperidine-1-carboxylate (600.0 mg, 1.46 mmol) and (1S)-1-(5-fluoropyridin-2-yl)ethyl methanesulfonate (382.66 mg, 1.75 mmol) in DMF (10.0 mL) is added $Cs_2CO_3$ (1.42 g, 4.37 mmol) RT under $N_2$. The reaction is stirred at 120° C. for 2 hr. Upon cooling to RT, the mixture is diluted with $H_2O$ (100 mL) and extracted with EtOAc (3×100 mL). The combined organic layers are washed with brine (3×100 mL), dried over $Na_2SO_4$, filtered, and concentrated in vacuo. The residue is purified by Prep-TLC (DCM/MeOH 20:1) to afford the title compound as a yellow solid (240 mg, 30.8%). ES/MS m/z 536.3 [M+H]+.

The following compounds are prepared essentially as described for tert-butyl 4-[4-[5-[(1R)-1-(5-fluoro-2-pyridyl)ethoxy]-3-methyl-imidazo[1,2-a]pyridin-7-yl]-5-methyl-triazol-1-yl]piperidine-1-carboxylate using the appropriate reagents, adjusting the reaction times and temperature, and adjusting the purification system as appropriate.

TABLE 43

| Prep No. | Chemical Name | Structure | ES/MS m/z [M + H]+ |
|---|---|---|---|
| 539[1,2] | tert-Butyl 4-[4-[3-cyano-4-[1-(2-methoxycarbonylphenyl)ethoxy]pyrazolo[1,5-a]pyridin-6-yl]-5-methyl-triazol-1-yl]piperidine-1-carboxylate | 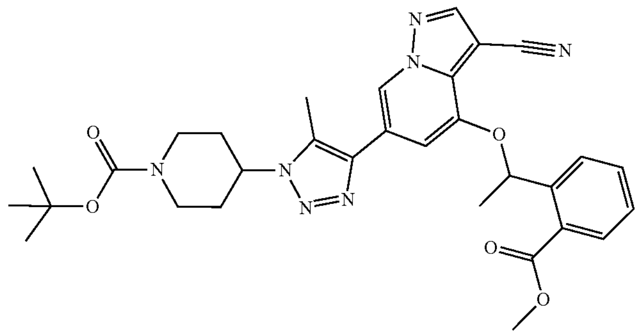 [SMILES: COC(=O)c1ccccc1C(C)Oc1cc(-c2nnn(C3CCN(C(=O)OC(C)(C)C)CC3)c2C)cn2ncc(C#N)c12] | 586.3 |
| 540[3] | tert-Butyl 4-[4-[3-cyano-4-[1-[2-(dimethylcarbamoyl)phenyl]ethoxy]pyrazolo[1,5-a]pyridin-6-yl]-5-methyl-triazol-1-yl]piperidine-1-carboxylate | 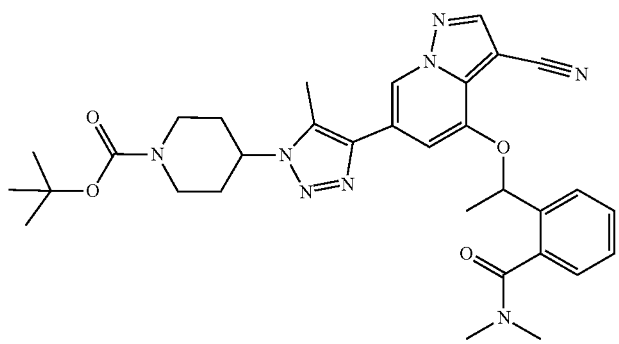 [SMILES: Cc1c(-c2cc(OC(C)c3ccccc3C(=O)N(C)C)c3c(C#N)cnn3c2)nnn1C1CCN(C(=O)OC(C)(C)C)CC1] | 599.3 |
| 541[3] | tert-Butyl 4-[4-[3-cyano-4-[2-(5-fluoro-2-pyridyl)-2-oxo-ethoxy]pyrazolo[1,5-a]pyridin-6-yl]-5-methyl-triazol-1-yl]piperidine-1-carboxylate | 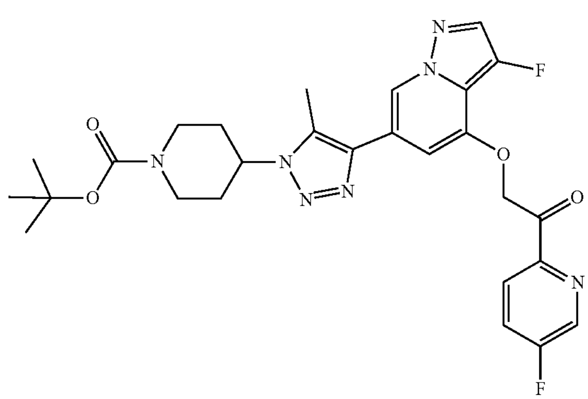 [SMILES: Cc1c(-c2cc(OCC(=O)c3ccc(F)cn3)c3c(F)cnn3c2)nnn1C1CCN(C(=O)OC(C)(C)C)CC1] | 554.4 |

TABLE 43-continued

| Prep No. | Chemical Name | Structure | ES/MS m/z [M + H]+ |
|---|---|---|---|
| 542[3] | tert-Butyl 4-[4-[3-chloro-4-[2-(5-fluoro-2-pyridyl)-2-oxo-ethoxy]pyrazolo[1,5-a]pyridin-6-yl]-5-methyl-triazol-1-yl]piperidine-1-carboxylate | 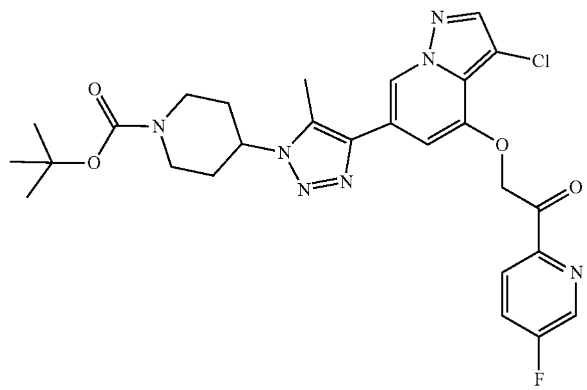 [SMILES: Cc1c(-c2cc(OCC(=O)c3ccc(F)cn3)c3c(Cl)cnn3c2)nnn1C1CCN(C(=O)OC(C)(C)C)CC1] | 514.2 [M + H − tBu]+ |
| 543[4] | tert-Butyl 4-[4-[3-cyano-5-[(1R)-1-(5-fluoro-2-pyridyl)ethoxy]imidazo[1,2-a]pyridin-7-yl]-3-(2-hydroxyethyl)-5-methyl-pyrazol-1-yl]piperidine-1-carboxylate | 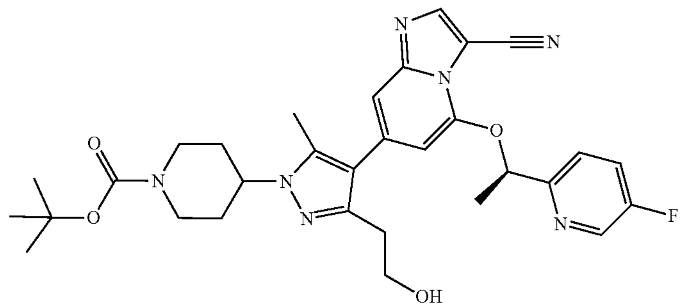 [SMILES: Cc1c(-c2cc(O[C@H](C)c3ccc(F)cn3)n3c(C#N)cnc3c2)c(CCO)nn1C1CCN(C(=O)OC(C)(C)C)CC1] | 590.1 |
| 544[5] | tert-Butyl 4-[4-[3-cyano-5-[(1R)-1-[4-(2,2,2-trifluoroethyl)-1,2,4-triazol-3-yl]ethoxy]imidazo[1,2-a]pyridin-7-yl]-5-methyl-triazol-1-yl]piperidine-1-carboxylate | 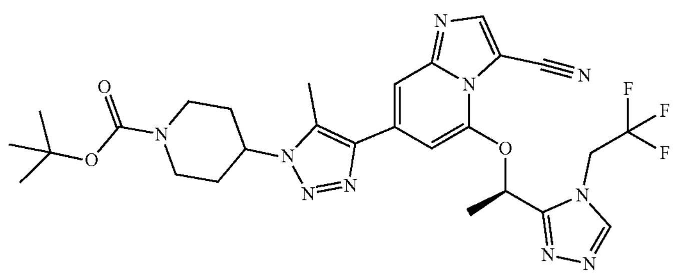 [SMILES: Cc1c(-c2cc(O[C@H](C)c3nncn3CC(F)(F)F)n3c(C#N)cnc3c2)nnn1C1CCN(C(=O)OC(C)(C)C)CC1] | 601.5 |
| 545[6] | (1s,3r)-3-(4-(4-((S)-2-((tert-Butyldimethylsilyl)oxy)-1-(5-fluoropyridin-2-yl)ethoxy)-3-chloropyrazolo[1,5-a]pyridin-6-yl)-5-methyl-1H-1,2,3-triazol-1-yl)cyclobutan-1-ol | 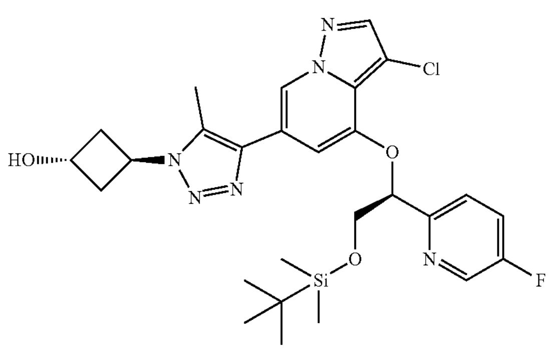 [SMILES: Cc1c(-c2cc(O[C@H](CO[Si](C)(C)C(C)(C)C)c3ccc(F)cn3)c3c(Cl)cnn3c2)nnn1[C@H]1C[C@H](O)C1] | 573.0 |

[1]Methyl 2-(1-bromoethyl)benzoate used as starting material.
[2]Purified by reverse phase chromatography eluting with a gradient of 0% to 100% ACN in H₂O.
[3]Purified by reverse phase chromatography eluting with a gradient of 10% to 100% ACN in H₂O.
[4]Purified by Prep-TLC 2:1 EtOAc:PE.
[5]Purified by Prep-TLC 10:1 DCM:MeOH.
[6]Purified by silica gel chromatography eluting with a gradient of 0% to 20% MeOH in DCM.

Preparation 546 tert-Butyl 4-[4-[3-fluoro-4-[2-(5-fluoro-2-pyridyl)-2-hydroxy-ethoxy]pyrazolo[1,5-a]pyridin-6-yl]-5-methyl-triazol-1-yl]piperidine-1-carboxylate

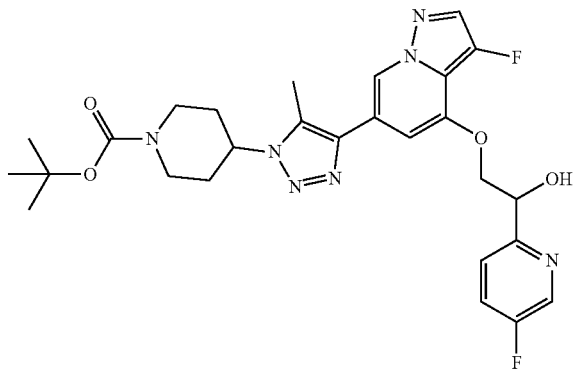 [SMILES: Cc1c(-c2cc(OCC(O)c3ccc(F)cn3)c3c(F)cnn3c2)nnn1C1CCN(C(=O)OC(C)(C)C)CC1]

To a solution of tert-butyl 4-[4-[3-fluoro-4-[2-(5-fluoro-2-pyridyl)-2-oxo-ethoxy]pyrazolo[1,5-a]pyridin-6-yl]-5-methyl-triazol-1-yl]piperidine-1-carboxylate (45 mg, 0.08 mmol) in MeOH (5 mL) is added $NaBH_4$ (3.7 mg, 0.098 mmol). The reaction is stirred for 30 min. at RT then concentrated under reduced pressure. The residue is treated with EtOAc and $H_2O$. The organic layer is separated, and the aqueous layer is extracted with EtOAc (2×10 mL). The combined organic layers are washed brine, dried over $Na_2SO_4$, and concentrated to afford the title compound (45 mg, 0.08 mmol) as a white solid. The crude product is used in the next without further purification. ES/MS m/z 556.2 [M+H]$^+$.

The following compound is prepared essentially as described for tert-Butyl 4-[4-[3-cyano-4-[2-(5-fluoro-2-pyridyl)-2-hydroxy-ethoxy]pyrazolo[1,5-a]pyridin-6-yl]-5-methyl-triazol-1-yl]piperidine-1-carboxylate using the appropriate reagents, adjusting the reaction time and temperature, and adjusting the purification system as appropriate.

TABLE 44

| Prep No. | Chemical Name | Structure | ES/MS m/z [M + H]$^+$ |
|---|---|---|---|
| 547 | tert-Butyl 4-[4-[3-chloro-4-[2-(5-fluoro-2-pyridyl)-2-hydroxy-ethoxy]pyrazolo[1,5-a]pyridin-6-yl]-5-methyl-triazol-1-yl]piperidine-1-carboxylate | 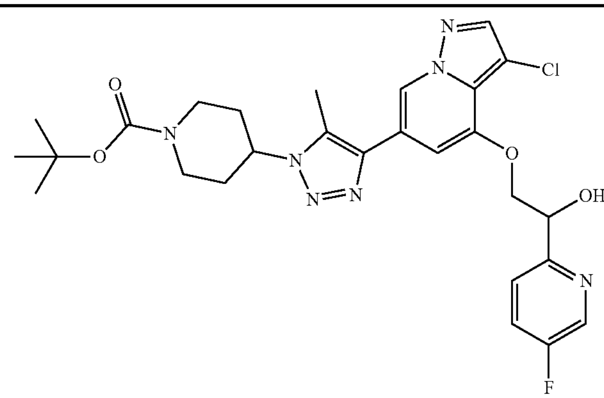 | 572.2 |

Preparation 548 tert-Butyl 4-[4-[3-chloro-4-[2-(5-fluoro-2-pyridyl)-2-hydroxy-propoxy]pyrazolo[1,5-a]pyridin-6-yl]-5-methyl-triazol-1-yl]piperidine-1-carboxylate

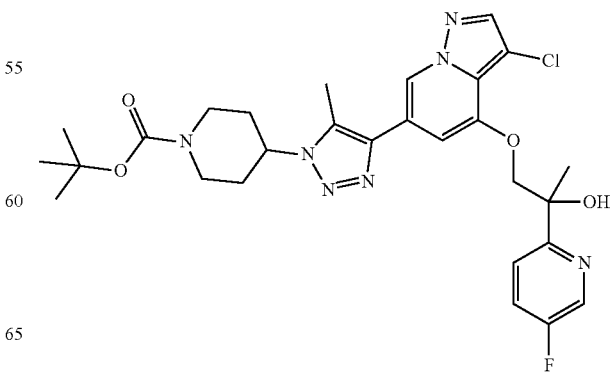

To a solution of tert-butyl 4-[4-[3-chloro-4-[2-(5-fluoro-2-pyridyl)-2-oxo-ethoxy]pyrazolo[1,5-a]pyridin-6-yl]-5-methyl-triazol-1-yl]piperidine-1-carboxylate (200 mg, 0.35 mmol) in THF (10 mL) at RT is added a solution of MeMgBr (3M in Et2O) (50.2 mg, 0.42 mmol). After stirring at RT for 60 min. the reaction is quenched with sat. NH₄Cl, extracted with EtOAc (2×), dried over Na₂SO₄ and concentrated. The residue is purified by silica gel chromatography eluting with 0% to 100% EtOAc in heptane to afford the title compound (170 mg, 82.7%) as a white solid. ES/MS, m/z 586.4 [M+H]⁺.

Preparation 549 tert-Butyl 4-[4-[3-fluoro-4-[2-(5-fluoro-2-pyridyl)-2-hydroxy-propoxy]pyrazolo[1,5-a]pyridin-6-yl]-5-methyl-triazol-1-yl]piperidine-1-carboxylate

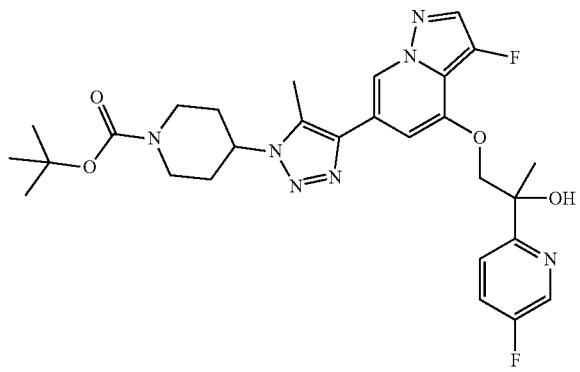 [SMILES: Cc1c(-c2cc(OCC(C)(O)c3ccc(F)cn3)c3c(Cl)cnn3c2)nnn1C1CCN(C(=O)OC(C)(C)C)CC1]

To a solution of tert-butyl 4-[4-[3-fluoro-4-[2-(5-fluoro-2-pyridyl)-2-oxo-ethoxy]pyrazolo[1,5-a]pyridin-6-yl]-5-methyl-triazol-1-yl]piperidine-1-carboxylate (180 mg, 0.33 mmol) in THF (8 mL) at RT is added MeMgBr (3M solution) (58.2 mg, 0.49 mmol) and the reaction is stirred at RT for 30 min. Next, the reaction is quenched with sat. NH₄Cl, extracted into EtOAc (2×), dried over Na₂SO₄ and concentrated. The residue is purified by silica gel chromatography eluting with 0% to 100% EtOAc in heptane to afford the title compound (90 mg, 49%) as a white solid. ES/MS, m/z 570.4 [M+H]f.

Preparation 550 tert-Butyl4-(4-{4-[2-[(tert-butyldimethylsilyl)oxy]-1-(5-fluoropyridin-2-yl)ethoxy]-3-cyanopyrazolo[1,5-a]pyridin-6-yl}-5-methylpyrazol-1-yl)piperidine-1-carboxylate

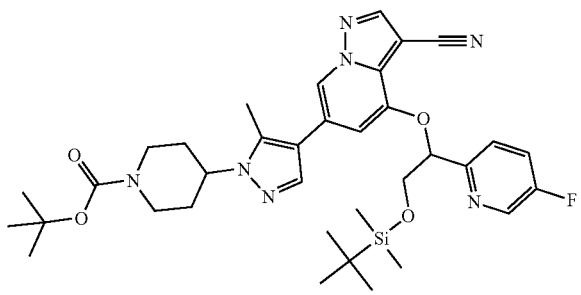 [SMILES: Cc1c(-c2cc(OC(CO[Si](C)(C)C(C)(C)C)c3ccc(F)cn3)c3c(C#N)cnn3c2)cnn1C1CCN(C(=O)OC(C)(C)C)CC1]

To a stirred mixture of PPh₃ (9.93 g, 97.87 mmol) in THF (30 mL) is added DIAD (7.66 g, 37.87 mmol) dropwise at 0° C. under N₂. The reaction is stirred at 0° C. for 0.5 hr under N₂. To the mixture is added 2-[(tert-butyldimethylsilyl)oxy]-1-(5-fluoropyridin-2-yl)ethanol (1.93 g, 7.10 mmol) and tert-butyl 4-(4-{3-cyano-4-hydroxypyrazolo[1,5-a]pyridin-6-yl}-5-methylpyrazol-1-yl)piperidine-1-carboxylate (2 g, 4.73 mmol) in THF (20 mL). The resulting mixture is stirred for 2 hr at RT then concentrated in vacuo. The residue is purified by reverse phase chromatography with the following conditions: Column, C18; eluting with 80% to 100% ACN in H₂O (0.1% NH₄HCO₃) to give the title compound as a white solid (2.7 g, 85.9%). ES/MS, m/z 676.4 [M+H]⁺.

Preparation 551 tert-Butyl 4-[4-[4-[2-[tert-butyl(dimethyl)silyl]oxy-1-(5-fluoro-2-pyridyl)ethoxy]pyrazolo[1,5-a]pyridin-6-yl]-5-methyl-triazol-1-yl]piperidine-1-carboxylate

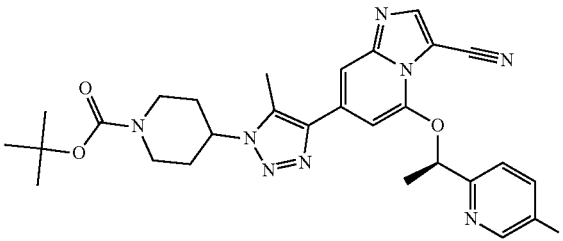

To PPh₃ (789.88 mg, 3.01 mmol) in THF (15 mL) is added DIAD (568.36 mg, 2.811 mmol) dropwise at 0° C. under N₂. The reaction is stirred at 0° C. for 0.5 hr. To the mixture is added to tert-butyl 4-[4-(4-hydroxypyrazolo[1,5-a]pyridin-6-yl)-5-methyl-triazol-1-yl]piperidine-1-carboxylate (400 mg, 1.00 mmol) and 2-[(tert-butyldimethylsilyl)oxy]-1-(5-fluoropyridin-2-yl)ethanol (408.68 mg, 1.51 mmol) in THF (10 mL). After stirring 2 hr at RT, the reaction is concentrated in vacuo. The residue is purified by reverse phase chromatography with the following conditions: Column, C18; eluting with 70% to 80% ACN in H2O (0.1% NH₄HCO₃) to give the title compound as a light-brown oil (450 mg, 68.77%). ES/MS, m/z 652.4 [M+H]⁺.

Preparation 552 tert-Butyl 4-(4-[3-cyano-5-[(1R)-1-(5-fluoropyridin-2-yl)ethoxy]imidazo[1,2-a]pyridin-7-yl]-5-methyl-1,2,3-triazol-1-yl)piperidine-1-carboxylate DEAD (185.1 mg, 1.06 mmol) is added to a stirred solution of PPh₃ (278.7 mg, 1.06 mmol) in THF (5.0 mL) at 0° C. under N₂ After the mixture is stirred for 30 min at 0° C. under N₂, a solution of tert-butyl 4-(4-[3-cyano-5-hydroxyimidazo[1,2-a]pyridin-7-yl]-5-methyl-1,2,3-triazol-1-yl)piperidine-1-carboxylate (150.0 mg, 0.35 mmol) and (1S)-1-(5-fluoropyridin-2-yl)ethanol (60.0 mg, 0.425 mmol) in THF (5.0 mL) is added to the mixture at RT under N₂ and stirred overnight at RT. The mixture is concentrated under reduced pressure. The residue is purified by reverse Combiflash chromatography with the following conditions: Column, C18; eluting with a gradient of 50% to 70% ACN in H₂O (0.1% NH₄HCO₃) to give the title compound as a yellow solid (80.0 mg, 41.3%). ES/MS m/z 547.2 [M+H]⁺.

Preparation 553 tert-Butyl 4-[4-[3-cyano-5-[1-[5-(trifluoromethyl)-3-pyridyl]ethoxy]imidazo[1,2-a]pyridin-7-yl]-5-methyl-triazol-1-yl]piperidine-1-carboxylate

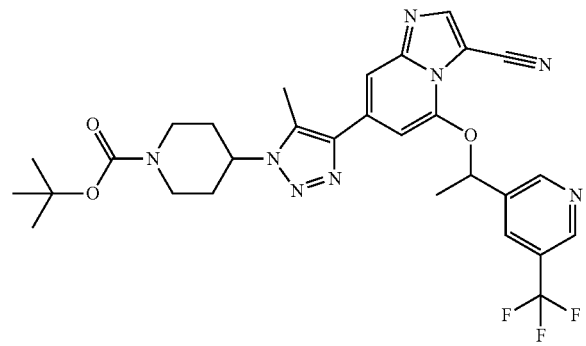 [SMILES: Cc1c(-c2cc(OC(C)c3cncc(C(F)(F)F)c3)n3c(C#N)cnc3c2)nnn1C1CCN(C(=O)OC(C)(C)C)CC1]

DIAD (334.25 mg, 1.65 mmol) is added dropwise to a stirred mixture of PPh₃ (464.52 mg, 1.77 mmol) in THF (10 mL) at 0° C. under N₂ and the mixture is stirred for 30 min. at 0° C. under N₂. To the mixture is added to 1-[5-(trifluoromethyl)pyridin-3-yl]ethanol (135.42 mg, 0.71 mmol) and tert-butyl 4-(4-[3-cyano-5-hydroxyimidazo[1,2-a]pyridin-7-yl]-5-methyl-1,2,3-triazol-1-yl)piperidine-1-carboxylate (250.00 mg, 0.59 mmol) in THF (20 mL). The mixture is stirred overnight at RT and concentrated under reduced pressure. The residue is purified by reversed Combi-flash chromatography with the following conditions: Column, C18; eluting with 0 to 100% ACN in H₂O (0.1% FA) give the title compound (150 mg, 42.59%) as an off-white solid. ES+H, m/z 596.9 [M+H]⁺

Preparation 554 tert-Butyl 4-[4-[3-cyano-5-[1-(5-fluoro-2-pyridyl)-2-methoxy-ethoxy]imidazo[1,2-a]pyridin-7-yl]-5-methyl-triazol-1-yl]piperidine-1-carboxylate

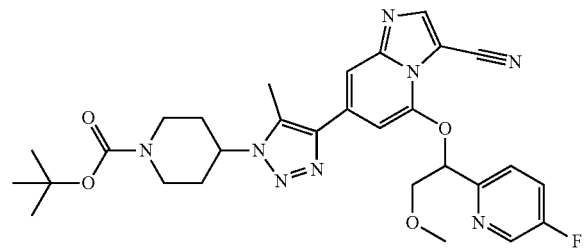 [SMILES: COCC(Oc1cc(-c2nnn(C3CCN(C(=O)OC(C)(C)C)CC3)c2C)cc2ncc(C#N)n12)c1ccc(F)cn1]

DIAD (171.90 mg, 0.85 mmol) is added dropwise to a stirred mixture of PPh₃ (241.55 mg, 0.92 mmol) in THF (10.00 mL) at 0° C. under N₂. The mixture is stirred for 30 min. at 0° C. under N₂, then the mixture is added to 1-(5-fluoropyridin-2-yl)-2-methoxyethanol (133.39 mg, 0.78 mmol) and tert-butyl 4-(4-[3-cyano-5-hydroxyimidazo[1,2-a]pyridin-7-yl]-5-methyl-1,2,3-triazol-1-yl)piperidine-1-carboxylate (300.00 mg, 0.71 mmol) in THF (10 mL). The mixture is stirred for 2 hr at RT under N₂ and concentrated under vacuum. The residue is purified by reversed Combiflash chromatography with the following conditions: Eluting with 55% to 60% ACN in H₂O (0.1% NH₄HCO₃) to give the title compound (160 mg, 39.17%) as an off-white solid. ES/MS, m/z 577.3 [M+H]⁺.

Preparation 555 tert-Butyl 4-[4-[3-cyano-5-[1-(5-fluoro-2-pyridyl)propoxy]imidazo[1,2-a]pyridin-7-yl]-5-methyl-triazol-1-yl]piperidine-1-carboxylate

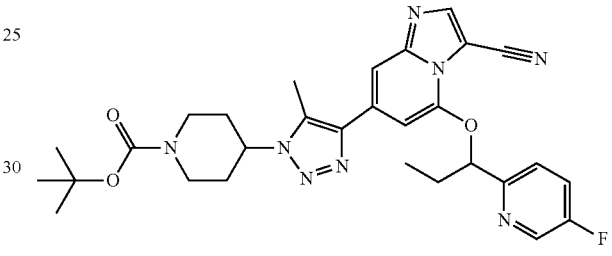

DIAD (171.90 mg, 0.85 mmol) is added dropwise to a stirred mixture of PPh₃ (241.55 mg, 0.92 mmol) in THF (10.0 mL) at 0° C. under N₂ and the mixture is stirred for 30 min at 0° C. under N₂. The mixture is added to 1-(5-fluoropyridin-2-yl)propan-1-ol (120.92 mg, 0.78 mmol) and tert-butyl-4-(4-[3-cyano-5-hydroxyimidazo[1,2-a]pyridin-7-yl]-5-methyl-1,2,3-triazol-1-yl)piperidine-1-carboxylate (300.00 mg, 0.71 mmol) in THF (10 mL). The mixture is stirred for 2 hr at RT under N₂. The mixture is concentrated under reduced pressure and the residue is purified by reversed Combi-flash chromatography with the following conditions: Eluting with 55% to 60% ACN in H₂O (0.1% NH₄HCO₃) to give the title compound (210 mg, 52.87%) as a grey solid. ES/MS m/z 561.5 [M+H]⁺.

Preparation 556 tert-Butyl 4-[4-[3-cyano-4-[1-(5-fluoro-2-pyridyl)-2-methoxy-ethoxy]pyrazolo[1,5-a]pyridin-6-yl]-5-methyl-triazol-1-yl]piperidine-1-carboxylate

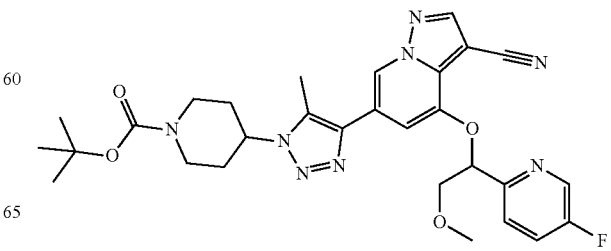

DIAD (143.25 mg, 0.71 mmol) is added dropwise to a stirred mixture of PPh₃ (201.29 mg, 0.77 mmol) in THF (15.00 mL) at 0° C. under N₂ and the mixture is stirred for 30 min at 0° C. under N₂. To the mixture is added to 1-(5-fluoropyridin-2-yl)-2-methoxyethanol (111.16 mg, 0.65 mmol) and tert-butyl 4-(4-[3-cyano-4-hydroxypyrazolo[1,5-a]pyridin-6-yl]-5-methyl-1,2,3-triazol-1-yl)piperidine-1-carboxylate (250.00 mg, 0.59 mmol) in THF (15 mL). The mixture is stirred for 2 hr at RT under N₂ and concentrated under reduced pressure. The residue is purified by reversed Combi-flash chromatography with the following conditions: Eluting with 55% to 60% ACN in H₂O (0.1% NH₄HCO₃) to give the title compound (200 mg, 58.75%) as an off-white solid. ES/MS m/z 577.1⁺.

The following compounds are prepared essentially as described for tert-butyl 4-(4-[3-cyano-5-[(1R)-1-(5-fluoropyridin-2-yl)ethoxy]imidazo[1,2-a]pyridin-7-yl]-5-methyl-1,2,3-triazol-1-yl)piperidine-1-carboxylate using the appropriate reagents, adjusting the reaction times to determine completion of the reactions, and adjusting the purification system as appropriate. DIAD, DIEA and DMAP can also be used in lieu of DEAD. Temperature is varied from 0° C. to 80° C. Polymer supported PPh₃ can be used in place of PPh₃.

TABLE 45

| Prep No. | Chemical Name | Structure | ES/MS m/z [M + H]⁺ |
|---|---|---|---|
| 557[1] | tert-Butyl 4-(4-[3-cyano-4-[(1R)-1-(oxan-4-yl)ethoxy]pyrazolo[1,5-a]pyridin-6-yl]-5-methylpyrazol-1-yl)piperidine-1-carboxylate | 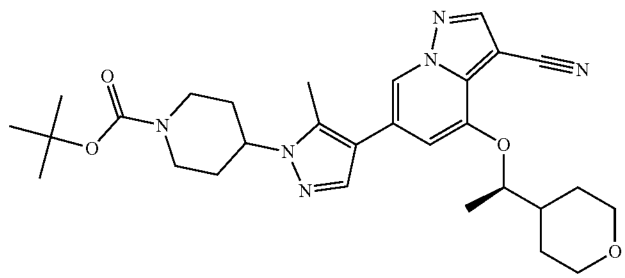 [SMILES: Cc1c(-c2cc(O[C@H](C)C3CCOCC3)c3c(C#N)cnn3c2)cnn1C1CCN(C(=O)OC(C)(C)C)CC1] | 535.3 |
| 558[1] | tert-Butyl 4-(4-[3-cyano-4-[(3-fluoropyridin-2-yl)methoxy]pyrazolo[1,5-a]pyridin-6-yl]-5-methylpyrazol-1-yl)piperidine-1-carboxylate | 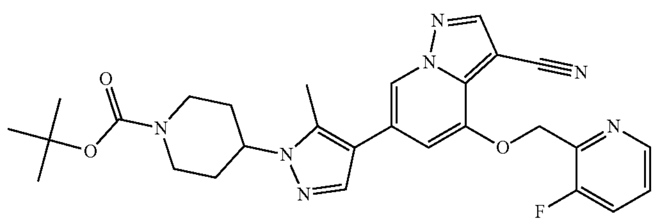 [SMILES: Cc1c(-c2cc(OCc3ncccc3F)c3c(C#N)cnn3c2)cnn1C1CCN(C(=O)OC(C)(C)C)CC1] | 532.3 |
| 559 | tert-Butyl 4-(4-[3-cyano-4-[(1R)-1-(3-fluoropyridin-2-yl)ethoxy]pyrazolo[1,5-a]pyridin-6-yl]-5-methylpyrazol-1-yl)piperidine-1-carboxylate | 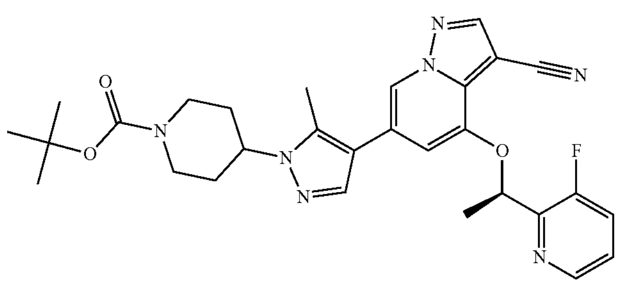 [SMILES: Cc1c(-c2cc(O[C@H](C)c3ncccc3F)c3c(C#N)cnn3c2)cnn1C1CCN(C(=O)OC(C)(C)C)CC1] | 546.2 |
| 560[1] | tert-Butyl 4-(4-[3-cyano-4-[(1R)-1-(pyrazin-2-yl)ethoxy]pyrazolo[1,5-a]pyridin-6-yl]-5-methylpyrazol-1-yl)piperidine-1-carboxylate | 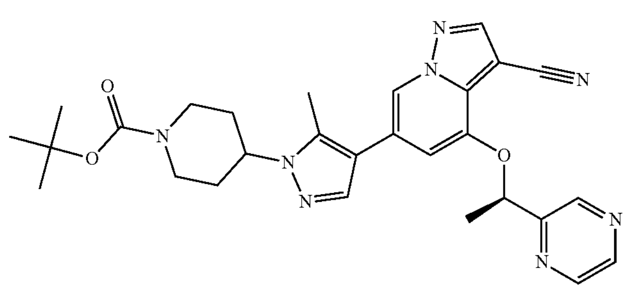 [SMILES: Cc1c(-c2cc(O[C@H](C)c3cnccn3)c3c(C#N)cnn3c2)cnn1C1CCN(C(=O)OC(C)(C)C)CC1] | 529.3 |

TABLE 45-continued

| Prep No. | Chemical Name | Structure | ES/MS m/z [[M + H]+ |
|---|---|---|---|
| 561[1] | tert-Butyl 4-(4-[3-cyano-4-[(1R)-1-(2-methylpyrazol-3-yl)ethoxy]pyrazolo[1,5-a]pyridin-6-yl]-5-methylpyrazol-1-yl)piperidine-1-carboxylate | 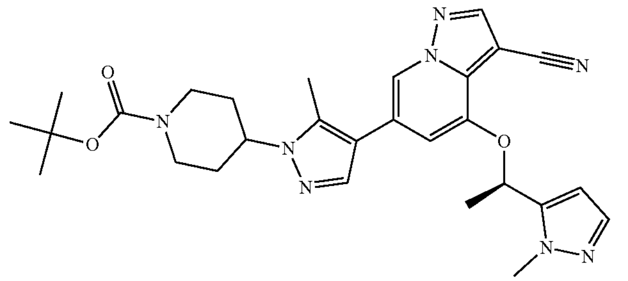 [SMILES: Cc1c(-c2cc(O[C@H](C)c3ccnn3C)c3c(C#N)cnn3c2)cnn1C1CCN(C(=O)OC(C)(C)C)CC1] | 531.3 |
| 562 | tert-Butyl 4-(4-[3-cyano-4-[(1R)-1-(pyridin-2-yl)propoxy]pyrazolo[1,5-a]pyridin-6-yl]-5-methylpyrazol-1-yl)piperidine-1-carboxylate | 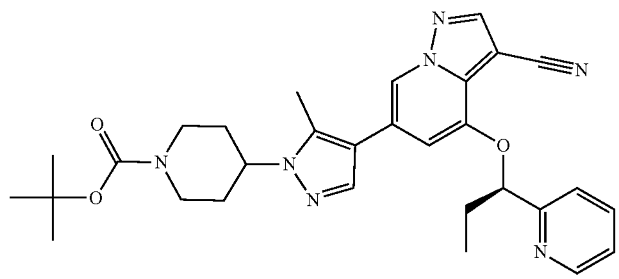 [SMILES: CC[C@@H](Oc1cc(-c2cnn(C3CCN(C(=O)OC(C)(C)C)CC3)c2C)cn2ncc(C#N)c12)c1ccccn1] | 542.3 |
| 563 | tert-Butyl 4-(4-[3-cyano-4-[(1R)-1-(1-methylpyrazol-3-yl)ethoxy]pyrazolo[1,5-a]pyridin-6-yl]-5-methylpyrazol-1-yl)piperidine-1-carboxylate | 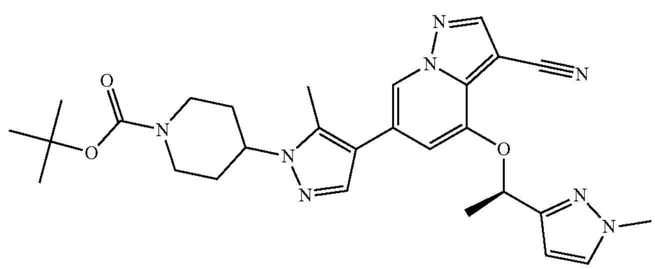 [SMILES: Cc1c(-c2cc(O[C@H](C)c3ccn(C)n3)c3c(C#N)cnn3c2)cnn1C1CCN(C(=O)OC(C)(C)C)CC1] | 531.4 |
| 564 | tert-Butyl 4-(4-(3-cyano-4-(((7R)-6,7-dihydro-5H-cyclopenta[b]pyridin-7-yl)oxy)pyrazolo[1,5-a]pyridin-6-yl)-5-methyl-1H-1,2,3-triazol-1-yl)piperidine-1-carboxylate | 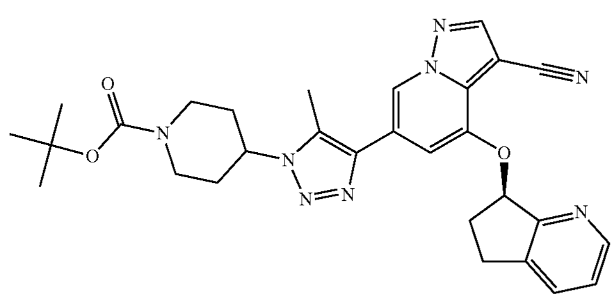 [SMILES: Cc1c(-c2cc(O[C@@H]3CCc4cccnc43)c3c(C#N)cnn3c2)nnn1C1CCN(C(=O)OC(C)(C)C)CC1] | 541.3 |
| 565[2] | tert-Butyl 4-(4-[3-cyano-4-[(1R)-1-cyclohexylethoxy]pyrazolo[1,5-a]pyridin-6-yl]-5-methyl-1,2,3-triazol-1-yl)piperidine-1-carboxylate | 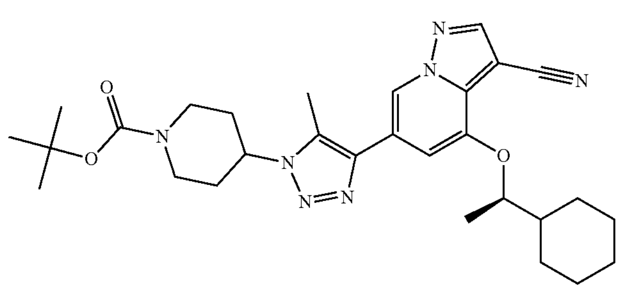 [SMILES: Cc1c(-c2cc(O[C@H](C)C3CCCCC3)c3c(C#N)cnn3c2)nnn1C1CCN(C(=O)OC(C)(C)C)CC1] | 534.5 |

TABLE 45-continued

| Prep No. | Chemical Name | Structure | ES/MS m/z [[M + H]+ |
|---|---|---|---|
| 566[1] | tert-Butyl 4-[4-(3-cyano-4-[[2-(pyridin-2-yl)propan-2-yl]oxy]pyrazolo[1,5-a]pyridin-6-yl)-5-methylpyrazol-1-yl]piperidine-1-carboxylate | 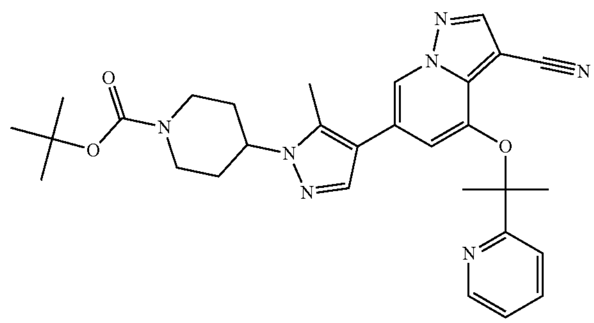 [SMILES: Cc1c(-c2cc(OC(C)(C)c3ccccn3)c3c(C#N)cnn3c2)cnn1C1CCN(C(=O)OC(C)(C)C)CC1] | 542.4 |
| 567 | tert-Butyl 4-[4-[3-cyano-4-[2-methoxy-1-[5-(trifluoromethyl)-3-pyridyl]ethoxy]-pyrazolo[1,5-a]pyridin-6-yl]-5-methyl-triazol-1-yl]piperidine-1-carboxylate | 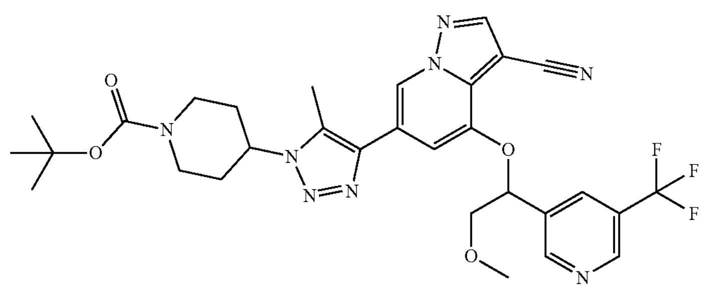 [SMILES: COCC(Oc1cc(-c2nnn(C3CCN(C(=O)OC(C)(C)C)CC3)c2C)cn2ncc(C#N)c12)c1cncc(C(F)(F)F)c1] | 627.2 |
| 568 | tert-Butyl 4-[4-[3-cyano-5-[(1R)-1-(5-fluoro-2-pyridyl)ethoxy]imidazo[1,2-a]pyridin-7-yl]-5-methyl-pyrazol-1-yl]piperidine-1-carboxylate | 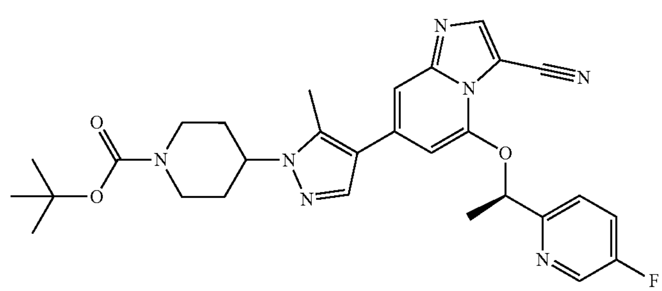 [SMILES: Cc1c(-c2cc(O[C@H](C)c3ccc(F)cn3)n3c(C#N)cnc3c2)cnn1C1CCN(C(=O)OC(C)(C)C)CC1] | 546.4 |
| 569 | tert-Butyl 4-[4-[5-[2-[tert-butyl(dimethyl)silyl]oxy-1-(5-fluoro-2-pyridyl)ethoxy]-3-cyano-imidazo[1,2-a]pyridin-7-yl]-5-methyl-pyrazol-1-yl]piperidine-1-carboxylate | 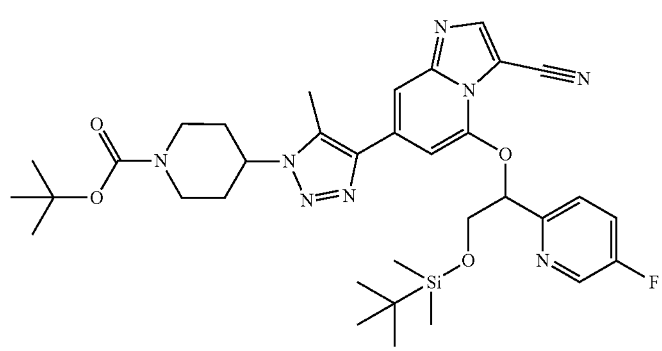 [SMILES: Cc1c(-c2cc(OC(CO[Si](C)(C)C(C)(C)C)c3ccc(F)cn3)n3c(C#N)cnc3c2)nnn1C1CCN(C(=O)OC(C)(C)C)CC1] | 677.5 |

TABLE 45-continued

| Prep No. | Chemical Name | Structure | ES/MS m/z [[M + H]+ |
|---|---|---|---|
| 570[5] | tert-Butyl 4-[4-[4-[3-[tert-butyl(dimethyl)silyl]oxy-1-(5-fluoro-2-pyridyl)propoxy]-3-cyano-pyrazolo[1,5-a]pyridin-6-yl]-5-methyl-triazol-1-yl]piperidine-1-carboxylate | 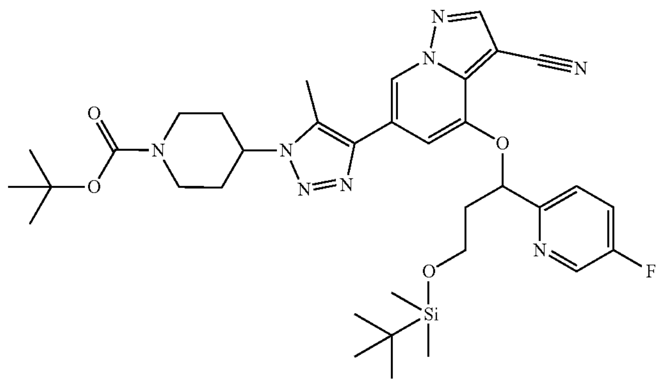 [SMILES: Cc1c(-c2cc(OC(CCO[Si](C)(C)C(C)(C)C)c3ccc(F)cn3)c3c(C#N)cnn3c2)nnn1C1CCN(C(=O)OC(C)(C)C)CC1] | 691.4 |
| 571 | tert-Butyl 4-[4-[4-[(1R)-1-(5-fluoro-2-pyridyl)ethoxy]pyrazolo[1,5-a]pyridin-6-yl]-5-methyl-triazol-1-yl]piperidine-1-carboxylate | 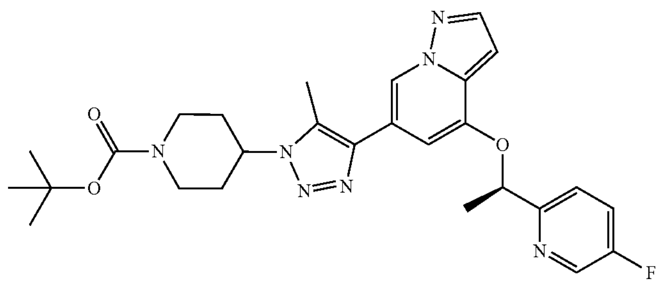 [SMILES: Cc1c(-c2cc(O[C@H](C)c3ccc(F)cn3)c3ccnn3c2)nnn1C1CCN(C(=O)OC(C)(C)C)CC1] | 522.4 |
| 572[6] | tert-Butyl 4-[4-[3-cyano-4-[1-(5-methylpyridazin-3-yl)ethoxy]pyrazolo[1,5-a]pyridin-6-yl]-5-methyl-triazol-1-yl]piperidine-1-carboxylate | 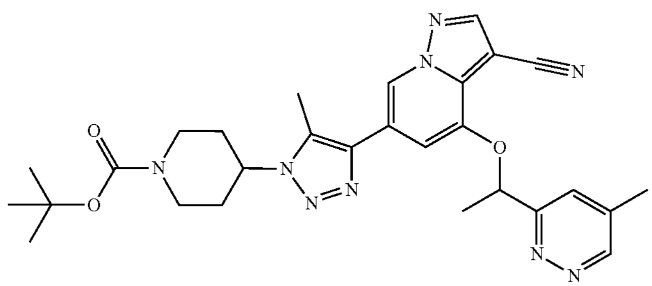 [SMILES: Cc1cnnc(C(C)Oc2cc(-c3nnn(C4CCN(C(=O)OC(C)(C)C)CC4)c3C)cn3ncc(C#N)c23)c1] | 544.3 |
| 573[1] | tert-Butyl 4-[4-[3-cyano-5-[[(7R)-6,7-dihydro-5H-cyclopenta[b]pyridin-7-yl]oxy]imidazo[1,2-a]pyridin-7-yl]-5-methyl-triazol-1-yl]piperidine-1-carboxylate | 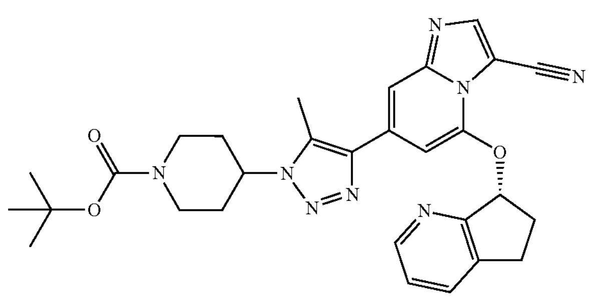 [SMILES: Cc1c(-c2cc(O[C@@H]3CCc4cccnc43)n3c(C#N)cnc3c2)nnn1C1CCN(C(=O)OC(C)(C)C)CC1] | 541.3 |
| 574[7] | tert-Butyl 4-[4-[3-cyano-4-[1-(4-isoquinolyl)ethoxy]pyrazolo[1,5-a]pyridin-6-yl]-5-methyl-triazol-1-yl]piperidine-1-carboxylate | 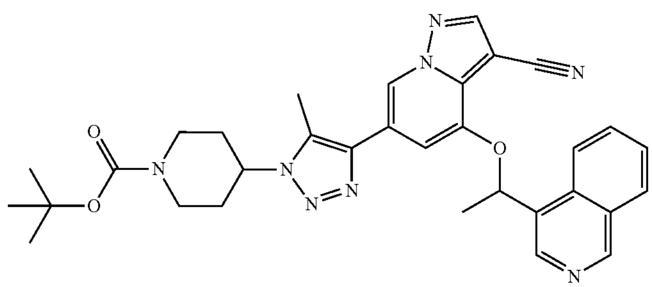 [SMILES: Cc1c(-c2cc(OC(C)c3cncc4ccccc34)c3c(C#N)cnn3c2)nnn1C1CCN(C(=O)OC(C)(C)C)CC1] | 579.3 |

TABLE 45-continued

| Prep No. | Chemical Name | Structure | ES/MS m/z [[M + H]+ |
|---|---|---|---|
| 575[6] | tert-Butyl 4-[4-[3-cyano-4-[1-(7-fluoro-4-isoquinolyl)ethoxy]pyrazolo[1,5-a]pyridin-6-yl]-5-methyl-triazol-1-yl]piperidine-1-carboxylate | 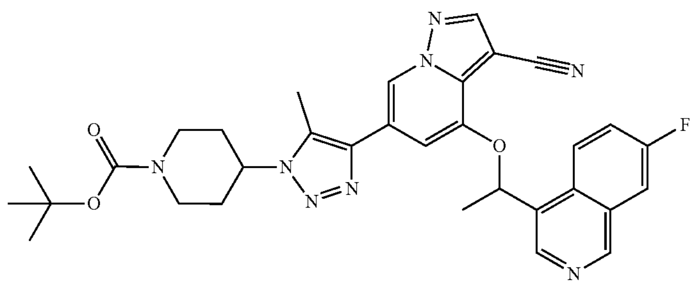 [SMILES: Cc1c(-c2cc(OC(C)c3cncc4cc(F)ccc34)c3c(C#N)cnn3c2)nnn1C1CCN(C(=O)OC(C)(C)C)CC1] | 596.3 |
| 576[7] | tert-Butyl 4-[4-[4-[2-[tert-butyl(dimethyl)silyl]oxy-1-(4-isoquinolyl)ethoxy]-3-cyano-pyrazolo[1,5-a]pyridin-6-yl]-5-methyl-triazol-1-yl]piperidine-1-carboxylate | 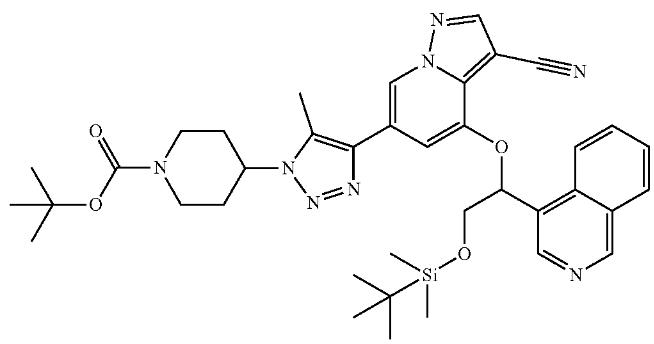 [SMILES: Cc1c(-c2cc(OC(CO[Si](C)(C)C(C)(C)C)c3cncc4ccccc34)c3c(C#N)cnn3c2)nnn1C1CCN(C(=O)OC(C)(C)C)CC1] | 709.3 |
| 577[5] | tert-Butyl 4-[4-[3-cyano-4-[1-(5-methylthiazol-2-yl)ethoxy]pyrazolo[1,5-a]pyridin-6-yl]-5-methyl-triazol-1-yl]piperidine-1-carboxylate | 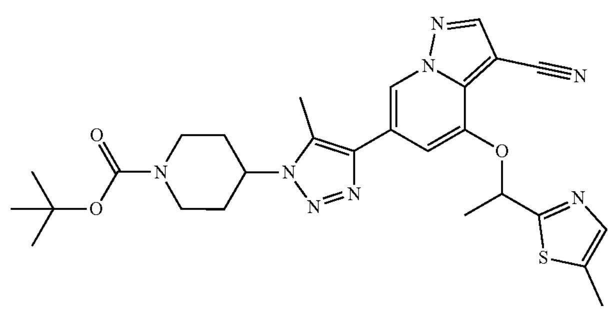 [SMILES: Cc1cnc(C(C)Oc2cc(-c3nnn(C4CCN(C(=O)OC(C)(C)C)CC4)c3C)cn3ncc(C#N)c23)s1] | 549.3 |
| 578[8] | tert-Butyl 4-[4-[3-cyano-5-[(1R)-1-(2-pyridyl)propoxy]imidazo[1,2-a]pyridin-7-yl]-5-methyl-triazol-1-yl]piperidine-1-carboxylate, Isomer 2 | 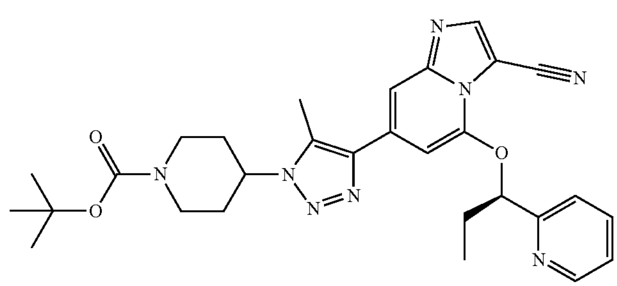 [SMILES: CC[C@@H](Oc1cc(-c2nnn(C3CCN(C(=O)OC(C)(C)C)CC3)c2C)cc2ncc(C#N)n12)c1ccccn1] | 543.3 |
| 579[9] | tert-Butyl 4-[4-[3-cyano-4-[2-fluoro-1-(5-fluoro-2-pyridyl)ethoxy]pyrazolo[1,5-a]pyridin-6-yl]-5-methyl-triazol-1-yl]piperidine-1-carboxylate | 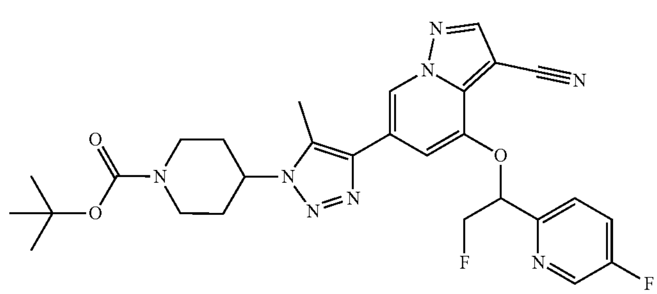 [SMILES: Cc1c(-c2cc(OC(CF)c3ccc(F)cn3)c3c(C#N)cnn3c2)nnn1C1CCN(C(=O)OC(C)(C)C)CC1] | 508.7 [M + H − C4H9]+ |

TABLE 45-continued

| Prep No. | Chemical Name | Structure | ES/MS m/z [[M + H]+ |
|---|---|---|---|
| 580[7] | tert-butyl 4-[4-[3-cyano-4-[cyclopropyl-(5-fluoro-2-pyridyl)methoxy]pyrazolo[1,5-a]pyridin-6-yl]-5-methyl-triazol-1-yl]piperidine-1-carboxylate | 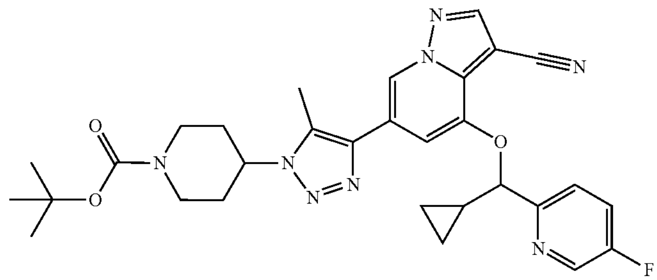 [SMILES: Cc1c(-c2cc(OC(c3ccc(F)cn3)C3CC3)c3c(C#N)cnn3c2)nnn1C1CCN(C(=O)OC(C)(C)C)CC1] | 572.8 |
| 581[7] | tert-Butyl 4-[4-[3-cyano-4-[(1-fluorocyclopropyl)-(5-fluoro-2-pyridyl)methoxy]pyrazolo[1,5-a]pyridin-6-yl]-5-methyl-triazol-1-yl]piperidine-1-carboxylate | 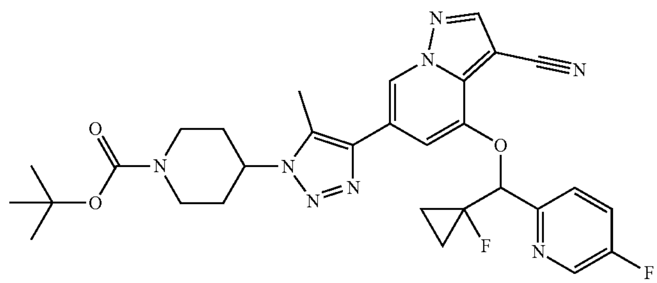 [SMILES: Cc1c(-c2cc(OC(c3ccc(F)cn3)C3(F)CC3)c3c(C#N)cnn3c2)nnn1C1CCN(C(=O)OC(C)(C)C)CC1] | 590.8 |
| 582[10] | tert-Butyl 4-[4-[3-cyano-4-[(5-fluoro-2-pyridyl)-[1-(trifluoromethyl)cyclopropyl]methoxy]pyrazolo[1,5-a]pyridin-6-yl]-5-methyl-triazol-1-yl]piperidine-1-carboxylate | 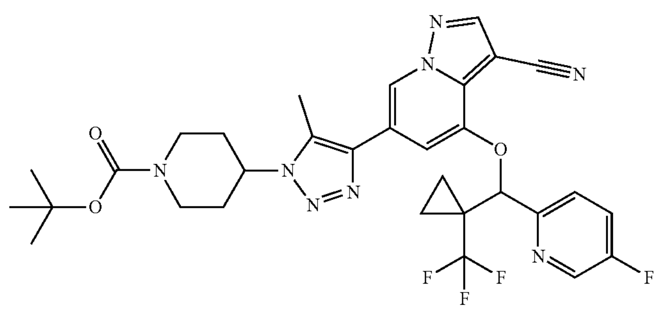 [SMILES: Cc1c(-c2cc(OC(c3ccc(F)cn3)C3(C(F)(F)F)CC3)c3c(C#N)cnn3c2)nnn1C1CCN(C(=O)OC(C)(C)C)CC1] | 641.3 |
| 583[15] | tert-Butyl 2-[4-[4-[2-[tert-butyl(dimethyl)silyl]oxy-1-(5-fluoro-2-pyridyl)ethoxy]-3-cyano-pyrazolo[1,5-a]pyridin-6-yl]-5-methyl-pyrazol-1-yl]-7-azaspiro[3.5]nonane-7-carboxylate | 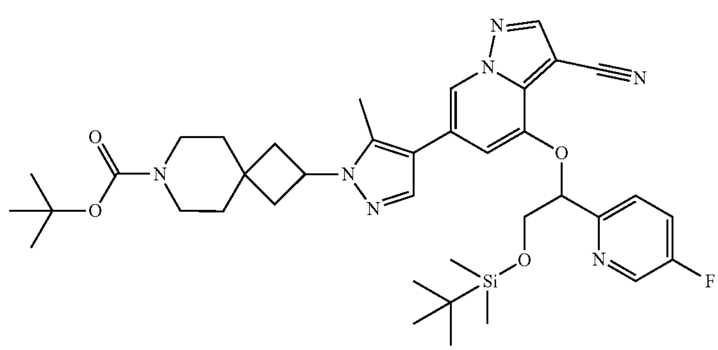 [SMILES: Cc1c(-c2cc(OC(CO[Si](C)(C)C(C)(C)C)c3ccc(F)cn3)c3c(C#N)cnn3c2)cnn1C1CC2(CCN(C(=O)OC(C)(C)C)CC2)C1] | 716.5 |
| 584[7] | tert-Butyl 4-[4-[3-cyano-4-[1-(2-methyltriazol-4-yl)ethoxy]pyrazolo[1,5-a]pyridin-6-yl]-5-methyl-triazol-1-yl]piperidine-1-carboxylate | 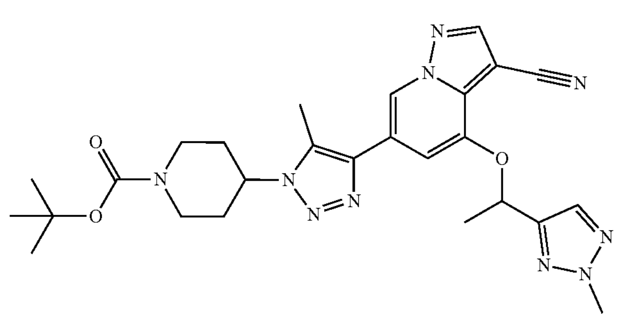 [SMILES: Cc1c(-c2cc(OC(C)c3cnn(C)n3)c3c(C#N)cnn3c2)nnn1C1CCN(C(=O)OC(C)(C)C)CC1] | 533.2 |

TABLE 45-continued

| Prep No. | Chemical Name | Structure | ES/MS m/z [[M + H]+ |
|---|---|---|---|
| 585[7] | tert-Butyl 4-[4-[3-cyano-4-[1-(1-isopropyltriazol-4-yl)ethoxy]pyrazolo[1,5-a]pyridin-6-yl]-5-methyl-triazol-1-yl]piperidine-1-carboxylate | 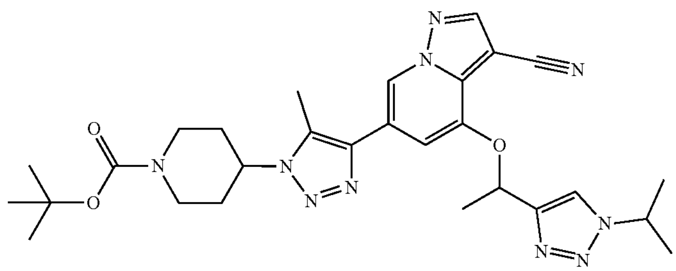 [SMILES: Cc1c(-c2cc(OC(C)c3cn(C(C)C)nn3)c3c(C#N)cnn3c2)nnn1C1CCN(C(=O)OC(C)(C)C)CC1] | 533.2 |
| 586[4] | tert-Butyl 4-[4-[5-[2-[tert-butyl(dimethyl)silyl]oxy-1-[5-(trifluoromethyl)-3-pyridyl]ethoxy]-3-cyano-imidazo[1,2-a]pyridin-7-yl]-5-methyl-triazol-1-yl]piperidine-1-carboxylate | 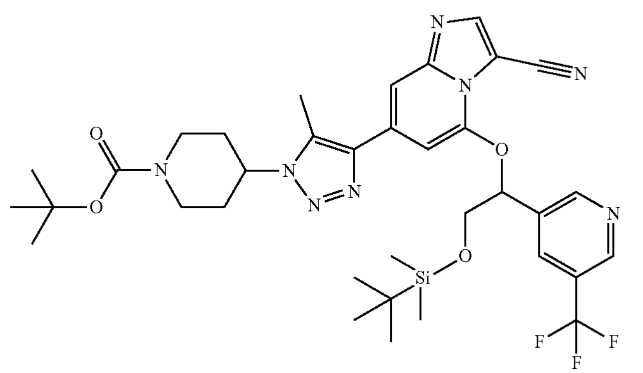 [SMILES: Cc1c(-c2cc(OC(CO[Si](C)(C)C(C)(C)C)c3cncc(C(F)(F)F)c3)n3c(C#N)cnc3c2)nnn1C1CCN(C(=O)OC(C)(C)C)CC1] | 727.4 |
| 587[4] | tert-Butyl 4-[4-[5-[2-[tert-butyl(dimethyl)silyl]oxy-1-(3,5-difluoro-2-pyridyl)ethoxy]-3-cyano-imidazo[1,2-a]pyridin-7-yl]-5-methyl-triazol-1-yl]piperidine-1-carboxylate | 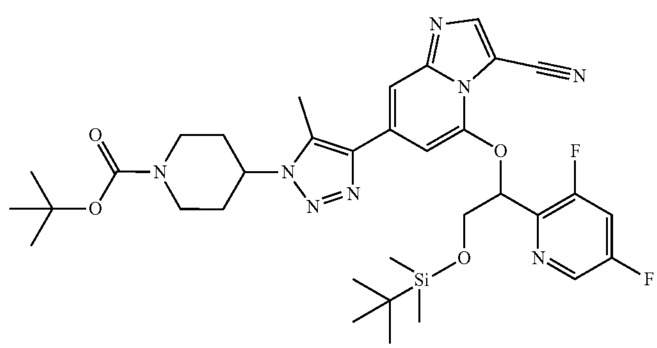 [SMILES: Cc1c(-c2cc(OC(CO[Si](C)(C)C(C)(C)C)c3ncc(F)cc3F)n3c(C#N)cnc3c2)nnn1C1CCN(C(=O)OC(C)(C)C)CC1] | 695.4 |
| 588[11] | tert-Butyl 2-[4-[5-[2-[tert-butyl(dimethyl)silyl]oxy-1-(5-fluoro-2-pyridyl)ethoxy]-3-cyano-imidazo[1,2-a]pyridin-7-yl]-5-methyl-triazol-1-yl]-7-azaspiro[3.5]nonane-7-carboxylate | 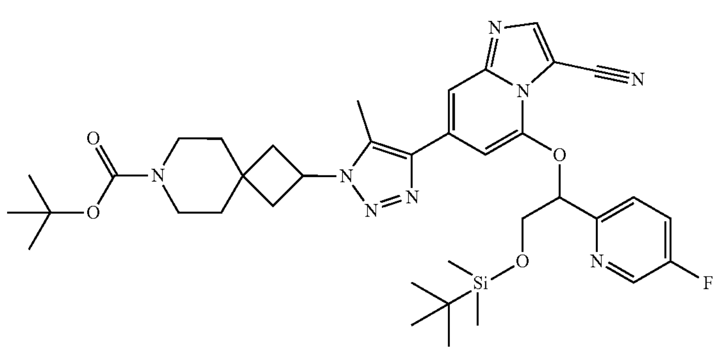 [SMILES: Cc1c(-c2cc(OC(CO[Si](C)(C)C(C)(C)C)c3ccc(F)cn3)n3c(C#N)cnc3c2)nnn1C1CC2(CCN(C(=O)OC(C)(C)C)CC2)C1] | 717.4 |

TABLE 45-continued

| Prep No. | Chemical Name | Structure | ES/MS m/z [[M + H]+ |
|---|---|---|---|
| 589[12] | tert-Butyl 4-[4-[4-[2-[tert-butyl(dimethyl)silyl]oxy-1-(5-fluoro-2-pyridyl)ethoxy]-3-cyano-pyrazolo[1,5-a]pyridin-6-yl]-5-methyl-triazol-1-yl]piperidine-1-carboxylate | 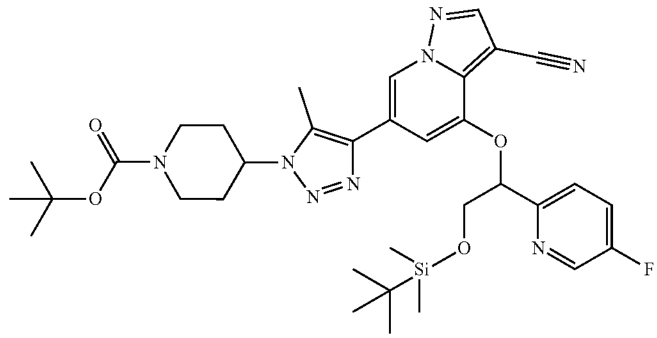 [SMILES: Cc1c(-c2cc(OC(CO[Si](C)(C)C(C)(C)C)c3ccc(F)cn3)c3c(C#N)cnn3c2)nnn1C1CCN(C(=O)OC(C)(C)C)CC1] | 677.4 |
| 590[13] | tert-Butyl 4-[4-[5-[2-[tert-butyl(dimethyl)silyl]oxy-1-(5-chloro-2-pyridyl)ethoxy]-3-cyano-imidazo[1,2-a]pyridin-7-yl]-5-methyl-triazol-1-yl]piperidine-1-carboxylate | 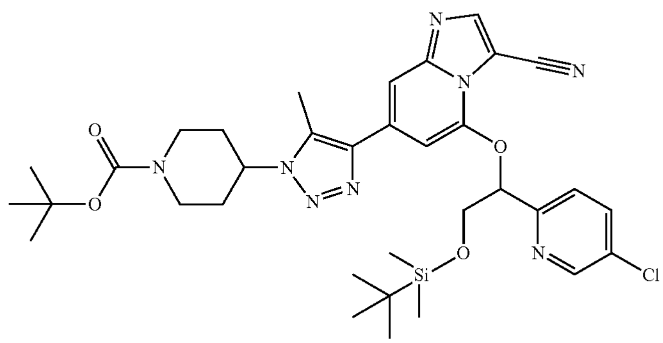 [SMILES: Cc1c(-c2cc(OC(CO[Si](C)(C)C(C)(C)C)c3ccc(Cl)cn3)n3c(C#N)cnc3c2)nnn1C1CCN(C(=O)OC(C)(C)C)CC1] | 693.6 |
| 591[5] | tert-Butyl 4-[4-[4-[2-[tert-butyl(dimethyl)silyl]oxy-1-[5-(trifluoromethyl)-3-pyridyl]ethoxy]-3-cyano-pyrazolo[1,5-a]pyridin-6-yl]-5-methyl-triazol-1-yl]piperidine-1-carboxylate | 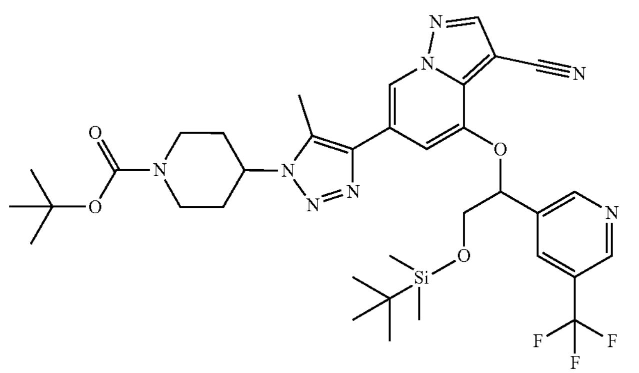 [SMILES: Cc1c(-c2cc(OC(CO[Si](C)(C)C(C)(C)C)c3cncc(C(F)(F)F)c3)c3c(C#N)cnn3c2)nnn1C1CCN(C(=O)OC(C)(C)C)CC1] | 727.4 |
| 592[14] | tert-Butyl 4-[4-[5-[3-[tert-butyl(dimethyl)silyl]oxy-1-(5-fluoro-2-pyridyl)propoxy]-3-cyano-imidazo[1,2-a]pyridin-7-yl]-5-methyl-triazol-1-yl]piperidine-1-carboxylate | 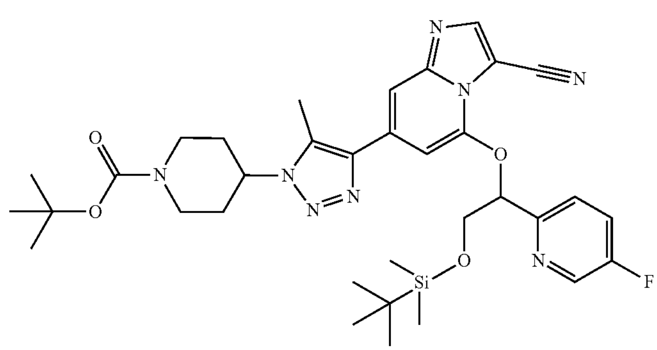 [SMILES: Cc1c(-c2cc(OC(CO[Si](C)(C)C(C)(C)C)c3ccc(F)cn3)n3c(C#N)cnc3c2)nnn1C1CCN(C(=O)OC(C)(C)C)CC1] | 691.5 |

TABLE 45-continued

| Prep No. | Chemical Name | Structure | ES/MS m/z [[M + H]+ |
|---|---|---|---|
| 593[8] | tert-Butyl 4-[4-[3-cyano-5-[2-methoxy-1-(2-pyridyl)ethoxy]imidazo[1,2-a]pyridin-7-yl]-5-methyl-triazol-1-yl]piperidine-1-carboxylate, Isomer 1 | 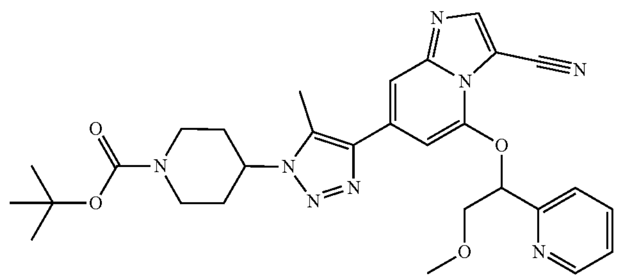 [SMILES: COCC(Oc1cc(-c2nnn(C3CCN(C(=O)OC(C)(C)C)CC3)c2C)cc2ncc(C#N)n12)c1ccccn1] | 559.3 |
| 594[8] | tert-Butyl 4-[4-[3-cyano-5-[3-methyl-1-(2-pyridyl)butoxy]imidazo[1,2-a]pyridin-7-yl]-5-methyl-triazol-1-yl]piperidine-1-carboxylate | 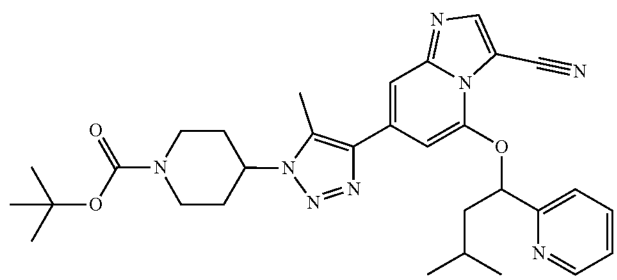 [SMILES: Cc1c(-c2cc(OC(CC(C)C)c3ccccn3)n3c(C#N)cnc3c2)nnn1C1CCN(C(=O)OC(C)(C)C)CC1] | 571.4 |
| 595[16] | tert-Butyl 4-[4-[3-cyano-5-[(1R)-1-(3-pyridyl)ethoxy]imidazo[1,2-a]pyridin-7-yl]-5-methyl-triazol-1-yl]piperidine-1-carboxylate | 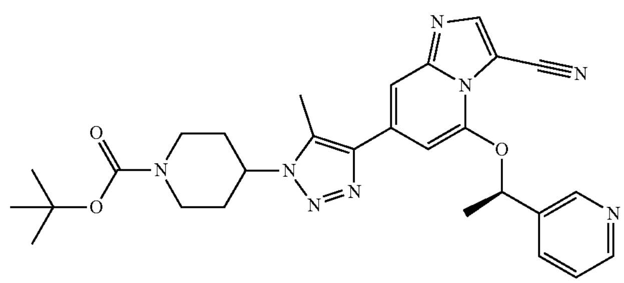 [SMILES: Cc1c(-c2cc(O[C@H](C)c3cccnc3)n3c(C#N)cnc3c2)nnn1C1CCN(C(=O)OC(C)(C)C)CC1] | 529.2 |
| 596[8] | tert-Butyl 4-[4-[3-cyano-5-[2-cyclopropyl-1-(2-pyridyl)ethoxy]imidazo[1,2-a]pyridin-7-yl]-5-methyl-triazol-1-yl]piperidine-1-carboxylate | 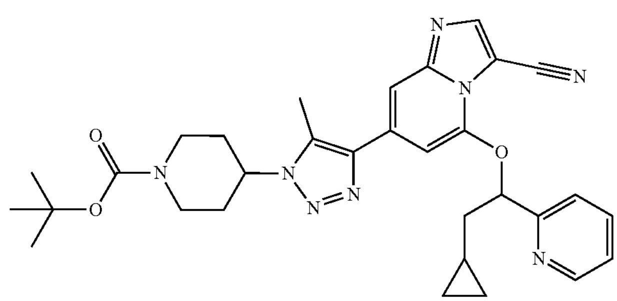 [SMILES: Cc1c(-c2cc(OC(CC3CC3)c3ccccn3)n3c(C#N)cnc3c2)nnn1C1CCN(C(=O)OC(C)(C)C)CC1] | 569.3 |
| 597[17] | tert-Butyl 4-[4-[3-cyano-5-(3,4-dihydro-2H-pyrano[3,2-b]pyridin-4-yloxy)imidazo[1,2-a]pyridin-7-yl]-5-methyl-triazol-1-yl]piperidine-1-carboxylate | 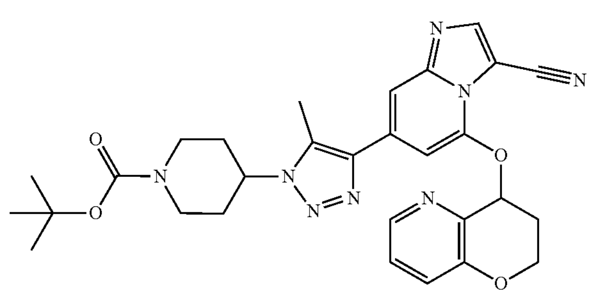 [SMILES: Cc1c(-c2cc(OC3CCOc4cccnc43)n3c(C#N)cnc3c2)nnn1C1CCN(C(=O)OC(C)(C)C)CC1] | 557.25 |

TABLE 45-continued

| Prep No. | Chemical Name | Structure | ES/MS m/z [[M + H]+ |
|---|---|---|---|
| 598[8] | tert-Butyl 4-[4-[3-cyano-5-[(1R)-1-(3-fluoro-2-pyridyl)ethoxy]imidazo[1,2-a]pyridin-7-yl]-5-methyl-triazol-1-yl]piperidine-1-carboxylate | 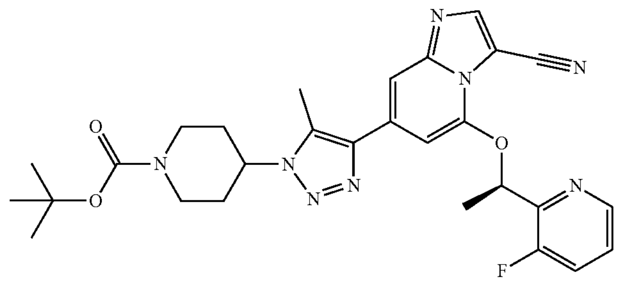 [SMILES: Cc1c(-c2cc(O[C@H](C)c3ncccc3F)n3c(C#N)cnc3c2)nnn1C1CCN(C(=O)OC(C)(C)C)CC1] | 547.1 |
| 599[8] | tert-Butyl 4-[4-[3-cyano-5-[(1R)-1-(2-fluorophenyl)ethoxy]imidazo[1,2-a]pyridin-7-yl]-5-methyl-triazol-1-yl]piperidine-1-carboxylate | 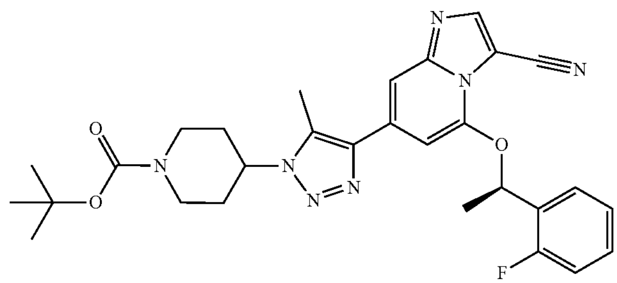 [SMILES: Cc1c(-c2cc(O[C@H](C)c3ccccc3F)n3c(C#N)cnc3c2)nnn1C1CCN(C(=O)OC(C)(C)C)CC1] | 546.2 |
| 600[18] | tert-Butyl 4-[4-[3-cyano-5-[(6,6-dimethyl-5,7-dihydrocyclopenta[b]pyridin-7-yl)oxy]imidazo[1,2-a]pyridin-7-yl]-5-methyl-triazol-1-yl]piperidine-1-carboxylate | 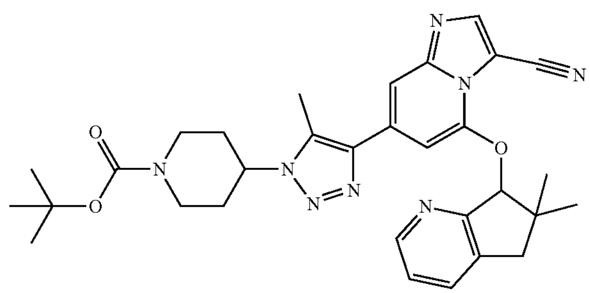 [SMILES: Cc1c(-c2cc(OC3c4ncccc4CC3(C)C)n3c(C#N)cnc3c2)nnn1C1CCN(C(=O)OC(C)(C)C)CC1] | 569.3 |
| 601[19] | tert-Butyl 4-[4-[3-cyano-5-[1-(3,5-difluoro-2-pyridyl)ethoxy]imidazo[1,2-a]pyridin-7-yl]-5-methyl-triazol-1-yl]piperidine-1-carboxylate | 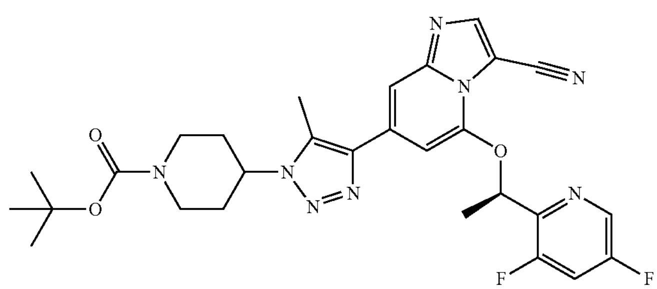 [SMILES: Cc1c(-c2cc(O[C@H](C)c3ncc(F)cc3F)n3c(C#N)cnc3c2)nnn1C1CCN(C(=O)OC(C)(C)C)CC1] | 565.1 |
| 602[8] | tert-Butyl 4-[4-[3-cyano-5-[2-pyridyl-[1-(trifluoromethyl)cyclopropyl]methoxy]imidazo[1,2-a]pyridin-7-yl]-5-methyl-triazol-1-yl]piperidine-1-carboxylate | 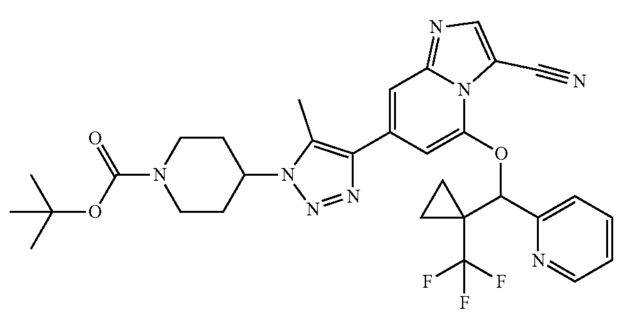 [SMILES: Cc1c(-c2cc(OC(c3ccccn3)C3(C(F)(F)F)CC3)n3c(C#N)cnc3c2)nnn1C1CCN(C(=O)OC(C)(C)C)CC1] | 623.0 |

TABLE 45-continued

| Prep No. | Chemical Name | Structure | ES/MS m/z [[M + H]+ |
|---|---|---|---|
| 603[20] | tert-Butyl 4-[4-[3-cyano-5-[1-(5-methyl-2-pyridyl)ethoxy]imidazo[1,2-a]pyridin-7-yl]-5-methyl-triazol-1-yl]piperidine-1-carboxylate | 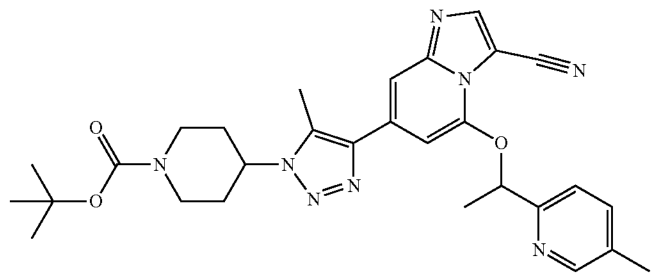 [SMILES: Cc1ccc(C(C)Oc2cc(-c3nnn(C4CCN(C(=O)OC(C)(C)C)CC4)c3C)cc3ncc(C#N)n23)nc1] | 543.3 |
| 604[21] | tert-Butyl 4-[4-[3-cyano-5-(1-isothiazol-4-ylethoxy)imidazo[1,2-a]pyridin-7-yl]-5-methyl-triazol-1-yl]piperidine-1-carboxylate | 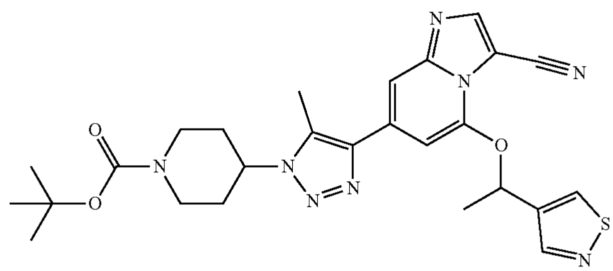 [SMILES: Cc1c(-c2cc(OC(C)c3cnsc3)n3c(C#N)cnc3c2)nnn1C1CCN(C(=O)OC(C)(C)C)CC1] | 535.1 |
| 605[22] | tert-Butyl 4-[4-[3-cyano-5-(1-isothiazol-3-ylethoxy)imidazo[1,2-a]pyridin-7-yl]-5-methyl-triazol-1-yl]piperidine-1-carboxylate | 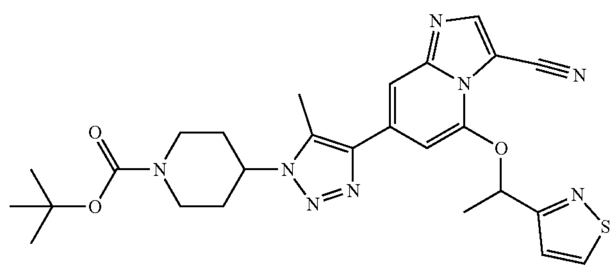 [SMILES: Cc1c(-c2cc(OC(C)c3ccsn3)n3c(C#N)cnc3c2)nnn1C1CCN(C(=O)OC(C)(C)C)CC1] | 535.10 |
| 606[20] | tert-Butyl 4-[4-[3-cyano-4-[1-[5-(trifluoromethyl)-3-pyridyl]ethoxy]pyrazolo[1,5-a]pyridin-6-yl]-5-methyl-triazol-1-yl]piperidine-1-carboxylate | 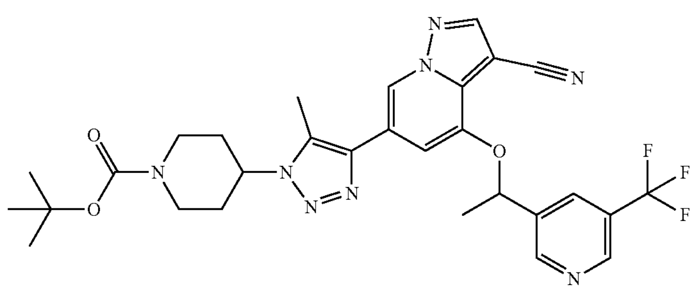 [SMILES: Cc1c(-c2cc(OC(C)c3cncc(C(F)(F)F)c3)c3c(C#N)cnn3c2)nnn1C1CCN(C(=O)OC(C)(C)C)CC1] | 597.3 |
| 607[23] | tert-Butyl 4-[4-[3-cyano-5-(1-isothiazol-5-ylethoxy)imidazo[1,2-a]pyridin-7-yl]-5-methyl-triazol-1-yl]piperidine-1-carboxylate | 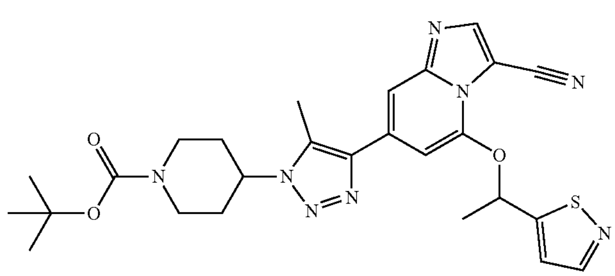 [SMILES: Cc1c(-c2cc(OC(C)c3ccns3)n3c(C#N)cnc3c2)nnn1C1CCN(C(=O)OC(C)(C)C)CC1] | 535.2 |

TABLE 45-continued

| Prep No. | Chemical Name | Structure | ES/MS m/z [[M + H]+ |
|---|---|---|---|
| 608[24] | tert-Butyl 4-[4-[4-[(1R)-1-(2-bromophenyl)ethoxy]pyrazolo[1,5-a]pyridin-6-yl]-5-methyl-pyrazol-1-yl]piperidine-1-carboxylate | 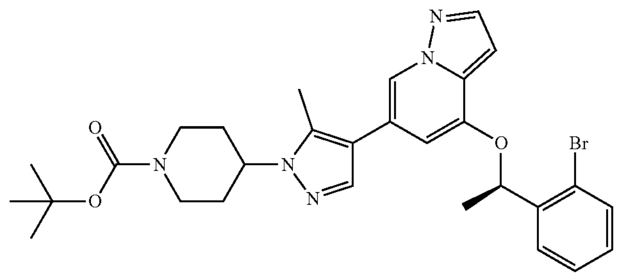 [SMILES: Cc1c(-c2cc(O[C@H](C)c3ccccc3Br)c3ccnn3c2)cnn1C1CCN(C(=O)OC(C)(C)C)CC1] | 582.2 |
| 609 | tert-Butyl 4-[4-[3-cyano-4-[1-(2-methylsulfonylphenyl)ethoxy]pyrazolo[1,5-a]pyridin-6-yl]-5-methyl-pyrazol-1-yl]piperidine-1-carboxylate | 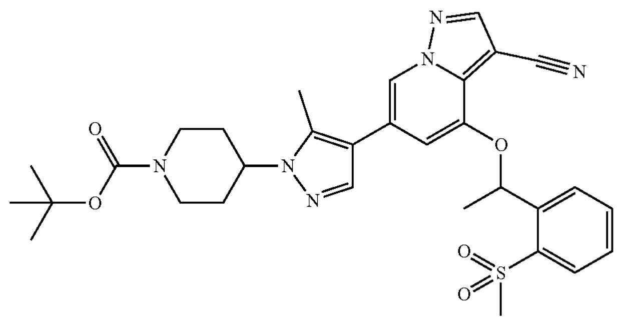 [SMILES: Cc1c(-c2cc(OC(C)c3ccccc3S(C)(=O)=O)c3c(C#N)cnn3c2)cnn1C1CCN(C(=O)OC(C)(C)C)CC1] | 627.2 [M + Na]+ |
| 610[9] | tert-Butyl 4-[4-[5-[1-(1,3-benzothiazol-7-yl)ethoxy]-3-cyano-imidazo[1,2-a]pyridin-7-yl]-5-methyl-triazol-1-yl]piperidine-1-carboxylate | 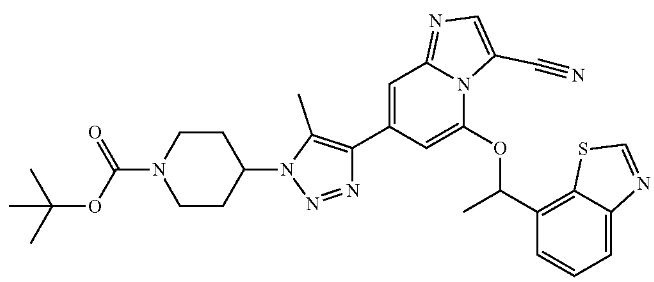 [SMILES: Cc1c(-c2cc(OC(C)c3cccc4ncsc34)n3c(C#N)cnc3c2)nnn1C1CCN(C(=O)OC(C)(C)C)CC1] | 585.2 |
| 611[25] | tert-Butyl 4-[4-[3-cyano-5-[(1R)-1-(2-pyridyl)ethoxy]imidazo[1,2-a]pyridin-7-yl]-5-methyl-triazol-1-yl]azepane-1-carboxylate | 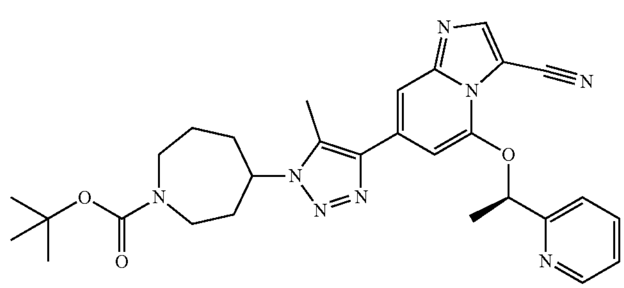 [SMILES: Cc1c(-c2cc(O[C@H](C)c3ccccn3)n3c(C#N)cnc3c2)nnn1C1CCCN(C(=O)OC(C)(C)C)CC1] | 543.3 |
| 612[8] | tert-Butyl (3S)-3-[4-[3-cyano-5-[(1R)-1-(5-fluoro-2-pyridyl)ethoxy]imidazo[1,2-a]pyridin-7-yl]-5-methyl-triazol-1-yl]piperidine-1-carboxylate | 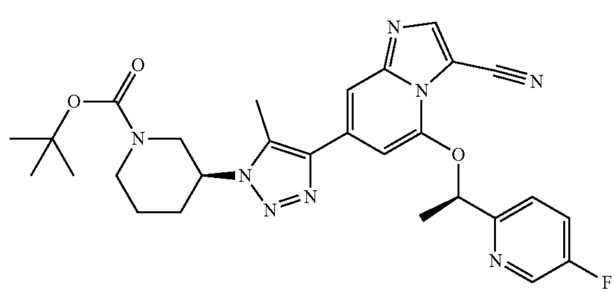 [SMILES: Cc1c(-c2cc(O[C@H](C)c3ccc(F)cn3)n3c(C#N)cnc3c2)nnn1[C@H]1CCCN(C(=O)OC(C)(C)C)C1] | 547.2 |

TABLE 45-continued

| Prep No. | Chemical Name | Structure | ES/MS m/z [[M + H]+ |
|---|---|---|---|
| 613[26] | tert-Butyl 4-[4-[3-cyano-5-[(1R)-1-(5-fluoro-2-pyridyl)ethoxy]imidazo[1,2-a]pyridin-7-yl]-5-methyl-triazol-1-yl]azepane-1-carboxylate | 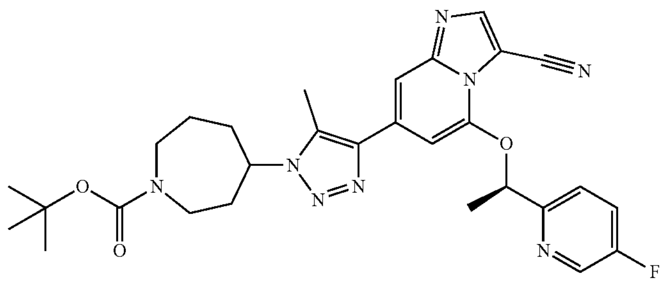 [SMILES: Cc1c(-c2cc(O[C@H](C)c3ccc(F)cn3)n3c(C#N)cnc3c2)nnn1C1CCCN(C(=O)OC(C)(C)C)CC1] | 561.5 |
| 614[27] | tert-Butyl (3R)-3-[4-[3-cyano-5-[(1R)-1-(5-fluoro-2-pyridyl)ethoxy]imidazo[1,2-a]pyridin-7-yl]-5-methyl-triazol-1-yl]piperidine-1-carboxylate | 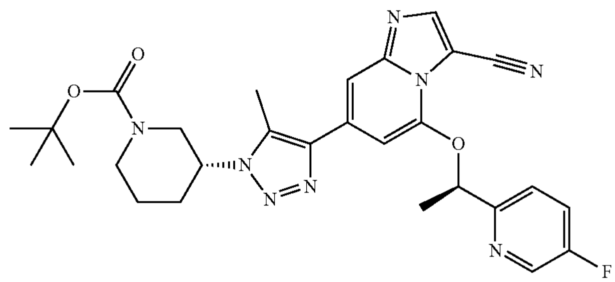 [SMILES: Cc1c(-c2cc(O[C@H](C)c3ccc(F)cn3)n3c(C#N)cnc3c2)nnn1[C@@H]1CCCN(C(=O)OC(C)(C)C)C1] | 547.2 |
| 615[6] | tert-Butyl 4-[4-[3-cyano-5-[(1R)-1-pyrimidin-4-ylethoxy]imidazo[1,2-a]pyridin-7-yl]-5-methyl-triazol-1-yl]piperidine-1-carboxylate | 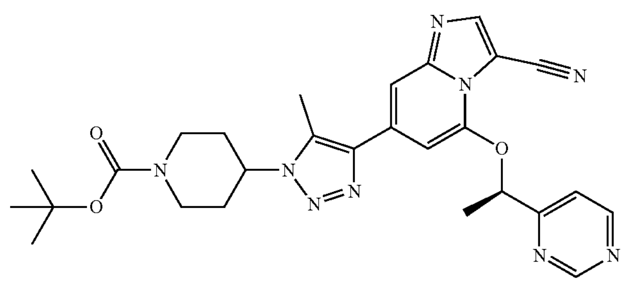 | 530.2 |
| 616[7] | tert-Butyl 4-[4-[3-cyano-4-[1-(2-ethyltriazol-4-yl)ethoxy]pyrazolo[1,5-a]pyridin-6-yl]-5-methyl-triazol-1-yl]piperidine-1-carboxylate | 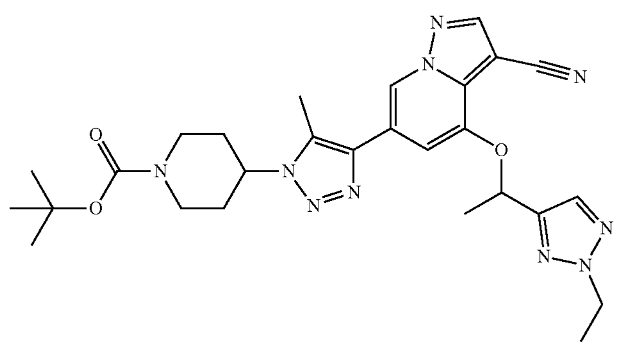 [SMILES: CCn1ncc(C(C)Oc2cc(-c3nnn(C4CCN(C(=O)OC(C)(C)C)CC4)c3C)cn3ncc(C#N)c23)n1] | 547.3 |
| 617[29] | tert-Butyl 4-[4-[3-cyano-5-[1-(5-methoxy-3-pyridyl)ethoxy]imidazo[1,2-a]pyridin-7-yl]-5-methyl-triazol-1-yl]piperidine-1-carboxylate | 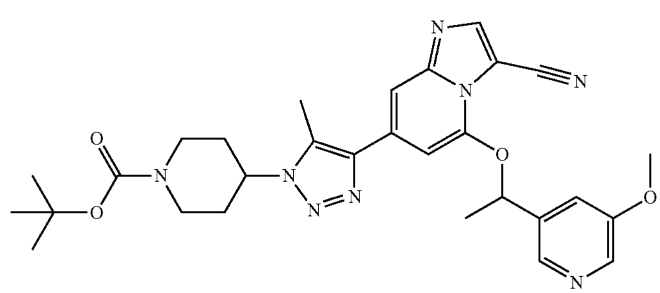 [SMILES: COc1cncc(C(C)Oc2cc(-c3nnn(C4CCN(C(=O)OC(C)(C)C)CC4)c3C)cc3ncc(C#N)n23)c1] | 559.4 |

TABLE 45-continued

| Prep No. | Chemical Name | Structure | ES/MS m/z [[M + H]+ |
|---|---|---|---|
| 618[30] | tert-Butyl 4-[4-[5-[1-(6-chloro-3-pyridyl)ethoxy]-3-cyano-imidazo[1,2-a]pyridin-7-yl]-5-methyl-triazol-1-yl]piperidine-1-carboxylate | 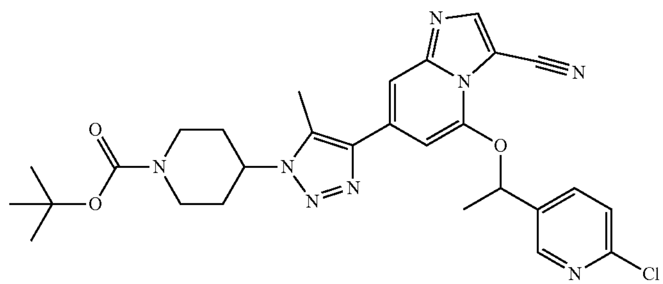 [SMILES: Cc1c(-c2cc(OC(C)c3ccc(Cl)nc3)n3c(C#N)cnc3c2)nnn1C1CCN(C(=O)OC(C)(C)C)CC1] | ($^{35}$Cl/$^{37}$Cl) 563.3/ 565.3 |
| 619[31] | tert-Butyl 4-[4-[3-cyano-5-[1-[5-(trifluoromethyl)isoxazol-3-yl]ethoxy]imidazo[1,2-a]pyridin-7-yl]-5-methyl-triazol-1-yl]piperidine-1-carboxylate | 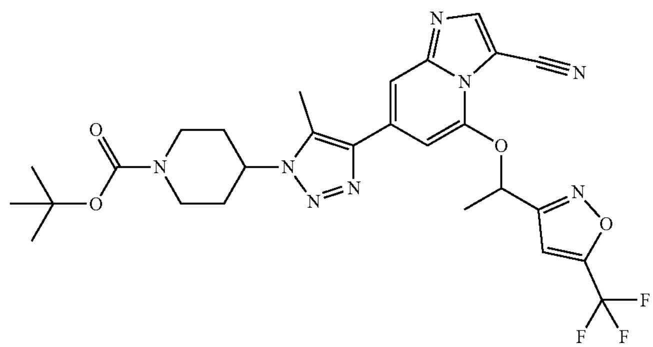 [SMILES: Cc1c(-c2cc(OC(C)c3cc(C(F)(F)F)on3)n3c(C#N)cnc3c2)nnn1C1CCN(C(=O)OC(C)(C)C)CC1] | 587.2 |
| 620[32] | tert-Butyl 4-[4-[3-cyano-5-[2,2-dimethyl-1-(2-pyridyl)propoxy]imidazo[1,2-a]pyridin-7-yl]-5-methyl-triazol-1-yl]piperidine-1-carboxylate, Isomer 1 | 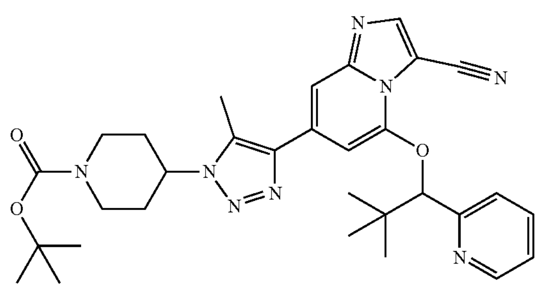 [SMILES: Cc1c(-c2cc(OC(c3ccccn3)C(C)(C)C)n3c(C#N)cnc3c2)nnn1C1CCN(C(=O)OC(C)(C)C)CC1] | 571.2 |
| 621[8] | tert-Butyl 4-[4-[3-cyano-5-[(1R)-1-(2,6-difluorophenyl)ethoxy]imidazo[1,2-a]pyridin-7-yl]-5-methyl-triazol-1-yl]piperidine-1-carboxylate | 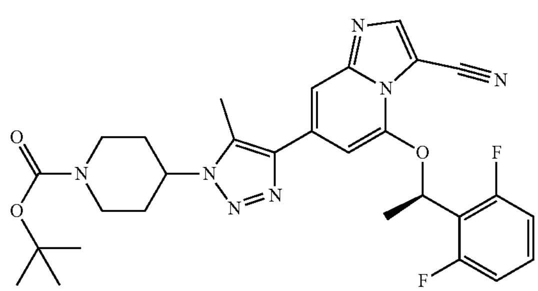 [SMILES: Cc1c(-c2cc(O[C@H](C)c3c(F)cccc3F)n3c(C#N)cnc3c2)nnn1C1CCN(C(=O)OC(C)(C)C)CC1] | 564.3 |
| 622[7] | tert-Butyl 4-[4-[3-cyano-4-[1-[5-(difluoromethyl)-3-pyridyl]ethoxy]pyrazolo[1,5-a]pyridin-6-yl]-5-methyl-triazol-1-yl]piperidine-1-carboxylate | 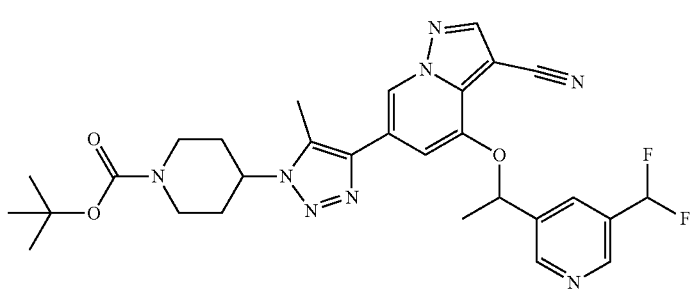 [SMILES: Cc1c(-c2cc(OC(C)c3cncc(C(F)F)c3)c3c(C#N)cnn3c2)nnn1C1CCN(C(=O)OC(C)(C)C)CC1] | 579.2 |

TABLE 45-continued

| Prep No. | Chemical Name | Structure | ES/MS m/z [[M + H]+ |
|---|---|---|---|
| 623[9] | tert-Butyl 4-[4-[3-cyano-4-[1-(5-methyl-3-pyridyl)ethoxy]pyrazolo[1,5-a]pyridin-6-yl]-5-methyl-triazol-1-yl]piperidine-1-carboxylate | 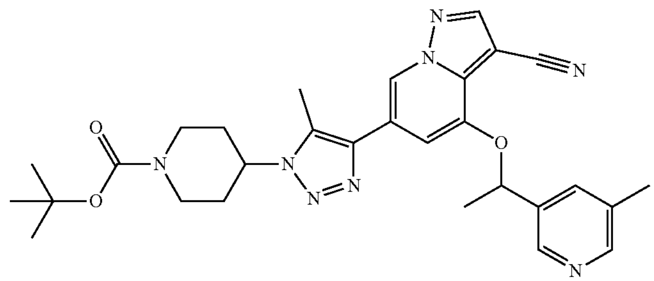 [SMILES: Cc1cncc(C(C)Oc2cc(-c3nnn(C4CCN(C(=O)OC(C)(C)C)CC4)c3C)cn3ncc(C#N)c23)c1] | 543.3 |
| 624[9] | tert-Butyl 4-[4-[3-cyano-4-[1-(5-methyl-1,3,4-thiadiazol-2-yl)ethoxy]pyrazolo[1,5-a]pyridin-6-yl]-5-methyl-triazol-1-yl]piperidine-1-carboxylate | 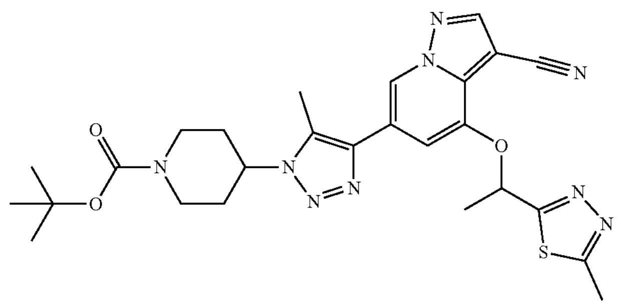 [SMILES: Cc1nnc(C(C)Oc2cc(-c3nnn(C4CCN(C(=O)OC(C)(C)C)CC4)c3C)cn3ncc(C#N)c23)s1] | 548.3 [M − H]+ |
| 625[9] | tert-Butyl 4-[4-[3-cyano-4-[1-[2-morpholino-5-(trifluoromethyl)-3-pyridyl]ethoxy]pyrazolo[1,5-a]pyridin-6-yl]-5-methyl-triazol-1-yl]piperidine-1-carboxylate | 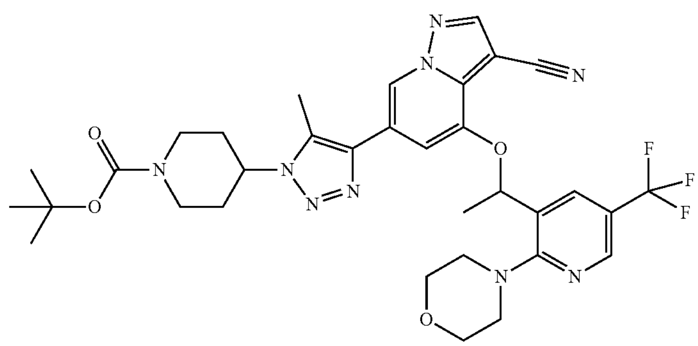 [SMILES: Cc1c(-c2cc(OC(C)c3cc(C(F)(F)F)cnc3N3CCOCC3)c3c(C#N)cnn3c2)nnn1C1CCN(C(=O)OC(C)(C)C)CC1] | a |
| 626[9] | tert-Butyl 4-[4-[3-cyano-5-[1-(1-isopropyltriazol-4-yl)ethoxy]imidazo[1,2-a]pyridin-7-yl]-5-methyl-triazol-1-yl]piperidine-1-carboxylate | 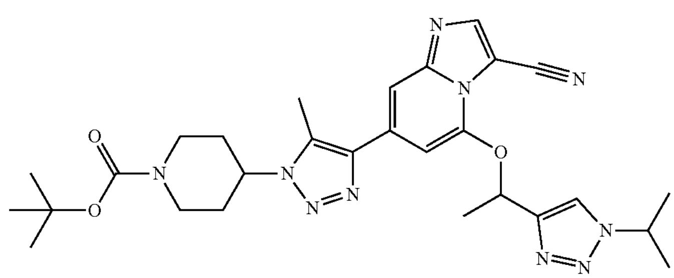 [SMILES: Cc1c(-c2cc(OC(C)c3cn(C(C)C)nn3)n3c(C#N)cnc3c2)nnn1C1CCN(C(=O)OC(C)(C)C)CC1] | 561.3 |
| 627[9] | tert-Butyl 4-[4-[3-cyano-5-[1-(6-methylpyrazin-2-yl)ethoxy]imidazo[1,2-a]pyridin-7-yl]-5-methyl-triazol-1-yl]piperidine-1-carboxylate | 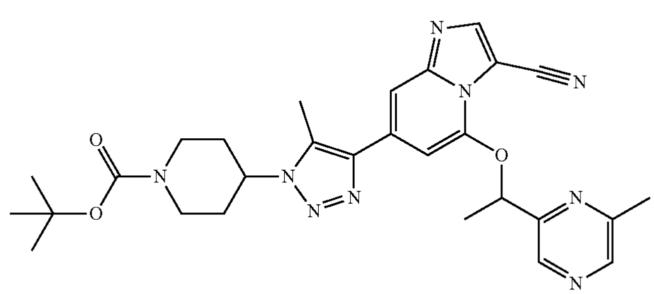 [SMILES: Cc1cncc(C(C)Oc2cc(-c3nnn(C4CCN(C(=O)OC(C)(C)C)CC4)c3C)cc3ncc(C#N)n23)n1] | 544.3 |

TABLE 45-continued

| Prep No. | Chemical Name | Structure | ES/MS m/z [[M + H]+ |
|---|---|---|---|
| 628[6] | tert-Butyl 4-[4-[3-cyano-5-[1-(3,3-difluorocyclobutyl)ethoxy]imidazo[1,2-a]pyridin-7-yl]-5-methyl-triazol-1-yl]piperidine-1-carboxylate | 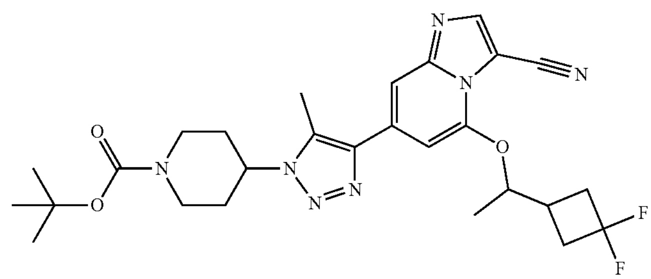 [SMILES: Cc1c(-c2cc(OC(C)C3CC(F)(F)C3)n3c(C#N)cnc3c2)nnn1C1CCN(C(=O)OC(C)(C)C)CC1] | 542.2 |
| 629[6] | tert-Butyl 4-[4-[5-[(1R)-1-(2-chloro-4-fluoro-phenyl)ethoxy]-3-cyano-imidazo[1,2-a]pyridin-7-yl]-5-methyl-triazol-1-yl]piperidine-1-carboxylate | 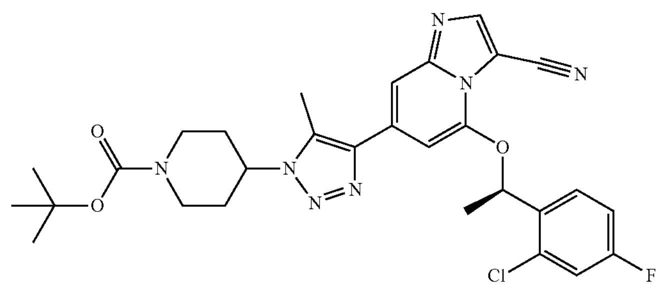 [SMILES: Cc1c(-c2cc(O[C@H](C)c3ccc(F)cc3Cl)n3c(C#N)cnc3c2)nnn1C1CCN(C(=O)OC(C)(C)C)CC1] | 580.2 |
| 630[33] | tert-Butyl 4-[4-[3-cyano-5-[(1R)-1-(5-fluoro-3-methyl-2-pyridyl)ethoxy]imidazo[1,2-a]pyridin-7-yl]-5-methyl-triazol-1-yl]piperidine-1-carboxylate | 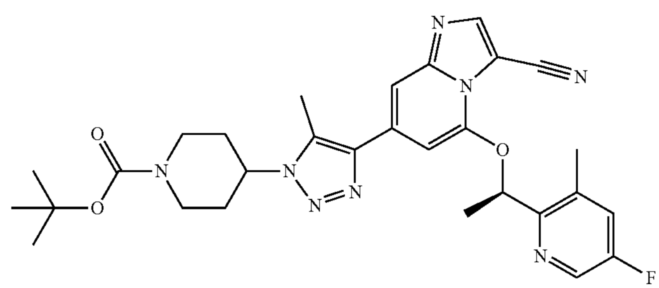 [SMILES: Cc1cc(F)cnc1[C@@H](C)Oc1cc(-c2nnn(C3CCN(C(=O)OC(C)(C)C)CC3)c2C)cc2ncc(C#N)n12] | 561.3 |
| 631[34] | tert-Butyl 4-[4-[3-cyano-5-[2,2-difluoro-1-(5-fluoro-2-pyridyl)ethoxy]imidazo[1,2-a]pyridin-7-yl]-5-methyl-triazol-1-yl]piperidine-1-carboxylate | 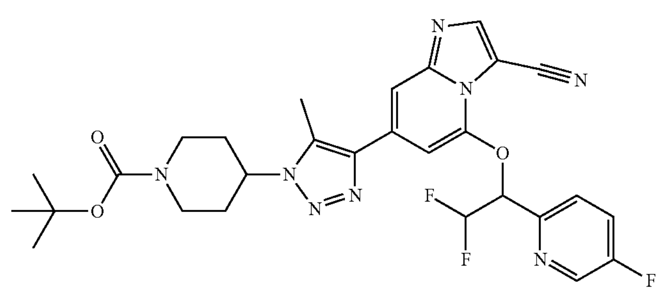 [SMILES: Cc1c(-c2cc(OC(c3ccc(F)cn3)C(F)F)n3c(C#N)cnc3c2)nnn1C1CCN(C(=O)OC(C)(C)C)CC1] | 583.2 |
| 632[7] | tert-Butyl 4-[4-[3-cyano-4-[(1R)-1-(2-methylthiazol-4-yl)ethoxy]pyrazolo[1,5-a]pyridin-6-yl]-5-methyl-triazol-1-yl]piperidine-1-carboxylate | 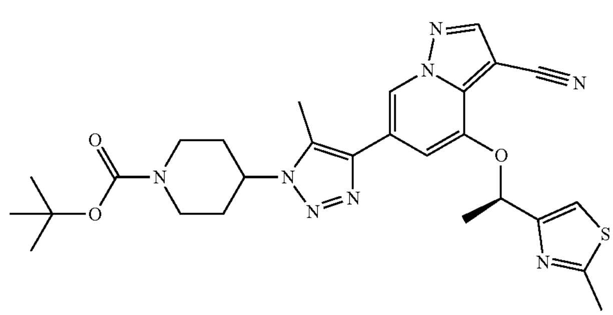 [SMILES: Cc1nc([C@@H](C)Oc2cc(-c3nnn(C4CCN(C(=O)OC(C)(C)C)CC4)c3C)cn3ncc(C#N)c23)cs1] | 549.2 |

TABLE 45-continued

| Prep No. | Chemical Name | Structure | ES/MS m/z [[M + H]+ |
|---|---|---|---|
| 663[7] | tert-Butyl 4-[4-[3-cyano-4-[(1R)-1-(1-methylpyrazol-3-yl)ethoxy]pyrazolo[1,5-a]pyridin-6-yl]-5-methyl-triazol-1-yl]piperidine-1-carboxylate | 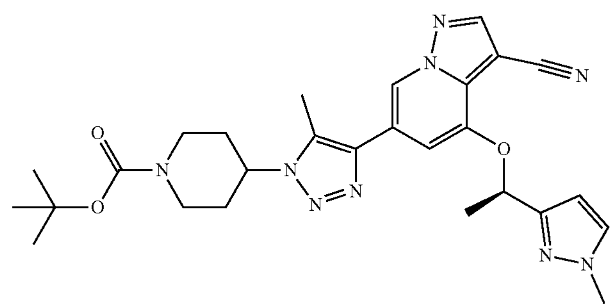 [SMILES: Cc1c(-c2cc(O[C@H](C)c3ccn(C)n3)c3c(C#N)cnn3c2)nnn1C1CCN(C(=O)OC(C)(C)C)CC1] | 532.2 |
| 634[35] | tert-Butyl 4-[4-[3-cyano-5-[(5-fluoro-2-pyridyl)methoxy]imidazo[1,2-a]pyridin-7-yl]-5-methyl-triazol-1-yl]piperidine-1-carboxylate | 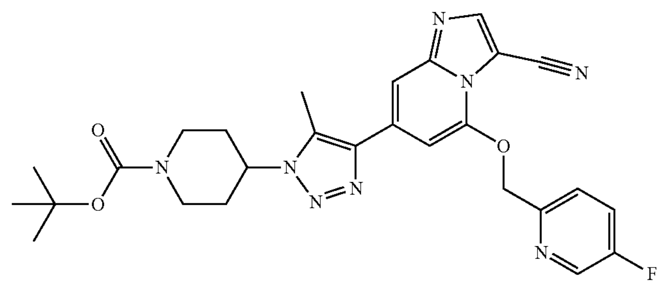 [SMILES: Cc1c(-c2cc(OCc3ccc(F)cn3)n3c(C#N)cnc3c2)nnn1C1CCN(C(=O)OC(C)(C)C)CC1] | 533.2 |
| 635[35] | tert-Butyl 4-[4-[3-cyano-5-[(1R)-1-(2,4-difluorophenyl)ethoxy]imidazo[1,2-a]pyridin-7-yl]-5-methyl-triazol-1-yl]piperidine-1-carboxylate | 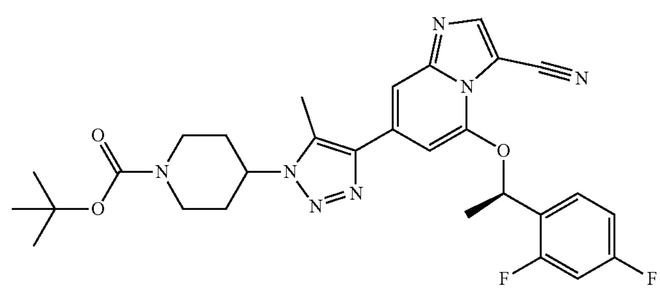 [SMILES: Cc1c(-c2cc(O[C@H](C)c3ccc(F)cc3F)n3c(C#N)cnc3c2)nnn1C1CCN(C(=O)OC(C)(C)C)CC1] | 564.2 |
| 636[26] | tert-Butyl 4-[4-[3-cyano-5-[(5-fluoro-2-pyridyl)-[1-(trifluoromethyl)cyclopropyl]methoxy]imidazo[1,2-a]pyridin-7-yl]-5-methyl-triazol-1-yl]piperidine-1-carboxylate | 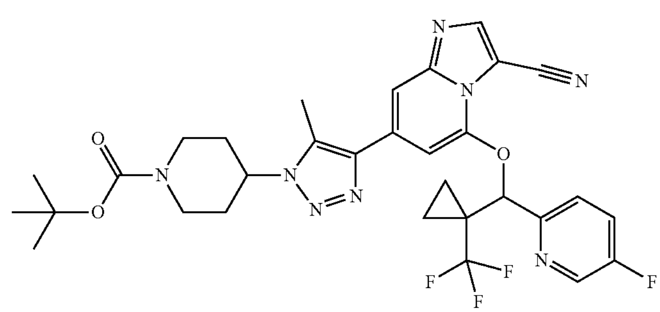 [SMILES: Cc1c(-c2cc(OC(c3ccc(F)cn3)C3(C(F)(F)F)CC3)n3c(C#N)cnc3c2)nnn1C1CCN(C(=O)OC(C)(C)C)CC1] | 641.5 |
| 637[6] | tert-Butyl 4-[4-[4-[1-(1,2-benzothiazol-7-yl)ethoxy]-3-cyano-pyrazolo[1,5-a]pyridin-6-yl]-5-methyl-triazol-1-yl]piperidine-1-carboxylate | 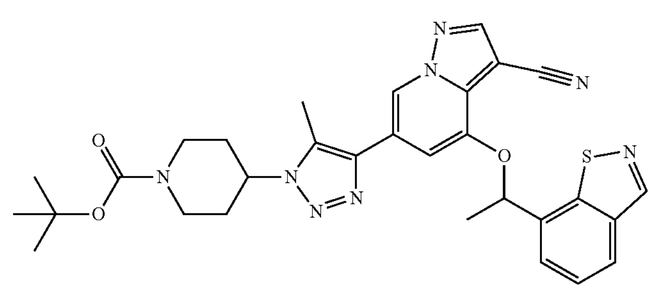 [SMILES: Cc1c(-c2cc(OC(C)c3cccc4cnsc34)c3c(C#N)cnn3c2)nnn1C1CCN(C(=O)OC(C)(C)C)CC1] | 585.2 |

TABLE 45-continued

| Prep No. | Chemical Name | Structure | ES/MS m/z [[M + H]+ |
|---|---|---|---|
| 638[7] | tert-Butyl 4-[4-[5-[1-(1,2-benzothiazol-7-yl)ethoxy]-3-cyano-imidazo[1,2-a]pyridin-7-yl]-5-methyl-triazol-1-yl]piperidine-1-carboxylate | 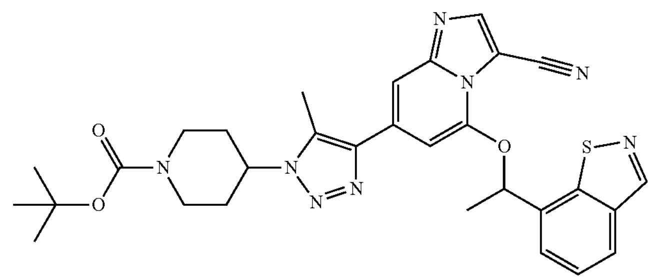 [SMILES: Cc1c(-c2cc(OC(C)c3cccc4cnsc34)n3c(C#N)cnc3c2)nnn1C1CCN(C(=O)OC(C)(C)C)CC1] | 585.2 |
| 639[5] | tert-Butyl 4-[4-[3-cyano-5-[(1R)-1-(4-fluorophenyl)ethoxy]imidazo[1,2-a]pyridin-7-yl]-5-methyl-triazol-1-yl]piperidine-1-carboxylate | 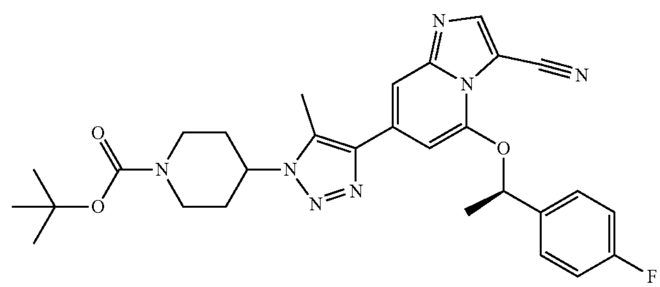 [SMILES: Cc1c(-c2cc(O[C@H](C)c3ccc(F)cc3)n3c(C#N)cnc3c2)nnn1C1CCN(C(=O)OC(C)(C)C)CC1] | 546.1 |
| 640[31] | tert-Butyl 4-[4-[3-cyano-5-[2-methoxy-1-[5-(trifluoromethyl)-3-pyridyl]ethoxy]imidazo[1,2-a]pyridin-7-yl]-5-methyl-triazol-1-yl]piperidine-1-carboxylate | 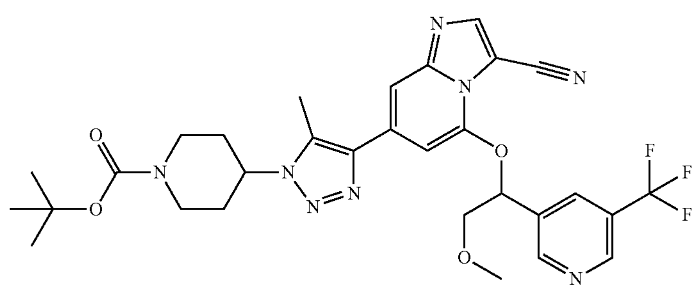 [SMILES: COCC(Oc1cc(-c2nnn(C3CCN(C(=O)OC(C)(C)C)CC3)c2C)cc2ncc(C#N)n12)c1cncc(C(F)(F)F)c1] | 627.2 |
| 641[4] | tert-Butyl 4-[4-[3-cyano-5-[1-(2-isoxazol-3-ylphenyl)ethoxy]imidazo[1,2-a]pyridin-7-yl]-5-methyl-triazol-1-yl]piperidine-1-carboxylate | 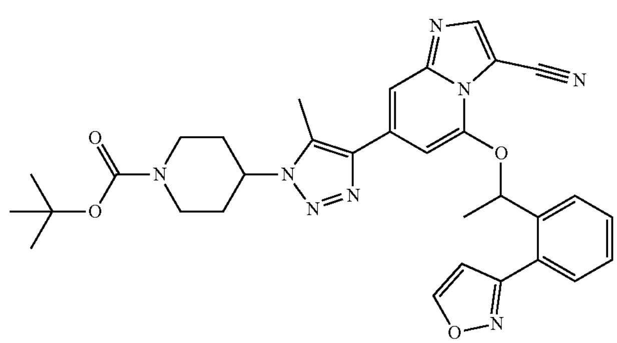 [SMILES: Cc1c(-c2cc(OC(C)c3ccccc3-c3ccon3)n3c(C#N)cnc3c2)nnn1C1CCN(C(=O)OC(C)(C)C)CC1] | 595.3 |
| 642[36] | tert-Butyl 4-[4-[3-cyano-4-[1-(3-methylsulfonylphenyl)ethoxy]pyrazolo[1,5-a]pyridin-6-yl]-5-methyl-pyrazol-1-yl]piperidine-1-carboxylate | 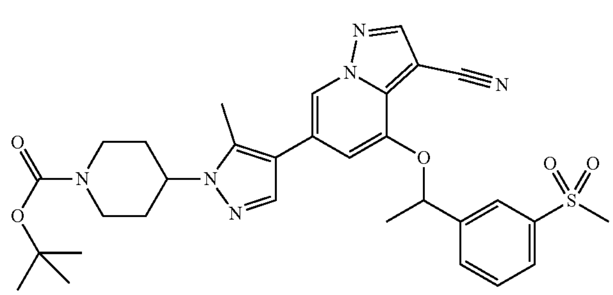 [SMILES: Cc1c(-c2cc(OC(C)c3cccc(S(C)(=O)=O)c3)c3c(C#N)cnn3c2)cnn1C1CCN(C(=O)OC(C)(C)C)CC1] | 505.20 [M + H − $C_5H_9O_2$]+ |

TABLE 45-continued

| Prep No. | Chemical Name | Structure | ES/MS m/z [[M + H]+ |
|---|---|---|---|
| 643[26] | tert-Butyl 4-[4-[3-cyano-5-[1-(5-fluoro-3-pyridyl)ethoxy]imidazo[1,2-a]pyridin-7-yl]-5-methyl-triazol-1-yl]piperidine-1-carboxylate | 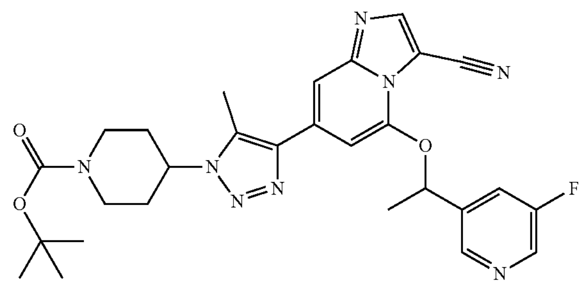 [SMILES: Cc1c(-c2cc(OC(C)c3cncc(F)c3)n3c(C#N)cnc3c2)nnn1C1CCN(C(=O)OC(C)(C)C)CC1] | 547.4 |
| 644[37] | tert-Butyl 4-[4-[3-cyano-4-[1-(5-fluoro-2-pyridyl)-2-methoxy-ethoxy]pyrazolo[1,5-a]pyridin-6-yl]-5-methyl-triazol-1-yl]piperidine-1-carboxylate | 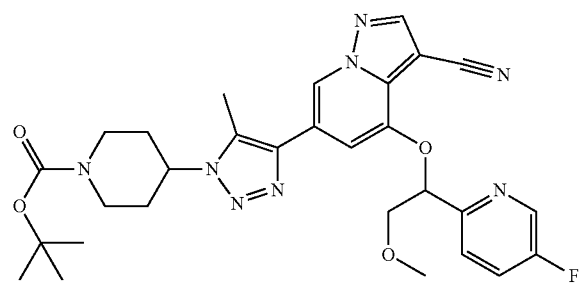 [SMILES: COCC(Oc1cc(-c2nnn(C3CCN(C(=O)OC(C)(C)C)CC3)c2C)cn2ncc(C#N)c12)c1ccc(F)cn1] | 577.1 |
| 645[38] | tert-Butyl 4-[4-[5-[(1R)-1-(5-chloro-2-pyridyl)ethoxy]-3-cyano-imidazo[1,2-a]pyridin-7-yl]-5-methyl-triazol-1-yl]piperidine-1-carboxylate | 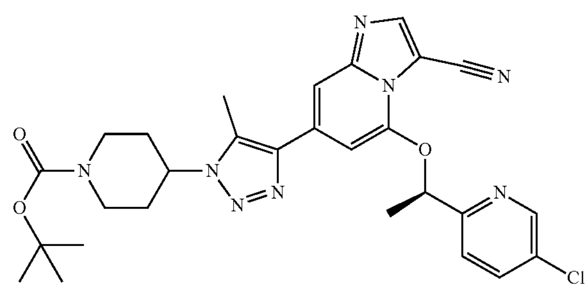 [SMILES: Cc1c(-c2cc(O[C@H](C)c3ccc(Cl)cn3)n3c(C#N)cnc3c2)nnn1C1CCN(C(=O)OC(C)(C)C)CC1] | 563.3 |
| 646[29] | tert-Butyl 4-[4-[5-[1-(5-chloro-3-pyridyl)ethoxy]-3-cyano-imidazo[1,2-a]pyridin-7-yl]-5-methyl-triazol-1-yl]piperidine-1-carboxylate | 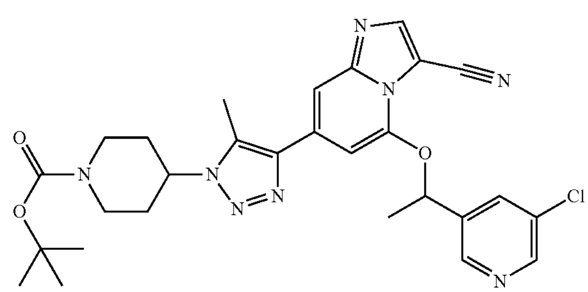 [SMILES: Cc1c(-c2cc(OC(C)c3cncc(Cl)c3)n3c(C#N)cnc3c2)nnn1C1CCN(C(=O)OC(C)(C)C)CC1] | 563.4 |
| 647[35] | tert-Butyl 4-[4-[3-cyano-5-[1-(3-methylsulfonylphenyl)ethoxy]imidazo[1,2-a]pyridin-7-yl]-5-methyl-triazol-1-yl]piperidine-1-carboxylate | 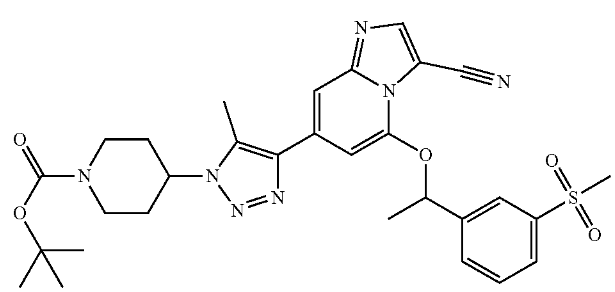 [SMILES: Cc1c(-c2cc(OC(C)c3cccc(S(C)(=O)=O)c3)n3c(C#N)cnc3c2)nnn1C1CCN(C(=O)OC(C)(C)C)CC1] | 606.2 |

TABLE 45-continued

| Prep No. | Chemical Name | Structure | ES/MS m/z [[M + H]+ |
|---|---|---|---|
| 648[35] | tert-Butyl 4-[4-[3-cyano-5-[1-(2-isothiazol-3-yl)phenyl)ethoxy]imidazo[1,2-a]pyridin-7-yl]-5-methyl-triazol-1-yl]piperidine-1-carboxylate | 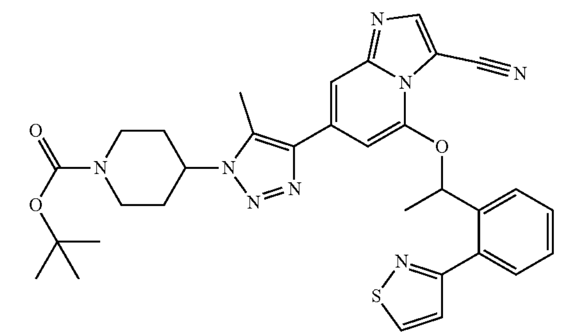 [SMILES: Cc1c(-c2cc(OC(C)c3ccccc3-c3ccsn3)n3c(C#N)cnc3c2)nnn1C1CCN(C(=O)OC(C)(C)C)CC1] | 611.2 |
| 649[9] | tert-Butyl 4-[4-[3-cyano-5-[1-(5-methyl-1,3,4-thiadiazol-2-yl)ethoxy]imidazo[1,2-a]pyridin-7-yl]-5-methyl-triazol-1-yl]piperidine-1-carboxylate | 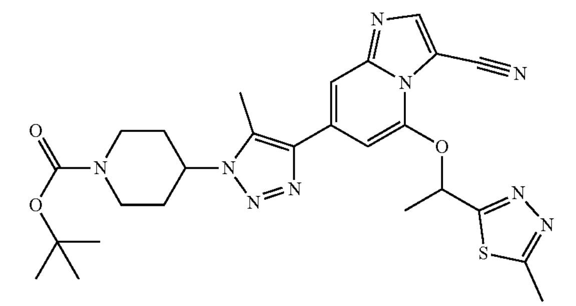 [SMILES: Cc1nnc(C(C)Oc2cc(-c3nnn(C4CCN(C(=O)OC(C)(C)C)CC4)c3C)cc3ncc(C#N)n23)s1] | 550.2 |
| 650[7] | tert-butyl 4-[4-[3-cyano-4-[1-(4-methylisothiazol-5-yl)ethoxy]pyrazolo[1,5-a]pyridin-6-yl]-5-methyl-triazol-1-yl]piperidine-1-carboxylate | 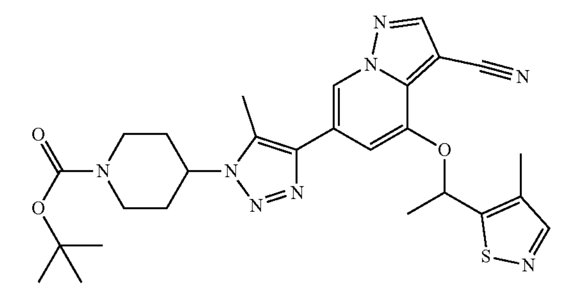 [SMILES: Cc1cnsc1C(C)Oc1cc(-c2nnn(C3CCN(C(=O)OC(C)(C)C)CC3)c2C)cn2ncc(C#N)c12] | 547.3 [M − H]+ |
| 651[33] | tert-Butyl 4-[4-[3-cyano-4-[(1R)-1-(5-fluoro-2-pyridyl)ethoxy]pyrazolo[1,5-a]pyridin-6-yl]-5-methyl-triazol-1-yl]piperidine-1-carboxylate | 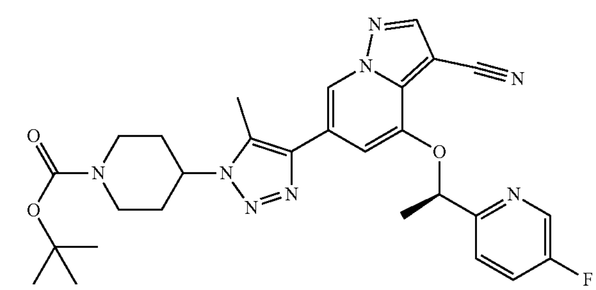 [SMILES: Cc1c(-c2cc(O[C@H](C)c3ccc(F)cn3)c3c(C#N)cnn3c2)nnn1C1CCN(C(=O)OC(C)(C)C)CC1] | 547.2 |
| 652[17] | tert-Butyl 4-[4-[3-cyano-5-[1-(5-methylthiazol-2-yl)ethoxy]imidazo[1,2-a]pyridin-7-yl]-5-methyl-triazol-1-yl]piperidine-1-carboxylate | 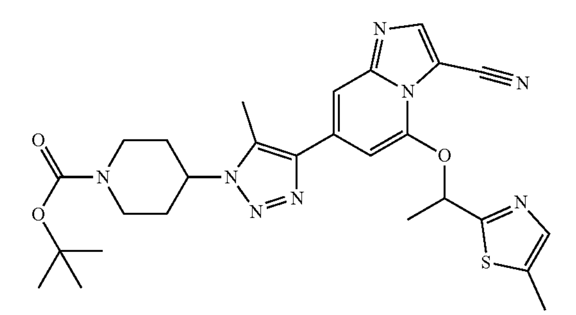 [SMILES: Cc1cnc(C(C)Oc2cc(-c3nnn(C4CCN(C(=O)OC(C)(C)C)CC4)c3C)cc3ncc(C#N)n23)s1] | 549.3 |

TABLE 45-continued

| Prep No. | Chemical Name | Structure | ES/MS m/z [[M + H]+ |
|---|---|---|---|
| 653[39] | tert-Butyl 4-[4-[3-cyano-4-[2-methoxy-1-[5-(trifluoromethyl)-3-pyridyl]ethoxy]pyrazolo[1,5-a]pyridin-6-yl]-5-methyl-triazol-1-yl]piperidine-1-carboxylate | 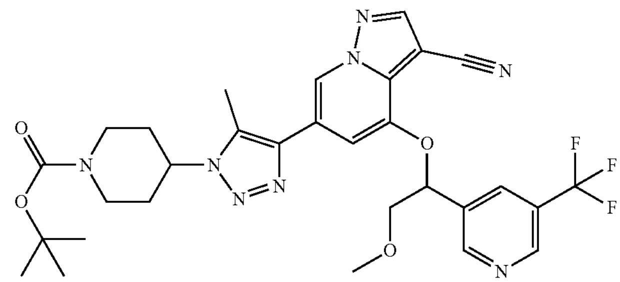 [SMILES: COCC(Oc1cc(-c2nnn(C3CCN(C(=O)OC(C)(C)C)CC3)c2C)cn2ncc(C#N)c12)c1cncc(C(F)(F)F)c1] | 627.2 |
| 654[40] | tert-Butyl 4-[4-[5-[1-(5-chloropyridazin-3-yl)ethoxy]-3-cyano-imidazo[1,2-a]pyridin-7-yl]-5-methyl-triazol-1-yl]piperidine-1-carboxylate | 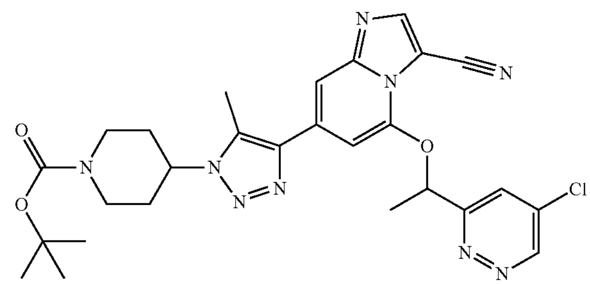 [SMILES: Cc1c(-c2cc(OC(C)c3cc(Cl)cnn3)n3c(C#N)cnc3c2)nnn1C1CCN(C(=O)OC(C)(C)C)CC1] | 564.2 |
| 655[6] | tert-Butyl 4-[4-[4-[1-(5-chloropyridazin-3-yl)ethoxy]-3-cyano-pyrazolo[1,5-a]pyridin-6-yl]-5-methyl-triazol-1-yl]piperidine-1-carboxylate | 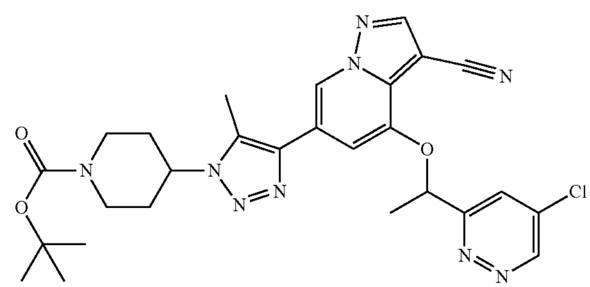 [SMILES: Cc1c(-c2cc(OC(C)c3cc(Cl)cnn3)c3c(C#N)cnn3c2)nnn1C1CCN(C(=O)OC(C)(C)C)CC1] | [Cl$^{35}$/Cl$^{37}$] 564.2/ 566.2 |
| 656[41] | tert-Butyl 4-[4-[3-cyano-5-[1-(5-methyl-3-pyridyl)ethoxy]imidazo[1,2-a]pyridin-7-yl]-5-methyl-triazol-1-yl]piperidine-1-carboxylate | 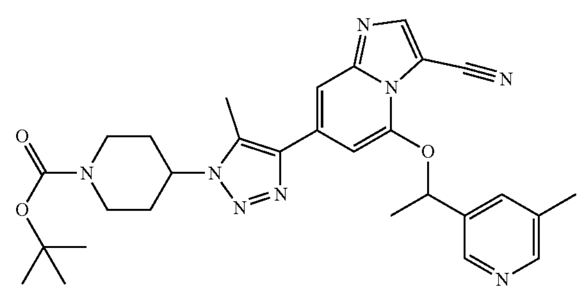 [SMILES: Cc1cncc(C(C)Oc2cc(-c3nnn(C4CCN(C(=O)OC(C)(C)C)CC4)c3C)cc3ncc(C#N)n23)c1] | 543.3 |
| 657[41] | tert-Butyl 4-[4-[3-cyano-5-[1-[5-(difluoromethyl)-3-pyridyl]ethoxy]imidazo[1,2-a]pyridin-7-yl]-5-methyl-triazol-1-yl]piperidine-1-carboxylate | 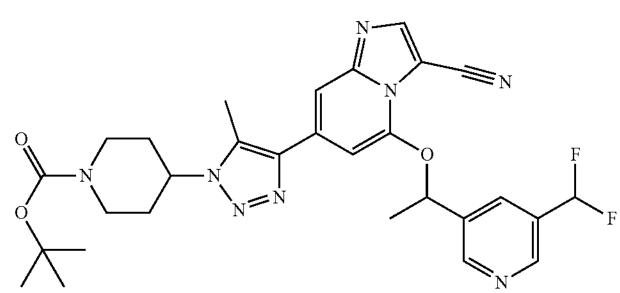 [SMILES: Cc1c(-c2cc(OC(C)c3cncc(C(F)F)c3)n3c(C#N)cnc3c2)nnn1C1CCN(C(=O)OC(C)(C)C)CC1] | 579.2 |

TABLE 45-continued

| Prep No. | Chemical Name | Structure | ES/MS m/z [[M + H]+ |
|---|---|---|---|
| 658[7] | tert-Butyl 4-[4-[3-cyano-4-[1-(1-methylpyrrolo[2,3-c]pyridin-4-yl)ethoxy]pyrazolo[1,5-a]pyridin-6-yl]-5-methyl-triazol-1-yl]piperidine-1-carboxylate | 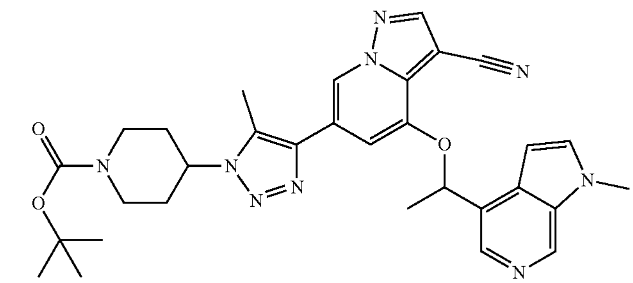 [SMILES: Cc1c(-c2cc(OC(C)c3cncc4c3ccn4C)c3c(C#N)cnn3c2)nnn1C1CCN(C(=O)OC(C)(C)C)CC1] | 582.3 |
| 659[9] | tert-Butyl 4-[4-[3-cyano-4-[1-(6-methylpyrazin-2-yl)ethoxy]pyrazolo[1,5-a]pyridin-6-yl]-5-methyl-triazol-1-yl]piperidine-1-carboxylate | 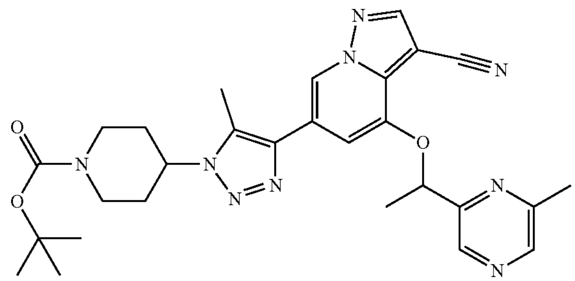 [SMILES: Cc1cncc(C(C)Oc2cc(-c3nnn(C4CCN(C(=O)OC(C)(C)C)CC4)c3C)cn3ncc(C#N)c23)n1] | 544.3 |
| 660[6] | tert-Butyl 4-[4-[3-cyano-5-[1-(5-methylpyridazin-3-yl)ethoxy]imidazo[1,2-a]pyridin-7-yl]-5-methyl-triazol-1-yl]piperidine-1-carboxylate | 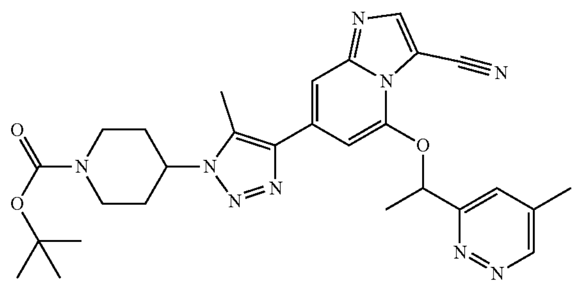 [SMILES: Cc1cnnc(C(C)Oc2cc(-c3nnn(C4CCN(C(=O)OC(C)(C)C)CC4)c3C)cc3ncc(C#N)n23)c1] | 544.3 |
| 661[42] | tert-Butyl 4-[4-[3-cyano-5-[1-(3-ethyltriazol-4-yl)ethoxy]imidazo[1,2-a]pyridin-7-yl]-5-methyl-triazol-1-yl]piperidine-1-carboxylate | 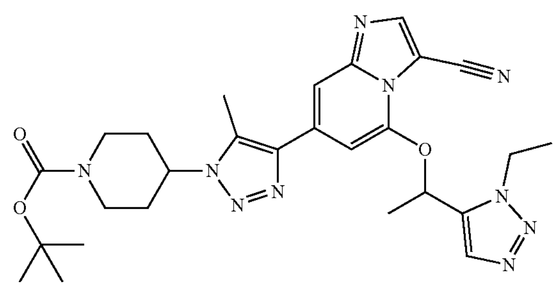 [SMILES: CCn1nncc1C(C)Oc1cc(-c2nnn(C3CCN(C(=O)OC(C)(C)C)CC3)c2C)cc2ncc(C#N)n12] | 547.2 |
| 662[43] | tert-Butyl 4-[4-[4-[2-[tert-butyl(dimethyl)silyl]oxy-1-(5-fluoro-2-pyridyl)ethoxy]-3-fluoro-pyrazolo[1,5-a]pyridin-6-yl]-5-methyl-triazol-1-yl]piperidine-1-carboxylate | 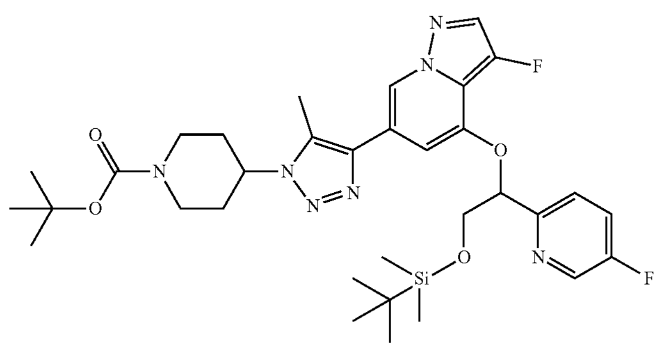 [SMILES: Cc1c(-c2cc(OC(CO[Si](C)(C)C(C)(C)C)c3ccc(F)cn3)c3c(F)cnn3c2)nnn1C1CCN(C(=O)OC(C)(C)C)CC1] | 670.3 |

TABLE 45-continued

| Prep No. | Chemical Name | Structure | ES/MS m/z [[M + H]+ |
|---|---|---|---|
| 663[44,45] | tert-Butyl 4-[4-[4-[2-[tert-butyl(dimethyl)silyl]oxy-1-(2-pyridyl)ethoxy]pyrazolo[1,5-a]pyridin-6-yl]-5-methyl-triazol-1-yl]piperidine-1-carboxylate | 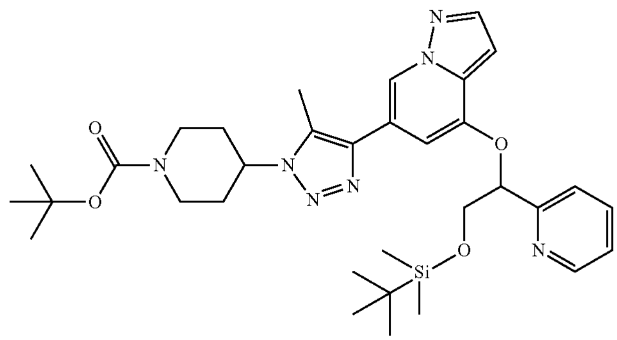 [SMILES: Cc1c(-c2cc(OC(CO[Si](C)(C)C(C)(C)C)c3ccccn3)c3ccnn3c2)nnn1C1CCN(C(=O)OC(C)(C)C)CC1] | 634.4 |
| 664[46] | Cis-tert-Butyl 4-[3-[4-[2-[tert-butyl(dimethyl)silyl]oxy-1-(5-fluoro-2-pyridyl)ethoxy]pyrazolo[1,5-a]pyridin-6-yl]-5-methyl-triazol-1-yl]cyclobutyl]piperazine-1-carboxylate | 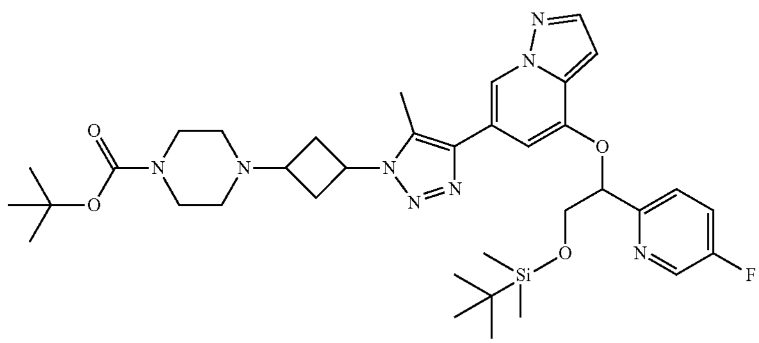 [SMILES: Cc1c(-c2cc(OC(CO[Si](C)(C)C(C)(C)C)c3ccc(F)cn3)c3ccnn3c2)nnn1C1CC(N2CCN(C(=O)OC(C)(C)C)CC2)C1] | 707.1 |
| 665[7] | tert-Butyl 4-[4-[3-cyclopropyl-4-[(1R)-1-(5-fluoro-2-pyridyl)ethoxy]pyrazolo[1,5-a]pyridin-6-yl]-5-methyl-triazol-1-yl]piperidine-1-carboxylate | 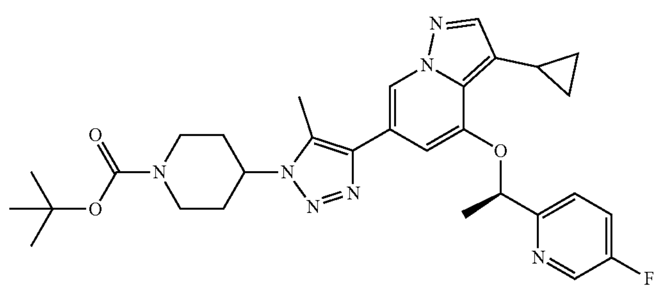 [SMILES: Cc1c(-c2cc(O[C@H](C)c3ccc(F)cn3)c3c(C4CC4)cnn3c2)nnn1C1CCN(C(=O)OC(C)(C)C)CC1] | 561.8 |
| 666[9] | tert-Butyl 4-[4-[2-cyano-1-(5-fluoro-2-pyridyl)-2-methyl-propoxy]pyrazolo[1,5-a]pyridin-6-yl]-5-methyl-triazol-1-yl]piperidine-1-carboxylate | 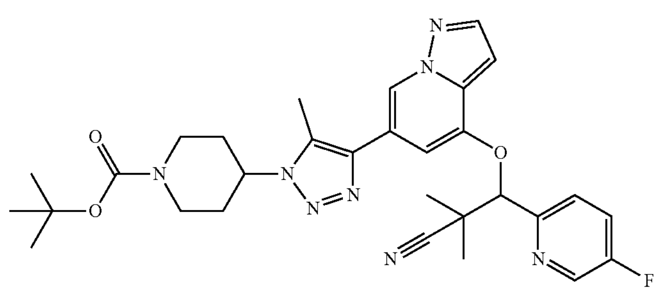 [SMILES: Cc1c(-c2cc(OC(c3ccc(F)cn3)C(C)(C)C#N)c3ccnn3c2)nnn1C1CCN(C(=O)OC(C)(C)C)CC1] | 575.7 |

TABLE 45-continued

| Prep No. | Chemical Name | Structure | ES/MS m/z [[M + H]+ |
|---|---|---|---|
| 667[9] | tert-Butyl 4-[4-[3-cyano-4-[1-[2-(2-methoxyethylamino)-5-(trifluoromethyl)-3-pyridyl]ethoxy]pyrazolo[1,5-a]pyridin-6-yl]-5-methyl-triazol-1-yl]piperidine-1-carboxylate | 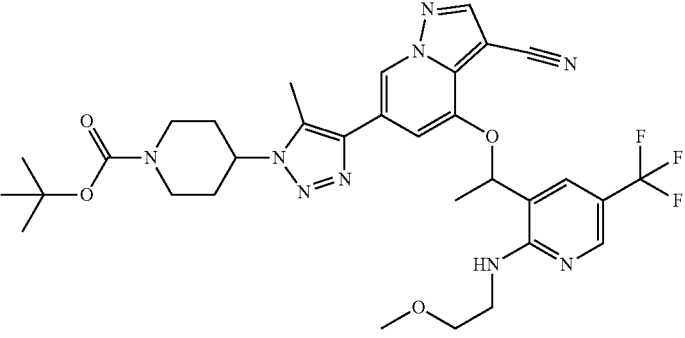 [SMILES: COCCNc1ncc(C(F)(F)F)cc1C(C)Oc1cc(-c2nnn(C3CCN(C(=O)OC(C)(C)C)CC3)c2C)cn2ncc(C#N)c12] | 670.3 |
| 668 | tert-Butyl 4-[4-[4-[1-[2-[3-[tert-butyl(dimethyl)silyl]oxyazetidin-1-yl]-5-(trifluoromethyl)-3-pyridyl]ethoxy]-3-cyano-pyrazolo[1,5-a]pyridin-6-yl]-5-methyl-triazol-1-yl]piperidine-1-carboxylate | 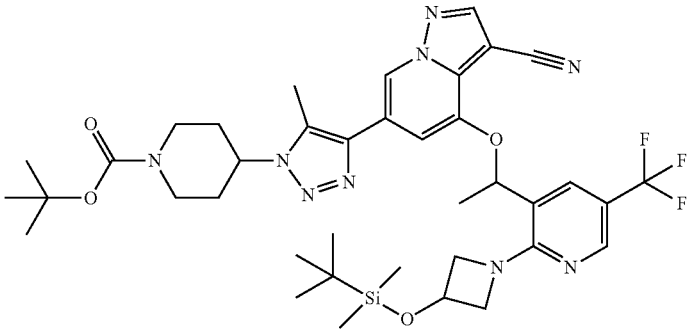 [SMILES: Cc1c(-c2cc(OC(C)c3cc(C(F)(F)F)cnc3N3CC(O[Si](C)(C)C(C)(C)C)C3)c3c(C#N)cnn3c2)nnn1C1CCN(C(=O)OC(C)(C)C)CC1] | b |
| 669[47] | tert-Butyl 4-[4-[3-cyano-5-[1-(5-fluoro-2-pyridyl)-2-(trifluoromethoxy)ethoxy]imidazo[1,2-a]pyridin-7-yl]-5-methyl-triazol-1-yl]piperidine-1-carboxylate | 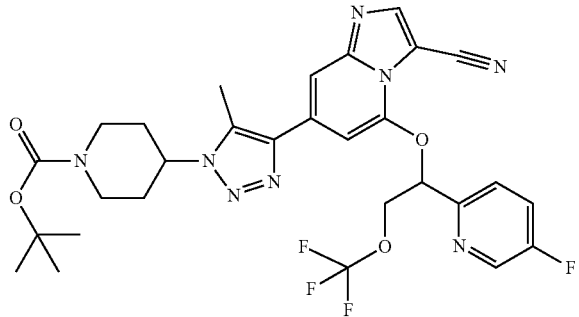 [SMILES: Cc1c(-c2cc(OC(COC(F)(F)F)c3ccc(F)cn3)n3c(C#N)cnc3c2)nnn1C1CCN(C(=O)OC(C)(C)C)CC1] | 631.1 |

TABLE 45-continued

| Prep No. | Chemical Name | Structure | ES/MS m/z [[M + H]+ |
|---|---|---|---|
| 670[5] | tert-Butyl 4-[4-[3-cyano-5-[1-[5-fluoro-6-(2-methoxyethoxy)-2-pyridyl]ethoxy]imidazo[1,2-a]pyridin-7-yl]-5-methyl-triazol-1-yl]piperidine-1-carboxylate | 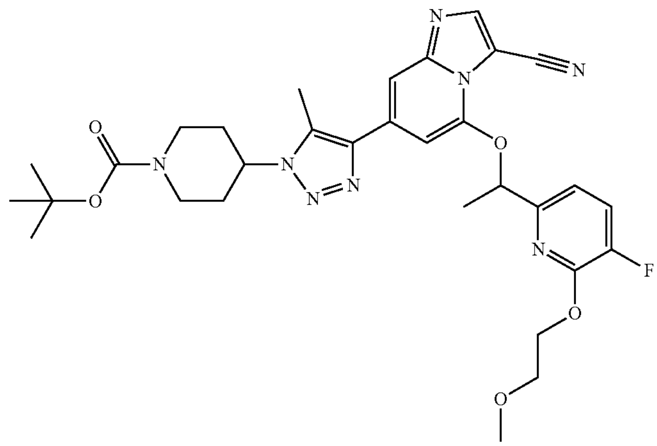 [SMILES: COCCOc1nc(C(C)Oc2cc(-c3nnn(C4CCN(C(=O)OC(C)(C)C)CC4)c3C)cc3ncc(C#N)n23)ccc1F] | 621.5 |
| 671[9] | tert-Butyl 4-[4-[3-cyano-5-[1-[5-(trifluoromethoxy)-3-pyridyl]ethoxy]imidazo[1,2-a]pyridin-7-yl]-5-methyl-triazol-1-yl]piperidine-1-carboxylate | 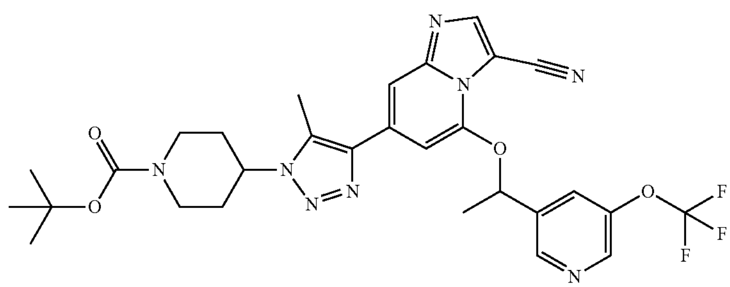 [SMILES: Cc1c(-c2cc(OC(C)c3cncc(OC(F)(F)F)c3)n3c(C#N)cnc3c2)nnn1C1CCN(C(=O)OC(C)(C)C)CC1] | 613.1 |
| 672[26] | tert-Butyl (2SR,4RS)-4-[4-[3-cyano-5-[(1R)-1-(2-pyridyl)ethoxy]imidazo[1,2-a]pyridin-7-yl]-5-methyl-triazol-1-yl]-2-cyclopropyl-piperidine-1-carboxylate | 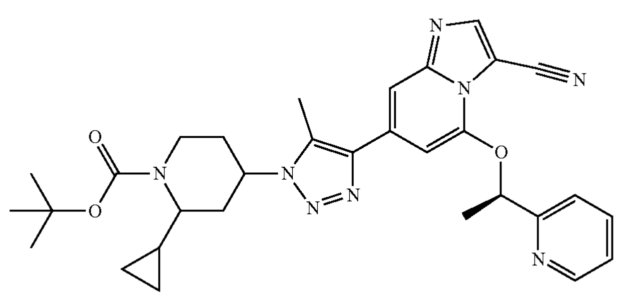 [SMILES: Cc1c(-c2cc(O[C@H](C)c3ccccn3)n3c(C#N)cnc3c2)nnn1C1CCN(C(=O)OC(C)(C)C)C(C2CC2)C1] | 569.2 |
| 673[9] | tert-Butyl 4-[4-[4-[[(4R)-2,2-dimethyl-1,3-dioxolan-4-yl]-(5-fluoro-2-pyridyl)methoxy]pyrazolo[1,5-a]pyridin-6-yl]-5-methyl-triazol-1-yl]piperidine-1-carboxylate | 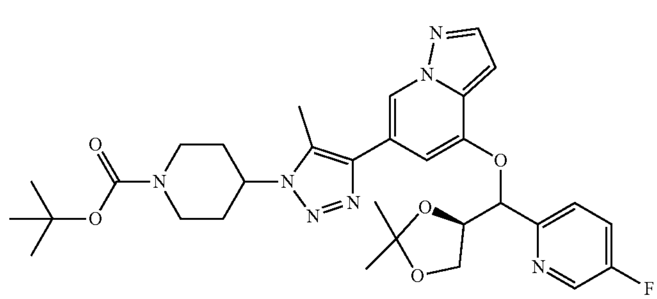 [SMILES: Cc1c(-c2cc(OC(c3ccc(F)cn3)[C@H]3COC(C)(C)O3)c3ccnn3c2)nnn1C1CCN(C(=O)OC(C)(C)C)CC1] | 608.8 |

TABLE 45-continued

| Prep No. | Chemical Name | Structure | ES/MS m/z [[M + H]+ |
|---|---|---|---|
| 674[48] | tert-Butyl 4-[4-[5-[(1R)-1-(5-fluoro-2-pyridyl)ethoxy]imidazo[1,2-c]pyrimidin-7-yl]-5-methyl-pyrazol-1-yl]piperidine-1-carboxylate | 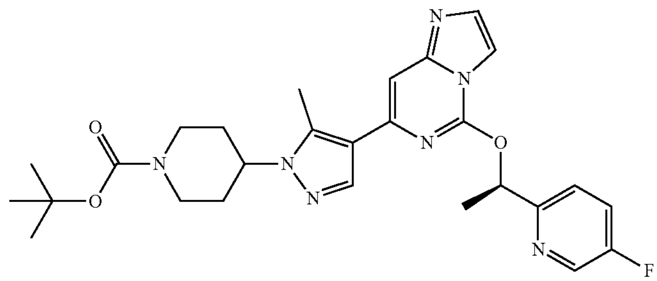 [SMILES: Cc1c(-c2cc3nccn3c(O[C@H](C)c3ccc(F)cn3)n2)cnn1C1CCN(C(=O)OC(C)(C)C)CC1] | 522.2 |

[1] Purified by silica gel column chromatography, eluting with a gradient of PE:EtOAc (2:1 to 1:1)
[2] Flash chromatography eluting with 71% PE in EtOAc.
[3] Purified by reversed Combi-flash chromatography, C18 column, eluting with 80% to 100% ACN in H$_2$O (0.1% NH$_4$HCO$_3$).
[4] Purified by reverse phase chromatography, C18 column, eluting with 70% to 80% ACN in H$_2$O (0.1% NH$_4$HCO$_3$).
[5] Purified by reverse phase chromatography, C18 column, eluting with 50% to 60% ACN in H$_2$O (0.1% NH$_4$HCO$_3$).
[6] Purified by reverse phase chromatography, C18 column, eluting ACN in H$_2$O.
[7] Purified by reverse phase chromatography, C18 column, eluting with 0% to 100% ACN in H$_2$O.
[8] Purified by prep-TLC, eluting with a gradient of PE:EtOAc (1:1).
[9] Purified by reverse phase chromatography, C18 column, eluting with 10% to 100% ACN in H$_2$O.
[10] Purified by silica gel column chromatography, eluting with a gradient of PE:EtOAc (8:1).
[11] Purified by reverse phase chromatography, C18 column, eluting with 45% to 50% ACN in H$_2$O (0.1% FA).
[12] Purified by reverse phase chromatography, C18 column, eluting with 56% to 60% ACN in H$_2$O (0.1% NH$_4$HCO$_3$).
[13] Purified by reverse phase chromatography, C18 column, eluting with 70% to 75% ACN in H2O (0.1% NH$_4$OH).
[14] Purified by reverse phase chromatography, C18 column, eluting with 70% to 90% ACN in H2O (0.1% NH$_4$HCO$_3$).
[15] Purified by reverse phase chromatography, C18 column, eluting with 80% to 100% ACN in H$_2$O (0.1% NH$_4$HCO$_3$).
[16] Purified by prep-TLC, eluting with EtOAc.
[17] Purified by silica gel column chromatography, eluting with PE:EtOAc (5:1 to 2:1).
[18] Purified by prep-TLC, eluting with a gradient of PE:EtOAc (2:1).
[19] Purified by reverse phase chromatography, C18 column, eluting with 0% to 100% ACN in H$_2$O (0.1% FA).
[20] Purified by reverse phase chromatography, C18 column, eluting with 60% to 70% ACN in H$_2$O (0.1% NH$_4$HCO$_3$).
[21] Purified by reverse phase chromatography, C18 column, eluting with 30% to 50% ACN in H2O (0.1% NH$_4$OH).
[22] Purified by reverse phase chromatography, C18 column, eluting with 20% to 60% ACN in H$_2$O (NH$_4$HCO$_3$).
[23] Purified by silica gel column chromatography, eluting with a gradient of DCM:MeOH (9:1).
[24] Purified by silica gel column chromatography, eluting with 10% to 50% EtOAc in PE.
[25] Purified by reverse phase chromatography, C18 column, eluting with 10% to 50% ACN in H$_2$O (0.1% FA).
[26] Purified by reverse phase chromatography, C18 column, eluting with 10% to 50% ACN in H2O (0.1% NH$_4$HCO$_3$).
[27] Purified by reverse phase chromatography, C18 column, eluting with 30% to 45% ACN in H$_2$O (0.1% NH$_3$ H$_2$O).
[28] Purified by reverse phase chromatography, C18 column, eluting with 0% to 100% ACN in H$_2$O (0.1% NH$_4$HCO$_3$).
[29] Purified by reverse phase chromatography, C18 column, eluting with 10% to 70% ACN in H$_2$O (0.1% NH$_4$HCO$_3$).
[30] Purified by reverse phase chromatography, C18 column, eluting with 40% to 80% ACN in H$_2$O (0.05% NH$_4$HCO$_3$).
[31] Purified by reverse phase chromatography, C18 column, eluting with 45% to 50% ACN in H$_2$O (0.1% NH$_4$HCO$_3$).
[32] Purified by reverse phase chromatography, C18 column, eluting with 50% to 70% ACN in H$_2$O (0.1% FA).
[33] Purified by reverse phase chromatography, C18 column, eluting with 30% to 50% ACN in H2O (0.1% NH$_4$HCO$_3$).
[34] Purified by reverse phase chromatography, C18 column, eluting with 25% to 50% ACN in H2O (0.1% NH$_4$OH).
[35] Purified by reverse phase chromatography, C18 column, eluting ACN in H$_2$O (0.1% FA).
[36] Purified by silica gel chromatography, eluting with EtOAc:Hepane.
[37] Purified by reversed Combi-flash chromatography, C18 column, eluting with 55% to 60% ACN in H$_2$O (0.1% NH$_4$HCO$_3$).
[38] Purified by reverse phase chromatography, C18 column, eluting with 40% to 50% ACN in H$_2$O.
[39] Purified by reverse phase chromatography, C18 column, eluting with 10% to 50% ACN in H$_2$O.
[40] Purified by reverse phase chromatography, C18 column, eluting with 0% to 50% ACN in H$_2$O.
[41] Purified by reverse phase chromatography, C18 column, eluting with 10% to 100% ACN in H$_2$O.
[42] Purified by silica gel column chromatography, eluting with a gradient of PE:EtOAc (4:1 to 3:1).
[43] Purified by reverse phase chromatography, C18 column, eluting with 85% to 95% ACN in H$_2$O (0.1% FA).
[44] Purified by silica gel column chromatography, eluting with a gradient of PE:EtOAc (1:1).
[45] Purified by reverse phase chromatography, C18 column, eluting with 60% to 90% ACN in H2O.
[46] Purified by reverse phase chromatography, C18 column, eluting with 85% to 95% ACN in H2O (0.1% NH$_4$HCO$_3$).
[47] Purified by reverse phase chromatography, C18 column, eluting with 50% to 55% ACN in H2O (0.1% NH$_4$HCO$_3$).
[48] Purified by silica gel column chromatography, eluting with a gradient of 0% to 100% acetone in DCM.

a[1]H NMR (400 MHz, CDCl$_3$) δ 1.49-1.54 (m, 9 H), 1.91-1.97 (m, 3 H), 2.00 (s, 3 H), 2.20-2.33 (m, 2 H), 2.43-2.49 (m, 3 H), 2.89-3.01 (m, 2 H), 3.25-3.34 (m, 4 H), 3.93-4.01 (m, 3 H), 4.25-4.37 (m, 3 H), 5.78-5.88 (m, 1 H), 7.35-7.42 (m, 1 H,) 8.13-8.18 (m, 2H), 8.18-8.24 (m, 1 H), 8.48-8.54 (m, 1 H).
b[1]H NMR (400 MHz, CDCl$_3$) δ 0.00 (br s, 6 H) 0.81 (br s, 9H) 1.39 (br s, 9H) 1.71-1.83 (m, 3 H) 1.92 (br d, J = 15.53 Hz, 3 H) 2.08-2.21 (m, 2 H) 2.26 (br s, 3 H) 2.77-2.95 (m, 2 H) 3.91-4.12 (m, 2 H) 4.15-4.33 (m, 4 H) 4.39-4.52 (m, 1 H) 4.68-4.79 (m, 1 H) 5.43-5.54 (m, 1 H) 6.85-6.99 (m, 1 H) 7.79-7.94 (m, 1 H) 8.05-8.17 (m, 1 H) 8.22-8.37 (m, 2 H).

Preparation 675 tert-Butyl (3R)-3-(3-(4-(3-cyano-4-(((trifluoromethyl)sulfonyl)oxy)pyrazolo[1,5-a]pyridin-6-yl)-5-methyl-1H-pyrazol-1-yl)azetidin-1-yl)pyrrolidine-1-carboxylate

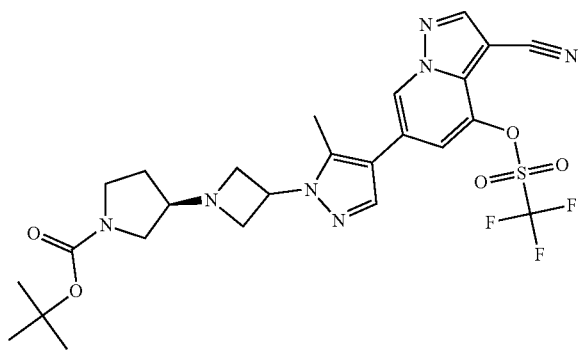 [SMILES: Cc1c(-c2cc(OS(=O)(=O)C(F)(F)F)c3c(C#N)cnn3c2)cnn1C1CN([C@@H]2CCN(C(=O)OC(C)(C)C)C2)C1]

A stirred mixture of tert-butyl (R)-3-(3-(4-(3-cyano-4-hydroxypyrazolo[1,5-a]pyridin-6-yl)-5-methyl-1H-pyrazol-1-yl)azetidin-1-yl)pyrrolidine-1-carboxylate (300 mg, 0.64 mmol) and 1,1,1-trifluoro-N-phenyl-N-trifluoromethanesulfonylmethanesulfonamide (346 mg, 0.97 mmol) in DCM (10.00 mL) is treated with TEA (196.00 mg, 1.94 mmol) and DMAP (7.00 mg, 0.06 mmol) and stirred for 1 hr at RT under $N_2$. The mixture is concentrated under reduced pressure. The residue is purified by Prep-TLC, eluting with a gradient of DCM:MeOH (10:1) to give the title compound as a light-yellow oil (350 mg, 90.8%). ES/MS m/z 596.3 [M+H]$^+$.

The following compounds are prepared essentially as described for tert-butyl (R)-3-(3-(4-(3-cyano-4-(((trifluoromethyl)sulfonyl)oxy)pyrazolo[1,5-a]pyridin-6-yl)-5-methyl-1H-pyrazol-1-yl)azetidin-1-yl)pyrrolidine-1-carboxylate using the appropriate reagents, adjusting the reaction times to determine completion of the reactions, and adjusting the purification system as appropriate. DMF can also be used as the solvent and DIEA can be used as the base. Temperature is varied from 0° C. to RT.

TABLE 46

| Prep No. | Chemical Name | Structure | ES/MS m/z [[M + H]$^+$ |
|---|---|---|---|
| 676[1] | tert-Butyl (3S)-3-(4-(3-cyano-4-(((trifluoromethyl)sulfonyl)oxy)pyrazolo[1,5-a]pyridin-6-yl)-5-methylpyrazol-1-yl)pyrrolidine-1-carboxylate | 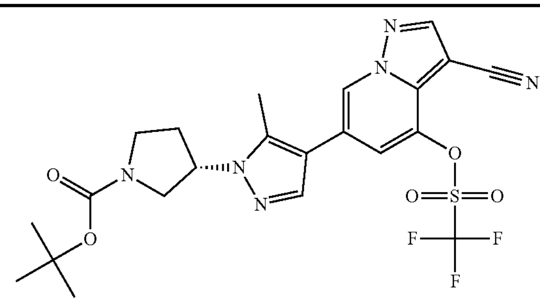 | 541.3 |
| 677[2] | tert-Butyl (3R)-3-[4-[3-cyano-4-(trifluoromethanesulfonyloxy)pyrazolo[1,5-a]pyridin-6-yl]-5-methylpyrazol-1-yl]pyrrolidine-1-carboxylate | 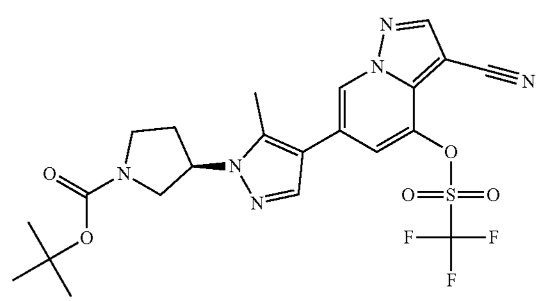 [SMILES: Cc1c(-c2cc(OS(=O)(=O)C(F)(F)F)c3c(C#N)cnn3c2)cnn1[C@@H]1CCN(C(=O)OC(C)(C)C)C1] | 541.0 |
| 678[3] | tert-Butyl 4-[4-[3-cyano-4-(trifluoromethylsulfonyloxy)pyrazolo[1,5-a]pyridin-6-yl]-5-methyl-pyrazol-1-yl]piperidine-1-carboxylate | 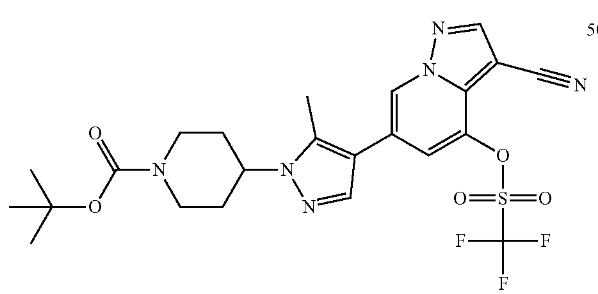 | 506.4 |

[1]Purification with reverse Combi-flash chromatography with C18 column; eluting with 70-75% ACN in H$_2$O.
[2]Purification with reverse flash chromatography with C18 column eluting with 60-70% ACN in H2O (1% NH$_4$HCO$_3$).
[3]Purified by silica gel column chromatography, eluting with PE:EtOAc (10:1)

Preparation 679 tert-Butyl (3R)-3-[4-(3-cyano-4-[[(1R)-1-(pyridin-2-yl)ethyl]amino]pyrazolo[1,5-a]pyridin-6-yl)-5-methylpyrazol-1-yl]pyrrolidine-1-carboxylate

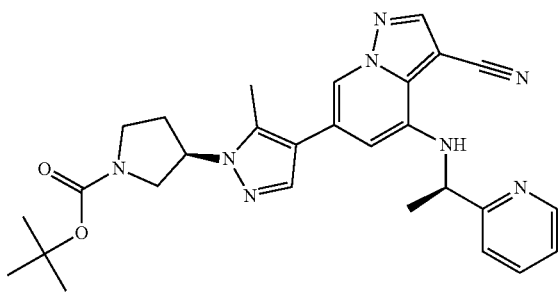 [SMILES: Cc1c(-c2cc(N[C@H](C)c3ccccn3)c3c(C#N)cnn3c2)cnn1[C@@H]1CCN(C(=O)OC(C)(C)C)C1]

A stirred mixture of tert-butyl (3R)-3-[4-[3-cyano-4-(trifluoromethanesulfonyloxy)pyrazolo[1,5-a]pyridin-6-yl]-5-methylpyrazol-1-yl]pyrrolidine-1-carboxylate (102.00 mg, 0.19 mmol) and (1R)-1-(pyridin-2-yl)ethanamine (27.67 mg, 0.23 mmol) in toluene (20.00 mL) is treated with $Cs_2CO_3$ (184.45 mg, 0.57 mmol), Xantphos (65.51 mg, 0.11 mmol) and $Pd_2(dba)_3$ (86.40 mg, 0.094 mmol) added in portions at RT under $N_2$. The mixture is stirred for 4 hrs at 80° C. under $N_2$. The solution is cooled to RT, filtered, the filter cake washed with EtOAc (5×50 mL), and the filtrate concentrated under reduced pressure. The residue is purified by reverse flash chromatography with the following conditions: C18 silica gel; $H_2O$ (0.1% $NH_4HCO_3$) in ACN, eluting with a gradient of 70% to 80%. The mixture is concentrated under reduced pressure to give the title compound as a white solid (50 mg, 51.69%). ES/MS m/z 513.3 $[M+H]^+$.

The following compounds are prepared essentially as described for tert-butyl (3R)-3-[4-(3-cyano-4-[[(1R)-1-(pyridin-2-yl)ethyl]amino]pyrazolo[1,5-a]pyridin-6-yl)-5-methylpyrazol-1-yl]pyrrolidine-1-carboxylate using the appropriate reagents, adjusting the reaction times to determine completion of the reactions, and adjusting the purification system as appropriate. The catalyst can also be $Pd(OAc)_2$, $Pd(dba)_2$. Temperature is varied from 80° C. to 100° C.

TABLE 47

| Prep No. | Chemical Name | Structure | ES/MS m/z $[M + H]^+$ |
|---|---|---|---|
| 680[1] | tert-Butyl (R)-3-(3-(4-(3-cyano-4-(((R)-1-(pyridin-2-yl)ethyl)amino)pyrazolo[1,5-a]pyridin-6-yl)-5-methyl-1H-pyrazol-1-yl)azetidin-1-yl)pyrrolidine-1-carboxylate | 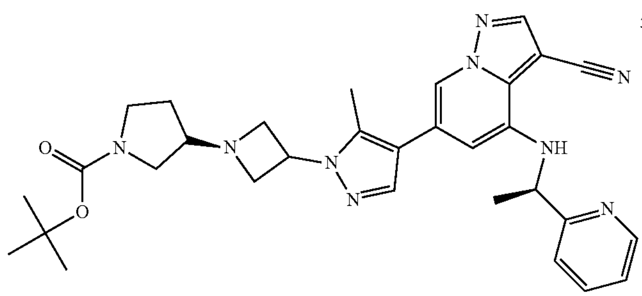 | 568.4 |
| 681[2] | tert-Butyl (3S)-3-[4-(3-cyano-4-[[(1R)-1-(pyridin-2-yl)ethyl]amino]pyrazolo[1,5-a]pyridin-6-yl)-5-methylpyrazol-1-yl]pyrrolidine-1-carboxylate | 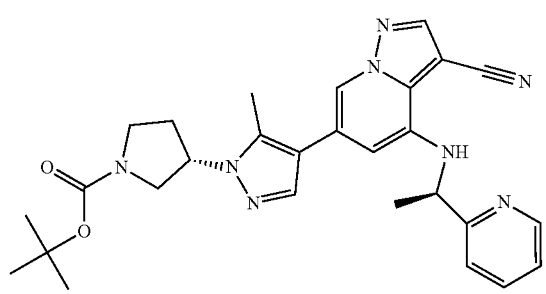 [SMILES: Cc1c(-c2cc(N[C@H](C)c3ccccn3)c3c(C#N)cnn3c2)cnn1[C@H]1CCN(C(=O)OC(C)(C)C)C1] | 513.1 |
| 682[3] | tert-Butyl 4-[4-[3-cyano-4-[[(1R)-1-(2-pyridyl)ethyl]amino]pyrazolo[1,5-a]pyridin-6-yl]-5-methyl-pyrazol-1-yl]piperidine-1-carboxylate | 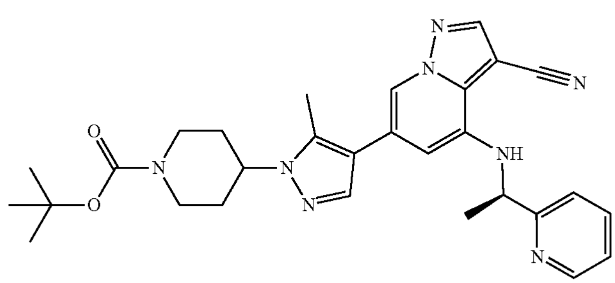 [SMILES: Cc1c(-c2cc(N[C@H](C)c3ccccn3)c3c(C#N)cnn3c2)cnn1C1CCN(C(=O)OC(C)(C)C)CC1] | 527.4 |

TABLE 47-continued

| Prep No. | Chemical Name | Structure | ES/MS m/z [M + H]+ |
|---|---|---|---|
| 683[4] | tert-Butyl 4-[4-[3-cyano-5-[[(1R)-1-(2-pyridyl)ethyl]amino]imidazo[1,2-a]pyridin-7-yl]-5-methyl-pyrazol-1-yl]piperidine-1-carboxylate | 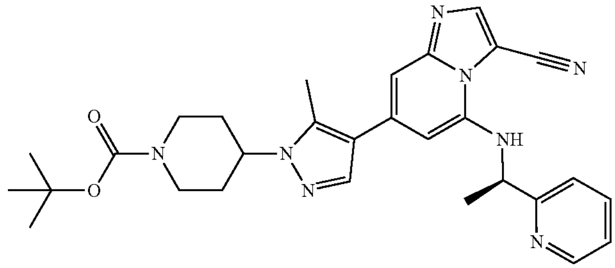 [SMILES: Cc1c(-c2cc(N[C@H](C)c3ccccn3)n3c(C#N)cnc3c2)cnn1C1CCN(C(=O)OC(C)(C)C)CC1] | 527.4 |

[1]After the mixture is cooled to RT it is concentrated under reduced pressure and purifiedby silica gel column chromatography, eluting with a gradient of DCM:MeOH (20:1).
[2]Prior to purification, the mixture is diluted with H₂O (30 mL), extracted with EtOAc (3 × 50 mL). The combined organic extracts are washed with brine (2 × 30 mL), driedover anhydrous Na₂SO₄, filtered, and the filtrate is concentrated under reduced pressure.
[3]Purified by silica gel column chromatography, eluting with DCM:MeOH (20:1).
[4]Purified by Prep-TLC PE:EtOAc (1:1).

Preparation 684 tert-Butyl 7-((1s,3s)-3-(4-(4-(2-((tert-butyldimethyl-silyl)oxy)-1-(5-fluoropyridin-2-yl)ethoxy)-3-chloropyrazolo[1,5-a]pyridin-6-yl)-5-methyl-1H-1,2,3-triazol-1-yl)cyclobutyl)-3-oxa-7,9-diazabicyclo[3.3.1]nonane-9-carboxylate, Isomer 2

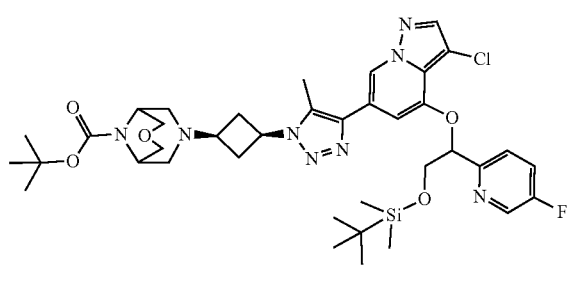 [SMILES: Cc1c(-c2cc(OC(CO[Si](C)(C)C(C)(C)C)c3ccc(F)cn3)c3c(Cl)cnn3c2)nnn1[C@H]1C[C@@H](N2CC3COCC(C2)N3C(=O)OC(C)(C)C)C1]

A solution of (1S,3r)-3-(4-(4-((S)-2-((tert-Butyldimethyl-silyl)oxy)-1-(5-fluoropyridin-2-yl)ethoxy)-3-chloropyrazolo[1,5-a]pyridin-6-yl)-5-methyl-1H-1,2,3-triazol-1-yl)cyclobutan-1-ol (190 mg, 0.33 mmol) and DIPEA (214 mg, 1.66 mmol) in DCM (4.0 ml) is cooled to −78° C. is treated with (CF₃SO₂)₂O (1.40 g, 0.50 mmol). The reaction is stirred at −78° C. for 15 minutes. The reaction consequently treated with a solution of DIPEA (214 mg, 1.66 mmol) and 9-boc-3-oxa-7,9-diazabicyclo[3.3.1]nonane (151 mg, 0.66 mmol) in DCM (4 mL). The mixture is heated to 40° C. for 16 hr. Then, the reaction is cooled to RT and stirred for 2 days. The reaction is diluted with H₂O then extracted with 4:1 DCM:IPA. The layers are separated, and the organic layer is washed with H₂O, brine, dried over Na₂SO₄, filtered, and concentrated in vacuo. The residue is purified by silica gel chromatography eluting with 0% to 100% EtOAc in DCM to afford the title compound (100 mg, 38.5%) as a tan solid. ES/MS m/z 783.4 [M+H]+.

Preparation 685 tert-Butyl 4-[4-[3-cyano-5-[2,2,2-trifluoro-1-(5-fluoro-2-pyridyl)ethoxy]imidazo[1,2-a]pyridin-7-yl]-5-methyl-triazol-1-yl]piperidine-1-carboxylate

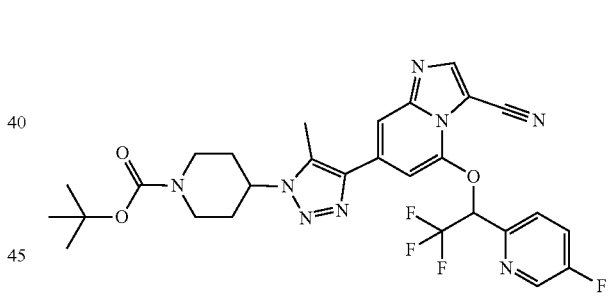

To tert-butyl 4-(4-[3-cyano-5-hydroxyimidazo[1,2-a]pyridin-7-yl]-5-methyl-1,2,3-triazol-1-yl)piperidine-1-carboxylate (600.00 mg, 1.42 mmol) and 2,2,2-trifluoro-1-(5-fluoropyridin-2-yl)ethyl trifluoromethanesulfonate (0.927 g, 2.83 mmol) in ACN (5.00 mL) is added K₂CO₃ (587.45 mg, 4.25 mmol) at RT under N₂. The resulting mixture is stirred at 80° C. for 3 hr. Upon cooling to RT, the aq. layer is extracted with EtOAc (3×5 mL). The combined organic layers are concentrated in vacuo. The residue is purified by reversed flash chromatography with the following conditions: Column, C18; eluting with a gradient of 50% to 60% ACN in water (0.1% NH₄HCO₃): UV 254 nm to afford the title compound as a white solid (450 mg, 52.88%). ES/MS m/z 601.3 [M+H]+.

Preparation 686 tert-Butyl 4-(4-[3-cyano-4-[2,2,2-trifluoro-1-(oxan-4-yl)ethoxy]pyrazolo[1,5-a]pyridin-6-yl]-5-methylpyrazol-1-yl)piperidine-1-carboxylate

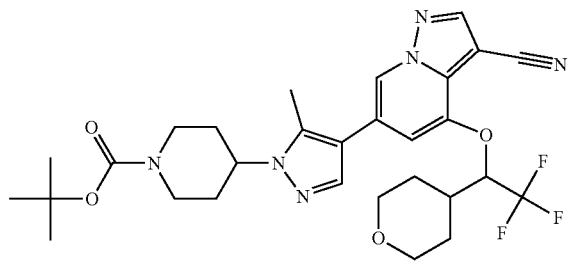 [SMILES: Cc1c(-c2cc(OC(C3CCOCC3)C(F)(F)F)c3c(C#N)cnn3c2)cnn1C1CCN(C(=O)OC(C)(C)C)CC1]

A stirred solution of 2,2,2-trifluoro-1-(oxan-4-yl)ethyl trifluoromethanesulfonate (204.12 mg, 0.65 mmol) and $K_2CO_3$ (267.64 mg, 1.94 mmol) in ACN (5.00 mL) is treated with tert-butyl 4-(4-[3-cyano-4-hydroxypyrazolo[1,5-a]pyridin-6-yl]-5-methylpyrazol-1-yl)piperidine-1-carboxylate (300.00 mg, 0.71 mmol) at RT under $N_2$ and the mixture is stirred for 3 hrs at 80° C. under $N_2$. The solution is filtered, the filter cake is washed with DCM (2×10 mL), and the filtrate is concentrated under reduced pressure. The residue is purified by reverse Combi-flash chromatography with the following conditions: Column, C18; ACN in $H_2O$, eluting with a gradient of 60% to 65% to give the title compound as a yellow solid (320 mg, 84.22%). ES/MS m/z 589.1 [M+H]$^+$.

The following compounds are prepared essentially as described for tert-butyl 4-(4-[3-cyano-4-[2,2,2-trifluoro-1-(oxan-4-yl)ethoxy]pyrazolo[1,5-a]pyridin-6-yl]-5-methylpyrazol-1-yl)piperidine-1-carboxylate using the appropriate reagents, adjusting the reaction times to determine completion of the reactions, and adjusting the purification system as appropriate. The filter cake can also be washed with EtOAc.

TABLE 48

| Prep No. | Chemical Name | Structure | ES/MS m/z [M + H]$^+$ |
|---|---|---|---|
| 687[1] | tert-Butyl 4-(4-[3-cyano-4-[(1S)-2,2,2-trifluoro-1-(pyridin-2-yl)ethoxy]pyrazolo[1,5-a]pyridin-6-yl]-5-methyl-1,2,3-triazol-1-yl)piperidine-1-carboxylate | 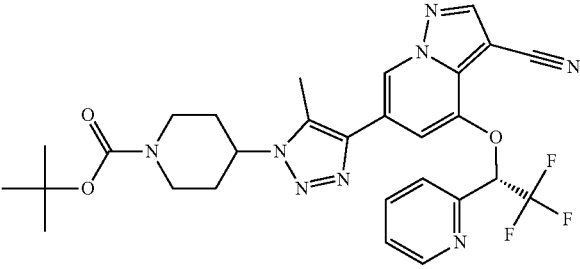 [SMILES: Cc1c(-c2cc(O[C@@H](c3ccccn3)C(F)(F)F)c3c(C#N)cnn3c2)nnn1C1CCN(C(=O)OC(C)(C)C)CC1] | 583.4 |
| 688 | tert-Butyl 4-(4-(3-cyano-4-((6,6-difluoro-6,7-dihydro-5H-cyclopenta[b]pyridin-7-yl)oxy)pyrazolo[1,5-a]pyridin-6-yl)-5-methyl-1H-1,2,3-triazol-1-yl)piperidine-1-carboxylate | 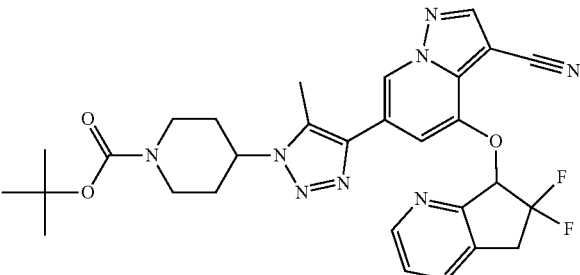 | 577.3 |
| 689[2] | tert-Butyl 4-[4-[3-cyano-5-[(6,6-difluoro-5,7-dihydrocyclopenta[b]pyridin-7-yl)oxy]imidazo[1,2-a]pyridin-7-yl]-5-methyl-triazol-1-yl]piperidine-1-carboxylate | 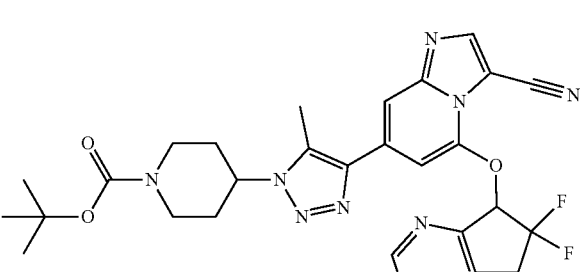 | 577.1 |

[1] After stirring, the solution is cooled to RT, diluted with EtOAc (50 mL), washed with brine (2 × 20 mL), dried over anhydrous $Na_2SO_4$, filtered, and the filtrate is concentrated under reduced pressure.

[2] Purified by reverse phase chromatography: Column, C18; eluting with 55% to 60% ACN in $H_2O$ (0.1% $NH_4HCO_3$).

Preparation 690 tert-Butyl 4-[4-[4-[(1R)-1-(2-cyanophenyl)ethoxy]pyrazolo[1,5-a]pyridin-6-yl]-5-methyl-pyrazol-1-yl]piperidine-1-carboxylate

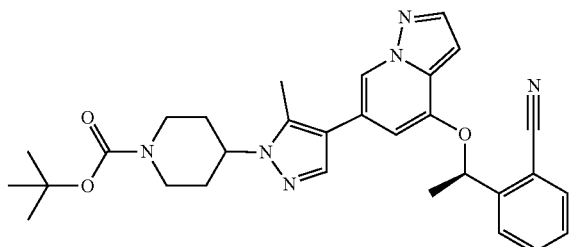

A mixture of tert-butyl 4-(4-[4-[(1R)-1-(2-bromophenyl)ethoxy]pyrazolo[1,5-a]pyridin-6-yl]-5-methylpyrazol-1-yl)piperidine-1-carboxylate (550 mg, 0.94 mmol), Zn(CN)$_2$ (334 mg, 2.84 mmol), Zn (62 mg, 0.95 mmol), X-Phos (226 mg, 0.47 mmol) and Pd$_2$(dba)$_3$ (434 mg, 0.47 mmol) in DMA (100 mL) is stirred overnight at 100° C. under N$_2$. Upon cooling to RT, the reaction is extracted with EtOAc (500 mL). The organic layer is washed with brine (100 mL), dried over Na$_2$SO$_4$, filtered, and concentrated in vacuo. The residue is purified by flash silica gel chromatography eluting with 10% to 100% EtOAc in PE to afford the title compound as a yellow solid (390 mg, 78%). ES/MS m/z 527.3 [M+H]$^+$.

Preparation 691 tert-Butyl 4-[4-[3-cyano-4-((1S)-2,2,2-trifluoro-1-phenyl-ethoxy)pyrazolo[1,5-a]pyridin-6-yl]-5-methyl-1,2,3-triazol-1-yl]piperidine-1-carboxylate

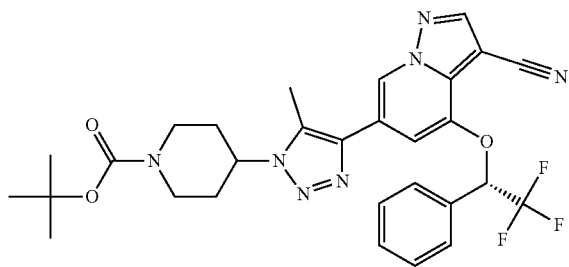 [SMILES: Cc1c(-c2cc(O[C@@H](c3ccccc3)C(F)(F)F)c3c(C#N)cnn3c2)nnn1C1CCN(C(=O)OC(C)(C)C)CC1]

tert-Butyl 4-(4-[3-cyano-4-hydroxypyrazolo[1,5-a]pyridin-6-yl]-5-methyl-1H-1,2,3-triazol-1-yl)piperidine-1-carboxylate (250 mg, 590 µmol), (R)-2,2,2-trifluoro-1-phenylethan-1-ol (208 mg, 1.18 mmol), PPh$_3$ (310 mg, 1.18 mmol), DCM (4 ml), and di-tert-butyl (E)-diazene-1,2-dicarboxylate (299 mg, 1.30 mmol) are sequentially added together and the mixture is stirred for 2 hrs at 50° C. The mixture is concentrated and diluted with NMP. The residue is purified using prep-HPLC, eluting with a gradient of ACN:H$_2$O (10-90%, 0.5% HCl) to give the title compound as a white solid (94 mg, 0.14 mmol, 23%). ES/MS m/z 582.4 [M+H]$^+$.

Preparation 692 tert-Butyl 4-[4-[4-[(1R)-1-(5-fluoro-2-pyridyl)ethoxy]-3-formyl-pyrazolo[1,5-a]pyridin-6-yl]-5-methyl-triazol-1-yl]piperidine-1-carboxylate

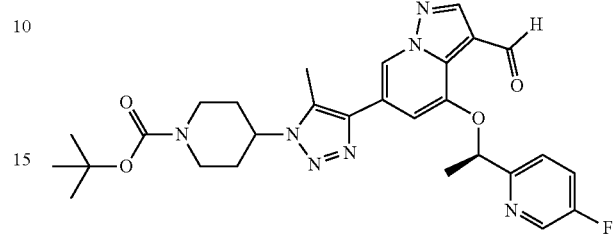

To ZnCl$_2$ (56.1 mg, 0.41 mmol) and NaH (32.9 mg, 60% wt, 0.82 mmol) in a sealed vial under N$_2$, tert-butyl (R)-4-(4-(3-cyano-4-(1-(5-fluoropyridin-2-yl)ethoxy)pyrazolo[1,5-a]pyridin-6-yl)-5-methyl-1H-1,2,3-triazol-1-yl)piperidine-1-carboxylate (150 mg, 0.27 mmol) in THF (3 mL) is added and the reaction mixture is stirred for 1.5 hr at 40° C. At this point, additional ZnCl$_2$ (56.1 mg, 0.41 mmol) and NaH (32.9 mg, 60% wt, 0.82 mmol) is added and continued stirring 1.5 hr at 40° C. The reaction is cooled to 0° C., silica (1.0 g) is added, diluted with hexanes (5 mL) and stirred for 1 hr at RT. The suspension is filtered, washing with EtOAc followed by 20% MeOH in DCM and concentrating in vacuo. The residue is purified by reverse phase C18 chromatography eluting with a linear gradient of 10% to 100% ACN in H$_2$O to afford the title compound (30 mg, 20%) as off-white solid. ES/MS 550.8 m/z [M+H]$^+$.

Preparation 693 tert-Butyl 4-[4-[4-[(1R)-1-(5-fluoro-2-pyridyl)ethoxy]-3-(hydroxymethyl)pyrazolo[1,5-a]pyridin-6-yl]-5-methyl-triazol-1-yl]piperidine-1-carboxylate

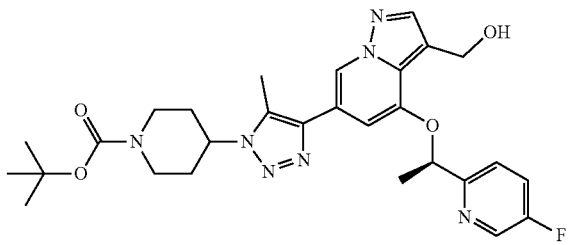 [SMILES: Cc1c(-c2cc(O[C@H](C)c3ccc(F)cn3)c3c(CO)cnn3c2)nnn1C1CCN(C(=O)OC(C)(C)C)CC1]

NaBH$_4$ (2.8 mg, 0.07 Mmol) is added to a solution of tert-butyl (R)-4-(4-(4-(1-(5-fluoropyridin-2-yl)ethoxy)-3-formylpyrazolo[1,5-a]pyridin-6-yl)-5-methyl-1H-1,2,3-triazol-1-yl)piperidine-1-carboxylate (20 mg, 0.04 mmol) in MeOH (3 mL) at RT. After stirring for 10 minutes the reaction is concentrated in vacuo. The residue is suspended in EtOAC and H$_2$O, layers are separated, and the aqueous layer is extracted with EtOAC (2x). Organic layers are combined, washed with brine, dried over Na$_2$SO$_4$ and concentrated in vacuo. The residue is used in a subsequent step without additional purification. ES/MS 553.8 m/z [M+H]$^+$.

Preparation 694 tert-Butyl 3-[4-[3-chloro-5-[(1R)-1-(2-pyridyl)ethoxy]imidazo[1,2-a]pyridin-7-yl]-5-methyl-triazol-1-yl]azetidine-1-carboxylate

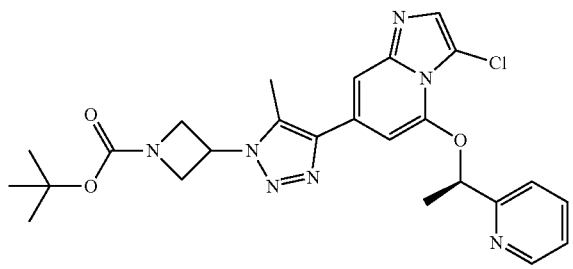 [SMILES: Cc1c(-c2cc(O[C@H](C)c3ccccn3)n3c(Cl)cnc3c2)nnn1C1CN(C(=O)OC(C)(C)C)C1]

To tert-butyl 3-[5-methyl-4-[5-[(1R)-1-(2-pyridyl)ethoxy]imidazo[1,2-a]pyridin-7-yl]triazol-1-yl]azetidine-1-carboxylate (200.00 mg, 0.421 mmol) in DMF (2.00 mL) is added 1,3-dichloro-5,5-dimethylimidazolidine-2,4-dione (41.43 mg, 0.21 mmol) at RT under $N_2$. The reaction is stirred at RT for 2 hr, quenched with $H_2O$ (10 mL) and extracted with DCM (2×10 mL). The combined organic layers are washed with brine (2×10 mL), dried over $Na_2SO_4$, and filtered. The filtrate is concentrated in vacuo. The residue is purified by Prep-TLC (5% MeOH in DCM) to afford the title compound as a yellow solid (140 mg, 65.27%). ES/MS, m/z 510.0 [M+H]$^+$.

Preparation 695 tert-Butyl 4-[4-[4-[2-[tert-butyl(dimethyl)silyl]oxy-1-(2-pyridyl)ethoxy]-3-chloro-pyrazolo[1,5-a]pyridin-6-yl]-5-methyl-triazol-1-yl]piperidine-1-carboxylate

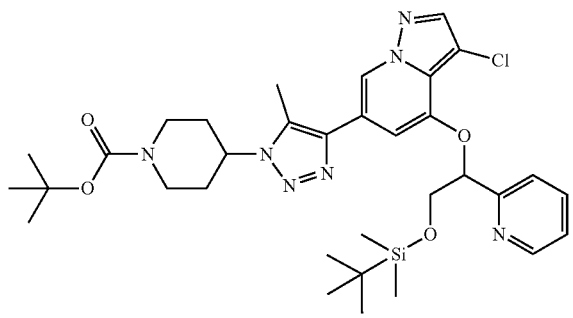 [SMILES: Cc1c(-c2cc(OC(CO[Si](C)(C)C(C)(C)C)c3ccccn3)c3c(Cl)cnn3c2)nnn1C1CCN(C(=O)OC(C)(C)C)CC1]

A mixture of tert-butyl 4-(4-{4-[(1R)-2-[(tert-butyldimethylsilyl)oxy]-1-(pyridin-2-yl)ethoxy]pyrazolo[1,5-a]pyridin-6-yl}-5-methyl-1,2,3-triazol-1-yl)piperidine-1-carboxylate (770 mg, 1.22 mmol) and NCS (146 mg, 1.09 mmol) in DCM (10 mL) is stirred for 3 hr at RT under $N_2$. The reaction is diluted with $H_2O$ (30 mL), extracted with DCM (3×50 mL). The combined organic layers are washed with brine (2×50 mL), dried over $Na_2SO_4$, filtered, and concentrated in vacuo. The residue is purified by silica gel column chromatography, eluting with 50% PE in EA to afford the title compound (700 mg, 86.22%) as a light-yellow solid. %). ES/MS, m/z 668.4 [M+H]$^+$.

Preparation 696 tert-Butyl 4-[4-[5-[2-[tert-butyl(dimethyl)silyl]oxy-1-(5-fluoro-2-pyridyl)ethoxy]-3-chloro-imidazo[1,2-a]pyridin-7-yl]-5-methyl-triazol-1-yl]piperidine-1-carboxylate

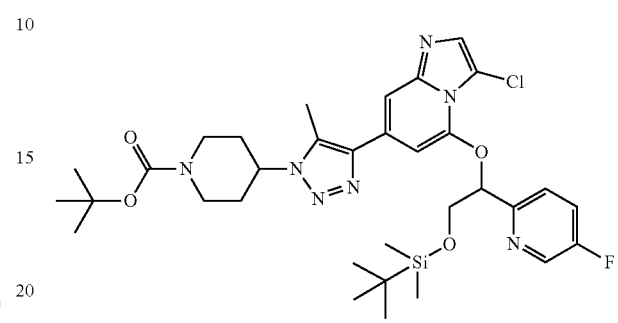

A mixture of tert-butyl 4-[4-[5-[2-[tert-butyl(dimethyl)silyl]oxy-1-(5-fluoro-2-pyridyl)ethoxy]imidazo[1,2-a]pyridin-7-yl]-5-methyl-triazol-1-yl]piperidine-1-carboxylate (1 g, 1.53 mmol) and 1,3-dichloro-5,5-dimethylimidazolidine-2,4-dione (0.272 g, 1.38 mmol) in DCM (10 mL) is stirred at RT for 2 hr under $N_2$. The reaction is quenched with $H_2O$ (20 mL) then extracted with DCM (2×40 mL). The combined organic layers are washed with brine (2×20 mL), dried over $Na_2SO_4$, filtered, and concentrated in vacuo. The residue is purified by silica gel column chromatography, eluting with PE/EtOAc (2:1-1:1) to afford the title compound as an off-white solid (460 mg, 43.69%). ES/MS m/z 686.3 [M+H]$^+$.

Preparation 697 tert-Butyl 4-[4-[4-[2-[tert-butyl(dimethyl)silyl]oxy-1-(5-fluoro-2-pyridyl)ethoxy]-3-chloro-pyrazolo[1,5-a]pyridin-6-yl]-5-methyl-triazol-1-yl]piperidine-1-carboxylate

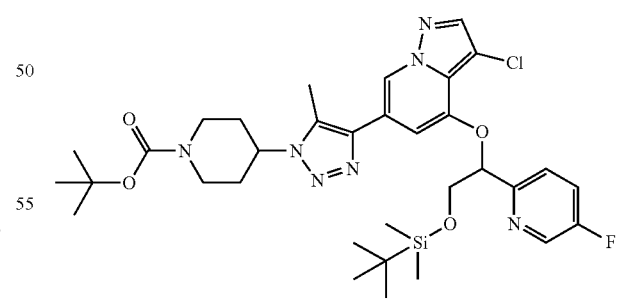

To tert-butyl 4-[4-[4-[2-[tert-butyl(dimethyl)silyl]oxy-1-(5-fluoro-2-pyridyl)ethoxy]pyrazolo[1,5-a]pyridin-6-yl]-5-methyl-triazol-1-yl]piperidine-1-carboxylate (330 mg, 0.51 mmol) in DCM (5 mL) is added NCS (64.22 mg, 0.481 mmol) at RT under $N_2$. The reaction is concentrated in vacuo and the residue is purified by reverse phase chromatography with the following conditions: Column, C18; eluting with 65% to 75% ACN in H₂O (0.1% FA) to give the title compound (185 mg, 53.25%) as a light-yellow oil. ES/MS m/z 686.0 [M+H]⁺.

The following compounds are prepared essentially as described for tert-butyl 4-[4-[4-[2-[tert-butyl(dimethyl)silyl]oxy-1-(5-fluoro-2-pyridyl)ethoxy]-3-chloro-pyrazolo[1,5-a]pyridin-6-yl]-5-methyl-triazol-1-yl]piperidine-1-carboxylate using the appropriate reagents, adjusting the reaction times to determine completion of the reactions, and adjusting the purification system as appropriate.

TABLE 49

| Prep No. | Chemical Name | Structure | ES/MS m/z [[M + H]⁺ |
|---|---|---|---|
| 698[1] | Cis-tert-Butyl 4-[3-[4-[4-[2-[tert-butyl(dimethyl)silyl]oxy-1-(5-fluoro-2-pyridyl)ethoxy]-3-chloro-pyrazolo[1,5-a]pyridin-6-yl]-5-methyl-triazol-1-yl]cyclobutyl]piperazine-1-carboxylate | 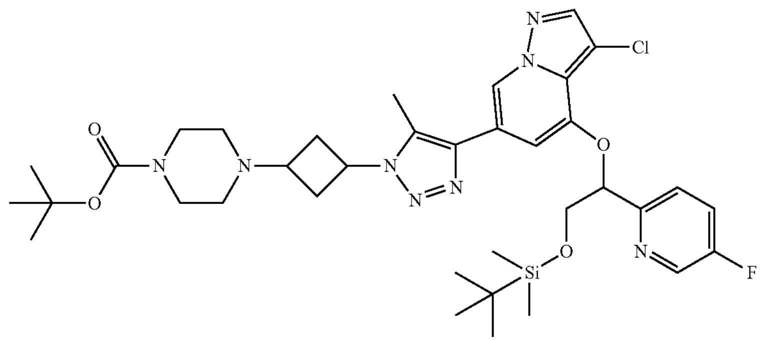 [SMILES: Cc1c(-c2cc(OC(CO[Si](C)(C)C(C)(C)C)c3ccc(F)cn3)c3c(Cl)cnn3c2)nnn1C1CC(N2CCN(C(=O)OC(C)(C)C)CC2)C1] | 741.3 |
| 699[2] | tert-Butyl 4-[4-[3-chloro-4-[2-cyano-1-(5-fluoro-2-pyridyl)-2-methyl-propoxy]pyrazolo[1,5-a]pyridin-6-yl]-5-methyl-triazol-1-yl]piperidine-1-carboxylate | 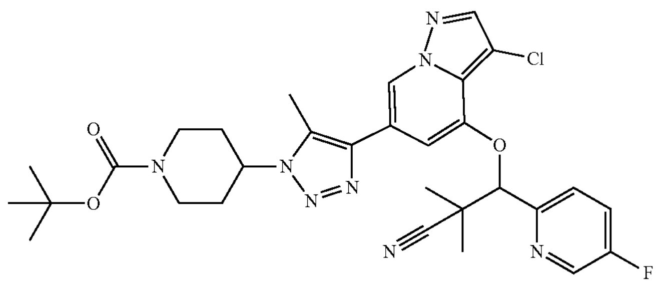 [SMILES: Cc1c(-c2cc(OC(c3ccc(F)cn3)C(C)(C)C#N)c3c(Cl)cnn3c2)nnn1C1CCN(C(=O)OC(C)(C)C)CC1] | [Cl³⁵/Cl³⁷] 553.8/555.7 (M-tBu) |
| 700 | tert-Butyl 4-[4-[4-[(1R)-1-(5-fluoro-2-pyridyl)ethoxy]-3-iodo-pyrazolo[1,5-a]pyridin-6-yl]-5-methyl-triazol-1-yl]piperidine-1-carboxylate | 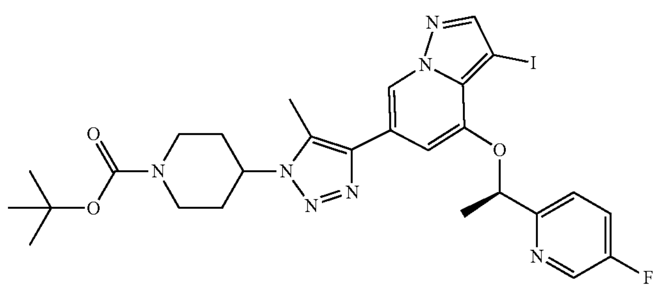 [SMILES: Cc1c(-c2cc(O[C@H](C)c3ccc(F)cn3)c3c(I)cnn3c2)nnn1C1CCN(C(=O)OC(C)(C)C)CC1] | 648.4 |
| 701[2] | tert-Butyl 4-[4-[3-bromo-4-[[(4R)-2,2-dimethyl-1,3-dioxolan-4-yl]-(5-fluoro-2-pyridyl)methoxy]pyrazolo[1,5-a]pyridin-6-yl]-5-methyl-triazol-1-yl]piperidine-1-carboxylate | 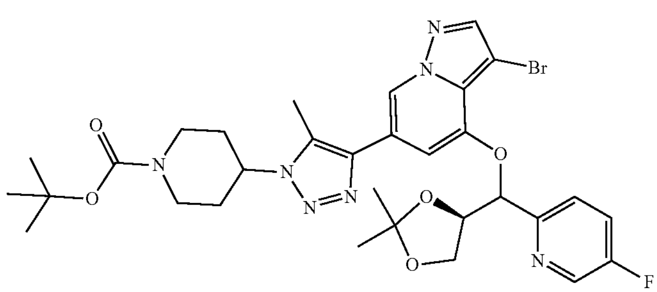 [SMILES: Cc1c(-c2cc(OC(c3ccc(F)cn3)[C@H]3COC(C)(C)O3)c3c(Br)cnn3c2)nnn1C1CCN(C(=O)OC(C)(C)C)CC1] | (⁷⁹Br/⁸¹Br) 685.6/ 687.6 |

TABLE 49-continued

| Prep No. | Chemical Name | Structure | ES/MS m/z [[M + H]+ |
|---|---|---|---|
| 702[3] | tert-Butyl 4-[4-[3-chloro-5-[(1R)-1-(5-fluoro-2-pyridyl)ethoxy]imidazo[1,2-c]pyrimidin-7-yl]-5-methyl-pyrazol-1-yl]piperidine-1-carboxylate | 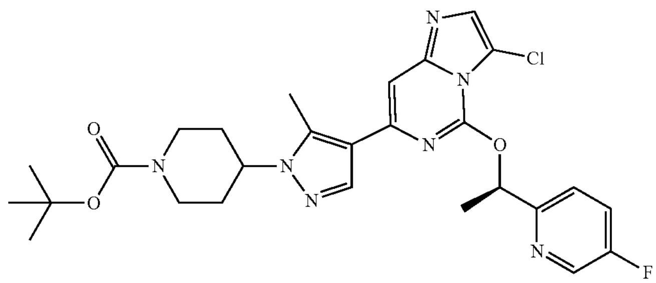 [SMILES: Cc1c(-c2cc3ncc(Cl)n3c(O[C@H](C)c3ccc(F)cn3)n2)cnn1C1CCN(C(=O)OC(C)(C)C)CC1] | 556.2 |
| 703[3] | tert-Butyl 4-[4-[5-[(1R)-1-(5-fluoro-2-pyridyl)ethoxy]-3-iodo-imidazo[1,2-c]pyrimidin-7-yl]-5-methyl-pyrazol-1-yl]piperidine-1-carboxylate | 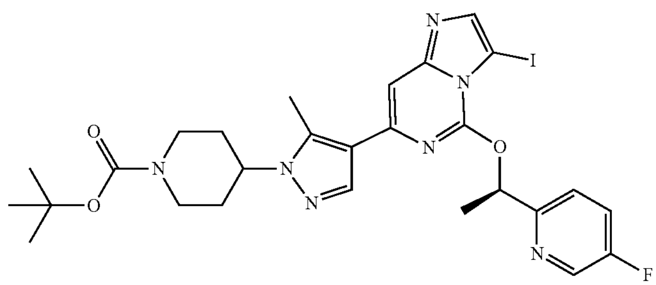 [SMILES: Cc1c(-c2cc3ncc(I)n3c(O[C@H](C)c3ccc(F)cn3)n2)cnn1C1CCN(C(=O)OC(C)(C)C)CC1] | 648.2 |
| 704[4] | tert-Butyl (3R,4S)-4-[4-[4-[2-[tert-butyl(dimethyl)silyl]oxy-1-(5-fluoro-2-pyridyl)ethoxy]-3-chloro-pyrazolo[1,5-a]pyridin-6-yl]-5-methyl-triazol-1-yl]-3-fluoro-piperidine-1-carboxylate, Isomer 2 | 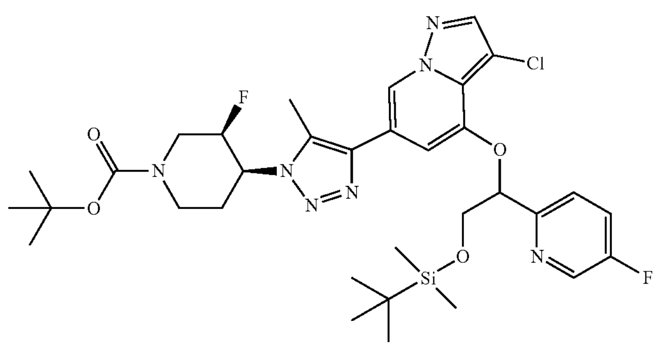 [SMILES: Cc1c(-c2cc(OC(CO[Si](C)(C)C(C)(C)C)c3ccc(F)cn3)c3c(Cl)cnn3c2)nnn1[C@H]1CCN(C(=O)OC(C)(C)C)C[C@H]1F] | 704.3 |
| 705[5] | tert-Butyl (3S,4S)-4-[4-[4-[2-[tert-butyl(dimethyl)silyl]oxy-1-(5-fluoro-2-pyridyl)ethoxy]-3-chloro-pyrazolo[1,5-a]pyridin-6-yl]-5-methyl-triazol-1-yl]-3-fluoro-piperidine-1-carboxylate, Isomer 2 | 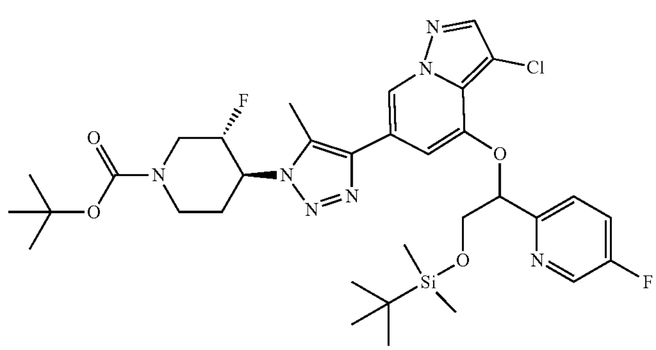 [SMILES: Cc1c(-c2cc(OC(CO[Si](C)(C)C(C)(C)C)c3ccc(F)cn3)c3c(Cl)cnn3c2)nnn1[C@H]1CCN(C(=O)OC(C)(C)C)C[C@@H]1F] | 704.2 |

TABLE 49-continued

| Prep No. | Chemical Name | Structure | ES/MS m/z [[M + H]+ |
|---|---|---|---|
| 706[4] | tert-Butyl (3S,4R)-4-[4-[4-[2-[tert-butyl(dimethyl)silyl]oxy-1-(5-fluoro-2-pyridyl)ethoxy]-3-chloro-pyrazolo[1,5-a]pyridin-6-yl]-5-methyl-triazol-1-yl]-3-fluoro-piperidine-1-carboxylate, Isomer 2 | 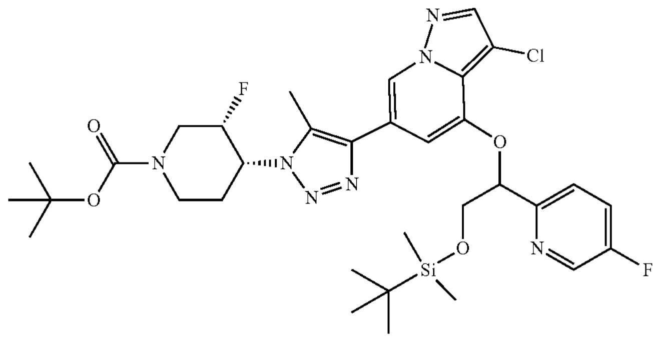 [SMILES: Cc1c(-c2cc(OC(CO[Si](C)(C)C(C)(C)C)c3ccc(F)cn3)c3c(Cl)cnn3c2)nnn1[C@@H]1CCN(C(=O)OC(C)(C)C)C[C@@H]1F] | 704.4 |
| 707[5] | tert-Butyl (3R,4R)-4-[4-[4-[2-[tert-butyl(dimethyl)silyl]oxy-1-(5-fluoro-2-pyridyl)ethoxy]-3-chloro-pyrazolo[1,5-a]pyridin-6-yl]-5-methyl-triazol-1-yl]-3-fluoro-piperidine-1-carboxylate, Isomer 2 | 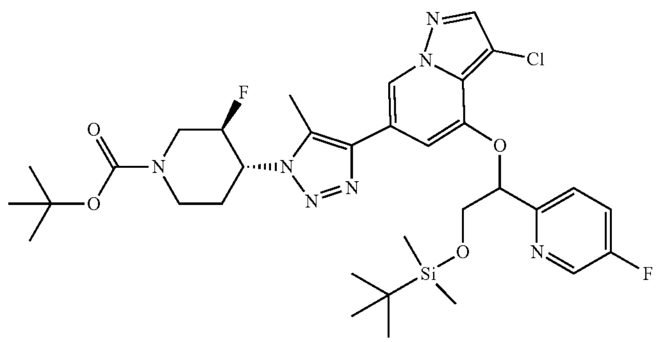 [SMILES: Cc1c(-c2cc(OC(CO[Si](C)(C)C(C)(C)C)c3ccc(F)cn3)c3c(Cl)cnn3c2)nnn1[C@@H]1CCN(C(=O)OC(C)(C)C)C[C@H]1F] | 704.4 |
| 708[5] | tert-Butyl (3S,4S)-4-[4-[4-[2-[tert-butyl(dimethyl)silyl]oxy-1-(5-fluoro-2-pyridyl)ethoxy]-3-chloro-pyrazolo[1,5-a]pyridin-6-yl]-5-methyl-triazol-1-yl]-3-hydroxy-piperidine-1-carboxylate, Isomer 2 | 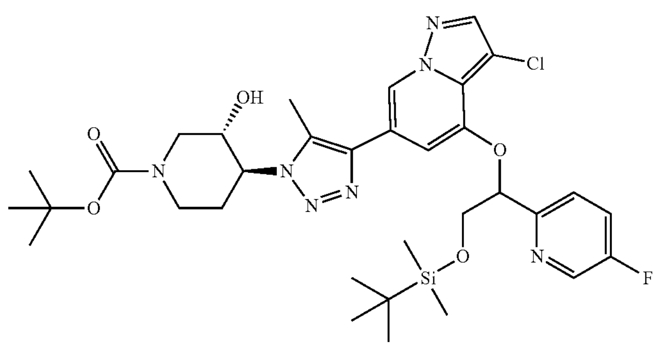 [SMILES: Cc1c(-c2cc(OC(CO[Si](C)(C)C(C)(C)C)c3ccc(F)cn3)c3c(Cl)cnn3c2)nnn1[C@H]1CCN(C(=O)OC(C)(C)C)C[C@@H]1O] | 702.4 |
| 709[5] | tert-Butyl (3R,4S)-4-[4-[4-[2-[tert-butyl(dimethyl)silyl]oxy-1-(5-fluoro-2-pyridyl)ethoxy]-3-chloro-pyrazolo[1,5-a]pyridin-6-yl]-5-methyl-triazol-1-yl]-3-hydroxy-piperidine-1-carboxylate, Isomer 2 | 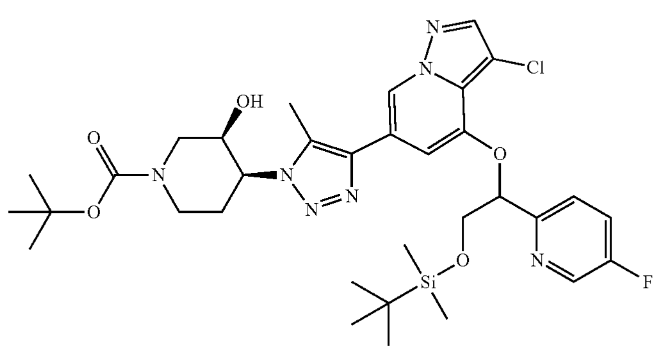 [SMILES: Cc1c(-c2cc(OC(CO[Si](C)(C)C(C)(C)C)c3ccc(F)cn3)c3c(Cl)cnn3c2)nnn1[C@H]1CCN(C(=O)OC(C)(C)C)C[C@H]1O] | 702.2 |

TABLE 49-continued

| Prep No. | Chemical Name | Structure | ES/MS m/z [[M + H]+ |
|---|---|---|---|
| 710[6] | tert-Butyl (3S,4R)-4-[4-[4-[2-[tert-butyl(dimethyl)silyl]oxy-1-(5-fluoro-2-pyridyl)ethoxy]-3-chloro-pyrazolo[1,5-a]pyridin-6-yl]-5-methyl-triazol-1-yl]-3-hydroxy-piperidine-1-carboxylate, Isomer 2 | 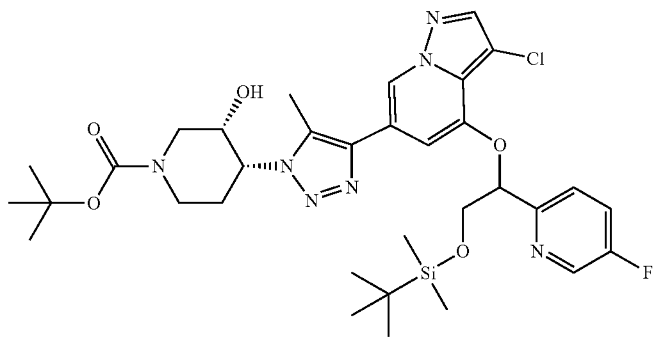 [SMILES: Cc1c(-c2cc(OC(CO[Si](C)(C)C(C)(C)C)c3ccc(F)cn3)c3c(Cl)cnn3c2)nnn1[C@@H]1CCN(C(=O)OC(C)(C)C)C[C@@H]1O] | 702.4 |
| 711[7] | tert-Butyl (3R,4R)-4-[4-[4-[2-[tert-butyl(dimethyl)silyl]oxy-1-(5-fluoro-2-pyridyl)ethoxy]-3-chloro-pyrazolo[1,5-a]pyridin-6-yl]-5-methyl-triazol-1-yl]-3-hydroxy-piperidine-1-carboxylate, Isomer 2 | 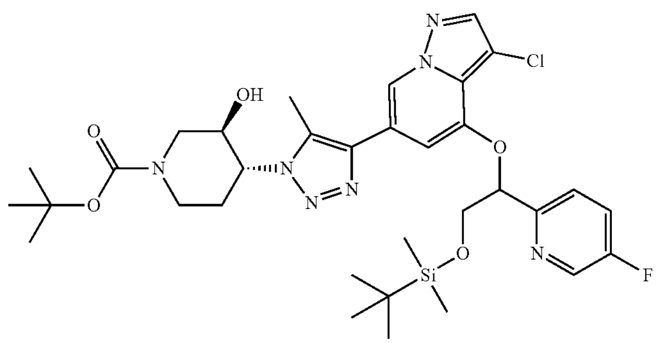 [SMILES: Cc1c(-c2cc(OC(CO[Si](C)(C)C(C)(C)C)c3ccc(F)cn3)c3c(Cl)cnn3c2)nnn1[C@@H]1CCN(C(=O)OC(C)(C)C)C[C@H]1O] | 702.4 |
| 712[5] | tert-butyl (3RS,4RS)-4-[4-[4-2-[tert-butyl(dimethyl)silyl]oxy-1-(5-fluoro-2-pyridyl)ethoxy]-3-chloro-pyrazolo[1,5-a]pyridin-6-yl]-5-methyl-triazol-1-yl]-3-methyl-piperidine-1-carboxylate, Isomer 2 | 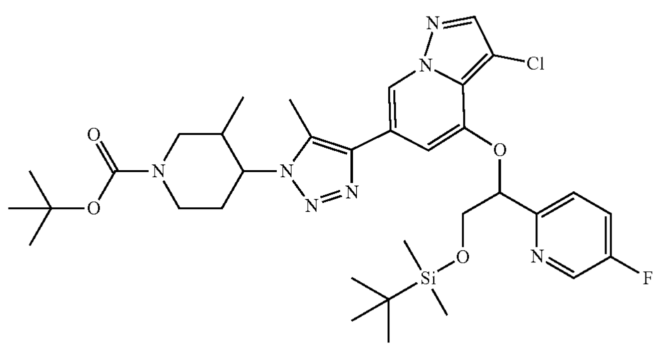 [SMILES: Cc1c(-c2cc(OC(CO[Si](C)(C)C(C)(C)C)c3ccc(F)cn3)c3c(Cl)cnn3c2)nnn1C1CCN(C(=O)OC(C)(C)C)CC1C] | 700.2 |
| 713[5] | tert-butyl (3RS,4SR)-4-[4-[4-[2-[tert-butyl(dimethyl)silyl]oxy-1-(5-fluoro-2-pyridyl)ethoxy]-3-chloro-pyrazolo[1,5-a]pyridin-6-yl]-5-methyl-triazol-1-yl]-3-methyl-piperidine-1-carboxylate, Isomer 2 | 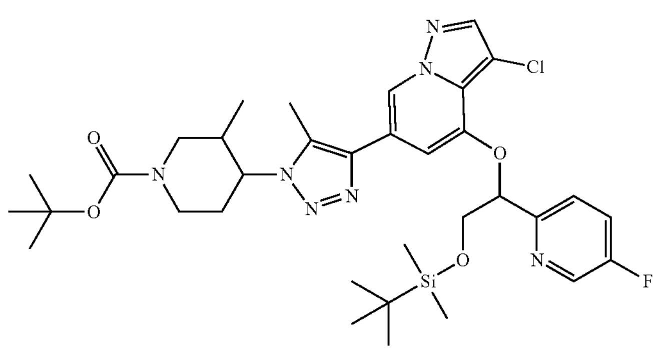 [SMILES: Cc1c(-c2cc(OC(CO[Si](C)(C)C(C)(C)C)c3ccc(F)cn3)c3c(Cl)cnn3c2)nnn1C1CCN(C(=O)OC(C)(C)C)CC1C] | 700.2 |

[1]Purified by reverse phase chromatography with the following conditions: Column, C18 eluting with 70% to 80% ACN in H₂O (0.1% NH₄HCO₃).
[2]Purified by reverse phase chromatography with the following conditions: Column, C18; eluting with 10% to 100% ACN in H₂O.
[3]Purified by silica gel chromatography, eluting with 0% to 100% EtOAc in DCM.
[4]Purified by silica gel chromatography, eluting with PE:EA (1:2).
[5]Purified by Prep-TLC PE:EA (2:1).
[6]Purified by silica gel chromatography, eluting with PE:EA (1:1:1:2).
[7]Purified by Prep-TLC PE:EA (1:1).

Preparation 714 tert-Butyl 4-[4-[3-cyano-5-[(1R)-1-(5-fluoro-2-pyridyl)ethoxy]imidazo[1,2-c]pyrimidin-7-yl]-5-methyl-pyrazol-1-yl]piperidine-1-carboxylate

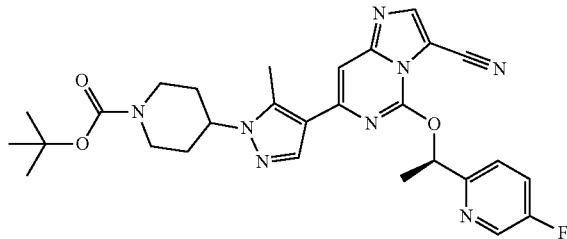 [SMILES: Cc1c(-c2cc3ncc(C#N)n3c(O[C@H](C)c3ccc(F)cn3)n2)cnn1C1CCN(C(=O)OC(C)(C)C)CC1]

A solution of tert-butyl 4-[4-[5-[(1R)-1-(5-fluoro-2-pyridyl)ethoxy]-3-iodo-imidazo[1,2-c]pyrimidin-7-yl]-5-methyl-pyrazol-1-yl]piperidine-1-carboxylate (74.0 mg, 0.11 mmol) and CuCN (11.0 mg, 0.13 mmol) in DMF (2.5 mL) is stirred at 100° C. for 1 hr. Upon cooling to RT, the reaction is quenched with aq. NH$_4$OH and extracted with EtOAc. The organic layer is washed with H$_2$O, brine, dried over Na$_2$SO$_4$, filtered and concentrated in vacuo. The residue is purified by silica gel chromatography eluting with 0% to 100% EtOAc in DCM to afford the title compound (57 mg, 91%) as a colorless foam. ES/MS m/z 547.2 [M+H]$^+$.

Preparation 715 tert-Butyl 4-[4-[3-cyano-4-[1-[2-(1-hydroxy-1-methyl-ethyl)phenyl]ethoxy]pyrazolo[1,5-a]pyridin-6-yl]-5-methyl-triazol-1-yl]piperidine-1-carboxylate

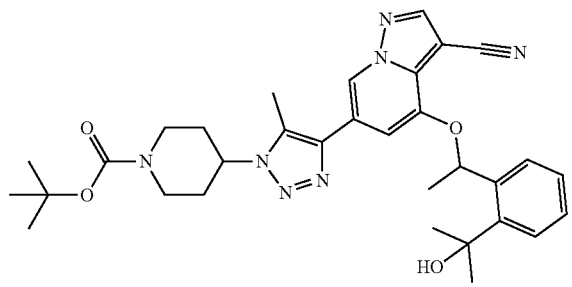 [SMILES: Cc1c(-c2cc(OC(C)c3ccccc3C(C)(C)O)c3c(C#N)cnn3c2)nnn1C1CCN(C(=O)OC(C)(C)C)CC1]

A solution of MeMgBr (178 mg, 3 molar, 1.50 mmol) in THF is added dropwise to a solution of tert-butyl 4-(4-(3-cyano-4-(1-(2-(methoxycarbonyl)phenyl)ethoxy) pyrazolo[1,5-a]pyridin-6-yl)-5-methyl-1H-1,2,3-triazol-1-yl)piperidine-1-carboxylate (292 mg, 0.50 mmol) in THF (3 mL) at 0° C. The reaction is stirred for 2 hr at 0° C. H$_2$O (3 mL) is slowly added, and the mixture is allowed warm to RT. The mixture is diluted with DCM (20 mL) and H$_2$O (20 mL) and the layers are separated. The aqueous layer is extracted with DCM (20 mL). The combined organic layers are concentrated in vacuo. The residue is purified by reverse phase chromatography eluting with a gradient of 0% to 100% ACN in H$_2$O to afford the title compound (192 mg, 65.7%). ES/MS m/z 585.8 [M+H]$^+$.

Preparation of 716

2-[1-[6-[1-(1-tert-Butoxycarbonyl-4-piperidyl)-5-methyl-triazol-4-yl]-3-cyano-pyrazolo[1,5-a]pyridin-4-yl]oxyethyl]benzoic acid

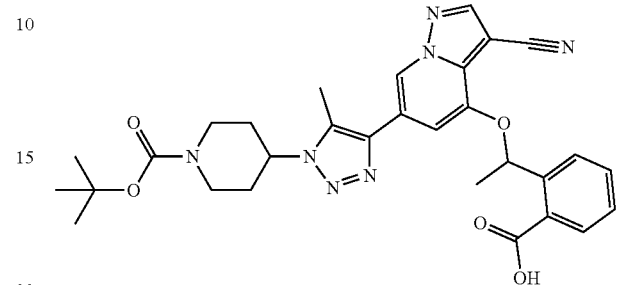

To tert-butyl 4-(4-(3-cyano-4-(1-(2-(methoxycarbonyl) phenyl) ethoxy)pyrazolo[1,5-a]pyridin-6-yl)-5-methyl-1H-1,2,3-triazol-1-yl)piperidine-1-carboxylate (274 mg, 468 µmol) in THF (12 mL) is added an aq. solution of LiOH (112 mg, 4.68 mmol) and the mixture is stirred for 3 hr. The pH is adjusted to 5 using aq. HCl (0.1 M) then EtOAc (10 mL) is added. The layers are separated and the aq. phase is extracted with EtOAc (3×10 mL). The combined organics are dried over Na$_2$SO$_4$, filtered, and concentrated in vacuo to afford the title compound (260 mg, 97.2%). ES/MS m/z 572.2 [M+H]f.

Preparation 717 tert-Butyl 4-[4-[4-[1-(2-carbamoylphenyl)ethoxy]-3-cyano-pyrazolo[1,5-a]pyridin-6-yl]-5-methyl-triazol-1-yl]piperidine-1-carboxylate

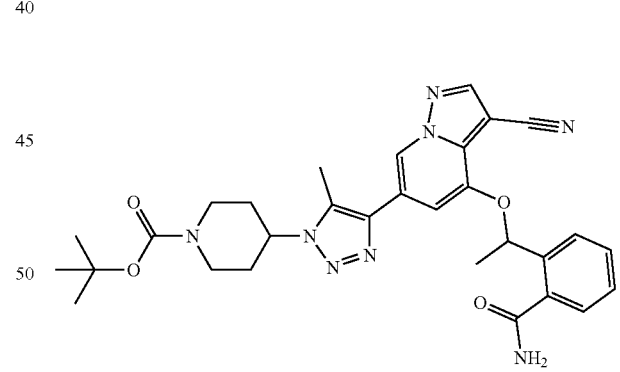

To 2-(1-((6-(1-(1-(tert-butoxycarbonyl)piperidin-4-yl)-5-methyl-1H-1,2,3-triazol-4-yl)-3-cyanopyrazolo[1,5-a]pyridin-4-yl)oxy)ethyl)benzoic acid (260 mg, 455 µmol) and NH$_4$Cl (122 mg, 2.27 mmol) in DMF (4 mL) is added T3P (868 mg, 50% Wt, 1.36 mmol) in DMF, followed by DIEA (588 mg, 4.55 mmol) and the reaction is stirred for 3 hr. The mixture is diluted with DCM (10 mL) and H$_2$O (10 mL) and the layers are separated. The aq. layer is extracted with DCM (3×10 mL) and the combined organics are concentrated in vacuo. The residue is purified by reverse phase chromatography eluting with 0% to 100% ACN in H$_2$O to afford the title compound (80 mg, 31%). ES/MS m/z 571.3 [M+H]$^+$.

Preparation 718 tert-Butyl 4-[4-[4-[(1R)-1-(5-fluoro-2-pyridyl)ethoxy]-3-isothiazol-4-yl-pyrazolo[1,5-a]pyridin-6-yl]-5-methyl-triazol-1-yl]piperidine-1-carboxylate

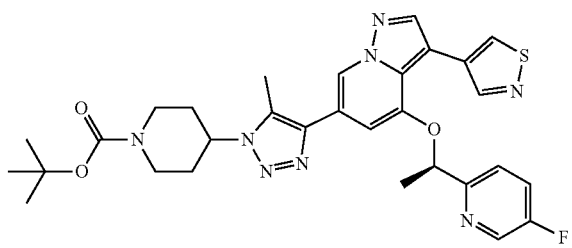 [SMILES: Cc1c(-c2cc(O[C@H](C)c3ccc(F)cn3)c3c(-c4cnsc4)cnn3c2)nnn1C1CCN(C(=O)OC(C)(C)C)CC1]

A mixture of tert-butyl 4-[4-[4-[(1R)-1-(5-fluoro-2-pyridyl)ethoxy]-3-iodo-pyrazolo[1,5-a]pyridin-6-yl]-5-methyl-triazol-1-yl]piperidine-1-carboxylate (600 mg, 0.93 mmol), 4-(4,4,5,5-tetramethyl-1,3,2-dioxaborolan-2-yl)-1,2-thiazole (293 mg, 1.39 mmol), CsF (422 mg, 2.78 mmol) and Pd(DtBPF)Cl$_2$ (60.39 mg, 0.09 mmol) in dioxane (4 mL) is stirred for 3 hr at 60° C. under N$_2$. The reaction is concentrated in vacuo. The mixture is diluted with water (50 mL), extracted with EtOAc (2×50 mL). The combined organic layers are washed with brine (1×50 mL), dried over Na$_2$SO$_4$, filtered and the filtrate is concentrated in vacuo. The residue is purified by reverse phase chromatography using the following conditions: column, C18; mobile phase, eluting with a linear gradient of 30% to 50% ACN in H$_2$O to afford the title compound (400 mg, 71.4%) as a white solid. ES/MS m/z 605.5 [M+H]$^+$.

Preparation 719

7-[1-(Azetidin-3-yl)-5-methyl-triazol-4-yl]-3-chloro-5-[(1R)-1-(2-pyridyl)ethoxy]imidazo[1,2-a]pyridine. TFA

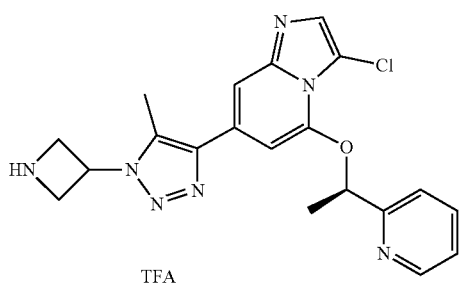 [SMILES: Cc1c(-c2cc(O[C@H](C)c3ccccn3)n3c(Cl)cnc3c2)nnn1C1CNC1]

To a stirred solution of tert-butyl 3-(4-[3-chloro-5-[(1R)-1-(pyridin-2-yl)ethoxy]imidazo[1,2-a]pyridin-7-yl]-5-methyl-1,2,3-triazol-1-yl)azetidine-1-carboxylate (140.00 mg, 0.28 mmol) in DCM (2.00 mL) is added TFA (1.00 mL) at RT under N$_2$. The reaction is stirred 1 hr at RT then concentrated in vacuo to afford the title compound (120 mg, crude) as a yellow solid, which is carried forward without a further purification. ES/MS m/z 410.0 [M+H]$^+$.

Preparation 720

4-[1-(5-Fluoro-2-pyridyl)-2-hydroxy-ethoxy]-6-[5-methyl-1-(4-piperidyl)pyrazol-4-yl]pyrazolo[1,5-a]pyridine-3-carbonitrile. HCl

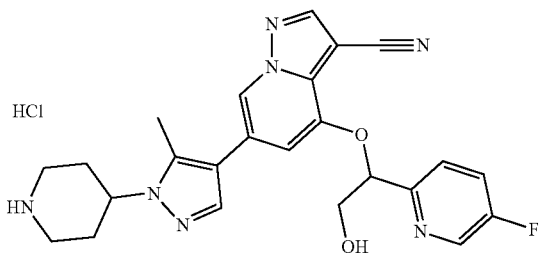 [SMILES: Cl ; Cc1c(-c2cc(OC(CO)c3ccc(F)cn3)c3c(C#N)cnn3c2)cnn1C1CCNCC1]

A mixture of tert-butyl 4-[4-[4-[2-[tert-butyl(dimethyl)silyl]oxy-1-(5-fluoro-2-pyridyl)ethoxy]-3-cyano-pyrazolo[1,5-a]pyridin-6-yl]-5-methyl-pyrazol-1-yl]piperidine-1-carboxylate (2.7 g, 4.00 mmol) in DCM (50 ml) and 4M HCl in 1,4-dioxane (25 mL) is stirred for 1 hr at RT under N$_2$. The resulting mixture is concentrated in vacuo to give the title compound (2.3 g, crude, HCl salt), which is carried forward without a further purification. ES/MS m/z 462.2 [M+H]$^+$.

Preparation 721

2-[3-Chloro-6-[5-methyl-1-(4-piperidyl)triazol-4-yl]pyrazolo[1,5-a]pyridin-4-yl]oxy-2-(5-fluoro-2-pyridyl)ethanol. HCl

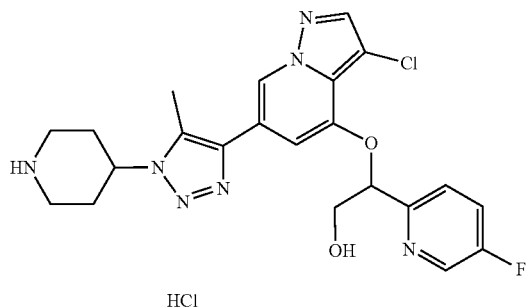 [SMILES: Cc1c(-c2cc(OC(CO)c3ccc(F)cn3)c3c(Cl)cnn3c2)nnn1C1CCNCC1 ; Cl]

A solution of tert-butyl 4-[4-[4-[2-[tert-butyl(dimethyl)silyl]oxy-1-(5-fluoro-2-pyridyl)ethoxy]-3-chloro-pyrazolo[1,5-a]pyridin-6-yl]-5-methyl-triazol-1-yl]piperidine-1-carboxylate (175 mg, 0.26 mmol) in DCM (3 mL) and 4M HCl in 1,4-dioxane (1.5 mL) is stirred at RT for 1 hr under N$_2$. The resulting mixture is concentrated in vacuo to give the title compound (165 mg) which is carried forward without a further purification. ES/MS m/z 472.2 [M+H]$^+$.

Preparation 722

2-[3-Chloro-7-[5-methyl-1-(4-piperidyl)triazol-4-yl]imidazo[1,2-a]pyridin-5-yl]oxy-2-(5-fluoro-2-pyridyl)ethanol. HCl

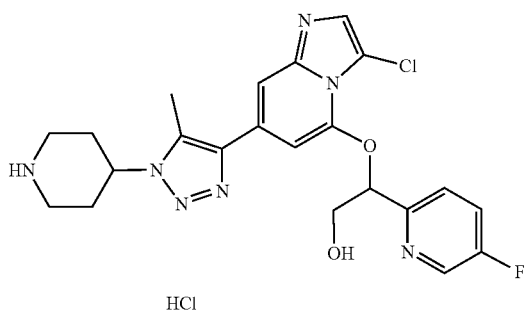 [SMILES: Cc1c(-c2cc(OC(CO)c3ccc(F)cn3)n3c(Cl)cnc3c2)nnn1C1CCNCC1 ; Cl]

To tert-butyl 4-[4-[5-[2-[tert-butyl(dimethyl)silyl]oxy-1-(5-fluoro-2-pyridyl)ethoxy]-3-chloro-imidazo[1,2-a]pyridin-7-yl]-5-methyl-triazol-1-yl]piperidine-1-carboxylate (450 mg, 0.66 mmol) in DCM (4 mL) is added 4M HCl in 1,4-dioxane (4 mL). After stirring 1 hr at RT the reaction is concentrated in vacuo to afford the title compound (300 mg, HCl salt) which is carried forward without a further purification. ES/MS m/z 472.2 [M+H]⁺.

The following compounds are prepared essentially as described for 2-[3-Chloro-7-[5-methyl-1-(4-piperidyl)triazol-4-yl]imidazo[1,2-a]pyridin-5-yl]oxy-2-(5-fluoro-2-pyridyl)ethanol HCl using the appropriate reagents, adjusting the reaction times to determine completion of the reactions, and adjusting the purification system as appropriate. For compounds where the amine salt was isolated, the formation of the mono-, di-, or trivalent salt is dependent on the pKa of the amine and the acid used to form the salt. The exact mono-, di-, or trivalent salt form for each example was not identified.

TABLE 50

| Prep No. | Chemical Name | Structure | ES/MS m/z [M + H]⁺ |
|---|---|---|---|
| 723 | 4-[1-(5-Fluoro-2-pyridyl)-3-hydroxy-propoxy]-6-[5-methyl-1-(4-piperidyl)triazol-4-yl]pyrazolo[1,5-a]pyridine-3-carbonitrile. HCl | 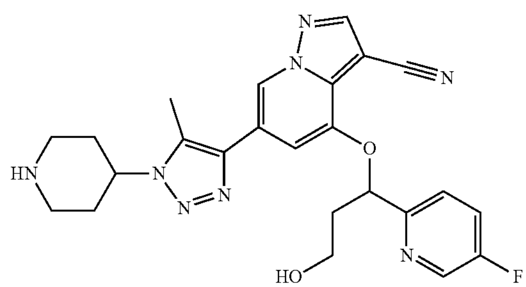 | 477.4 |
| 724 | 5-[2-Hydroxy-1-[5-(trifluoromethyl)-3-pyridyl]ethoxy]-7-[5-methyl-1-(4-piperidyl)triazol-4-yl]imidazo[1,2-a]pyridine-3-carbonitrile. HCl | 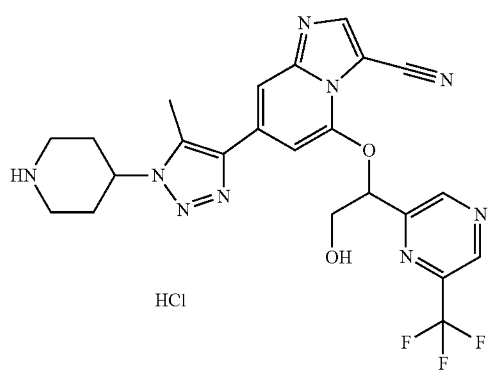 [SMILES: Cc1c(-c2cc(OC(CO)c3cncc(C(F)(F)F)n3)n3c(C#N)cnc3c2)nnn1C1CCNCC1 ; Cl] | 513.3 |
| 725 | 5-[1-(3,5-Difluoro-2-pyridyl)-2-hydroxy-ethoxy]-7-[5-methyl-1-(4-piperidyl)triazol-4-yl]imidazo[1,2-a]pyridine-3-carbonitrile. HCl | 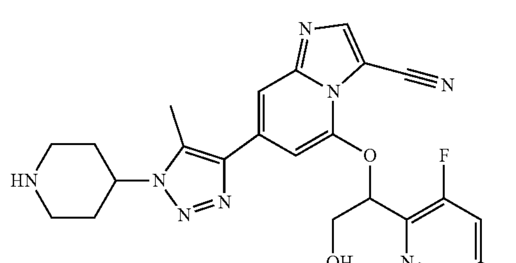 | 481.1 |

TABLE 50-continued

| Prep No. | Chemical Name | Structure | ES/MS m/z [M + H]+ |
|---|---|---|---|
| 726 | 7-[1-(7-Azaspiro[3.5]nonan-2-yl)-5-methyl-triazol-4-yl]-5-[1-(5-fluoro-2-pyridyl)-2-hydroxy-ethoxy]imidazo[1,2-a]pyridine-3-carbonitrile. HCl | 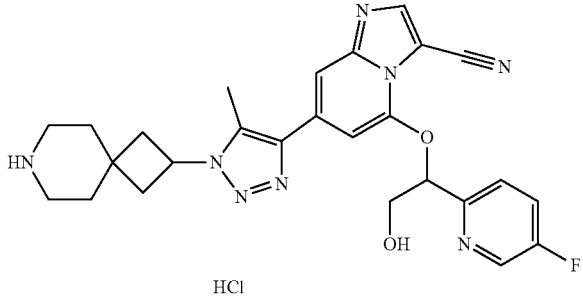 [SMILES: Cc1c(-c2cc(OC(CO)c3ccc(F)cn3)n3c(C#N)cnc3c2)nnn1C1CC2(CCNCC2)C1 ; Cl] | 503.3 |
| 727 | 4-[1-(5-Fluoro-2-pyridyl)-2-hydroxy-ethoxy]-6-[5-methyl-1-(4-piperidyl)triazol-4-yl]pyrazolo[1,5-a]pyridine-3-carbonitrile. HCl | 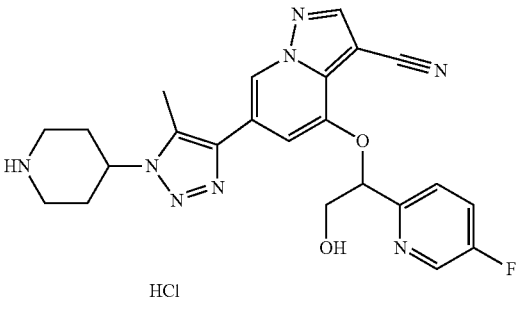 [SMILES: Cc1c(-c2cc(OC(CO)c3ccc(F)cn3)c3c(C#N)cnn3c2)nnn1C1CCNCC1 ; Cl] | 463.1 |
| 728 | 4-[2-Hydroxy-1-[5-(trifluoromethyl)-3-pyridyl]ethoxy]-6-[5-methyl-1-(4-piperidyl)triazol-4-yl]pyrazolo[1,5-a]pyridine-3-carbonitrile. HCl | 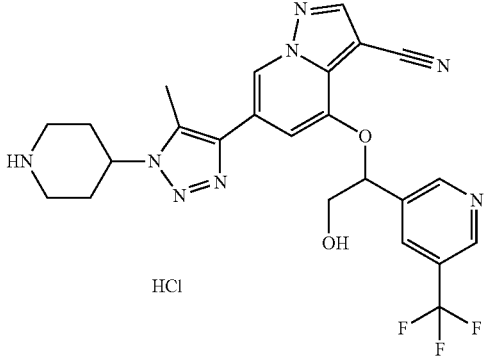 [SMILES: Cc1c(-c2cc(OC(CO)c3cncc(C(F)(F)F)c3)c3c(C#N)cnn3c2)nnn1C1CCNCC1 ; Cl] | 513.3 |
| 729 | 5-[1-(5-Fluoro-2-pyridyl)-3-hydroxy-propoxy]-7-[5-methyl-1-(4-piperidyl)triazol-4-yl]imidazo[1,2-a]pyridine-3-carbonitrile. HCl | 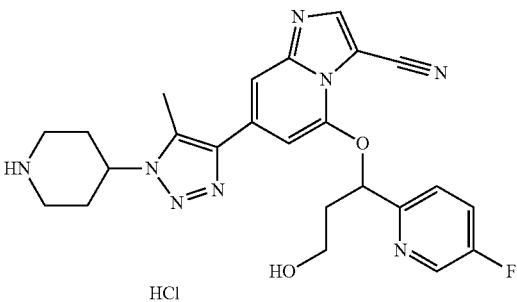 [SMILES: Cc1c(-c2cc(OC(CCO)c3ccc(F)cn3)n3c(C#N)cnc3c2)nnn1C1CCNCC1 ; Cl] | 477.2 |

TABLE 50-continued

| Prep No. | Chemical Name | Structure | ES/MS m/z [M + H]+ |
|---|---|---|---|
| 730 | 6-[1-(7-Azaspiro[3.5]nonan-2-yl)-5-methyl-pyrazol-4-yl]-4-[1-(5-fluoro-2-pyridyl)-2-hydroxy-ethoxy]pyrazolo[1,5-a]pyridine-3-carbonitrile.HCl | 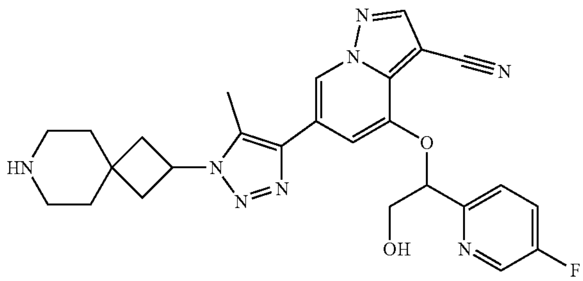 | 502.3 |
| 731 | 2-[3-Fluoro-6-[5-methyl-1-(4-piperidyl)triazol-4-yl]pyrazolo[1,5-a]pyridin-4-yl]oxy-2-(5-fluoro-2-pyridyl)ethanol HCl | 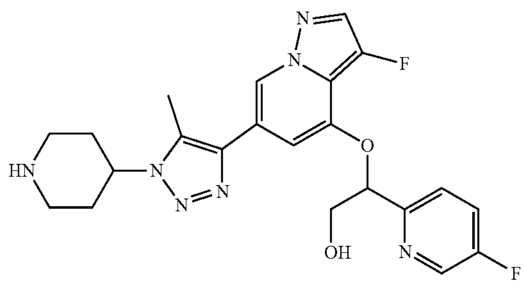 | 456.2 |
| 732 | 2-[3-Chloro-6-[5-methyl-1-(4-piperidyl)triazol-4-yl]pyrazolo[1,5-a]pyridin-4-yl]oxy-2-(2-pyridyl)ethanol HCl | 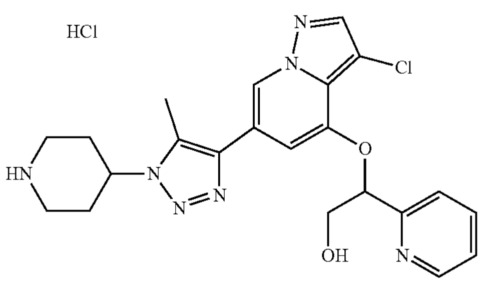 [SMILES: Cc1c(-c2cc(OC(CO)c3ccccn3)c3c(Cl)cnn3c2)nnn1C1CCNCC1 ; Cl] | 454.2 |
| 733 | 4-[1-[2-(3-Hydroxyazetidin-1-yl)-5-(trifluoromethyl)-3-pyridyl]ethoxy]-6-[5-methyl-1-(4-piperidyl)triazol-4-yl]pyrazolo[1,5-a]pyridine-3-carbonitrile HCl | 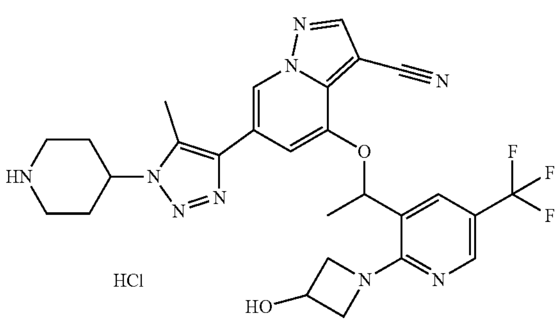 [SMILES: Cc1c(-c2cc(OC(C)c3cc(C(F)(F)F)cnc3N3CC(O)C3)c3c(C#N)cnn3c2)nnn1C1CCNCC1 ; Cl] | 568.2 |
| 734 | 2-[3-Chloro-6-[1-[(3R,4S)-3-fluoro-4-piperidyl]-5-methyl-triazol-4-yl]pyrazolo[1,5-a]pyridin-4-yl]oxy-2-(5-fluoro-2-pyridyl)ethanol HCl, Isomer 2 | 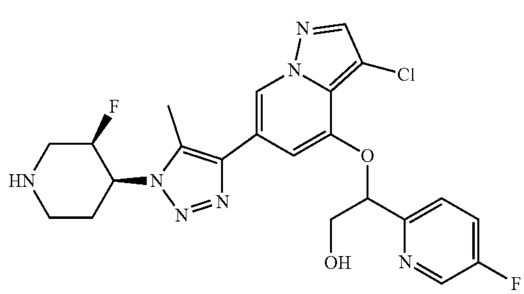 | 490.2 |

TABLE 50-continued

| Prep No. | Chemical Name | Structure | ES/MS m/z [M + H]+ |
|---|---|---|---|
| 735 | 2-[3-Chloro-6-[1-[(3S,4S)-3-fluoro-4-piperidyl]-5-methyl-triazol-4-yl]pyrazolo[1,5-a]pyridin-4-yl]oxy-2-(5-fluoro-2-pyridyl)ethanol HCl, Isomer 2 | 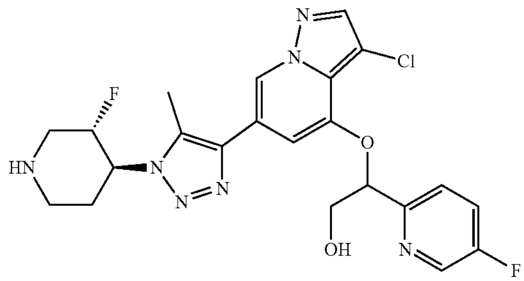 | 490.2 |
| 736 | 2-[3-Chloro-6-[1-[(3S,4R)-3-fluoro-4-piperidyl]-5-methyl-triazol-4-yl]pyrazolo[1,5-a]pyridin-4-yl]oxy-2-(5-fluoro-2-pyridyl)ethanol HCl, Isomer 2 | 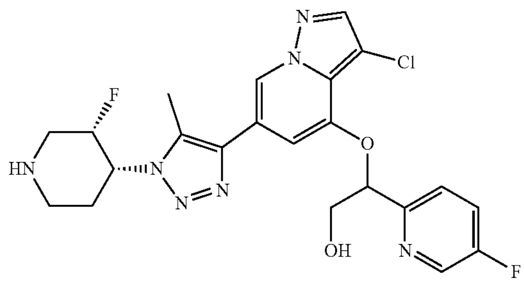 | 490.2 |
| 737 | 2-[3-Chloro-6-[1-[(3R,4R)-3-fluoro-4-piperidyl]-5-methyl-triazol-4-yl]pyrazolo[1,5-a]pyridin-4-yl]oxy-2-(5-fluoro-2-pyridyl)ethanol HCl, Isomer 2 | 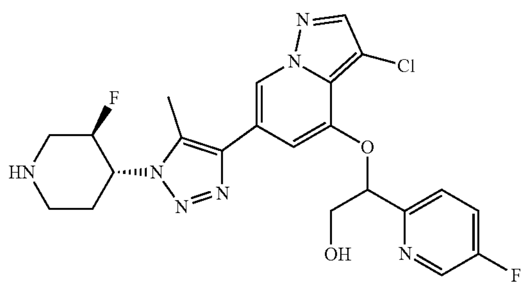 | 490.1 |
| 738 | (3S,4S)-4-[4-[3-Chloro-4-[1-(5-fluoro-2-pyridyl)-2-hydroxy-ethoxy]pyrazolo[1,5-a]pyridin-6-yl]-5-methyl-triazol-1-yl]piperidin-3-ol HCl, Isomer 2 | 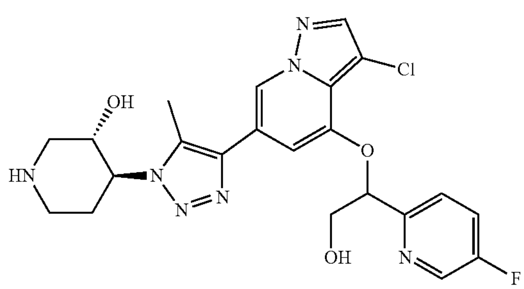 | 488.2 |
| 739 | (3R,4S)-4-[4-[3-chloro-4-[1-(5-fluoro-2-pyridyl)-2-hydroxy-ethoxy]pyrazolo[1,5-a]pyridin-6-yl]-5-methyl-triazol-1-yl]piperidin-3-ol HCl, Isomer 2 | 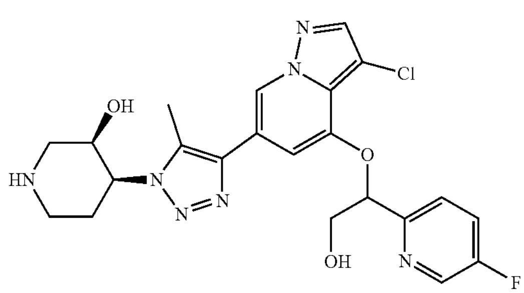 | 488.2 |

TABLE 50-continued

| Prep No. | Chemical Name | Structure | ES/MS m/z [M + H]+ |
|---|---|---|---|
| 740 | (3S,4R)-4-[4-[3-Chloro-4-[1-(5-fluoro-2-pyridyl)-2-hydroxy-ethoxy]pyrazolo[1,5-a]pyridin-6-yl]-5-methyl-triazol-1-yl]piperidin-3-ol HCl, Isomer 2 | 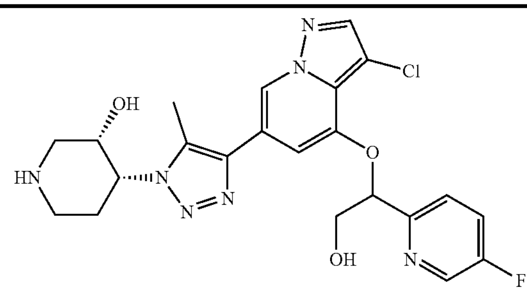 | 488.1 |
| 741 | (3R,4R)-4-[4-[3-Chloro-4-[1-(5-fluoro-2-pyridyl)-2-hydroxy-ethoxy]pyrazolo[1,5-a]pyridin-6-yl]-5-methyl-triazol-1-yl]piperidin-3-ol HCl, Isomer 2 | 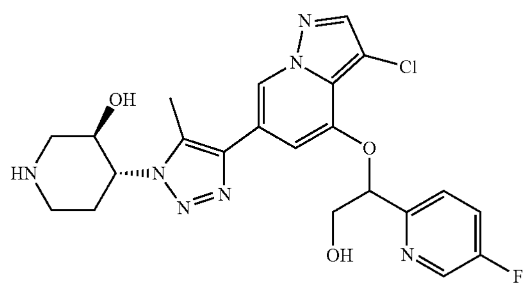 | 488.2 |
| 743 | 2-[3-Chloro-6-[5-Methyl-1-[(3RS,4SR)-3-methyl-4-piperidyl]triazol-4-yl]pyrazolo[1,5-a]pyridin-4-yl]oxy-2-(5-fluoro-2-pyridyl)ethanol HCl | 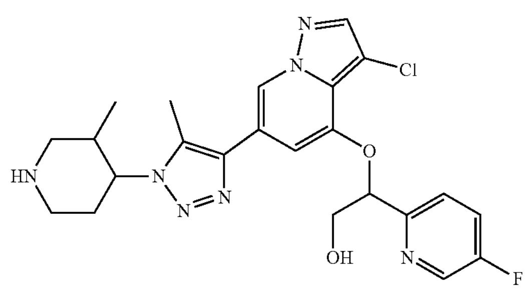 | 486.2 |
| 744 | Cis-2-[3-Chloro-6-[5-methyl-1-(3-piperazin-1-ylcyclobutyl)triazol-4-yl]pyrazolo[1,5-a]pyridin-4-yl]oxy-2-(5-fluoro-2-pyridyl)ethanol HCl | 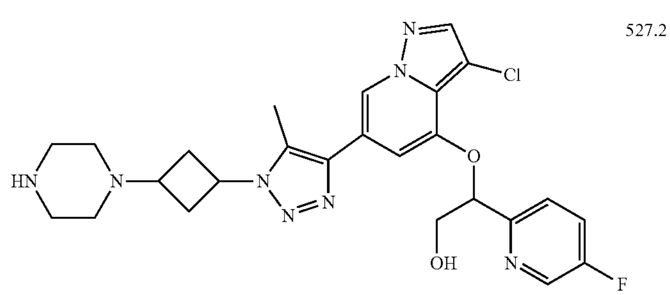 | 527.2 |

| Prep No. | Chemical Name | Structure | ES/MS m/z [M + H]⁺ |
|---|---|---|---|
| 745 | 4-[2-Hydroxy-1-(4-isoquinolyl)ethoxy]-6-[5-methyl-1-(4-piperidyl)triazol-4-yl]pyrazolo[1,5-a]pyridine-3-carbonitrile HCl | 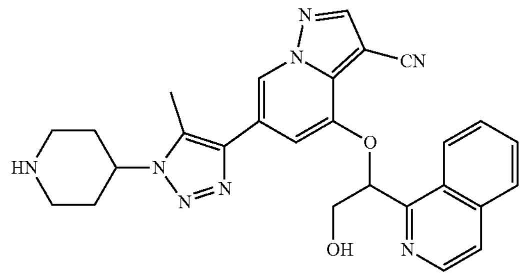 | 495.2 |

Preparation 746

7-[5-Methyl-1-(4-piperidyl)triazol-4-yl]-5-[2,2,2-trifluoro-1-(5-fluoro-2-pyridyl)ethoxy]imidazo[1,2-a]pyridine-3-carbonitrile. HCl

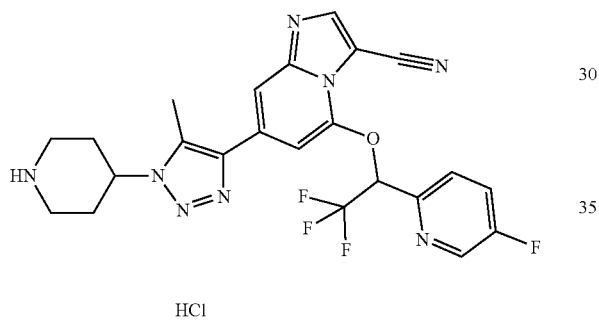

HCl

To a stirred solution of tert-butyl 4-[4-[3-cyano-5-[2,2,2-trifluoro-1-(5-fluoro-2-pyridyl)ethoxy]imidazo[1,2-a]pyridin-7-yl]-5-methyl-triazol-1-yl]piperidine-1-carboxylate (450.00 mg, 0.75 mmol) in DCM (5.00 mL) is added 4M HCl in 1,4-dioxane (2 mL) at RT under N₂. The resulting mixture is stirred at RT for 1 hr, then is concentrated in vacuo to afford the title compound (300 mg). The title compound is carried forward without a further purification. ES/MS m/z 501.2 [M+H]⁺.

Preparation 747

5-Methoxy-7-[5-methyl-1-(piperidin-4-yl)-1,2,3-triazol-4-yl]imidazo[1,2-a]pyridine-3-carbonitrile.HCl

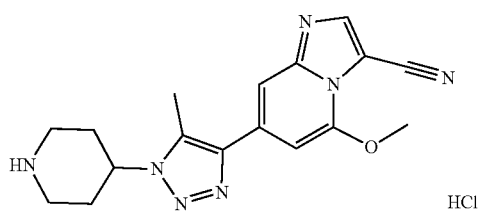 [SMILES: COc1cc(-c2nnn(C3CCNCC3)c2C)cc2ncc(C#N)n12 ; Cl]

HCl

A solution of tert-butyl 4-(4-[3-ethynyl-5-methoxyimidazo[1,2-a]271yridine-7-yl]-5-methyl-1,2,3-triazol-1-yl)piperidine-1-carboxylate (450.00 mg, 1.03 mmol), DCM (10 mL), and HCl (4 M) in 1,4-dioxane (10.00 mL) is stirred for 2 hrs at RT. The mixture is concentrated under reduced pressure, diluted with EtOAc (3 mL) and hexanes (20 mL), and stirred 5 min. The solid is collected by filtration, and the filter cake is washed with hexanes (2×10 mL) and lyophilized to give the title compound as a brown solid (110 mg, 28.6%). ES/MS m/z 338.0 [M+H]⁺.

Preparation 748

4-Isopropoxy-6-[5-methyl-1-[piperidin-4-yl]pyrazol-4-yl]pyrazolo[1,5-a]pyridine-3-carbonitrile. TFA

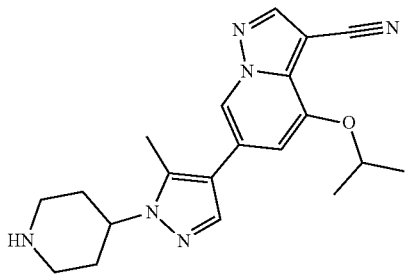 [SMILES: Cc1c(-c2cc(OC(C)C)c3c(C#N)cnn3c2)cnn1C1CCNCC1]

tert-Butyl 4-[4-(3-cyano-4-isopropoxy-pyrazolo[1,5-a]271yridine-6-yl)-5-methyl-pyrazol-1-yl]piperidine-1-carboxylate (75 mg, 0.16 mmol) is stirred at RT in TFA (1 mL) for 30 min. The mixture is concentrated to dryness to give the title compound (54.2 mg, 92.12%) which is used without further purification. ES/MS m/z 365.2 [M+H]⁺

The following compounds are prepared essentially as described for 4-isopropoxy-6-[5-methyl-1-[piperidin-4-yl]pyrazol-4-yl]pyrazolo[1,5-a]pyridine-3-carbonitrile using the appropriate reagents, adjusting the reaction times to determine completion of the reactions, and adjusting the purification system as appropriate. Temperature is varied from RT to 50° C. The mixture can also be quenched with saturated Na₂CO₃ aq and extracted with EtOAc. For compounds where the amine salt was isolated, the formation of the mono-, di-, or trivalent salt is dependent on the pKa of the amine and the acid used to form the salt. The exact mono-, di-, or trivalent salt form for each example was not identified.

TABLE 51

| Prep No. | Chemical Name | Structure | ES/MS m/z [M + H]+ |
|---|---|---|---|
| 749[1] | 4-Methoxy-6-[5-methyl-1-[(3S)-piperidin-3-yl]pyrazol-4-yl]pyrazolo[1,5-a]pyridine-3-carbonitrile.FA | 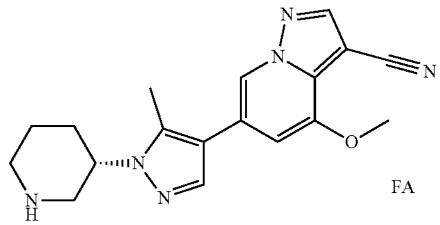 | 337.20 |
| 750 | 6-[5-Methyl-1-(4-piperidyl)pyrazol-4-yl]-4-[1-(2-methylsulfonylphenyl)ethoxy]pyrazolo[1,5-a]pyridine-3-carbonitrile, TFA | 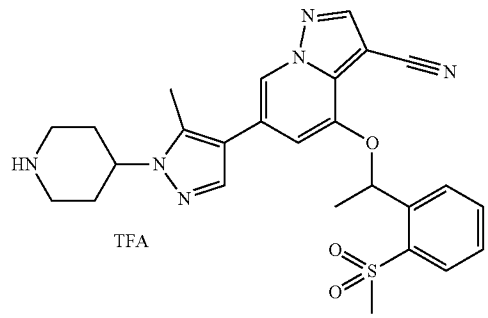 [SMILES: Cc1c(-c2cc(OC(C)c3ccccc3S(C)(=O)=O)c3c(C#N)cnn3c2)cnn1C1CCNCC1 ; "TFA"] | 505.2 |
| 751 | 5-[1-(1,3-Benzothiazol-7-yl)ethoxy]-7-[5-methyl-1-(4-piperidyl)triazol-4-yl]imidazo[1,2-a]pyridine-3-carbonitrile. TFA | 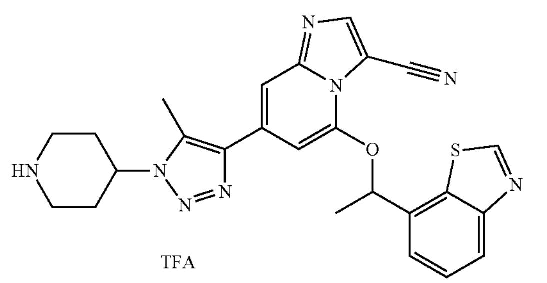 [SMILES: Cc1c(-c2cc(OC(C)c3cccc4ncsc34)n3c(C#N)cnc3c2)nnn1C1CCNCC1] | 485.1 |
| 752 | 6-[1-[1-(6-Azabicyclo[3.2.1]octan-3-yl)azetidin-3-yl]-5-methyl-pyrazol-4-yl]-4-methoxy-pyrazolo[1,5-a]pyridine-3-carbonitrile. TFA | 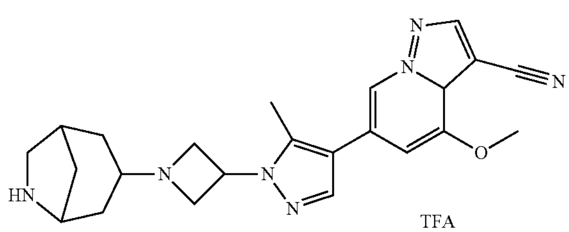 | 418.2 |
| 753 | 7-[1-(Azetidin-3-yl)-5-methyl-pyrazol-4-yl]-5-[(1R)-1-(2-pyridyl)ethoxy]imidazo[1,2-a]pyridine-3-carbonitrile. TFA | 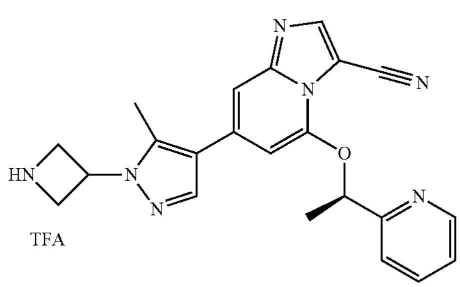 [SMILES: Cc1c(-c2cc(O[C@H](C)c3ccccn3)n3c(C#N)cnc3c2)cnn1C1CNC1] | 400.0 |

TABLE 51-continued

| Prep No. | Chemical Name | Structure | ES/MS m/z [M + H]+ |
|---|---|---|---|
| 754 | 7-[1-(Azepan-4-yl)-5-methyl-triazol-4-yl]-5-[(1R)-1-(2-pyridyl)ethoxy]imidazo[1,2-a]pyridine-3-carbonitrile. TFA | 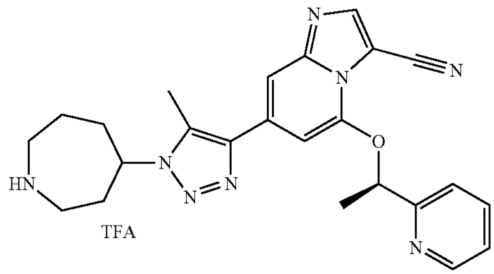 [SMILES: Cc1c(-c2cc(O[C@H](C)c3ccccn3)n3c(C#N)cnc3c2)nnn1C1CCCNCC1] | 443.2 |
| 755 | 5-[[(1R)-1-(5-Fluoro-2-pyridyl)ethyl]amino]-7-[5-methyl-1-(4-piperidyl)triazol-4-yl]imidazo[1,2-a]pyridine-3-carbonitrile. TFA | 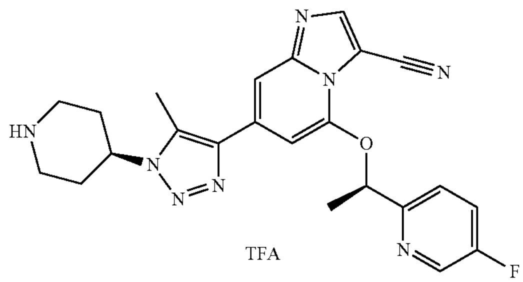 | 446.2 |
| 756 | 5-[(5-Fluoro-2-pyridyl)methoxy]-7-[5-methyl-1-(4-piperidyl)triazol-4-yl]imidazo[1,2-a]pyridine-3-carbonitrile. 2 TFA | 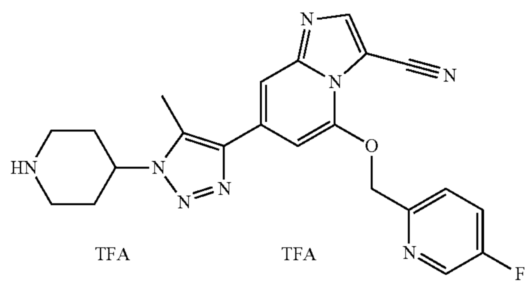 [SMILES: Cc1c(-c2cc(OCc3ccc(F)cn3)n3c(C#N)cnc3c2)nnn1C1CCNCC1] | 433.2 |

[1]Reverse Combi-flash chromatography with the following conditions: C18; eluting with a gradient of 50-70% ACN in H$_2$O (0.1% FA).

Preparation 757

6-[1-(Azetidin-3-yl)-5-methylpyrazol-4-yl]-4-methoxypyrazolo[1,5-a]pyridine-3-carbonitrile.FA

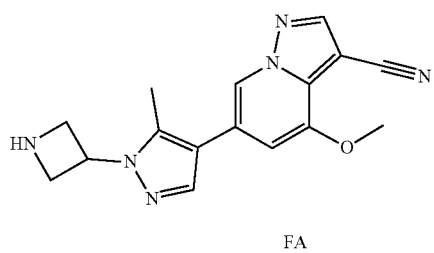 [SMILES: COc1cc(-c2cnn(C3CNC3)c2C)cn2ncc(C#N)c12 ; "FA"]

FA

A solution of tert-butyl 3-(4-[3-cyano-4-methoxypyrazolo[1,5-a]273yridine-6-yl]-5-methylpyrazol-1-yl)azetidine-1-carboxylate (480 mg, 1.18 mmol) and TFA (20 mL) in DCM (20 mL) is stirred for 30 min at RT under N$_2$. The mixture is concentrated under reduced pressure. The pH of the residue is adjusted to pH 8 with aq., sat'd. NaHCO$_3$ and extracted with DCM:iPrOH (3:1) (3×100 mL). The combined organic extracts are washed with brine (1×10 mL), dried over anhydrous Na$_2$SO$_4$, filtered, and the filtrate is concentrated under reduced pressure. The residue is purified by reverse Combi-flash chromatography with the following conditions: Column, C18; eluting with a gradient of 0% to 30% ACN in H$_2$O (0.1% FA), to give the title compound as a white solid (210 mg, 57%). ES/MS m/z 309.05 [M+H]+.

Preparation 758

5-[(1R)-1-(5-Fluoropyridin-2-yl)ethoxy]-7-[5-methyl-1-(piperidin-4-yl)-1,2,3-triazol-4-yl]imidazo[1,2-a]pyridine-3-carbonitrile.HCl

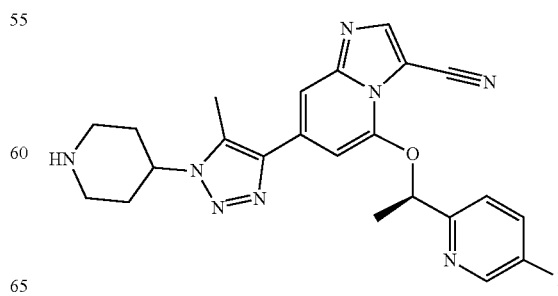

HCl

A stirred solution of tert-butyl 4-(4-[3-cyano-5-[(1R)-1-(5-fluoropyridin-2-yl)ethoxy]imidazo[1,2-a]274yridine-7-yl]-5-methyl-1,2,3-triazol-1-yl)piperidine-1-carboxylate (70.0 mg, 0.128 mmol) in DCM (3.0 mL) is treated with 4 M HCl in 1,4-dioxane (1.0 mL) and stirred for 30 min at RT under N$_2$. The mixture is concentrated under reduced pressure and washed with EtOAc (3×20 mL) to give the title compound as a yellow solid (95 mg, crude). ES/MS m/z 447.2 [M+H]$^+$.

Preparation 759

6-[5-Methyl-1-(piperidin-4-yl)-1,2,3-triazol-4-yl]-4-[(1R)-1-(274yridine-2-yl)ethoxy]pyrazolo[1,5-a]pyridine-3-carbonitrile.TFA

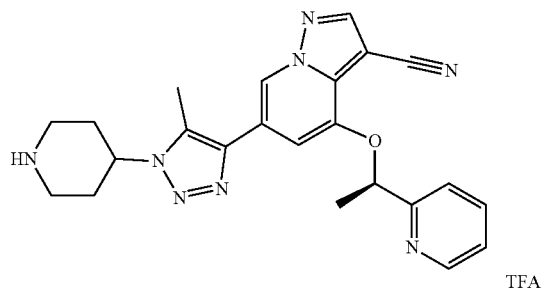 [SMILES: Cc1c(-c2cc(O[C@H](C)c3ccccn3)c3c(C#N)cnn3c2)nnn1C1CCNCC1]

TFA

A solution of tert-butyl 4-(4-[3-cyano-4-[(1R)-1-(274yridine-2-yl)ethoxy]pyrazolo[1,5-a]274yridine-6-yl]-5-methyl-1,2,3-triazol-1-yl)piperidine-1-carboxylate (354 mg, 0.67 mmol) and TFA (1 mL) is stirred for 1 hr at RT under N$_2$. The mixture is concentrated under reduced pressure, and the residue is purified by trituration with MTBE (5 mL). The precipitated solids are collected by filtration and washed with MTBE (2×2 mL) to give the title compound as a brown solid (456 mg), which is used directly without further purification. ES/MS m/z 429.3 [M+H]$^+$.

Preparation 760

7-[5-Methyl-1-(4-piperidyl)triazol-4-yl]-5-[1-[5-(trifluoromethyl)-3-pyridyl]ethylamino]imidazo[1,2-a]pyridine-3-carbonitrile. TFA

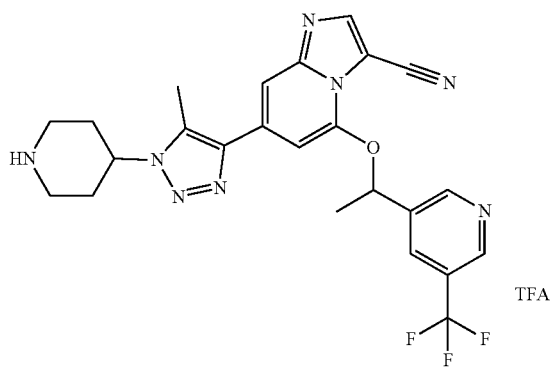 [SMILES: Cc1c(-c2cc(OC(C)c3cncc(C(F)(F)F)c3)n3c(C#N)cnc3c2)nnn1C1CCNCC1]

TFA

A solution of tert-butyl 4-[4-[3-cyano-5-[1-[5-(trifluoromethyl)-3-pyridyl]ethoxy]imidazo[1,2-a]275yridine-7-yl]-5-methyl-triazol-1-yl]piperidine-1-carboxylate (150.00 mg, 0.251 mmol), TFA (5 mL) and DCM (10 mL) is stirred for 1 hr at RT under N$_2$. The mixture is concentrated under reduced pressure to give the title compound. ES+H, m/z 497.3 [M+H]$^+$.

Preparation 761

5-[1-(5-Fluoro-2-pyridyl)-2-methoxy-ethoxy]-7-[5-methyl-1-(4-piperidyl)triazol-4-yl]imidazo[1,2-a]pyridine-3-carbonitrile.TFA

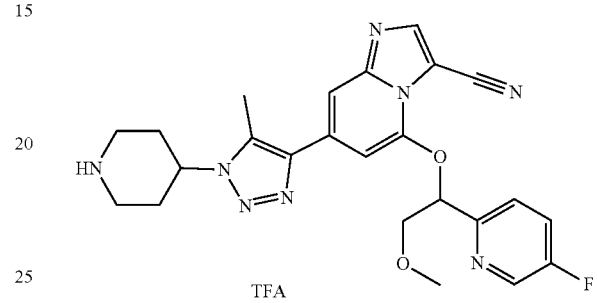

TFA

A mixture of tert-butyl 4-[4-[3-cyano-5-[1-(5-fluoro-2-pyridyl)-2-methoxy-ethoxy]imidazo[1,2-a]275yridine-7-yl]-5-methyl-triazol-1-yl]piperidine-1-carboxylate (150.00 mg, 0.26 mmol) in TFA (2.00 mL) and DCM (4.00 mL) is stirred for 1 hr at RT under N$_2$. The mixture is concentrated under reduced pressure to give the title compound which is used directly without further purification (140 mg). ES/MS m/z 477.2 [M+H]$^+$.

Preparation 762

5-[1-(5-Fluoro-2-pyridyl)propoxy]-7-[5-methyl-1-(4-piperidyl)triazol-4-yl]imidazo[1,2-a]pyridine-3-carbonitrile.HCl

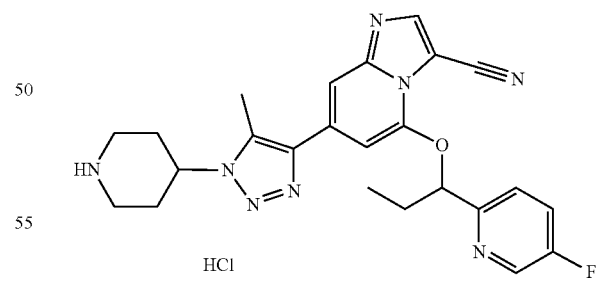

HCl

A mixture of (200.00 mg, 0.36 mmol) tert-butyl 4-[4-[3-cyano-5-[1-(5-fluoro-2-pyridyl)propoxy]imidazo[1,2-a]pyridine-7-yl]-5-methyl-triazol-1-yl]piperidine-1-carboxylate in 4 M HCl (gas) in 1,4-dioxane (2.00 mL) and DCM (3.00 mL) is stirred for 1 hr at RT under N$_2$. The mixture is concentrated under reduced pressure to give the title compound (200 mg) which is used directly without further purification. ES/MS m/z 461.3 [M+H]$^+$.

Preparation 763

4-[1-(5-Fluoro-2-pyridyl)-2-methoxy-ethoxy]-6-[5-methyl-1-(4-piperidyl)triazol-4-yl]pyrazolo[1,5-a]pyridine-3-carbonitrile.HCl

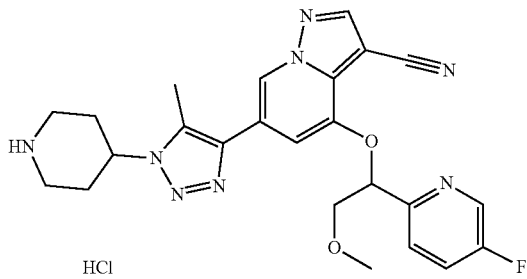 [SMILES: COCC(Oc1cc(-c2nnn(C3CCNCC3)c2C)cn2ncc(C#N)c12)c1ccc(F)cn1 ; Cl]

A mixture of tert-butyl 4-[4-[3-cyano-4-[1-(5-fluoro-2-pyridyl)-2-methoxy-ethoxy]pyrazolo[1,5-a]pyridine-6-yl]-5-methyl-triazol-1-yl]piperidine-1-carboxylate (180.00 mg, 0.31 mmol) in 4 M HCl (gas) in 1,4-dioxane (2.00 mL) and DCM (4.00 mL) is stirred for 1 hr at RT under $N_2$. The mixture is concentrated under reduced pressure to give the title compound (160 mg) which is used directly without further purification. ES/MS m/z 477.2 [M+H]$^+$.

The following compounds are prepared essentially as described for 4-[1-(5-fluoro-2-pyridyl)-2-methoxy-ethoxy]-6-[5-methyl-1-(4-piperidyl)triazol-4-yl]pyrazolo[1,5-a]pyridine-3-carbonitrile.HCl using the appropriate reagents, adjusting the reaction times to determine completion of the reactions, and adjusting the purification system as appropriate. TFA and trifluoroacetaldehyde can be substituted for HCl. The precipitated solids can also be triturated with $Et_2O$ and DCM. For compounds where the amine salt was isolated, the formation of the mono-, di-, or trivalent salt is dependent on the pKa of the amine and the acid used to form the salt. The exact mono-, di-, or trivalent salt form for each example was not identified.

TABLE 52

| Prep No. | Chemical Name | Structure | ES/MS m/z [M + H]$^+$ |
|---|---|---|---|
| 764 | 6-[1-(Azetidin-3-yl)-5-methyl-1,2,3-triazol-4-yl]-4-[(1R)-1-(pyridine-2-yl)ethoxy]pyrazolo[1,5-a]pyridine-3-carbonitrile. TFA | 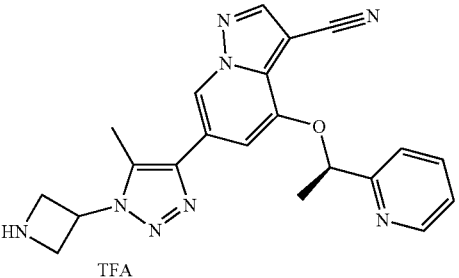 [SMILES: Cc1c(-c2cc(O[C@H](C)c3ccccn3)c3c(C#N)cnn3c2)nnn1C1CNC1] | 400.1 |
| 765 | 6-[1-(Azetidin-3-yl)pyrazol-4-yl]-4-methoxypyrazolo[1,5-a]pyridine-3-carbonitrile. TFA | 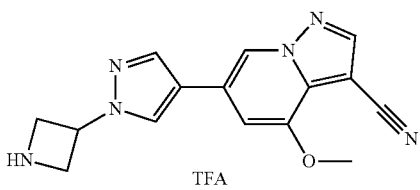 [SMILES: COc1cc(-c2cnn(C3CNC3)c2)cn2ncc(C#N)c12] | 295.2 |
| 766 | 6-[5-Methyl-1-(piperidin-4-yl)pyrazol-4-yl]-4-[(1R)-1-(pyrazin-2-yl)ethoxy]pyrazolo[1,5-a]pyridine-3-carbonitrile. HCl | 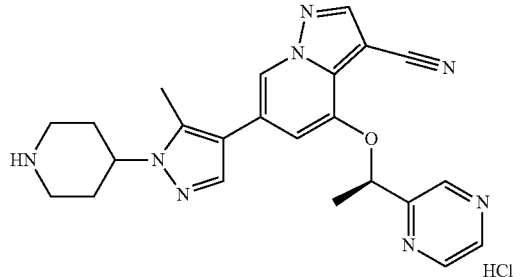 [SMILES: Cc1c(-c2cc(O[C@H](C)c3cnccn3)c3c(C#N)cnn3c2)cnn1C1CCNCC1 ; Cl] | 429.2 |

TABLE 52-continued

| Prep No. | Chemical Name | Structure | ES/MS m/z [M + H]+ |
|---|---|---|---|
| 767 | 6-[5-Methyl-1-(piperidin-4-yl)pyrazol-4-yl]-4-[(1R)-1-(277yridine-2-yl)propoxy]pyrazolo[1,5-a]pyridine-3-carbonitrile. HCl | 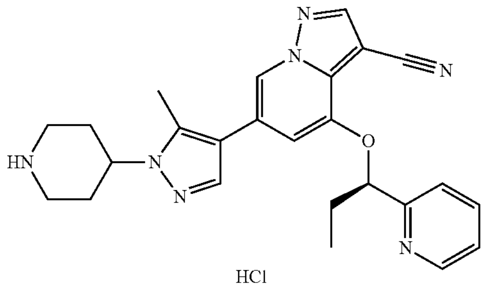 [SMILES: CC[C@@H](Oc1cc(-c2cnn(C3CCNCC3)c2C)cn2ncc(C#N)c12)c1ccccn1 ; Cl] | 442.4 |
| 768 | 4-[(1R)-1-Cyclobutylethoxy]-6-[5-methyl-1-(piperidin-4-yl)-1,2,3-triazol-4-yl]pyrazolo[1,5-a]pyridine-3-carbonitrile. HCl | 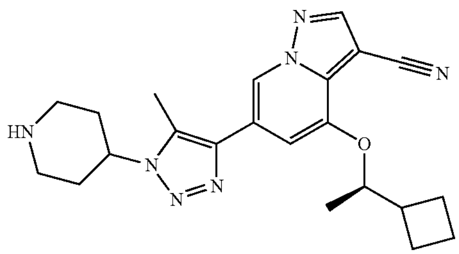 | 406.3 |
| 769 | 4-Methoxy-6-(5-methyl-1-((3S,5R)-5-methylpyrrolidin-3-yl)-1H-pyrazol-4-yl)pyrazolo[1,5-a]pyridine-3-carbonitrile. HCl | 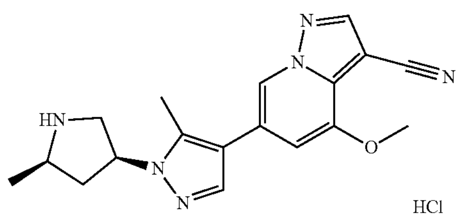 [SMILES: COc1cc(-c2cnn([C@@H]3CN[C@H](C)C3)c2C)cn2ncc(C#N)c12 ; Cl] | 337.2 |
| 770 | 4-Methoxy-6-[5-methyl-1-[(3S,5S)-5-methylpyrrolidin-3-yl]pyrazol-4-yl]pyrazolo[1,5-a]pyridine-3-carbonitrile. HCl | 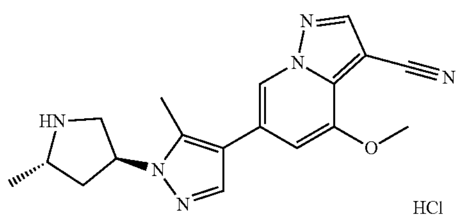 [SMILES: COc1cc(-c2cnn([C@@H]3CN[C@@H](C)C3)c2C)cn2ncc(C#N)c12 ; Cl] | 337.1 |
| 771 | 6-[1-(5,5-Dimethylpyrrolidin-3-yl)-5-methylpyrazol-4-yl]-4-methoxypyrazolo[1,5-a]pyridine-3-carbonitrile. HCl | 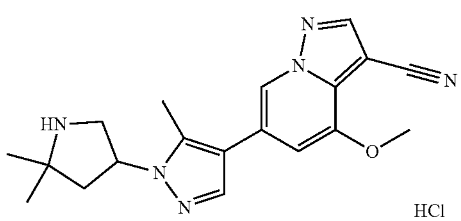 [SMILES: COc1cc(-c2cnn(C3CNC(C)(C)C3)c2C)cn2ncc(C#N)c12 ; Cl] | 351.2 |
| 772 | 6-[5-Methyl-1-(piperidin-4-yl)pyrazol-4-yl]-4-[2,2,2-trifluoro-1-(oxan-4-yl)ethoxy]pyrazolo[1,5-a]pyridine-3-carbonitrile. HCl | 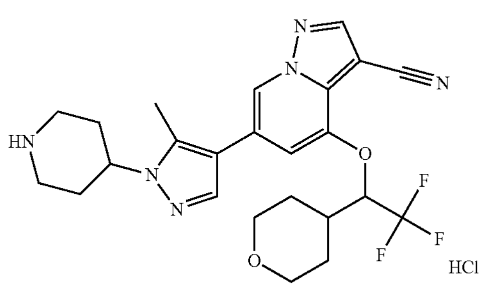 [SMILES: Cc1c(-c2cc(OC(C3CCOCC3)C(F)(F)F)c3c(C#N)cnn3c2)cnn1C1CCNCC1 ; Cl] | 489.1 |

TABLE 52-continued

| Prep No. | Chemical Name | Structure | ES/MS m/z [M + H]+ |
|---|---|---|---|
| 773 | 6-[5-Methyl-1-[(3S)-pyrrolidin-3-yl]pyrazol-4-yl]-4-[[(1R)-1-(278yridine-2-yl)ethyl]amino]pyrazolo[1,5-a]pyridine-3-carbonitrile. HCl | 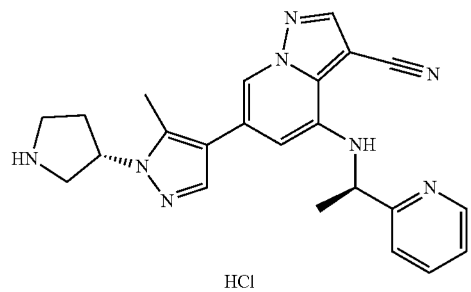 [SMILES: Cc1c(-c2cc(N[C@H](C)c3ccccn3)c3c(C#N)cnn3c2)cnn1[C@H]1CCNC1 ; Cl] | 413.1 |
| 774 | 4-[2-methoxy-1-[5-(trifluoromethyl)-3-pyridyl]ethoxy]-6-[5-methyl-1-(4-piperidyl)triazol-4-yl]pyrazolo[1,5-a]pyridine-3-carbonitrile. HCl | 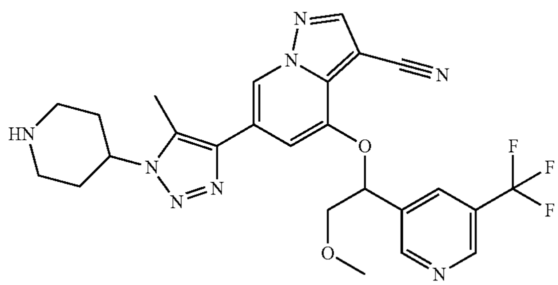 | 527.2 |
| 775 | 5-[1-(5-Fluoro-2-pyridyl)-2-hydroxy-ethoxy]-7-[5-methyl-1-(4-piperidyl)triazol-4-yl]imidazo[1,2-a]pyridine-3-carbonitrile. HCl | 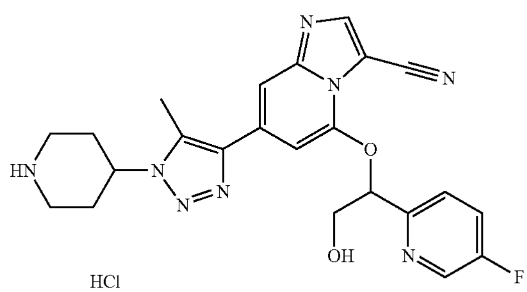 [SMILES: Cc1c(-c2cc(OC(CO)c3ccc(F)cn3)n3c(C#N)cnc3c2)nnn1C1CCNCC1 ; Cl] | 463.1 |
| 776 | 5-[(1R)-1-(5-Fluoro-2-pyridyl)ethoxy]-7-[5-methyl-1-(4-piperidyl)pyrazol-4-yl]imidazo[1,2-a]pyridine-3-carbonitrile. HCl | 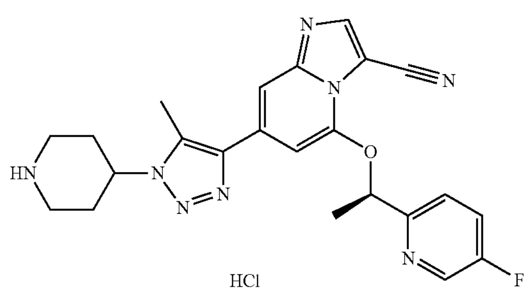 [SMILES: Cc1c(-c2cc(O[C@H](C)c3ccc(F)cn3)n3c(C#N)cnc3c2)nnn1C1CCNCC1 ; Cl] | 446.4 |
| 777 | 3-Chloro-5-[(1R)-1-(5-fluoro-2-pyridyl)ethoxy]-7-[5-methyl-1-(4-piperidyl)triazol-4-yl]imidazo[1,2-a]pyridine. TFA | 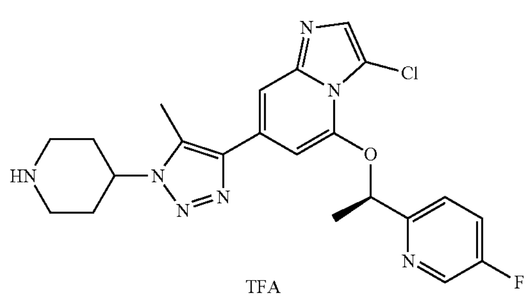 [SMILES: Cc1c(-c2cc(O[C@H](C)c3ccc(F)cn3)n3c(Cl)cnc3c2)nnn1C1CCNCC1 ; "TFA"] | 456.1 |

TABLE 52-continued

| Prep No. | Chemical Name | Structure | ES/MS m/z [M + H]+ |
|---|---|---|---|
| 778 | 7-[1-(7-Azaspiro[3.5]nonan-2-yl)-5-methyl-triazol-4-yl]-5-[(1R)-1-(5-fluoro-2-pyridyl)ethoxy]imidazo[1,2-a]pyridine-3-carbonitrile HCl | 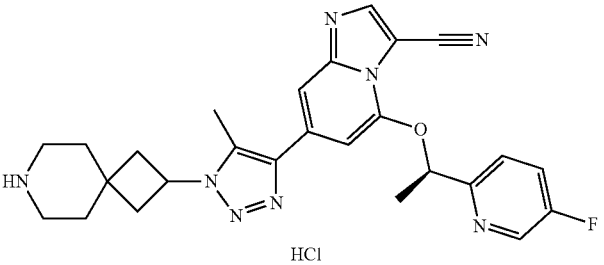 [SMILES: Cc1c(-c2cc(O[C@H](C)c3ccc(F)cn3)n3c(C#N)cnc3c2)nnn1C1CC2(CCNCC2)C1 ; Cl] | 487.2 |
| 779 | 4-[2-fluoro-1-(5-fluoro-2-pyridyl)ethoxy]-6-[5-methyl-1-(4-piperidyl)triazol-4-yl]pyrazolo[1,5-a]pyridine-3-carbonitrile Di-HCl | 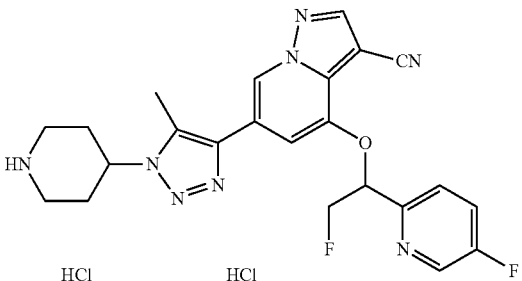 [SMILES: Cc1c(-c2cc(OC(CF)c3ccc(F)cn3)c3c(C#N)cnn3c2)nnn1C1CCNCC1 ; Cl ; Cl] | 464.8 |
| 780 | 7-[5-methyl-1-(4-piperidyl)triazol-4-yl]-5-[(1R)-1-(2-pyridyl)propoxy]imidazo[1,2-a]pyridine-3-carbonitrile, Isomer 2 TFA | 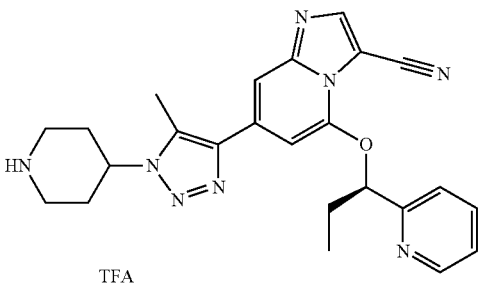 [SMILES: CC[C@@H](Oc1cc(-c2nnn(C3CCNCC3)c2C)cc2ncc(C#N)n12)c1ccccn1 ; "TFA"] | 442.9 |
| 781 | 4-[cyclopropyl-(5-fluoro-2-pyridyl)methoxy]-6-[5-methyl-1-(4-piperidyl)triazol-4-yl]pyrazolo[1,5-a]pyridine-3-carbonitrile TFA | 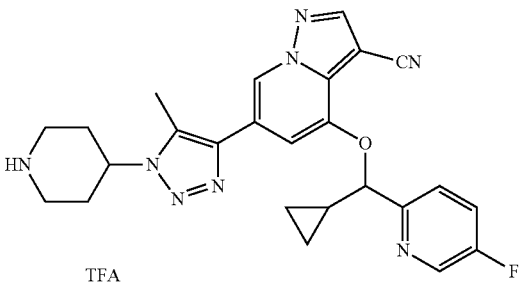 [SMILES: Cc1c(-c2cc(OC(c3ccc(F)cn3)C3CC3)c3c(C#N)cnn3c2)nnn1C1CCNCC1 ; "TFA"] | a |
| 782 | 4-[(1-fluorocyclopropyl)-(5-fluoro-2-pyridyl)methoxy]-6-[5-methyl-1-(4-piperidyl)triazol-4-yl]pyrazolo[1,5-a]pyridine-3-carbonitrile TFA | 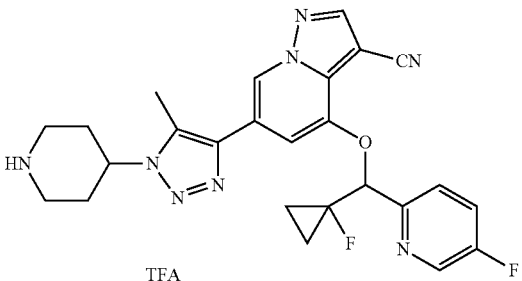 [SMILES: Cc1c(-c2cc(OC(c3ccc(F)cn3)C3(F)CC3)c3c(C#N)cnn3c2)nnn1C1CCNCC1 ; "TFA"] | 492.8 |

| Prep No. | Chemical Name | Structure | ES/MS m/z [M + H]+ |
|---|---|---|---|
| 783 | 4-[(5-fluoro-2-pyridyl)-[1-(trifluoromethyl)cyclopropyl]methoxy]-6-[5-methyl-1-(4-piperidyl)triazol-4-yl]pyrazolo[1,5-a]pyridine-3-carbonitrile HCl | 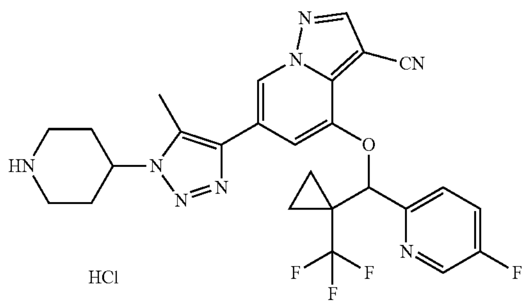 [SMILES: Cc1c(-c2cc(OC(c3ccc(F)cn3)C3(C(F)(F)F)CC3)c3c(C#N)cnn3c2)nnn1C1CCNCC1 ; Cl] | 541.1 |
| 784 | 5-[2-Cyclopropyl-1-(2-pyridyl)ethoxy]-7-[5-methyl-1-(4-piperidyl)triazol-4-yl]imidazo[1,2-a]pyridine-3-carbonitrile HCl | 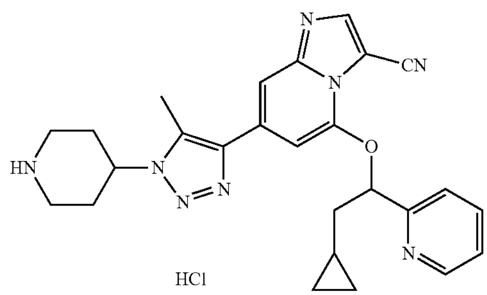 [SMILES: Cc1c(-c2cc(OC(CC3CC3)c3ccccn3)n3c(C#N)cnc3c2)nnn1C1CCNCC1 ; Cl] | 469.2 |
| 785 | 5-[(1R)-1-(3-Fluoro-2-pyridyl)ethoxy]-7-[5-methyl-1-(4-piperidyl)triazol-4-yl]imidazo[1,2-a]pyridine-3-carbonitrile HCl | 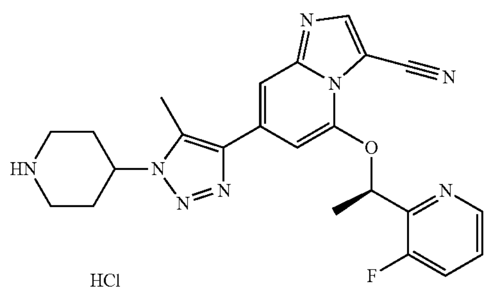 [SMILES: Cc1c(-c2cc(O[C@H](C)c3ncccc3F)n3c(C#N)cnc3c2)nnn1C1CCNCC1 ; Cl] | 447.2 |
| 786 | 5-[(6,6-Dimethyl-5,7-dihydrocyclopenta[b]pyridin-7-yl)oxy]-7-[5-methyl-1-(4-piperidyl)triazol-4-yl]imidazo[1,2-a]pyridine-3-carbonitrile HCl | 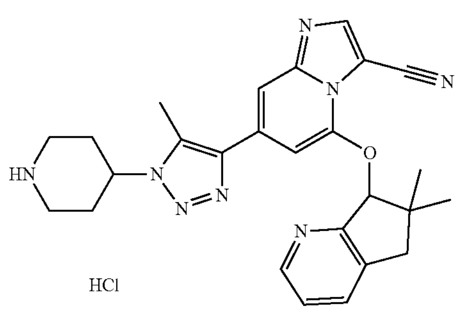 [SMILES: Cc1c(-c2cc(OC3c4ncccc4CC3(C)C)n3c(C#N)cnc3c2)nnn1C1CCNCC1 ; Cl] | 469.2 |
| 787 | 5-[1-(3,5-Difluoro-2-pyridyl)ethoxy]-7-[5-methyl-1-(4-piperidyl)triazol-4-yl]imidazo[1,2-a]pyridine-3-carbonitrile HCl | 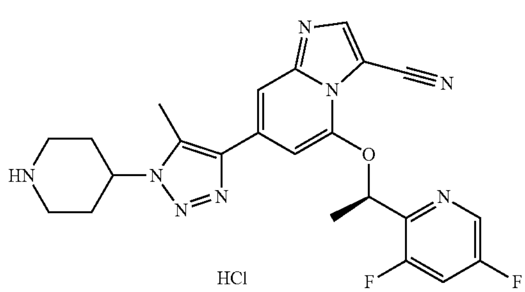 [SMILES: Cc1c(-c2cc(O[C@H](C)c3ncc(F)cc3F)n3c(C#N)cnc3c2)nnn1C1CCNCC1 ; Cl] | 464.8 |

TABLE 52-continued

| Prep No. | Chemical Name | Structure | ES/MS m/z [M + H]+ |
|---|---|---|---|
| 788 | 6-[1-(3,3-Difluoro-4-piperidyl)-5-methyl-pyrazol-4-yl]-4-methoxy-pyrazolo[1,5-a]pyridine-3-carbonitrile HCl | 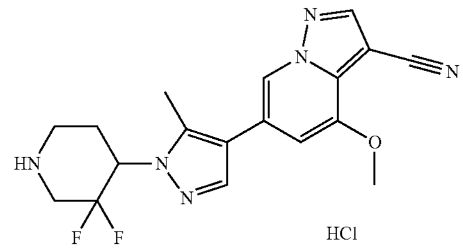 [SMILES: COc1cc(-c2cnn(C3CCNCC3(F)F)c2C)cn2ncc(C#N)c12 ; Cl] | 373.3 |
| 789 | 5-(1-Isothiazol-3-ylethoxy)-7-[5-methyl-1-(4-piperidyl)triazol-4-yl]imidazo[1,2-a]pyridine-3-carbonitrile HCl | 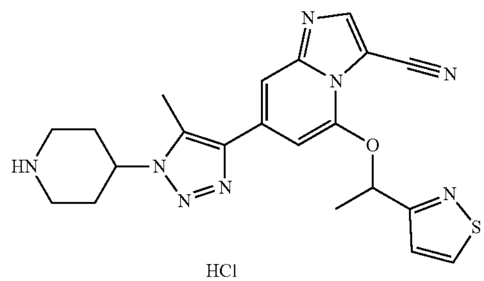 [SMILES: Cc1c(-c2cc(OC(C)c3ccsn3)n3c(C#N)cnc3c2)nnn1C1CCNCC1 ; Cl] | 435.10 |
| 790 | 6-[5-Methyl-1-(4-piperidyl)triazol-4-yl]-4-[1-[5-(trifluoromethyl)-3-pyridyl]ethoxy]pyrazolo[1,5-a]pyridine-3-carbonitrile HCl | 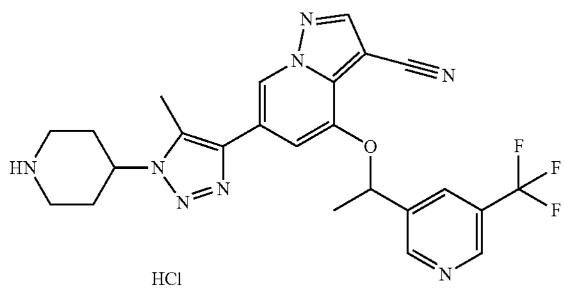 [SMILES: Cc1c(-c2cc(OC(C)c3cncc(C(F)(F)F)c3)c3c(C#N)cnn3c2)nnn1C1CCNCC1 ; Cl] | 497.1 |
| 791 | 2-[(1R)-1-[6-[5-Methyl-1-(4-piperidyl)pyrazol-4-yl]pyrazolo[1,5-a]pyridin-4-yl]oxyethyl]benzonitrile HCl | 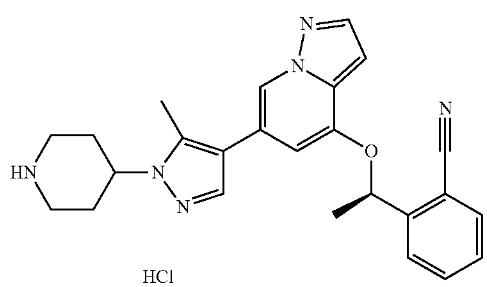 [SMILES: Cc1c(-c2cc(O[C@H](C)c3ccccc3C#N)c3ccnn3c2)cnn1C1CCNCC1 ; Cl] | 427.2 |
| 792 | 7-[1-(7-Azaspiro[3.5]nonan-2-yl)-5-methyl-triazol-4-yl]-5-[(1R)-1-(2-pyridyl)ethoxy]imidazo[1,2-a]pyridine-3-carbonitrile HCl | 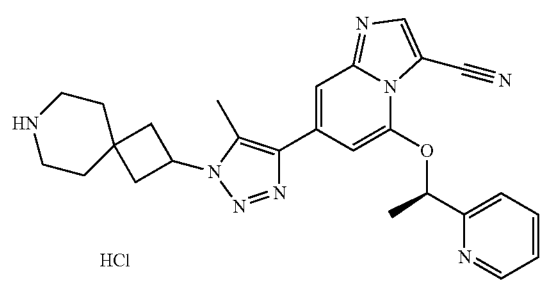 [SMILES: Cc1c(-c2cc(O[C@H](C)c3ccccn3)n3c(C#N)cnc3c2)nnn1C1CC2(CCNCC2)C1 ; Cl] | 469.3 |

TABLE 52-continued

| Prep No. | Chemical Name | Structure | ES/MS m/z [M + H]+ |
|---|---|---|---|
| 793 | 6-[1-(3,3-Difluoro-4-piperidyl)-5-methyl-pyrazol-4-yl]-4-methoxy-pyrazolo[1,5-a]pyridine-3-carbonitrile HCl | 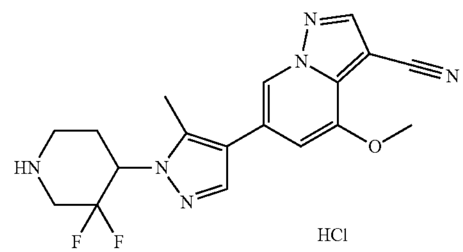 [SMILES: COc1cc(-c2cnn(C3CCNCC3(F)F)c2C)cn2ncc(C#N)c12 ; Cl] | 373.3 |
| 794 | 5-[(1R)-1-(5-Fluoro-2-pyridyl)ethoxy]-7-[5-methyl-1-[(3S)-3-piperidyl]triazol-4-yl]imidazo[1,2-a]pyridine-3-carbonitrile HCl | 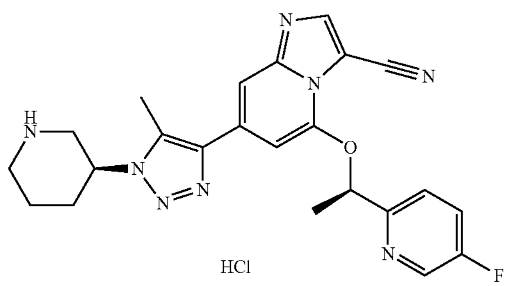 [SMILES: Cc1c(-c2cc(O[C@H](C)c3ccc(F)cn3)n3c(C#N)cnc3c2)nnn1[C@H]1CCCNC1 ; Cl] | 447.1 |
| 795 | 5-[(1R)-1-(5-Fluoro-2-pyridyl)ethoxy]-7-[5-methyl-1-[(3R)-3-piperidyl]triazol-4-yl]imidazo[1,2-a]pyridine-3-carbonitrile HCl | 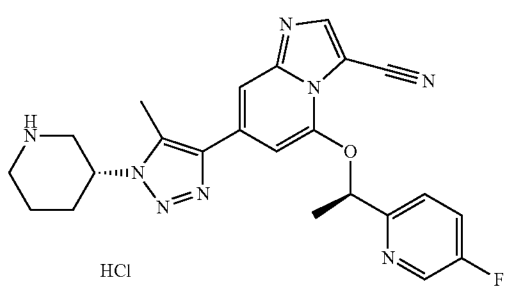 [SMILES: Cc1c(-c2cc(O[C@H](C)c3ccc(F)cn3)n3c(C#N)cnc3c2)nnn1[C@@H]1CCCNC1 ; Cl] | 447.2 |
| 796 | 7-[5-Methyl-1-(4-piperidyl)pyrazol-4-yl]-5-[[(1R)-1-(2-pyridyl)ethyl]amino]imidazo[1,2-a]pyridine-3-carbonitrile HCl | 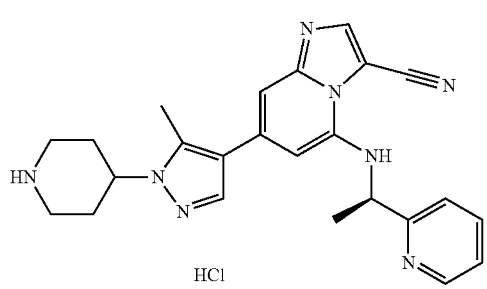 [SMILES: Cc1c(-c2cc(N[C@H](C)c3ccccn3)n3c(C#N)cnc3c2)cnn1C1CCNCC1 ; Cl] | 427.1 |
| 797 | 7-[5-Methyl-1-(4-piperidyl)triazol-4-yl]-5-[(1R)-1-pyrimidin-4-ylethoxy]imidazo[1,2-a]pyridine-3-carbonitrile HCl | 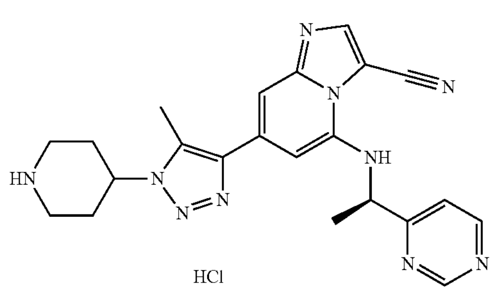 [SMILES: Cc1c(-c2cc(N[C@H](C)c3ccncn3)n3c(C#N)cnc3c2)nnn1C1CCNCC1 ; Cl] | 430.2 |

TABLE 52-continued

| Prep No. | Chemical Name | Structure | ES/MS m/z [M + H]+ |
|---|---|---|---|
| 798 | 5-[1-(6-Chloro-3-pyridyl)ethoxy]-7-[5-methyl-1-(4-piperidyl)triazol-4-yl]imidazo[1,2-a]pyridine-3-carbonitrile HCl | 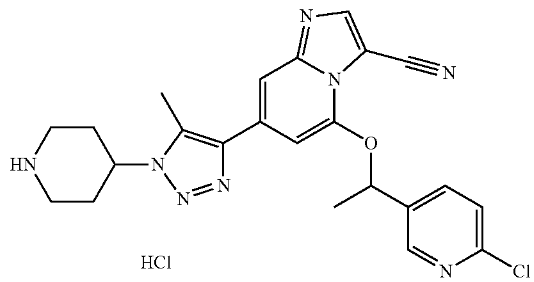 [SMILES: Cc1c(-c2cc(OC(C)c3ccc(Cl)nc3)n3c(C#N)cnc3c2)nnn1C1CCNCC1 ; Cl] | a |
| 799 | 7-[5-Methyl-1-(4-piperidyl)triazol-4-yl]-5-(trifluoromethyl)isoxazol-3-yl]ethoxy]imidazo[1,2-a]pyridine-3-carbonitrile HCl | 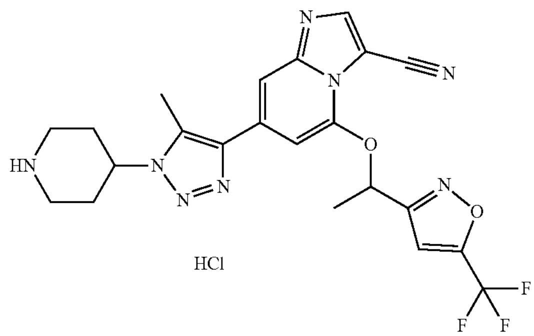 [SMILES: Cc1c(-c2cc(OC(C)c3cc(C(F)(F)F)on3)n3c(C#N)cnc3c2)nnn1C1CCNCC1 ; Cl] | 487.2 |
| 800 | 6-[5-Methyl-1-(4-piperidyl)triazol-4-yl]-4-[1-(5-methyl-1,3,4-thiadiazol-2-yl)ethoxy]pyrazolo[1,5-a]pyridine-3-carbonitrile HCl | 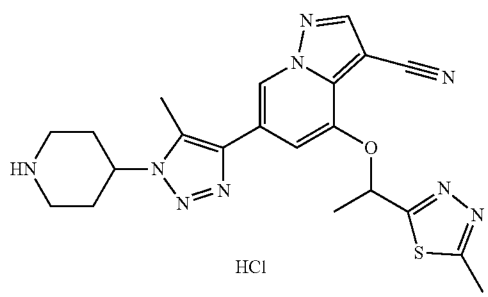 [SMILES: Cc1nnc(C(C)Oc2cc(-c3nnn(C4CCNCC4)c3C)cn3ncc(C#N)c23)s1 ; Cl] | 450.1 |
| 801 | 6-[5-Methyl-1-(4-piperidyl)triazol-4-yl]-4-[1-[2-morpholino-5-(trifluoromethyl)-3-pyridyl]ethoxy]pyrazolo[1,5-a]pyridine-3-carbonitrile 2 HCl | 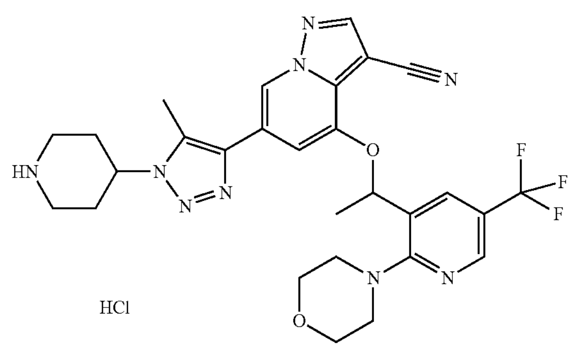 [SMILES: Cc1c(-c2cc(OC(C)c3cc(C(F)(F)F)cnc3N3CCOCC3)c3c(C#N)cnn3c2)nnn1C1CCNCC1 ; Cl] | 582.3 |
| 802 | 5-[1-(1-Isopropyltriazol-4-yl)ethoxy]-7-[5-methyl-1-(4-piperidyl)triazol-4-yl]imidazo[1,2-a]pyridine-3-carbonitrile HCl | 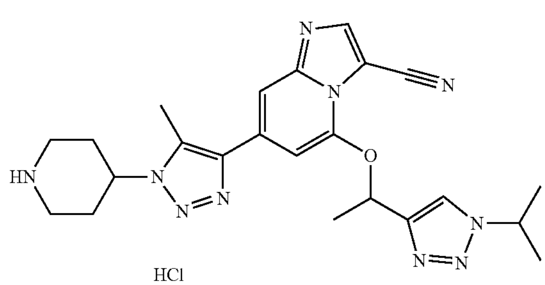 [SMILES: Cc1c(-c2cc(OC(C)c3cn(C(C)C)nn3)n3c(C#N)cnc3c2)nnn1C1CCNCC1 ; Cl] | 461.2 |

TABLE 52-continued

| Prep No. | Chemical Name | Structure | ES/MS m/z [M + H]+ |
|---|---|---|---|
| 803 | 7-[5-Methyl-1-(4-piperidyl)triazol-4-yl]-5-[1-(6-methylpyrazin-2-yl)ethoxy]imidazo[1,2-a]pyridine-3-carbonitrile 2 HCl | 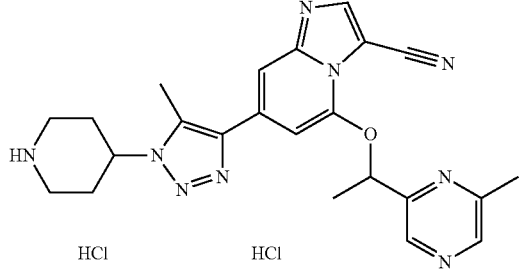 [SMILES: Cc1cncc(C(C)Oc2cc(-c3nnn(C4CCNCC4)c3C)cc3ncc(C#N)n23)n1 ; Cl ; Cl] | 444.2 |
| 804 | 5-[1-(3,3-Difluorocyclobutyl)ethoxy]-7-[5-methyl-1-(4-piperidyl)triazol-4-yl]imidazo[1,2-a]pyridine-3-carbonitrile HCl | 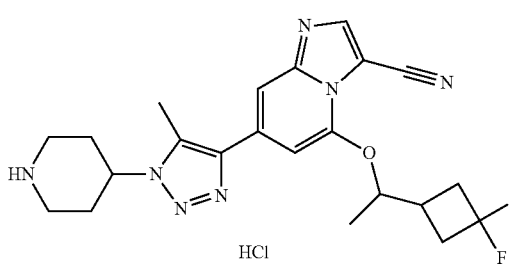 | 442.2 |
| 805 | 5-[(1R)-1-(2-Chloro-4-fluoro-phenyl)ethoxy]-7-[5-methyl-1-(4-piperidyl)triazol-4-yl]imidazo[1,2-a]pyridine-3-carbonitrile HCl | 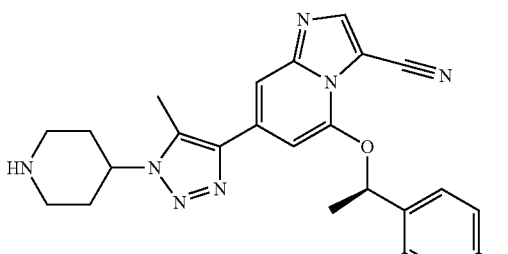 | 479.2 [M]+ |
| 806 | 5-[(1R)-1-(5-Fluoro-3-methyl-2-pyridyl)ethoxy]-7-[5-methyl-1-(4-piperidyl)triazol-4-yl]imidazo[1,2-a]pyridine-3-carbonitrile HCl | 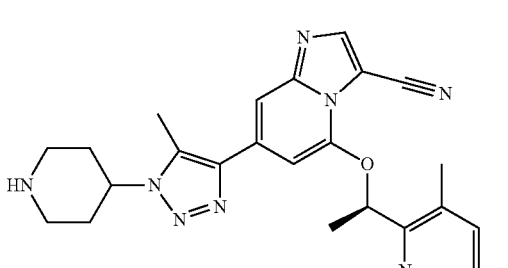 | 461.1 |
| 807 | 5-[2,2-Difluoro-1-(5-fluoro-2-pyridyl)ethoxy]-7-[5-methyl-1-(4-piperidyl)triazol-4-yl]imidazo[1,2-a]pyridine-3-carbonitrile di-HCl | 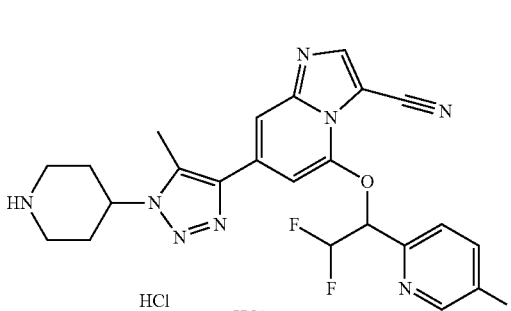 | 483.2 |

TABLE 52-continued

| Prep No. | Chemical Name | Structure | ES/MS m/z [M + H]+ |
|---|---|---|---|
| 808 | 5-[(5-Fluoro-2-pyridyl)-(trifluoromethyl)cyclopropyl]methoxy]-7-[5-methyl-1-(4-piperidyl)triazol-4-yl]imidazo[1,2-a]pyridine-3-carbonitrile HCl | 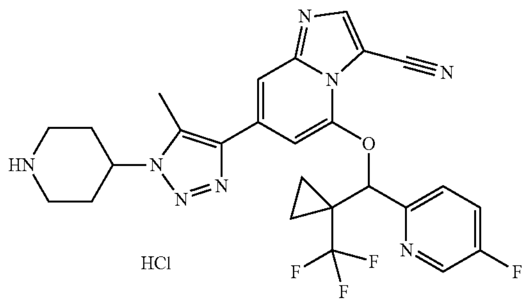 [SMILES: Cc1c(-c2cc(OC(c3ccc(F)cn3)C3(C(F)(F)F)CC3)n3c(C#N)cnc3c2)nnn1C1CCNCC1 ; Cl] | 541.2 |
| 809 | 5-[2-Methoxy-1-[5-(trifluoromethyl)-3-pyridyl]ethoxy]-7-[5-methyl-1-(4-piperidyl)triazol-4-yl]imidazo[1,2-a]pyridine-3-carbonitrile HCl | 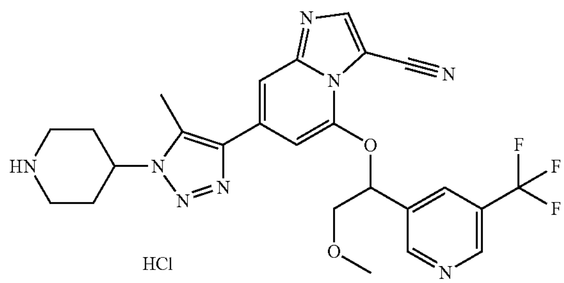 [SMILES: COCC(Oc1cc(-c2nnn(C3CCNCC3)c2C)cc2ncc(C#N)n12)c1cncc(C(F)(F)F)c1 ; Cl] | 527.1 |
| 810 | 5-[1-(5-Fluoro-3-pyridyl)ethoxy]-7-[5-methyl-1-(4-piperidyl)triazol-4-yl]imidazo[1,2-a]pyridine-3-carbonitrile HCl | 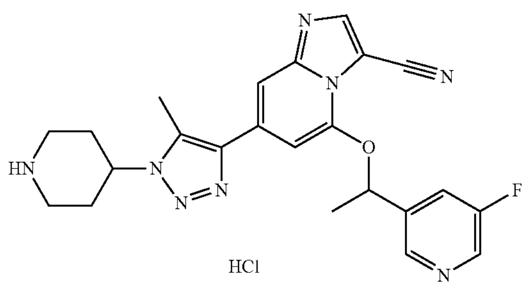 [SMILES: Cc1c(-c2cc(OC(C)c3cncc(F)c3)n3c(C#N)cnc3c2)nnn1C1CCNCC1 ; Cl] | 447.3 |
| 811 | 7-[5-Methyl-1-(4-piperidyl)triazol-4-yl]-5-[(1R)-1-(5-methyl-1,3,4-thiadiazol-2-yl)ethoxy]imidazo[1,2-a]pyridine-3-carbonitrile HCl | 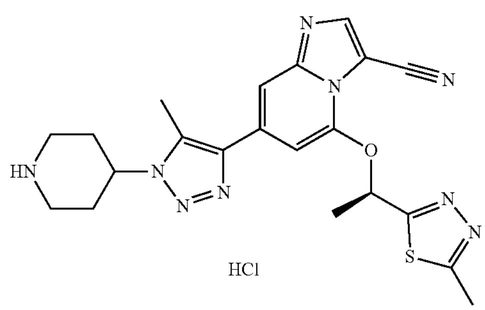 [SMILES: Cc1nnc([C@@H](C)Oc2cc(-c3nnn(C4CCNCC4)c3C)cc3ncc(C#N)n23)s1 ; Cl] | 450.1 |
| 812 | 4-[1-(4-methylisothiazol-5-yl)ethoxy]-6-[5-methyl-1-(4-piperidyl)triazol-4-yl]pyrazolo[1,5-a]pyridine-3-carbonitrile HCl | 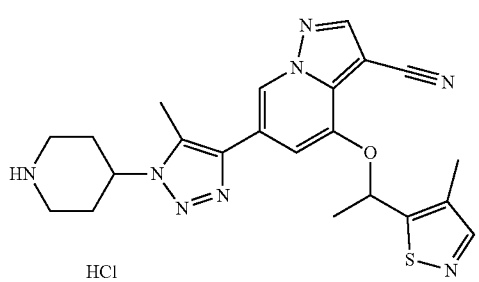 [SMILES: Cc1cnsc1C(C)Oc1cc(-c2nnn(C3CCNCC3)c2C)cn2ncc(C#N)c12 ; Cl] | 449.20 |

TABLE 52-continued

| Prep No. | Chemical Name | Structure | ES/MS m/z [M + H]+ |
|---|---|---|---|
| 813 | 4-[(1R)-1-(5-Fluoro-2-pyridyl)ethoxy]-6-[5-methyl-1-(4-piperidyl)triazol-4-yl]pyrazolo[1,5-a]pyridine-3-carbonitrile HCl | 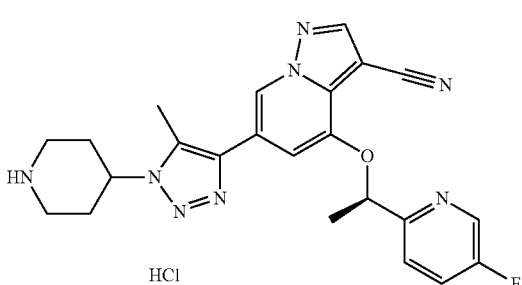 | 447.2 |
| 814 | 4-[2-methoxy-1-[5-(trifluoromethyl)-3-pyridyl]ethoxy]-6-[5-methyl-1-(4-piperidyl)triazol-4-yl]pyrazolo[1,5-a]pyridine-3-carbonitrile HCl | 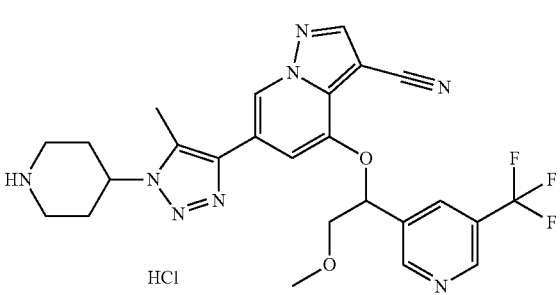 [SMILES: COCC(Oc1cc(-c2nnn(C3CCNCC3)c2C)cn2ncc(C#N)c12)c1cncc(C(F)(F)F)c1 ; Cl] | 527.2 |
| 815 | 5-[(6,6-Difluoro-5,7-dihydrocyclopenta[b]pyridin-7-yl)oxy]-7-[5-methyl-1-(4-piperidyl)triazol-4-yl]imidazo[1,2-a]pyridine-3-carbonitrile HCl | 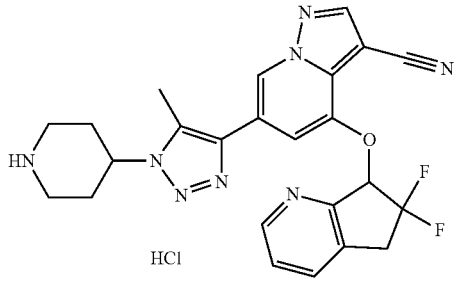 [SMILES: Cc1c(-c2cc(OC3c4ncccc4CC3(F)F)c3c(C#N)cnn3c2)nnn1C1CCNCC1 ; Cl] | 477.1 |
| 816 | 5-[1-(5-Chloropyridazin-3-yl)ethoxy]-7-[5-methyl-1-(4-piperidyl)triazol-4-yl]imidazo[1,2-a]pyridine-3-carbonitrile. HCl | 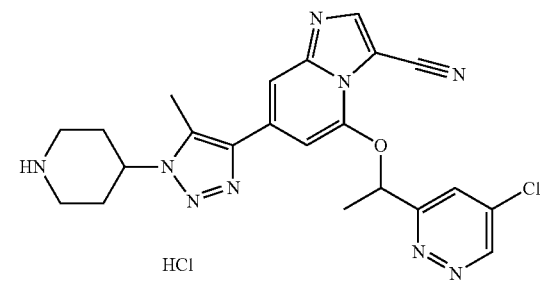 [SMILES: Cc1c(-c2cc(OC(C)c3cc(Cl)cnn3)n3c(C#N)cnc3c2)nnn1C1CCNCC1 ; Cl] | 464.1 |
| 817 | 4-[1-(5-Chloropyridazin-3-yl)ethoxy]-6-[5-methyl-1-(4-piperidyl)triazol-4-yl]pyrazolo[1,5-a]pyridine-3-carbonitrile. HCl | 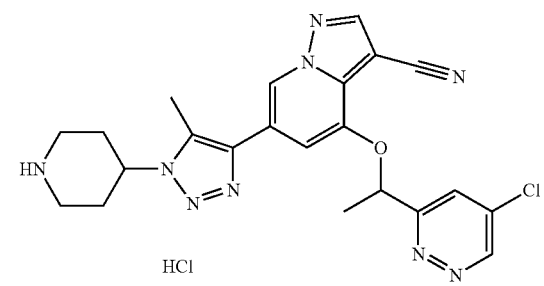 [SMILES: Cc1c(-c2cc(OC(C)c3cc(Cl)cnn3)c3c(C#N)cnn3c2)nnn1C1CCNCC1 ; Cl] | 464.1 |

TABLE 52-continued

| Prep No. | Chemical Name | Structure | ES/MS m/z [M + H]+ |
|---|---|---|---|
| 818 | 7-[5-Methyl-1-(4 piperidyl)triazol-4-yl]-5-[1-(5-methyl-3-pyridyl)ethoxy]imidazo[1,2-a]pyridine-3-carbonitrile. HCl | 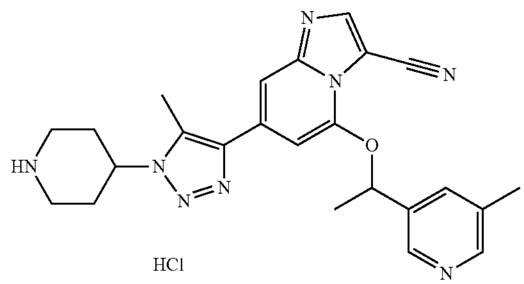 [SMILES: Cc1cncc(C(C)Oc2cc(-c3nnn(C4CCNCC4)c3C)cc3ncc(C#N)n23)c1 ; Cl] | 443.2 |
| 819 | 5-[1-[5-(Difluoromethyl)-3-pyridyl]ethoxy]-7-[5-methyl-1-(4-piperidyl)triazol-4-yl]imidazo[1,2-a]pyridine-3-carbonitrile. HCl | 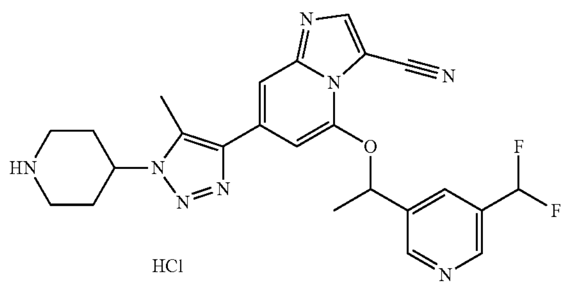 [SMILES: Cc1c(-c2cc(OC(C)c3cncc(C(F)F)c3)n3c(C#N)cnc3c2)nnn1C1CCNCC1 ; Cl] | 479.1 |
| 820 | 6-[5-Methyl-1-(4-piperidyl)triazol-4-yl]-4-[1-(6-methylpyrazin-2-yl)ethoxy]pyrazolo[1,5-a]pyridine-3-carbonitrile. 2 HCl | 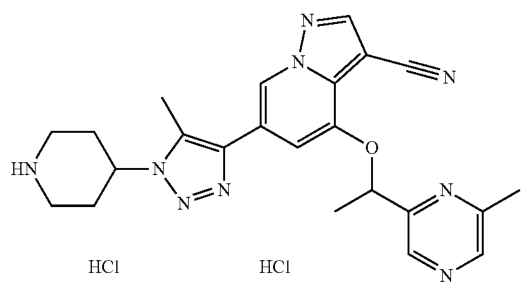 [SMILES: Cc1cncc(C(C)Oc2cc(-c3nnn(C4CCNCC4)c3C)cn3ncc(C#N)c23)n1 ; Cl ; Cl] | 444.2 |
| 821 | 6-[5-Methyl-1-(4-piperidyl)triazol-4-yl]-4-[1-(5-methylthiazol-2-yl)ethoxy]pyrazolo[1,5-a]pyridine-3-carbonitrile HCl | 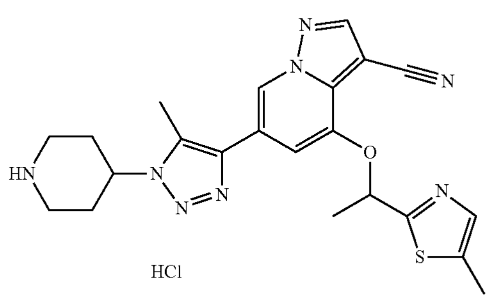 [SMILES: Cc1cnc(C(C)Oc2cc(-c3nnn(C4CCNCC4)c3C)cn3ncc(C#N)c23)s1 ; Cl] | 449.2 |
| 822 | 2-[3-Fluoro-6-[5-methyl-1-(4-piperidyl)triazol-4-yl]pyrazolo[1,5-a]pyridin-4-yl]oxy-1-(5-fluoro-2-pyridyl)ethanol HCl | 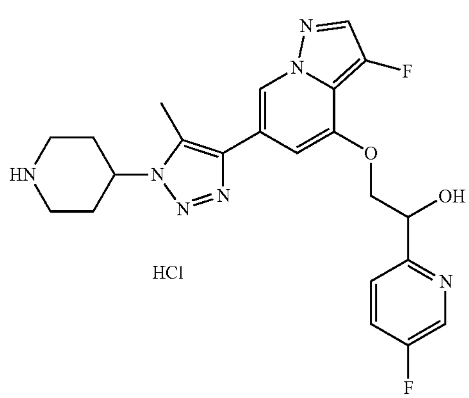 [SMILES: Cc1c(-c2cc(OCC(O)c3ccc(F)cn3)c3c(F)cnn3c2)nnn1C1CCNCC1 ; Cl] | 456.2 |

| Prep No. | Chemical Name | Structure | ES/MS m/z [M + H]+ |
|---|---|---|---|
| 823 | 2-[3-Chloro-6-[5-methyl-1-(4-piperidyl)triazol-4-yl]pyrazolo[1,5-a]pyridin-4-yl]oxy-1-(5-fluoro-2-pyridyl)ethanol HCl | 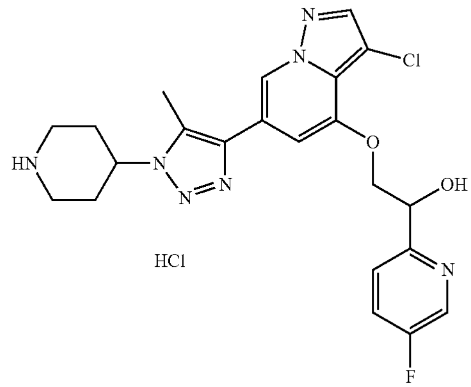 [SMILES: Cc1c(-c2cc(OCC(O)c3ccc(F)cn3)c3c(Cl)cnn3c2)nnn1C1CCNCC1 ; Cl] | 472.2 |
| 824 | 1-[3-Chloro-6-[5-methyl-1-(4-piperidyl)triazol-4-yl]pyrazolo[1,5-a]pyridin-4-yl]oxy-2-(5-fluoro-2-pyridyl)propan-2-ol HCl | 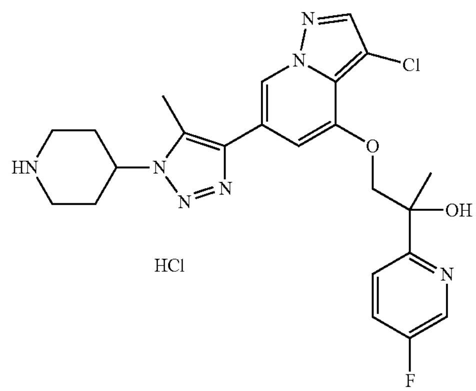 [SMILES: Cc1c(-c2cc(OCC(C)(O)c3ccc(F)cn3)c3c(Cl)cnn3c2)nnn1C1CCNCC1 ; Cl] | 486.2 |
| 825 | 1-[3-Fluoro-6-[5-methyl-1-(4-piperidyl)triazol-4-yl]pyrazolo[1,5-a]pyridin-4-yl]oxy-2-(5-fluoro-2-pyridyl)propan-2-ol HCl | 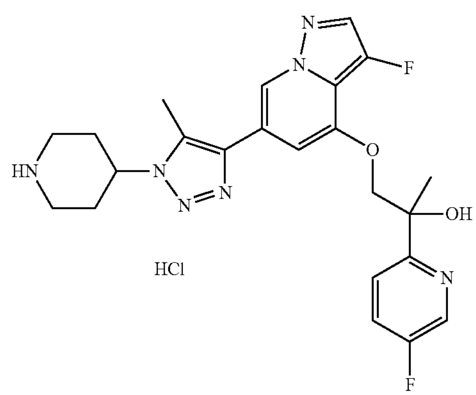 [SMILES: Cc1c(-c2cc(OCC(C)(O)c3ccc(F)cn3)c3c(F)cnn3c2)nnn1C1CCNCC1 ; Cl] | 470.2 |
| 826 | 7-[5-Methyl-1-(4-piperidyl)triazol-4-yl]-5-[(1R)-1-[4-(2,2,2-trifluoroethyl)-1,2,4-triazol-3-yl]ethoxy]imidazo[1,2-a]pyridine-3-carbonitrile TFA | 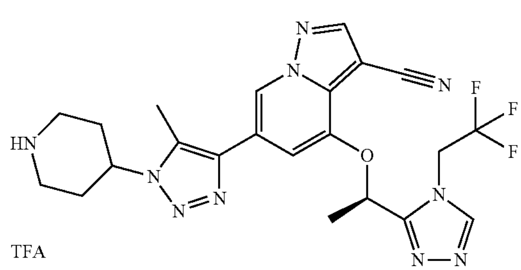 [SMILES: Cc1c(-c2cc(O[C@H](C)c3nncn3CC(F)(F)F)c3c(C#N)cnn3c2)nnn1C1CCNCC1 ; "TFA"] | 501.2 |

TABLE 52-continued

| Prep No. | Chemical Name | Structure | ES/MS m/z [M + H]+ |
|---|---|---|---|
| 827 | 2-[3-Fluoro-6-[5-methyl-1-(4-methyl-4-piperidyl)triazol-4-yl]pyrazolo[1,5-a]pyridin-4-yl]oxy-2-(5-fluoro-2-pyridyl)ethanol HCl, Isomer 2 | 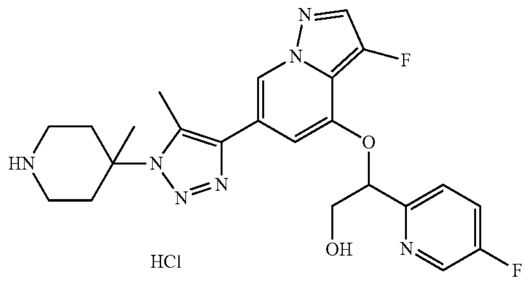 [SMILES: Cc1c(-c2cc(OC(CO)c3ccc(F)cn3)c3c(F)cnn3c2)nnn1C1(C)CCNCC1 ; Cl] | 470.2 |
| 828 | 3-Cyclopropyl-4-[(1R)-1-(5-fluoro-2-pyridyl)ethoxy]-6-[5-methyl-1-(4-piperidyl)triazol-4-yl]pyrazolo[1,5-a]pyridine HCl | 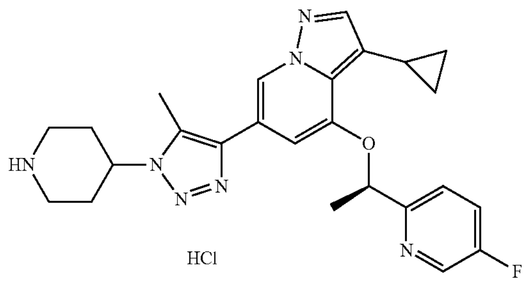 [SMILES: Cc1c(-c2cc(O[C@H](C)c3ccc(F)cn3)c3c(C4CC4)cnn3c2)nnn1C1CCNCC1 ; Cl] | 461.9 |
| 829 | 4-[1-[2-(1-Hydroxy-1-methyl-ethyl)phenyl]ethoxy]-6-[5-methyl-1-(4-piperidyl)triazol-4-yl]pyrazolo[1,5-a]pyridine-3-carbonitrile HCl | 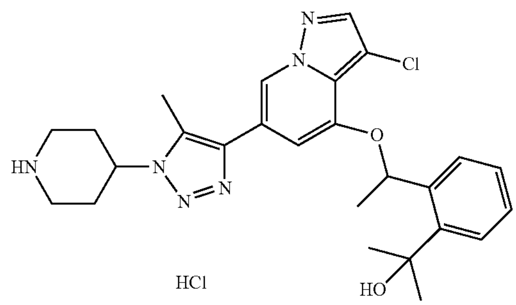 [SMILES: Cc1c(-c2cc(OC(C)c3ccccc3C(C)(C)O)c3c(Cl)cnn3c2)nnn1C1CCNCC1 ; Cl] | 485.9 |
| 830 | 3-[3-Chloro-6-[5-methyl-1-(4-piperidyl)triazol-4-yl]pyrazolo[1,5-a]pyridin-4-yl]oxy-3-(5-fluoro-2-pyridyl)-2,2-dimethyl-propanenitrile 2HCl | 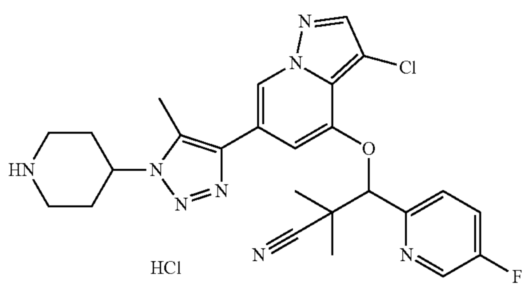 [SMILES: Cc1c(-c2cc(OC(c3ccc(F)cn3)C(C)(C)C#N)c3c(Cl)cnn3c2)nnn1C1CCNCC1 ; Cl] | 481.7 [M − 2H − CN]+ |
| 831 | 4-[1-[2-(2-Methoxyethylamino)-5-(trifluoromethyl)-3-pyridyl]ethoxy]-6-[5-methyl-1-(4-piperidyl)triazol-4-yl]pyrazolo[1,5-a]pyridine-3-carbonitrile 2HCl | 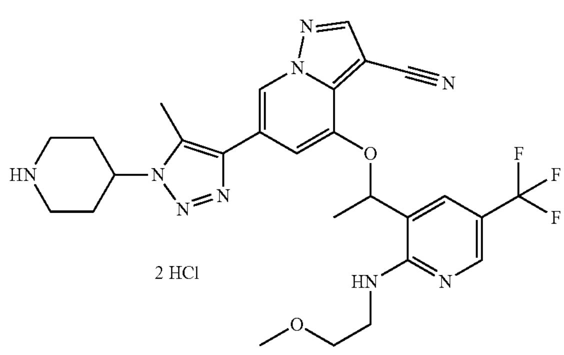 [SMILES: COCCNc1ncc(C(F)(F)F)cc1C(C)Oc1cc(-c2nnn(C3CCNCC3)c2C)cn2ncc(C#N)c12 ; "2 HCl"] | 570.2 |

TABLE 52-continued

| Prep No. | Chemical Name | Structure | ES/MS m/z [M + H]+ |
|---|---|---|---|
| 821 | 5-[(1R)-1-(5-Fluoro-2-pyridyl)ethoxy]-743-(2-hydroxyethyl)-5-methyl-1-(4-piperidyl)pyrazol-4-yl]imidazo[1,2-a]pyridine-3-carbonitrile HCl | | 490.3 | a Material taken on to next step without further purifcation.

Preparation 833

4-Methoxy-6-(5-methyl-1-[1-[(3S)-pyrrolidin-3-yl]pyridine289-3-yl]pyrazol-4-yl)pyrazolo[1,5-a]pyridine-3-carbonitrile

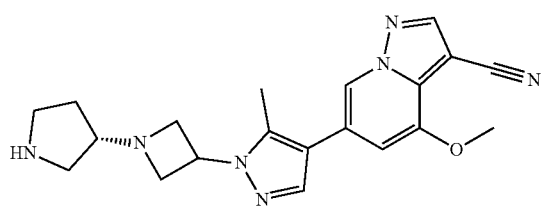 [SMILES: COc1cc(-c2cnn(C3CN([C@H]4CCNC4)C3)c2C)cn2ncc(C#N)c12]

A mixture of tert-butyl (3S)-3-[3-(4-[3-cyano-4-methoxy-pyrazolo[1,5-a]289yridine-6-yl]-5-methylpyrazol-1-yl pyridine289-1-yl]pyrrolidine-1-carboxylate (190 mg, 0.42 mmol) in TFA (5 mL) and DCM (5 mL) is stirred for 2 hrs at RT. The mixture is concentrated under reduced pressure to give the title compound as a dark green oil (260 mg). The pH of the crude product (60 mg) is adjusted with NaHCO$_3$ and purified by Prep-HPLC with the following conditions: Column, Xbridge Shield RP18 OBD, 19*150 mm, 5 μm; eluting with a gradient of 20% to 35% ACN in H$_2$O (10 mmol/L NH$_4$HCO$_3$), flow rate: 25 mL/min; 254 nm; t$_{(R)}$ 5.57 min to give the title compound as a white solid (20 mg, 12.7%). ES/MS m/z 378.3 [M+H]+.

The following compounds are prepared essentially as described for (S)-4-methoxy 6-(5-methyl-1-[1-[(3S)-pyrrolidin-3-yl]pyridine289-3-yl]pyrazol-4-yl)pyrazolo[1,5-a]pyridine-3-carbonitrile using the appropriate reagents, adjusting the reaction times to determine completion of the reactions, and adjusting the purification system as appropriate. The crude product can also be dissolved in MeOH and Na$_2$CO$_3$ can also be used as an alternate base. 2,6-Lutidine in DCM can also be used as the base and solvent combination. HCl in 1,4-dioxane can also be used in lieu of TFA. For compounds where the amine salt was isolated, the formation of the mono-, di-, or trivalent salt is dependent on the pKa of the amine and the acid used to form the salt. The exact mono-, di-, or trivalent salt form for each example was not identified.

TABLE 53

| Prep No. | Chemical Name | Structure | ES/MS m/z [M + H]+ |
|---|---|---|---|
| 834[1] | 4-Methoxy-6-[5-methyl-1-[1-[(3S)-3-piperidyl]pyridine-3-yl]pyrazol-4-yl]pyrazolo[1,5-a]pyridine-3-carbonitrile | 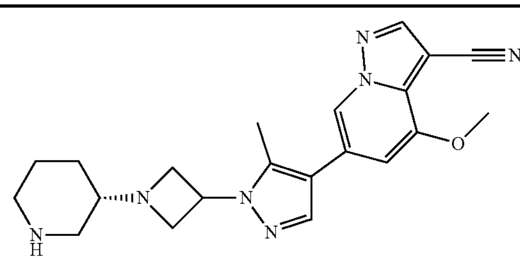 | 392.05 |
| 835[2] | 4-Methoxy-6-[5-methyl-1-[1-[(3R)-3-piperidyl]pyridine-3-yl]pyrazol-4-yl]pyrazolo[1,5-a]pyridine-3-carbonitrile | 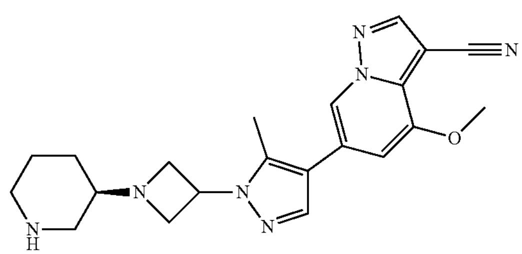 [SMILES: COc1cc(-c2cnn(C3CN([C@@H]4CCCNC4)C3)c2C)cn2ncc(C#N)c12] | 392.20 |

| Prep No. | Chemical Name | Structure | ES/MS m/z [M + H]⁺ |
|---|---|---|---|
| 836[3] | 4-[1-(2-Ethyltriazol-4-yl)ethoxy]-6-[5-methyl-1-(4-piperidyl)triazol-4-yl]pyrazolo[1,5-a]pyridine-3-carbonitrile | 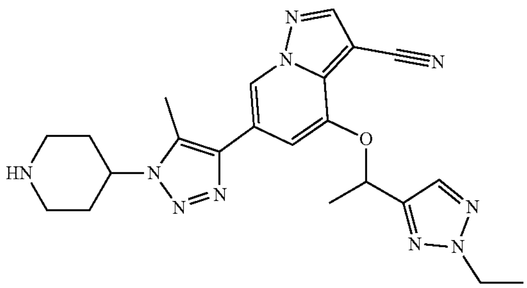 [SMILES: CCn1ncc(C(C)Oc2cc(-c3nnn(C4CCNCC4)c3C)cn3ncc(C#N)c23)n1] | 447.2 |
| 837[3] | 4-[(1-fluorocyclopropyl)-(5-fluoro-2-pyridyl)methoxy]-6-[5-methyl-1-(4-piperidyl)triazol-4-yl]pyrazolo[1,5-a]pyridine-3-carbonitrile | 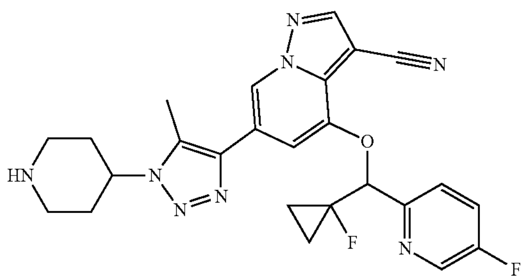 [SMILES: Cc1c(-c2cc(OC(c3ccc(F)cn3)C3(F)CC3)c3c(C#N)cnn3c2)nnn1C1CCNCC1] | 492.8 |
| 838[4] | 5-[1-(5-Chloro-2-pyridyl)-2-hydroxy-ethoxy]-7-[5-methyl-1-(4-piperidyl)triazol-4-yl]imidazo[1,2-a]pyridine-3-carbonitrile | 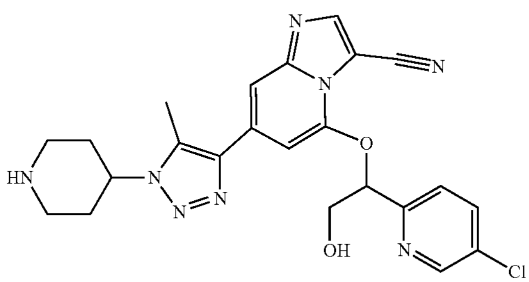 [SMILES: Cc1c(-c2cc(OC(CO)c3ccc(Cl)cn3)n3c(C#N)cnc3c2)nnn1C1CCNCC1] | 479.1 |
| 839[5,6,7] | 4-methoxy-6-(4-methyl-5-piperazin-1-yl-1,2,4-triazol-3-yl)pyrazolo[1,5-a]pyridine-3-carbonitrile | 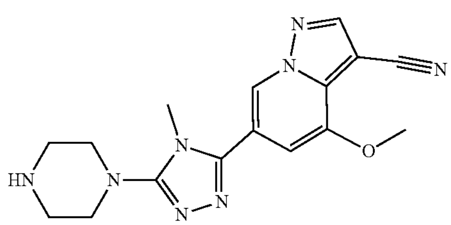 [SMILES: COc1cc(-c2nnc(N3CCNCC3)n2C)cn2ncc(C#N)c12] | 339.2 |
| 840[8] | 6-[5-Methyl-1-(4-piperidyl)triazol-4-yl]-4-[(1R)-1-(2-methylthiazol-4-yl)ethoxy]pyrazolo[1,5-a]pyridine-3-carbonitrile | 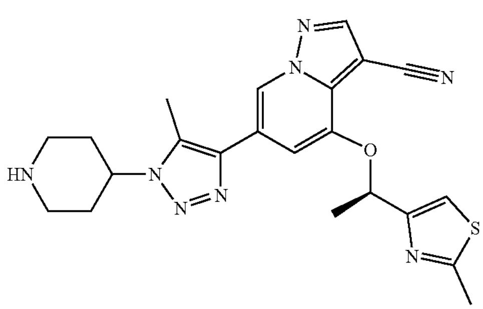 [SMILES: Cc1nc([C@@H](C)Oc2cc(-c3nnn(C4CCNCC4)c3C)cn3ncc(C#N)c23)cs1] | 449.2 |

TABLE 53-continued

| Prep No. | Chemical Name | Structure | ES/MS m/z [M + H]+ |
|---|---|---|---|
| 841[8] | 6-[5-Methyl-1-(4-piperidyl)triazol-4-yl]-4-[(1R)-1-(1-methylpyrazol-3-yl)ethoxy]pyrazolo[1,5-a]pyridine-3-carbonitrile | 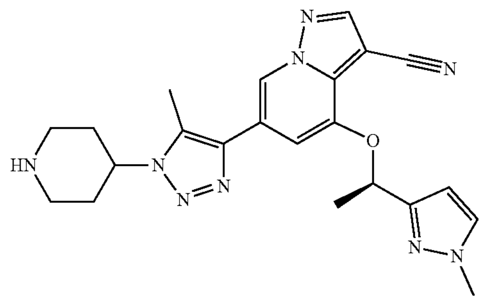 [SMILES: Cc1c(-c2cc(O[C@H](C)c3ccn(C)n3)c3c(C#N)cnn3c2)nnn1C1CCNCC1] | 432.2 |
| 842[9] | 5-[1-(1,2-Benzothiazol-7-yl)ethoxy]-7-[5-methyl-1-(4-piperidyl)triazol-4-yl]imidazo[1,2-a]pyridine-3-carbonitrile | 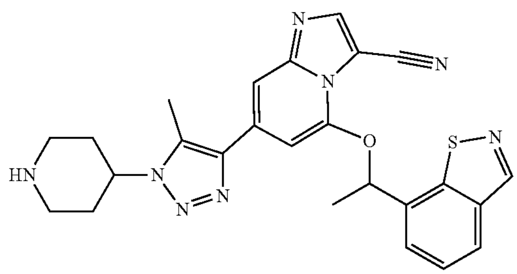 [SMILES: Cc1c(-c2cc(OC(C)c3cccc4cnsc34)n3c(C#N)cnc3c2)nnn1C1CCNCC1] | 485.1 |
| 843[9] | 4-[1-(1,2-Benzothiazol-7-yl)ethoxy]-6-[5-methyl-1-(4-piperidyl)triazol-4-yl]pyrazolo[1,5-a]pyridine-3-carbonitrile | 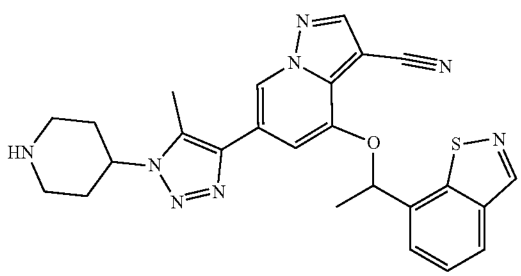 [SMILES: Cc1c(-c2cc(OC(C)c3cccc4cnsc34)c3c(C#N)cnn3c2)nnn1C1CCNCC1] | 485.2 |
| 844[10] | 5-[(1R)-1-(4-Fluorophenyl)ethoxy]-7-[5-methyl-1-(4-piperidyl)triazol-4-yl]imidazo[1,2-a]pyridine-3-carbonitrile | 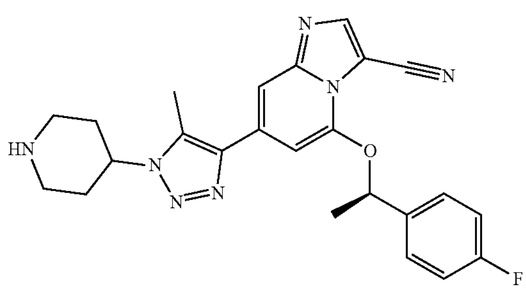 [SMILES: Cc1c(-c2cc(O[C@H](C)c3ccc(F)cc3)n3c(C#N)cnc3c2)nnn1C1CCNCC1] | 446.2 |
| 845[11] | 7-[5-Methyl-1-(4-piperidyl)triazol-4-yl]-5-[1-(5-methylpyridazin-3-yl)ethoxy]imidazo[1,2-a]pyridine-3-carbonitrile | 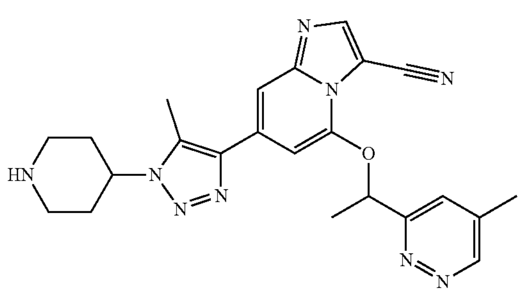 [SMILES: Cc1cnnc(C(C)Oc2cc(-c3nnn(C4CCNCC4)c3C)cc3ncc(C#N)n23)c1] | 444.2 |

TABLE 53-continued

| Prep No. | Chemical Name | Structure | ES/MS m/z [M + H]+ |
|---|---|---|---|
| 846[12] | 3-Chloro-5-[(1R)-1-(5-fluoro-2-pyridyl)ethoxy]-7-[5-methyl-1-(4-piperidyl)pyrazol-4-yl]imidazo[1,2-c]pyrimidine | 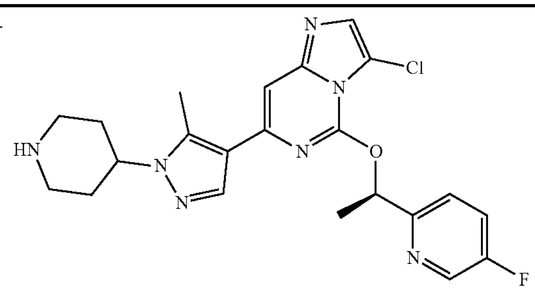 | 439.2 |

[1]Prep-HPLC with the following conditions: Column, Xbridge Prep C18 OBD, 19 * 150 mm, 5 μm; eluting with 38-50% MeOH in H$_2$O (0.05% NH$_3$H$_2$O).
[2]Reverse Combi-flash chromatography with the following conditions: Column, C18, eluting with a gradient of 30-60% ACN in H$_2$O (0.1% NH$_3$H$_2$O).
[3]Reverse phase chromatography eluting with a gradient of 0-100% ACN in H$_2$O.
[4]Purified by reverse flash chromatography: Column, C18; eluting with 50% to 55% ACN in H$_2$O (0.1% NH$_4$OH), 50% to 55% gradient.
[5]Reaction is diluted with 3:1 CHCl$_3$:iPrOH and concentrated in vacuo. Residue is dissolved into 4:1 DCM:iPrOH, washed with NaHCO$_3$, washed with H$_2$O, brine, dried over Na$_2$SO$_4$, filtered and concentrated.
[6]Reverse phase C18 chromatography eluting with 10% to 95% ACN in H$_2$O.
[7]Reverse phase C18 chromatography eluting with 10% to 100% ACN in H$_2$O.
[8]Volatiles are removed, and residue is filtered through a carbonate cartridge.
[9]The reaction is quenched by the addition of aq NaHCO$_3$, and the mixture is extracted with DCM.
[10]Purified by reverse phase chromatography: Column, C18; eluting with 50% to 60% ACN in H$_2$O (0.1% NH$_4$HCO$_3$).
[11]Purified by reverse phase chromatography: Column, C18; eluting with 0% to 50% ACN in H$_2$O (0.1% FA).
[12]Reaction concentrated in vacuo. Residue is dissolved into 3:1 CHCl$_3$:IPA, washed with aq NaHCO$_3$, H$_2$O, brine, dried over Na$_2$SO$_4$, filtered and concentrated.

Preparation 847

5-Methoxy-7-[5-methyl-1-(piperidin-4-yl)-1,2,3-triazol-4-yl]imidazo[1,2-a]pyridine-3-carbonitrile.HCl

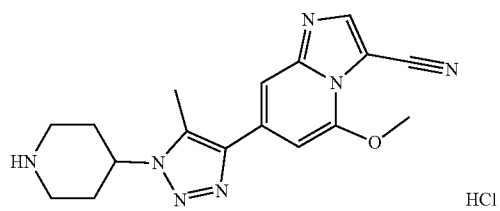 [SMILES: COc1cc(-c2nnn(C3CCNCC3)c2C)cc2ncc(C#N)n12 ; Cl]

A solution of tert-butyl 4-(4-[3-ethynyl-5-methoxyimidazo[1,2-a]pyridine-7-yl]-5-methyl-1,2,3-triazol-1-yl)piperidine-1-carboxylate (450.00 mg, 1.03 mmol), DCM (10 mL), HCl (4 M) in 1,4-dioxane (10.00 mL) is stirred for 2 hrs at RT. The mixture is concentrated under reduced pressure, diluted with EtOAc (3 mL) and hexanes (20 mL), and stirred 5 min. The solid is collected by filtration, and the filter cake is washed with hexanes (2×10 mL) and lyophilized to give the title compound as a brown solid (110 mg, 28.6%). ES/MS m/z 338.0 [M+H]+.

Preparation 848

6-[1-[1-(Azetidin-3-yl)piperidin-4-yl]-5-methylpyrazol-4-yl]-4-methoxypyrazolo[1,5-a]pyridine-3-carbonitrile

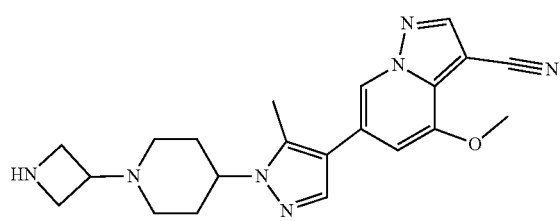 [SMILES: COc1cc(-c2cnn(C3CCN(C4CNC4)CC3)c2C)cn2ncc(C#N)c12]

TFA (2 mL) is added dropwise to a stirred solution of tert-butyl 3-[4-(4-[3-cyano-4-methoxypyrazolo[1,5-a]pyridine-6-yl]-5-methylpyrazol-1-yl)piperidin-1-yl]azetidine-1-carboxylate (100.00 mg, 0.20 mmol) in DCM (2.00 mL) and the solution is stirred for 1 hr at RT. The mixture is concentrated under reduced pressure to give the title compound (120 mg, crude). The product is used directly without further purification. ES/MS m/z 392.2 [M+H]+.

The following compounds are prepared essentially as described for 6-[1-[1-(azetidin-3-yl)piperidin-4-yl]-5-methylpyrazol-4-yl]-4-methoxypyrazolo[1,5-a]pyridine-3-carbonitrile using the appropriate reagents and adjusting the reaction times to determine completion of the reactions. 2,6-Lutidine in DCM can also be used as the solvent. HCl in 1,4-dioxane or TMSOTf can also be used in lieu of TFA. For compounds where the amine salt was isolated, the formation of the mono-, di-, or trivalent salt is dependent on the pKa of the amine and the acid used to form the salt. The exact mono-, di-, or trivalent salt form for each example was not identified.

TABLE 54

| Prep No. | Chemical Name | Structure | ES/MS m/z [M + H]+ |
|---|---|---|---|
| 849 | 4-Methoxy-6-(5-methyl-1-[1-[(3R)-pyrrolidin-3-yl]pyridine-3-yl]pyrazol-4-yl)pyrazolo[1,5-a]pyridine-3-carbonitrile. TFA | 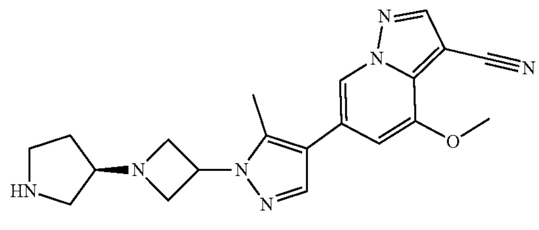 | 378.2 |
| 850[1] | 6-[1-(Azetidin-3-yl)-5-methyl-1,2,3-triazol-4-yl]-4-methoxypyrazolo[1,5-a]pyridine-3-carbonitrile. TFA | 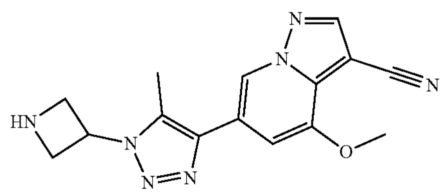 | 310.2 |
| 851 | 4-Methoxy-6-[5-methyl-1-(piperidin-4-yl)-1,2,3-triazol-4-yl]pyrazolo[1,5-a]pyridine-3-carbonitrile. TFA | 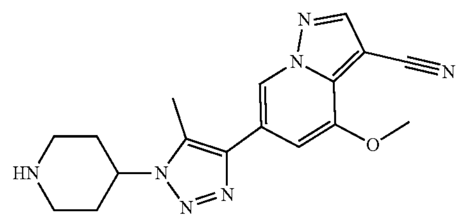 | 338.1 |
| 852[2] | 4-Methoxy-6-(5-methyl-1-(7-azaspiro[3.5]nonan-2-yl)-1H-pyrazol-4-yl)pyrazolo[1,5-a]pyridine-3-carbonitrile. HCl | 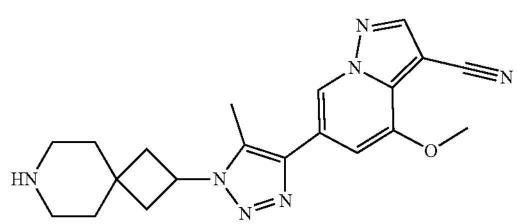 | 377.3 |
| 853 | 6-[1-(Azetidin-3-yl)-5-methyl-1,2,3-triazol-4-yl]-4-isopropoxypyrazolo[1,5-a]pyridine-3-carbonitrile. TFA | 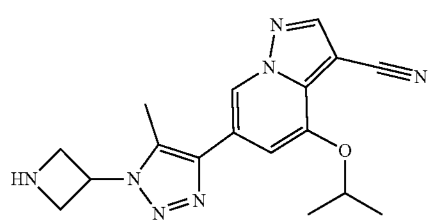 | 338.2 |
| 854[3] | 6-(1-((1R,3r,5S)-8-Azabicyclo[3.2.1]octan-3-yl)-5-methyl-1H-pyrazol-4-yl)-4-methoxypyrazolo[1,5-a]pyridine-3-carbonitrile. HCl | 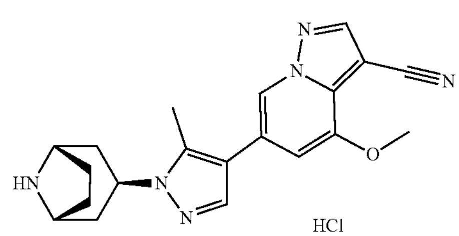 [SMILES: COc1cc(-c2cnn([C@H]3C[C@H]4CC[C@@H](C3)N4)c2C)cn2ncc(C#N)c12 ; Cl] | 363.2 |

TABLE 54-continued

| Prep No. | Chemical Name | Structure | ES/MS m/z [M + H]+ |
|---|---|---|---|
| 855[4] | 6-(1-((1R,3s,5S)-8-Azabicyclo[3.2.1]octan-3-yl)-5-methyl-1H-pyrazol-4-yl)-4-methoxypyrazolo[1,5-a]pyridine-3-carbonitrile. HCl | 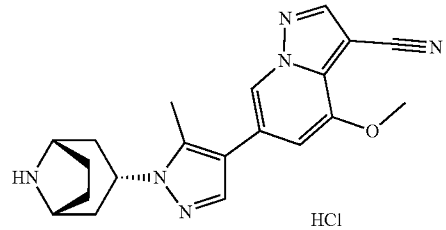 [SMILES: COc1cc(-c2cnn([C@@H]3C[C@H]4CC[C@@H](C3)N4)c2C)cn2ncc(C#N)c12 ; Cl] | 363.15 |
| 856 | 4-Methoxy-6-(5-methyl-1-(1-((3S)-pyrrolidin-3-yl)piperidin-4-yl)-1H-pyrazol-4-yl)pyrazolo[1,5-a]pyridine-3-carbonitrile. TFA | 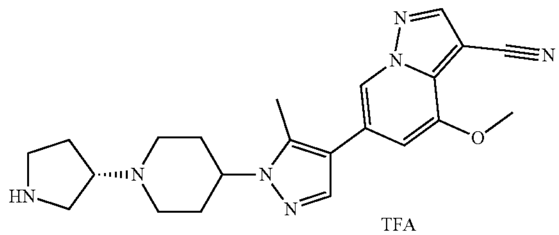 [SMILES: COc1cc(-c2cnn(C3CCN([C@H]4CCNC4)CC3)c2C)cn2ncc(C#N)c12] | 406.1 |
| 857 | 6-[5-Methyl-1-(piperidin-4-yl)pyrazol-4-yl]-4-[(1R)-1-(pyridin-2-yl)ethoxy]pyrazolo[1,5-a]pyridine-3-carbonitrile. TFA | 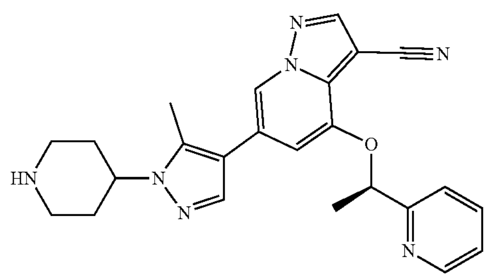 | 428.3 |
| 858 | 6-[1-(Azetidin-3-yl)-5-methylpyrazol-4-yl]-4-[(1R)-1-(pyridin-2-yl)ethoxy]pyrazolo[1,5-a]pyridine-3-carbonitrile. TFA | 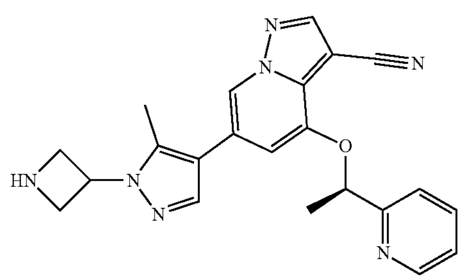 | 400.2 |
| 859 | 4-Methoxy-6-(5-methyl-1-[1-[(3R)-pyrrolidin-3-yl]piperidin-4-yl]pyrazol-4-yl)pyrazolo[1,5-a]pyridine-3-carbonitrile. TFA | 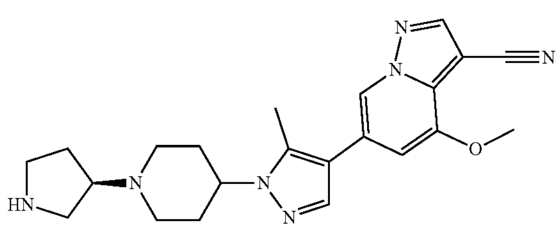 | 406.1 |

TABLE 54-continued

| Prep No. | Chemical Name | Structure | ES/MS m/z [M + H]+ |
|---|---|---|---|
| 860 | 6-[1-[(4S)-Azepan-4-yl]-5-methylpyrazol-4-yl]-4-methoxypyrazolo[1,5-a]pyridine-3-carbonitrile. HCl | 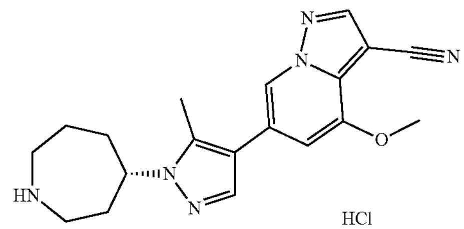 [SMILES: COc1cc(-c2cnn([C@H]3CCCNCC3)c2C)cn2ncc(C#N)c12 ; Cl] | 351.3 |
| 861[5] | 6-[1-[(4R)-Azepan-4-yl]-5-methylpyrazol-4-yl]-4-methoxypyrazolo[1,5-a]pyridine-3-carbonitrile. HCl | 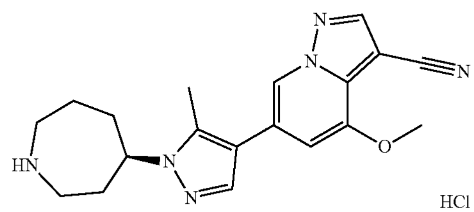 [SMILES: COc1cc(-c2cnn([C@@H]3CCCNCC3)c2C)cn2ncc(C#N)c12 ; Cl] | 351.2 |
| 862 | 6-[5-Methyl-1-(piperidin-4-yl)pyrazol-4-yl]-4-[(1S)-1-(pyridin-2-yl)ethoxy]pyrazolo[1,5-a]pyridine-3-carbonitrile. TFA | 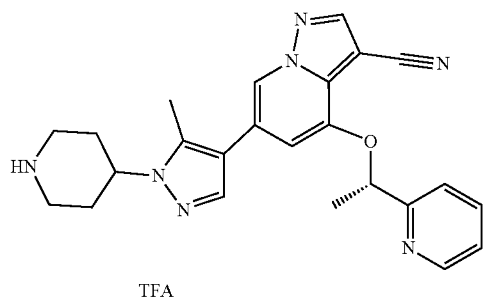 [SMILES: Cc1c(-c2cc(O[C@@H](C)c3ccccn3)c3c(C#N)cnn3c2)cnn1C1CCNCC1 ; "TFA"] | 428.2 |
| 863 | 6-(5-Methyl-1-[1-[(3S)-pyrrolidin-3-yl]azetidin-3-yl]pyrazol-4-yl)-4-[(1R)-1-(pyridin-2-yl)ethoxy]pyrazolo[1,5-a]pyridine-3-carbonitrile. TFA | 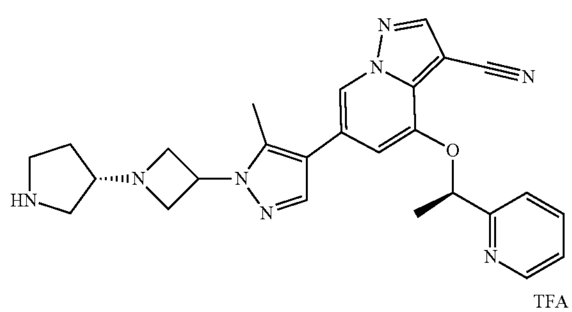 [SMILES: Cc1c(-c2cc(O[C@H](C)c3ccccn3)c3c(C#N)cnn3c2)cnn1C1CN([C@H]2CCNC2)C1] | 469.3 |
| 864 | 6-(5-Methyl-1-[1-[(3R)-pyrrolidin-3-yl]azetidin-3-yl]pyrazol-4-yl)-4-[(1R)-1-(pyridin-2-yl)ethoxy]pyrazolo[1,5-a]pyridine-3-carbonitrile. TFA | 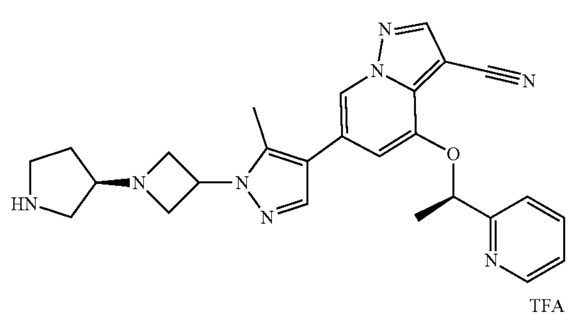 [SMILES: Cc1c(-c2cc(O[C@H](C)c3ccccn3)c3c(C#N)cnn3c2)cnn1C1CN([C@@H]2CCNC2)C1] | 469.2 |

TABLE 54-continued

| Prep No. | Chemical Name | Structure | ES/MS m/z [M + H]+ |
|---|---|---|---|
| 865 | 6-(1-(Azetidin-3-yl)-3-methyl-1H-pyrazol-4-yl)-4-methoxypyrazolo[1,5-a]pyridine-3-carbonitrile. TFA | 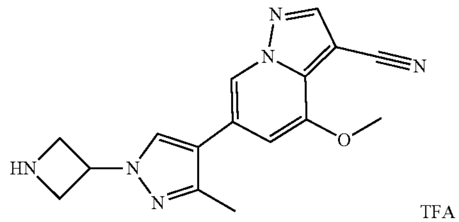 [SMILES: COc1cc(-c2cn(C3CNC3)nc2C)cn2ncc(C#N)c12] | 309.3 |
| 866[6] | 6-[5-Methyl-1-(piperidin-4-yl)pyrazol-4-yl]-4-[(1R)-1-(oxan-4-yl)ethoxy]pyrazolo[1,5-a]pyridine-3-carbonitrile. HCl | 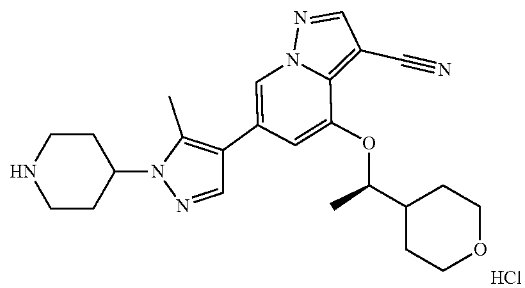 [SMILES: Cc1c(-c2cc(O[C@H](C)C3CCOCC3)c3c(C#N)cnn3c2)cnn1C1CCNCC1 ; Cl] | 435.4 |
| 867 | 4-[(3-Fluoropyridin-2-yl)methoxy]-6-[5-methyl-1-(piperidin-4-yl)pyrazol-4-yl]pyrazolo[1,5-a]pyridine-3-carbonitrile. HCl | 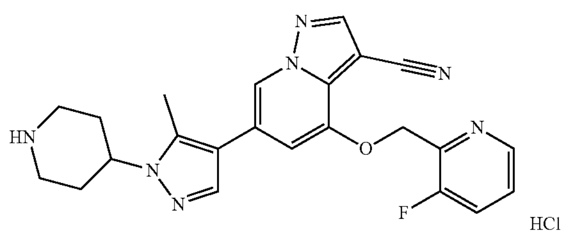 [SMILES: Cc1c(-c2cc(OCc3ncccc3F)c3c(C#N)cnn3c2)cnn1C1CCNCC1 ; Cl] | 432.2 |
| 868[4] | 4-[(1R)-1-(3-Fluoropyridin-2-yl)ethoxy]-6-[5-methyl-1-(piperidin-4-yl)pyrazol-4-yl]pyrazolo[1,5-a]pyridine-3-carbonitrile. HCl | 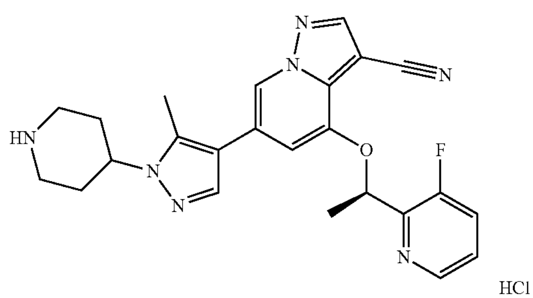 [SMILES: Cc1c(-c2cc(O[C@H](C)c3ncccc3F)c3c(C#N)cnn3c2)cnn1C1CCNCC1 ; Cl] | 446.3 |
| 869 | 6-[5-Methyl-1-(piperidin-4-yl)pyrazol-4-yl]-4-[(1R)-1-(2-methylpyrazol-3-yl)ethoxy]pyrazolo[1,5-a]pyridine-3-carbonitrile. HCl | 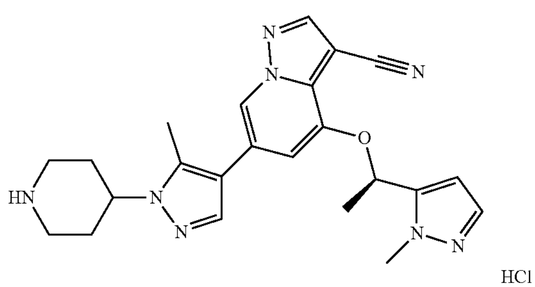 [SMILES: Cc1c(-c2cc(O[C@H](C)c3ccnn3C)c3c(C#N)cnn3c2)cnn1C1CCNCC1 ; Cl] | 431.2 |

TABLE 54-continued

| Prep No. | Chemical Name | Structure | ES/MS m/z [M + H]+ |
|---|---|---|---|
| 870 | 7-[5-Methyl-1-(piperidin-4-yl)pyrazol-4-yl]-5-[(1R)-1-(pyridin-2-yl)ethoxy]imidazo[1,2-a]pyridine-3-carbonitrile. TFA | 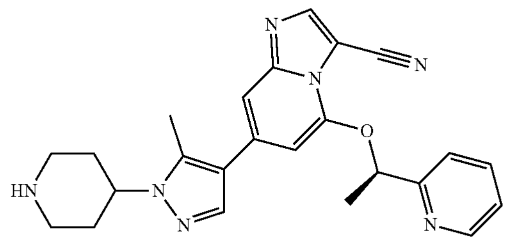 | 428.3 |
| 871 | 4-Methoxy-6-(5-methyl-1-[1-[(3R,5S)-5-methylpyrrolidin-3-yl]azetidin-3-yl]pyrazol-4-yl)pyrazolo[1,5-a]pyridine-3-carbonitrile. TFA | 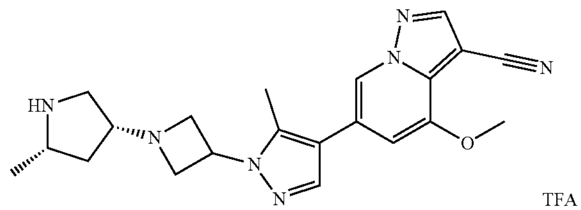 [SMILES: COc1cc(-c2cnn(C3CN([C@H]4CN[C@@H](C)C4)C3)c2C)cn2ncc(C#N)c12] | 392.1 |
| 872 | 4-Methoxy-6-(5-methyl-1-((3R,5S)-5-methylpyrrolidin-3-yl)-1H-pyrazol-4-yl)pyrazolo[1,5-a]pyridine-3-carbonitrile | 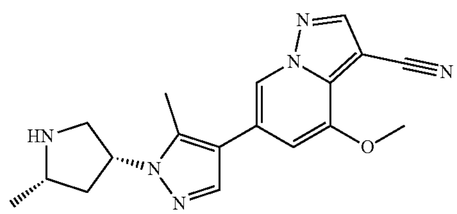 [SMILES: COc1cc(-c2cnn([C@H]3CN[C@@H](C)C3)c2C)cn2ncc(C#N)c12] | 337.2 |
| 873 | 4-Methoxy-6-[1-[1-(5,5-Dimethylpyrrolidin-3-yl)azetidin-3-yl]-5-methylpyrazol-4-yl]-pyrazolo[1,5-a]pyridine-3-carbonitrile. TFA | 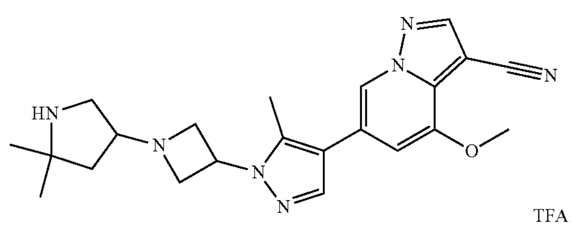 [SMILES: COc1cc(-c2cnn(C3CN(C4CNC(C)(C)C4)C3)c2C)cn2ncc(C#N)c12] | 406.1 |
| 874 | 4-Methoxy-6-(5-methyl-1-[1-[(3R,5R)-5-methylpyrrolidin-3-yl]azetidin-3-yl]pyrazol-4-yl)pyrazolo[1,5-a]pyridine-3-carbonitrile. TFA | 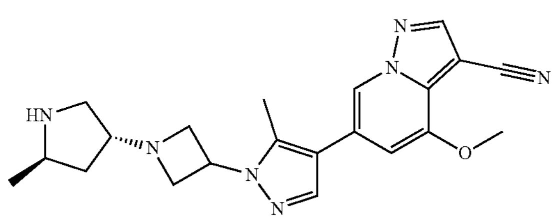 | 392.2 |
| 875 | 4-Methoxy-6-[5-methyl-1-[(3R,5R)-5-methylpyrrolidin-3-yl]pyrazol-4-yl]pyrazolo[1,5-a]pyridine-3-carbonitrile. HCl | 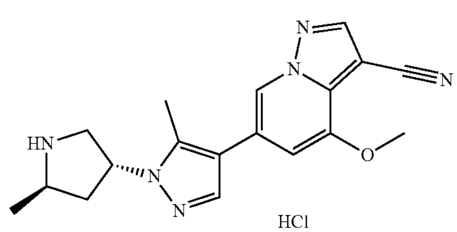 [SMILES: COc1cc(-c2cnn([C@H]3CN[C@H](C)C3)c2C)cn2ncc(C#N)c12 ; Cl] | 337.10 |

TABLE 54-continued

| Prep No. | Chemical Name | Structure | ES/MS m/z [M + H]⁺ |
|---|---|---|---|
| 876 | 4-[(1R)-1-Cyclopropylethoxy]-6-[5-methyl-1-(piperidin-4-yl)-1,2,3-triazol-4-yl]pyrazolo[1,5-a]pyridine-3-carbonitrile | 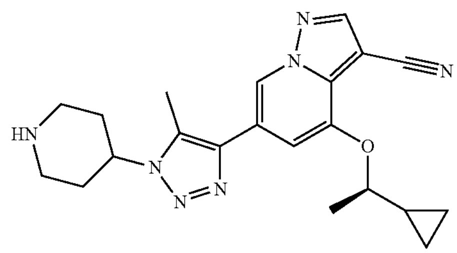 [SMILES: Cc1c(-c2cc(O[C@H](C)C3CC3)c3c(C#N)cnn3c2)nnn1C1CCNCC1] | 392.1 |
| 877 | 4-[(1R)-1-Cyclopropylethoxy]-6-[5-methyl-1-(piperidin-4-yl)pyrazol-4-yl]pyrazolo[1,5-a]pyridine-3-carbonitrile | 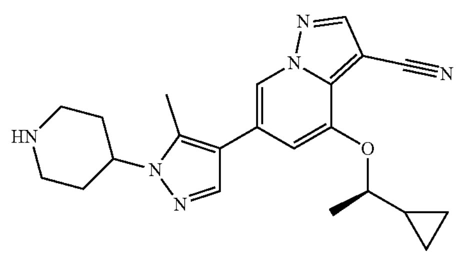 [SMILES: Cc1c(-c2cc(O[C@H](C)C3CC3)c3c(C#N)cnn3c2)cnn1C1CCNCC1] | 391.3 |
| 878[7] | 6-[5-Methyl-1-(piperidin-4-yl)-1,2,3-triazol-4-yl]-4-[(1R)-1-phenylethoxy]pyrazolo[1,5-a]pyridine-3-carbonitrile | 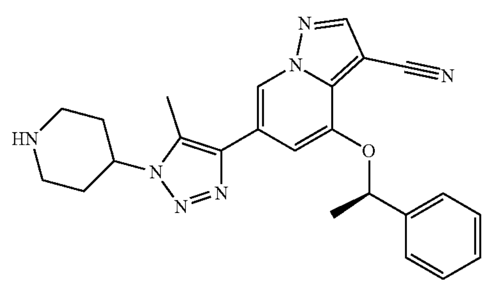 [SMILES: Cc1c(-c2cc(O[C@H](C)c3ccccc3)c3c(C#N)cnn3c2)nnn1C1CCNCC1] | 428.1 |
| 879 | 6-[5-Methyl-1-(piperidin-4-yl)pyrazol-4-yl]-4-[[(2S)-1,1,1-trifluoropropan-2-yl]oxy]pyrazolo[1,5-a]pyridine-3-carbonitrile. HCl | 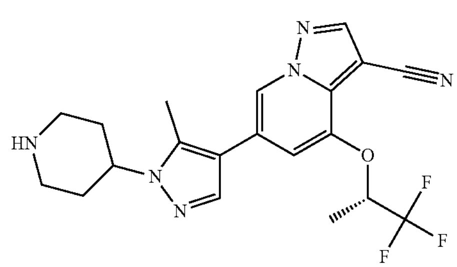 | 419.4 |
| 880 | 6-[5-Methyl-1-(piperidin-4-yl)pyrazol-4-yl]-4-[[(2R)-1,1,1-trifluoropropan-2-yl]oxy]pyrazolo[1,5-a]pyridine-3-carbonitrile. HCl | 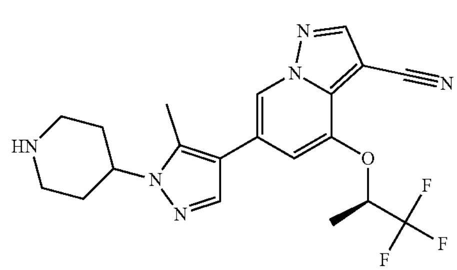 | 419.2 |

TABLE 54-continued

| Prep No. | Chemical Name | Structure | ES/MS m/z [M + H]+ |
|---|---|---|---|
| 881 | 7-[5-Methyl-1-(piperidin-4-yl)-1,2,3-triazol-4-yl]-5-[(1R)-1-(pyridin-2-yl)ethoxy]imidazo[1,2-a]pyridine-3-carbonitrile. TFA | 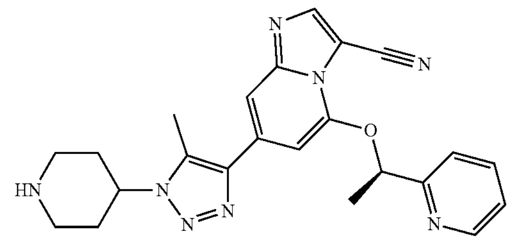 | 429.2 |
| 882 | 4-[[(7R)-6,7-dihydro-5H-cyclopenta[b]pyridin-7-yl]oxy]-6-[5-methyl-1-(4-piperidyl)triazol-4-yl]pyrazolo[1,5-a]pyridine-3-carbonitrile. HCl | 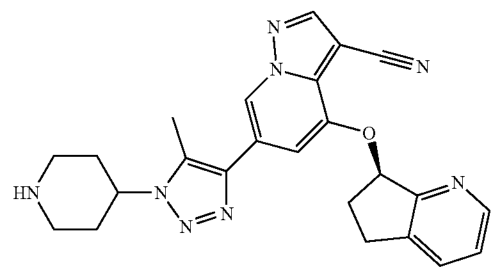 | 441.3 |
| 883 | 4-[(1R)-1-Cyclohexylethoxy]-6-[5-methyl-1-(piperidin-4-yl)-1,2,3-triazol-4-yl]pyrazolo[1,5-a]pyridine-3-carbonitrile | 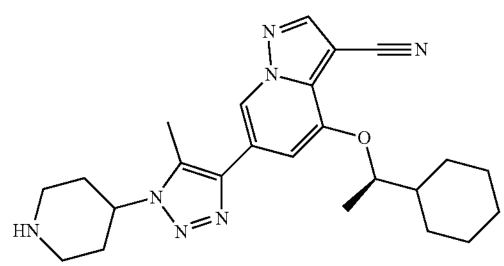 [SMILES: Cc1c(-c2cc(O[C@H](C)C3CCCCC3)c3c(C#N)cnn3c2)nnn1C1CCNCC1] | 434.4 |
| 884 | 6-[5-Methyl-1-[(3R)-pyrrolidin-3-yl]pyrazol-4-yl]-4-[[(1R)-1-(pyridin-2-yl)ethyl]amino]pyrazolo[1,5-a]pyridine-3-carbonitrile | 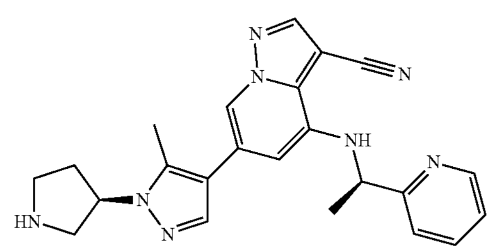 [SMILES: Cc1c(-c2cc(N[C@H](C)c3ccccn3)c3c(C#N)cnn3c2)cnn1[C@@H]1CCNC1] | 413.2 |
| 885 | 6-(5-Methyl-1-(1-((3R)-pyrrolidin-3-yl)azetidin-3-yl)-1H-pyrazol-4-yl)-4-(((R)-1-(pyridin-2-yl)ethyl)amino)pyrazolo[1,5-a]pyridine-3-carbonitrile | 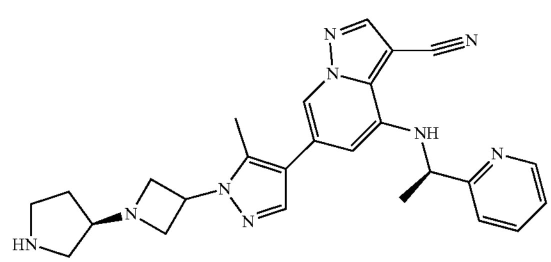 [SMILES: Cc1c(-c2cc(N[C@H](C)c3ccccn3)c3c(C#N)cnn3c2)cnn1C1CN([C@@H]2CCNC2)C1] | 468.4 |

TABLE 54-continued

| Prep No. | Chemical Name | Structure | ES/MS m/z [M + H]+ |
|---|---|---|---|
| 886 | 2-[(1R)-1-([3-Chloro-7-[5-methyl-1-(piperidin-4-yl)-1,2,3-triazol-4-yl]imidazo[1,2-a]300yridine-5-yl]oxy)ethyl]pyridine. TFA | 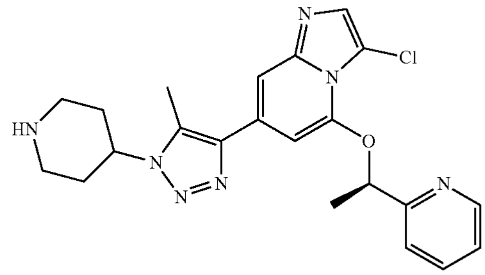 | 438.2 |
| 887[8] | 6-[5-Methyl-1-(piperidin-4-yl)pyrazol-4-yl]-4-[[2-(300yridine-2-yl)propan-2-yl]oxy]pyrazolo[1,5-a]pyridine-3-carbonitrile. HCl | 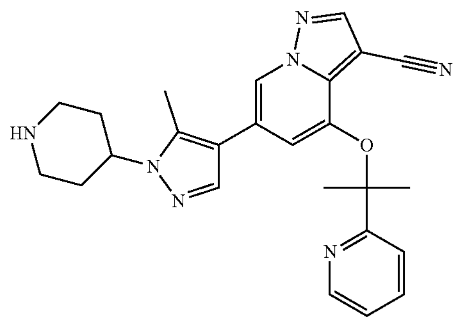 | 442.3 |
| 888 | 6-[5-Methyl-1-(piperidin-4-yl)-1,2,3-triazol-4-yl]-4-[(1S)-2,2,2-trifluoro-1-(300yridine-2-yl)ethoxy]pyrazolo[1,5-a]pyridine-3-carbonitrile | 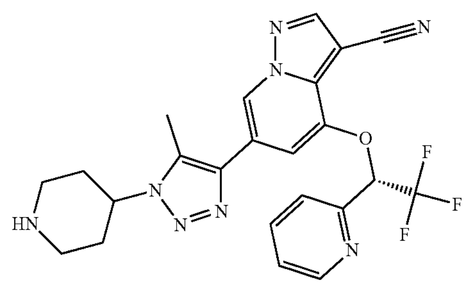 [SMILES: Cc1c(-c2cc(O[C@@H](c3ccccn3)C(F)(F)F)c3c(C#N)cnn3c2)nnn1C1CCNCC1] | 483.4 |
| 889[9] | 6-(1-[1-[3,3-Difluoropiperidin-4-yl]azetidin-3-yl]-5-methylpyrazol-4-yl)-4-methoxypyrazolo[1,5-a]pyridine-3-carbonitrile. TFA, Isomer 1 | 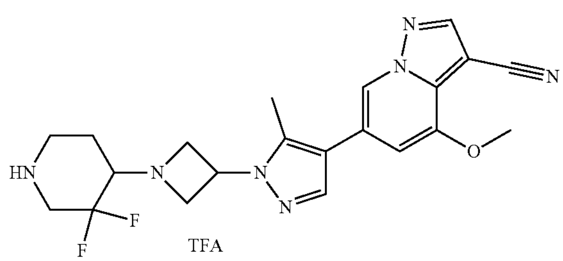 [SMILES: COc1cc(-c2cnn(C3CN(C4CCNCC4(F)F)C3)c2C)cn2ncc(C#N)c12] | 428.0 |
| 890[9] | 6-(1-[1-[3,3-Difluoropiperidin-4-yl]azetidin-3-yl]-5-methylpyrazol-4-yl)-4-methoxypyrazolo[1,5-a]pyridine-3-carbonitrile, Isomer 2 | 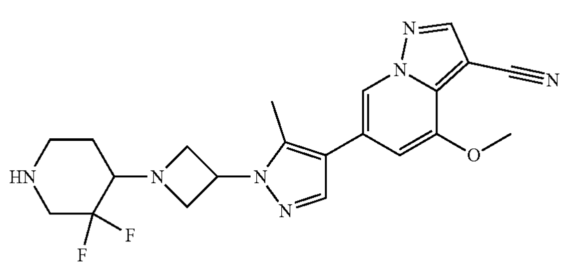 [SMILES: COc1cc(-c2cnn(C3CN(C4CCNCC4(F)F)C3)c2C)cn2ncc(C#N)c12] | 428.1 |

TABLE 54-continued

| Prep No. | Chemical Name | Structure | ES/MS m/z [M + H]+ |
|---|---|---|---|
| 891 | 4-((6,6-Difluoro-6,7-dihydro-5H-cyclopenta[b]pyridin-7-yl)oxy)-6-(5-methyl-1-(piperidin-4-yl)-1H-1,2,3-triazol-4-yl)pyrazolo[1,5-a]pyridine-3-carbonitrile. HCl | 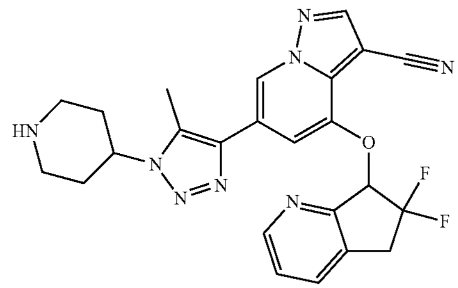 | 477.2 |
| 892 | 7-[1-(Azetidin-3-yl)-5-methyl-1,2,3-triazol-4-yl]-5-[(1R)-1-(pyridin-2-yl)ethoxy]imidazo[1,2-a]pyridine-3-carbonitrile. TFA | 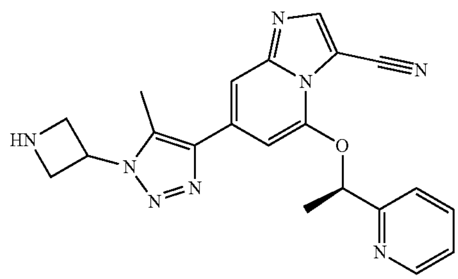 | 401.2 |
| 893 | 4-[(1R)-1-Cyclobutylethoxy]-6-[5-methyl-1-(piperidin-4-yl)pyrazol-4-yl]pyrazolo[1,5-a]pyridine-3-carbonitrile. HCl | 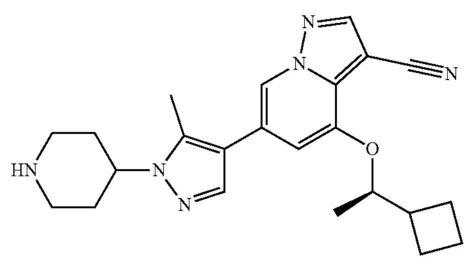 | 405.3 |
| 894[10] | 4-Methoxy-6-[5-methyl-1-[(3S)-pyrrolidin-3-yl]-1,2,3-triazol-4-yl]pyrazolo[1,5-a]pyridine-3-carbonitrile. HCl | 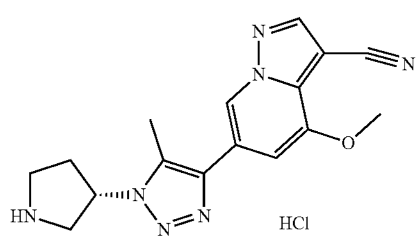 [SMILES: COc1cc(-c2nnn([C@H]3CCNC3)c2C)cn2ncc(C#N)c12 ; Cl] | 323.95 |
| 895 | 4-((1S)-2,2,2-trifluoro-1-phenyl-ethoxy)-6-[5-Methyl-1-(piperidin-4-yl)-1,2,3-triazol-4-yl]pyrazolo[1,5-a]pyridine-3-carbonitrile. TFA | 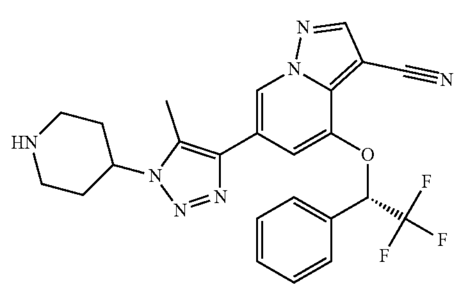 | 482.4 |

TABLE 54-continued

| Prep No. | Chemical Name | Structure | ES/MS m/z [M + H]+ |
|---|---|---|---|
| 896 | 6-[5-Methyl-1-(4-piperidyl)pyrazol-4-yl]-4-[[(1R)-1-(2-pyridyl)ethyl]amino]pyrazolo[1,5-a]pyridine-3-carbonitrile TFA | 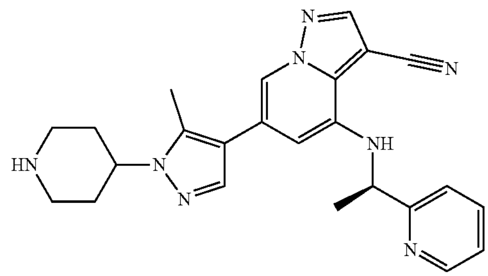 | 427.2 |
| 897 | 5-[2,2-Dimethyl-1-(2-pyridyl)propoxy]-7-[5-methyl-1-(4-piperidyl)triazol-4-yl]imidazo[1,2-a]pyridine-3-carbonitrile HCl, Isomer 1 | 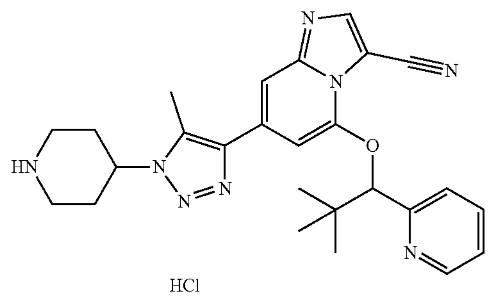 [SMILES: Cc1c(-c2cc(OC(c3ccccn3)C(C)(C)C)n3c(C#N)cnc3c2)nnn1C1CCNCC1 ; Cl] | 471.1 |
| 898 | 5-[[(7R)-6,7-Dihydro-5H-cyclopenta[b]pyridin-7-yl]oxy]-7-[5-methyl-1-(4-piperidyl)triazol-4-yl]imidazo[1,2-a]pyridine-3-carbonitrile HCl | 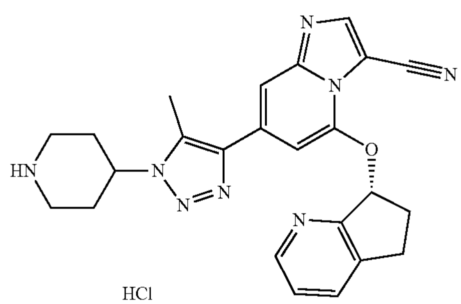 [SMILES: Cc1c(-c2cc(O[C@@H]3CCc4cccnc43)n3c(C#N)cnc3c2)nnn1C1CCNCC1 ; Cl] | 441.3 |
| 899 | 4-[1-(4-Isoquinolyl)ethoxy]-6-[5-methyl-1-(4-piperidyl)triazol-4-yl]pyrazolo[1,5-a]pyridine-3-carbonitrile HCl | 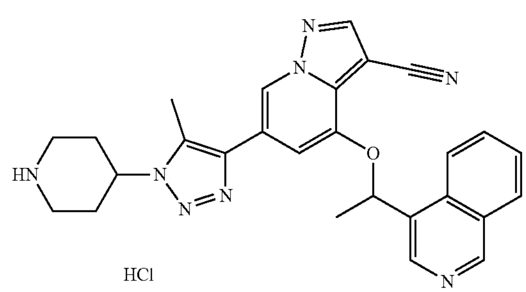 [SMILES: Cc1c(-c2cc(OC(C)c3cncc4ccccc34)c3c(C#N)cnn3c2)nnn1C1CCNCC1 ; Cl] | 479.2 |
| 900 | 4-[1-(7-Fluoro-4-isoquinolyl)ethoxy]-6-[5-methyl-1-(4-piperidyl)triazol-4-yl]pyrazolo[1,5-a]pyridine-3-carbonitrile HCl | 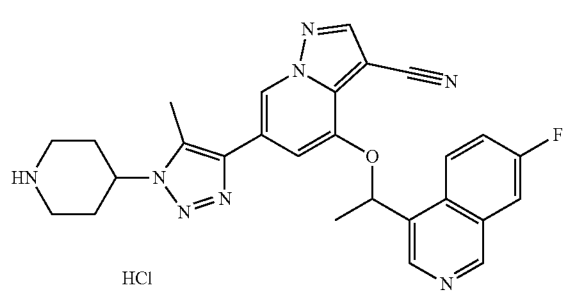 [SMILES: Cc1c(-c2cc(OC(C)c3cncc4cc(F)ccc34)c3c(C#N)cnn3c2)nnn1C1CCNCC1 ; Cl] | 497.2 |

TABLE 54-continued

| Prep No. | Chemical Name | Structure | ES/MS m/z [M + H]+ |
|---|---|---|---|
| 901 | 6-[5-Methyl-1-(4-piperidyl)triazol-4-yl]-4-[1-(5-methylpyridazin-3-yl)ethoxy]pyrazolo[1,5-a]pyridine-3-carbonitrile HCl | 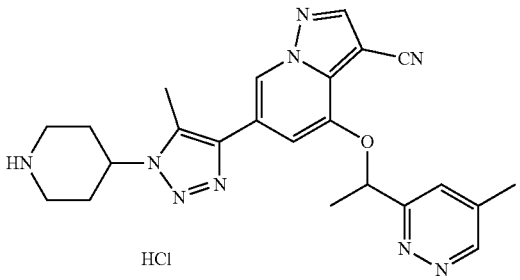 [SMILES: Cc1cnnc(C(C)Oc2cc(-c3nnn(C4CCNCC4)c3C)cn3ncc(C#N)c23)c1 ; Cl] HCl | 444.2 |
| 902 | 2-[1-[3-cyano-6-[5-methyl-1-(4-piperidyl)triazol-4-yl]pyrazolo[1,5-a]pyridin-4-yl]oxyethyl]benzamide TFA | 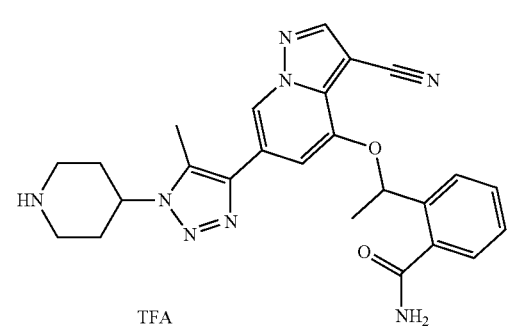 [SMILES: Cc1c(-c2cc(OC(C)c3ccccc3C(N)=O)c3c(C#N)cnn3c2)nnn1C1CCNCC1] TFA | 471.2 |
| 903 | 7-[5-Methyl-1-(4-piperidyl)triazol-4-yl]-5-[2-pyridyl-[1-(trifluoromethyl)cyclopropyl]methoxy]imidazo[1,2-a]pyridine-3-carbonitrile TFA | 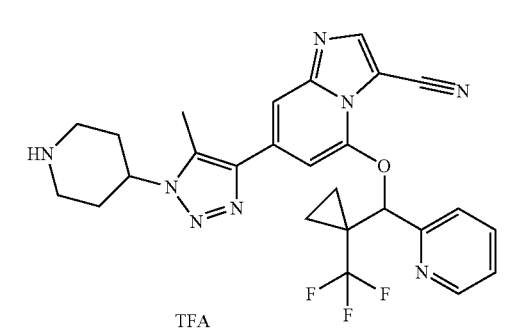 [SMILES: Cc1c(-c2cc(OC(c3ccccn3)C3(C(F)(F)F)CC3)n3c(C#N)cnc3c2)nnn1C1CCNCC1] TFA | 523.2 |
| 904 | 7-[5-methyl-1-(4-piperidyl)triazol-4-yl]-5-[1-(5-methyl-2-pyridyl)ethoxy]imidazo[1,2-a]pyridine-3-carbonitrile TFA | 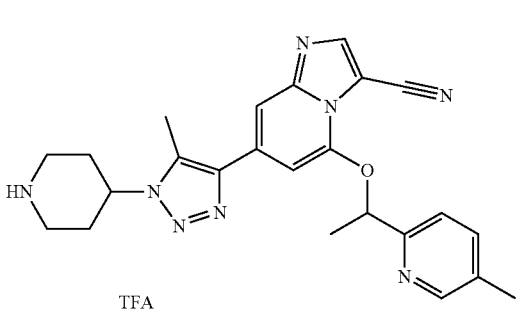 [SMILES: Cc1ccc(C(C)Oc2cc(-c3nnn(C4CCNCC4)c3C)cc3ncc(C#N)n23)nc1] TFA | 443.1 |
| 905 | 6-[5-Methyl-1-[1-[(3S)-pyrrolidin-3-yl]azetidin-3-yl]pyrazol-4-yl]-4-[[(1R)-1-(2-pyridyl)ethyl]amino]pyrazolo[1,5-a]pyridine-3-carbonitrile TFA | 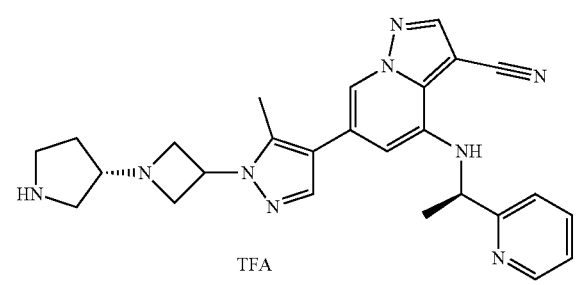 [SMILES: Cc1c(-c2cc(N[C@H](C)c3ccccn3)c3c(C#N)cnn3c2)cnn1C1CN([C@H]2CCNC2)C1] TFA | 468.1 |

TABLE 54-continued

| Prep No. | Chemical Name | Structure | ES/MS m/z [M + H]+ |
|---|---|---|---|
| 906 | 4-[1-(1-Isopropyltriazol-4-yl)ethoxy]-6-[5-methyl-1-(4-piperidyl)triazol-4-yl]pyrazolo[1,5-a]pyridine-3-carbonitrile Di-HCl | 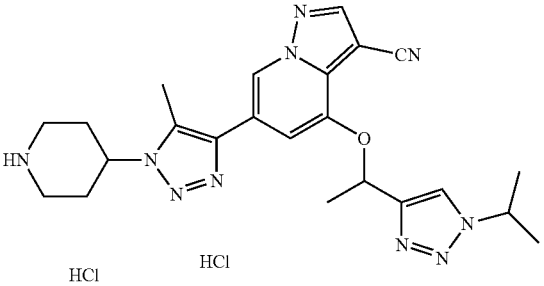 [SMILES: Cc1c(-c2cc(OC(C)c3cn(C(C)C)nn3)c3c(C#N)cnn3c2)nnn1C1CCNCC1 ; Cl ; Cl] | 461.2 |
| 907 | 6-[5-Methyl-1-(4-piperidyl)pyrazol-4-yl]-4-[1-(3-methylsulfonylphenyl)ethoxy]pyrazolo[1,5-a]pyridine-3-carbonitrile TFA | 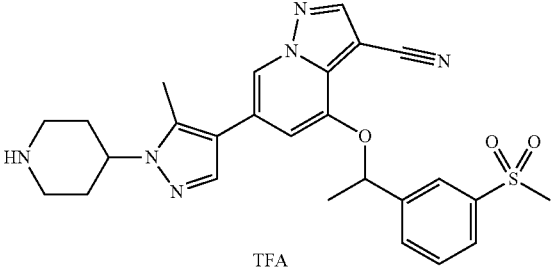 [SMILES: Cc1c(-c2cc(OC(C)c3cccc(S(C)(=O)=O)c3)c3c(C#N)cnn3c2)cnn1C1CCNCC1] | 505.2 |
| 908 | 7-[5-Methyl-1-(4-piperidyl)triazol-4-yl]-5-[1-(3-methylsulfonylphenyl)ethoxy]imidazo[1,2-a]pyridine-3-carbonitrile TFA | 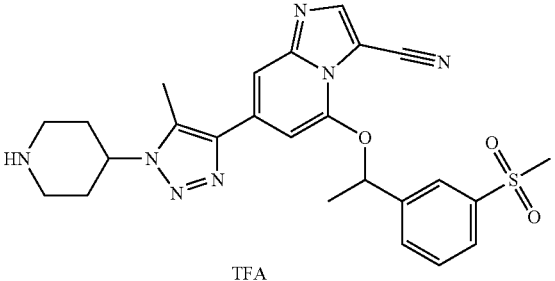 [SMILES: Cc1c(-c2cc(OC(C)c3cccc(S(C)(=O)=O)c3)n3c(C#N)cnc3c2)nnn1C1CCNCC1] | 506.2 |
| 909 | 7-[5-Methyl-1-(4-piperidyl)triazol-4-yl]-5-[1-(5-methylthiazol-2-yl)ethoxy]imidazo[1,2-a]pyridine-3-carbonitrile TFA | 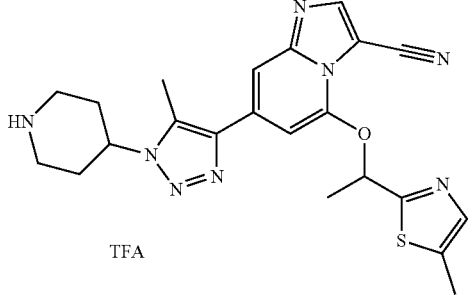 [SMILES: Cc1cnc(C(C)Oc2cc(-c3nnn(C4CCNCC4)c3C)cc3ncc(C#N)n23)s1] | 449.3 |
| 910 | 5-[(1R)-1-(5-Fluoro-2-pyridyl)ethoxy]-3-methyl-7-[5-methyl-1-(4-piperidyl)triazol-4-yl]imidazo[1,2-a]pyridine TFA | 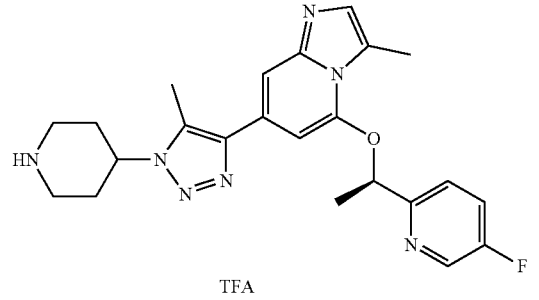 [SMILES: Cc1c(-c2cc(O[C@H](C)c3ccc(F)cn3)n3c(C)cnc3c2)nnn1C1CCNCC1] | 436.2 |

TABLE 54-continued

| Prep No. | Chemical Name | Structure | ES/MS m/z [M + H]+ |
|---|---|---|---|
| 911 | 6-[5-Methyl-1-(4-piperidyl)triazol-4-yl]-4-[1-(1-methylpyrrolo[2,3-c]pyridin-4-yl)ethoxy]pyrazolo[1,5-a]pyridine-3-carbonitrile. TFA | TFA | 482.2 |
| 912 | 4-Methoxy-6-[5-methyl-1-(4-piperidyl)pyrazol-4-yl]-3-(trifluoromethyl)pyrazolo[1,5-a]pyridine TFA | TFA | 379.9 |
| 913 | 4-[4-[(1R)-1-(5-Fluoro-2-pyridyl)ethoxy]-6-[5-methyl-1-(4-piperidyl)triazol-4-yl]pyrazolo[1,5-a]pyridin-3-yl]isothiazole HCl | HCl | 505.3 |
| 914 | [4-[(1R)-1-(5-Fluoro-2-pyridyl)ethoxy]-6-[5-methyl-1-(4-piperidyl)triazol-4-yl]pyrazolo[1,5-a]pyridin-3-yl]methanol HCl | HCl | 434.90 [M + H − H2O]+ |
| 915 | 5-[1-(5-Fluoro-2-pyridyl)-2-(trifluoromethoxy)ethoxy]-7-[5-methyl-1-(4-piperidyl)triazol-4-yl]imidazo[1,2-a]pyridine-3-carbonitrile HCl | HCl | 531.2 |

TABLE 54-continued

| Prep No. | Chemical Name | Structure | ES/MS m/z [M + H]+ |
|---|---|---|---|
| 916 | 5-[1-[5-Fluoro-6-(2-methoxyethoxy)-2-pyridyl]ethoxy]-7-[5-methyl-1-(4-piperidyl)triazol-4-yl]imidazo[1,2-a]pyridine-3-carbonitrile HCl | 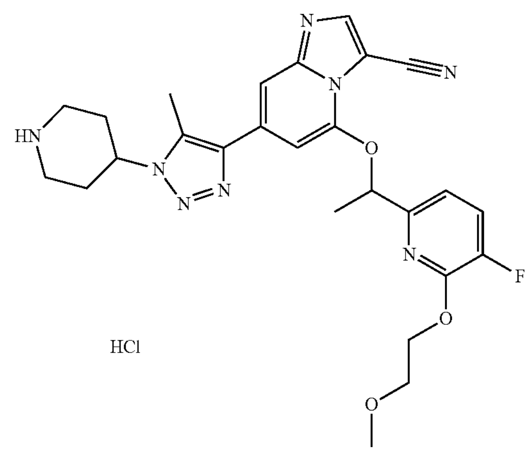 [SMILES: COCCOc1nc(C(C)Oc2cc(-c3nnn(C4CCNCC4)c3C)cc3ncc(C#N)n23)ccc1F ; Cl] | 521.2 |
| 917 | 7-[5-Methyl-1-(4-piperidyl)triazol-4-yl]-5-[1-[5-(trifluoromethoxy)-3-pyridyl]ethoxy]imidazo[1,2-a]pyridine-3-carbonitrile HCl | 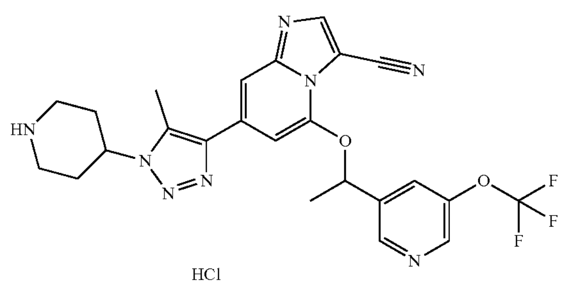 [SMILES: Cc1c(-c2cc(OC(C)c3cncc(OC(F)(F)F)c3)n3c(C#N)cnc3c2)nnn1C1CCNCC1 ; Cl] | 513.2 |
| 918 | 7-[1-[(2SR,4RS)-2-Cyclopropyl-4-piperidyl]-5-methyl-triazol-4-yl]-5-[(1R)-1-(2-pyridyl)ethoxy]imidazo[1,2-a]pyridine-3-carbonitrile HCl | 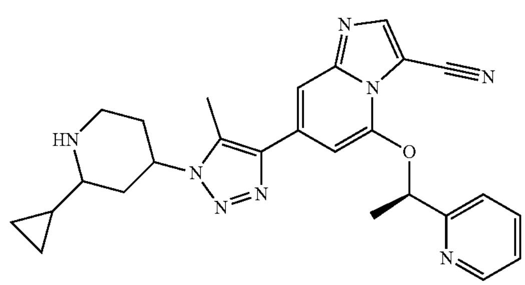 | 469.2 |
| 919 | (2R)-3-[3-Bromo-6-[5-methyl-1-(4-piperidyl)triazol-4-yl]pyrazolo[1,5-a]pyridin-4-yl]oxy-3-(5-fluoro-2-pyridyl)propane-1,2-diol HCl | 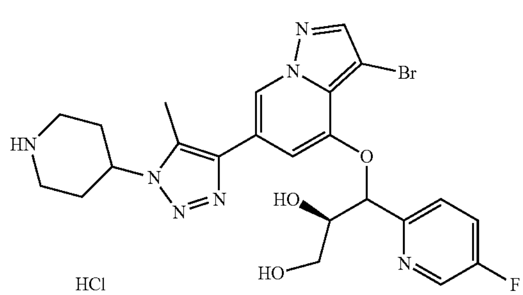 [SMILES: Cc1c(-c2cc(OC(c3ccc(F)cn3)[C@H](O)CO)c3c(Br)cnn3c2)nnn1C1CCNCC1 ; Cl] | ($^{79}$Br/$^{81}$Br) 545.7/ 547.7 |

TABLE 54-continued

| Prep No. | Chemical Name | Structure | ES/MS m/z [M + H]⁺ |
|---|---|---|---|
| 920 | 7-[5-Methyl-1-(2-methyl-2-piperazin-1-yl-propyl)triazol-4-yl]-5-[(1R)-1-(2-pyridyl)ethoxy]imidazo[1,2-a]pyridine-3-carbonitrile HCl | 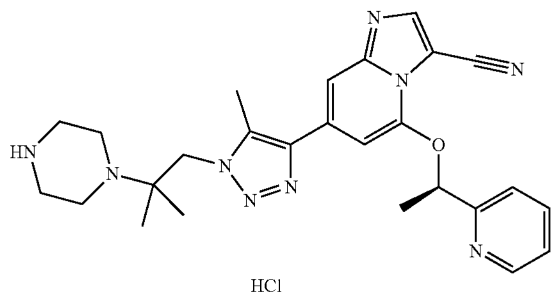 [SMILES: Cc1c(-c2cc(O[C@H](C)c3ccccn3)n3c(C#N)cnc3c2)nnn1CC(C)(C)N1CCNCC1 ; Cl] | 486.3 |
| 921[11] | 2-((6-(1-((1s,3s)-3-(3-oxa-7,9-diazabicyclo[3.3.1]nonan-7-yl)cyclobutyl)-5-methyl-1H-1,2,3-triazol-4-yl)-3-chloropyrazolo[1,5-a]pyridin-4-yl)oxy)-2-(5-fluoropyridin-2-yl)ethan-1-ol, 2 HCl, Isomer 2 | 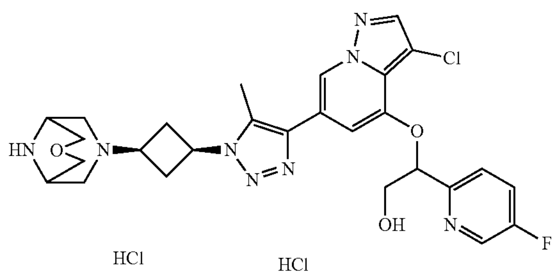 [SMILES: Cc1c(-c2cc(OC(CO)c3ccc(F)cn3)c3c(Cl)cnn3c2)nnn1[C@H]1C[C@@H](N2CC3COCC(C2)N3)C1 ; Cl ; Cl] | 569.2 |
| 922[12] | 6-[5-Methyl-1-(4-piperidyl)triazol-4-yl]-4-[1-(2-methyltriazol-4-yl)ethoxy]pyrazolo[1,5-a]pyridine-3-carbonitrile | 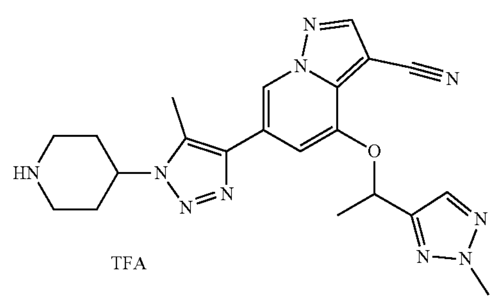 [SMILES: Cc1c(-c2cc(OC(C)c3cnn(C)n3)c3c(C#N)cnn3c2)nnn1C1CCNCC1] | 433.2 |

[1]Crude product is re-crystallized from EtOAc:PE (40:40 mL).
[2]Purified by reverse Combi-flash chromatography with the following conditions: Column, C18; eluting with a gradient of 20-30% ACN in H$_2$O (0.1% HCl).
[3]The crude product is re-crystallized from EtOAc.
[4]Mixture is filtered, and the filter cake washed with EtOAc.
[5]Crude product is triturated with DCM.
[6]Crude product is concentrated and re-crystallized from EtOAc:MTBE.
[7]The reaction is quenched by the addition of sat. NH$_4$Cl (10.0 mL) at RT and the mixture is extracted with CHCl$_3$ and iPrOH (3:1, 3 × 30 mL).
[8]Crude product is triturated in MTBE:EtOAc (5:1) and collected by filtration.
[9]Mixture is washed with Et$_2$O.
[10]The crude product is re-crystallized from MeOH/EtOAc.
[11]Reaction is diluted with MTBE and filtered to collect pale yellow solid as the title compound.
[12]Reverse phase chromatography eluting with a gradient of 0-100% ACN in H$_2$O.

Preparation 923

5-[(1R)-1-(2-Fluorophenyl)ethoxy]-7-[5-methyl-1-(4-piperidyl)triazol-4-yl]imidazo[1,2-a]pyridine-3-carbonitrile

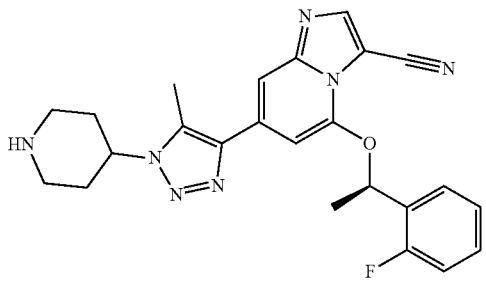 [SMILES: Cc1c(-c2cc(O[C@H](C)c3ccccc3F)n3c(C#N)cnc3c2)nnn1C1CCNCC1]

To a solution of tert-butyl 4-(4-[3-cyano-5-[(1R)-1-(2-fluorophenyl)ethoxy]imidazo[1,2-a]pyridin-7-yl]-5-methyl-1,2,3-triazol-1-yl)piperidine-1-carboxylate (110 mg, 0.20 mmol) in DCM (5.0 mL) is added 2,6-lutidine (216 mg, 2.0 mmol, 10.00) and TMSOTf (224 mg, 1.0 mmol) dropwise at RT under N₂ atmosphere. The reaction is stirred for 1 hr then concentrated in vacuo to afford the title compound (400 mg) as a yellow liquid. ES/MS m/z 446.1 [M+H]⁺.

The following compounds are prepared essentially as described for 5-[(1R)-1-(2-Fluorophenyl)ethoxy]-7-[5-methyl-1-(4-piperidyl)triazol-4-yl]imidazo[1,2-a]pyridine-3-carbonitrile using the appropriate reagents, adjusting the reaction times to determine completion of the reactions. For compounds where the amine salt was isolated, the formation of the mono-, di-, or trivalent salt is dependent on the pKa of the amine and the acid used to form the salt. The exact mono-, divalent triflic salt form for each example was not identified. The material was taken on to the next step as isolated.

TABLE 55

| Prep No. | Chemical Name | Structure | ES/MS m/z [M + H]⁺ |
|---|---|---|---|
| 924 | 5-[1-(3-Ethyltriazol-4-yl)ethoxy]-7-[5-methyl-1-(4-piperidyl)triazol-4-yl]imidazo[1,2-a]pyridine-3-carbonitrile | 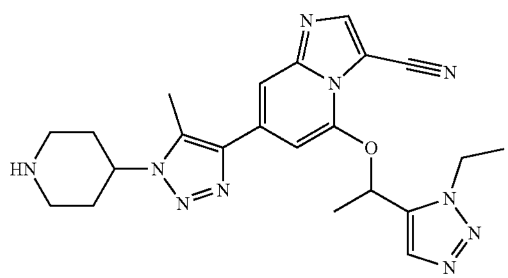 [SMILES: CCn1nncc1C(C)Oc1cc(-c2nnn(C3CCNCC3)c2C)cc2ncc(C#N)n12] | 447.2 |
| 925 | 5-[1-(2-Isothiazol-3-ylphenyl)ethoxy]-7-[5-methyl-1-(4-piperidyl)triazol-4-yl]imidazo[1,2-a]pyridine-3-carbonitrile | 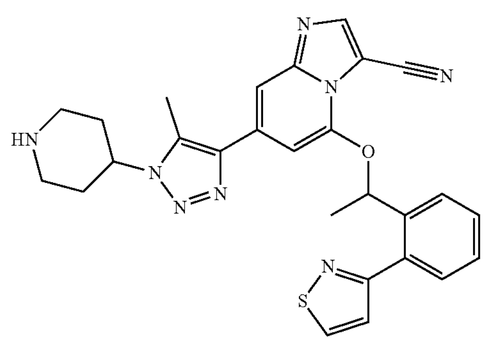 [SMILES: Cc1c(-c2cc(OC(C)c3ccccc3-c3ccsn3)n3c(C#N)cnc3c2)nnn1C1CCNCC1] | 511.2 |
| 926¹ | 5-[1-(5-Chloro-3-pyridyl)ethoxy]-7-[5-methyl-1-(4-piperidyl)triazol-4-yl]imidazo[1,2-a]pyridine-3-carbonitrile | | 463.1 |

TABLE 55-continued

| Prep No. | Chemical Name | Structure | ES/MS m/z [M + H]+ |
|---|---|---|---|
| 927 | 5-[(1R)-1-(2,4-Difluorophenyl)ethoxy]-7-[5-methyl-1-(4-piperidyl)triazol-4-yl]imidazo[1,2-a]pyridine-3-carbonitrile | 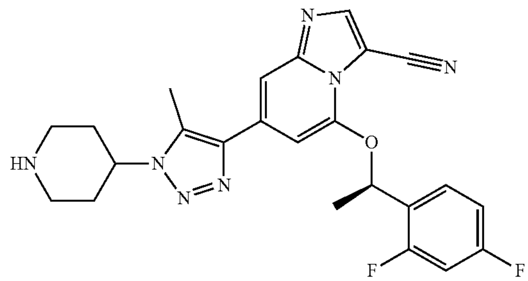 [SMILES: Cc1c(-c2cc(O[C@H](C)c3ccc(F)cc3F)n3c(C#N)cnc3c2)nnn1C1CCNCC1] | 464.1 |
| 928 | 5-[1-(2-Isoxazol-3-ylphenyl)ethoxy]-7-[5-methyl-1-(4-piperidyl)triazol-4-yl]imidazo[1,2-a]pyridine-3-carbonitrile | 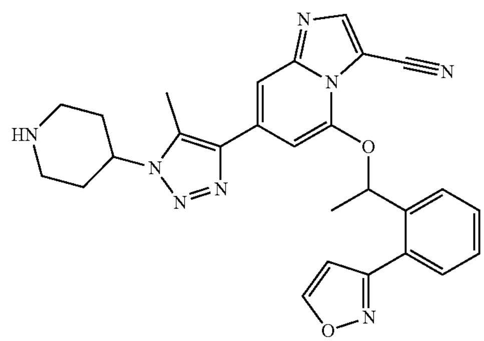 [SMILES: Cc1c(-c2cc(OC(C)c3ccccc3-c3ccon3)n3c(C#N)cnc3c2)nnn1C1CCNCC1] | 495.2 |
| 929 | 5-[1-(5-Methoxy-3-pyridyl)ethoxy]-7-[5-methyl-1-(4-piperidyl)triazol-4-yl]imidazo[1,2-a]pyridine-3-carbonitrile | 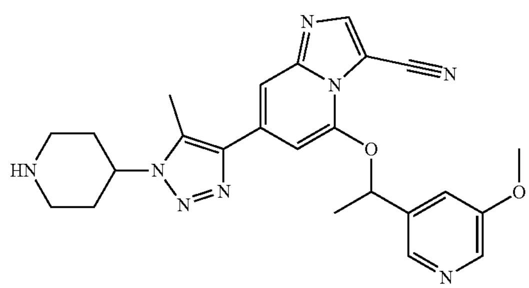 [SMILES: COc1cncc(C(C)Oc2cc(-c3nnn(C4CCNCC4)c3C)cc3ncc(C#N)n23)c1] | 459.2 |
| 930 | 5-[(1R)-1-(2,6-Difluorophenyl)ethoxy]-7-[5-methyl-1-(4-piperidyl)triazol-4-yl]imidazo[1,2-a]pyridine-3-carbonitrile | 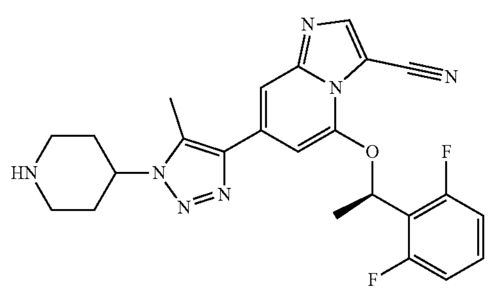 [SMILES: Cc1c(-c2cc(O[C@H](C)c3c(F)cccc3F)n3c(C#N)cnc3c2)nnn1C1CCNCC1] | 464.3 |
| 931 | 5-(1-Isothiazol-4-ylethoxy)-7-[5-methyl-1-(4-piperidyl)triazol-4-yl]imidazo[1,2-a]pyridine-3-carbonitrile | 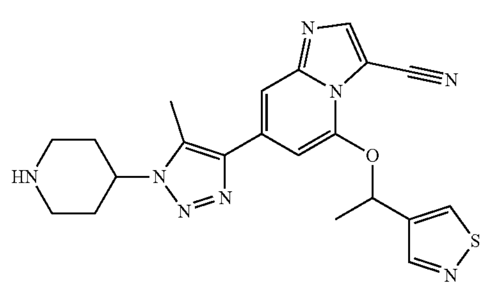 [SMILES: Cc1c(-c2cc(OC(C)c3cnsc3)n3c(C#N)cnc3c2)nnn1C1CCNCC1] | 435.1 |

TABLE 55-continued

| Prep No. | Chemical Name | Structure | ES/MS m/z [M + H]+ |
|---|---|---|---|
| 932 | 5-(1-Isothiazol-5-ylethoxy)-7-[5-methyl-1-(4-piperidyl)triazol-4-yl]imidazo[1,2-a]pyridine-3-carbonitrile | 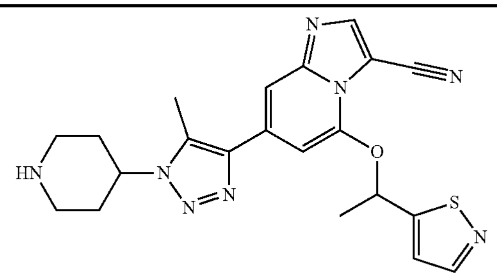 | 435.2 |
| 933 | 7-[1-(Azepan-4-yl)-5-methyl-triazol-4-yl]-5-[(1R)-1-(4-fluorophenyl)ethoxy]imidazo[1,2-a]pyridine-3-carbonitrile | 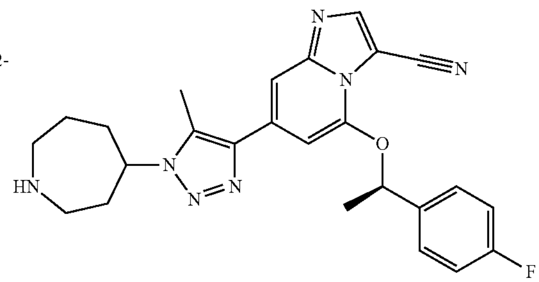 | 461.2 |

[1] TEA in DCM is used as the solvent. The reaction is quenched by addition of MeOH (5 mL).

Preparation 934

4-Methoxy-6-[5-methyl-1-[(3R)-pyrrolidin-3-yl]triazol-4-yl]pyrazolo[1,5-a]pyridine-3-carbonitrile.HCl

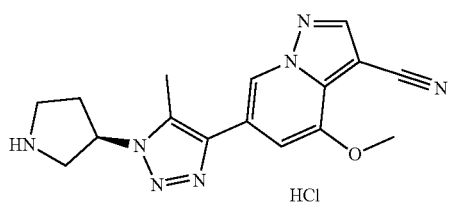 [SMILES: COc1cc(-c2nnn([C@@H]3CCNC3)c2C)cn2ncc(C#N)c12 ; Cl]

A stirred RT mixture of tert-butyl (3R)-3-(4-(3-cyano-4-methoxypyrazolo[1,5-a]310yridine-6-yl)-5-methyl-1H-1,2,3-triazol-1-yl)pyrrolidine-1-carboxylate (480 mg, 1.13 mmol) in DCM (5 mL) is treated with 4 M HCl in 1,4-dioxane (5 mL) and stirred for 2 hrs at RT to give white precipitated solids. The precipitated solids are collected by filtration and washed with EtOAc (3×20 mL) to give the title compound as a white solid (350 mg, 84.1%). ES/MS m/z 324.1 [M+H]+.

The following compounds are prepared essentially as described for 4-methoxy-6-[5-methyl-1-[(3R)-pyrrolidin-3-yl]triazol-4-yl]pyrazolo[1,5-a]pyridine-3-carbonitrile.HCl using the appropriate reagents, adjusting the reaction times to determine completion of the reactions, and adjusting the purification system as appropriate. The residue can also be concentrated under reduced pressure and the crude product washed with DCM. For compounds where the amine salt was isolated, the formation of the mono-, di-, or trivalent salt is dependent on the pKa of the amine and the acid used to form the salt. The exact mono-, di-, or trivalent salt form for each example was not identified.

TABLE 56

| Prep No. | Chemical Name | Structure | ES/MS m/z [M + H]+ |
|---|---|---|---|
| 935[1] | 6-(1-[1-[2,2-Dimethylazetidin-3-yl]piperidin-4-yl]-5-methylpyrazol-4-yl)-4-methoxypyrazolo[1,5-a]pyridine-3-carbonitrile, Isomer 1 | 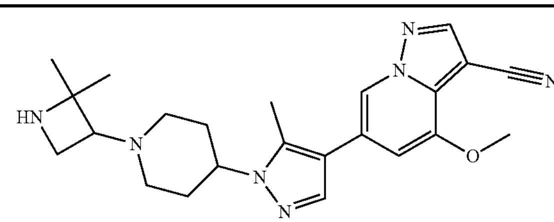 | 420.30 |
| 936[2] | 6-(1-[1-[2,2-Dimethylazetidin-3-yl]piperidin-4-yl]-5-methylpyrazol-4-yl)-4-methoxypyrazolo[1,5-a]pyridine-3-carbonitrile, Isomer 2 | 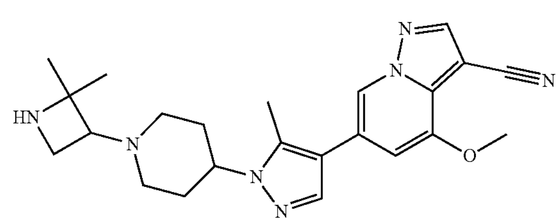 [SMILES: COc1cc(-c2cnn(C3CCN(C4CNC4(C)C)CC3)c2C)cn2ncc(C#N)c12] | 420.35 |

TABLE 56-continued

| Prep No. | Chemical Name | Structure | ES/MS m/z [M + H]+ |
|---|---|---|---|
| 937[1] | 4-Methoxy-6-[5-methyl-1-[(3R)-piperidin-3-yl]pyrazol-4-yl]pyrazolo[1,5-a]pyridine-3-carbonitrile. FA | FA | 337.2 |
| 938[3] | 4-Isopropoxy-6-(5-methyl-1-(piperidin-4-yl)-1H-1,2,3-triazol-4-yl)pyrazolo[1,5-a]pyridine-3-carbonitrile. HCl | HCl | 366.2 |
| 939 | 4-Methoxy-6-[1-(piperidin-4-yl)pyrazol-4-yl]pyrazolo[1,5-a]pyridine-3-carbonitrile. HCl | HCl | 323.1 |
| 940 | 4-Methoxy-6-[3-methyl-1-(piperidin-4-yl)pyrazol-4-yl]pyrazolo[1,5-a]pyridine-3-carbonitrile. HCl | HCl | 337.2 |
| 941 | 6-[5-Methyl-1-(piperidin-4-yl)pyrazol-4-yl]-4-[(1R)-1-(1-methylpyrazol-3-yl)ethoxy]pyrazolo[1,5-a]pyridine-3-carbonitrile. HCl | HCl | 431.2 |
| 942[4] | 7-[5-Methyl-1-(4-piperidyl)triazol-4-yl]-5-[3-methyl-1-(2-pyridyl)butoxy]imidazo[1,2-a]pyridine-3-carbonitrile HCl | HCl | 471.2 |

TABLE 56-continued

| Prep No. | Chemical Name | Structure | ES/MS m/z [M + H]+ |
|---|---|---|---|
| 943[5] | 5-[(1R)-1-(5-Fluoro-2-pyridyl)ethoxy]-7-[5-methyl-1-(4-piperidyl)pyrazol-4-yl]imidazo[1,2-c]pyrimidine-3-carbonitrile | 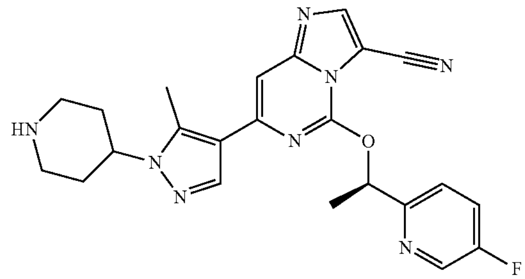 [SMILES: Cc1c(-c2cc3ncc(C#N)n3c(O[C@H](C)c3ccc(F)cn3)n2)cnn1C1CCNCC1] | 447.2 |

[1]Reverse Combi-flash chromatography with the following conditions: Column, Xbridge Shield RP18 OBD, 19 * 150 mm, 5 μm, 5-25% ACN in H2O (10 mmol/L, NH4HCO3).
[2]Prep-HPLC with the following conditions: Column, Xbridge Prep C18 OBD, 19 * 150 mm, 5 μm, 2-14% ACN in H2O (10 mmol/L NH4HCO3).
[3]Reverse Combi-flash chromatography with the following conditions: Column, C18, 20-30% ACN in H2O (0.1% HCl).
[4]Residue is triturated in MTBE, filtered, and the filter cake is dried.
[5]Residue is taken up into 3:1 CHCl3:IPA, washed with NaHCO3 solution, H2O and brine. Dried over Na2SO4, filtered, and concentrated in vacuo.

Preparation 944

4-Methoxy-6-[5-methyl-1-[(3R)-pyrrolidin-3-yl]pyrazol-4-yl]pyrazolo[1,5-a]pyridine-3-carbonitrile

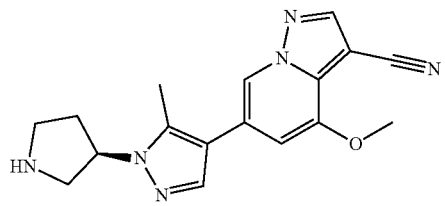 [SMILES: COc1cc(-c2cnn([C@@H]3CCNC3)c2C)cn2ncc(C#N)c12]

A solution of tert-butyl (3R)-3-(4-[3-cyano-4-methoxy-pyrazolo[1,5-a]pyridine-6-yl]-5-methylpyrazol-1-yl)pyrrolidine-1-carboxylate (950.00 mg, 2.25 mmol) in TFA (5 mL) and DCM (5 mL) is stirred for 1 hr at RT and concentrated under reduced pressure. The residue is purified directly by reverse Combi-flash chromatography with the following conditions: Column, C18 gel; eluting with a gradient of 25% to 30% ACN in H2O (0.1% TFA). The purified residue is concentrated under vacuum, the pH is adjusted to 10 with sat. Na2CO3 (aq.) and extracted with EtOAc (3×100 mL). The combined organic extracts are washed with brine (2×50 mL), dried over anhydrous Na2SO4, filtered, and the filtrate is concentrated under reduced pressure to give the title compound as a white solid (490 mg, 67.6%). The product (50 mg) is repurified by reverse Combi-flash chromatography with the following conditions: Column, C18 gel; eluting with a gradient of 60% to 70% ACN in H2O (0.1% NH4HCO3). The solution is concentrated under vacuum to give the title compound as a white solid (36.2 mg, 72.4%). ES/MS m/z 323.05 [M+H]+.

The following compounds are prepared essentially as described for 4-methoxy-6-[5-methyl-1-[(3R)-pyrrolidin-3-yl]pyrazol-4-yl]pyrazolo[1,5-a]pyridine-3-carbonitrile adjusting the reaction time to determine completion of the reaction. For compounds where the amine salt was isolated, the formation of the mono-, di-, or trivalent salt is dependent on the pKa of the amine and the acid used to form the salt. The exact mono-, di-, or trivalent salt form for each example was not identified.

TABLE 57

| Prep No. | Chemical Name | Structure | ES/MS m/z [M + H]+ |
|---|---|---|---|
| 945 | 4-Methoxy-6-[5-methyl-methyl-1-[(3S)-pyrrolidin-3-yl]pyrazol-4-yl]pyrazolo[1,5-a]pyridine-3-carbonitrile | 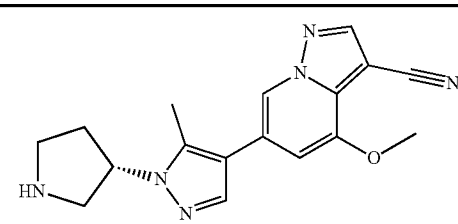 | 323.2 |
| 946 | 5-[2-Methoxy-1-(2-pyridyl)ethoxy]-7-[5-methyl-1-(4-piperidyl)triazol-4-yl]imidazo[1,2-a]pyridine-3-carbonitrile TFA, Isomer 1 | 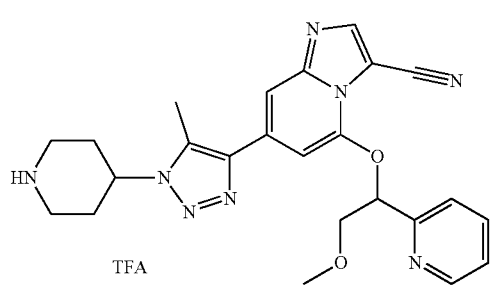 [SMILES: COCC(Oc1cc(-c2nnn(C3CCNCC3)c2C)cc2ncc(C#N)n12)c1ccccn1] | 458.9 |

TABLE 57-continued

| Prep No. | Chemical Name | Structure | ES/MS m/z [M + H]+ |
|---|---|---|---|
| 947 | 5-(3,4-Dihydro-2H-pyrano[3,2-b]pyridin-4-yloxy)-7-[5-methyl-1-(4-piperidyl)triazol-4-yl]imidazo[1,2-a]pyridine-3-carbonitrile TFA | 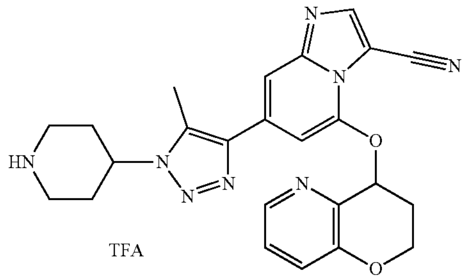 [SMILES: Cc1c(-c2cc(OC3CCOc4cccnc43)n3c(C#N)cnc3c2)nnn1C1CCNCC1] | 457.2 |

Preparation 948 tert-Butyl 3-[4-[4-[3-cyano-4-[[(1R)-1-(2-pyridyl)ethyl]amino]pyrazolo[1,5-a]pyridin-6-yl]-5-methyl-pyrazol-1-yl]-1-piperidyl]-2,2-dimethyl-azetidine-1-carboxylate

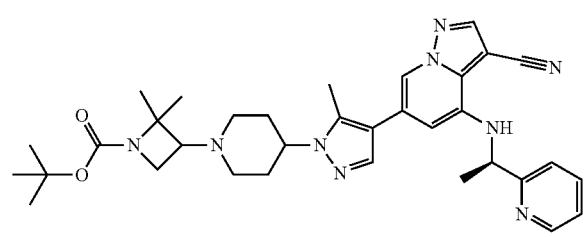 [SMILES: Cc1c(-c2cc(N[C@H](C)c3ccccn3)c3c(C#N)cnn3c2)cnn1C1CCN(C2CN(C(=O)OC(C)(C)C)C2(C)C)CC1]

To 6-[5-methyl-1-(piperidin-4-yl)pyrazol-4-yl]-4-[[(1R)-1-(pyridin-2-yl)ethyl]amino]pyrazolo[1,5-a]pyridine-3-carbonitrile TFA (250 mg, 0.59 mmol) and tert-butyl 2,2-dimethyl-3-oxoazetidine-1-carboxylate (234 mg, 1.17 mmol) in MeOH (5.0 mL) is added AcOH (71 mg, 1.17 mmol) at RT under $N_2$. The reaction mixture is stirred for 1 hr at 50° C. then $NaBH_3CN$ (111 mg, 1.76 mmol) is added and stirred overnight at 50° C. The suspension is filtered, the filter cake is washed with EtOAc (3×100 mL), organic layers combined and concentrated in vacuo. The residue is purified by Prep-TLC PE:EtOAc (1:1) to afford the title compound as a yellow solid (90 mg, 26%). ES/MS m/z 610.3 [M+H]+.

The following compounds are prepared essentially as described for tert-butyl 3-[4-[4-[3-cyano-4-[[(1R)-1-(2-pyridyl)ethyl]amino]pyrazolo[1,5-a]pyridin-6-yl]-5-methyl-pyrazol-1-yl]-1-piperidyl]-2,2-dimethyl-azetidine-1-carboxylate adjusting the reaction time to determine completion of the reaction.

TABLE 58

| Prep No. | Chemical Name | Structure | ES/MS m/z [M + H]+ |
|---|---|---|---|
| 949[1] | tert-Butyl 2-[3-[4-[3-cyano-5-[(1R)-1-(2-pyridyl)ethoxy]imidazo[1,2-a]pyridin-7-yl]-5-methyl-pyrazol-1-yl]azetidin-1-yl]-7-azabicyclo[2.2.1]heptane-7-carboxylate | 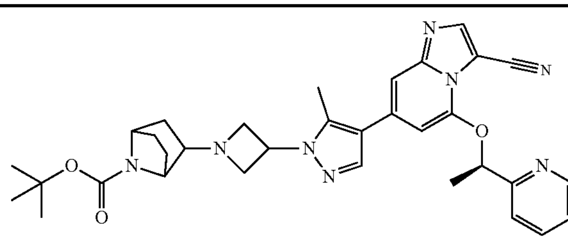 | 595.1 |
| 950[2] | tert-Butyl 2-[3-[4-(3-cyano-4-methoxy-pyrazolo[1,5-a]pyridin-6-yl)-5-methyl-pyrazol-1-yl]azetidin-1-yl]-7-azabicyclo[2.2.1]heptane-7-carboxylate | 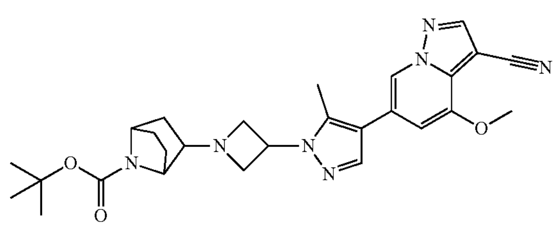 [SMILES: COc1cc(-c2cnn(C3CN(C4CC5CCC4N5C(=O)OC(C)(C)C)C3)c2C)cn2ncc(C#N)c12] | 504.2 |

[1]Purified by Prep-TLC, PE/EtOAc (1:1)
[2]Purified by silica gel column chromatography, eluting with PE:EtOAc (1:1).

Preparation 951

6-[1-[1-(2,2-Dimethylazetidin-3-yl)-4-piperidyl]-5-methyl-pyrazol-4-yl]-4-[[(1R)-1-(2-pyridyl)ethyl]amino]pyrazolo[1,5-a]pyridine-3-carbonitrile TFA

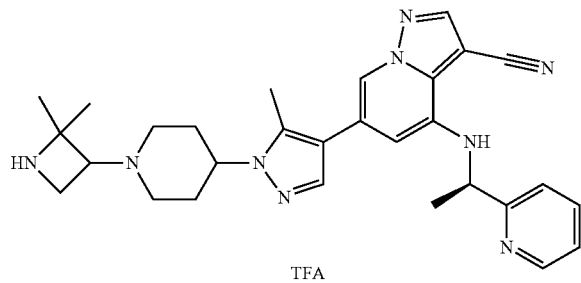 [SMILES: Cc1c(-c2cc(N[C@H](C)c3ccccn3)c3c(C#N)cnn3c2)cnn1C1CCN(C2CNC2(C)C)CC1]

To tert-butyl 3-[4-[4-(3-cyano-4-[[(1R)-1-(pyridin-2-yl)ethyl]amino]pyrazolo[1,5-a]pyridin-6-yl)-5-methylpyrazol-1-yl]piperidin-1-yl]-2,2-dimethylazetidine-1-carboxylate (90 mg, 0.15 mmol) in DCM (3.0 mL) is added TFA (1.0 mL) at RT under N$_2$. The reaction is stirred 1 hr at RT then concentrated in vacuo to afford the title compound as a yellow solid (110 mg). ES/MS m/z 510.3 [M+H]$^+$.

The following compounds are prepared essentially as described for 6-[1-[1-(2,2-dimethylazetidin-3-yl)-4-piperidyl]-5-methyl-pyrazol-4-yl]-4-[[(1R)-1-(2-pyridyl)ethyl]amino]pyrazolo[1,5-a]pyridine-3-carbonitrile TFA adjusting the reaction time to determine completion of the reaction. HCl in 1,4-dioxane can be used instead of TFA. For compounds where the amine salt was isolated, the formation of the mono-, di-, or trivalent salt is dependent on the pKa of the amine and the acid used to form the salt. The exact mono-, di-, or trivalent salt form for each example was not identified.

TABLE 59

| Prep No. | Chemical Name | Structure | ES/MS m/z [M + H]$^+$ |
|---|---|---|---|
| 952 | 7-[1-[1-(7-Azabicyclo[2.2.1]heptan-2-yl)azetidine-3-yl]-5-methyl-pyrazol-4-yl]-5-[(1R)-1-(2-pyridyl)ethoxy]imidazo[1,2-a]pyridine-3-carbonitrile HCl | 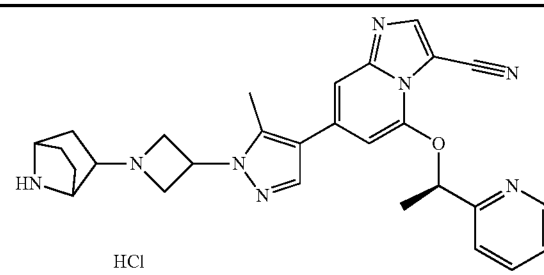 | 495.1 |
| 953 | 6-[1-[1-(7-Azabicyclo[2.2.1]heptan-2-yl)azetidin-3-yl]-5-methyl-pyrazol-4-yl]-4-methoxy-pyrazolo[1,5-a]pyridine-3-carbonitrile TFA | 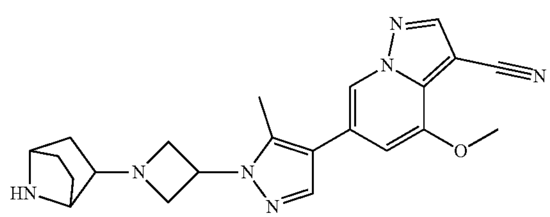 | 404.2 |

Preparation 954

6-[1-(1-Cyano-4-piperidyl)-5-methyl-pyrazol-4-yl]-4-[1-(5-fluoro-2-pyridyl)-2-hydroxy-ethoxy]pyrazolo[1,5-a]pyridine-3-carbonitrile

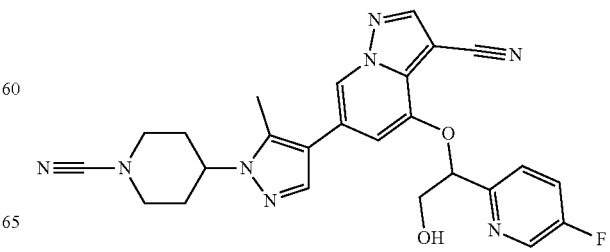

A mixture of 4-[1-(5-Fluoro-2-pyridyl)-2-hydroxyethoxy]-6-[5-methyl-1-(4-piperidyl)pyrazol-4-yl]pyrazolo[1,5-a]pyridine-3-carbonitrile (2.3 g, HCl salt), DIEA (6.44 g, 49.84 mmol) and BrCN (0.63 g, 5.98 mmol) in DCM (50 mL) is stirred for 1 hr at RT under N₂. The reaction is quenched with H₂O (400 mL) then extracted with EtOAc (3×100 mL). The combined organic layers are washed with brine (200 mL) and dried over anhydrous Na₂SO₄. After filtration, the filtrate is concentrated in vacuo. The residue is purified by reverse phase chromatography with the following conditions: Column, C18; eluting with 40% to 60% ACN in H₂O (0.1% NH₄HCO₃) to give the title compound (1.46 g, 60.2%) as a white solid. ES/MS m/z 487.3 [M+H]⁺.

Preparation 955

4-[4-[3-Chloro-4-[1-(5-fluoro-2-pyridyl)-2-hydroxyethoxy]pyrazolo[1,5-a]pyridine-6-yl]-5-methyl-triazol-1-yl]piperidine-1-carbonitrile

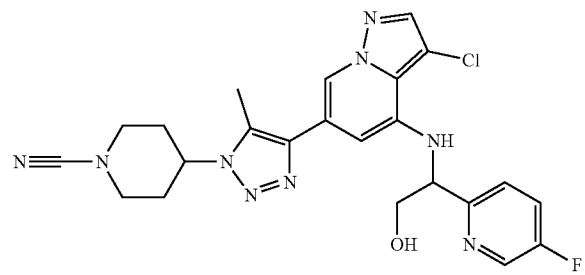 [SMILES: Cc1c(-c2cc(NC(CO)c3ccc(F)cn3)c3c(Cl)cnn3c2)nnn1C1CCN(C#N)CC1]

To a stirred solution of 2-[3-Chloro-6-[5-methyl-1-(4-piperidyl)triazol-4-yl]pyrazolo[1,5-a]pyridin-4-yl]oxy-2-(5-fluoro-2-pyridyl)ethanol. HCl (165 mg, crude) and DIEA (452 mg, 3.50 mmol) in DCM (1 mL) is added BrCN (44 mg, 0.42 mmol) at RT under N₂. After stirring 1 hr at RT, the reaction is concentrated in vacuo. The residue is purified by Prep-TLC (PE/EtOAc 1:5 to afford the title compound as a light-yellow solid (110 mg, 63.31%). ES/MS m/z 497.2 [M+H]⁺.

Preparation 956

4-[4-[3-Chloro-5-[1-(5-fluoro-2-pyridyl)-2-hydroxyethoxy]imidazo[1,2-a]pyridine-7-yl]-5-methyl-triazol-1-yl]piperidine-1-carbonitrile

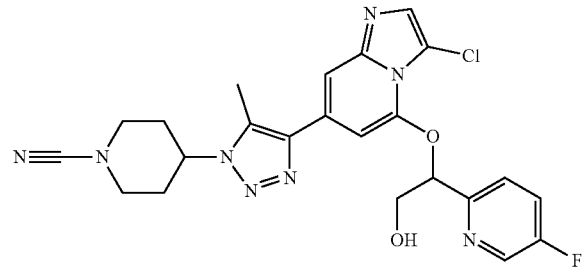 [SMILES: Cc1c(-c2cc(OC(CO)c3ccc(F)cn3)n3c(Cl)cnc3c2)nnn1C1CCN(C#N)CC1]

A mixture of 2-[3-chloro-7-[5-methyl-1-(4-piperidyl)triazol-4-yl]imidazo[1,2-a]pyridin-5-yl]oxy-2-(5-fluoro-2-pyridyl)ethanol HCl (300 mg, 0.64 mmol), DIEA (0.82 g, 6.36 mmol) and BrCN (74 mg, 0.70 mmol) in DCM (12.00 mL) is stirred at RT for 1 hr under N₂. The reaction is concentrated in vacuo. The residue is purified by reverse phase chromatography with the following conditions: Column, C18; eluting with a gradient of 50% to 70% ACN in H₂O (0.1% NH₄HCO₃; UV 254 nm; to afford the title compound as an off-white solid (120 mg, 37.99%). ES/MS m/z 497.2 [M+H]⁺.

Preparation 957

7-[1-(1-Cyano-4-piperidyl)-5-methyl-triazol-4-yl]-5-[2,2,2-trifluoro-1-(5-fluoro-2-pyridyl)ethoxy]imidazo[1,2-a]pyridine-3-carbonitrile

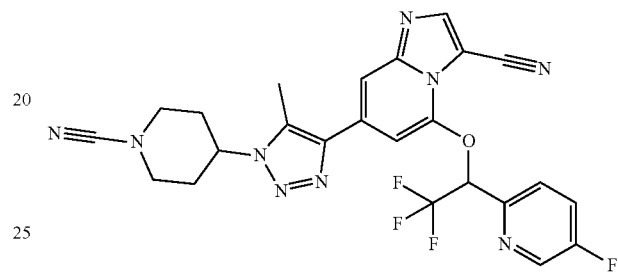

To 7-[5-Methyl-1-(4-piperidyl)triazol-4-yl]-5-[2,2,2-trifluoro-1-(5-fluoro-2-pyridyl)ethoxy]imidazo[1,2-a]pyridine-3-carbonitrile HCl (300.00 mg, 0.60 mmol) in DCM (5.00 mL) is added DIEA (0.774 g, 5.99 mmol) and BrCN (76.19 mg, 0.72 mmol) in portions at RT under N₂. The resulting mixture is stirred for 1 hr at RT then concentrated in vacuo. The residue is purified by reverse phase chromatography with the following conditions: Column, C18; mobile phase; eluting with a gradient of 50% to 60% ACN in water (0.1% NH₄HCO₃); UV 254 nm; to afford the title compound as a grey solid (200 mg, 63.49%). ES/MS m/z 526.2 [M+H]⁺.

Preparation 958

4-(4-[3-Cyano-4-[2,2,2-trifluoro-1-(oxan-4-yl)ethoxy]pyrazolo[1,5-a]pyridine-6-yl]-5-methylpyrazol-1-yl)piperidine-1-carbonitrile

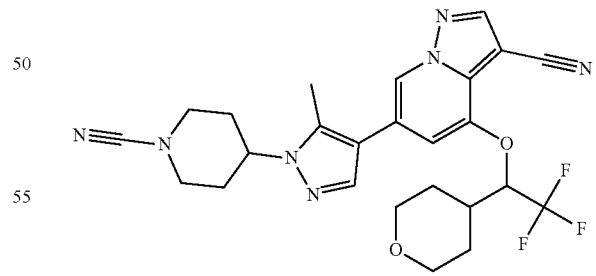

A stirred solution of 6-[5-methyl-1-(piperidin-4-yl)pyrazol-4-yl]-4-[2,2,2-trifluoro-1-(oxan-4-yl)ethoxy]pyrazolo[1,5-a]pyridine-3-carbonitrile.HCl (250.00 mg, crude) and DIEA (661.41 mg, 5.12 mmol) in DCM (5.00 mL) is treated with BrCN (65.05 mg, 0.61 mmol) in portions at RT under N₂ and the mixture is stirred for 1 hr at RT under N₂. The solution is diluted with DCM (80 mL), washed with sat. NaHCO₃ (2×20 mL) and brine (15 mL), and the H₂O phase is quenched by sodium hypochlorite soln (100 mL). The combined organic layers are dried over anhydrous Na$_2$SO$_4$, filtered, and the filtrate is concentrated under reduced pressure. The residue is purified by reverse Combi-flash chromatography with the following conditions: Column, C18; eluting with a gradient of 50% to 55% ACN in H$_2$O (0.1% NH$_4$HCO$_3$) to give the title compound as a white solid (100 mg, 38.05%). ES/MS m/z 514.3 [M+H]$^+$.

Preparation 959

4-[3-(4-[3-Cyano-4-methoxypyrazolo[1,5-a]pyridine-6-yl]-5-methylpyrazol-1-yl)319yridine319-1-yl]-2,2-dimethylpyrrolidine-1-carbonitrile

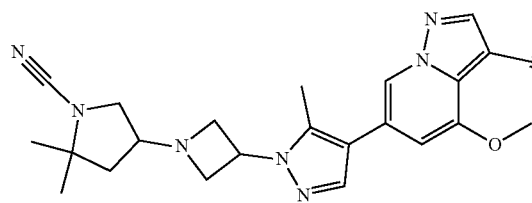

A stirred solution of 6-[1-[1-(5,5-dimethylpyrrolidin-3-yl)319yridine319-3-yl]-5-methylpyrazol-4-yl]-4-methoxy-pyrazolo[1,5-a]pyridine-3-carbonitrile.TFA (250.0 mg, 0.62 mmol) in DCM (5.0 mL) at RT under N$_2$ is treated with DIEA (796.8 mg, 6.17 mmol) and BrCN (58.8 mg, 0.56 mmol), and the mixture is stirred for 1 hr at RT under N$_2$. The mixture is concentrated under reduced pressure. The residue is purified by reverse Combi-flash chromatography with the following conditions: Column, C18; eluting with a gradient of 40% to 70% ACN in H$_2$O (0.1% NH$_4$HCO$_3$) to give the title compound as a white solid (100 mg, 37.4%). ES/MS m/z 431.2 [M+H]$^+$.

Preparation 960

7-[1-(1-Cyano-4-piperidyl)-5-methyl-triazol-4-yl]-5-[1-[5-(trifluoromethyl)-3-pyridyl]ethoxy]imidazo[1,2-a]pyridine-3-carbonitrile

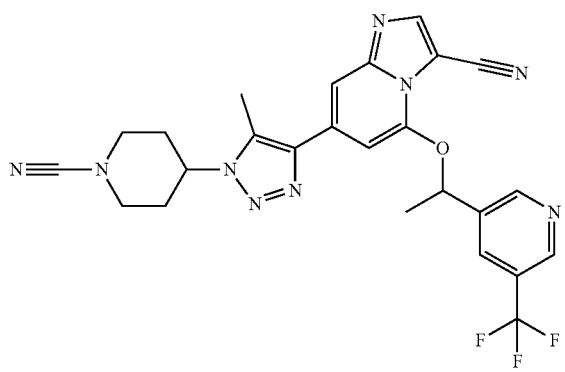 [SMILES: Cc1c(-c2cc(OC(C)c3cncc(C(F)(F)F)c3)n3c(C#N)cnc3c2)nnn1C1CCN(C#N)CC1]

A mixture of 7-[5-methyl-1-(4-piperidyl)triazol-4-yl]-5-[1-[5-(trifluoromethyl)-3-pyridyl]ethoxy]imidazo[1,2-a]pyridine-3-carbonitrile.TFA (140.00 mg, 0.28 mmol) in DCM (15.00 mL) at RT under N$_2$ is treated with DIEA (364.43 mg, 2.82 mmol) and BrCN (35.84 mg, 0.34 mmol). The mixture is stirred for 2 hr at RT under N$_2$ and is concentrated under reduced pressure. The residue is purified by reversed Combi-flash chromatography with the following conditions: Column, C18; eluting with a gradient of 0 to 100% ACN in H$_2$O (0.1% FA) to give the title compound as a light-yellow solid. ES+H m/z 522.2 [M+H]$^+$.

Preparation 961

7-[1-(1-Cyano-4-piperidyl)-5-methyl-triazol-4-yl]-5-[1-(5-fluoro-2-pyridyl)-2-methoxy-ethoxy]imidazo[1,2-a]pyridine-3-carbonitrile

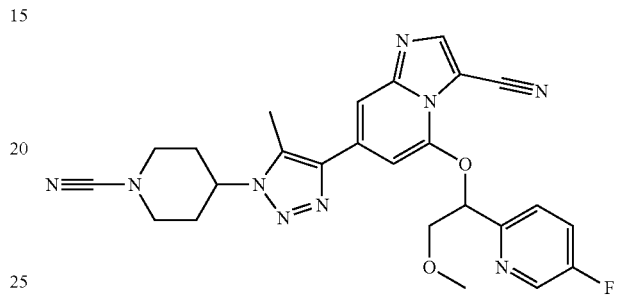

A mixture of 5-[1-(5-fluoro-2-pyridyl)-2-methoxy-ethoxy]-7-[5-methyl-1-(4-piperidyl)triazol-4-yl]imidazo[1,2-a]pyridine-3-carbonitrile.TFA (150.00 mg), DIEA (542.45 mg, 4.20 mmol) and BrCN (48.90 mg, 0.462 mmol) in DCM (6.00 mL) is stirred for 2 hr at RT under N$_2$ and concentrated under reduced pressure. The residue is purified by reversed Combi-flash chromatography eluting with 50% to 55% ACN in H$_2$O (0.1% NH$_4$HCO$_3$), to give the title compound (110 mg, 69.68%) as an off-white solid. ES/MS m/z 502.2 [M+H]$^+$ Preparation 962

7-[1-(1-Cyano-4-piperidyl)-5-methyl-triazol-4-yl]-5-[1-(5-fluoro-2-pyridyl)propoxy]imidazo[1,2-a]pyridine-3-carbonitrile

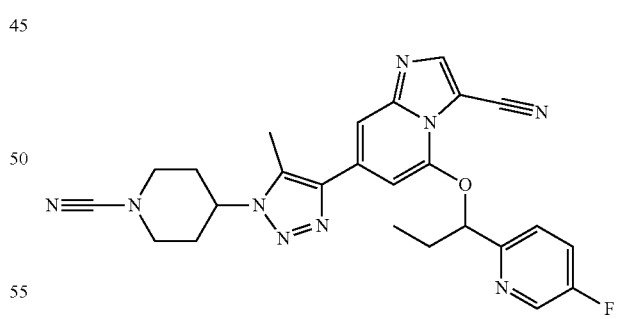

A mixture of 5-[1-(5-fluoro-2-pyridyl)propoxy]-7-[5-methyl-1-(4-piperidyl)triazol-4-yl]imidazo[1,2-a]pyridine-3-carbonitrile.HCl (200 mg), DIEA (561 mg, 4.34 mmol) and BrCN (55 mg, 0.52 mmol) in DCM (6.00 mL) is stirred for 2 hr at RT under N$_2$. The resulting mixture is concentrated under reduced pressure. The residue is purified by reversed Combi-flash chromatography eluting with 45% to 50% ACN in H$_2$O (0.1% NH$_4$HCO$_3$) to give the title compound (150 mg, 71.14%) as an off-white solid. ES/MS m/z 486.4 [M+H]$^+$.

Preparation 963

6-[1-(1-Cyano-4-piperidyl)-5-methyl-triazol-4-yl]-4-[1-(5-fluoro-2-pyridyl)-2-methoxy-ethoxy]pyrazolo[1,5-a]pyridine-3-carbonitrile

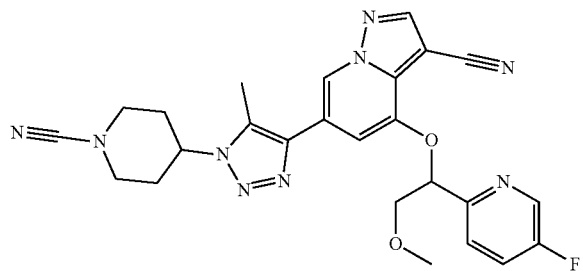 [SMILES: COCC(Oc1cc(-c2nnn(C3CCN(C#N)CC3)c2C)cn2ncc(C#N)c12)c1ccc(F)cn1]

A mixture of 4-[1-(5-fluoro-2-pyridyl)-2-methoxy-ethoxy]-6-[5-methyl-1-(4-piperidyl)triazol-4-yl]pyrazolo[1,5-a]pyridine-3-carbonitrile HCl, DIEA (406.84 mg, 3.15 mmol) and BrCN (36.68 mg, 0.35 mmol) in DCM (4.00 mL) is stirred for 2 hr at RT under $N_2$. The mixture is concentrated under reduced pressure and then is purified by reversed Combi-flash chromatography eluting with 50% to 60% ACN in $H_2O$ (0.1% $NH_4HCO_3$) to give the title compound (140 mg, 88.63%) as an off-white solid. ES/MS m/z 502.2 [M+H]$^+$.

The following compounds are prepared essentially as described for 6-[1-(1-cyano-4-piperidyl)-5-methyl-triazol-4-yl]-4-[1-(5-fluoro-2-pyridyl)-2-methoxy-ethoxy]pyrazolo[1,5-a]pyridine-3-carbonitrile using the appropriate reagents and adjusting the reaction times to determine completion of the reactions.

TABLE 60

| Prep No. | Chemical Name | Structure | ES/MS m/z [M + H]+ |
|---|---|---|---|
| 964 | 4-(4-[3-Cyano-4-methoxypyrazolo[1,5-a]pyridin-6-yl]-5-methylpyrazol-1-yl)-2,2-dimethylpyrrolidine-1-carbonitrile | 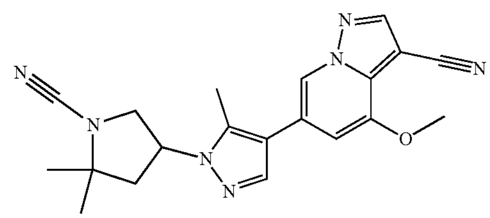 [SMILES: COc1cc(-c2cnn(C3CN(C#N)C(C)(C)C3)c2C)cn2ncc(C#N)c12] | 376.0 |
| 965[1] | 6-(1-(1-Cyanopiperidin-4-yl)-5-methyl-1H-1,2,3-triazol-4-yl)-4-((6,6-difluoro-6,7-dihydro-5H-cyclopenta[b]pyridin-7-yl)oxy)pyrazolo[1,5-a]pyridine-3-carbonitrile | 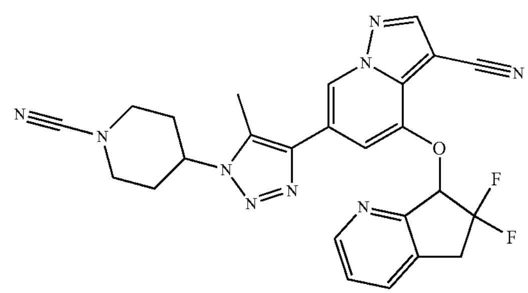 [SMILES: Cc1c(-c2cc(OC3c4ncccc4CC3(F)F)c3c(C#N)cnn3c2)nnn1C1CCN(C#N)CC1] | 502.3 |
| 966 | 6-[1-(1-cyano-4-piperidyl)-5-methyl-triazol-4-yl]-4-[2-methoxy-1-[5-(trifluoromethyl)-3-pyridyl]ethoxy]pyrazolo[1,5-a]pyridine-3-carbonitrile | 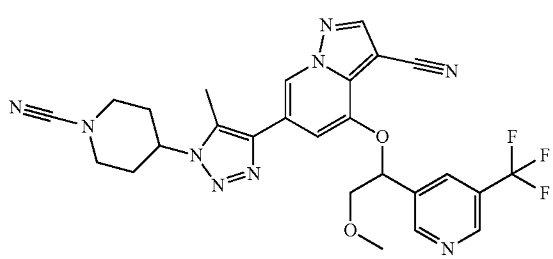 [SMILES: COCC(Oc1cc(-c2nnn(C3CCN(C#N)CC3)c2C)cn2ncc(C#N)c12)c1cncc(C(F)(F)F)c1] | 552.2 |
| 967[2] | 7-[1-(1-Cyano-4-piperidyl)-5-methyl-triazol-4-yl]-5-[1-(5-fluoro-2-pyridyl)-2-hydroxy-ethoxy]imidazo[1,2-a]pyridine-3-carbonitrile | 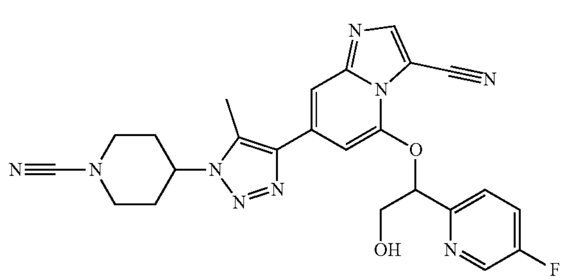 [SMILES: Cc1c(-c2cc(OC(CO)c3ccc(F)cn3)n3c(C#N)cnc3c2)nnn1C1CCN(C#N)CC1] | 488.1 |

TABLE 60-continued

| Prep No. | Chemical Name | Structure | ES/MS m/z [M + H]+ |
|---|---|---|---|
| 968[5] | 4-(4-bromo-5-methyl-triazol-1-yl)piperidine-1-carbonitrile | 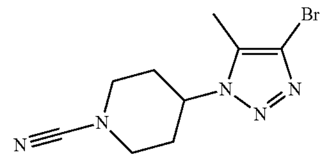 | ($^{79}$Br/$^{81}$Br) 270.0/272.0 |

[1]Purified by Prep-TLC (PE:EtOAc 2:1).
[2]Purified by Xbridge C18 Column, 50*250 mm, 10 μm; eluting with 10% to 40% ACN in H$_2$O (10 mmol/L NH$_4$HCO$_3$), B; flow rate: 25 mL/min; 254/220 nm.
[3]Purified by Prep-TLC (PE:EtOAc 1:2).
[4]Purified by Prep-TLC (PE:EtOAc 1:1).
[5]Purified by reverse phase chromatography eluting with 38% to 48% ACN in H$_2$O (0.1% NH$_4$HCO$_3$), 254 nm.

Example 1

2-[1-[3-Cyano-6-[1-(1-cyano-4-piperidyl)-5-methyl-triazol-4-yl]pyrazolo[1,5-a]pyridine-4-yl]oxyethyl]benzamide

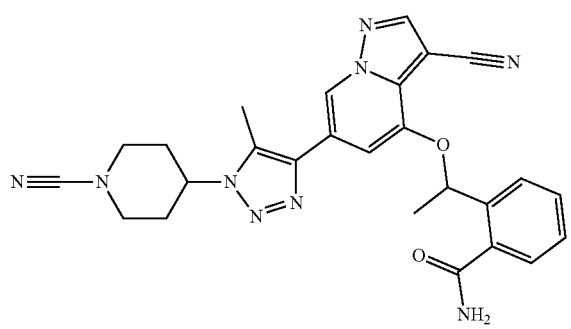 [SMILES: Cc1c(-c2cc(OC(C)c3ccccc3C(N)=O)c3c(C#N)cnn3c2)nnn1C1CCN(C#N)CC1]

2-[1-[3-cyano-6-[5-methyl-1-(4-piperidyl)triazol-4-yl]pyrazolo[1,5-a]pyridin-4-yl]oxyethyl]benzamide (63 mg, 0.13 mmol) and DIEA (52 mg, 0.40 mmol) in DCM (0.9 mL) is added a solution of BrCN (14 mg, 0.13 mmol) in DCM (0.1 mL). The mixture is stirred for 10 m then concentrated in vacuo. The residue is purified by reverse phase chromatography to afford the title compound (33 mg) LCMS m/z: [M+H]: 496.2; Rt=0.84 min The following compounds are prepared essentially as described for 2-[1-[3-Cyano-6-[1-(1-cyano-4-piperidyl)-5-methyl-triazol-4-yl]pyrazolo[1,5-a]pyridine-4-yl]oxyethyl]benzamide using the appropriate reagents and adjusting the reaction times to determine completion of the reactions.

TABLE 61

| Example No. | Chemical Name | Structure | ES/MS m/z [M + H]+ |
|---|---|---|---|
| 2[1] | 6-[1-(1-Cyano-4-piperidyl)-5-methyl-triazol-4-yl]-4-[1-(5-methylpyridazin-3-yl)ethoxy]pyrazolo[1,5-a]pyridine-3-carbonitrile | 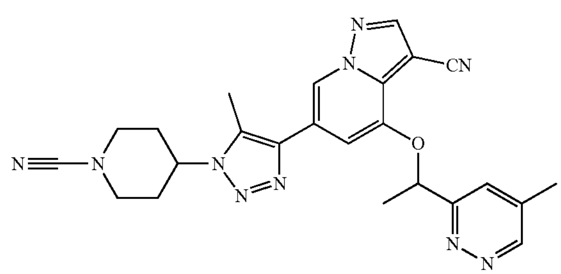 [SMILES: Cc1cnnc(C(C)Oc2cc(-c3nnn(C4CCN(C#N)CC4)c3C)cn3ncc(C#N)c23)c1] | 469.2 |
| 3[2] | 4-[1-(5-Chloropyridazin-3-yl)ethoxy]-6-[1-(1-cyano-4-piperidyl)-5-methyl-triazol-4-yl]pyrazolo[1,5-a]pyridine-3-carbonitrile | 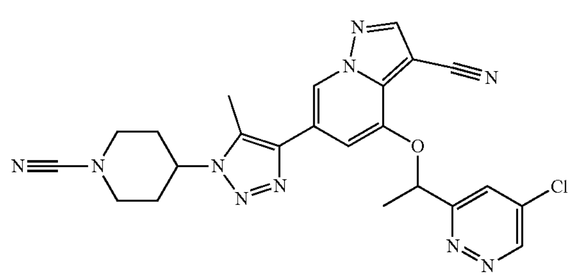 [SMILES: Cc1c(-c2cc(OC(C)c3cc(Cl)cnn3)c3c(C#N)cnn3c2)nnn1C1CCN(C#N)CC1] | 489.10 |

TABLE 61-continued

| Example No. | Chemical Name | Structure | ES/MS m/z [M + H]⁺ |
|---|---|---|---|
| 4[3] | 7-[1-(1-Cyano-4-piperidyl)-5-methyl-triazol-4-yl]-5-[1-(5-methylpyridazin-3-yl)ethoxy]imidazo[1,2-a]pyridine-3-carbonitrile | 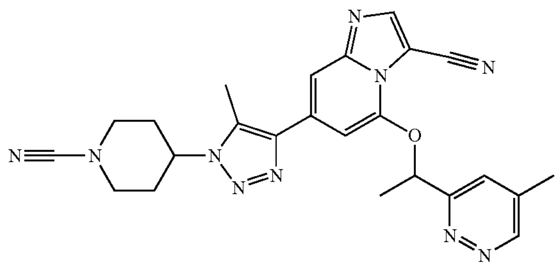 [SMILES: Cc1cnnc(C(C)Oc2cc(-c3nnn(C4CCN(C#N)CC4)c3C)cc3ncc(C#N)n23)c1] | 469.20 |
| 5[4] | 7-[1-(1-Cyano-4-piperidyl)-5-methyl-triazol-4-yl]-5-[1-(5-methyl-3-pyridyl)ethoxy]imidazo[1,2-a]pyridine-3-carbonitrile | 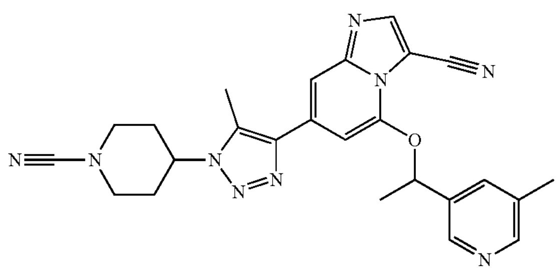 | 468.20 |
| 6[4] | 7-[1-(1-Cyano-4-piperidyl)-5-methyl-triazol-4-yl]-5-[1-[5-(difluoromethyl)-3-pyridyl]ethoxy]imidazo[1,2-a]pyridine-3-carbonitrile | 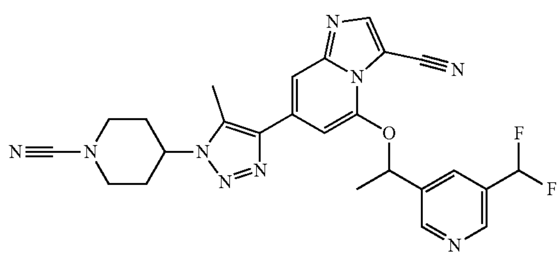 [SMILES: Cc1c(-c2cc(OC(C)c3cncc(C(F)F)c3)n3c(C#N)cnc3c2)nnn1C1CCN(C#N)CC1] | 504.2 |
| 7[2] | 6-[1-(1-Cyano-4-piperidyl)-5-methyl-triazol-4-yl]-4-[1-(1-methylpyrrolo[2,3-c]pyridin-4-yl)ethoxy]pyrazolo[1,5-a]pyridine-3-carbonitrile | 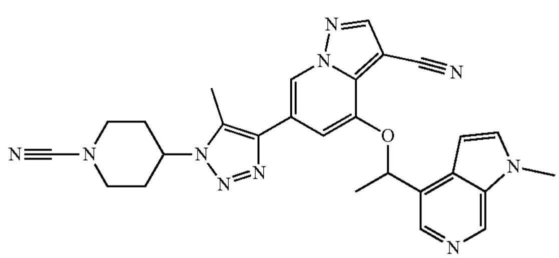 [SMILES: Cc1c(-c2cc(OC(C)c3cncc4c3ccn4C)c3c(C#N)cnn3c2)nnn1C1CCN(C#N)CC1] | 507.2 |
| 8[5] | 2-[1-[3-cyano-6-[1-(1-cyano-4-piperidyl)-5-methyl-triazol-4-yl]pyrazolo[1,5-a]pyridin-4-yl]oxyethyl]-N,N-dimethyl-benzamide | 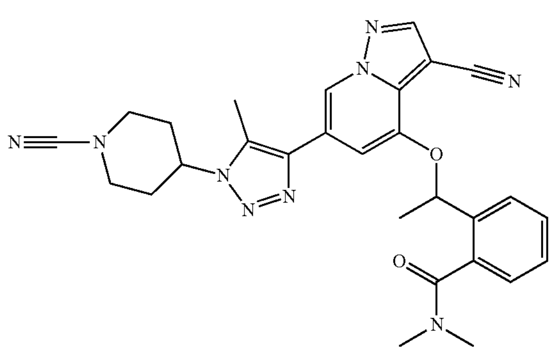 [SMILES: Cc1c(-c2cc(OC(C)c3ccccc3C(=O)N(C)C)c3c(C#N)cnn3c2)nnn1C1CCN(C#N)CC1] | 524.2 |

TABLE 61-continued

| Example No. | Chemical Name | Structure | ES/MS m/z [M + H]+ |
|---|---|---|---|
| 9[2] | 6-[1-(1-Cyano-4-piperidyl)-5-methyl-triazol-4-yl]-4-[1-(2-ethyltriazol-4-yl)ethoxy]pyrazolo[1,5-a]pyridine-3-carbonitrile | 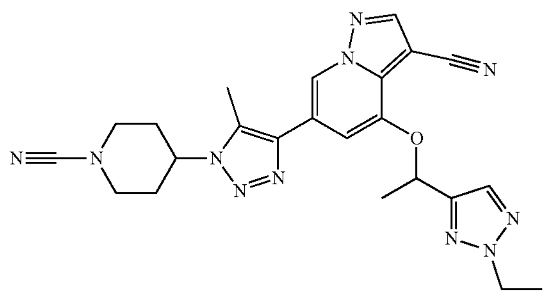 [SMILES: CCn1ncc(C(C)Oc2cc(-c3nnn(C4CCN(C#N)CC4)c3C)cn3ncc(C#N)c23)n1] | 472.2 |
| 10[4] | 6-[1-(1-Cyano-4-piperidyl)-5-methyl-triazol-4-yl]-4-[1-(5-methyl-3-pyridyl)ethoxy]pyrazolo[1,5-a]pyridine-3-carbonitrile | 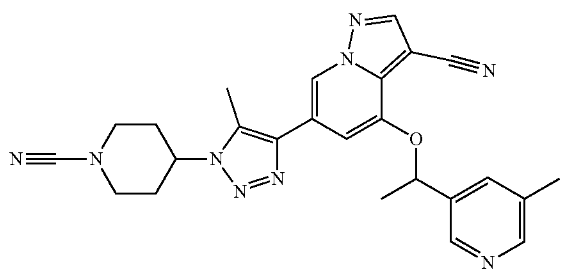 [SMILES: Cc1cncc(C(C)Oc2cc(-c3nnn(C4CCN(C#N)CC4)c3C)cn3ncc(C#N)c23)c1] | 468.2 |
| 11[4] | 6-[1-(1-Cyano-4-piperidyl)-5-methyl-triazol-4-yl]-4-[1-[5-(difluoromethyl)-3-pyridyl]ethoxy]pyrazolo[1,5-a]pyridine-3-carbonitrile | 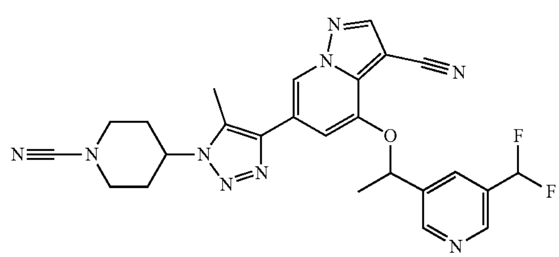 [SMILES: Cc1c(-c2cc(OC(C)c3cncc(C(F)F)c3)c3c(C#N)cnn3c2)nnn1C1CCN(C#N)CC1] | 504.2 |
| 12[3] | 5-[1-(5-Chloropyridazin-3-yl)ethoxy]-7-[1-(1-cyano-4-piperidyl)-5-methyl-triazol-4-yl]imidazo[1,2-a]pyridine-3-carbonitrile | 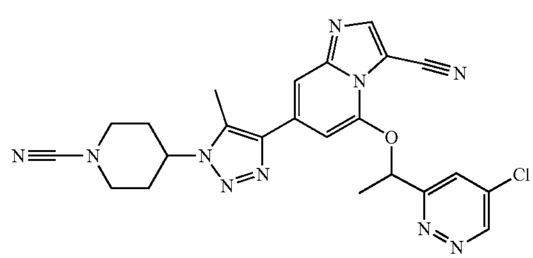 [SMILES: Cc1c(-c2cc(OC(C)c3cc(Cl)cnn3)n3c(C#N)cnc3c2)nnn1C1CCN(C#N)CC1] | 489.2 |
| 13[4] | 6-[1-(1-Cyano-4-piperidyl)-5-methyl-triazol-4-yl]-4-[1-[2-morpholino-5-(trifluoromethyl)-3-pyridyl]ethoxy]pyrazolo[1,5-a]pyridine-3-carbonitrile | 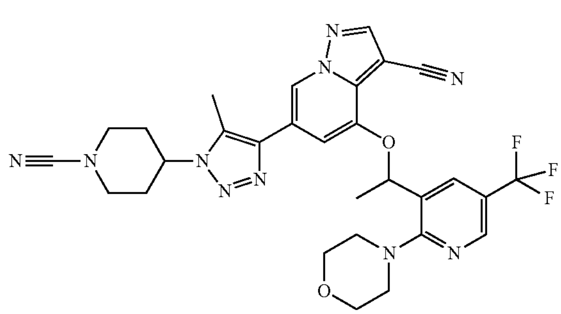 [SMILES: Cc1c(-c2cc(OC(C)c3cc(C(F)(F)F)cnc3N3CCOCC3)c3c(C#N)cnn3c2)nnn1C1CCN(C#N)CC1] | 607.20 |

TABLE 61-continued

| Example No. | Chemical Name | Structure | ES/MS m/z [M + H]+ |
|---|---|---|---|
| 14[4] | 6-[1-(1-Cyano-4-piperidyl)-5-methyl-triazol-4-yl]-4-[1-(5-methyl-1,3,4-thiadiazol-2-yl)ethoxy]pyrazolo[1,5-a]pyridine-3-carbonitrile | 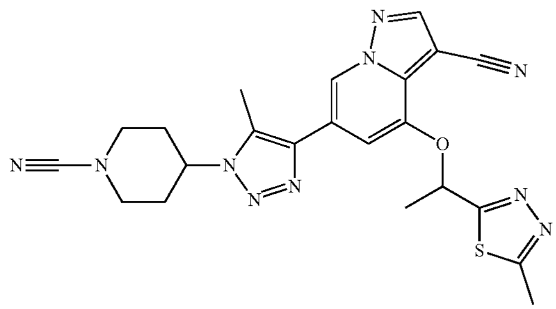 [SMILES: Cc1nnc(C(C)Oc2cc(-c3nnn(C4CCN(C#N)CC4)c3C)cn3ncc(C#N)c23)s1] | 475.2 |
| 15[4] | 7-[1-(1-Cyano-4-piperidyl)-5-methyl-triazol-4-yl]-5-[1-(1-isopropyltriazol-4-yl)ethoxy]imidazo[1,2-a]pyridine-3-carbonitrile | 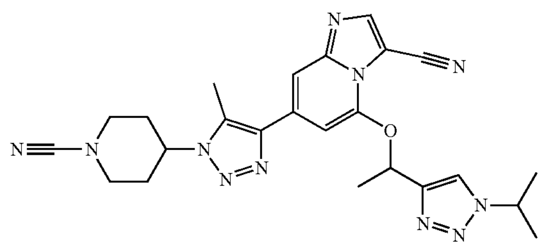 [SMILES: Cc1c(-c2cc(OC(C)c3cn(C(C)C)nn3)n3c(C#N)cnc3c2)nnn1C1CCN(C#N)CC1] | 486.2 |
| 16[6] | 6-[1-(1-Cyano-4-piperidyl)-5-methyl-triazol-4-yl]-4-[1-(6-methylpyrazin-2-yl)ethoxy]pyrazolo[1,5-a]pyridine-3-carbonitrile | 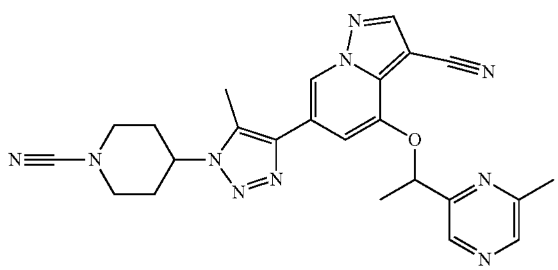 [SMILES: Cc1cncc(C(C)Oc2cc(-c3nnn(C4CCN(C#N)CC4)c3C)cn3ncc(C#N)c23)n1] | 469.1 |
| 17 | 7-[1-(1-Cyano-4-piperidyl)-5-methyl-triazol-4-yl]-5-[1-(6-methylpyrazin-2-yl)ethoxy]imidazo[1,2-a]pyridine-3-carbonitrile | 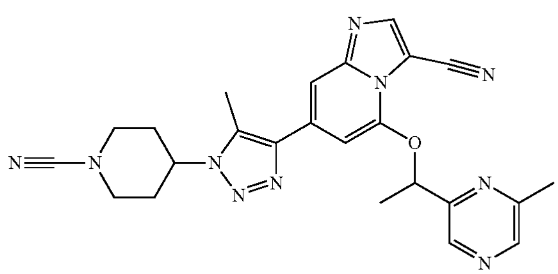 [SMILES: Cc1cncc(C(C)Oc2cc(-c3nnn(C4CCN(C#N)CC4)c3C)cc3ncc(C#N)n23)n1] | 469.20 |
| 18[2] | 6-[1-(1-cyano-4-piperidyl)-5-methyl-triazol-4-yl]-4-[2-hydroxy-1-(4-isoquinolyl)ethoxy]pyrazolo[1,5-a]pyridine-3-carbonitrile | 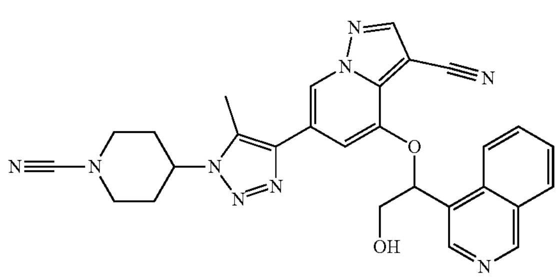 [SMILES: Cc1c(-c2cc(OC(CO)c3cncc4ccccc34)c3c(C#N)cnn3c2)nnn1C1CCN(C#N)CC1] | 520.2 |

TABLE 61-continued

| Example No. | Chemical Name | Structure | ES/MS m/z [M + H]+ |
|---|---|---|---|
| 19[2] | 6-[1-(1-Cyano-4-piperidyl)-5-methyl-pyrazol-4-yl]-4-[1-(2-methylsulfonylphenyl)ethoxy]pyrazolo[1,5-a]pyridine-3-carbonitrile | 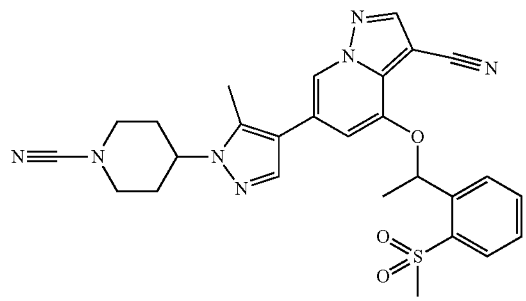 [SMILES: Cc1c(-c2cc(OC(C)c3ccccc3S(C)(=O)=O)c3c(C#N)cnn3c2)cnn1C1CCN(C#N)CC1] | 530.1 |
| 20[2] | 5-[1-(1,3-Benzothiazol-7-yl)ethoxy]-7-[1-(1-cyano-4-piperidyl)-5-methyl-triazol-4-yl]imidazo[1,2-a]pyridine-3-carbonitrile | 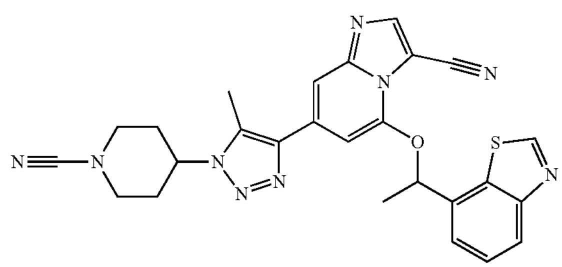 [SMILES: Cc1c(-c2cc(OC(C)c3cccc4ncsc34)n3c(C#N)cnc3c2)nnn1C1CCN(C#N)CC1] | 532.2 |
| 21[2] | 6-[1-(1-Cyano-4-piperidyl)-5-methyl-triazol-4-yl]-4-[1-(7-fluoro-4-isoquinolyl)ethoxy]pyrazolo[1,5-a]pyridine-3-carbonitrile | 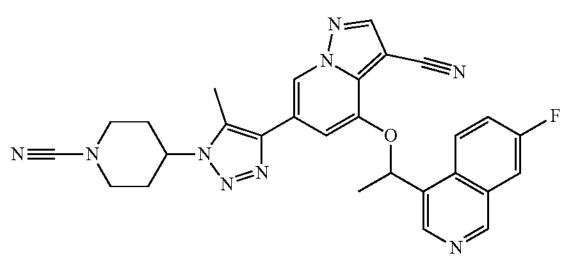 [SMILES: Cc1c(-c2cc(OC(C)c3cncc4cc(F)ccc34)c3c(C#N)cnn3c2)nnn1C1CCN(C#N)CC1] | 522.2 |
| 22[5] | 6-[1-(1-Cyano-4-piperidyl)-5-methyl-triazol-4-yl]-4-[2-fluoro-1-(5-fluoro-2-pyridyl)ethoxy]pyrazolo[1,5-a]pyridine-3-carbonitrile | 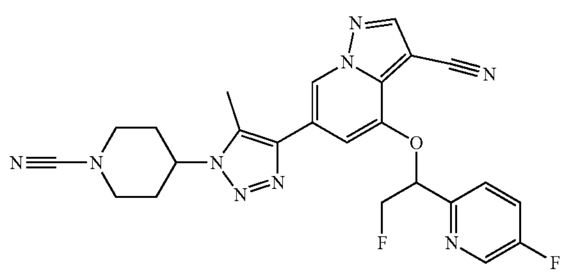 [SMILES: Cc1c(-c2cc(OC(CF)c3ccc(F)cn3)c3c(C#N)cnn3c2)nnn1C1CCN(C#N)CC1] | 490.8 |
| 23[7] | 6-[1-(1-Cyano-4-piperidyl)-5-methyl-triazol-4-yl]-4-[cyclopropyl-(5-fluoro-2-pyridyl)methoxy]pyrazolo[1,5-a]pyridine-3-carbonitrile | 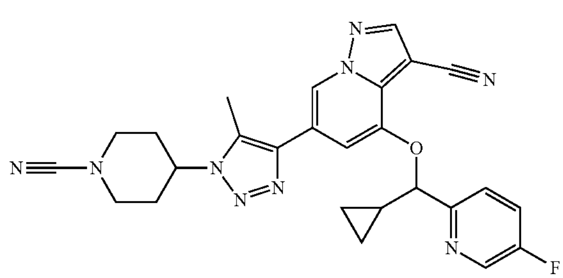 [SMILES: Cc1c(-c2cc(OC(c3ccc(F)cn3)C3CC3)c3c(C#N)cnn3c2)nnn1C1CCN(C#N)CC1] | 497.8 |

TABLE 61-continued

| Example No. | Chemical Name | Structure | ES/MS m/z [M + H]+ |
|---|---|---|---|
| 24[2] | 6-[1-(1-Cyano-4-piperidyl)-5-methyl-triazol-4-yl]-4-[1-(4-isoquinolyl)ethoxy]pyrazolo[1,5-a]pyridine-3-carbonitrile | 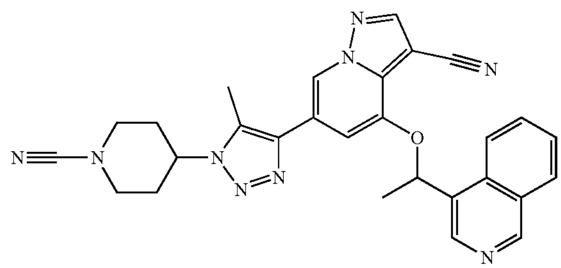 [SMILES: Cc1c(-c2cc(OC(C)c3cncc4ccccc34)c3c(C#N)cnn3c2)nnn1C1CCN(C#N)CC1] | 504.20 |
| 25[4] | 6-[1-(1-Cyano-4-piperidyl)-5-methyl-triazol-4-yl]-4-[1-(2-methyltriazol-4-yl)ethoxy]pyrazolo[1,5-a]pyridine-3-carbonitrile | 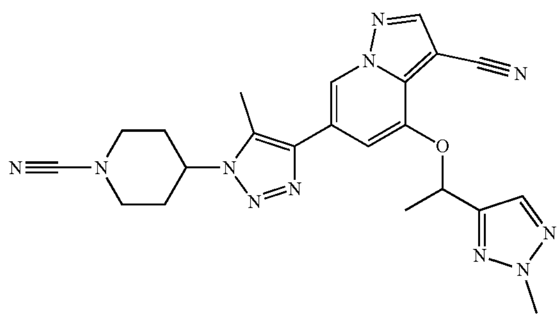 [SMILES: Cc1c(-c2cc(OC(C)c3cnn(C)n3)c3c(C#N)cnn3c2)nnn1C1CCN(C#N)CC1] | 458.2 |
| 26[2] | 6-[1-(1-Cyano-4-piperidyl)-5-methyl-triazol-4-yl]-4-[(1-fluorocyclopropyl)-(5-fluoro-2-pyridyl)methoxy]pyrazolo[1,5-a]pyridine-3-carbonitrile | 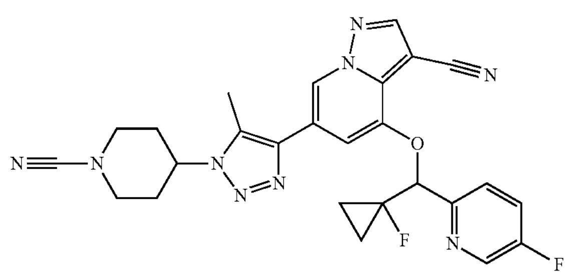 [SMILES: Cc1c(-c2cc(OC(c3ccc(F)cn3)C3(F)CC3)c3c(C#N)cnn3c2)nnn1C1CCN(C#N)CC1] | 515.8 |
| 27[7] | 4-[1-(1,2-Benzothiazol-7-yl)ethoxy]-6-[1-(1-cyano-4-piperidyl)-5-methyl-triazol-4-yl]pyrazolo[1,5-a]pyridine-3-carbonitrile | 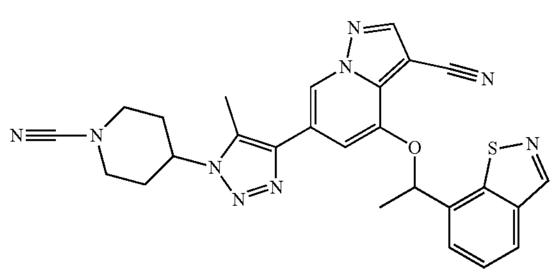 [SMILES: Cc1c(-c2cc(OC(C)c3cccc4cnsc34)c3c(C#N)cnn3c2)nnn1C1CCN(C#N)CC1] | 510.2 |
| 28[7] | 5-[1-(1,2-Benzothiazol-7-yl)ethoxy]-7-[1-(1-cyano-4-piperidyl)-5-methyl-triazol-4-yl]imidazo[1,2-a]pyridine-3-carbonitrile | 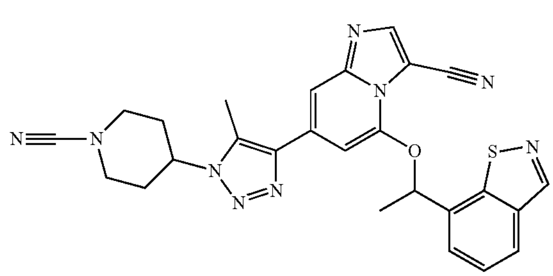 [SMILES: Cc1c(-c2cc(OC(C)c3cccc4cnsc34)n3c(C#N)cnc3c2)nnn1C1CCN(C#N)CC1] | 510.1 |

TABLE 61-continued

| Example No. | Chemical Name | Structure | ES/MS m/z [M + H]+ |
|---|---|---|---|
| 29[8] | 7-[1-(1-Cyano-4-piperidyl)-5-methyl-triazol-4-yl]-5-[1-(3-methylsulfonylphenyl)ethoxy]imidazo[1,2-a]pyridine-3-carbonitrile | 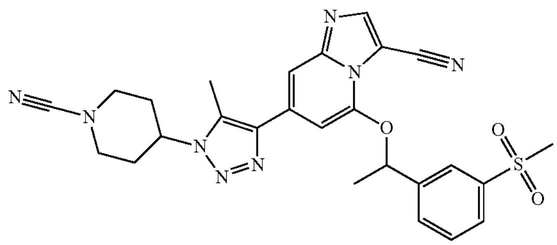 [SMILES: Cc1c(-c2cc(OC(C)c3cccc(S(C)(=O)=O)c3)n3c(C#N)cnc3c2)nnn1C1CCN(C#N)CC1] | 531.1 |
| 30[8] | 7-[1-(1-Cyano-4-piperidyl)-5-methyl-triazol-4-yl]-5-[1-(2-isothiazol-3-ylphenyl)ethoxy]imidazo[1,2-a]pyridine-3-carbonitrile | 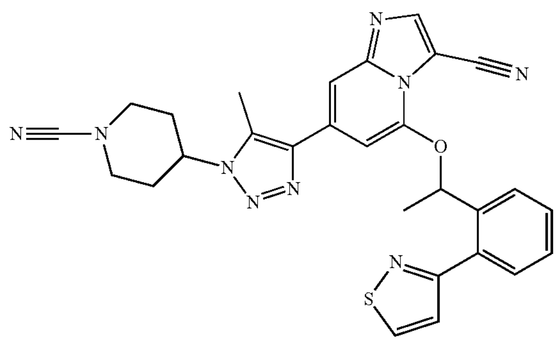 [SMILES: Cc1c(-c2cc(OC(C)c3ccccc3-c3ccsn3)n3c(C#N)cnc3c2)nnn1C1CCN(C#N)CC1] | 534.2 [M − H]+ |
| 31[5] | 7-[1-(1-Cyano-4-piperidyl)-5-methyl-triazol-4-yl]-5-[1-(3,3-difluorocyclobutyl)ethoxy]imidazo[1,2-a]pyridine-3-carbonitrile | 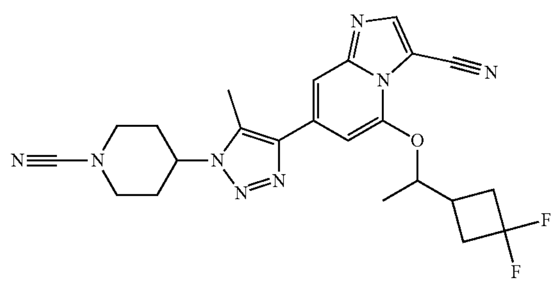 [SMILES: Cc1c(-c2cc(OC(C)C3CC(F)(F)C3)n3c(C#N)cnc3c2)nnn1C1CCN(C#N)CC1] | 467.2 |
| 32[5] | 7-[1-(1-Cyano-4-piperidyl)-5-methyl-triazol-4-yl]-5-[1-(5-methyl-1,3,4-thiadiazol-2-yl)ethoxy]imidazo[1,2-a]pyridine-3-carbonitrile | 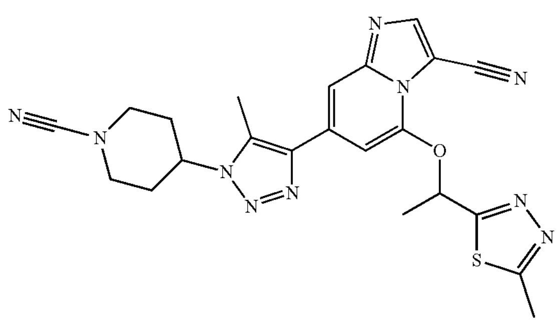 [SMILES: Cc1nnc(C(C)Oc2cc(-c3nnn(C4CCN(C#N)CC4)c3C)cc3ncc(C#N)n23)s1] | 475.1 |
| 33[7] | 6-[1-(1-cyano-4-piperidyl)-5-methyl-triazol-4-yl]-4-[1-(4-methylisothiazol-5-yl)ethoxy]pyrazolo[1,5-a]pyridine-3-carbonitrile | 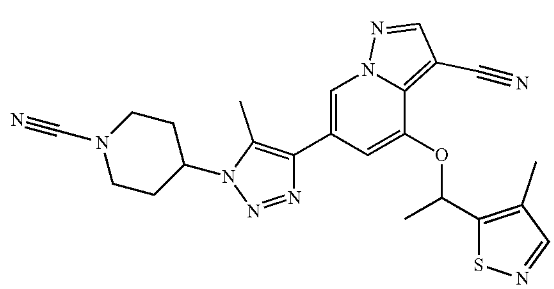 [SMILES: Cc1cnsc1C(C)Oc1cc(-c2nnn(C3CCN(C#N)CC3)c2C)cn2ncc(C#N)c12] | 474.2 |

TABLE 61-continued

| Example No. | Chemical Name | Structure | ES/MS m/z [M + H]+ |
|---|---|---|---|
| 34[2] | 6-[1-(1-Cyano-4-piperidyl)-5-methyl-triazol-4-yl]-4-[1-[2-(1-hydroxy-1-methyl-ethyl)phenyl]ethoxy]pyrazolo[1,5-a]pyridine-3-carbonitrile | 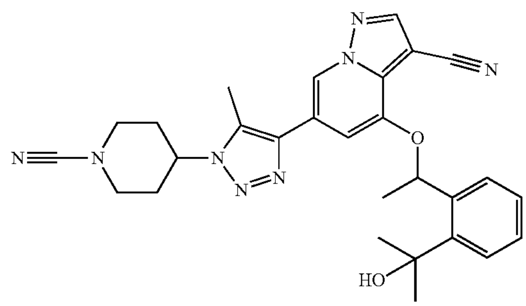 [SMILES: Cc1c(-c2cc(OC(C)c3ccccc3C(C)(C)O)c3c(C#N)cnn3c2)nnn1C1CCN(C#N)CC1] | 510.8 |
| 35[4] | 4-[4-[3-Chloro-4-[2-cyano-1-(5-fluoro-2-pyridyl)-2-methyl-propoxy]pyrazolo[1,5-a]pyridin-6-yl]-5-methyl-triazol-1-yl]piperidine-1-carbonitrile | 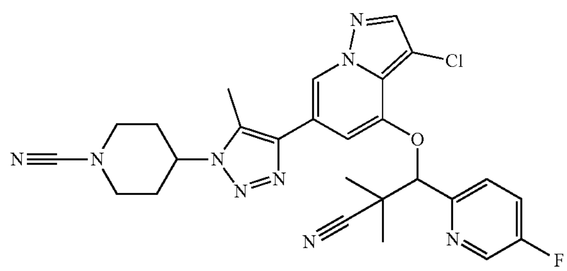 [SMILES: Cc1c(-c2cc(OC(c3ccc(F)cn3)C(C)(C)C#N)c3c(Cl)cnn3c2)nnn1C1CCN(C#N)CC1] | 535.7 |
| 36[4] | 6-[1-(1-Cyano-4-piperidyl)-5-methyl-triazol-4-yl]-4-[1-[2-(2-methoxyethylamino)-5-(trifluoromethyl)-3-pyridyl]ethoxy]pyrazolo[1,5-a]pyridine-3-carbonitrile | 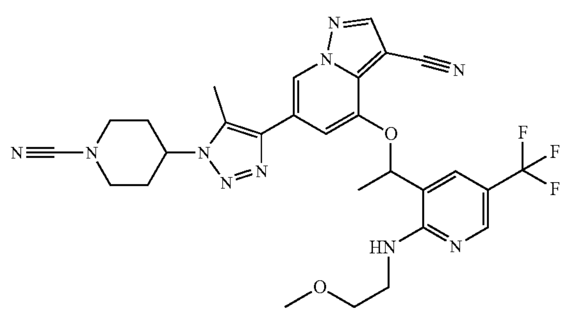 [SMILES: COCCNc1ncc(C(F)(F)F)cc1C(C)Oc1cc(-c2nnn(C3CCN(C#N)CC3)c2C)cn2ncc(C#N)c12] | 595.3 |
| 37[4] | 6-[1-(1-Cyano-4-piperidyl)-5-methyl-triazol-4-yl]-4-[1-[2-(3-hydroxyazetidin-1-yl)-5-(trifluoromethyl)-3-pyridyl]ethoxy]pyrazolo[1,5-a]pyridine-3-carbonitrile | 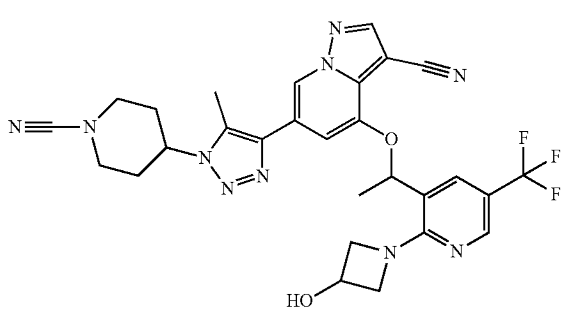 [SMILES: Cc1c(-c2cc(OC(C)c3cc(C(F)(F)F)cnc3N3CC(O)C3)c3c(C#N)cnn3c2)nnn1C1CCN(C#N)CC1] | 593.3 |

TABLE 61-continued

| Example No. | Chemical Name | Structure | ES/MS m/z [M + H]+ |
|---|---|---|---|
| 38[6] | 4-[4-[3-Bromo-4-[(2R)-1-(5-fluoro-2-pyridyl)-2,3-dihydroxy-propoxy]pyrazolo[1,5-a]pyridin-6-yl]-5-methyl-triazol-1-yl]piperidine-1-carbonitrile | 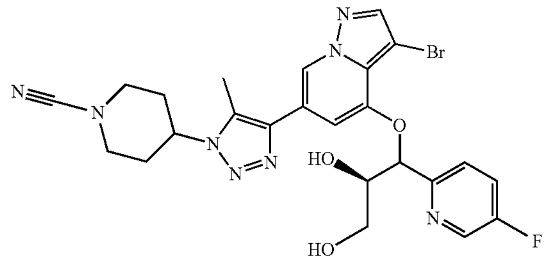 [SMILES: Cc1c(-c2cc(OC(c3ccc(F)cn3)[C@H](O)CO)c3c(Br)cnn3c2)nnn1C1CCN(C#N)CC1] | ($^{79}$Br/$^{81}$Br) 570.6/ 572.6 |

[1]Purification: Prep-TLC (PE/EtOAc 1:2)
[2]Reverse phase flash chromatography eluting with 0% to 100% ACN in H$_2$O.
[3]Reverse phase flash chromatography eluting with 0% to 50% ACN in H$_2$O.
[4]Reverse phase C18 chromatography eluting with 10% to 100% ACN in H$_2$O.
[5]Reverse phase flash chromatography eluting ACN in H$_2$O.
[6]Reverse phase C18 chromatography eluting with 10% to 100% ACN in H$_2$O followed by Prep HPLC system eluting with 10% to 100% ACN in H$_2$O.
[7]Reverse phase C18 chromatography eluting with 0% to 100% ACN in H$_2$O.
[8]Reverse phase C18 chromatography eluting with ACN in H$_2$O (0.1% FA).

Example 39

4-[3-(4-[3-Cyano-4-methoxypyrazolo[1,5-a]pyridin-6-yl]-5-methylpyrazol-1-yl)azetidin-1-yl]-2,2-dimethyl-pyrrolidine-1-carbonitrile, Isomer 1 and

Example 40

4-[3-(4-[3-Cyano-4-methoxypyrazolo[1,5-a]pyridin-6-yl]-5-methylpyrazol-1-yl)azetidin-1-yl]-2,2-dimethyl-pyrrolidine-1-carbonitrile, Isomer 2

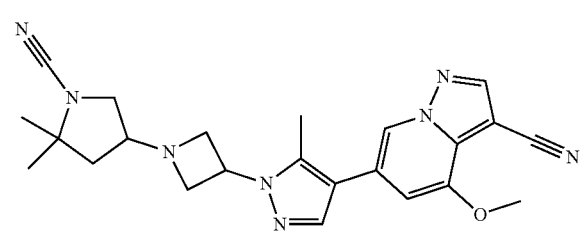 [SMILES: COc1cc(-c2cnn(C3CN(C4CN(C#N)C(C)(C)C4)C3)c2C)cn2ncc(C#N)c12]

4-[3-(4-[3-cyano-4-methoxypyrazolo[1,5-a]pyridin-6-yl]-5-methylpyrazol-1-yl)azetidin-1-yl]-2,2-dimethylpyrrolidine-1-carbonitrile (100 mg) is separated by Chiral-HPLC with the following conditions: Column, CHIRAL ART Cellulose-SC, 2*25 cm, 5 μm; eluting with 1:1 hexanes:DCM and 30% iPrOH, 254/210 nm; $t_{(R)}$ Isomer 1 is 6.15 min (33.1 mg, 32.9%) as a white solid with 100% ee, $t_{(R)}$ Isomer 2 is 9.07 min (35.5 mg, 35.2%) as a white solid with 100% ee. ES/MS m/z 431.20 [M+H]+.

Example 41

7-[1-(1-Cyano-4-piperidyl)-5-methyl-triazol-4-yl]-5-[1-[5-(trifluoromethyl)-3-pyridyl]ethoxy]imidazo[1,2-a]pyridine-3-carbonitrile, Isomer 1 and

Example 42

7-[1-(1-Cyano-4-piperidyl)-5-methyl-triazol-4-yl]-5-[1-[5-(trifluoromethyl)-3-pyridyl]ethoxy]imidazo[1,2-a]pyridine-3-carbonitrile, Isomer 2

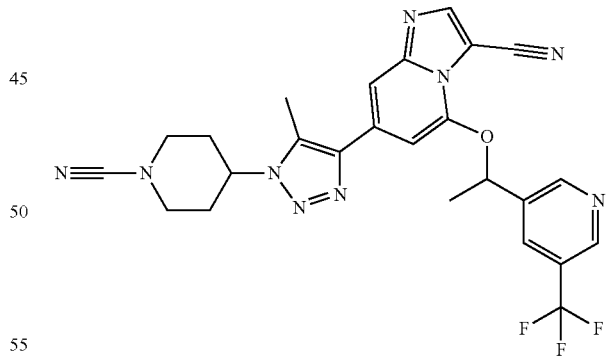

7-[5-Methyl-1-(4-piperidyl)triazol-4-yl]-5-[1-[5-(trifluoromethyl)-3-pyridyl]ethoxy]imidazo[1,2-a]pyridine-3-carbonitrile.TFA (90.00 mg) is separated by Chiral-HPLC with the following conditions: Column CHIRALPAK ID, 2*25 cm, 5 μm; eluting with 30% MTBE (0.1% diethylamine) and EtOH, 254/210 nm; 20 mL/min; $t_{(R)}$ Isomer 1 is 6 min (35.3 mg, 38.83%) with 100% ee, $t_{(R)}$ Isomer 2 is 10.4 min (34.6 mg, 37.87%) with 100% ee, ES/MS m/z 522.20 [M+H]+.

Example 43

6-[1-(1-Cyano-4-piperidyl)-5-methyl-pyrazol-4-yl]-4-[1-(5-fluoro-2-pyridyl)-2-hydroxy-ethoxy]pyrazolo[1,5-a]pyridine-3-carbonitrile, Isomer 1 and

Example 44

6-[1-(1-Cyano-4-piperidyl)-5-methyl-pyrazol-4-yl]-4-[1-(5-fluoro-2-pyridyl)-2-hydroxy-ethoxy]pyrazolo[1,5-a]pyridine-3-carbonitrile, Isomer 2

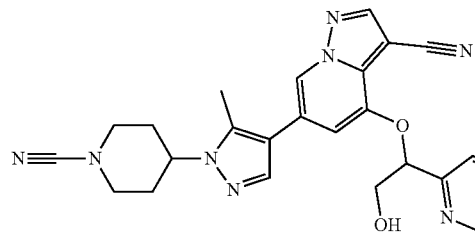

6-[1-(1-Cyano-4-piperidyl)-5-methyl-pyrazol-4-yl]-4-[1-(5-fluoro-2-pyridyl)-2-hydroxy-ethoxy]pyrazolo[1,5-a]pyridine-3-carbonitrile is separated by prep-chiral-HPLC with the following conditions: Column: CHIRALPAK ID, 2*25 cm, 5 μm; eluting with 50% hexanes (10 mM $NH_3$ in MeOH) in iPrOH, 254/270 nm, $t_{(R)}$ Isomer 1 is 11.90 min (319 mg, 35.4%) with 99% ee, ES/MS m/z 487.2 [M+H]$^+$, $t_{(R)}$ Isomer 2 is 16.12 min (320 mg, 35.4%) with 96.1% ee, ES/MS m/z 487.2 [M+H]$^+$.

Example 45

4-[4-[3-Chloro-4-[1-(5-fluoro-2-pyridyl)-2-hydroxy-ethoxy]pyrazolo[1,5-a]pyridin-6-yl]-5-methyl-triazol-1-yl]piperidine-1-carbonitrile, Isomer 1 and

Example 46

4-[4-[3-Chloro-4-[1-(5-fluoro-2-pyridyl)-2-hydroxy-ethoxy]pyrazolo[1,5-a]pyridin-6-yl]-5-methyl-triazol-1-yl]piperidine-1-carbonitrile, Isomer 2

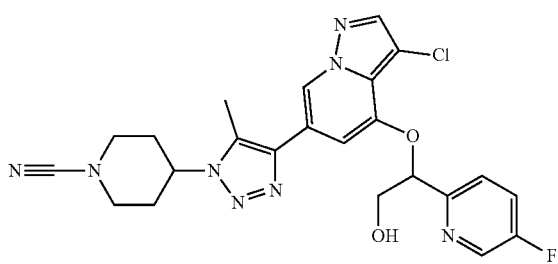 [SMILES: Cc1c(-c2cc(OC(CO)c3ccc(F)cn3)c3c(Cl)cnn3c2)nnn1C1CCN(C#N)CC1]

4-[4-[3-Chloro-4-[1-(5-fluoro-2-pyridyl)-2-hydroxy-ethoxy]pyrazolo[1,5-a]pyridin-6-yl]-5-methyl-triazol-1-yl]piperidine-1-carbonitrile is separated by prep-chiral-HPLC with the following conditions: Column: ART Cellulose-SB, 2*25 cm, 5 μm; eluting with 20% 5:1 Hex:DCM (0.5% 2M $NH_3$ in MeOH) in EtOH, 210/244 nm; $t_{(R)}$ Isomer 1 is 6.81 min (32 mg, 29.1%) with 100% ee, ES/MS m/z 497.2 [M+H]$^+$, $t_{(R)}$ Isomer 2 is 8.00 min (31 mg, 28.2%) with 96.7% ee, ES/MS m/z 497.2 [M+H]$^+$.

Example 47

4-[4-[3-Chloro-5-[1-(5-fluoro-2-pyridyl)-2-hydroxy-ethoxy]imidazo[1,2-a]pyridine-7-yl]-5-methyl-triazol-1-yl]piperidine-1-carbonitrile, Isomer 2

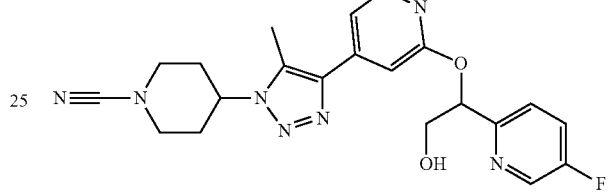

4-[4-[3-chloro-5-[1-(5-fluoro-2-pyridyl)-2-hydroxy-ethoxy]imidazo[1,2-a]pyridin-7-yl]-5-methyl-triazol-1-yl]piperidine-1-carbonitrile is separated with the following conditions: Column: CHIRALPAK IF, 2*25 cm, 5 μm; eluting with 30% EtOH:ACN (2:1) in hexanes (10 mM $NH_3$ in MeOH); 246/310 nm; $t_{(R)}$ Isomer 1 is 14.56 min (39.6 mg, 12.5%) as an off-white solid with 99.5% ee, $t_{(R)}$ Isomer 2 is 17.6 min (44.6 mg, 14.1%) as an off-white solid with 95.12% ee. ES/MS m/z 497.2 [M+H]$^+$.

Example 48

7-[1-(1-Cyano-4-piperidyl)-5-methyl-triazol-4-yl]-5-[2,2,2-trifluoro-1-(5-fluoro-2-pyridyl)ethoxy]imidazo[1,2-a]pyridine-3-carbonitrile, Isomer 1

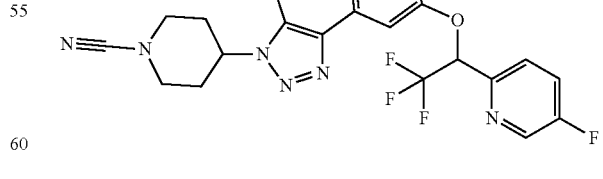

7-[1-(1-Cyano-4-piperidyl)-5-methyl-triazol-4-yl]-5-[2,2,2-trifluoro-1-(5-fluoro-2-pyridyl)ethoxy]imidazo[1,2-a]pyridine-3-carbonitrile is separated with the following condition: Column: NB Lux i-Cellulose-5, 2.12*25 cm, 5 μm; eluting with 30% MTBE (10 mM $NH_3$ in MeOH) in EtOH;

254/320 nm; t$_{(R)}$ Isomer 1 is 11.61 min (52.3 mg, 26.15%) with 100% ee, ES/MS m/z 526.2 [M+H]$^+$.

Example 49

7-[1-(1-Cyano-4-piperidyl)-5-methyl-triazol-4-yl]-5-[1-(5-fluoro-2-pyridyl)-2-methoxy-ethoxy]imidazo[1,2-a]pyridine-3-carbonitrile, Isomer 1 and Example 50

7-[1-(1-Cyano-4-piperidyl)-5-methyl-triazol-4-yl]-5-[1-(5-fluoro-2-pyridyl)-2-methoxy-ethoxy]imidazo[1,2-a]pyridine-3-carbonitrile, Isomer 2

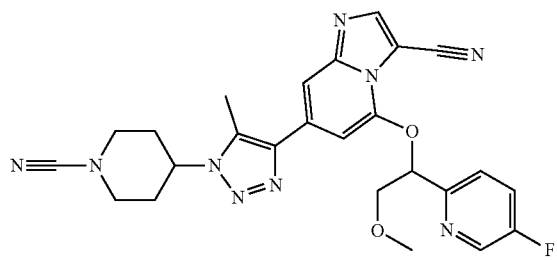 [SMILES: COCC(Oc1cc(-c2nnn(C3CCN(C#N)CC3)c2C)cc2ncc(C#N)n12)c1ccc(F)cn1]

7-[1-(1-Cyano-4-piperidyl)-5-methyl-triazol-4-yl]-5-[1-(5-fluoro-2-pyridyl)-2-methoxy-ethoxy]imidazo[1,2-a]pyridine-3-carbonitrile (110.00 mg) is separated by prep-chiral-HPLC with the following conditions: Column CHIRALPAK ID, 2*25 cm, 5 m; eluting with 30% MTBE (10 mM NH$_3$-MeOH) and EtOH, 254/320 nm, t$_{(R)}$ Isomer 1 is 8.65 min (36.6 mg) with 100% ee, t$_{(R)}$ Isomer 2 is 11.51 min (30.9 mg) with 100% ee, ES/MS m/z 502.35 [M+H]$^+$.

Example 51

7-[1-(1-Cyano-4-piperidyl)-5-methyl-triazol-4-yl]-5-[1-(5-fluoro-2-pyridyl)propoxy]imidazo[1,2-a]pyridine-3-carbonitrile, Isomer 1 and Example 52

7-[1-(1-Cyano-4-piperidyl)-5-methyl-triazol-4-yl]-5-[1-(5-fluoro-2-pyridyl)propoxy]imidazo[1,2-a]pyridine-3-carbonitrile, Isomer 2

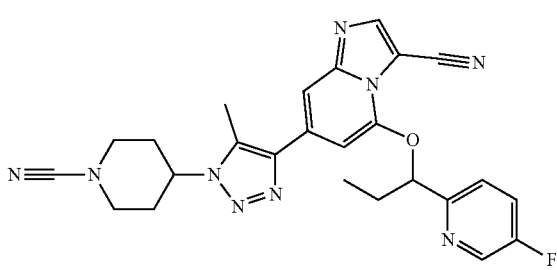 [SMILES: CCC(Oc1cc(-c2nnn(C3CCN(C#N)CC3)c2C)cc2ncc(C#N)n12)c1ccc(F)cn1]

7-[1-(1-Cyano-4-piperidyl)-5-methyl-triazol-4-yl]-5-[1-(5-fluoro-2-pyridyl)propoxy]imidazo[1,2-a]pyridine-3-carbonitrile (120 mg) is separated by prep-chiral-HPLC with the following conditions: Column: (R,R)-WHELK-01-Kromasil, 5*25 cm, 5 um; eluting with 50% hexanes (10 mM NH$_3$-MeOH) and EtOH, 254/220 nm, t$_{(R)}$ Isomer 1 is 7.27 min (52.9 mg) with 100% ee, t$_{(R)}$ Isomer 2 is 14.52 min (53.1 mg) with 100% ee, ES/MS m/z 486.20 [M+H]$^+$.

Example 53

6-[1-(1-Cyano-4-piperidyl)-5-methyl-triazol-4-yl]-4-[1-(5-fluoro-2-pyridyl)-2-methoxy-ethoxy]pyrazolo[1,5-a]pyridine-3-carbonitrile, Isomer 1

Example 54

6-[1-(1-Cyano-4-piperidyl)-5-methyl-triazol-4-yl]-4-[1-(5-fluoro-2-pyridyl)-2-methoxy-ethoxy]pyrazolo[1,5-a]pyridine-3-carbonitrile, Isomer 2

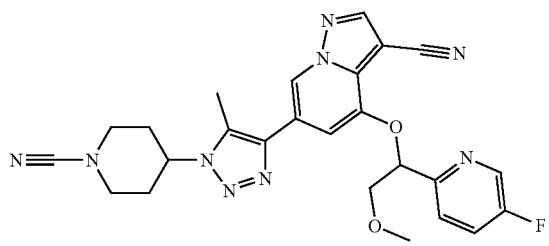 [SMILES: COCC(Oc1cc(-c2nnn(C3CCN(C#N)CC3)c2C)cn2ncc(C#N)c12)c1ccc(F)cn1]

6-[1-(1-Cyano-4-piperidyl)-5-methyl-triazol-4-yl]-4-[1-(5-fluoro-2-pyridyl)-2-methoxy-ethoxy]pyrazolo[1,5-a]pyridine-3-carbonitrile (160 mg) is isolated by prep-chiral-HPLC with the following conditions: Column: CHIRALPAK ID, 2*25 cm, 5 μm; eluting with 30% MTBE (10 mM NH3-MeOH) and EtOH, 250/215 nm, t$_{(R)}$ Isomer 1 is 7.06 min (61.5 mg) with 100% ee, t$_{(R)}$ Isomer 2 is 9.34 min (70.6 mg) with 100% ee, ES/MS m/z 502.20 [M+H]$^+$.

The following compounds are prepared essentially as described for 4-[3-(4-[3-cyano-4-methoxypyrazolo[1,5-a]pyridine-6-yl]-5-methylpyrazol-1-yl)pyridine-1-yl]-2,2-dimethylpyrrolidine-1-carbonitrile, Isomer 1 and Isomer 2, and adjusting the purification system as appropriate.

TABLE 62

| Ex. No. | Chemical name | Structure | ES/MS m/z [M + H]+ | tR min |
|---|---|---|---|---|
| 55[1] | 4-(4-[3-Cyano-4-[2,2,2-trifluoro-1-(oxan-4-yl)ethoxy]pyrazolo[1,5-a]pyridin-6-yl]-5-methylpyrazol-1-yl)piperidine-1-carbonitrile, Isomer 1 | 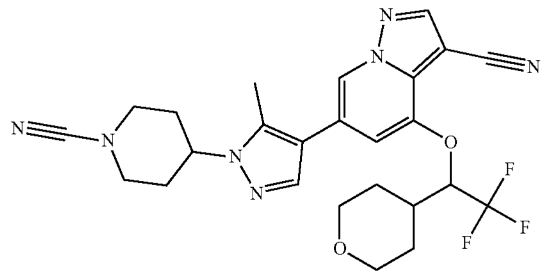 [SMILES: Cc1c(-c2cc(OC(C3CCOCC3)C(F)(F)F)c3c(C#N)cnn3c2)cnn1C1CCN(C#N)CC1] | 513.9 | 6.36 |
| 56[1] | 4-(4-[3-Cyano-4-[2,2,2-trifluoro-1-(oxan-4-yl)ethoxy]pyrazolo[1,5-a]pyridin-6-yl]-5-methylpyrazol-1-yl)piperidine-1-carbonitrile, Isomer 2 | 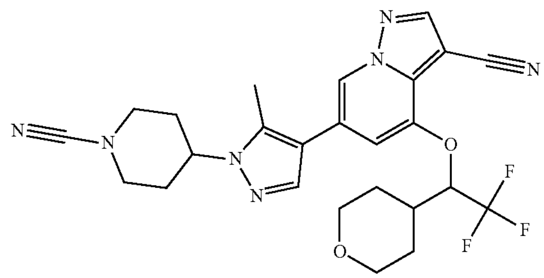 [SMILES: Cc1c(-c2cc(OC(C3CCOCC3)C(F)(F)F)c3c(C#N)cnn3c2)cnn1C1CCN(C#N)CC1] | 513.9 | 8.04 |
| 57[2] | 4-(4-[3-Cyano-4-[(6,6-difluoro-6,7-dihydro-5H-cyclopenta[b]pyridin-7-yl)oxy]pyrazolo[1,5-a]pyridin-6-yl]-5-methyl-1H-1,2,3-triazol-1-yl)piperidine-carbonitrile, Isomer 1 | 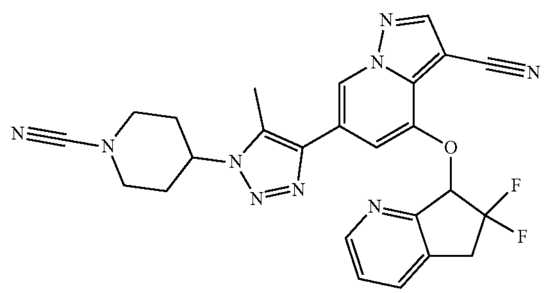 [SMILES: Cc1c(-c2cc(OC3c4ncccc4CC3(F)F)c3c(C#N)cnn3c2)nnn1C1CCN(C#N)CC1] | 502.0 | 15.61 |
| 58[2] | 4-(4-[3-Cyano-4-[(6,6-difluoro-6,7-dihydro-5H-cyclopenta[b]pyridin-7-yl)oxy]pyrazolo[1,5-a]pyridin-6-yl]-5-methyl-1H-1,2,3-triazol-1-yl)piperidine-carbonitrile, Isomer 2 | 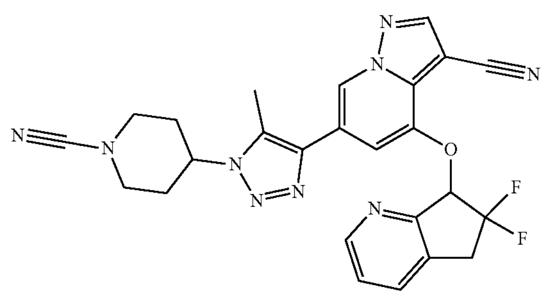 [SMILES: Cc1c(-c2cc(OC3c4ncccc4CC3(F)F)c3c(C#N)cnn3c2)nnn1C1CCN(C#N)CC1] | 502.0 | 19.2 |
| 59[3] | 4-(4-[3-Cyano-4-methoxypyrazolo[1,5-a]pyridin-6-yl]-5-methylpyrazol-1-yl)-2,2-dimethylpyrrolidine-1-carbonitrile, Isomer 1 | 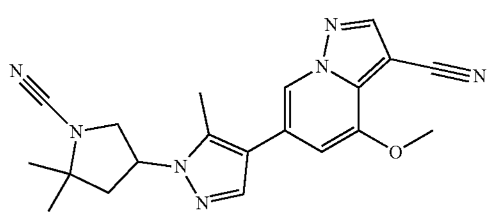 [SMILES: COc1cc(-c2cnn(C3CN(C#N)C(C)(C)C3)c2C)cn2ncc(C#N)c12] | 376.0 | 6.3 |
| 60[3] | 4-(4-[3-Cyano-4-methoxypyrazolo[1,5-a]pyridin-6-yl]-5-methylpyrazol-1-yl)-2,2-dimethylpyrrolidine-1-carbonitrile, Isomer 2 | 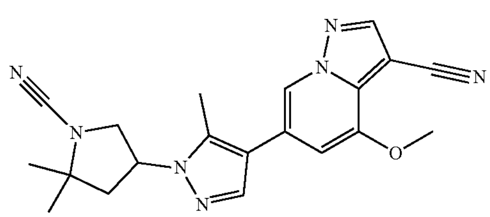 [SMILES: COc1cc(-c2cnn(C3CN(C#N)C(C)(C)C3)c2C)cn2ncc(C#N)c12] | 376.0 | 8.6 |

TABLE 62-continued

| Ex. No. | Chemical name | Structure | ES/MS m/z [M + H]+ | tR min |
|---|---|---|---|---|
| 61[4] | 6-[1-(1-cyano-4-piperidyl)-5-methyl-triazol-4-yl]-4-[2-methoxy-1-[5-(trifluoromethyl)-3-pyridyl]ethoxy]pyrazolo[1,5-a]pyridine-3-carbonitrile, Isomer 1 | 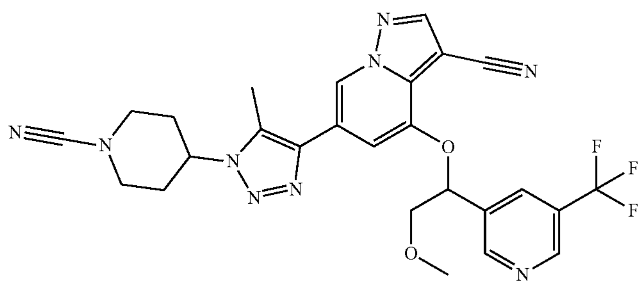 [SMILES: COCC(Oc1cc(-c2nnn(C3CCN(C#N)CC3)c2C)cn2ncc(C#N)c12)c1cncc(C(F)(F)F)c1] | 552.3 | 4.47 |
| 62[4] | 6-[1-(1-cyano-4-piperidyl)-5-methyl-triazol-4-yl]-4-[2-methoxy-1-[5-(trifluoromethyl)-3-pyridyl]ethoxy]pyrazolo[1,5-a]pyridine-3-carbonitrile, Isomer 2 | 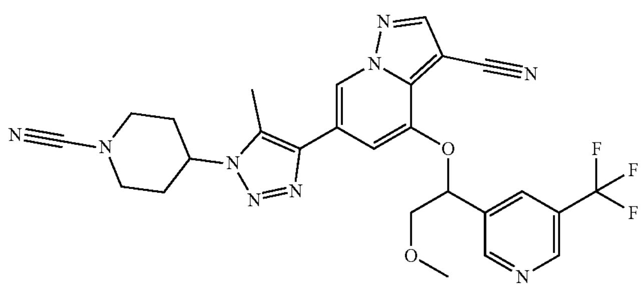 [SMILES: COCC(Oc1cc(-c2nnn(C3CCN(C#N)CC3)c2C)cn2ncc(C#N)c12)c1cncc(C(F)(F)F)c1] | 552.3 | 7.66 |
| 63[5] | 7-[1-(1-Cyano-4-piperidyl)-5-methyl-triazol-4-yl]-5-[1-(5-fluoro-2-pyridyl)-2-hydroxy-ethoxy]imidazo[1,2-a]pyridine-3-carbonitrile, Isomer 1 | 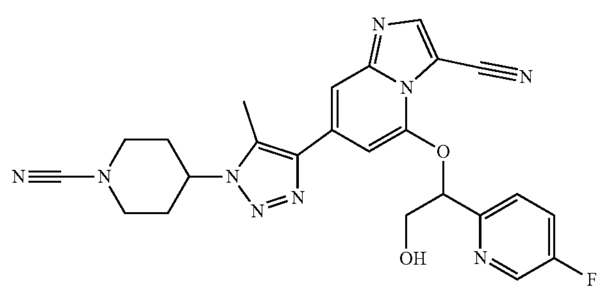 [SMILES: Cc1c(-c2cc(OC(CO)c3ccc(F)cn3)n3c(C#N)cnc3c2)nnn1C1CCN(C#N)CC1] | 488.2 | 6.99 |
| 64[5] | 7-[1-(1-Cyano-4-piperidyl)-5-methyl-triazol-4-yl]-5-[1-(5-fluoro-2-pyridyl)-2-hydroxy-ethoxy]imidazo[1,2-a]pyridine-3-carbonitrile, Isomer 2 | 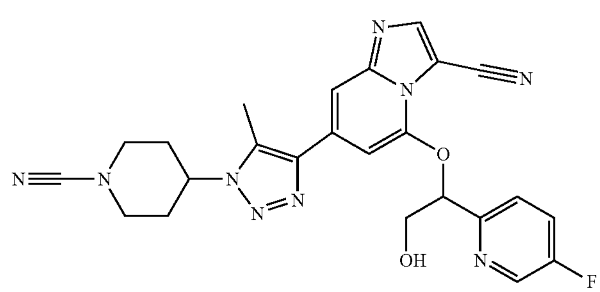 [SMILES: Cc1c(-c2cc(OC(CO)c3ccc(F)cn3)n3c(C#N)cnc3c2)nnn1C1CCN(C#N)CC1] | 488.3 | 10.75 |
| 65[6] | 2-[1-[3-Cyano-6-[1-(1-cyano-4-piperidyl)-5-methyl-triazol-4-yl]pyrazolo[1,5-a]pyridin-4-yl]oxyethyl]benzamide, Isomer 1 | 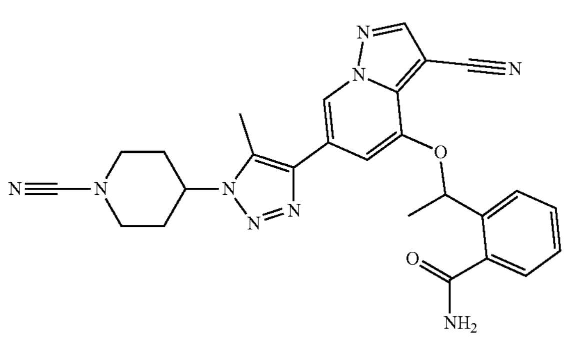 [SMILES: Cc1c(-c2cc(OC(C)c3ccccc3C(N)=O)c3c(C#N)cnn3c2)nnn1C1CCN(C#N)CC1] | 496.4 | 3.18[5] |

TABLE 62-continued

| Ex. No. | Chemical name | Structure | ES/MS m/z [M + H]+ | tR min |
|---|---|---|---|---|
| 66[7] | 6-[1-(1-Cyano-4-piperidyl)-5-methyl-triazol-4-yl]-4-[1-(5-methylpyridazin-3-yl)ethoxy]pyrazolo[1,5-a]pyridine-3-carbonitrile, Isomer 1 | 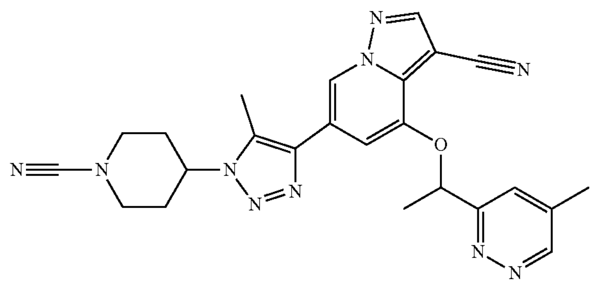 [SMILES: Cc1cnnc(C(C)Oc2cc(-c3nnn(C4CCN(C#N)CC4)c3C)cn3ncc(C#N)c23)c1] | 469.2 | 1.53 |
| 67[7] | 6-[1-(1-Cyano-4-piperidyl)-5-methyl-triazol-4-yl]-4-[1-(5-methylpyridazin-3-yl)ethoxy]pyrazolo[1,5-a]pyridine-3-carbonitrile, Isomer 2 | 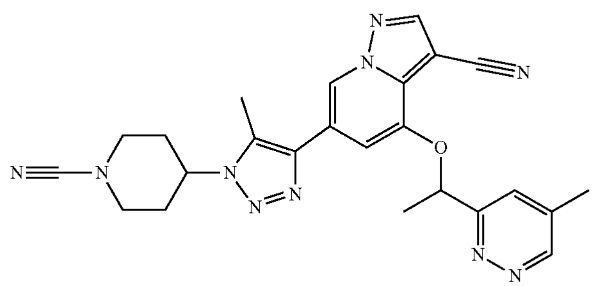 [SMILES: Cc1cnnc(C(C)Oc2cc(-c3nnn(C4CCN(C#N)CC4)c3C)cn3ncc(C#N)c23)c1] | 469.2 | 2.03 |
| 68[8] | 4-[1-(5-Chloropyridazin-3-yl)ethoxy]-6-[1-(1-cyano-4-piperidyl)-5-methyl-triazol-4-yl]pyrazolo[1,5-a]pyridine-3-carbonitrile, Isomer 1 | 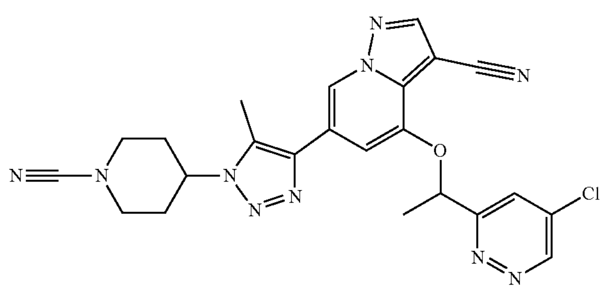 [SMILES: Cc1c(-c2cc(OC(C)c3cc(Cl)cnn3)c3c(C#N)cnn3c2)nnn1C1CCN(C#N)CC1] | 489.1 | 1.66 |
| 69[9] | 7-[1-(1-Cyano-4-piperidyl)-5-methyl-triazol-4-yl]-5-[1-(5-methylpyridazin-3-yl)ethoxy]imidazo[1,2-a]pyridine-3-carbonitrile, Isomer 1 | 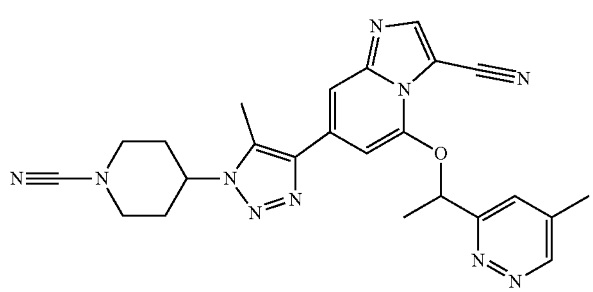 [SMILES: Cc1cnnc(C(C)Oc2cc(-c3nnn(C4CCN(C#N)CC4)c3C)cc3ncc(C#N)n23)c1] | 469.2 | 1.56 |
| 70[10] | 7-[1-(1-Cyano-4-piperidyl)-5-methyl-triazol-4-yl]-5-[1-(5-methyl-3-pyridyl)ethoxy]imidazo[1,2-a]pyridine-3-carbonitrile, Isomer 1 | 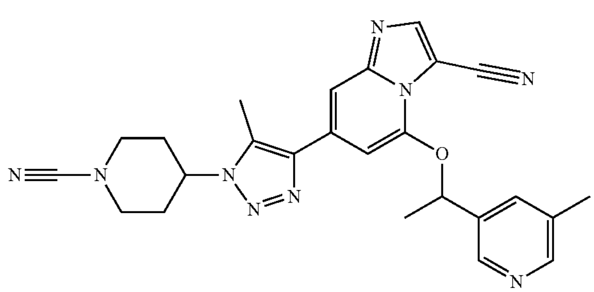 [SMILES: Cc1cncc(C(C)Oc2cc(-c3nnn(C4CCN(C#N)CC4)c3C)cc3ncc(C#N)n23)c1] | 468.2 | 2.42 |

TABLE 62-continued

| Ex. No. | Chemical name | Structure | ES/MS m/z [M + H]+ | tR min |
|---|---|---|---|---|
| 71[10] | 7-[1-(1-Cyano-4-piperidyl)-5-methyl-triazol-4-yl]-5-[1-(5-methyl-3-pyridyl)ethoxy]imidazo[1,2-a]pyridine-3-carbonitrile, Isomer 2 | 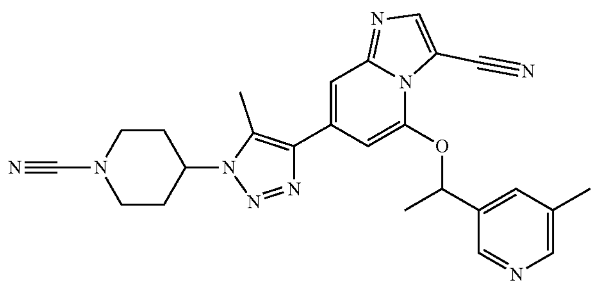 [SMILES: Cc1cncc(C(C)Oc2cc(-c3nnn(C4CCN(C#N)CC4)c3C)cc3ncc(C#N)n23)c1] | 468.3 | 3.03 |
| 72[11] | 7-[1-(1-Cyano-4-piperidyl)-5-methyl-triazol-4-yl]-5-[1-[5-(difluoromethyl)-3-pyridyl]ethoxy]imidazo[1,2-a]pyridine-3-carbonitrile, Isomer 1 | 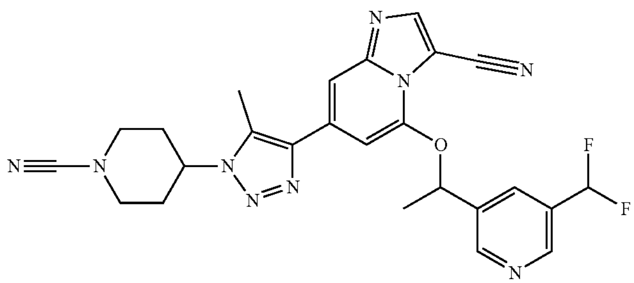 [SMILES: Cc1c(-c2cc(OC(C)c3cncc(C(F)F)c3)n3c(C#N)cnc3c2)nnn1C1CCN(C#N)CC1] | 504.3 | 1.94 |
| 73[11] | 7-[1-(1-Cyano-4-piperidyl)-5-methyl-triazol-4-yl]-5-[1-[5-(difluoromethyl)-3-pyridyl]ethoxy]imidazo[1,2-a]pyridine-3-carbonitrile, Isomer 2 | 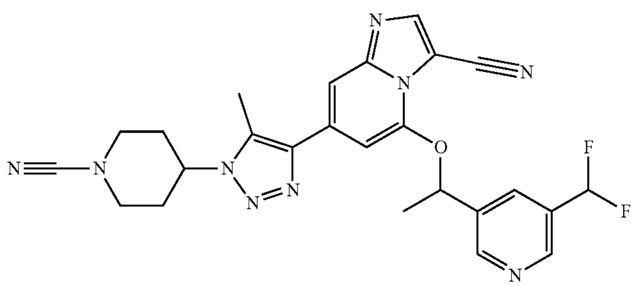 [SMILES: Cc1c(-c2cc(OC(C)c3cncc(C(F)F)c3)n3c(C#N)cnc3c2)nnn1C1CCN(C#N)CC1] | 504.4 | 2.47 |
| 74[12] | 6-[1-(1-Cyano-4-piperidyl)-5-methyl-triazol-4-yl]-4-[1-(1-methylpyrrolo[2,3-c]pyridin-4-yl)ethoxy]pyrazolo[1,5-a]pyridine-3-carbonitrile, Isomer 1 | 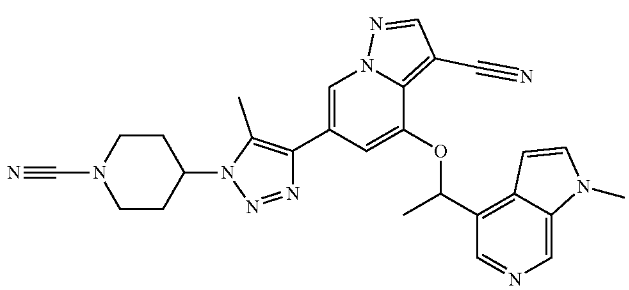 [SMILES: Cc1c(-c2cc(OC(C)c3cncc4c3ccn4C)c3c(C#N)cnn3c2)nnn1C1CCN(C#N)CC1] | 507.4 | 1.42 |
| 75[13] | 2-[1-[3-cyano-6-[1-(1-cyano-4-piperidyl)-5-methyl-triazol-4-yl]pyrazolo[1,5-a]pyridin-4-yl]oxyethyl]-N,N-dimethyl-benzamide, Isomer 2 | 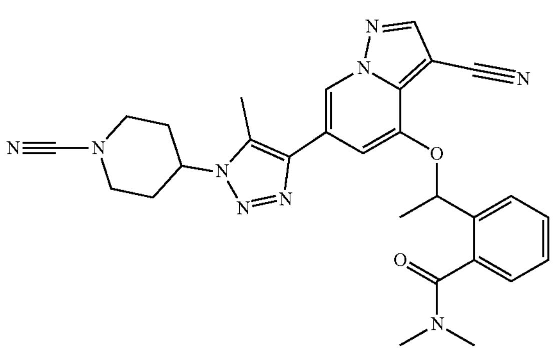 [SMILES: Cc1c(-c2cc(OC(C)c3ccccc3C(=O)N(C)C)c3c(C#N)cnn3c2)nnn1C1CCN(C#N)CC1] | 524.2 | 4.23 |

TABLE 62-continued

| Ex. No. | Chemical name | Structure | ES/MS m/z [M + H]+ | tR min |
|---|---|---|---|---|
| 76[14] | 6-[1-(1-Cyano-4-piperidyl)-5-methyl-pyrazol-4-yl]-4-[1-(2-methylsulfonylphenyl)ethoxy]pyrazolo[1,5-a]pyridine-3-carbonitrile, Isomer 1 | 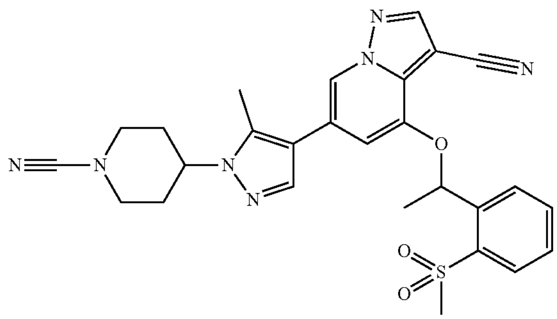 [SMILES: Cc1c(-c2cc(OC(C)c3ccccc3S(C)(=O)=O)c3c(C#N)cnn3c2)cnn1C1CCN(C#N)CC1] | 530.2 | 2.22 |
| 77[14,15] | 6-[1-(1-Cyano-4-piperidyl)-5-methyl-pyrazol-4-yl]-4-[1-(2-methylsulfonylphenyl)ethoxy]pyrazolo[1,5-a]pyridine-3-carbonitrile, Isomer 2 | 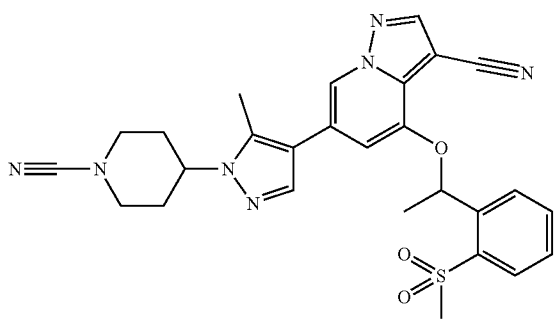 [SMILES: Cc1c(-c2cc(OC(C)c3ccccc3S(C)(=O)=O)c3c(C#N)cnn3c2)cnn1C1CCN(C#N)CC1] | 530.2 | 2.85 |
| 78[12,16] | 5-[1-(1,3-Benzothiazol-7-yl)ethoxy]-7-[1-(1-cyano-4-piperidyl)-5-methyl-triazol-4-yl]imidazo[1,2-a]pyridine-3-carbonitrile, Isomer 1 | 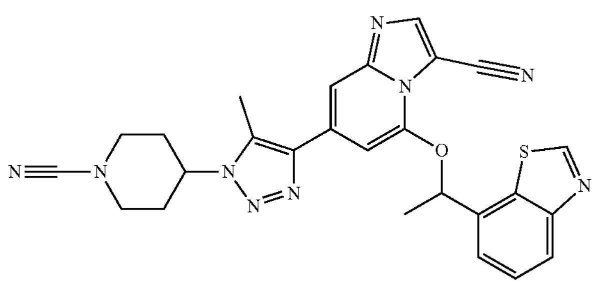 [SMILES: Cc1c(-c2cc(OC(C)c3cccc4ncsc34)n3c(C#N)cnc3c2)nnn1C1CCN(C#N)CC1] | 510.2 | 1.94 |
| 79[17,18] | 4-[1-(1,2-benzothiazol-7-yl)ethoxy]-6-[1-(1-cyano-4-piperidyl)-5-methyl-triazol-4-yl]pyrazolo[1,5-a]pyridine-3-carbonitrile, Isomer 1 | 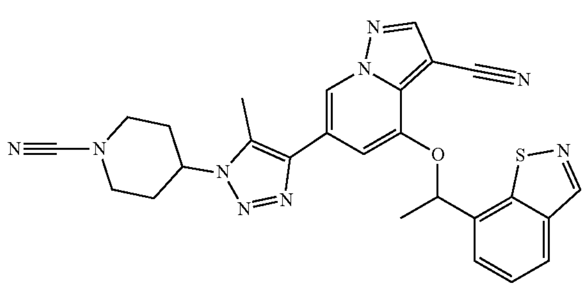 [SMILES: Cc1c(-c2cc(OC(C)c3cccc4cnsc34)c3c(C#N)cnn3c2)nnn1C1CCN(C#N)CC1] | 510.9 | 1.87 |

TABLE 62-continued

| Ex. No. | Chemical name | Structure | ES/MS m/z [M + H]+ | tR min |
|---|---|---|---|---|
| 80[17,18] | 4-[1-(1,2-benzothiazol-7-yl)ethoxy]-6-[1-(1-cyano-4-piperidyl)-5-methyl-triazol-4-yl]pyrazolo[1,5-a]pyridine-3-carbonitrile, Isomer 2 | 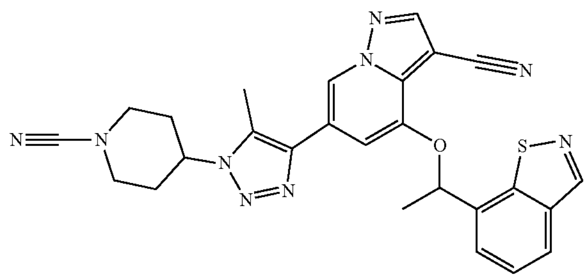 [SMILES: Cc1c(-c2cc(OC(C)c3cccc4cnsc34)c3c(C#N)cnn3c2)nnn1C1CCN(C#N)CC1] | 510.8 | 2.85 |
| 81[19] | 6-[1-(1-Cyano-4-piperidyl)-5-methyl-pyrazol-4-yl]-4-[1-(3-methylsulfonylphenyl)ethoxy]pyrazolo[1,5-a]pyridine-3-carbonitrile, Isomer 2 | 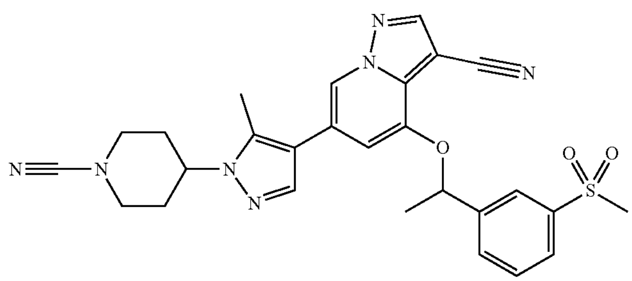 [SMILES: Cc1c(-c2cc(OC(C)c3cccc(S(C)(=O)=O)c3)c3c(C#N)cnn3c2)cnn1C1CCN(C#N)CC1] | 531.0 | 1.57 |
| 82[20,21] | 7-[1-(1-Cyano-4-piperidyl)-5-methyl-triazol-4-yl]-5-[1-(3,3-difluorocyclobutyl)ethoxy]imidazo[1,2-a]pyridine-3-carbonitrile, Isomer 1 | 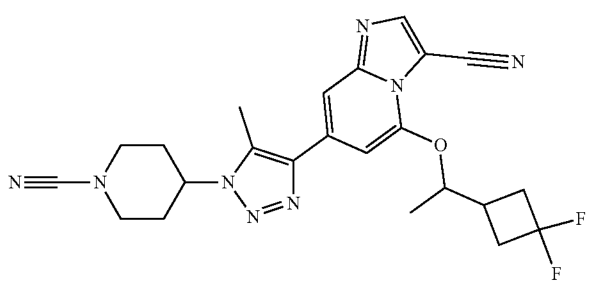 [SMILES: Cc1c(-c2cc(OC(C)C3CC(F)(F)C3)n3c(C#N)cnc3c2)nnn1C1CCN(C#N)CC1] | 467.2 | 0.75 |
| 83[20,21] | 7-[1-(1-Cyano-4-piperidyl)-5-methyl-triazol-4-yl]-5-[1-(3,3-difluorocyclobutyl)ethoxy]imidazo[1,2-a]pyridine-3-carbonitrile, Isomer 2 | 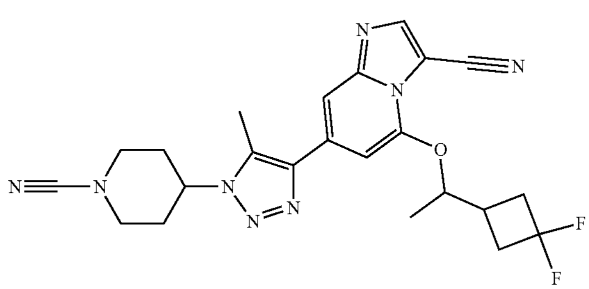 [SMILES: Cc1c(-c2cc(OC(C)C3CC(F)(F)C3)n3c(C#N)cnc3c2)nnn1C1CCN(C#N)CC1] | 467.2 | 0.84 |

TABLE 62-continued

| Ex. No. | Chemical name | Structure | ES/MS m/z [M + H]⁺ | tR min |
|---|---|---|---|---|
| 84[22,23] | 7-[1-(1-Cyano-4-piperidyl)-5-methyl-triazol-4-yl]-5-[1-(5-methyl-1,3,4-thiadiazol-2-yl)ethoxy]imidazo[1,2-a]pyridine-3-carbonitrile, Isomer 2 | 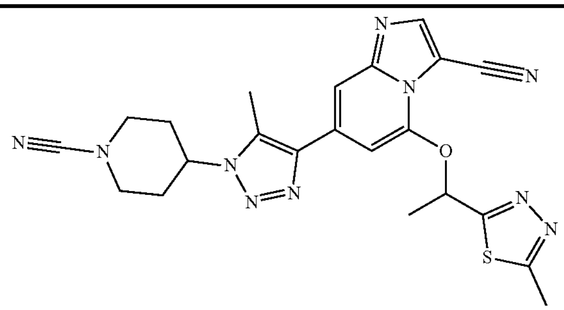 | 475.2 | 2.65 |

[1] Column CHIRAL ART Amylose-SA, 2*25 cm, 5 μm, eluting with hexanes:DCM (5:1) (0.1% DEA) in 50% EtOH, flow rate 20 mL/min, 220/254 nm.
[2] Column CHIRALPAK IE, 2*25 cm, 5 μm, eluting with 50% EtOH in MTBE:hexanes (1:1, 0.1% DEA additive) in 22 min, 210/250 nm.
[3] Column CHIRAL ART Cellulose-SB, 2*25 cm, 5 μm, 40% EtOH in hexanes (10 mM NH₃?MeOH), 25 mL/min, 250/210 nm.
[4] Column CHIRAL ART Cellulose-SC, 2*25 cm, 5 μm; eluting with 40% EtOH in MTBE (10 mM NH₃-MeOH); 20 mL/min; 250/215 nm.
[5] Column CHIRALPAK IE, 2*25 cm, 5 μm, eluting with 50% EtOH in MTBE (10 mM NH₃?MeOH); flow rate: 20 mL/min; 254/210.
[6] Column: (S,S) Whelk-01, 21 x 250 mm; eluting with an 65% CO₂ in MeOH (0.5% DMEA); flow rate 80 mL/min; UV at 225 nm.
[7] Column: CHIRALPAK AD-H, 21*150 mm; eluting with a 65% CO₂ in EtOH (0.5% DMEA); flow rate 80 mL/min; UV at 245 nm.
[8] Column: CHIRALPAK AD-H, 21*150 mm; eluting with a 60% CO₂ in MeOH (0.5% DMEA); flow rate 80 mL/min; UV at 245 nm.
[9] Column: CHIRALPAK AD-H, 21*250 mm; eluting with a 60% CO₂ in MeOH (0.5% DMEA); flow rate 70 mL/min; UV at 225 nm.
[10] Column: CHIRALPAK AD-H, 20*150 mm; eluting with a 70% CO₂ in EtOH (0.5% DMEA); flow rate 80 mL/min; UV at 254 nm.
[11] Column: CHIRALPAK AD-H, 21*250 mm; eluting with a 70% CO₂ in EtOH (0.5% DMEA); flow rate 70 mL/min; UV at 225 nm.
[12] Column: Chiralpak AD-H, 21*150 mm; eluting with an 70% CO₂ in iPrOH (0.5% DMEA); flow rate 80 mL/min; 310 nm.
[13] Column CHIRALPAK AS-H, 21*150 cm, eluting with 85% CO₂ in EtOH (0.5% DMEA additive), flow rate 70 mL/min, 242 nm.
[14] Column: Lux Sum Cellulose-4, 2.12*250 mm, eluting with 60% CO₂ in EtOH (0.5% DMEA).
[15] Reported $t_{(R)}$'s are obtained using the following analytical conditions: SFC, Lux 5 μm Cellulose-4, 4.6*100 mm, 40% EtOH (0.5% DMEA)/CO₂.
[16] Reported $t_{(R)}$'s are obtained using the following analytical conditions: SFC, Chiralpak AD-H, 4.6 x 150 mm, 30% iPrOH (0.5% DMEA)/CO₂, 5 mL/min, 225 nm.
[17] Column: CHIRALPAK AD-H, 21*150 mm; eluting with a 60% CO₂ in MeOH; 225 nm.
[18] Reported $t_{(R)}$'s are obtained using the following analytical conditions: SFC, Chiralpak AD-H, 4.6 x 150 mm, 40% MeOH/CO₂, 5 mL/min, 225 nm.
[19] Column CHIRALPAK AS-H, 21*150 cm, eluting with 75% CO₂ in MeOH, flow rate 80 mL/min, 225 nm.
[20] Column: CHIRALPAK AD-H, 21*250 mm; eluting with a 75% CO₂ in EtOH (0.5% DMEA); flow rate 70 mL/min; UV at 255 nm.
[21] Reported $t_{(R)}$'s are obtained using the following analytical conditions: SFC, Chiralpak AD-H, 4.6 x 150 mm, 25% EtOH (0.5% DMEA)/CO₂, 5 mL/min, 225 nm.
[22] Column: Chiralcel-OD-H, 21*250 mm; eluting with a 60% CO₂ in MeOH (0.5% DMEA); flow rate 80 mL/min; UV at 225 nm.
[23] Reported $t_{(R)}$'s are obtained using the following analytical conditions: Column: Chiralcel-OD-H, 4.6*150 mm; eluting with a 40% MeOH (0.5% DMEA)/CO₂; flow rate 5 mL/min; UV at 225 nm.

Example 85

6-[1-(1-cyano-4-piperidyl)-5-methyl-triazol-4-yl]-4-[1-[5-(trifluoromethyl)-3-pyridyl]ethoxy]pyrazolo[1,5-a]pyridine-3-carbonitrile, Isomer 1 and

Example 86

6-[1-(1-cyano-4-piperidyl)-5-methyl-triazol-4-yl]-4-[1-[5-(trifluoromethyl)-3-pyridyl]ethoxy]pyrazolo[1,5-a]pyridine-3-carbonitrile, Isomer 2

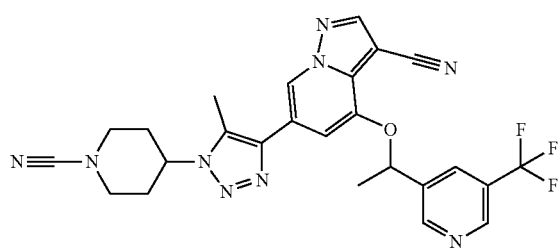 [SMILES: Cc1c(-c2cc(OC(C)c3cncc(C(F)(F)F)c3)c3c(C#N)cnn3c2)nnn1C1CCN(C#N)CC1]

To 6-[5-methyl-1-(4-piperidyl)triazol-4-yl]-4-[1-[5-(trifluoromethyl)-3-pyridyl]ethoxy]pyrazolo[1,5-a]pyridine-3-carbonitrile (200.00 mg, 0.40 mmol) in DCM (5 mL) is added DIEA (520.62 mg, 4.03 mmol) and BrCN (51.20 mg, 0.48 mmol) in portions at RT under N₂. The reaction is stirred 2 hr at RT then concentrated in vacuo. The residue is purified by reverse phase chromatography with the following conditions: Column, C18; mobile phase, eluting with 50% to 60% ACN in H₂O (0.1% NH₄HCO₃) to afford the titled compound as a white solid (170 mg, 80.92%). ES/MS m/z 522.1 [M+H]⁺.

6-[1-(1-Cyano-4-piperidyl)-5-methyl-triazol-4-yl]-4-[1-[5-(trifluoromethyl)-3-pyridyl]ethoxy]pyrazolo[1,5-a]pyridine-3-carbonitrile is subjected to prep-chiral-HPLC: Column, CHIRAL ART Amylose-SA, 2*25 cm, 5 m; eluting with 10% EtOH in Hex:DCM (5:1) (0.5% 2M NH₃-MeOH) to afford 6-[1-(1-cyano-4-piperidyl)-5-methyl-triazol-4-yl]-4-[1-[5-(trifluoromethyl)-3-pyridyl]ethoxy] pyrazolo[1,5-a]pyridine-3-carbonitrile, Isomer 1, $t_{(R)}$ is 16.5 min (30.5 mg, 17.9%) with 99.7% ee, ES/MS m/z 522.15 [M+H]⁺ and 6-[1-(1-cyano-4-piperidyl)-5-methyl-triazol-4-yl]-4-[1-[5-(trifluoromethyl)-3-pyridyl]ethoxy] pyrazolo[1,5-a]pyridine-3-carbonitrile, Isomer 2, $t_{(R)}$ Isomer 2 is 22.5 min (42.1 mg, 24.8%) with 98.0% ee, ES/MS m/z 522.10 [M+H]⁺.

The following compounds are prepared essentially as described for 6-[1-(1-cyano-4-piperidyl)-5-methyl-triazol-4-yl]-4-[1-[5-(trifluoromethyl)-3-pyridyl]ethoxy]pyrazolo[1,5-a]pyridine-3-carbonitrile, Isomer 1, and Isomer 2, and adjusting the purification system as appropriate. Retention times reported in Table 57 are for the separated enantiomers.

TABLE 63

| Ex. No. | Chemical name | Structure | ES/MS m/z [M + H]+ | t(R) min |
|---|---|---|---|---|
| 87[1,2] | 6-[1-(1-Cyano-4-piperidyl)-5-methyl-triazol-4-yl]-4-[(5-fluoro-2-pyridyl)-[1-(trifluoromethyl)cyclopropyl]methoxy]pyrazolo[1,5-a]pyridine-3-carbonitrile, Isomer 2 | 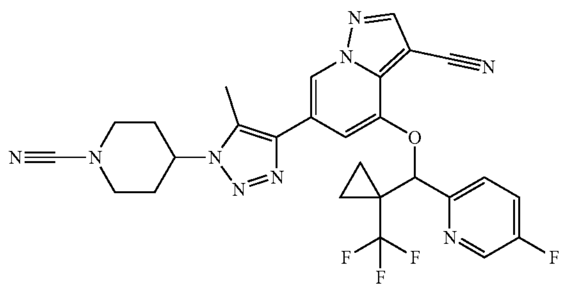 [SMILES: Cc1c(-c2cc(OC(c3ccc(F)cn3)C3(C(F)(F)F)CC3)c3c(C#N)cnn3c2)nnn1C1CCN(C#N)CC1] | 566.4 | 12.8 |
| 88[3,4] | 6-[1-(7-Cyano-7-azaspiro[3.5]nonan-2-yl)-5-methyl-pyrazol-4-yl]-4-[1-(5-fluoro-2-pyridyl)-2-hydroxy-ethoxy]pyrazolo[1,5-a]pyridine-3-carbonitrile, Isomer 1 | 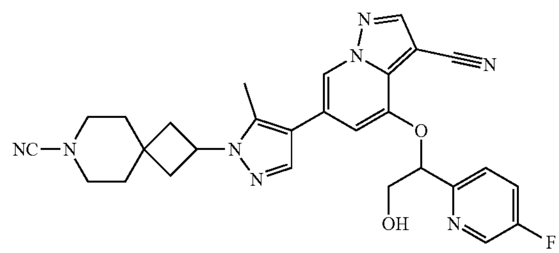 [SMILES: Cc1c(-c2cc(OC(CO)c3ccc(F)cn3)c3c(C#N)cnn3c2)cnn1C1CC2(CCN(C#N)CC2)C1] | 527.2 | 4.6 |
| 89[5,6] | 6-[1-(1-Cyano-4-piperidyl)-5-methyl-triazol-4-yl]-4-[1-(5-methylthiazol-2-yl)ethoxy]pyrazolo[1,5-a]pyridine-3-carbonitrile, Isomer 1 | 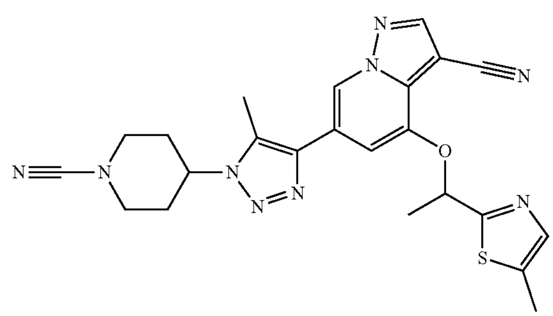 [SMILES: Cc1cnc(C(C)Oc2cc(-c3nnn(C4CCN(C#N)CC4)c3C)cn3ncc(C#N)c23)s1] | 474.2 | 14.6 |
| 90[5,6] | 6-[1-(1-Cyano-4-piperidyl)-5-methyl-triazol-4-yl]-4-[1-(5-methylthiazol-2-yl)ethoxy]pyrazolo[1,5-a]pyridine-3-carbonitrile, Isomer 2 | 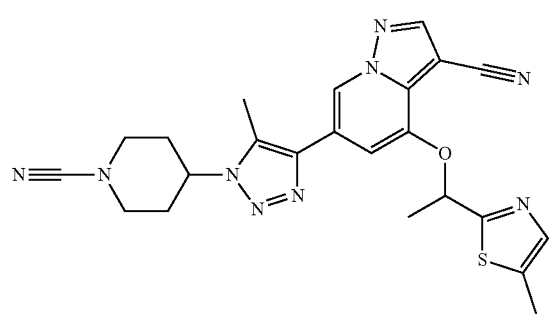 [SMILES: Cc1cnc(C(C)Oc2cc(-c3nnn(C4CCN(C#N)CC4)c3C)cn3ncc(C#N)c23)s1] | 474.2 | 17.6 |
| 91[7,8] | 6-[1-(1-Cyano-4-piperidyl)-5-methyl-triazol-4-yl]-4-[1-(5-fluoro-2-pyridyl)-2-hydroxy-ethoxy]pyrazolo[1,5-a]pyridine-3-carbonitrile, Isomer 1 | 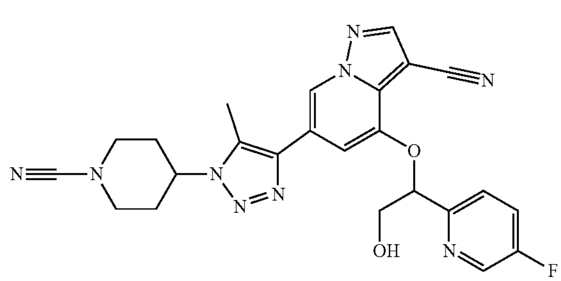 [SMILES: Cc1c(-c2cc(OC(CO)c3ccc(F)cn3)c3c(C#N)cnn3c2)nnn1C1CCN(C#N)CC1] | 488.2 | 5.1 |

TABLE 63-continued

| Ex. No. | Chemical name | Structure | ES/MS m/z [M + H]+ | t(R) min |
|---|---|---|---|---|
| 92[7,8] | 6-[1-(1-Cyano-4-piperidyl)-5-methyl-triazol-4-yl]-4-[1-(5-fluoro-2-pyridyl)-2-hydroxy-ethoxy]pyrazolo[1,5-a]pyridine-3-carbonitrile, Isomer 2 | 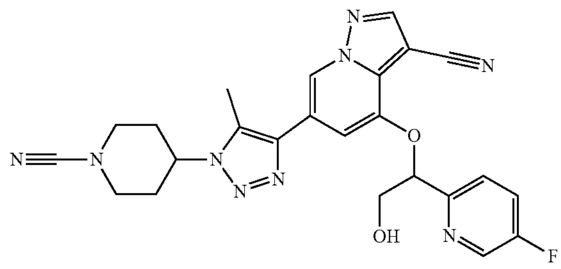 [SMILES: Cc1c(-c2cc(OC(CO)c3ccc(F)cn3)c3c(C#N)cnn3c2)nnn1C1CCN(C#N)CC1] | 488.2 | 8.9 |
| 93[9,10] | 6-[1-(1-Cyano-4-piperidyl)-5-methyl-triazol-4-yl]-4-[1-(1-isopropyltriazol-4-yl)ethoxy]pyrazolo[1,5-a]pyridine-3-carbonitrile, Isomer I | 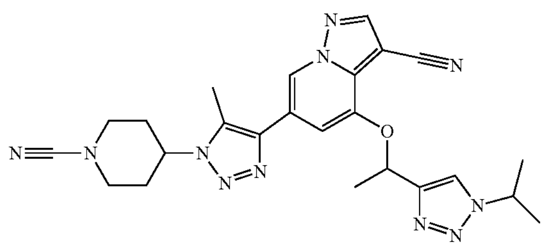 [SMILES: Cc1c(-c2cc(OC(C)c3cn(C(C)C)nn3)c3c(C#N)cnn3c2)nnn1C1CCN(C#N)CC1] | 486.4 | 1.2 |
| 94[11,12] | 6-[1-[1-(1-Cyano-2,2-dimethyl-azetidin-3-yl)-4-piperidyl]-5-methyl-pyrazol-4-yl]-4-[[(1R)-1-(2-pyridyl)ethyl]amino]pyrazolo[1,5-a]pyridine-3-carbonitrile, Isomer 1 | 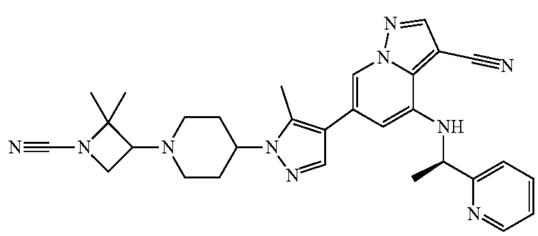 [SMILES: Cc1c(-c2cc(N[C@H](C)c3ccccn3)c3c(C#N)cnn3c2)cnn1C1CCN(C2CN(C#N)C2(C)C)CC1] | 535.4 | 10.1 |
| 95[11,12] | 6-[1-[1-(1-Cyano-2,2-dimethyl-azetidin-3-yl)-4-piperidyl]-5-methyl-pyrazol-4-yl]-4-[[(1R)-1-(2-pyridyl)ethyl]amino]pyrazolo[1,5-a]pyridine-3-carbonitrile, Isomer 2 | 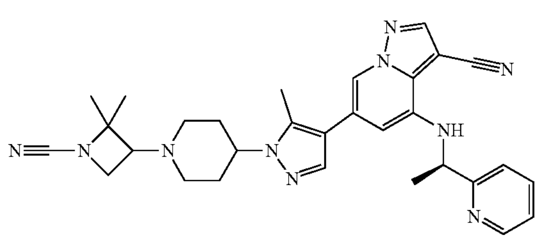 [SMILES: Cc1c(-c2cc(N[C@H](C)c3ccccn3)c3c(C#N)cnn3c2)cnn1C1CCN(C2CN(C#N)C2(C)C)CC1] | 535.4 | 12.8 |
| 96[13,14] | 7-[1-(1-Cyano-4-piperidyl)-5-methyl-triazol-4-yl]-5-[3,3,3-trifluoro-1-(5-fluoro-2-pyridyl)propoxy]imidazo[1,2-a]pyridine-3-carbonitrile, Isomer 2 | 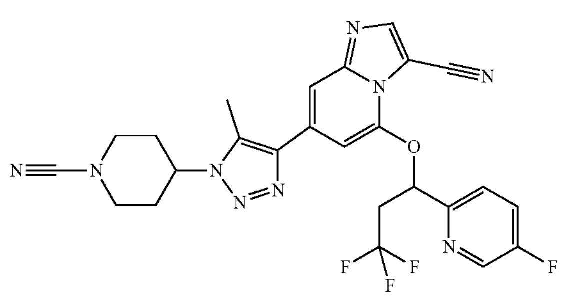 [SMILES: Cc1c(-c2cc(OC(CC(F)(F)F)c3ccc(F)cn3)n3c(C#N)cnc3c2)nnn1C1CCN(C#N)CC1] | 540.3 | 8.3 |
| 97[15,16] | 7-[1-(1-Cyano-4-piperidyl)-5-methyl-triazol-4-yl]-5-[1-(3-ethyltriazol-4-yl)ethoxy]imidazo[1,2-a]pyridine-3-carbonitrile, Isomer 1 | 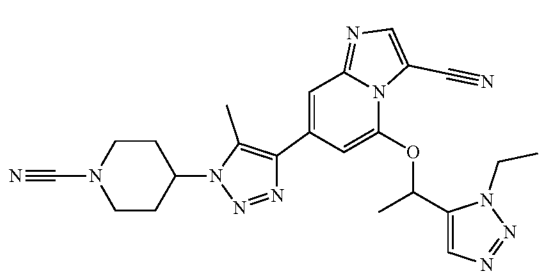 [SMILES: CCn1nncc1C(C)Oc1cc(-c2nnn(C3CCN(C#N)CC3)c2C)cc2ncc(C#N)n12] | 472.2 | 13.6 |

TABLE 63-continued

| Ex. No. | Chemical name | Structure | ES/MS m/z [M + H]+ | t(R) min |
|---|---|---|---|---|
| 98[17,18] | 6-[1-(1-Cyano-4-piperidyl)-5-methyl-triazol-4-yl]-4-[1-(5-fluoro-2-pyridyl)-3-hydroxy-propoxy]pyrazolo[1,5-a]pyridine-3-carbonitrile, Isomer 2 | 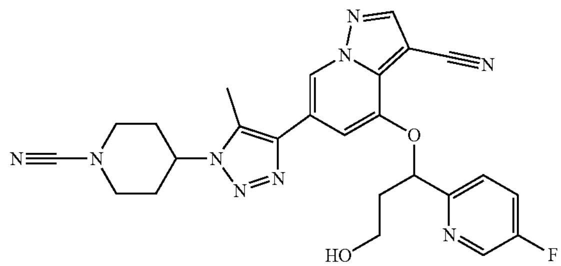 [SMILES: Cc1c(-c2cc(OC(CCO)c3ccc(F)cn3)c3c(C#N)cnn3c2)nnn1C1CCN(C#N)CC1] | 502.2 | 12.2 |
| 99[11,19] | 7-[1-(1-Cyano-4-piperidyl)-5-methyl-triazol-4-yl]-5-[1-[6-(trifluoromethyl)pyrazin-2-yl]ethoxy]imidazo[1,2-a]pyridine-3-carbonitrile, Isomer 1 | 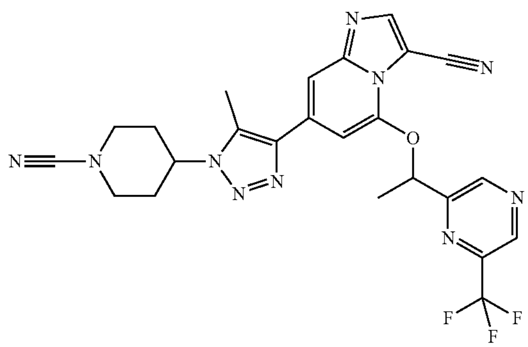 [SMILES: Cc1c(-c2cc(OC(C)c3cncc(C(F)(F)F)n3)n3c(C#N)cnc3c2)nnn1C1CCN(C#N)CC1] | 523.3 | 11.4 |
| 100[20,21] | 7-[1-(1-Cyano-4-piperidyl)-5-methyl-triazol-4-yl]-5-[2-hydroxy-1-[5-(trifluoromethyl)-3-pyridyl]ethoxy]imidazo[1,2-a]pyridine-3-carbonitrile, Isomer 2 | 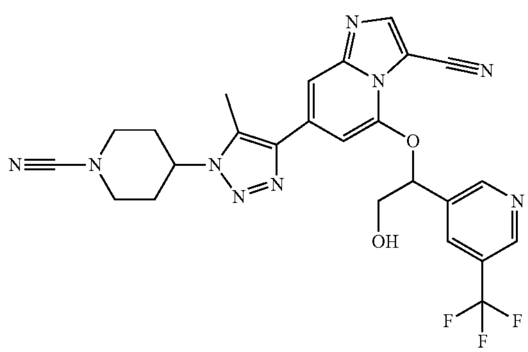 [SMILES: Cc1c(-c2cc(OC(CO)c3cncc(C(F)(F)F)c3)n3c(C#N)cnc3c2)nnn1C1CCN(C#N)CC1] | 538.1 | 7.0 |
| 101[13,22] | 7-[1-(1-Cyano-4-piperidyl)-5-methyl-triazol-4-yl]-5-[1-(3,5-difluoro-2-pyridyl)-2-hydroxy-ethoxy]imidazo[1,2-a]pyridine-3-carbonitrile, Isomer 1 | 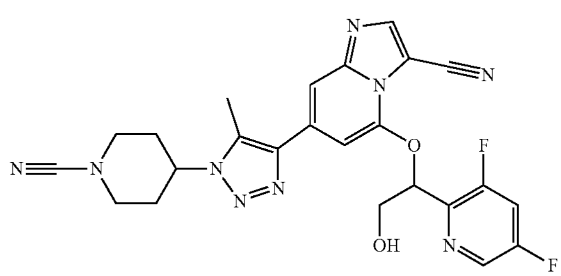 [SMILES: Cc1c(-c2cc(OC(CO)c3ncc(F)cc3F)n3c(C#N)cnc3c2)nnn1C1CCN(C#N)CC1] | 506.1 | 7.3 |
| 102[13,22] | 7-[1-(1-Cyano-4-piperidyl)-5-methyl-triazol-4-yl]-5-[1-(3,5-difluoro-2-pyridyl)-2-hydroxy-ethoxy]imidazo[1,2-a]pyridine-3-carbonitrile, Isomer 2 | 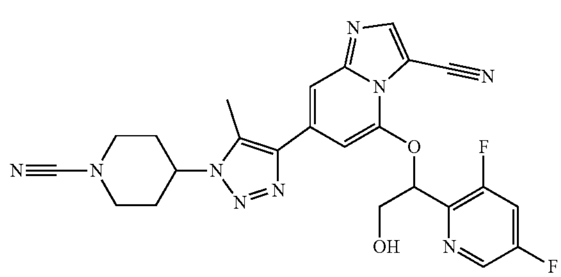 | 506.1 | 8.8 |

TABLE 63-continued

| Ex. No. | Chemical name | Structure | ES/MS m/z [M + H]+ | t(R) min |
|---|---|---|---|---|
| 103[23,24] | 7-[1-(7-Cyano-7-azaspiro[3.5]nonan-2-yl)-5-methyl-triazol-4-yl]-5-[1-(5-fluoro-2-pyridyl)-2-hydroxy-ethoxy]imidazo[1,2-a]pyridine-3-carbonitrile, Isomer 1 | 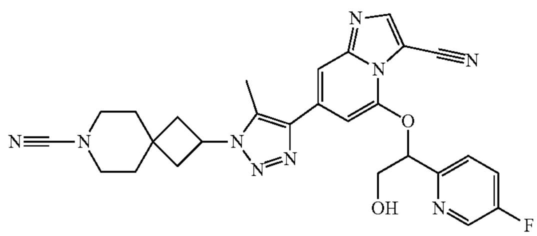 [SMILES: Cc1c(-c2cc(OC(CO)c3ccc(F)cn3)n3c(C#N)cnc3c2)nnn1C1CC2(CCN(C#N)CC2)C1] | 528.2 | 8.0 |
| 104[23,24] | 7-[1-(7-Cyano-7-azaspiro[3.5]nonan-2-yl)-5-methyl-triazol-4-yl]-5-[1-(5-fluoro-2-pyridyl)-2-hydroxy-ethoxy]imidazo[1,2-a]pyridine-3-carbonitrile, Isomer 2 | 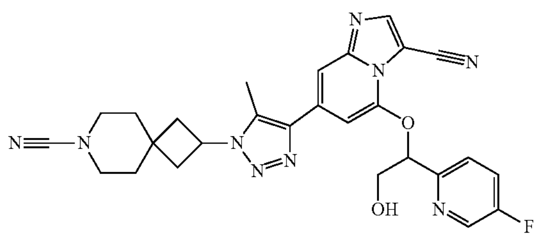 [SMILES: Cc1c(-c2cc(OC(CO)c3ccc(F)cn3)n3c(C#N)cnc3c2)nnn1C1CC2(CCN(C#N)CC2)C1] | 528.3 | 13.0 |
| 105[15,82] | 7-[1-(1-cyano-4-piperidyl)-5-methyl-pyrazol-4-yl]-5-[1-(5-fluoro-2-pyridyl)-2-hydroxy-ethoxy]imidazo[1,2-a]pyridine-3-carbonitrile, Isomer 1 | 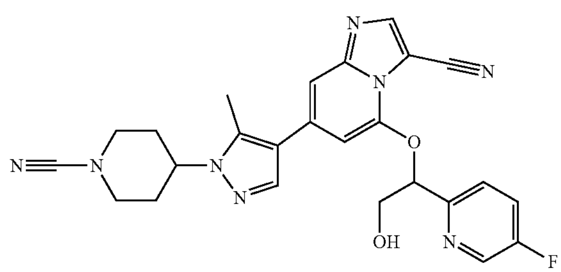 [SMILES: Cc1c(-c2cc(OC(CO)c3ccc(F)cn3)n3c(C#N)cnc3c2)cnn1C1CCN(C#N)CC1] | 487.2 | 12.7 |
| 106[26,24] | 5-[1-(5-Chloro-2-pyridyl)-2-hydroxy-ethoxy]-7-[1-(1-cyano-4-piperidyl)-5-methyl-triazol-4-yl]imidazo[1,2-a]pyridine-3-carbonitrile, Isomer 2 | 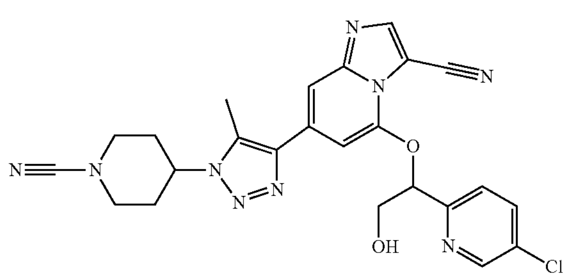 [SMILES: Cc1c(-c2cc(OC(CO)c3ccc(Cl)cn3)n3c(C#N)cnc3c2)nnn1C1CCN(C#N)CC1] | 504.3 | 9.0 |
| 107[17,27] | 6-[1-(1-Cyano-4-piperidyl)-5-methyl-triazol-4-yl]-4-[2-hydroxy-1-[5-(trifluoromethyl)-3-pyridyl]ethoxy]pyrazolo[1,5-a]pyridine-3-carbonitrile, Isomer 2 | 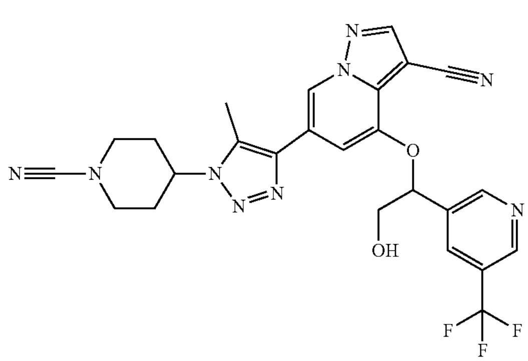 [SMILES: Cc1c(-c2cc(OC(CO)c3cncc(C(F)(F)F)c3)c3c(C#N)cnn3c2)nnn1C1CCN(C#N)CC1] | 538.3 | 10.1 |

TABLE 63-continued

| Ex. No. | Chemical name | Structure | ES/MS m/z [M + H]+ | t(R) min |
|---|---|---|---|---|
| 108[28,29] | 7-[1-(1-Cyano-4-piperidyl)-5-methyl-triazol-4-yl]-5-[1-(5-fluoro-2-pyridyl)-3-hydroxy-propoxy]imidazo[1,2-a]pyridine-3-carbonitrile, Isomer 1 | 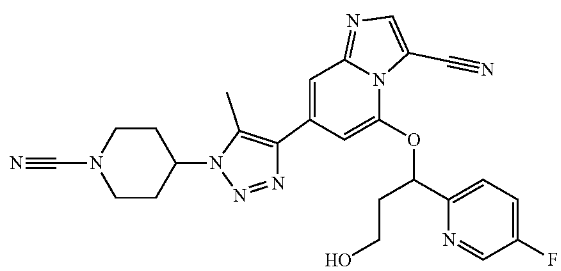 [SMILES: Cc1c(-c2cc(OC(CCO)c3ccc(F)cn3)n3c(C#N)cnc3c2)nnn1C1CCN(C#N)CC1] | 502.2 | 10.2 |
| 109[28,29] | 7-[1-(1-Cyano-4-piperidyl)-5-methyl-triazol-4-yl]-5-[1-(5-fluoro-2-pyridyl)-3-hydroxy-propoxy]imidazo[1,2-a]pyridine-3-carbonitrile, Isomer 2 | 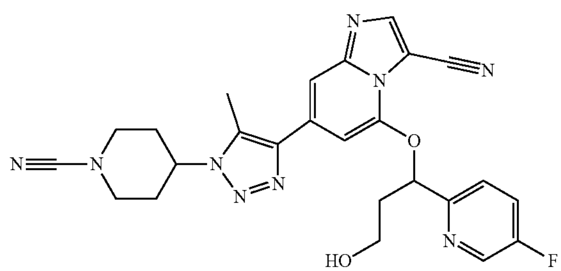 [SMILES: Cc1c(-c2cc(OC(CCO)c3ccc(F)cn3)n3c(C#N)cnc3c2)nnn1C1CCN(C#N)CC1] | 502.2 | 12.8 |
| 110[32,33] | 7-[1-(1-Cyano-4-piperidyl)-5-methyl-triazol-4-yl]-5-[3-methyl-1-(2-pyridyl)butoxy]imidazo[1,2-a]pyridine-3-carbonitrile, Isomer 2 | 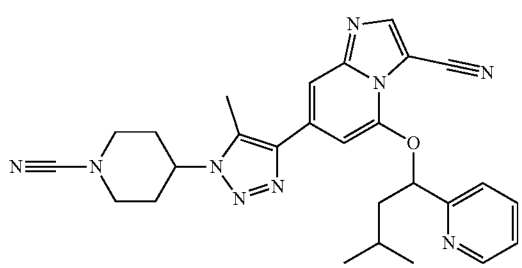 [SMILES: Cc1c(-c2cc(OC(CC(C)C)c3ccccn3)n3c(C#N)cnc3c2)nnn1C1CCN(C#N)CC1] | 496.2 | 30.1 |
| 111[34,35] | 7-[1-(1-Cyano-4-piperidyl)-5-methyl-triazol-4-yl]-5-[2-cyclopropyl-1-(2-pyridyl)ethoxy]imidazo[1,2-a]pyridine-3-carbonitrile, Isomer 1 | 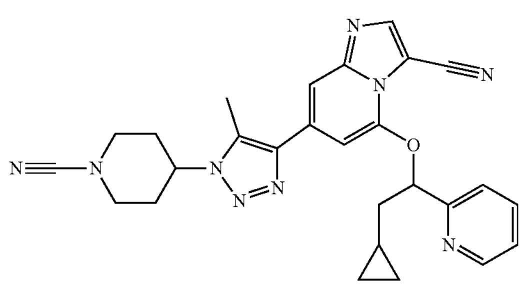 [SMILES: Cc1c(-c2cc(OC(CC3CC3)c3ccccn3)n3c(C#N)cnc3c2)nnn1C1CCN(C#N)CC1] | 494.2 | 9.8 |
| 112[34,35] | 7-[1-(1-Cyano-4-piperidyl)-5-methyl-triazol-4-yl]-5-[2-cyclopropyl-1-(2-pyridyl)ethoxy]imidazo[1,2-a]pyridine-3-carbonitrile, Isomer 2 | 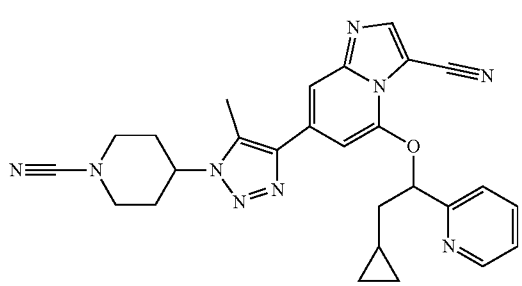 [SMILES: Cc1c(-c2cc(OC(CC3CC3)c3ccccn3)n3c(C#N)cnc3c2)nnn1C1CCN(C#N)CC1] | 494.2 | 11.8 |

TABLE 63-continued

| Ex. No. | Chemical name | Structure | ES/MS m/z [M + H]+ | t(R) min |
|---|---|---|---|---|
| 113[36,37] | 7-[1-(1-Cyano-4-piperidyl)-5-methyl-triazol-4-yl]-5-(3,4-dihydro-2H-pyrano[3,2-b]pyridin-4-yloxy)imidazo[1,2-a]pyridine-3-carbonitrile, Isomer 1 | 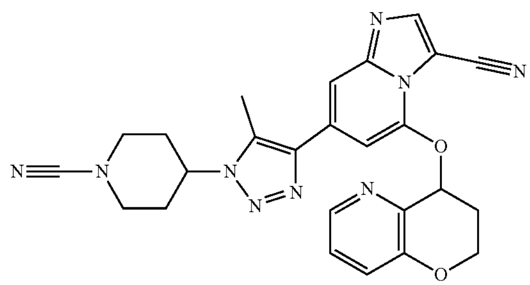 [SMILES: Cc1c(-c2cc(OC3CCOc4cccnc43)n3c(C#N)cnc3c2)nnn1C1CCN(C#N)CC1] | 481.2 | 1.5 |
| 114[38,39] | 7-[1-(1-Cyano-4-piperidyl)-5-methyl-triazol-4-yl]-5-[(6,6-dimethyl-5,7-dihydrocyclopenta[b]pyridin-7-yl)oxy]imidazo[1,2-a]pyridine-3-carbonitrile, Isomer 1 | 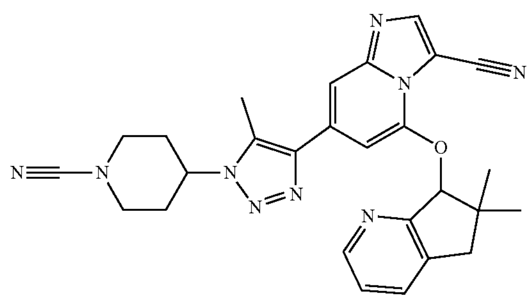 [SMILES: Cc1c(-c2cc(OC3c4ncccc4CC3(C)C)n3c(C#N)cnc3c2)nnn1C1CCN(C#N)CC1] | 494.3 | 10.3 |
| 115[38,39] | 7-[1-(1-Cyano-4-piperidyl)-5-methyl-triazol-4-yl]-5-[(6,6-dimethyl-5,7-dihydrocyclopenta[b]pyridin-7-yl)oxy]imidazo[1,2-a]pyridine-3-carbonitrile, Isomer 2 | 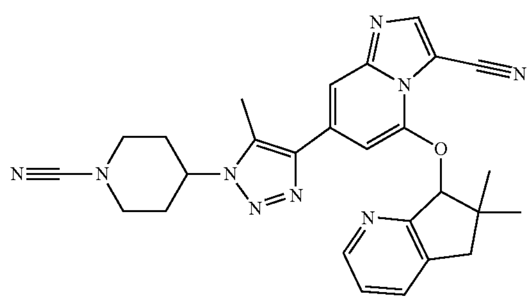 [SMILES: Cc1c(-c2cc(OC3c4ncccc4CC3(C)C)n3c(C#N)cnc3c2)nnn1C1CCN(C#N)CC1] | 494.3 | 12.1 |
| 116[40,41] | 7-[1-(1-Cyano-4-piperidyl)-5-methyl-triazol-4-yl]-5-[1-(3,5-difluoro-2-pyridyl)ethoxy]imidazo[1,2-a]pyridine-3-carbonitrile, Isomer 1 | 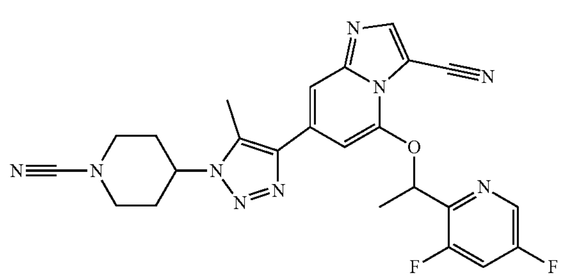 [SMILES: Cc1c(-c2cc(OC(C)c3ncc(F)cc3F)n3c(C#N)cnc3c2)nnn1C1CCN(C#N)CC1] | 489.8 | 18.6 |
| 117[40,41] | 7-[1-(1-Cyano-4-piperidyl)-5-methyl-triazol-4-yl]-5-[1-(3,5-difluoro-2-pyridyl)ethoxy]imidazo[1,2-a]pyridine-3-carbonitrile, Isomer 2 | 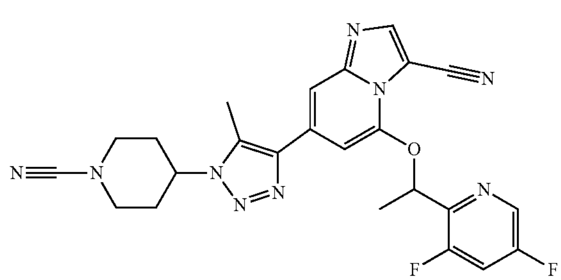 [SMILES: Cc1c(-c2cc(OC(C)c3ncc(F)cc3F)n3c(C#N)cnc3c2)nnn1C1CCN(C#N)CC1] | 489.8 | 21.9 |

| Ex. No. | Chemical name | Structure | ES/MS m/z [M + H]+ | t(R) min |
|---|---|---|---|---|
| 118[40,42] | 6-[1-(1-Cyano-3,3-difluoro-4-piperidyl)-5-methyl-pyrazol-4-yl]-4-methoxy-pyrazolo[1,5-a]pyridine-3-carbonitrile, Isomer 1 | 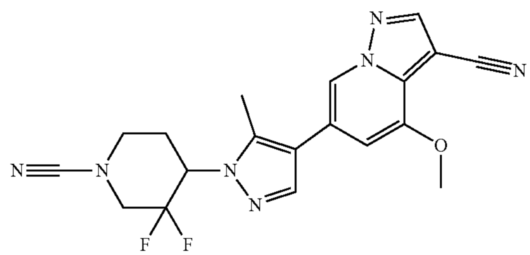 [SMILES: COc1cc(-c2cnn(C3CCN(C#N)CC3(F)F)c2C)cn2ncc(C#N)c12] | 398.1 | 4.2 |
| 119[40,42] | 6-[1-(1-Cyano-3,3-difluoro-4-piperidyl)-5-methyl-pyrazol-4-yl]-4-methoxy-pyrazolo[1,5-a]pyridine-3-carbonitrile, Isomer 2 | 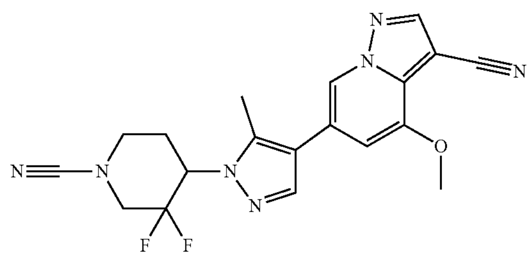 [SMILES: COc1cc(-c2cnn(C3CCN(C#N)CC3(F)F)c2C)cn2ncc(C#N)c12] | 398.1 | 7.3 |
| 120[43,44] | 7-[1-(1-Cyano-4-piperidyl)-5-methyl-triazol-4-yl]-5-[2-pyridyl-[1-(trifluoromethyl)cyclopropyl]methoxy]imidazo[1,2-a]pyridine-3-carbonitrile, Isomer 1 | 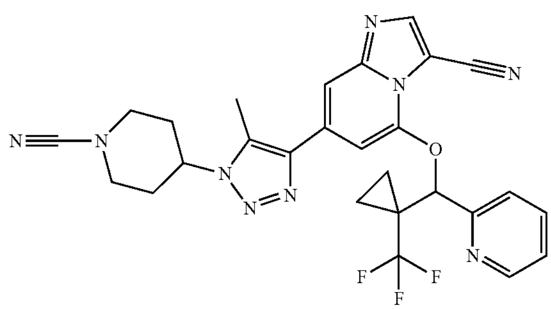 [SMILES: Cc1c(-c2cc(OC(c3ccccn3)C3(C(F)(F)F)CC3)n3c(C#N)cnc3c2)nnn1C1CCN(C#N)CC1] | 548.2 | 5.6 |
| 121[45,46] | 7-[1-(1-Cyano-4-piperidyl)-5-methyl-triazol-4-yl]-5-[1-(5-methyl-2-pyridyl)ethoxy]imidazo[1,2-a]pyridine-3-carbonitrile, Isomer 1 | 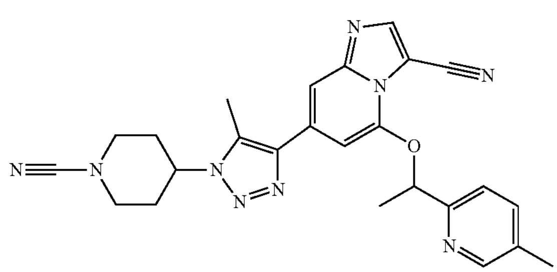 [SMILES: Cc1ccc(C(C)Oc2cc(-c3nnn(C4CCN(C#N)CC4)c3C)cc3ncc(C#N)n23)nc1] | 468.1 | 5.5 |
| 122[47,48] | 7-[1-(1-Cyano-4-piperidyl)-5-methyl-triazol-4-yl]-5-(1-isothiazol-4-ylethoxy)imidazo[1,2-a]pyridine-3-carbonitrile, Isomer 1 | 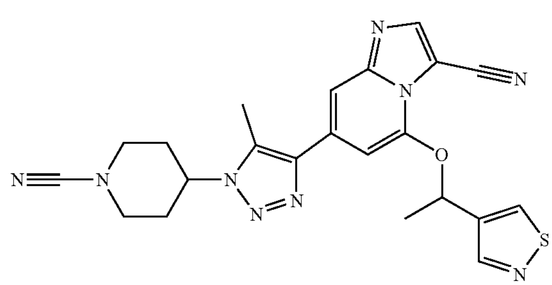 [SMILES: Cc1c(-c2cc(OC(C)c3cnsc3)n3c(C#N)cnc3c2)nnn1C1CCN(C#N)CC1] | 460.2 | 6.6 |

TABLE 63-continued

| Ex. No. | Chemical name | Structure | ES/MS m/z [M + H]+ | t(R) min |
|---|---|---|---|---|
| 123[47,48] | 7-[1-(1-Cyano-4-piperidyl)-5-methyl-triazol-4-yl]-5-(1-isothiazol-4-ylethoxy)imidazo[1,2-a]pyridine-3-carbonitrile, Isomer 2 | 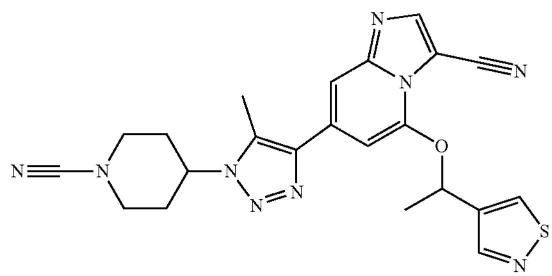 [SMILES: Cc1c(-c2cc(OC(C)c3cnsc3)n3c(C#N)cnc3c2)nnn1C1CCN(C#N)CC1] | 460.2 | 8.5 |
| 124[49,50] | 7-[1-(1-Cyano-4-piperidyl)-5-methyl-triazol-4-yl]-5-(1-isothiazol-3-ylethoxy)imidazo[1,2-a]pyridine-3-carbonitrile, Isomer 1 | 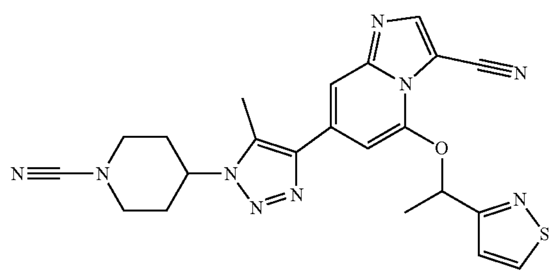 [SMILES: Cc1c(-c2cc(OC(C)c3ccsn3)n3c(C#N)cnc3c2)nnn1C1CCN(C#N)CC1] | 460.1 | 12.5 |
| 125[49,50] | 7-[1-(1-Cyano-4-piperidyl)-5-methyl-triazol-4-yl]-5-(1-isothiazol-3-ylethoxy)imidazo[1,2-a]pyridine-3-carbonitrile, Isomer 2 | 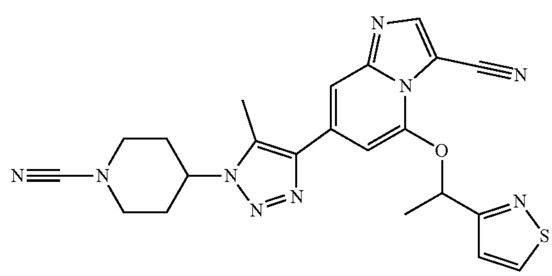 [SMILES: Cc1c(-c2cc(OC(C)c3ccsn3)n3c(C#N)cnc3c2)nnn1C1CCN(C#N)CC1] | 460.0 | 18.3 |
| 126[17,51] | 6-[1-(1-Cyano-4-piperidyl)-5-methyl-triazol-4-yl]-4-[1-[5-(trifluoromethyl)-3-pyridyl]ethoxy]pyrazolo[1,5-a]pyridine-3-carbonitrile, Isomer 1 | 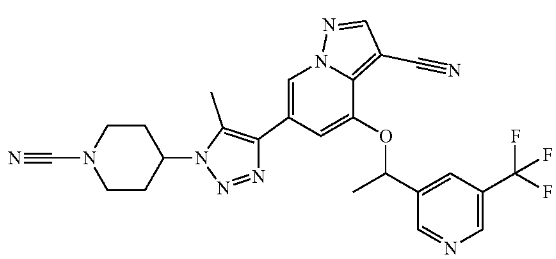 [SMILES: Cc1c(-c2cc(OC(C)c3cncc(C(F)(F)F)c3)c3c(C#N)cnn3c2)nnn1C1CCN(C#N)CC1] | 522.2 | 16.5 |
| 127[17,51] | 6-[1-(1-Cyano-4-piperidyl)-5-methyl-triazol-4-yl]-4-[1-[5-(trifluoromethyl)-3-pyridyl]ethoxy]pyrazolo[1,5-a]pyridine-3-carbonitrile, Isomer 2 | 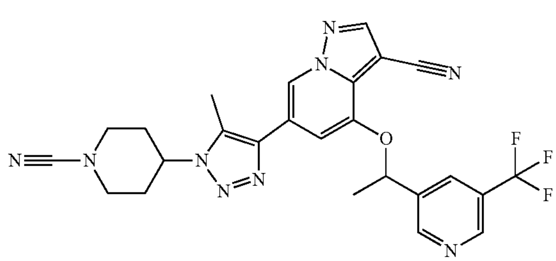 [SMILES: Cc1c(-c2cc(OC(C)c3cncc(C(F)(F)F)c3)c3c(C#N)cnn3c2)nnn1C1CCN(C#N)CC1] | 522.1 | 22.5 |

TABLE 63-continued

| Ex. No. | Chemical name | Structure | ES/MS m/z [M + H]+ | t(R) min |
|---|---|---|---|---|
| 128[52,53] | 7-[1-(1-Cyano-4-piperidyl)-5-methyl-triazol-4-yl]-5-(1-isothiazol-5-ylethoxy)imidazo[1,2-a]pyridine-3-carbonitrile, Isomer 1 | 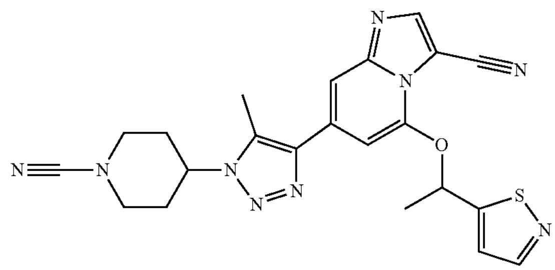 [SMILES: Cc1c(-c2cc(OC(C)c3ccns3)n3c(C#N)cnc3c2)nnn1C1CCN(C#N)CC1] | 460.1 | 7.1 |
| 129[40,56] | 6-[1-(1-Cyano-3,3-difluoro-4-piperidyl)-5-methyl-pyrazol-4-yl]-4-methoxy-pyrazolo[1,5-a]pyridine-3-carbonitrile, Isomer 2 | 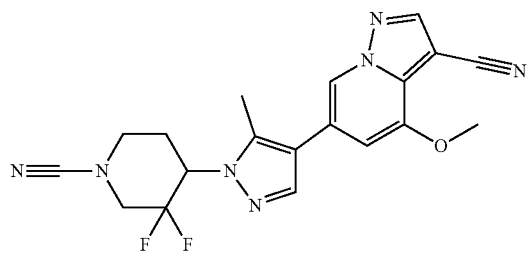 [SMILES: COc1cc(-c2cnn(C3CCN(C#N)CC3(F)F)c2C)cn2ncc(C#N)c12] | 398.1 | 7.3 |
| 130[54,55] | 7-[1-(1-Cyanoazepan-4-yl)-5-methyl-triazol-4-yl]-5-[1-(5-fluoro-2-pyridyl)ethoxy]imidazo[1,2-a]pyridine-3-carbonitrile, Isomer 1 | 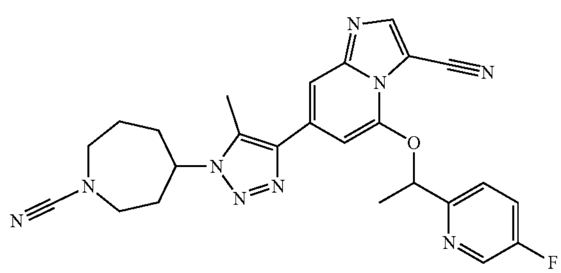 [SMILES: Cc1c(-c2cc(OC(C)c3ccc(F)cn3)n3c(C#N)cnc3c2)nnn1C1CCCN(C#N)CC1] | 486.3 | 10 |
| 131[54,55] | 7-[1-(1-Cyanoazepan-4-yl)-5-methyl-triazol-4-yl]-5-[1-(5-fluoro-2-pyridyl)ethoxy]imidazo[1,2-a]pyridine-3-carbonitrile, Isomer 2 | 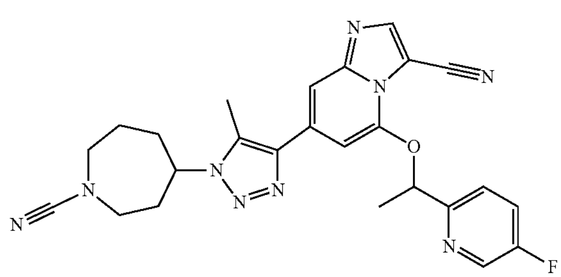 [SMILES: Cc1c(-c2cc(OC(C)c3ccc(F)cn3)n3c(C#N)cnc3c2)nnn1C1CCCN(C#N)CC1] | 486.3 | 26 |
| 132[49,58] | 7-[1-(1-Cyano-4-piperidyl)-5-methyl-triazol-4-yl]-5-[1-(5-methoxy-3-pyridyl)ethoxy]imidazo[1,2-a]pyridine-3-carbonitrile, Isomer 1 | 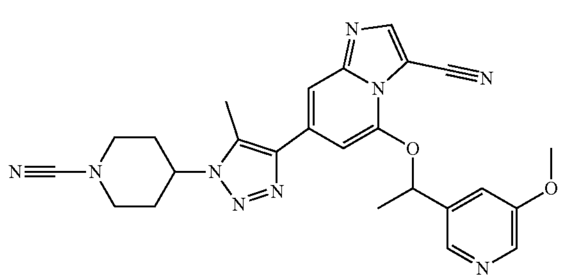 [SMILES: COc1cncc(C(C)Oc2cc(-c3nnn(C4CCN(C#N)CC4)c3C)cc3ncc(C#N)n23)c1] | 484.1 | 4.7 |

TABLE 63-continued

| Ex. No. | Chemical name | Structure | ES/MS m/z [M + H]+ | t(R) min |
|---|---|---|---|---|
| 133[49,58] | 7-[1-(1-Cyano-4-piperidyl)-5-methyl-triazol-4-yl]-5-[1-(5-methoxy-3-pyridyl)ethoxy]imidazo[1,2-a]pyridine-3-carbonitrile, Isomer 2 | 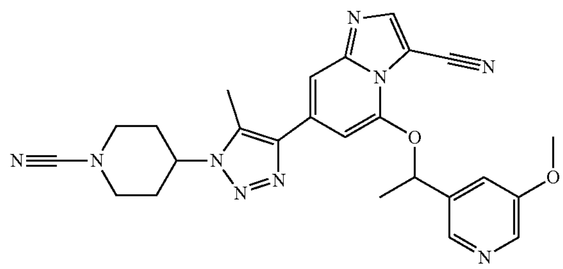 [SMILES: COc1cncc(C(C)Oc2cc(-c3nnn(C4CCN(C#N)CC4)c3C)cc3ncc(C#N)n23)c1] | 484.2 | 7.9 |
| 134[59,60] | 5-[1-(6-Chloro-3-pyridyl)ethoxy]-7-[1-(1-cyano-4-piperidyl)-5-methyl-triazol-4-yl]imidazo[1,2-a]pyridine-3-carbonitrile, Isomer 1 | 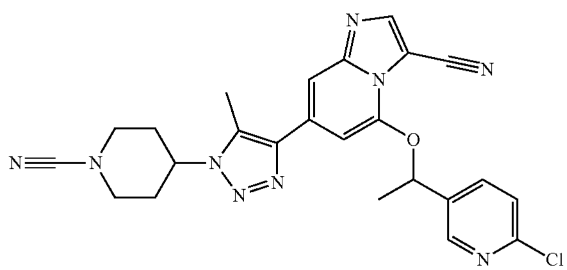 [SMILES: Cc1c(-c2cc(OC(C)c3ccc(Cl)nc3)n3c(C#N)cnc3c2)nnn1C1CCN(C#N)CC1] | ($^{35}$Cl/$^{37}$Cl) 488.4/ 490.4 | 6.8 |
| 135[59,60] | 5-[1-(6-Chloro-3-pyridyl)ethoxy]-7-[1-(1-cyano-4-piperidyl)-5-methyl-triazol-4-yl]imidazo[1,2-a]pyridine-3-carbonitrile, Isomer 2 | 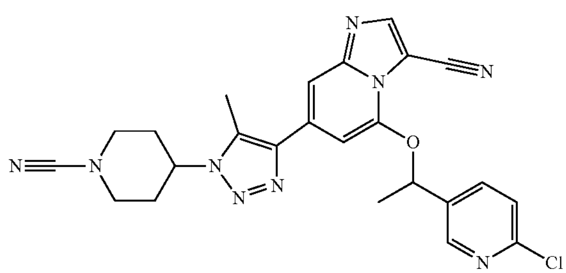 [SMILES: Cc1c(-c2cc(OC(C)c3ccc(Cl)nc3)n3c(C#N)cnc3c2)nnn1C1CCN(C#N)CC1] | ($^{35}$Cl/$^{37}$Cl) 488.4/ 490.4 | 10.1 |
| 136[61,62] | 7-[1-(1-Cyano-4-piperidyl)-5-methyl-triazol-4-yl]-5-[1-[5-(trifluoromethyl)isoxazol-3-yl]ethoxy]imidazo[1,2-a]pyridine-3-carbonitrile, Isomer 1 | 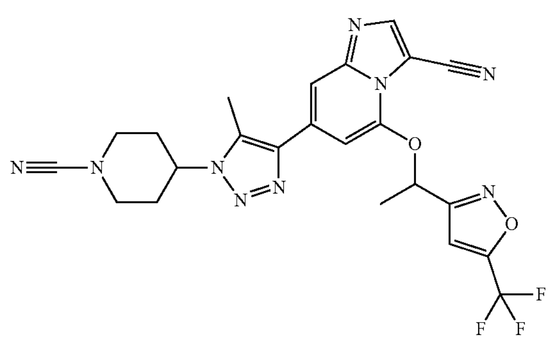 [SMILES: Cc1c(-c2cc(OC(C)c3cc(C(F)(F)F)on3)n3c(C#N)cnc3c2)nnn1C1CCN(C#N)CC1] | 512.1 | 16.4 |
| 137[61,62] | 7-[1-(1-Cyano-4-piperidyl)-5-methyl-triazol-4-yl]-5-[1-[5-(trifluoromethyl)isoxazol-3-yl]ethoxy]imidazo[1,2-a]pyridine-3-carbonitrile, Isomer 2 | 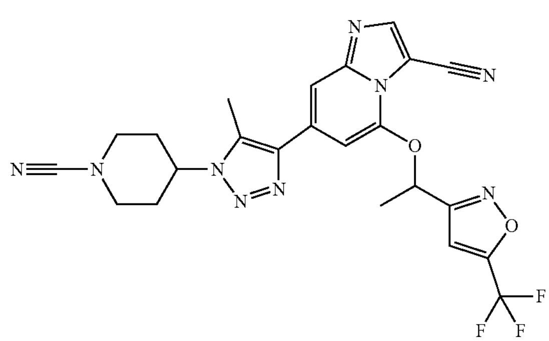 [SMILES: Cc1c(-c2cc(OC(C)c3cc(C(F)(F)F)on3)n3c(C#N)cnc3c2)nnn1C1CCN(C#N)CC1] | 512.1 | 19.4 |

TABLE 63-continued

| Ex. No. | Chemical name | Structure | ES/MS m/z [M + H]+ | t(R) min |
|---|---|---|---|---|
| 138[63,64] | 7-[1-(1-Cyano-4-piperidyl)-5-methyl-triazol-4-yl]-5-[2,2-difluoro-1-(5-fluoro-2-pyridyl)ethoxy]imidazo[1,2-a]pyridine-3-carbonitrile, Isomer 1 | 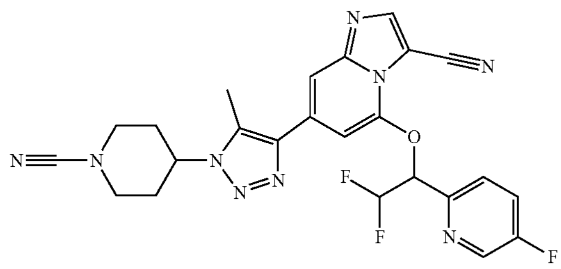 [SMILES: Cc1c(-c2cc(OC(c3ccc(F)cn3)C(F)F)n3c(C#N)cnc3c2)nnn1C1CCN(C#N)CC1] | 508.2 | 18.4 |
| 139[63,64] | 7-[1-(1-Cyano-4-piperidyl)-5-methyl-triazol-4-yl]-5-[2,2-difluoro-1-(5-fluoro-2-pyridyl)ethoxy]imidazo[1,2-a]pyridine-3-carbonitrile, Isomer 2 | 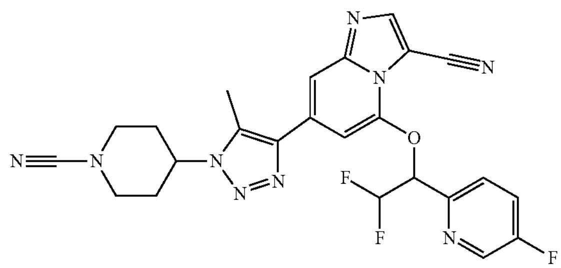 [SMILES: Cc1c(-c2cc(OC(c3ccc(F)cn3)C(F)F)n3c(C#N)cnc3c2)nnn1C1CCN(C#N)CC1] | 508.2 | 21.6 |
| 140[65,66] | 7-[1-(1-Cyano-4-piperidyl)-5-methyl-triazol-4-yl]-5-[(5-fluoro-2-pyridyl)-[1-(trifluoromethyl)cyclopropyl]methoxy]imidazo[1,2-a]pyridine-3-carbonitrile, Isomer 2 | 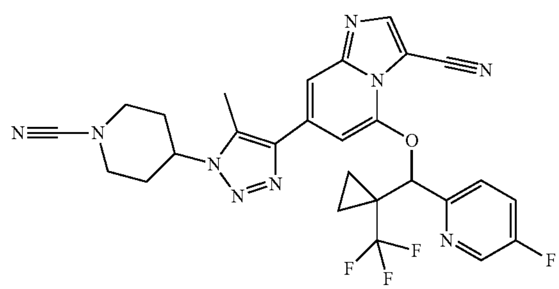 [SMILES: Cc1c(-c2cc(OC(c3ccc(F)cn3)C3(C(F)(F)F)CC3)n3c(C#N)cnc3c2)nnn1C1CCN(C#N)CC1] | 566.15 | 15.7 |
| 141[78,67] | 7-[1-(1-Cyano-4-piperidyl)-5-methyl-triazol-4-yl]-5-[2-methoxy-1-[5-(trifluoromethyl)-3-pyridyl]ethoxy]imidazo[1,2-a]pyridine-3-carbonitrile, Isomer 1 | 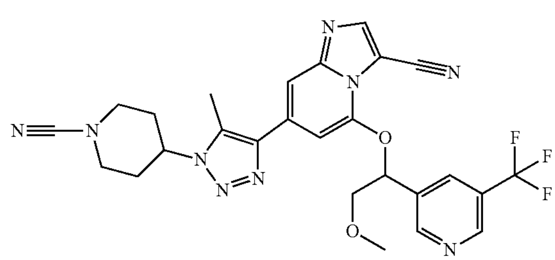 [SMILES: COCC(Oc1cc(-c2nnn(C3CCN(C#N)CC3)c2C)cc2ncc(C#N)n12)c1cncc(C(F)(F)F)c1] | 552.10 | 15.1 |
| 142[79,68] | 7-[1-(1-Cyano-4-piperidyl)-5-methyl-triazol-4-yl]-5-[1-(2-isoxazol-3-ylphenyl)ethoxy]imidazo[1,2-a]pyridine-3-carbonitrile, Isomer 2 | 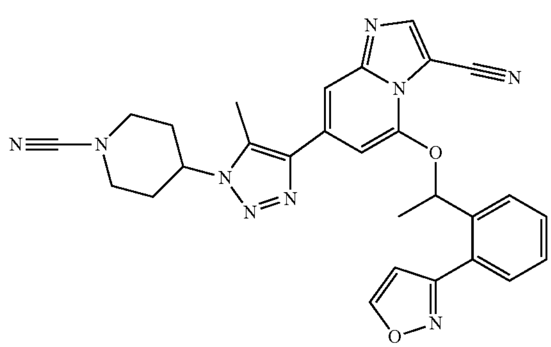 [SMILES: Cc1c(-c2cc(OC(C)c3ccccc3-c3ccon3)n3c(C#N)cnc3c2)nnn1C1CCN(C#N)CC1] | 520.20 | 14.6 |

TABLE 63-continued

| Ex. No. | Chemical name | Structure | ES/MS m/z [M + H]+ | t(R) min |
|---|---|---|---|---|
| 143[80,69] | 7-[1-(1-Cyano-4-piperidyl)-5-methyl-triazol-4-yl]-5-[1-(5-fluoro-3-pyridyl)ethoxy]imidazo[1,2-a]pyridine-3-carbonitrile, Isomer 1 | 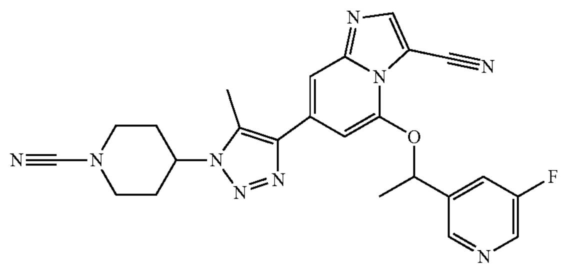 [SMILES: Cc1c(-c2cc(OC(C)c3cncc(F)c3)n3c(C#N)cnc3c2)nnn1C1CCN(C#N)CC1] | 472.2 | 6.0 |
| 144[17,70] | 6-[1-(1-Cyano-4-piperidyl)-5-methyl-triazol-4-yl]-4-[1-(5-fluoro-2-pyridyl)-2-methoxy-ethoxy]pyrazolo[1,5-a]pyridine-3-carbonitrile, Isomer 2 | 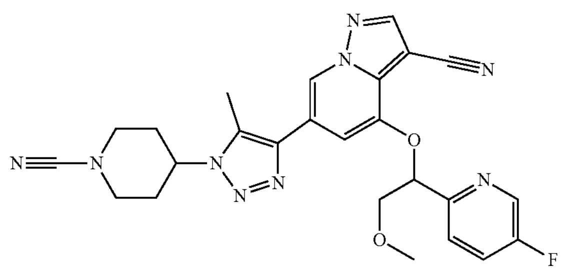 [SMILES: COCC(Oc1cc(-c2nnn(C3CCN(C#N)CC3)c2C)cn2ncc(C#N)c12)c1ccc(F)cn1] | 502.20 | 9.3 |
| 145[81,71] | 5-[1-(5-Chloro-3-pyridyl)ethoxy]-7-[1-(1-cyano-4-piperidyl)-5-methyl-triazol-4-yl]imidazo[1,2-a]pyridine-3-carbonitrile, Isomer 1 | 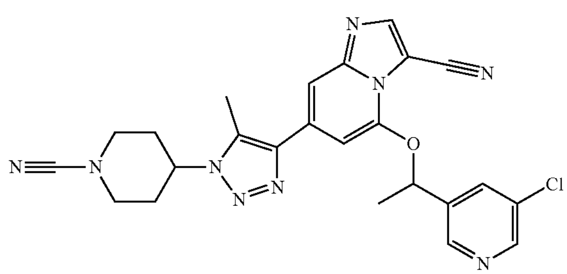 [SMILES: Cc1c(-c2cc(OC(C)c3cncc(Cl)c3)n3c(C#N)cnc3c2)nnn1C1CCN(C#N)CC1] | 488.1 | 6.5 |
| 146[72,73] | 7-[1-(1-Cyano-4-piperidyl)-5-methyl-triazol-4-yl]-5-[1-(5-methylthiazol-2-yl)ethoxy]imidazo[1,2-a]pyridine-3-carbonitrile, Isomer 1 | 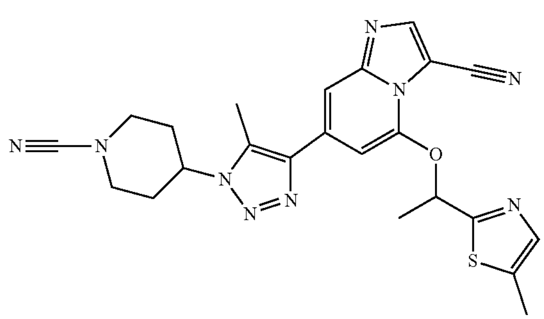 [SMILES: Cc1cnc(C(C)Oc2cc(-c3nnn(C4CCN(C#N)CC4)c3C)cc3ncc(C#N)n23)s1] | 474.15 | 7.7 |
| 147[74,75] | 6-[1-(1-Cyano-4-piperidyl)-5-methyl-triazol-4-yl]-4-[2-methoxy-1-[5-(trifluoromethyl)-3-pyridyl]ethoxy]pyrazolo[1,5-a]pyridine-3-carbonitrile, Isomer 1 | 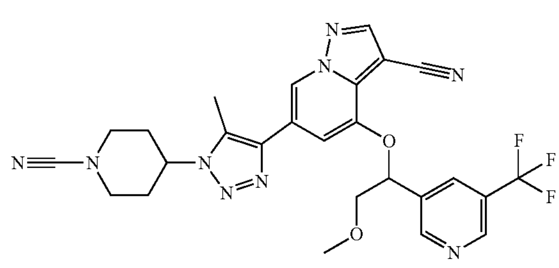 [SMILES: COCC(Oc1cc(-c2nnn(C3CCN(C#N)CC3)c2C)cn2ncc(C#N)c12)c1cncc(C(F)(F)F)c1] | 552.3 | 4.5 |

TABLE 63-continued

| Ex. No. | Chemical name | Structure | ES/MS m/z [M + H]+ | t(R) min |
|---|---|---|---|---|
| 148[76,77] | 7-[1-(1-Cyano-4-piperidyl)-5-methyl-triazol-4-yl]-5-[(6,6-difluoro-5,7-dihydrocyclopenta[b]pyridin-7-yl)oxy]imidazo[1,2-a]pyridine-3-carbonitrile, Isomer 1 | 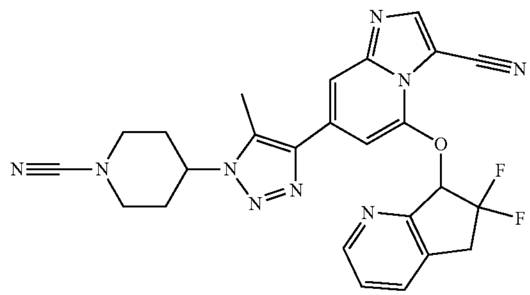 [SMILES: Cc1c(-c2cc(OC3c4ncccc4CC3(F)F)n3c(C#N)cnc3c2)nnn1C1CCN(C#N)CC1] | 502.3 | 19.5 |
| 149[76,77] | 7-[1-(1-Cyano-4-piperidyl)-5-methyl-triazol-4-yl]-5-[(6,6-difluoro-5,7-dihydrocyclopenta[b]pyridin-7-yl)oxy]imidazo[1,2-a]pyridine-3-carbonitrile, Isomer 2 | 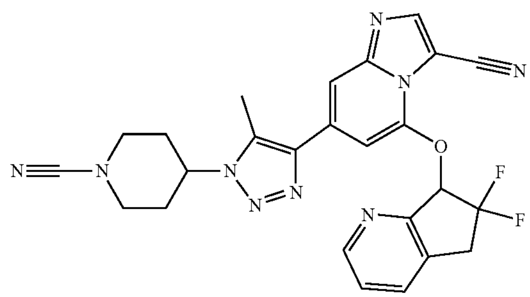 [SMILES: Cc1c(-c2cc(OC3c4ncccc4CC3(F)F)n3c(C#N)cnc3c2)nnn1C1CCN(C#N)CC1] | 502.3 | 26.5 |
| 150[15,84] | 4-[4-[3-Fluoro-4-[1-(5-fluoro-2-pyridyl)-2-hydroxy-ethoxy]pyrazolo[1,5-a]pyridin-6-yl]-5-methyl-triazol-1-yl]piperidine-1-carbonitrile, Isomer 1 | 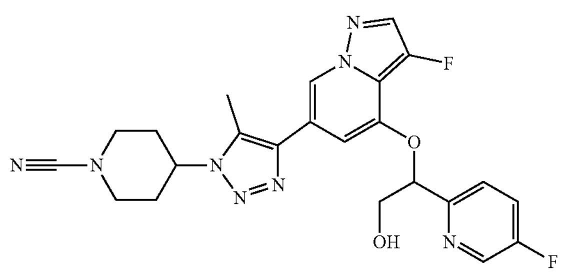 [SMILES: Cc1c(-c2cc(OC(CO)c3ccc(F)cn3)c3c(F)cnn3c2)nnn1C1CCN(C#N)CC1] | 481.2 | 6.35 |
| 151[85,86] | 4-[4-[3-Chloro-4-[2-hydroxy-1-(2-pyridyl)ethoxy]pyrazolo[1,5-a]pyridin-6-yl]-5-methyl-triazol-1-yl]piperidine-1-carbonitrile, Isomer 1 | 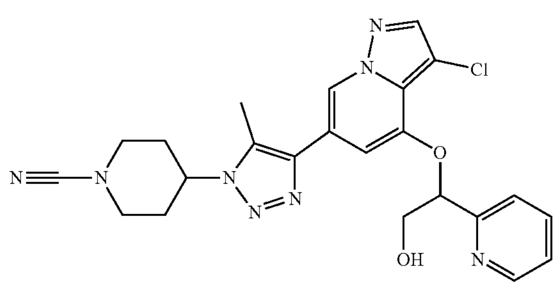 [SMILES: Cc1c(-c2cc(OC(CO)c3ccccn3)c3c(Cl)cnn3c2)nnn1C1CCN(C#N)CC1] | 478.9 | 6.18 |
| 152[45,87,97] | Cis-4-[3-[4-[3-Chloro-4-[1-(5-fluoro-2-pyridyl)-2-hydroxy-ethoxy]pyrazolo[1,5-a]pyridin-6-yl]-5-methyl-triazol-1-yl]cyclobutyl]piperazine-1-carbonitrile isomer 2 | 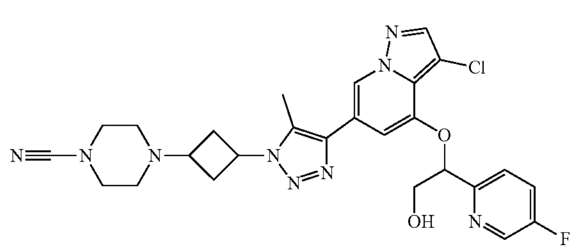 [SMILES: Cc1c(-c2cc(OC(CO)c3ccc(F)cn3)c3c(Cl)cnn3c2)nnn1C1CC(N2CCN(C#N)CC2)C1] | 552.2 | 15.7 |

TABLE 63-continued

| Ex. No. | Chemical name | Structure | ES/MS m/z [M + H]+ | t(R) min |
|---|---|---|---|---|
| 153[9,91] | 4-[4-[3-Fluoro-4-[2-(5-fluoro-2-pyridyl)-2-hydroxy-ethoxy]pyrazolo[1,5-a]pyridin-6-yl]-5-methyl-triazol-1-yl]piperidine-1-carbonitrile, Isomer 1 | 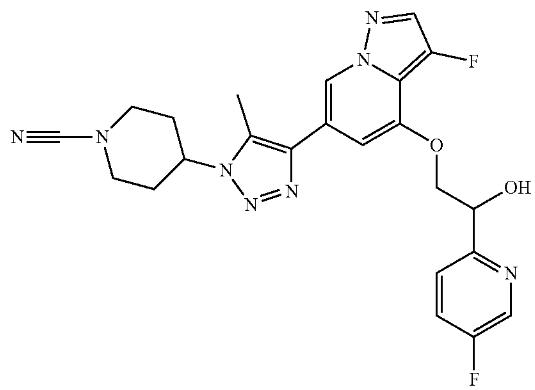 [SMILES: Cc1c(-c2cc(OCC(O)c3ccc(F)cn3)c3c(Cl)cnn3c2)nnn1C1CCN(C#N)CC1] | 481.2 | 0.85 |
| 154[9,93] | 4-[4-[3-Chloro-4-[2-(5-fluoro-2-pyridyl)-2-hydroxy-ethoxy]pyrazolo[1,5-a]pyridin-6-yl]-5-methyl-triazol-1-yl]piperidine-1-carbonitrile, Isomer 1 | 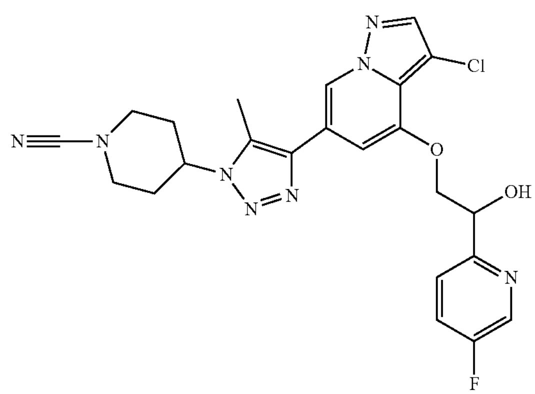 [SMILES: Cc1c(-c2cc(OCC(O)c3ccc(F)cn3)c3c(Cl)cnn3c2)nnn1C1CCN(C#N)CC1] | 497.4 | 1.40 |
| 155[9,93] | 4-[4-[3-Chloro-4-[2-(5-fluoro-2-pyridyl)-2-hydroxy-ethoxy]pyrazolo[1,5-a]pyridin-6-yl]-5-methyl-triazol-1-yl]piperidine-1-carbonitrile, Isomer 2 | 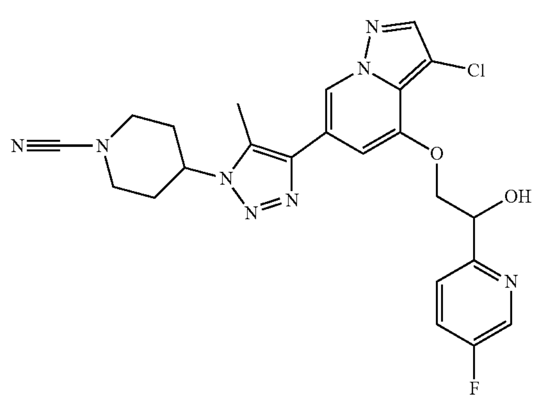 | 497.4 | 2.78 |
| 156[9,90] | 4-[4-[3-Chloro-4-[2-(5-fluoro-2-pyridyl)-2-hydroxy-propoxy]pyrazolo[1,5-a]pyridin-6-yl]-5-methyl-triazol-1-yl]piperidine-1-carbonitrile, Isomer 1 | 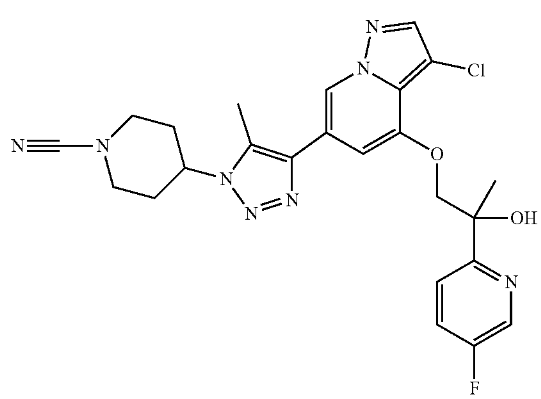 [SMILES: Cc1c(-c2cc(OCC(C)(O)c3ccc(F)cn3)c3c(Cl)cnn3c2)nnn1C1CCN(C#N)CC1] | 511.2 | 2.38 |

TABLE 63-continued

| Ex. No. | Chemical name | Structure | ES/MS m/z [M + H]+ | t(R) min |
|---|---|---|---|---|
| 157[103] | 4-[4-[3-Fluoro-4-[2-(5-fluoro-2-pyridyl)-2-hydroxy-propoxy]pyrazolo[1,5-a]pyridin-6-yl]-5-methyl-triazol-1-yl]piperidine-1-carbonitrile, Isomer 1 | 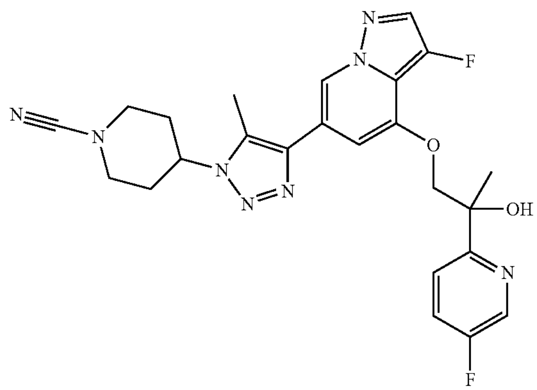 [SMILES: Cc1c(-c2cc(OCC(C)(O)c3ccc(F)cn3)c3c(F)cnn3c2)nnn1C1CCN(C#N)CC1] | 495.2 | 3.79 |
| 158[88,89] | 7-[1-(1-Cyano-4-piperidyl)-5-methyl-triazol-4-yl]-5-[1-(5-fluoro-2-pyridyl)-2-(trifluoromethoxy)ethoxy]imidazo[1,2-a]pyridine-3-carbonitrile, Isomer 1 | 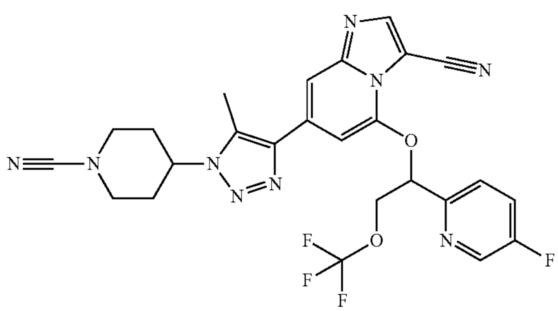 [SMILES: Cc1c(-c2cc(OC(COC(F)(F)F)c3ccc(F)cn3)n3c(C#N)cnc3c2)nnn1C1CCN(C#N)CC1] | 556.3 | 6.51 |
| 159[94,95] | 7-[1-(1-Cyano-4-piperidyl)-5-methyl-triazol-4-yl]-5-[1-[5-fluoro-6-(2-methoxyethoxy)-2-pyridyl]ethoxy]imidazo[1,2-a]pyridine-3-carbonitrile, Isomer 1 | 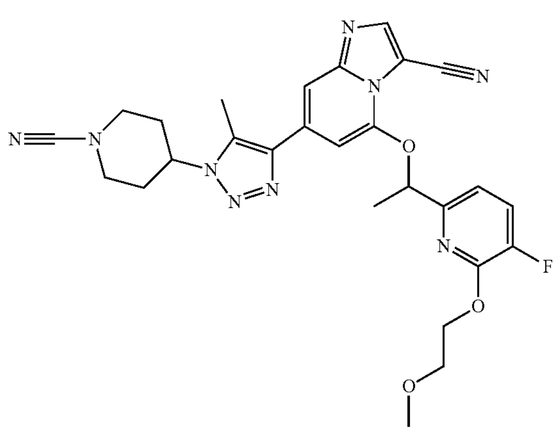 [SMILES: COCCOc1nc(C(C)Oc2cc(-c3nnn(C4CCN(C#N)CC4)c3C)cc3ncc(C#N)n23)ccc1F] | 546.2 | 8.44 |

TABLE 63-continued

| Ex. No. | Chemical name | Structure | ES/MS m/z [M + H]+ | t(R) min |
|---|---|---|---|---|
| 160[9,96] | 7-[1-(1-Cyano-4-piperidyl)-5-methyl-triazol-4-yl]-5-[1-[5-(trifluoromethoxy)-3-pyridyl]ethoxy]imidazo[1,2-a]pyridine-3-carbonitrile, Isomer 1 | 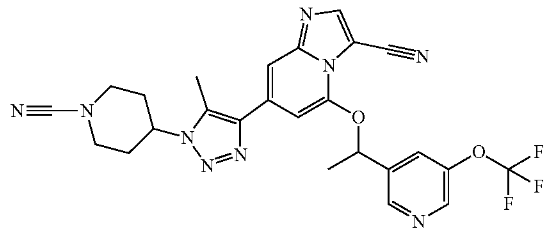 [SMILES: Cc1c(-c2cc(OC(C)c3cncc(OC(F)(F)F)c3)n3c(C#N)cnc3c2)nnn1C1CCN(C#N)CC1] | 538.2 | 9.21 |
| 161[99,100] | (3RS,4RS)-4-[4-[3-chloro-4-[1-(5-fluoro-2-pyridyl)-2-hydroxy-ethoxy]pyrazolo[1,5-a]pyridin-6-yl]-5-methyl-triazol-1-yl]-3-methyl-piperidine-1-carbonitrile, Isomer 2A | 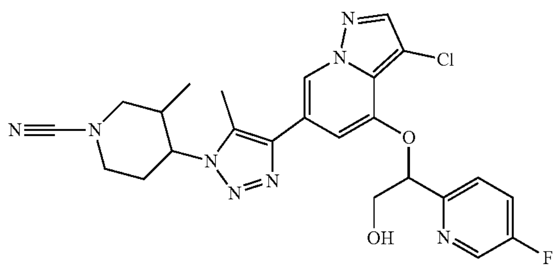 [SMILES: Cc1c(-c2cc(OC(CO)c3ccc(F)cn3)c3c(Cl)cnn3c2)nnn1C1CCN(C#N)CC1C] | 511.1 | 9.5 |
| 162[99,100] | (3RS,4RS)-4-[4-[3-chloro-4-[1-(5-fluoro-2-pyridyl)-2-hydroxy-ethoxy]pyrazolo[1,5-a]pyridin-6-yl]-5-methyl-triazol-1-yl]-3-methyl-piperidine-1-carbonitrile, Isomer 2B | 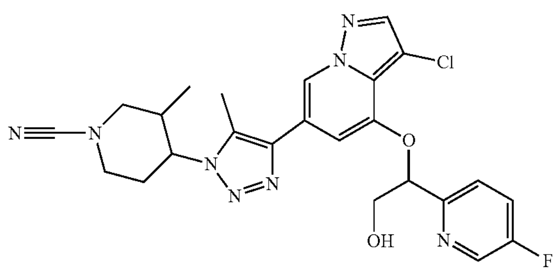 [SMILES: Cc1c(-c2cc(OC(CO)c3ccc(F)cn3)c3c(Cl)cnn3c2)nnn1C1CCN(C#N)CC1C] | 511.1 | 29.5 |
| 163[101,102] | (3RS,4SR)-4-[4-[3-chloro-4-[1-(5-fluoro-2-pyridyl)-2-hydroxy-ethoxy]pyrazolo[1,5-a]pyridin-6-yl]-5-methyl-triazol-1-yl]-3-methyl-piperidine-1-carbonitrile, Isomer 2A | 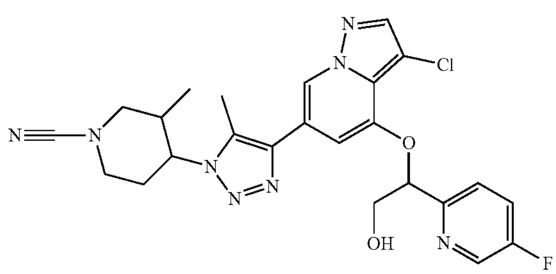 [SMILES: Cc1c(-c2cc(OC(CO)c3ccc(F)cn3)c3c(Cl)cnn3c2)nnn1C1CCN(C#N)CC1C] | 511.1 | 12.3 |
| 164[101,102] | (3RS,4SR)-4-[4-[3-chloro-4-[1-(5-fluoro-2-pyridyl)-2-hydroxy-ethoxy]pyrazolo[1,5-a]pyridin-6-yl]-5-methyl-triazol-1-yl]-3-methyl-piperidine-1-carbonitrile, Isomer 2B | 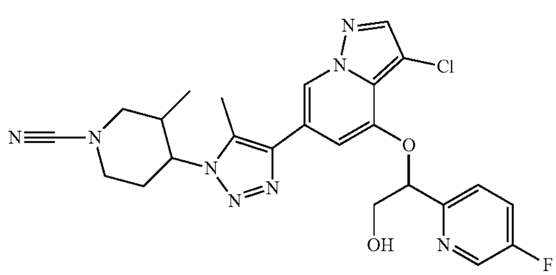 [SMILES: Cc1c(-c2cc(OC(CO)c3ccc(F)cn3)c3c(Cl)cnn3c2)nnn1C1CCN(C#N)CC1C] | 511.1 | 14.8 |

TABLE 63-continued

| Ex. No. | Chemical name | Structure | ES/MS m/z [M + H]+ | $t_{(R)}$ min |
|---|---|---|---|---|
| 165[104,105] | 6-[1-(1-Cyano-4-piperidyl)-5-methyl-pyrazol-4-yl]-4-[1-(3-methylsulfonylphenyl)ethoxy]pyrazolo[1,5-a]pyridine-3-carbonitrile, Isomer 2 | 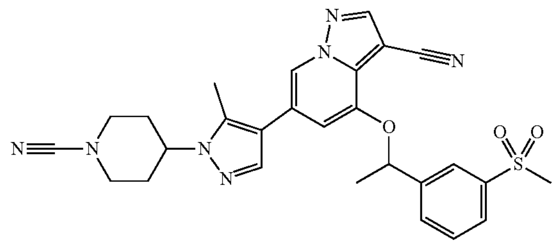 [SMILES: Cc1c(-c2cc(OC(C)c3cccc(S(C)(=O)=O)c3)c3c(C#N)cnn3c2)cnn1C1CCN(C#N)CC1] | 530.2 | 1.57 |

[1] Racemate purification: Column: XBridge Prep C18 OBD, 19*150 mm, 5 μm; eluting with 45% to 80% MeOH in H2O (10 mmol/L NH4HCO3).
[2] Column: CHIRALPAK IF, 2*25 cm, 5 μm, eluting with 30% EtOH:MeOH (1:3) in hexanes (10 mM NH3
[3] Racemate purification: Prep-TLC (PE/EtOAc 1:2)
[4] Chiral ART Cellulose-SA, 2*25 cm, 5 μm; eluting with 40% MeOH in MTBE (10 mM NH3 MeOH); flow rate 20 mL/min; 254/314 nm.
[5] Racemate purification: Reverse phase chromatography: Column, C18; eluting with 45% to 50% ACN in H2O (0.1% NH4HCO3), 254 nm.
[6] Column: CHIRALPAK IF, 2*25 cm, 5 μm, eluting with 30% EtOH:ACN (2:1) in hexanes (10 mM NH3 MeOH); flow rate: 20 mL/min; 246/310.
[7] Racemate purification: Reverse phase chromatography: Column, C18; eluting with 36% to 42% ACN in H2O (0.1% NH4HCO3), 254 nm.
[8] Column: CHIRALPAK IF, 2*25 cm, 5 μm, eluting with 40% EtOH:ACN (2:1) in hexanes (10 mM NH3 MeOH); flow rate: 20 mL/min; 246/310.
[9] Racemate purification: Reverse phase C18 chromatography eluting with 10% to 100% ACN in H2O.
[10] Column: Chiralpak AD-H, 250 x 21 mm; eluting with an 65% CO2 in EtOH (w/ 0.5% DMEA); flow rate 70 mL/min; UV at 225 nm. $t_{(R)}$ is obtained by SFC using the followinganalytical conditions: Chiralpak AD-H, 4.6 x 150 mm; 35% EtOH (0.5% DMEA)/CO2; 5 mL/min; UV at 225 nm.
[11] Racemate purification: Prep-TLC (PE/EtOAc = 1:1).
[12] Column: CHIRALPAK IC, 2*25 cm, 5 μm; eluting with 10% EtOH in MTBE (10 mM NH3 MeOH), flow rate:20 mL/min; 250/330 nm.
[13] Racemate purification: Reverse phase chromatography: Column, C18; eluting with 40% to 50% ACN in H2O (0.1% NH4HCO3), 254 nm.
[14] Column: Lux Cellulose-4, 2.12*25 cm, 5 μm; eluting with 50% EtOH:ACN (2:1) in Hex (10 mM NH3 MeOH); flow rate 25 mL/min; 254/318 nm.
[15] Racemate purification: Reverse phase chromatography: Column, C18; eluting with 30% to 40% ACN in H2O (0.1% NH4HCO3), 254 nm.
[16] Column: CHIRALPAK ID, 2*25 cm, 5 μm; eluting with 30% EtOH in Hex: DCM (3:1) (0.5% 2M NH3 MeOH); flow rate 20 mL/min; 254 nm.
[17] Racemate purification: Reverse phase chromatography: Column, C18; eluting with 50% to 60% ACN in H2O (0.1% NH4HCO3), 254 nm.
[18] Column: CHIRALPAK IA, 2*25 cm, 5 μm; eluting with 50% EtOH in Hex (10 mM NH3 MeOH), Flow rate: 20 mL/min; 254/210 nm
[19] Column: CHIRALPAK IA, 2*25 cm, 5 μm; eluting with 10% EtOH in hexanes:MTBE (1:1) (0.5% 2M NH3—MeOH).
[20] Racemate purification: Reverse phase chromatography: Column, C18; eluting with 70% to 80% ACN in H2O (0.1% NH4HCO3), 254 nm.
[21] Column:Chiral ART Cellulose-SC, 2*25 cm, 5 μm; eluting with 30% MeOH in MTBE (10 mM NH3 MeOH); flow rate 20 mL/min; 254/320 nm.
[22] Column: CHIRALPAK IF, 2*25 cm, 5 μm, eluting with 30% EtOH in MTBE (10 mM NH3 MeOH); flow rate: 18 mL/min; 254/230.
[23] Racemate purification: Reverse phase chromatography: Column, C18; eluting with 50% to 55% ACN in H2O (0.1% NH4HCO3), 254 nm.
[24] Column: CHIRALPAK IE, 2*25 cm, 5 μm; eluting with 50% MeOH in MTBE (10 mM NH3 MeOH); flow rate: 20 mL/min; 254/320.
[25] Column: CHIRALPAK IA, 2*25 cm, 20 μm; eluting with 50% EtOH in Hexanes:DCM (3:1) (0.5% 2M NH3 MeOH).
[26] Racemate purification: Reverse phase chromatography: Column, C18; eluting with 30% to 35% ACN in H2O (0.1% NH4OH), 254 nm.
[27] Column: Chiral ART Cellulose-SC, 2*25 cm, 5 μm; eluting with 30% MeOH in hexanes:MTBE 1:1 (2M NH3 MeOH); flow rate 20 mL/min; 256/212 nm.
[28] Racemate purification: Prep-TLC (EtOAc).
[29] Column: CHIRALPAK IG, 2*25 cm, 20 μm; eluting with 50% EtOH in hexanes:DCM (5:1) (0.5% 2M NH3 MeOH).
[30] Racemate purification: Reverse phase chromatography: Column, C18; eluting with 40% to 60% ACN in H2O (0.1% NH4HCO3), 254 nm.
[31] Column: CHIRALPAK ID, 2*25 cm, 5 μm; eluting with 50% iPrOH in hexanes (10 mM NH3 MeOH); flow rate 25 mL/min; 254/270 nm.
[32] Kinetex EVO C18 Column, 21.2*150, 5 μm; eluting with 30% to 52% ACN in H2O (10 mmol/L NH4HCO3); flow rate: 25 mL/min; 254/220 nm.
[33] Column: CHIRALPAK IC, 2*25 cm, 5 μm; eluting with 20% EtOH in MTBE (10 mM NH3 MeOH), flow rate:20 mL/min; 250/325 nm.
[34] Racemate purification: Column: )(Bridge Prep C18 OBD, 19*150 mm, 5 m; eluting with 34% to 45% ACN in H2O (10 mmol/L NH4OH).
[35] Column: CHIRALPAK IF, 2*25 cm, 5 m, eluting with 15% EtOH in MTBE (10 mM NH3-MeOH); flow rate: 20 mL/min; 254/325.
[36] Racemate purification: Reverse phase chromatography: Column, C18; eluting with 50% ACN in H2O (0.1% NH4HCO3), 254 nm.
[37] Column: CHIRALPAK IA-3, 4.6*50 cm, 3 μm, eluting with 50% EtOH in MTBE (0.1% diethylamine); flow rate: 1 mL/min.
[38] Racemate purification: Reverse phase chromatography: Column, C18; eluting with 40% to 60% ACN in H2O (0.1% FA), 254 nm.
[39] Column: CHIRALPAK IE, 2*25 cm, 5 μm; eluting with 50% EtOH in MTBE (10 mM NH3 MeOH); flow rate: 20 mL/min; 254/325.
[40] Racemate purification: Reverse phase C18 chromatography eluting with 0% to 100% ACN in H2O (0.1% NH4HCO3), 254 nm.
[41] Chiral ART Cellulose-SB, 2*25 cm, 5 μm; eluting with 30% EtOH in hexanes:MTBE (1:1) (0.5% NH3 MeOH)); flow rate 20 mL/min; 254/320 nm.
[42] Column: CHIRALPAK IA, 2*25 cm, 5 μm; eluting with 50% EtOH in hexanes:MTBE (1:1) (0.5% 2M NH3 MeOH).
[43] Racemate purification: Column: XBridge Prep C18 OBD, 19*150 mm, 5 μm; eluting with 32% to 48% ACN in H2O (10 mmol/L NH4HCO3).
[44] Column: CHIRALPAK IF, 2*25 cm, 5 μm, eluting with 50% EtOH in hexanes:DCM (5:1) (0.1% diethylamine); flow rate: 18 mL/min; 254/220.
[45] Racemate purification: Reverse phase chromatography: Column, C18; eluting with 60% to 70% ACN in H2O (0.1% NH4HCO3), 254 nm.
[46] Column: CHIRALPAK IA, 2*25 cm, 5 μm; eluting with 50% EtOH in MTBE (10 mM NH3 MeOH); flow rate: 20 mL/min., 254/320 nm.
[47] Racemate purification: Reverse phase chromatography: Column, C18; eluting with 30% to 50% ACN in H2O (0.1% NH4OH), 254 nm.
[48] Column: CHIRALPAK IA, 2.12*15 cm, 5 μm, eluting with 30% EtOH in MTBE (10 mM NH3 MeOH); flow rate: 20 mL/min., 254/300 nm.
[49] Racemate purification: Reverse phase chromatography: Column, C18; eluting with 10% to 50% ACN in H2O (NH4HCO3), 254 nm.
[50] Column: CHIRALPAK IA, 2*25 cm, 20 μm; eluting with 50% EtOH in hexanes:DCM (5:1) (0.5% 2M NH3 MeOH), flow rate: 18 mL/min., 254/220 nm.
[51] Column: CHIRAL ART Amylose-SA, 2*25 cm, 5 μm; eluting with 10% EtOH in hexanes:DCM (5:1)(0.5% 2M NH3—MeOH, flow rate:20 mL/min., 254/210 nm.
[52] Racemate purification: Column: XBridge Prep C18 OBD, 19*150 mm, 5 μm; eluting with 21% to 43% ACN in H2O (10 mmol/L NH4HCO3).
[53] Column: CHIRALPAK IA, 2*25 cm, 20 μm; eluting with 30% EtOH in hexanes:DCM (5:1) (0.5% 2M NH3 MeOH), flow rate: 20 mL/min., 254/220 nm.
[54] Racemate purification: Reverse phase chromatography: Column, C18; eluting with 10% to 50% ACN in H2O (0.1% FA), 254 nm.
[55] Column: Lux Cellulose-4, 2.12*25 cm, 5 μm; eluting with 90% ACN in H2O; flow rate 25 mL/min; 254/220 nm.
[56] Column: CHIRALPAK IA, 2*25 cm, 5 μm; eluting with 50% EtOH in hexanes:MTBE (0.5% 2M NH3 MeOH); flow rate: 18 mL/min; 250/210.
[58] Column: CHIRALPAK IA, 2.12*15 cm, 5 μm, eluting with 30% EtOH in MTBE (10 mM NH3 MeOH); flow rate: 20 mL/min., 254/220 nm.
[59] Racemate purification: Reverse phase chromatography: Column, C18; eluting with 40% to 70% ACN in H2O (0.05% NH4HCO3), 254 nm.
[60] Column: CHIRALPAK IE, 2*25 cm, 5 μm; eluting with 30% EtOH in MTBE (10 mM NH3 MeOH); flow rate: 20 mL/min; 254/220.
[61] Racemate purification: Reverse phase chromatography: Column, C18; eluting with 47% to 53% ACN in H2O (0.1% NH4HCO3), 254 nm.
[62] Column: CHIRALPAK IF, 2*25 cm, 5 μm, eluting with 20% iPrOH in hexanes:DCM (5:1) (0.5% 2M NH3 MeOH); flow rate: 20 mL/min; 254/210.
[63] Racemate purification: Reverse phase chromatography: Column, C18; eluting with 25% to 55% ACN in MTBE, 254 nm.
[64] Column: NB Lux i-Cellulose-5, 2.12*25 cm, 5 μm; eluting with 20% EtOH in MTBE (10 mM NH3 MeOH); flow rate 20 mL/min; 254/320 nm.

TABLE 63-continued

| Ex. No. | Chemical name | Structure | ES/MS m/z [M + H]+ | t(R) min |
|---|---|---|---|---|

[65]Racemate purification: Column: XBridge Prep C18 OBD, 19*150 mm, 5 μm; eluting with 43% to 53% MeOH in H₂O (10 mmol/L NH₄HCO₃).
[66]Column: Lux Cellulose-4, 2.12*25 cm, 5 μm; eluting with 80% ACN in H₂O; flow rate 25 mL/min; 254/220 nm.
[67]Column: CHIRALPAK IF, 2*25 cm, 5 μm, eluting with 20% EtOH in hexanes:DCM (3:1) (0.5% 2M NH₃ MeOH); flow rate: 20 mL/min; 254/210.
[68]Chiral ART Cellulose-SB, 2*25 cm, 5 μm; eluting with 10% EtOH in MTBE (10 mM NH₃ MeOH); flow rate 20 mL/min; 254/320 nm.
[69]Column: CHIRALPAK IA, 2*25 cm, 5 μm; eluting with 50% EtOH in hexanes:DCM (3:1) (0.5% 2M NH₃ MeOH).
[70]Column: CHIRALPAK ID, 2*25 cm, 5 μm; eluting with 30% EtOH in MTBE (10 mM NH₃ MeOH); flow rate 20 mL/min; 250/215 nm.
[71]Column: CHIRALPAK IA, 2*25 cm, 5 μm, eluting with 30% EtOH in MTBE (10 mM NH₃ MeOH); flow rate: 20 mL/min., 254/215 nm.
[72]Racemate purification: Reverse phase chromatography: Column, C18; eluting with 36% to 40% ACN in H₂O (0.1% NH₄HCO₃), 254 nm.
[73]Column CHIRALPAK IA, 2.12*15 cm, 5 μm, eluting with 20% EtOH in MTBE (10 mM NH₃ MeOH); flow rate: 20 mL/min., 254/220 nm.
[74]Racemate purification: Reverse phase chromatography: Column, C18; eluting with 10% to 50% ACN in H₂O, 254 nm.
[75]Column: Chiral ART Cellulose-SC, 2*25 cm, 5 μm; eluting with 40% EtOH in MTBE (10 mM NH₃ MeOH); flow rate 20 mL/min; 250/215 nm.
[76]Racemate purification: Reverse phase chromatography: Column, C18; eluting with 50% to 60% ACN in H₂O, 254 nm.
[77]Column:(R,R)-WRELK-01-Kromasil, 2.11*25 cm, 5 μm; eluting with 50% EtOH in hexanes:DCM (3:1)(0.5% 2M NH₃ MeOH, flow rate 20 mL/min; 254 nm.
[78]Racemate purification: Reverse phase chromatography: Column, C18; eluting with 40% to 50% ACN in H₂O (0.1% NH₄HCO₃), 254 nm.
[79]Racemate purification: Reverse phase chromatography: Column, C18; eluting with 85% to 90% ACN in H₂O (0.1% NH₄HCO₃), 254 nm.
[80]Racemate purification: Reverse phase chromatography: Column, C18; eluting with 30% to 70% ACN in H₂O (0.1% NH₄HCO₃), 254 nm.
[81]Racemate purification: Reverse phase chromatography: Column, C18; eluting with 10% to 50% ACN in H₂O (0.1% NH₄OH), 254 nm.
[83]Column, CHIRAL ART Amylose-SA, 2*25 cm, 5 μm, eluting with hexanes:DCM (5:1) (0.5% 2M NH₃ MeOH) in 20% EtOH, flow rate 20 mL/min, 254 nm.
[84]Column: CHIRALPAK ID, 2*25 cm, 5 μm; eluting with 50% MeOH in MTBE (10 mM NH₃ MeOH); flow rate 20 mL/min; 244/210 nm.
[85]Racemate purification: Reverse phase chromatography: Column, C18; eluting with 40% to 70% ACN in H₂O (0.1% NH₄HCO₃), 254 nm.
[86]Column: CHIRALPAK IE, 2*25 cm, 5 μm, eluting with 20% MeOH in 1:1 Hex:MTBE (1:1)(0.5% 2M NH₃ MeOH); flow rate: 20 mL/min; 246/310.
[87]Column: Chiral ART Cellulose-SA, 2*25 cm, 5 μm; eluting with 40% MeOH in Hex:MTBE (10 mM NH₃ MeOH); flow rate 20 mL/min; 254/314 nm.; 254/210.
[88]Racemate purification: Reverse phase chromatography: Column, C18; eluting with 55% to 60% ACN in H₂O (0.1% NH₄HCO₃), 254 nm.
[89]Column: CHIRALPAK ID, 2*25 cm, 5 μm; eluting with 10% i-PrOH in Hex: DCM (1:1) (diethylamine); flow rate 20 mL/min; 220/254 nm.
[90]Column: CHIRALPAK IA, 21.2*250 cm,; eluting with 50% MeOH in CO₂; flow rate 80 ml/min; 225 nm.
[91]Column: Chiralcel-OD-H, 21*250 mm; eluting with a 65% CO₂ in MeOH; flow rate 80 mL/min; UV at 225 nm.
[92]Column: Chiralpak AD-H, 250 x 21 mm; eluting with an 65% CO₂ in EtOH (0.5% DMEA); flow rate 70 mL/min; UV at 225 nm.
[93]Column: Chiralpak AD-H, 250 x 21 mm; eluting with an 50% CO₂ in EtOH (0.5% DMEA); flow rate 70 mL/min; 254 nm.
[94]Purified by reverse phase chromatography, C18 column, eluting with 40% to 50% ACN in H₂O.
[95]Column: NB Lux i-Cellulose-5, 2.12*25 cm, 5 μm; Mobile eluting with 30% MeOH in MtBE (10 mM NH₃ MeOH); Flow rate: 20 mL/min; 220/320 nm.
[96]Column: CHIRALPAK IF, 2*25 cm, 5 μm, eluting with 30% i-PrOH in hexanes:DCM (3:1) (0.5% 2M NH₃ MeOH); flow rate: 20 mL/min; 254/220.
[97]1H NMR (400 MHz, Chloroform-d) δ 8.47 (d, 1H), 8.25 (d, 1H), 7.86 (s, 1H), 7.61-7.52 (m, 1H), 7.46-7.37 (m, 1H), 6.74 (s, 1H), 5.62-5.56 (m, 1H), 4.56-4.44 (m, 1H), 4.20-04.05 (m, 2H), 3.42-3.25 (m, 4H), 2.98-2.67 (m, 6H), 2.64-2.44 (m, 4H), 2.32 (s, 3H).
[99]Racemate purification: flash reverse phase chromatography: Column: XB-C18, 250*50 mm, 10 μm; eluting with 20% to 50% CAN in aq. 10 mmol NH4HCO3; Flowrate:100mL/min; 254/220 nm.
[100]Column: CHIRAL ART Cellulose-SZ, 3*25 cm, 5 μm; eluting with 50% EtOH in Hex (0.1% 2M NH₃ MeOH); Flow rate: 40 mL/min; 244/280 nm.
[101]Purified by reverse phase chromatography, C18 column, eluting with 50% to 60% ACN in H₂O.
[102]CHIRALPAK IA, 2*25 cm, 5 μm; eluting with 15% MeOH in hexanes:MTBE (1:1) (0.5% 2M NH₃ MeOH); 286/214 nm.
[103]Chiralpak IA, 21.2 x 250 mm column, eluting with 60% 60% CO₂, in 40% MeOH (0.5% DMEA): 80 mL/min.
[104]Purified by reverse phase chromatography, C18 column
[105]Column: Chiralpak AS-H, 150 x 21 mm; eluting with an 75% CO₂ in EtOH; flow rate 80 mL/min; UV at 250 nm.

Example 166

7-[1-(1-Cyano-4-piperidyl)-5-methyl-triazol-4-yl]-5-[(5-fluoro-2-pyridyl)-(1-methoxycyclopropyl)methoxy]imidazo[1,2-a]pyridine-3-carbonitrile, Isomer 1 and

Example 167

7-[1-(1-Cyano-4-piperidyl)-5-methyl-triazol-4-yl]-5-[(5-fluoro-2-pyridyl)-(1-methoxycyclopropyl)methoxy]imidazo[1,2-a]pyridine-3-carbonitrile, Isomer 2

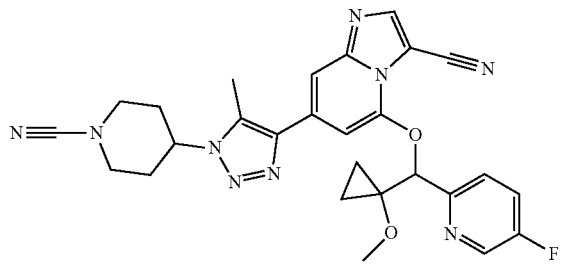 [SMILES: COC1(C(Oc2cc(-c3nnn(C4CCN(C#N)CC4)c3C)cc3ncc(C#N)n23)c2ccc(F)cn2)CC1]

To 3-cyano-5-[(5-fluoropyridin-2-yl)(1-methoxycyclopropyl)methoxy]imidazo[1,2-a]pyridin-7-ylboronic acid (400 mg, 1.05 mmol), 4-(4-bromo-5-methyl-1,2,3-triazol-1-yl)piperidine-1-carbonitrile (424 mg, 1.57 mmol), XPhos (49.90 mg, 0.105 mmol) and K₃PO₄ (667 mg, 3.14 mmol) in dioxane (5 mL) and H₂O (1 mL) is added XPhos Pd G3 (88.60 mg, 0.105 mmol) in portions at RT under N₂. The reaction is stirred for 2 hr at 60° C. Upon cooling to RT, the reaction is diluted with H₂O (20 mL) and extracted with EtOAc (2×30 mL). The combined organic layers are washed with brine (2×20 mL), dried over Na₂SO₄, and concentrated in vacuo. The residue is purified by Prep-TLC (EtOAc) to afford 7-[1-(1-Cyano-4-piperidyl)-5-methyl-triazol-4-yl]-5-[(5-fluoro-2-pyridyl)-(1-methoxycyclopropyl)methoxy]imidazo[1,2-a]pyridine-3-carbonitrile as a yellow solid (130 mg, 24%). ES/MS m/z 528.2 [M+H]+. 7-[1-(1-Cyano-4-piperidyl)-5-methyl-triazol-4-yl]-5-[(5-fluoro-2-pyridyl)-(1-methoxycyclopropyl)methoxy]imidazo[1,2-a]pyridine-3-carbonitrile is subjected to prep-chiral-HPLC: Column: CHIRALPAK IF, 2*25 cm, 5 m; eluting with 35% MeOH in hexanes:MTBE (1:1) (0.5% 2M NH₃-MeOH), 320/254 nm; to afford the title compound, Isomer 1, t(R) is 9.04 min (38.9 mg, 32.4%) with 97.6% ee, ES/MS m/z 528.15 [M+H]+ and the title compound, Isomer 2, t(R) is 10.79 min (18.9 mg, 15.8%) with 97.6% ee, ES/MS m/z 528.40 [M+H]+.

Example 168

4-[3-(4-[3-Cyano-4-methoxypyrazolo[1,5-a]pyridin-6-yl]-5-methylpyrazol-1-yl)azetidin-1-yl]piperidine-1-carbonitrile

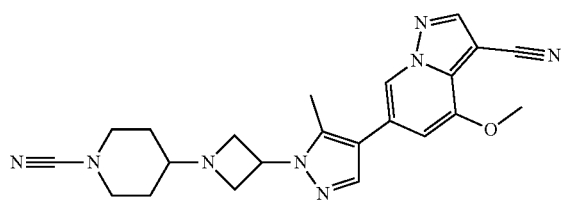 [SMILES: COc1cc(-c2cnn(C3CN(C4CCN(C#N)CC4)C3)c2C)cn2ncc(C#N)c12]

A solution of 4-oxopiperidine-1-carbonitrile (80 mg, 0.65 mmol) and 6-[1-(azetidin-3-yl)-5-methylpyrazol-4-yl]-4-methoxypyrazolo[1,5-a]pyridine-3-carbonitrile (100 mg, 0.32 mmol) in MeOH (3 mL) is treated with NaBH$_3$CN (102 mg, 1.62 mmol) and stirred overnight at RT under N$_2$. The mixture is quenched with H$_2$O (5 mL) and extracted with EtOAc (3×5 mL). The combined organic extracts are concentrated under reduced pressure. The crude product (100 mg) is purified by Prep-HPLC with the following conditions: Column, XBridge Shield RP18 OBD, 19*150 mm, 5 μm; eluting with a gradient of 30% to 50% ACN in H$_2$O (10 mmol/L NH$_4$HCO$_3$) to give the title compound as a white solid (26.3 mg, 19.4%). ES/MS m/z 417.30 [M+H]$^+$.

Example 169

4-(4-[3-Cyano-4-[(1R)-1-(pyridin-2-yl)ethoxy]pyrazolo[1,5-a]pyridin-6-yl]-5-methyl-1,2,3-triazol-1-yl)piperidine-1-carbonitrile

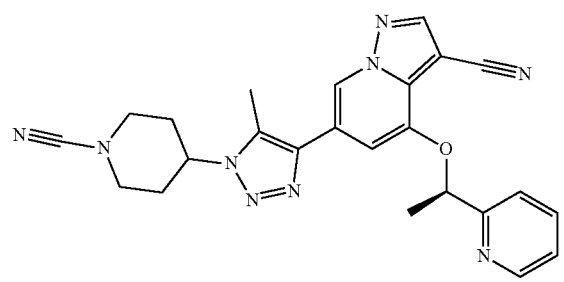 [SMILES: Cc1c(-c2cc(O[C@H](C)c3ccccn3)c3c(C#N)cnn3c2)nnn1C1CCN(C#N)CC1]

A solution of 6-[5-methyl-1-(piperidin-4-yl)-1,2,3-triazol-4-yl]-4-[(1R)-1-(pyridin-2-yl)ethoxy]pyrazolo[1,5-a]pyridine-3-carbonitrile.TFA (200 mg, 0.47 mmol), DIEA (603 mg, 4.67 mmol) in DCM (8 mL) is treated with BrCN (59 mg, 0.56 mmol) and stirred for 2 hrs at RT under N$_2$. The mixture is concentrated under reduced pressure. The residue is purified by reverse Combi-flash chromatography with the following conditions: Column, C18 silica; eluting with a gradient of 30% to 40% ACN in H$_2$O (0.1% NH$_4$HCO$_3$) to give the title compound as a white solid (90.5 mg, 42.8%). ES/MS m/z 454.15 [M+H]$^+$.

Example 170

4-(4-[3-Cyano-5-[(1R)-1-(5-fluoropyridin-2-yl)ethoxy]imidazo[1,2-a]pyridin-7-yl]-5-methyl-1,2,3-triazol-1-yl)piperidine-1-carbonitrile

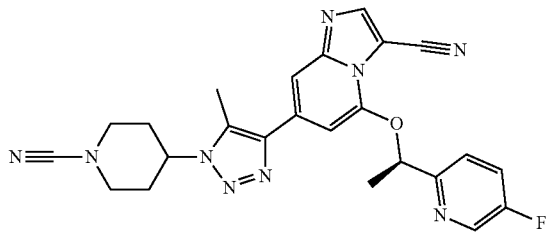 [SMILES: Cc1c(-c2cc(O[C@H](C)c3ccc(F)cn3)n3c(C#N)cnc3c2)nnn1C1CCN(C#N)CC1]

A stirred solution of 5-[(1R)-1-(5-fluoropyridin-2-yl)ethoxy]-7-[5-methyl-1-(piperidin-4-yl)-1,2,3-triazol-4-yl]imidazo[1,2-a]pyridine-3-carbonitrile.HCl (85.0 mg, 0.19 mmol) and DIEA (246.0 mg, 1.90 mmol) in DCM (5.0 mL) is treated with BrCN (24.2 mg, 0.23 mmol) and stirred for 30 min at 0° C. under N$_2$. The mixture is concentrated under reduced pressure. The residue is purified by reverse Combi-flash chromatography with the following conditions: Column, C18; eluting with a gradient of 3000 to 500% ACN in H$_2$O (0.10% NH$_4$HCO$_3$) to give the title compound as a white solid (32.9 mg, 36.20). ES/MS m/z 472.10 [M+H]$^+$.

The following compounds are prepared essentially as described for 4-(4-[3-cyano-5-[(1R)-1-(5-fluoropyridin-2-yl)ethoxy]imidazo[1,2-a]pyridin-7-yl]-5-methyl-1,2,3-triazol-1-yl)piperidine-1-carbonitrile using the appropriate reagents, adjusting reaction time to allow for completion of the reaction, and altering the purification system as appropriate. Temperature is varied from 0° C. to RT.

TABLE 64

| Ex. No. | Chemical name | Structure | ES/MS m/z [M + H]$^+$ | Elution Gradient |
| --- | --- | --- | --- | --- |
| 171 | 2-(4-[3-Cyano-4-methoxypyrazolo[1,5-a]pyridin-6-yl]-5-methylpyrazol-1-yl)-7-azaspiro[3.5]nonane-7-carbonitrile | 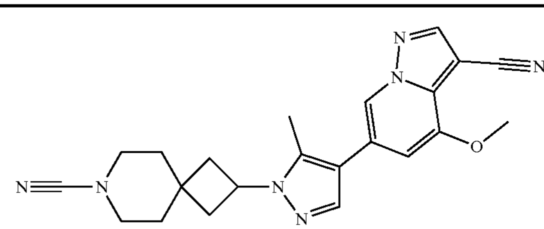 | 402.2 | 40-50% |

TABLE 64-continued

| Ex. No. | Chemical name | Structure | ES/MS m/z [M + H]+ | Elution Gradient |
|---|---|---|---|---|
| 172 | 3-[4-(4-[3-Cyano-4-methoxypyrazolo[1,5-a]pyridin-6-yl]-5-methylpyrazol-1-yl)piperidin-1-yl]-2,2-dimethylazetidine-1-carbonitrile, Isomer 1 | 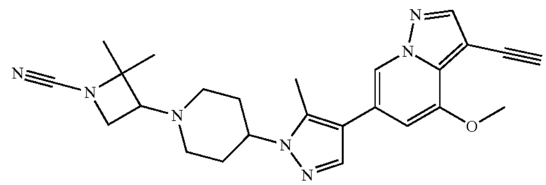 [SMILES: C#Cc1cnn2cc(-c3cnn(C4CCN(C5CN(C#N)C5(C)C)CC4)c3C)cc(OC)c12] | 445.30 | 18-22% |
| 173 | 3-[4-(4-[3-Cyano-4-methoxypyrazolo[1,5-a]pyridin-6-yl]-5-methylpyrazol-1-yl)piperidin-1-yl]-2,2-dimethylazetidine-1-carbonitrile, Isomer 2 | 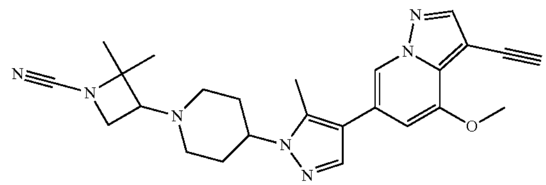 [SMILES: C#Cc1cnn2cc(-c3cnn(C4CCN(C5CN(C#N)C5(C)C)CC4)c3C)cc(OC)c12] | 445.35 | 40-50% |
| 174 | (3R)-3-(4-[3-Cyano-4-methoxypyrazolo[1,5-a]pyridin-6-yl]-5-methylpyrazol-1-yl)piperidine-1-carbonitrile | 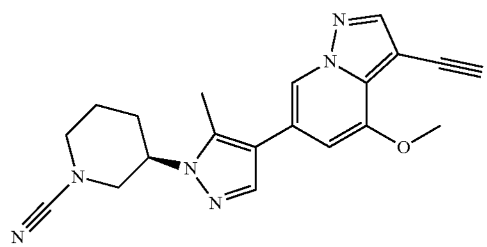 [SMILES: C#Cc1cnn2cc(-c3cnn([C@@H]4CCCN(C#N)C4)c3C)cc(OC)c12] | 362.1 | 33-37% B |
| 175 | 4-(4-[3-Cyano-4-[(1R)-1-(pyridin-2-yl)propoxy]pyrazolo[1,5-a]pyridin-6-yl]-5-methylpyrazol-1-yl)piperidine-1-carbonitrile | 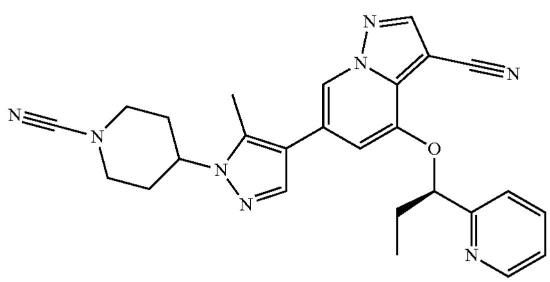 [SMILES: CC[C@@H](Oc1cc(-c2cnn(C3CCN(C#N)CC3)c2C)cn2ncc(C#N)c12)c1ccccn1] | 467.2 | 50-60% |
| 176 | 4-(4-[3-Cyano-4-[(1R)-1-(1-methylpyrazol-3-yl)ethoxy]pyrazolo[1,5-a]pyridin-6-yl]-5-methylpyrazol-1-yl)piperidine-1-carbonitrile | 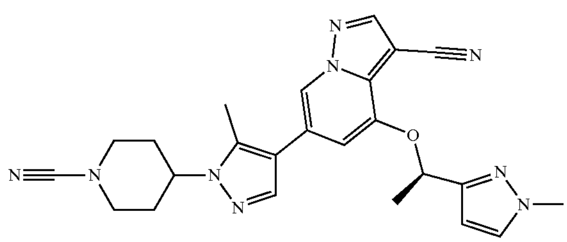 [SMILES: Cc1c(-c2cc(O[C@H](C)c3ccn(C)n3)c3c(C#N)cnn3c2)cnn1C1CCN(C#N)CC1] | 456.20 | 40-50% |
| 177 | (2R,4S)-4-(4-[3-Cyano-4-methoxypyrazolo[1,5-a]pyridin-6-yl]-5-methylpyrazol-1-yl)-2-methylpyrrolidine-1-carbonitrile | 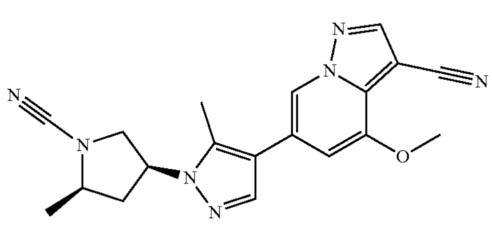 [SMILES: COc1cc(-c2cnn([C@H]3C[C@@H](C)N(C#N)C3)c2C)cn2ncc(C#N)c12] | 361.95 | 50-55% |

TABLE 64-continued

| Ex. No. | Chemical name | Structure | ES/MS m/z [M + H]+ | Elution Gradient |
|---|---|---|---|---|
| 178 | 4-[4-(3-Cyano-4-[[(2R)-1,1,1-trifluoropropan-2-yl]oxy]pyrazolo[1,5-a]pyridin-6-yl)-5-methylpyrazol-1-yl]piperidine-1-carbonitrile | 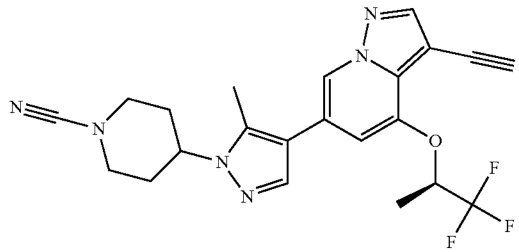 [SMILES: C#Cc1cnn2cc(-c3cnn(C4CCN(C#N)CC4)c3C)cc(O[C@H](C)C(F)(F)F)c12] | 444.15 | 30-70% |
| 179[2] | 4-[3-(4-[3-Cyano-4-methoxypyrazolo[1,5-a]pyridin-6-yl]-5-methylpyrazol-1-yl)azetidin-1-yl]-3,3-difluoropiperidine-1-carbonitrile, Isomer 1 | 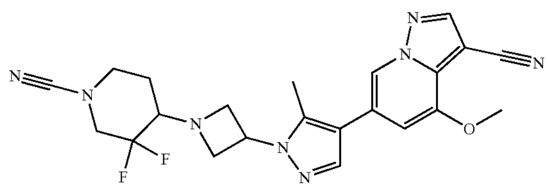 [SMILES: COc1cc(-c2cnn(C3CN(C4CCN(C#N)CC4(F)F)C3)c2C)cn2ncc(C#N)c12] | 453.2 | 36-42% B |
| 180[1] | 4-[3-(4-[3-Cyano-4-methoxypyrazolo[1,5-a]pyridin-6-yl]-5-methylpyrazol-1-yl)azetidin-1-yl]-3,3-difluoropiperidine-1-carbonitrile, Isomer 2 | 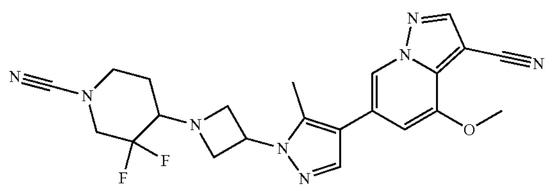 [SMILES: COc1cc(-c2cnn(C3CN(C4CCN(C#N)CC4(F)F)C3)c2C)cn2ncc(C#N)c12] | 453.2 | 33-46% B |
| 181 | 4-(4-[3-Cyano-4-isopropoxypyrazolo[1,5-a]pyridin-6-yl]-5-methylpyrazol-1-yl)piperidine-1-carbonitrile | 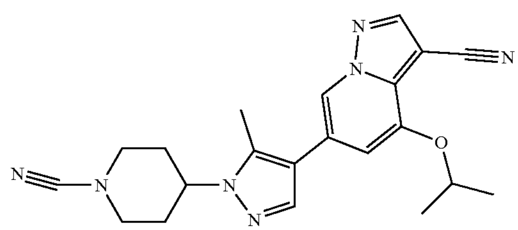 [SMILES: Cc1c(-c2cc(OC(C)C)c3c(C#N)cnn3c2)cnn1C1CCN(C#N)CC1] | 390.20 | |
| 182 | (3S)-3-(4-[3-Cyano-4-methoxypyrazolo[1,5-a]pyridin-6-yl]-5-methylpyrazol-1-yl)piperidine-1-carbonitrile | 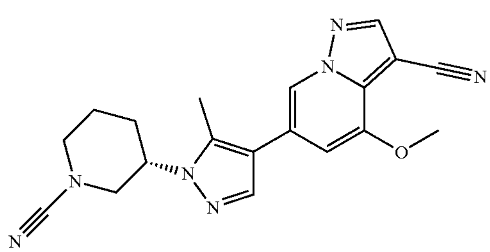 [SMILES: COc1cc(-c2cnn([C@H]3CCCN(C#N)C3)c2C)cn2ncc(C#N)c12] | 362.20 | 40-60% |
| 183[3] | 6-(1-((1R,3r,5S)-8-Cyano-8-azabicyclo[3.2.1]octan-3-yl)-5-methyl-1H-pyrazol-4-yl)-4-methoxypyrazolo[1,5-a]pyridine-3-carbonitrile | 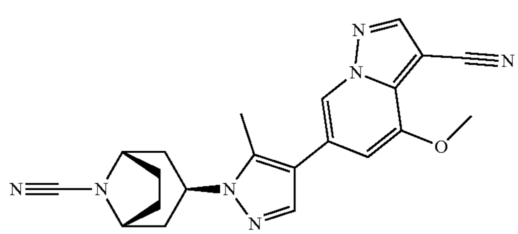 [SMILES: COc1cc(-c2cnn([C@H]3C[C@H]4CC[C@@H](C3)N4C#N)c2C)cn2ncc(C#N)c12] | 388.10 | |

TABLE 64-continued

| Ex. No. | Chemical name | Structure | ES/MS m/z [M + H]+ | Elution Gradient |
|---|---|---|---|---|
| 184 | 6-(1-((1R,3s,5S)-8-Cyano-8-azabicyclo[3.2.1]octan-3-yl)-5-methyl-1H-pyrazol-4-yl)-4-methoxypyrazolo[1,5-a]pyridine-3-carbonitrile | 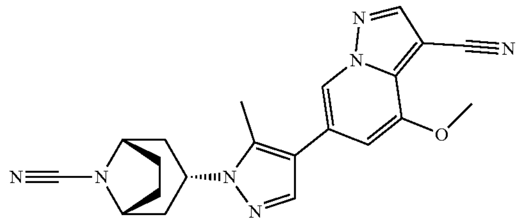 [SMILES: COc1cc(-c2cnn([C@@H]3C[C@H]4CC[C@@H](C3)N4C#N)c2C)cn2ncc(C#N)c12] | 388.15 | 40-60% |
| 185 | 6-[1-[1-[(3S)-1-Cyanopyrrolidin-3-yl]-4-piperidyl]-5-methyl-pyrazol-4-yl]-4-methoxy-pyrazolo[1,5-a]pyridine-3-carbonitrile | 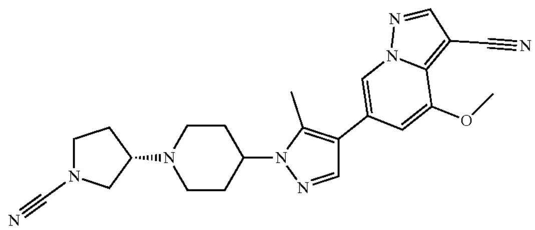 [SMILES: COc1cc(-c2cnn(C3CCN([C@H]4CCN(C#N)C4)CC3)c2C)cn2ncc(C#N)c12] | 431.15 | 25-45% |
| 186 | 4-(4-[3-Cyano-4-methoxypyrazolo[1,5-a]pyridin-6-yl]-3-methylpyrazol-1-yl)piperidine-1-carbonitrile | 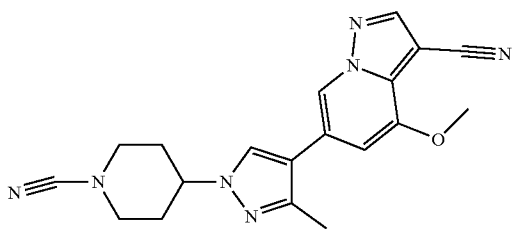 [SMILES: COc1cc(-c2cn(C3CCN(C#N)CC3)nc2C)cn2ncc(C#N)c12] | 362.1 | 40-60% |
| 187 | 4-(4-[3-Cyano-4-[(1R)-1-(3-fluoropyridin-2-yl)ethoxy]pyrazolo[1,5-a]pyridin-6-yl]-5-methylpyrazol-1-yl)piperidine-1-carbonitrile | 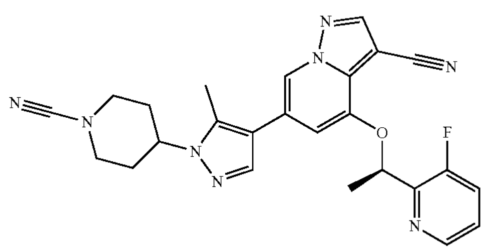 | 471.10 | 40-60% |
| 188 | 4-(4-[3-Cyano-4-[(1R)-1-(pyrazin-2-yl)ethoxy]pyrazolo[1,5-a]pyridin-6-yl]-5-methylpyrazol-1-yl)piperidine-1-carbonitrile | 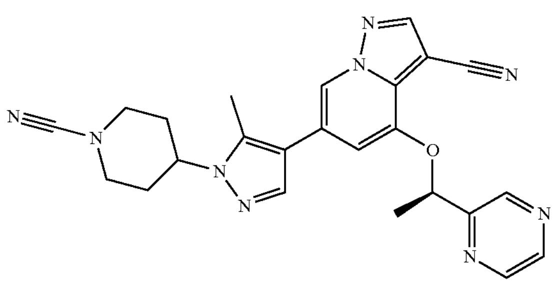 [SMILES: Cc1c(-c2cc(O[C@H](C)c3cnccn3)c3c(C#N)cnn3c2)cnn1C1CCN(C#N)CC1] | 453.95 | 36-40% |
| 189 | 4-(4-[3-Cyano-4-[(1R)-1-(2-methylpyrazol-3-yl)ethoxy]pyrazolo[1,5-a]pyridin-6-yl]-5-methylpyrazol-1-yl)piperidine-1-carbonitrile | 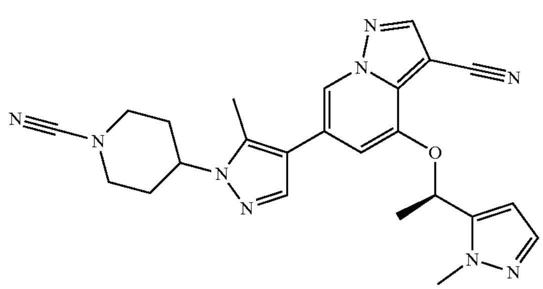 [SMILES: Cc1c(-c2cc(O[C@H](C)c3ccnn3C)c3c(C#N)cnn3c2)cnn1C1CCN(C#N)CC1] | 456.5 | 40-45% |

TABLE 64-continued

| Ex. No. | Chemical name | ES/MS m/z [M + H]+ | Elution Gradient |
|---|---|---|---|
| 190 | 4-(4-[3-Cyano-5-[(1R)-1-(pyridin-2-yl)ethoxy]imidazo[1,2-a]pyridin-7-yl]-5-methylpyrazol-1-yl)piperidine-1-carbonitrile | 453.1 | 10-50% |
| 191[4] | 6-(1-((3R,5S)-1-Cyano-5-methylpyrrolidin-3-yl)-5-methyl-1H-pyrazol-4-yl)-4-methoxypyrazolo[1,5-a]pyridine-3-carbonitrile | 362.15 | 30-46% B |
| 192 | 6-(1-((3S,5S)-1-cyano-5-methylpyrrolidin-3-yl)-5-methyl-1H-pyrazol-4-yl)-4-methoxypyrazolo[1,5-a]pyridine-3-carbonitrile | 361.95 | 38-42% |
| 193[5] | 4-(4-[3-Cyano-4-[(1R)-1-cyclopropylethoxy]pyrazolo[1,5-a]pyridin-6-yl]-5-methylpyrazol-1-yl)piperidine-1-carbonitrile | 416.2 | 42-62% B |
| 194 | 4-[4-(3-Cyano-4-[[(2S)-1,1,1-trifluoropropan-2-yl]oxy]pyrazolo[1,5-a]pyridin-6-yl)-5-methylpyrazol-1-yl]piperidine-1-carbonitrile | 444.15 | 30-70% |
| 195 | 4-(4-[3-cyano-4-[(1R)-1-cyclobutylethoxy]pyrazolo[1,5-a]pyridin-6-yl]-5-methylpyrazol-1-yl)piperidine-1-carbonitrile | 430.0 | 60-65% |

TABLE 64-continued

| Ex. No. | Chemical name | Structure | ES/MS m/z [M + H]+ | Elution Gradient |
|---|---|---|---|---|
| 196[6] | 4-(4-[3-Cyano-4-iso-propoxypyrazolo[1,5-a]pyridin-6-yl]-5-methyl-1,2,3-triazol-1-yl)piperidine-1-carbonitrile | 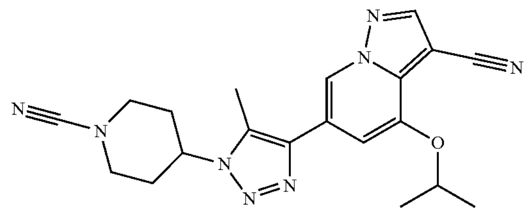 [SMILES: Cc1c(-c2cc(OC(C)C)c3c(C#N)cnn3c2)nnn1C1CCN(C#N)CC1] | 391.2 | None |
| 197 | 4-(4-[3-Cyano-4-[(1R)-1-cyclobutylethoxy]pyrazolo[1,5-a]pyridin-6-yl]-5-methyl-1,2,3-triazol-1-yl)piperidine-1-carbonitrile | 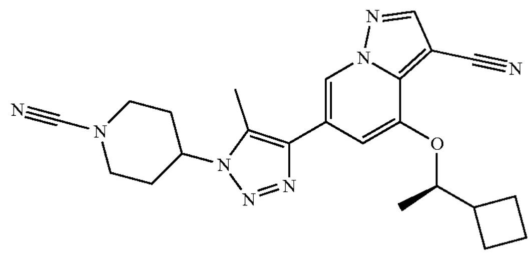 [SMILES: Cc1c(-c2cc(O[C@H](C)C3CCC3)c3c(C#N)cnn3c2)nnn1C1CCN(C#N)CC1] | 431.0 | 42-47% |
| 198[5] | 4-(4-[3-Cyano-4-[(1R)-1-cyclopropylethoxy]pyrazolo[1,5-a]pyridin-6-yl]-5-methyl-1,2,3-triazol-1-yl)piperidine-1-carbonitrile | 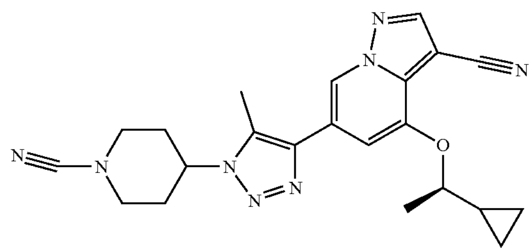 [SMILES: Cc1c(-c2cc(O[C@H](C)C3CC3)c3c(C#N)cnn3c2)nnn1C1CCN(C#N)CC1] | 417.2 | 36-61% B |
| 199 | 4-(4-[3-Cyano-4-[(1S)-2,2,2-trifluoro-1-(pyridin-2-yl)ethoxy]pyrazolo[1,5-a]pyridin-6-yl]-5-methyl-1,2,3-triazol-1-yl)piperidine-1-carbonitrile | 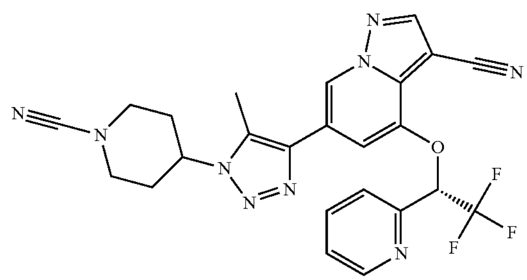 [SMILES: Cc1c(-c2cc(O[C@@H](c3ccccn3)C(F)(F)F)c3c(C#N)cnn3c2)nnn1C1CCN(C#N)CC1] | 508.05 | 40-60% |
| 200 | 4-(4-[3-Chloro-5-[(1R)-1-(pyridin-2-yl)ethoxy]imidazo[1,2-a]pyridin-7-yl]-5-methyl-1,2,3-triazol-1-yl)piperidine-1-carbonitrile | 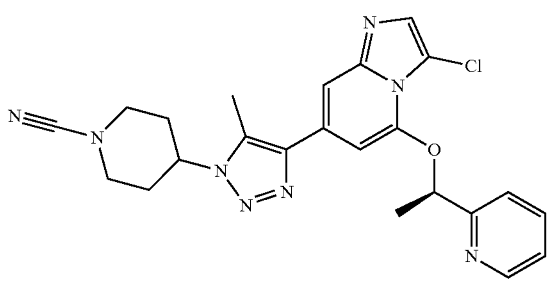 [SMILES: Cc1c(-c2cc(O[C@H](C)c3ccccn3)n3c(Cl)cnc3c2)nnn1C1CCN(C#N)CC1] | 463.05 | 43-48% |
| 201 | 4-(4-[3-Cyano-5-[(1R)-1-(pyridin-2-yl)ethoxy]imidazo[1,2-a]pyridin-7-yl]-5-methyl-1,2,3-triazol-1-yl)piperidine-1-carbonitrile | 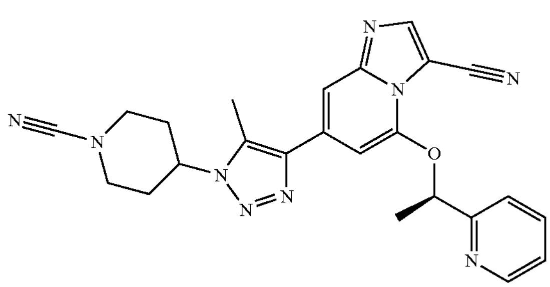 [SMILES: Cc1c(-c2cc(O[C@H](C)c3ccccn3)n3c(C#N)cnc3c2)nnn1C1CCN(C#N)CC1] | 454.05 | 33-37% |

TABLE 64-continued

| Ex. No. | Chemical name | Structure | ES/MS m/z [M + H]+ | Elution Gradient |
|---|---|---|---|---|
| 202 | 4-(4-[3-Cyano-4-[(1R)-1-cyclohexylethoxy]pyrazolo[1,5-a]pyridin-6-yl]-5-methyl-1,2,3-triazol-1-yl)piperidine-1-carbonitrile | 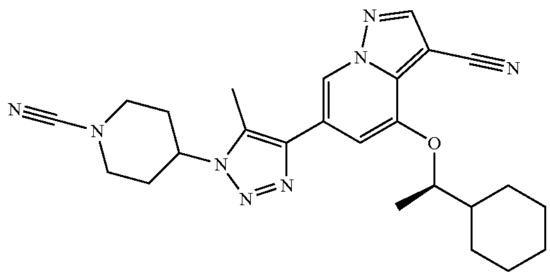 [SMILES: Cc1c(-c2cc(O[C@H](C)C3CCCCC3)c3c(C#N)cnn3c2)nnn1C1CCN(C#N)CC1] | 459.15 | 57-57% |
| 203 | (3R)-3-(4-[3-Cyano-4-methoxypyrazolo[1,5-a]pyridin-6-yl]-5-methyl-1,2,3-triazol-1-yl)pyrrolidine-1-carbonitrile | 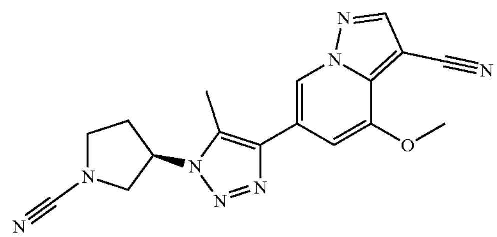 | 348.9 | 30-40% |
| 204 | (3S)-3-(4-[3-Cyano-4-methoxypyrazolo[1,5-a]pyridin-6-yl]-5-methyl-1,2,3-triazol-1-yl)pyrrolidine-1-carbonitrile | 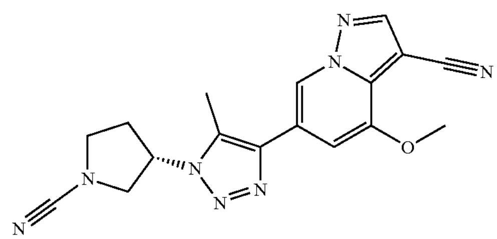 [SMILES: COc1cc(-c2nnn([C@H]3CCN(C#N)C3)c2C)cn2ncc(C#N)c12] | 348.9 | 30-50% |
| 205 | 4-(4-[3-Cyano-4-[(1R)-1-phenylethoxy]pyrazolo[1,5-a]pyridin-6-yl]-5-methyl-1,2,3-triazol-1-yl)piperidine-1-carbonitrile | 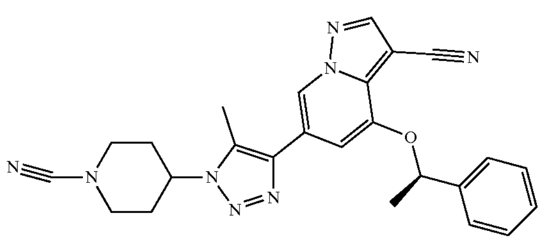 [SMILES: Cc1c(-c2cc(O[C@H](C)c3ccccc3)c3c(C#N)cnn3c2)nnn1C1CCN(C#N)CC1] | 453.20 | 30-50% |
| 206 | 4-(4-[3-Cyano-4-[(1S)-2,2,2-trifluoro-1-phenylethoxy]pyrazolo[1,5-a]pyridin-6-yl]-5-methyl-1,2,3-triazol-1-yl)piperidine-1-carbonitrile | 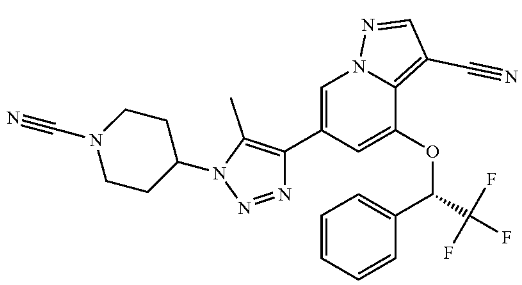 [SMILES: Cc1c(-c2cc(O[C@@H](c3ccccc3)C(F)(F)F)c3c(C#N)cnn3c2)nnn1C1CCN(C#N)CC1] | 507.4 | 5-100% |
| 207 | 4-(4-[3-Cyano-4-[[(7R)-6,7-dihydro-5H-cyclopenta[b]pyridin-7-yl]oxy]pyrazolo[1,5-a]pyridin-6-yl]-5-methyl-1,2,3-triazol-1-yl)piperidine-1-carbonitrile | 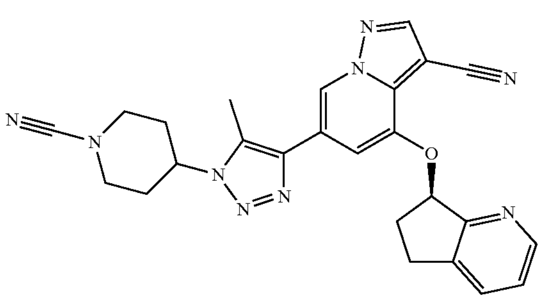 [SMILES: Cc1c(-c2cc(O[C@@H]3CCc4cccnc43)c3c(C#N)cnn3c2)nnn1C1CCN(C#N)CC1] | 466.2 | 30-50% |

TABLE 64-continued

| Ex. No. | Chemical name | Structure | ES/MS m/z [M + H]+ | Elution Gradient |
|---|---|---|---|---|
| 208[1] | 7-[1-(1-Cyano-4-piperidyl)-5-methyl-pyrazol-4-yl]-5-[(1R)-1-(5-fluoro-2-pyridyl)ethoxy]imidazo[1,2-a]pyridine-3-carbonitrile | 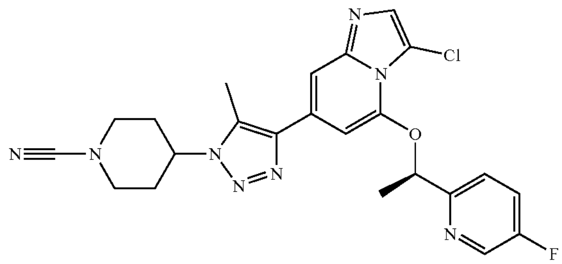 [SMILES: Cc1c(-c2cc(O[C@H](C)c3ccc(F)cn3)n3c(Cl)cnc3c2)nnn1C1CCN(C#N)CC1] | 481.15 | 36-37% |
| 209 | 7-[1-(1-cyano-4-piperidyl)-5-methyl-triazol-4-yl]-5-[(1R)-1-(2-pyridyl)propoxy]imidazo[1,2-a]pyridine-3-carbonitrile | 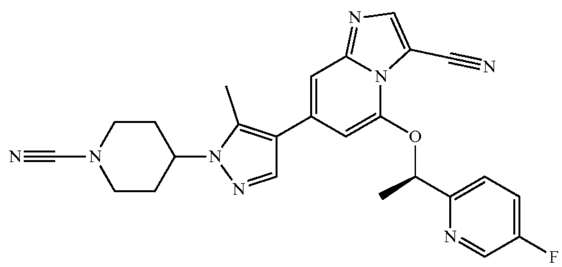 [SMILES: Cc1c(-c2cc(O[C@H](C)c3ccc(F)cn3)n3c(C#N)cnc3c2)cnn1C1CCN(C#N)CC1] | 471.3 | 45-55% |
| 210[4] | 7-[1-(1-cyano-4-piperidyl)-5-methyl-triazol-4-yl]-5-[(1R)-1-(2-pyridyl)propoxy]imidazo[1,2-a]pyridine-3-carbonitrile, Isomer 2 | 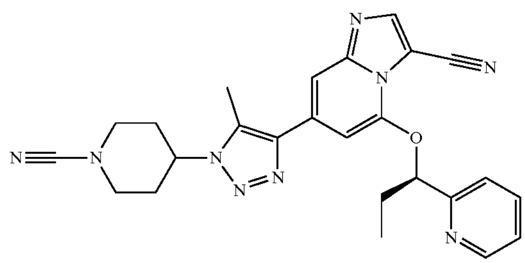 [SMILES: CC[C@@H](Oc1cc(-c2nnn(C3CCN(C#N)CC3)c2C)cc2ncc(C#N)n12)c1ccccn1] | 468.05 | 33-52% |
| 211[7] | 7-[1-(1-Cyano-4-piperidyl)-5-methyl-triazol-4-yl]-5-[[(7R)-6,7-dihydro-5H-cyclopenta[b]pyridin-7-yl]oxy]imidazo[1,2-a]pyridine-3-carbonitrile | 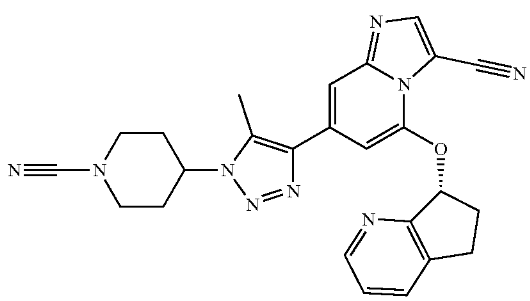 [SMILES: Cc1c(-c2cc(O[C@@H]3CCc4cccnc43)n3c(C#N)cnc3c2)nnn1C1CCN(C#N)CC1] | 466.3 | 19-50% |
| 212[4] | 7-[1-(7-Cyano-7-azaspiro[3.5]nonan-2-yl)-5-methyl-triazol-4-yl]-5-[(1R)-1-(2-pyridyl)ethoxy]imidazo[1,2-a]pyridine-3-carbonitrile | 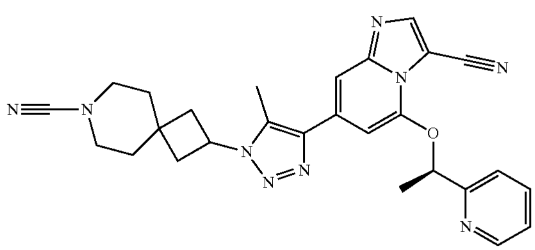 [SMILES: Cc1c(-c2cc(O[C@H](C)c3ccccn3)n3c(C#N)cnc3c2)nnn1C1CC2(CCN(C#N)CC2)C1] | 494.30 | 32-52% |
| 213[8] | 4-[4-[4-Methoxy-3-(trifluoromethyl)pyrazolo[1,5-a]pyridin-6-yl]-5-methyl-pyrazol-1-yl]piperidine-1-carbonitrile | 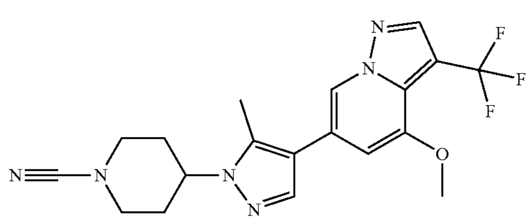 [SMILES: COc1cc(-c2cnn(C3CCN(C#N)CC3)c2C)cn2ncc(C(F)(F)F)c12] | 404.8 | 10-100% |

TABLE 64-continued

| Ex. No. | Chemical name | Structure | ES/MS m/z [M + H]+ | Elution Gradient |
|---|---|---|---|---|
| 214 | 4-[4-[4-[(1R)-1-(5-Fluoro-2-pyridyl)ethoxy]-3-(hydroxymethyl)pyrazolo[1,5-a]pyridin-6-yl]-5-methyl-triazol-1-yl]piperidine-1-carbonitrile | 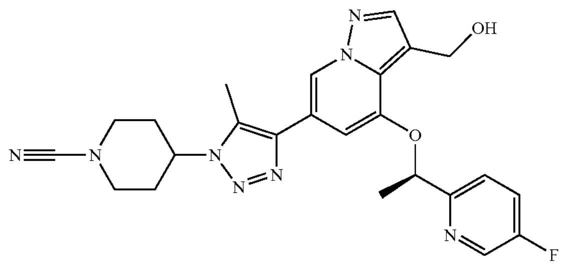 [SMILES: Cc1c(-c2cc(O[C@H](C)c3ccc(F)cn3)c3c(CO)cnn3c2)nnn1C1CCN(C#N)CC1] | 476.8 | 10-100% |

[1] Column: Kinetex EVO C18, 21.2*150, 5 μm, mobile phase A: H₂O (0.05% NH₃H₂O), mobile phase B: ACN.
[2] Column: XBridge Shield RP18 OBD, 19*150 mm, 5 μm, mobile phase A: H₂O (0.05% NH₃H₂O), mobile phase B: ACN.
[3] Crude product is re-crystallized from MTBE (20 mL).
[4] Column: XBridge Prep C18 OBD, 19*150 mm, 5 μm, mobile phase A: H₂O (10 mmol/L NH₄HCO₃), mobile phase B: ACN.
[5] Column: Gemini-NX C18 AXAI Packed, 21.2*150 mm, 5 μm, mobile phase A: H₂O (0.1% FA), mobile phase B: ACN.
[6] Prep-TLC (PE:EtOAc 1:1) followed by trituration in Et₂O (10 mL), filtration, and washing with Et₂O (3 × 15 mL).
[7] Column: SunFire Prep C18 OBD, 19 × 150 mm, 5 μm, mobile phase A: H₂O (0.1% FA), Mobile Phase B: ACN.

Example 215

(3S)-3-[3-(4-[3-Cyano-4-methoxypyrazolo[1,5-a]pyridin-6-yl]-5-methylpyrazol-1-yl)azetidin-1-yl]piperidine-1-carbonitrile

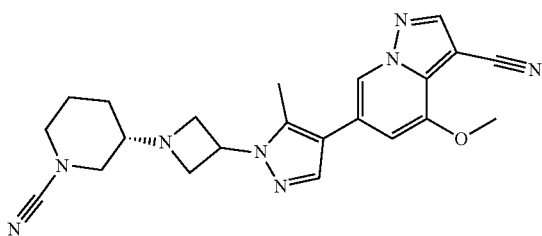 [SMILES: COc1cc(-c2cnn(C3CN([C@H]4CCCN(C#N)C4)C3)c2C)cn2ncc(C#N)c12]

A solution of 4-methoxy-6-(5-methyl-1-[1-[(3S)-piperidin-3-yl]azetidin-3-yl]pyrazol-4-yl)pyrazolo[1,5-a]pyridine-3-carbonitrile (100 mg, 0.26 mmol) and DIEA (330 mg, 2.55 mmol) in DCM (2 mL) is treated with BrCN (27 mg, 0.255 mmol) and stirred for 2 hrs at −60° C. under N₂. The mixture is warmed to RT, quenched with sat. NaHCO₃ (aq.) (10 mL) and extracted with DCM (2×15 mL). The combined organic extracts are washed with brine (2×10 mL), dried over anhydrous Na₂SO₄, filtered, and the filtrate is concentrated under reduced pressure. The residue is purified by reverse Combi-flash chromatography with the following conditions: Column, C18; eluting with a gradient of 44% to 49% ACN in H₂O (0.1% NH₄HCO₃) to give the title compound as a white solid (30 mg, 28.20%). ES/MS m/z 417.20 [M+H]+.

The following compounds are prepared essentially as described for (3S)-3-[3-(4-[3-cyano-4-methoxypyrazolo[1,5-a]pyridin-6-yl]-5-methylpyrazol-1-yl)azetidin-1-yl]piperidine-1-carbonitrile using the appropriate reagents, adjusting reaction time to determine completion of the reaction, and adjusting the purification system as appropriate. Temperature is varied from −60° C. to −75° C.

TABLE 65

| Ex. No. | Chemical name | Structure | ES/MS m/z [M + H]+ | Elution Gradient |
|---|---|---|---|---|
| 216 | (3R)-3-[3-(4-[3-Cyano-4-methoxypyrazolo[1,5-a]pyridin-6-yl]-5-methylpyrazol-1-yl)azetidin-1-yl]piperidine-1-carbonitrile | 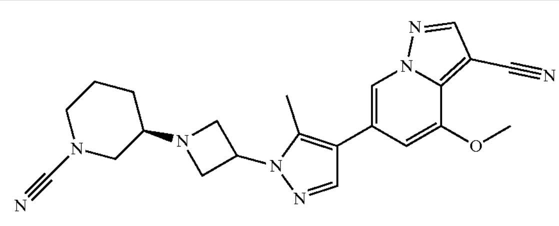 [SMILES: COc1cc(-c2cnn(C3CN([C@@H]4CCCN(C#N)C4)C3)c2C)cn2ncc(C#N)c12] | 417.15 | 30-70% |
| 217[1] | (2S,4R)-4-[3-(4-[3-Cyano-4-methoxypyrazolo[1,5-a]pyridin-6-yl]-5-methylpyrazol-1-yl)azetidin-1-yl]-2-methylpyrrolidine-1-carbonitrile | 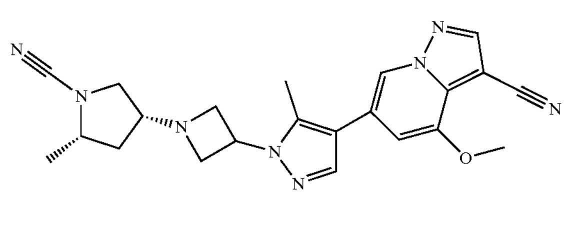 [SMILES: COc1cc(-c2cnn(C3CN([C@@H]4C[C@H](C)N(C#N)C4)C3)c2C)cn2ncc(C#N)c12] | 417.2 | 25-48% B |

TABLE 65-continued

| Ex. No. | Chemical name | Structure | ES/MS m/z [M + H]+ | Elution Gradient |
|---|---|---|---|---|
| 218[1] | (3R)-3-[3-(4-[3-Cyano-4-[(1R)-1-(pyridin-2-yl)ethoxy]pyrazolo[1,5-a]pyridin-6-yl]-5-methylpyrazol-1-yl)azetidin-1-yl]pyrrolidine-1-carbonitrile | 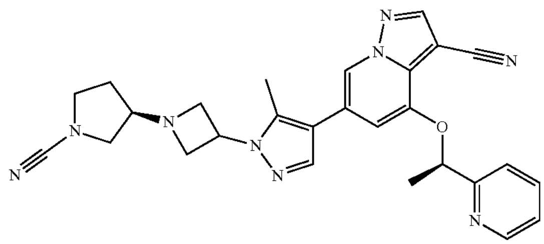 [SMILES: Cc1c(-c2cc(O[C@H](C)c3ccccn3)c3c(C#N)cnn3c2)cnn1C1CN([C@@H]2CCN(C#N)C2)C1] | 494.2 | 27-34% B |
| 219[2] | (3S)-3-[3-(4-[3-Cyano-4-[(1R)-1-(pyridin-2-yl)ethoxy]pyrazolo[1,5-a]pyridin-6-yl]-5-methylpyrazol-1-yl)azetidin-1-yl]pyrrolidine-1-carbonitrile | 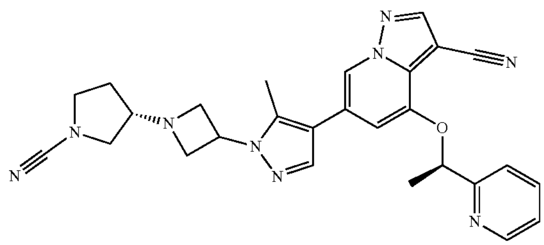 [SMILES: Cc1c(-c2cc(O[C@H](C)c3ccccn3)c3c(C#N)cnn3c2)cnn1C1CN([C@H]2CCN(C#N)C2)C1] | 493.35 | 33-47% B |
| 220 | (2R,4R)-4-[3-(4-[3-Cyano-4-methoxypyrazolo[1,5-a]pyridin-6-yl]-5-methylpyrazol-1-yl)azetidin-1-yl]-2-methylpyrrolidine-1-carbonitrile | 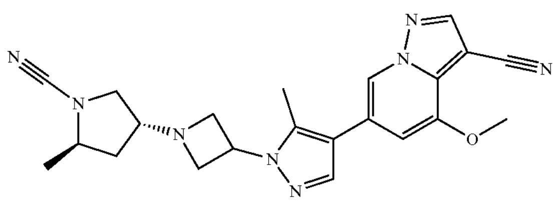 [SMILES: COc1cc(-c2cnn(C3CN([C@@H]4C[C@@H](C)N(C#N)C4)C3)c2C)cn2ncc(C#N)c12] | 417.15 | 40-60% |
| 221 | (3S)-3-[3-(4-[3-Cyano-4-[(1R)-1-(pyridin-2-yl)ethoxy]pyrazolo[1,5-a]pyridin-6-yl]-5-methylpyrazol-1-yl)azetidin-1-yl]pyrrolidine-1-carbonitrile | 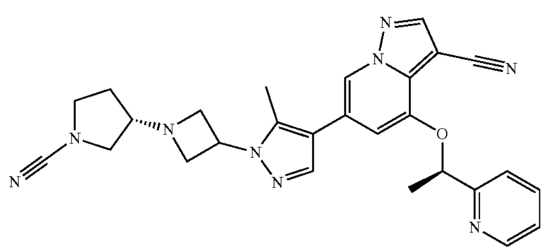 [SMILES: Cc1c(-c2cc(O[C@H](C)c3ccccn3)c3c(C#N)cnn3c2)cnn1C1CN([C@H]2CCN(C#N)C2)C1] | 494.30 | 41-45% |
| 222 | (3R)-3-[3-(4-[3-Cyano-4-methoxypyrazolo[1,5-a]pyridin-6-yl]-5-methylpyrazol-1-yl)azetidin-1-yl]pyrrolidine-1-carbonitrile | 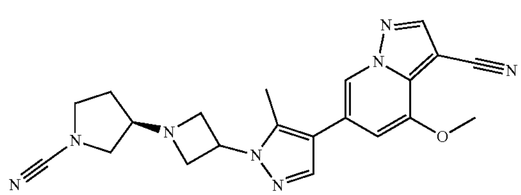 [SMILES: COc1cc(-c2cnn(C3CN([C@@H]4CCN(C#N)C4)C3)c2C)cn2ncc(C#N)c12] | 403.3 | 25-40% B |
| 223[1] | (3S)-3-[3-(4-[3-Cyano-4-methoxypyrazolo[1,5-a]pyridin-6-yl]-5-methylpyrazol-1-yl)azetidin-1-yl]pyrrolidine-1-carbonitrile | 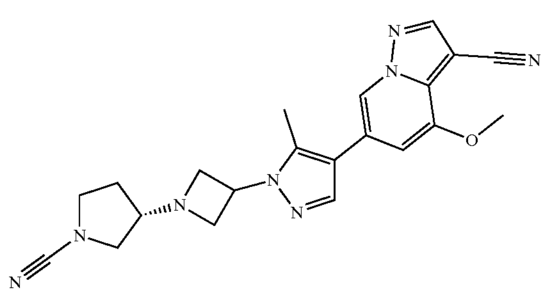 [SMILES: COc1cc(-c2cnn(C3CN([C@H]4CCN(C#N)C4)C3)c2C)cn2ncc(C#N)c12] | 403.1 | 20-50% B |

TABLE 65-continued

| Ex. No. | Chemical name | Structure | ES/MS m/z [M + H]+ | Elution Gradient |
|---|---|---|---|---|
| 224[2] | 6-[1-[1-[(3S)-1-Cyanopyrrolidin-3-yl]azetidin-3-yl]-5-methyl-pyrazol-4-yl]-4-[[(1R)-1-(2-pyridyl)ethyl]amino]pyrazolo[1,5-a]pyridine-3-carbonitrile | 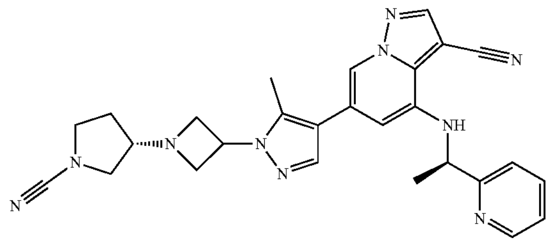 [SMILES: Cc1c(-c2cc(N[C@H](C)c3ccccn3)c3c(C#N)cnn3c2)cnn1C1CN([C@H]2CCN(C#N)C2)C1] | 493.2 | 33-47% |
| 225[3] | 6-(1-(1-(6-cyano-6-azabicyclo[3.2.1]octan-3-yl)azetidin-3-yl)-5-methyl-1H-pyrazol-4-yl)-4-methoxypyrazolo[1,5-a]pyridine-3-carbonitrile | 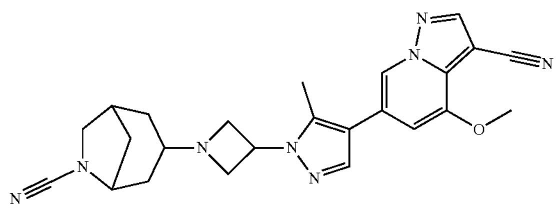 [SMILES: COc1cc(-c2cnn(C3CN(C4CC5CC(C4)N(C#N)C5)C3)c2C)cn2ncc(C#N)c12] | 443.1 | 20-50% |
| 226[1] | 7-[1-[1-(7-Cyano-7-azabicyclo[2.2.1]heptan-2-yl)azetidin-3-yl]-5-methyl-pyrazol-4-yl]-5-[(1R)-1-(2-pyridyl)ethoxy]imidazo[1,2-a]pyridine-3-carbonitrile | 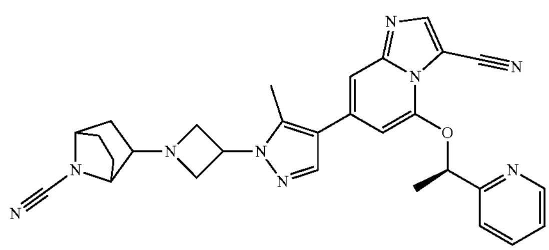 [SMILES: Cc1c(-c2cc(O[C@H](C)c3ccccn3)n3c(C#N)cnc3c2)cnn1C1CN(C2CC3CCC2N3C#N)C1] | 520.10 | 28-44% |

[1]Column: XBridge Prep C18 OBD, 19*150 mm, 5 μm, mobile phase A, H₂O (10 mmol/L NH₄HCO₃), mobile phase B, ACN.
[2]Column: XBridge Shield RP18 OBD, 19*150 mm, 5 μm, mobile phase A, H₂O (10 mmol/L NH₄HCO₃), mobile phase B, ACN.
[3]Column: Galaksil UP C18, 8 μm; mobile phase A: H₂O (10 mmol/L NH₄HCO₃), mobile phase B: ACN.

Example 227

4-(4-[3-Cyano-4-methoxypyrazolo[1,5-a]pyridin-6-yl]-5-methylpyrazol-1-yl)piperidine-1-carbonitrile

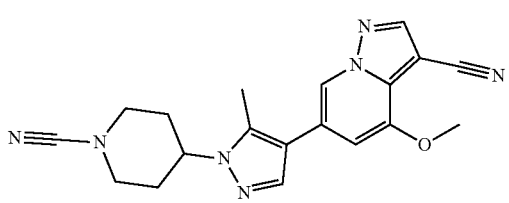 [SMILES: COc1cc(-c2cnn(C3CCN(C#N)CC3)c2C)cn2ncc(C#N)c12]

A solution of 4-methoxy-6-(5-methyl-1-(piperidin-4-yl)-1H-pyrazol-4-yl)pyrazolo[1,5-a]pyridine-3-carbonitrile (60 mg, 0.18 mmol) and K₂CO₃ (74 mg, 0.53 mmol) in DMF (1 mL) is treated with BrCN (23 mg, 0.21 mmol) and stirred for 16 hrs at 80° C. under N₂. The mixture is cooled to RT, quenched with H₂O (10 mL), and extracted with EtOAc (3×5 mL). The combined organic extracts are washed with brine (3×15 mL), dried over anhydrous Na₂SO₄, filtered, and the filtrate is concentrated under reduced pressure. The residue is purified by Prep-HPLC with the following conditions: Column, Kinetex EVO C18 Column, 21.2*E150, 5 μm; eluting with a gradient of 30% to 45% ACN in H₂O (0.05% N₃H₂O) to give the title compound as a white solid (9 mg, 14%). ES/MS m/z 362.15 [M+H]⁺.

The following compounds are prepared essentially as described for 4-(4-[3-cyano-4-methoxypyrazolo[1,5-a]pyridin-6-yl]-5-methylpyrazol-1-yl)piperidine-1-carbonitrile adjusting reaction time to allow for completion of the reaction and adjusting the purification system as appropriate. Temperature is varied from 80° C. to 100° C.

TABLE 66

| Ex. No. | Chemical name | Structure | ES/MS m/z [M + H]+ | Elution Gradient |
|---|---|---|---|---|
| 228 | 3-[4-(4-[3-Cyano-4-methoxypyrazolo[1,5-a]pyridin-6-yl]-5-methylpyrazol-1-yl)piperidin-1-yl]azetidine-1-carbonitrile | 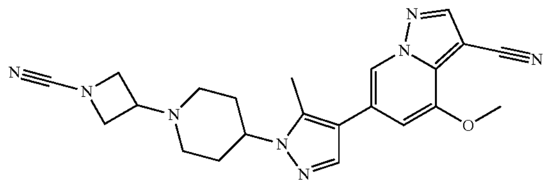 [SMILES: COc1cc(-c2cnn(C3CCN(C4CN(C#N)C4)CC3)c2C)cn2ncc(C#N)c12] | 417.2 | 5-45% B |
| 229[1] | (3R)-3-(4-[3-Cyano-4-methoxypyrazolo[1,5-a]pyridin-6-yl]-5-methylpyrazol-1-yl)pyrrolidine-1-carbonitrile | 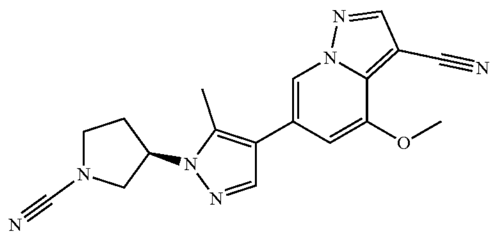 [SMILES: COc1cc(-c2cnn([C@@H]3CCN(C#N)C3)c2C)cn2ncc(C#N)c12] | 348.15 | 50-70% |
| 230[1] | (3S)-3-(4-[3-Cyano-4-methoxypyrazolo[1,5-a]pyridin-6-yl]-5-methylpyrazol-1-yl)pyrrolidine-1-carbonitrile | 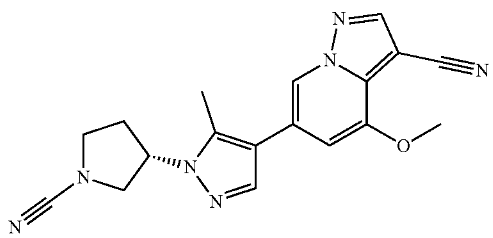 [SMILES: COc1cc(-c2cnn([C@H]3CCN(C#N)C3)c2C)cn2ncc(C#N)c12] | 348.20 | 40-55% |
| 231 | 4-(4-[3-Cyano-4-methoxypyrazolo[1,5-a]pyridin-6-yl]-5-methyl-1,2,3-triazol-1-yl)piperidine-1-carbonitrile | 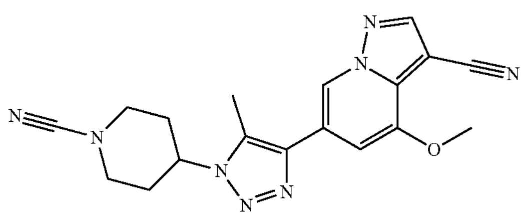 [SMILES: COc1cc(-c2nnn(C3CCN(C#N)CC3)c2C)cn2ncc(C#N)c12] | 363.15 | 20-30% B |

[1]Reverse Combi-flash chromatography with the following conditions: C18; H₂O (0.1% FA) in ACN.

Example 232

3-(4-[3-Cyano-4-methoxypyrazolo[1,5-a]pyridin-6-yl]-5-methylpyrazol-1-yl)azetidine-1-carbonitrile

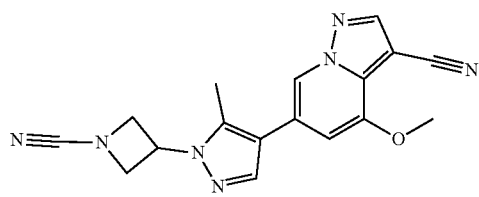 [SMILES: COc1cc(-c2cnn(C3CN(C#N)C3)c2C)cn2ncc(C#N)c12]

A solution of 6-[1-(azetidin-3-yl)-5-methylpyrazol-4-yl]-4-methoxypyrazolo[1,5-a]pyridine-3-carbonitrile (80 mg, 0.26 mmol), BrCN (33 mg, 0.31 mmol) and Cs₂CO₃ (254 mg, 0.78 mmol) in DMF (5 mL) is stirred for 2 hrs at 80° C. The mixture is cooled to RT and purified by reverse Combi-flash chromatography with the following conditions: Column, C18; 10-50% ACN in H₂O to give the title compound as an off-white solid (20.6 mg, 23.8%). ES/MS m/z 334.10 [M+H]+.

Example 233

4-[3-[4-[3-Chloro-5-[(1R)-1-(2-pyridyl)ethoxy]imidazo[1,2-a]pyridin-7-yl]-5-methyl-triazol-1-yl]azetidin-1-yl]piperidine-1-carbonitrile

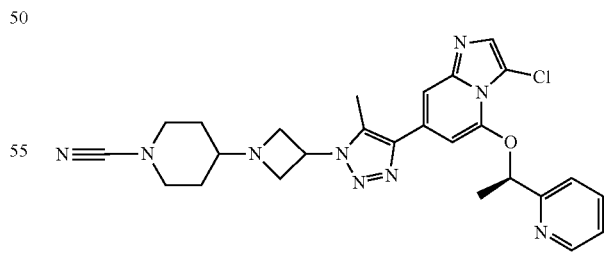

A mixture of 7-[1-(Azetidin-3-yl)-5-methyl-triazol-4-yl]-3-chloro-5-[(1R)-1-(2-pyridyl)ethoxy]imidazo[1,2-a]pyridine TFA (100.00 mg), 4-oxopiperidine-1-carbonitrile (90.86 mg, 0.73 mmol) and AcOH (1.47 mg, 0.02 mmol) in MeOH (5.00 mL) is stirred at 50° C. for 30 min under N₂. Upon cooling to RT, NaBH₃CN (23.00 mg, 0.37 mmol) is added in portions. The resulting mixture is stirred at 50° C.

for 2 hr then concentrated in vacuo. The residue is purified by Prep-HPLC with the following conditions: Column: Kinetex EVO C18 Column, 21.2*150, 5 µm; eluting with 21% to 47% ACN in H$_2$O (0.05% NH$_4$OH); 254/220 nm; to give the title compound as a white solid (16.3 mg, 12.9%). ES/MS m/z 518.20 [M+H]$^+$.

Example 234

4-[3-(4-[3-Cyano-4-methoxypyrazolo[1,5-a]pyridin-6-yl]pyrazol-1-yl)azetidin-1-yl]piperidine-1-carbonitrile

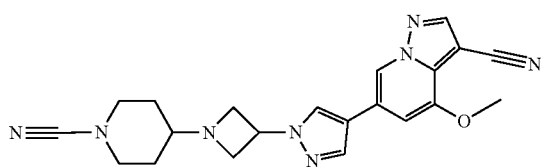 [SMILES: COc1cc(-c2cnn(C3CN(C4CCN(C#N)CC4)C3)c2)cn2ncc(C#N)c12]

A solution of 6-[1-(azetidin-3-yl)pyrazol-4-yl]-4-methoxypyrazolo[1,5-a]pyridine-3-carbonitrile.TFA (100.00 mg), 4-oxopiperidine-1-carbonitrile (210.90 mg, 1.70 mmol) and AcOH (2.04 mg, 0.034 mmol) in MeOH (3.00 mL) is stirred for 40 min at 50° C. under N$_2$. The solution is treated with NaBH$_3$CN (42.70 mg, 0.68 mmol) at RT, and stirred for 1 hr at 50° C. The mixture is concentrated under reduced pressure. The residue is purified by reverse Combi-flash chromatography with the following conditions: Column, C18; eluting with a gradient of 40% to 60% ACN in H$_2$O (0.1% NH$_4$HCO$_3$) to give the title compound as a white solid (23.8 mg, 17.40%). ES/MS m/z 403.25 [M+H]$^+$.

The following compounds are prepared essentially as described for 4-[3-(4-[3-cyano-4-methoxypyrazolo[1,5-a]pyridin-6-yl]pyrazol-1-yl)azetidin-1-yl]piperidine-1-carbonitrile using the appropriate reagents, adjusting reaction time to determine completion of the reaction, and adjusting the purification system as appropriate.

TABLE 67

| Ex. No. | Chemical name | Structure | ES/MS m/z [M + H]$^+$ | Elution Gradient |
|---|---|---|---|---|
| 235 | 4-[3-(4-[3-Cyano-4-[(1R)-1-(pyridin-2-yl)ethoxy]pyrazolo[1,5-a]pyridin-6-yl]-5-methyl-1,2,3-triazol-1-yl)azetidin-1-yl]piperidine-1-carbonitrile | 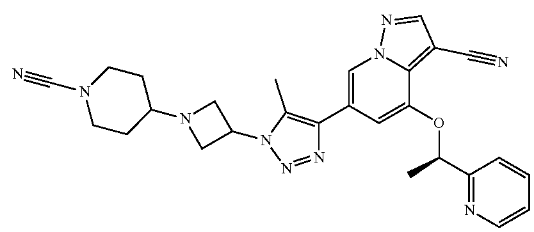 [SMILES: Cc1c(-c2cc(O[C@H](C)c3ccccn3)c3c(C#N)cnn3c2)cnn1C1CN(C2CCN(C#N)CC2)C1] | 509.2 | 30-50% |
| 236 | 4-[3-(4-[3-Cyano-4-[(1R)-1-(pyridin-2-yl)ethoxy]pyrazolo[1,5-a]pyridin-6-yl]-5-methylpyrazol-1-yl)azetidin-1-yl]piperidine-1-carbonitrile | 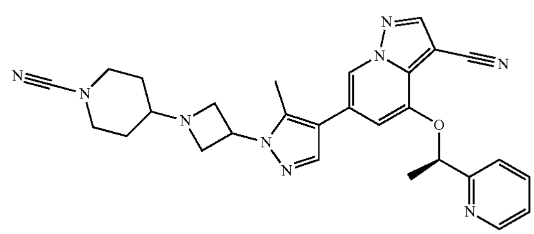 | 508.3 | 40-44% |
| 237[1] | 4-[3-(4-[3-Cyano-4-methoxypyrazolo[1,5-a]pyridin-6-yl]-5-methyl-1,2,3-triazol-1-yl)azetidin-1-yl]piperidine-1-carbonitrile. FA | 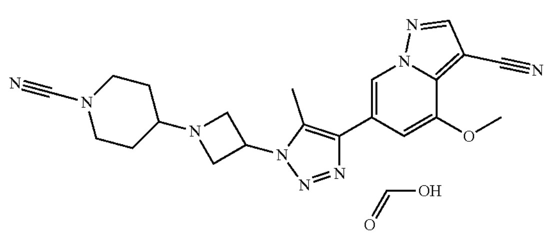 | 418.15 | 10-22% B |
| 238[2] | 4-[3-(4-[3-Cyano-5-[(1R)-1-(pyridin-2-yl)ethoxy]imidazo[1,2-a]pyridin-7-yl]-5-methyl-1,2,3-triazol-1-yl)azetidin-1-yl]piperidine-1-carbonitrile | 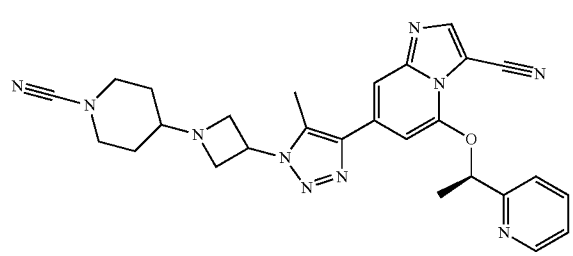 [SMILES: Cc1c(-c2cc(O[C@H](C)c3ccccn3)n3c(C#N)cnc3c2)nnn1C1CN(C2CCN(C#N)CC2)C1] | 509.05 | 25-40% B |

TABLE 67-continued

| Ex. No. | Chemical name | Structure | ES/MS m/z [M + H]+ | Elution Gradient |
|---|---|---|---|---|
| 239[3] | 4-[3-(4-[3-cyano-4-isopropoxypyrazolo[1,5-a]pyridin-6-yl]-5-methyl-1,2,3-triazol-1-yl)azetidin-1-yl]piperidine-1-carbonitrile | 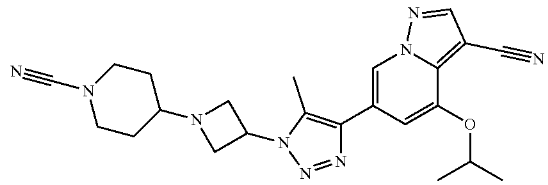 [SMILES: Cc1c(-c2cc(OC(C)C)c3c(C#N)cnn3c2)nnn1C1CN(C2CCN(C#N)CC2)C1] | 446.10 | 32-40% B |

[1]SunFire Prep C18 OBD Column; mobile phase A: H₂O (0.1% FA), mobile phase B: ACN.
[2]XBridge Shield RP18 OBD Column, 19*150 mm, 5 μm, mobile phase A: H₂O (0.05% NH₃H₂O), Mobile Phase B: ACN.
[3]XBridge Prep C18 OBD Column, 19*150 mm, 5 μm; mobile phase A: H₂O (10 mmol/L NH₄HCO₃), mobile phase B: ACN.

Example 240

4-[3-(4-[3-Cyano-4-methoxypyrazolo[1,5-a]pyridin-6-yl]-3-methylpyrazol-1-yl)azetidin-1-yl]piperidine-1-carbonitrile

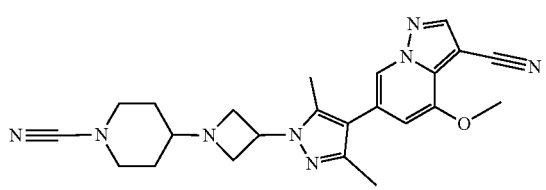 [SMILES: COc1cc(-c2c(C)nn(C3CN(C4CCN(C#N)CC4)C3)c2C)cn2ncc(C#N)c12]

AcOH (1.95 mg, 0.03 mmol) is added dropwise and NaBH₃CN (61.14 mg, 0.97 mmol) is added in portions to a mixture of 6-(1-(azetidin-3-yl)-3-methyl-1H-pyrazol-4-yl)-4-methoxypyrazolo[1,5-a]pyridine-3-carbonitrile.TFA (90.00 mg, 0.32 mmol) and 4-oxopiperidine-1-carbonitrile (201.31 mg, 1.62 mmol) in MeOH (3.00 mL) at RT under N₂. The mixture is stirred for 1 hr at 50° C. The reaction is quenched with NH₄Cl (50 mL) and extracted with DCM (3×50 mL). The combined organic extracts are washed with brine (2×100 mL), dried over anhydrous Na₂SO₄, filtered, and the filtrate is concentrated under reduced pressure. The residue is purified by reverse Combi-flash chromatography with the following conditions: Column, C18; eluting with a gradient of 40% to 50% ACN in H₂O (0.1% NH₄HCO₃) to give the title compound as a white solid (40.8 mg, 30%). ES/MS m/z 417.1 [M+H]⁺.

Example 241

4-(4-[3-Cyano-4-methoxypyrazolo[1,5-a]pyridin-6-yl]pyrazol-1-yl)piperidine-1-carbonitrile

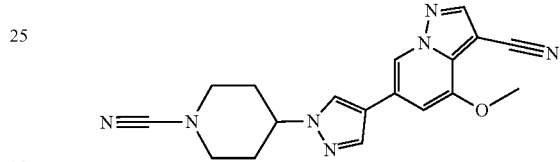

BrCN (42.71 mg, 0.40 mmol) is added in portions to a stirred solution of 4-methoxy-6-[1-(piperidin-4-yl)pyrazol-4-yl]pyrazolo[1,5-a]pyridine-3-carbonitrile.HCl (100.00 mg, 0.31 mmol) and DIEA (400.91 mg, 3.10 mmol) in DCM (5.00 mL), and the mixture is stirred for 1 hr at RT under N₂. The mixture is quenched with H₂O (10 mL) and extracted with EtOAc (2×50 mL). The combined organic extracts are washed with sat. NaHCO₃ (20 mL) and brine (2×20 mL), dried over anhydrous Na₂SO₄, filtered, and the filtrate is concentrated under reduced pressure. The residue is purified by reverse Combi-flash chromatography with the following conditions: column, C18; eluting with a gradient of 45% to 55% ACN in H₂O to give the title compound as a white solid (41.7 mg, 38.70%). ES/MS m/z 348.25 [M+H]⁺.

The following compounds are prepared essentially as described for 4-(4-[3-cyano-4-methoxypyrazolo[1,5-a]pyridin-6-yl]pyrazol-1-yl)piperidine-1-carbonitrile using the appropriate reagents, adjusting reaction time to determine completion of the reaction, and adjusting the purification system as appropriate.

TABLE 68

| Ex. No. | Chemical name | Structure | ES/M m/z [M + H]+ | Elution Gradient |
|---|---|---|---|---|
| 242 | 4-(4-[3-Cyano-4-[(1R)-1-(pyridin-2-yl)ethoxy]pyrazolo[1,5-a]pyridin-6-yl]-5-methylpyrazol-1-yl)piperidine-1-carbonitrile | 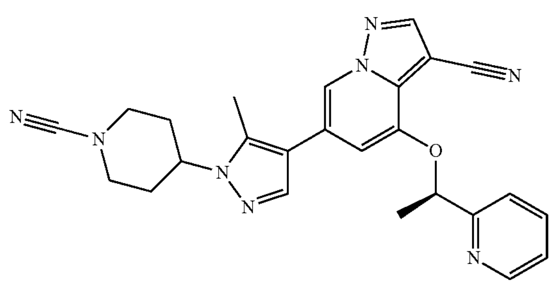 [SMILES: Cc1c(-c2cc(O[C@H](C)c3ccccn3)c3c(C#N)cnn3c2)cnn1C1CCN(C#N)CC1] | 453.2 | 50-60% |

TABLE 68-continued

| Ex. No. | Chemical name | Structure | ES/M m/z [M + H]+ | Elution Gradient |
|---|---|---|---|---|
| 243 | (2R,4R)-4-(4-[3-Cyano-4-methoxypyrazolo[1,5-a]pyridin-6-yl]-5-methylpyrazol-1-yl)-2-methyl pyrrolidine-1-carbonitrile | 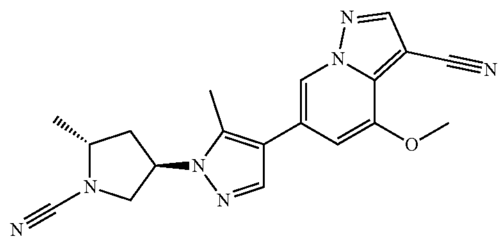 [SMILES: COc1cc(-c2cnn([C@@H]3C[C@@H](C)N(C#N)C3)c2C)cn2ncc(C#N)c12] | 362.10 | 10-60% |
| 244[1] | 4-(4-[3-Cyano-4-[(1S)-1-(pyridin-2-yl)ethoxy]pyrazolo[1,5-a]pyridin-6-yl]-5-methylpyrazol-1-yl)piperidine-1-carbonitrile | 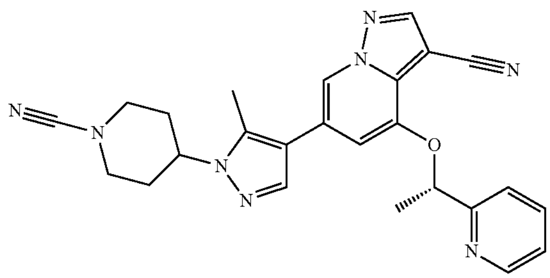 [SMILES: Cc1c(-c2cc(O[C@@H](C)c3ccccn3)c3c(C#N)cnn3c2)cnn1C1CCN(C#N)CC1] | 453.15 | 31-45% B |
| 245 | 4-(4-[3-Cyano-4-[(1R)-1-(oxan-4-yl)ethoxy]pyrazolo[1,5-a]pyridin-6-yl]-5-methylpyrazol-1-yl)piperidine-1-carbonitrile | 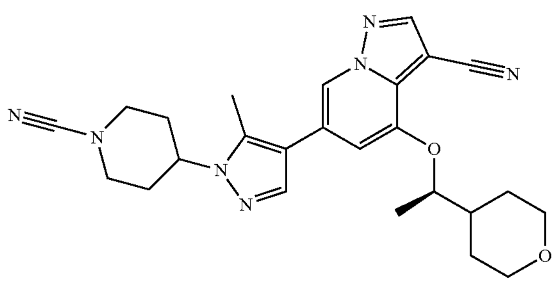 [SMILES: Cc1c(-c2cc(O[C@H](C)C3CCOCC3)c3c(C#N)cnn3c2)cnn1C1CCN(C#N)CC1] | 460.2 | 20-50% |
| 246 | 4-(4-[3-Cyano-4-[(3-fluoropyridin-2-yl)methoxy]pyrazolo[1,5-a]pyridin-6-yl]-5-methyl pyrazol-1-yl)piperidine-1-carbonitrile | 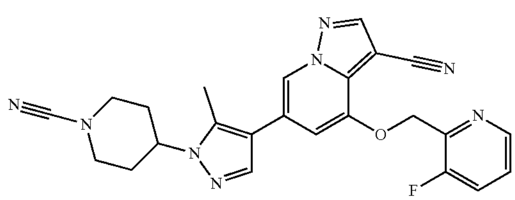 [SMILES: Cc1c(-c2cc(OCc3ncccc3F)c3c(C#N)cnn3c2)cnn1C1CCN(C#N)CC1] | 457.25 | 40-43% |
| 247[2] | (3R)-3-[4-(3-Cyano-4-[[(1R)-1-(pyridin-2-yl)ethyl]amino]pyrazolo[1,5-a]pyridin-6-yl)-5-methylpyrazol-1-yl]pyrrolidine-1-carbonitrile | 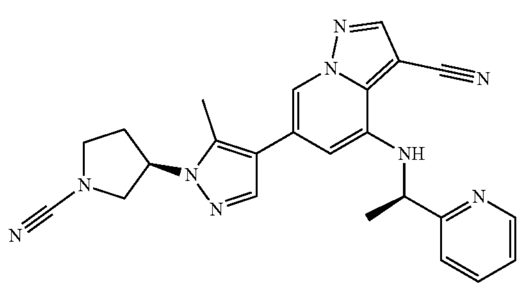 [SMILES: Cc1c(-c2cc(N[C@H](C)c3ccccn3)c3c(C#N)cnn3c2)cnn1[C@@H]1CCN(C#N)C1] | 438.1 | 30-35% |
| 248 | (3R)-3-[4-(4-[3-Cyano-4-methoxypyrazolo[1,5-a]pyridin-6-yl]-5-methylpyrazol-1-yl)piperidin-1-yl]pyrrolidine-1-carbonitrile | 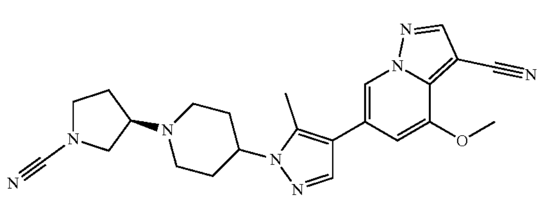 [SMILES: COc1cc(-c2cnn(C3CCN([C@@H]4CCN(C#N)C4)CC3)c2C)cn2ncc(C#N)c12] | 431.2 | 30-40% |

TABLE 68-continued

| Ex. No. | Chemical name | Structure | ES/M m/z [M + H]+ | Elution Gradient |
|---|---|---|---|---|
| 249[3] | 4-[4-(3-Cyano-4-[[2-(pyridin-2-yl)propan-2-yl]oxy]pyrazolo[1,5-a]pyridin-6-yl)-5-methylpyrazol-1-yl]piperidine-1-carbonitrile | 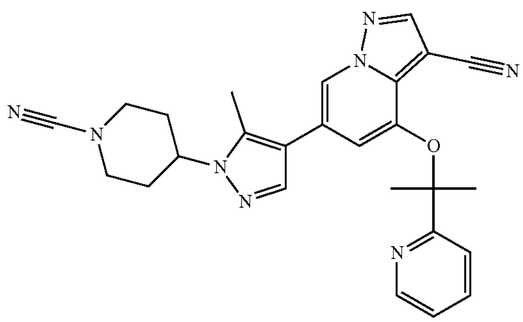 [SMILES: Cc1c(-c2cc(OC(C)(C)c3ccccn3)c3c(C#N)cnn3c2)cnn1C1CCN(C#N)CC1] | 467.2 | 30-48% B |
| 250[4] | (3S)-3-[4-(3-Cyano-4-[[(1R)-1-(pyridin-2-yl)ethyl]amino]pyrazolo[1,5-a]pyridin-6-yl)-5-methylpyrazol-1-yl]pyrrolidine-1-carbonitrile | 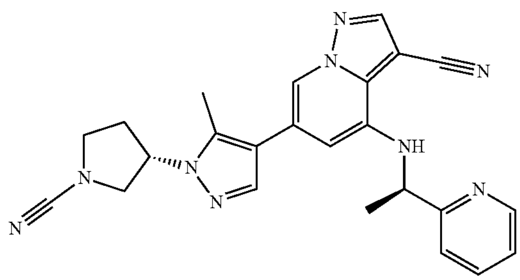 [SMILES: Cc1c(-c2cc(N[C@H](C)c3ccccn3)c3c(C#N)cnn3c2)cnn1[C@H]1CCN(C#N)C1] | 438.20 | |
| 251[5] | 4-[4-[5-[(1R)-1-(5-fluoro-2-pyridyl)ethoxy]-3-methyl-imidazo[1,2-a]pyridin-7-yl]-5-methyl-triazol-1-yl]piperidine-1-carbonitrile | 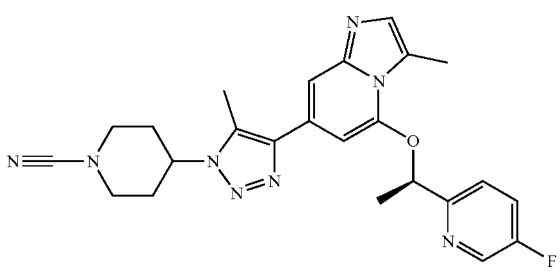 | 461.25 | |
| 252[6] | 7-[1-(7-cyano-7-azaspiro[3.5]nonan-2-yl)-5-methyl-triazol-4-yl]-5-[(1R)-1-(5-fluoro-2-pyridyl)ethoxy]imidazo[1,2-a]pyridine-3-carbonitrile | 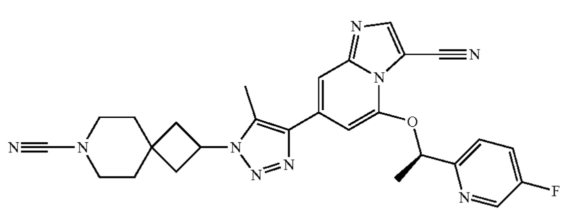 [SMILES: Cc1c(-c2cc(O[C@H](C)c3ccc(F)cn3)n3c(C#N)cnc3c2)nnn1C1CC2(CCN(C#N)CC2)C1] | 512.25 | 50-55% |
| 253[3] | 7-[1-(1-Cyano-4-piperidyl)-5-methyl-triazol-4-yl]-5-[2-methoxy-1-(2-pyridyl)ethoxy]imidazo[1,2-a]pyridine-3-carbonitrile, Isomer 1 | 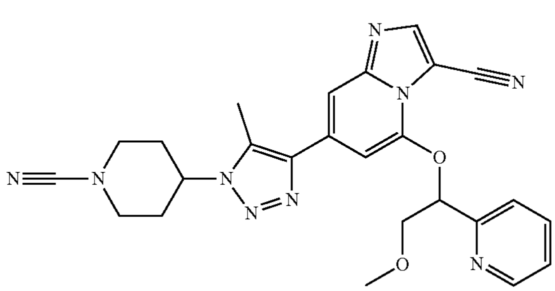 [SMILES: COCC(Oc1cc(-c2nnn(C3CCN(C#N)CC3)c2C)cc2ncc(C#N)n12)c1ccccn1] | 484.05 | 31-50% |

TABLE 68-continued

| Ex. No. | Chemical name | Structure | ES/M m/z [M + H]+ | Elution Gradient |
|---|---|---|---|---|
| 254[1] | 7-[1-(1-Cyano-4-piperidyl)-5-methyl-triazol-4-yl]-5-[(1R)-1-(3-fluoro-2-pyridyl)ethoxy]imidazo[1,2-a]pyridine-3-carbonitrile | 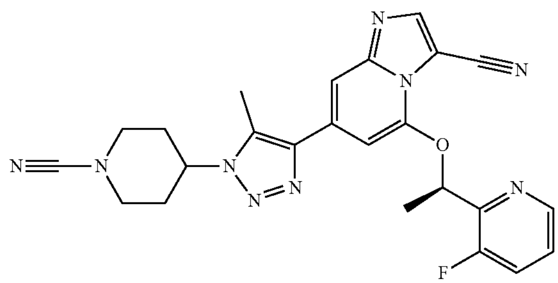 [SMILES: Cc1c(-c2cc(O[C@H](C)c3ncccc3F)n3c(C#N)cnc3c2)nnn1C1CCN(C#N)CC1] | 472.1 | 17-45% |
| 255[7] | 7-[1-(1-Cyano-4-piperidyl)-5-methyl-triazol-4-yl]-5-[(1R)-1-(2-fluorophenyl)ethoxy]imidazo[1,2-a]pyridine-3-carbonitrile | 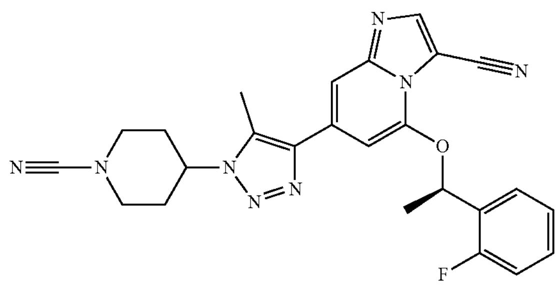 [SMILES: Cc1c(-c2cc(O[C@H](C)c3ccccc3F)n3c(C#N)cnc3c2)nnn1C1CCN(C#N)CC1] | 471.1 | 50-68% |
| 256[6] | 4-[4-[4-[(1R)-1-(2-Cyanophenyl)ethoxy]pyrazolo[1,5-a]pyridin-6-yl]-5-methyl-pyrazol-1-yl]piperidine-1-carbonitrile | 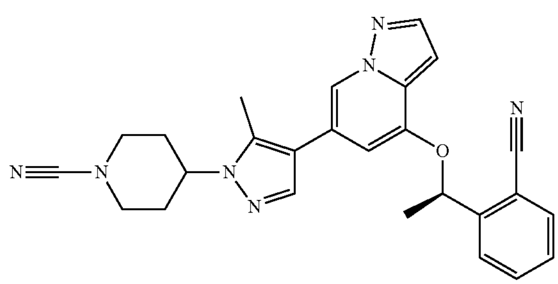 [SMILES: Cc1c(-c2cc(O[C@H](C)c3ccccc3C#N)c3ccnn3c2)cnn1C1CCN(C#N)CC1] | 452.15 | 10-50% |
| 257[1] | 7-[1-(1-Cyanoazepan-4-yl)-5-methyl-triazol-4-yl]-5-[(1R)-1-(2-pyridyl)ethoxy]imidazo[1,2-a]pyridine-3-carbonitrile | 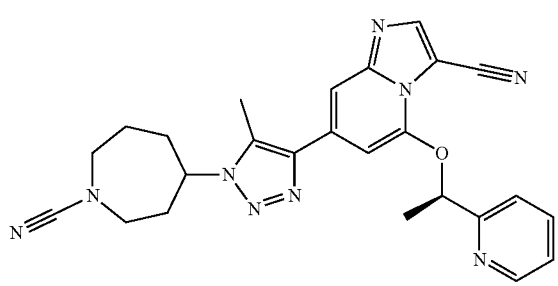 [SMILES: Cc1c(-c2cc(O[C@H](C)c3ccccn3)n3c(C#N)cnc3c2)nnn1C1CCCN(C#N)CC1] | 468.1 | 28-40% |
| 258[8] | 6-[1-[1-(7-Cyano-7-azabicyclo[2.2.1]heptan-2-yl)azetidin-3-yl]-5-methyl-pyrazol-4-yl]-4-methoxy-pyrazolo[1,5-a]pyridine-3-carbonitrile | 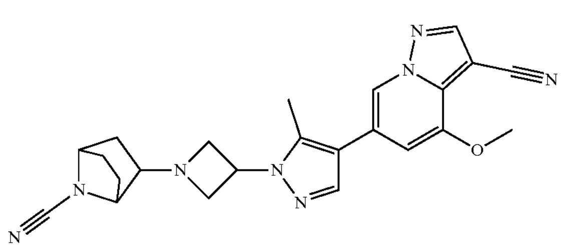 [SMILES: COc1cc(-c2cnn(C3CN(C4CC5CCC4N5C#N)C3)c2C)cn2ncc(C#N)c12] | 429.20 | 50-70% |

TABLE 68-continued

| Ex. No. | Chemical name | Structure | ES/M m/z [M + H]+ | Elution Gradient |
|---|---|---|---|---|
| 259[9] | 7-[1-[(3S)-1-Cyano-3-piperidyl]-5-methyl-triazol-4-yl]-5-[(1R)-1-(5-fluoro-2-pyridyl)ethoxy]imidazo[1,2-a]pyridine-3-carbonitrile | 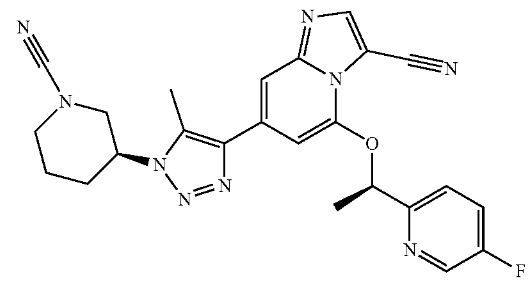 [SMILES: Cc1c(-c2cc(O[C@H](C)c3ccc(F)cn3)n3c(C#N)cnc3c2)nnn1[C@H]1CCCN(C#N)C1] | 472.35 | |
| 260[8] | 7-[1-[(3R)-1-Cyano-3-piperidyl]-5-methyl-triazol-4-yl]-5-[(1R)-1-(5-fluoro-2-pyridyl)ethoxy]imidazo[1,2-a]pyridine-3-carbonitrile | 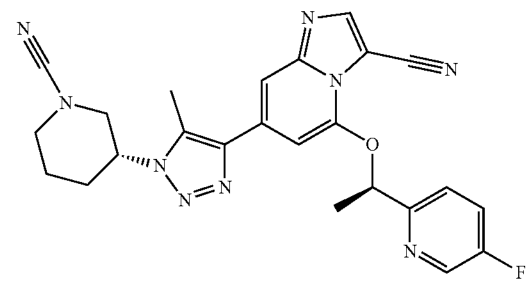 [SMILES: Cc1c(-c2cc(O[C@H](C)c3ccc(F)cn3)n3c(C#N)cnc3c2)nnn1[C@@H]1CCCN(C#N)C1] | 472.20 | 30-45% |
| 261[6,10] | 7-[1-(1-Cyano-4-piperidyl)-5-methyl-triazol-4-yl]-5-[[(1R)-1-(5-fluoro-2-pyridyl)ethyl]amino]imidazo[1,2-a]pyridine-3-carbonitrile | 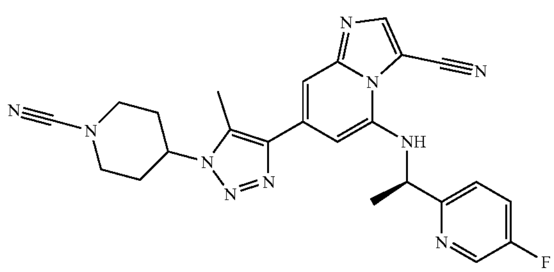 [SMILES: Cc1c(-c2cc(N[C@H](C)c3ccc(F)cn3)n3c(C#N)cnc3c2)nnn1C1CCN(C#N)CC1] | 471.2 | 30-38% |
| 262[6] | 7-[1-(1-Cyano-4-piperidyl)-5-methyl-pyrazol-4-yl]-5-[[(1R)-1-(2-pyridyl)ethyl]amino]imidazo[1,2-a]pyridine-3-carbonitrile | 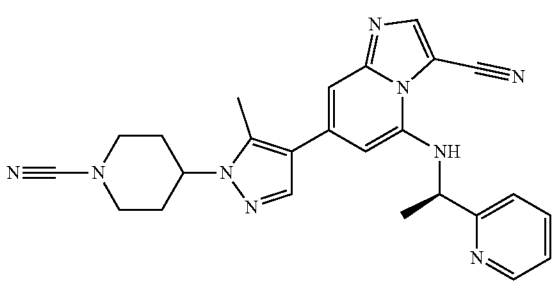 [SMILES: Cc1c(-c2cc(N[C@H](C)c3ccccn3)n3c(C#N)cnc3c2)cnn1C1CCN(C#N)CC1] | 452.30 | 40-60% |
| 263[8] | 7-[1-(1-Cyano-4-piperidyl)-5-methyl-triazol-4-yl]-5-[(1R)-1-pyrimidin-4-ylethoxy]imidazo[1,2-a]pyridine-3-carbonitrile | 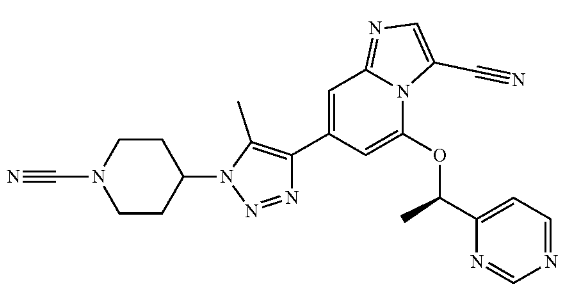 [SMILES: Cc1c(-c2cc(O[C@H](C)c3ccncn3)n3c(C#N)cnc3c2)nnn1C1CCN(C#N)CC1] | 455.20 | — |

TABLE 68-continued

| Ex. No. | Chemical name | Structure | ES/M m/z [M + H]+ | Elution Gradient |
|---|---|---|---|---|
| 264[6] | 7-[1-(1-Cyano-4-piperidyl)-5-methyl-triazol-4-yl]-5-[2,2-dimethyl-1-(2-pyridyl)propoxy]imidazo[1,2-a]pyridine-3-carbonitrile, Isomer 1 | 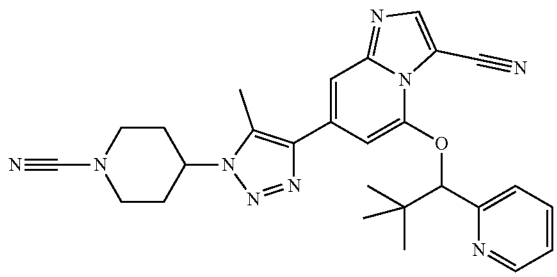 [SMILES: Cc1c(-c2cc(OC(c3ccccn3)C(C)(C)C)n3c(C#N)cnc3c2)nnn1C1CCN(C#N)CC1] | 496.3 | 30-50% |
| 265[11] | 7-[1-(1-Cyano-4-piperidyl)-5-methyl-triazol-4-yl]-5-[(1R)-1-(2,6-difluorophenyl)ethoxy]imidazo[1,2-a]pyridine-3-carbonitrile | 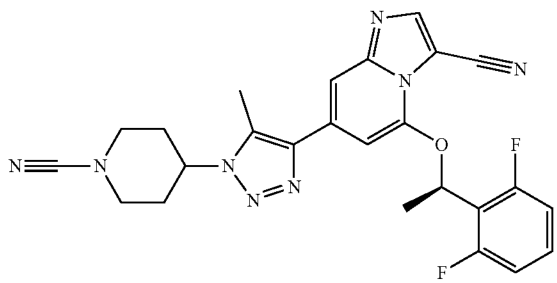 [SMILES: Cc1c(-c2cc(O[C@H](C)c3c(F)cccc3F)n3c(C#N)cnc3c2)nnn1C1CCN(C#N)CC1] | 489.1 | 10-50% |
| 266[11] | 5-[(1R)-1-(2-Chloro-4-fluorophenyl)ethoxy]-7-[1-(1-cyano-4-piperidyl)-5-methyl-triazol-4-yl]imidazo[1,2-a]pyridine-3-carbonitrile | 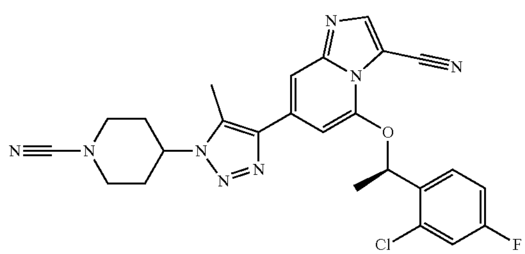 [SMILES: Cc1c(-c2cc(O[C@H](C)c3ccc(F)cc3Cl)n3c(C#N)cnc3c2)nnn1C1CCN(C#N)CC1] | 504.2 | 0-100% |
| 267[12] | 7-[1-(1-Cyano-4-piperidyl)-5-methyl-triazol-4-yl]-5-[(1R)-1-(5-fluoro-3-methyl-2-pyridyl)ethoxy]imidazo[1,2-a]pyridine-3-carbonitrile | 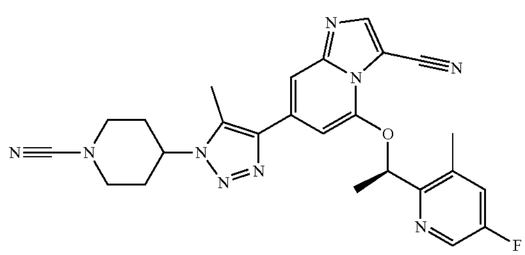 | 486.2 | 30-50% |
| 268[13] | 7-[1-(1-Cyano-4-piperidyl)-5-methyl-triazol-4-yl]-5-[(5-fluoro-2-pyridyl)methoxy]imidazo[1,2-a]pyridine-3-carbonitrile | 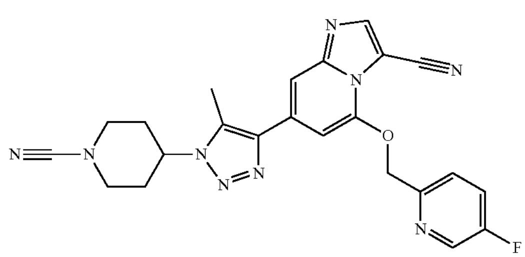 [SMILES: Cc1c(-c2cc(OCc3ccc(F)cn3)n3c(C#N)cnc3c2)nnn1C1CCN(C#N)CC1] | 458.2 | |
| 269[14] | 5-[(1R)-1-(5-Chloro-2-pyridyl)ethoxy]-7-[1-(1-cyano-4-piperidyl)-5-methyl-triazol-4-yl]imidazo[1,2-a]pyridine-3-carbonitrile | 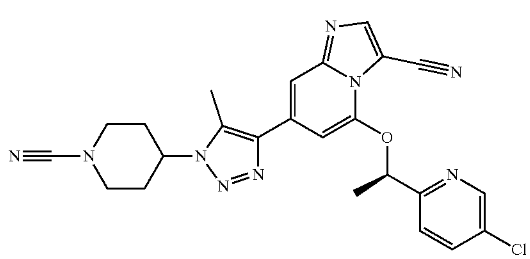 [SMILES: Cc1c(-c2cc(O[C@H](C)c3ccc(Cl)cn3)n3c(C#N)cnc3c2)nnn1C1CCN(C#N)CC1] | 488.15 | |

TABLE 68-continued

| Ex. No. | Chemical name | Structure | ES/M m/z [M + H]+ | Elution Gradient |
|---|---|---|---|---|
| 270[15] | 6-[1-(1-Cyano-4-piperidyl)-5-methyl-triazol-4-yl]-4-[(1R)-1-(5-fluoro-2-pyridyl)ethoxy]pyrazolo[1,5-a]pyridine-3-carbonitrile | 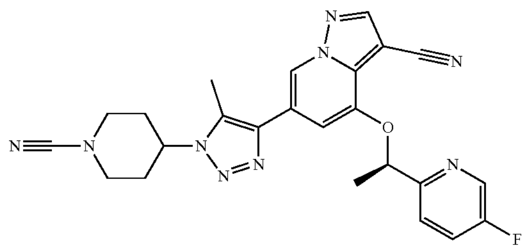 [SMILES: Cc1c(-c2cc(O[C@H](C)c3ccc(F)cn3)c3c(C#N)cnn3c2)nnn1C1CCN(C#N)CC1] | 472.2 | 33-52% |
| 271 | 4-[4-[4-[(1R)-1-(5-Fluoro-2-pyridyl)ethoxy]-3-isothiazol-4-yl-pyrazolo[1,5-a]pyridin-6-yl]-5-methyl-triazol-1-yl]piperidine-1-carbonitrile | 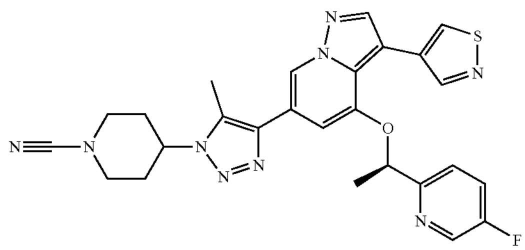 [SMILES: Cc1c(-c2cc(O[C@H](C)c3ccc(F)cn3)c3c(-c4cnsc4)cnn3c2)nnn1C1CCN(C#N)CC1] | 530.3 | 50-70% |
| 272 | 4-[4-[3-Cyclopropyl-4-[(1R)-1-(5-fluoro-2-pyridyl)ethoxy]pyrazolo[1,5-a]pyridin-6-yl]-5-methyl-triazol-1-yl]piperidine-1-carbonitrile | 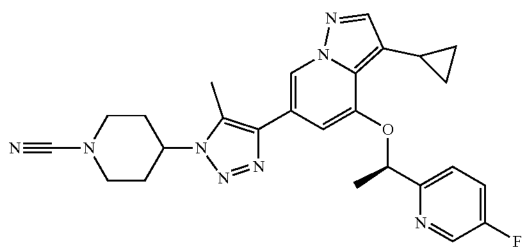 [SMILES: Cc1c(-c2cc(O[C@H](C)c3ccc(F)cn3)c3c(C4CC4)cnn3c2)nnn1C1CCN(C#N)CC1] | 486.8 | 0-100% |
| 273 | 7-[1-(1-Cyano-4-piperidyl)-3-(2-hydroxyethyl)-5-methyl-pyrazol-4-yl]-5-[(1R)-1-(5-fluoro-2-pyridyl)ethoxy]imidazo[1,2-a]pyridine-3-carbonitrile | 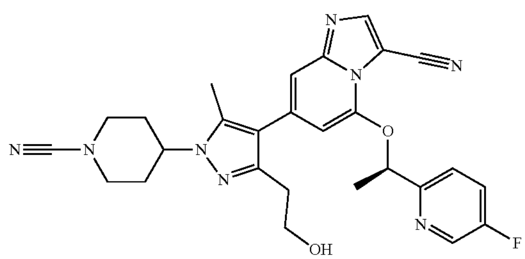 [SMILES: Cc1c(-c2cc(O[C@H](C)c3ccc(F)cn3)n3c(C#N)cnc3c2)c(CCO)nn1C1CCN(C#N)CC1] | 515.4 | 40-50% |
| 274[16] | 7-[1-(1-Cyano-4-piperidyl)-5-methyl-triazol-4-yl]-5-[(1R)-1-[4-(2,2,2-trifluoroethyl)-1,2,4-triazol-3-yl]ethoxy]imidazo[1,2-a]pyridine-3-carbonitrile | 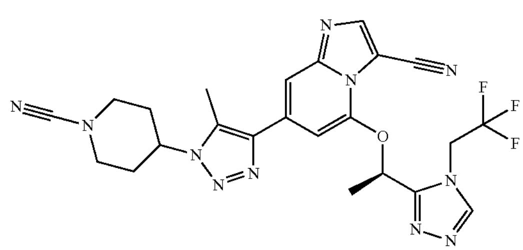 [SMILES: Cc1c(-c2cc(O[C@H](C)c3nncn3CC(F)(F)F)n3c(C#N)cnc3c2)nnn1C1CCN(C#N)CC1] | 526.1 | |
| 275[9] | 7-[1-[2-(4-Cyanopiperazin-1-yl)-2-methyl-propyl]-5-methyl-triazol-4-yl]-5-[(1R)-1-(2-pyridyl)ethoxy]imidazo[1,2-a]pyridine-3-carbonitrile | 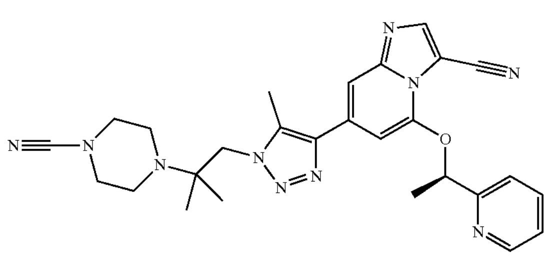 [SMILES: Cc1c(-c2cc(O[C@H](C)c3ccccn3)n3c(C#N)cnc3c2)nnn1CC(C)(C)N1CCN(C#N)CC1] | 511.4 | |

TABLE 68-continued

| Ex. No. | Chemical name | Structure | ES/M m/z [M + H]+ | Elution Gradient |
|---|---|---|---|---|
| 276[17] | (3R,4S)-4-[4-[3-chloro-4-[1-(5-fluoro-2-pyridyl)-2-hydroxy-ethoxy]pyrazolo[1,5-a]pyridin-6-yl]-5-methyl-triazol-1-yl]-3-fluoro-piperidine-1-carbonitrile, Isomer 2 | 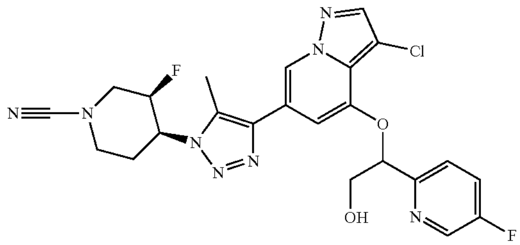 [SMILES: Cc1c(-c2cc(OC(CO)c3ccc(F)cn3)c3c(Cl)cnn3c2)nnn1[C@H]1CCN(C#N)C[C@H]1F] | 515.2 | 50-60% |
| 277 | (3S,4S)-4-[4-[3-Chloro-4-[1-(5-fluoro-2-pyridyl)-2-hydroxy-ethoxy]pyrazolo[1,5-a]pyridin-6-yl]-5-methyl-triazol-1-yl]-3-fluoro-piperidine-1-carbonitrile, Isomer 2 | 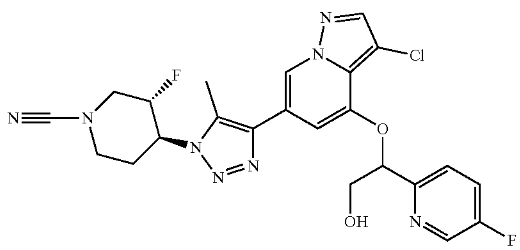 [SMILES: Cc1c(-c2cc(OC(CO)c3ccc(F)cn3)c3c(Cl)cnn3c2)nnn1[C@H]1CCN(C#N)C[C@@H]1F] | 515.1 | 40-60% |
| 278 | (3S,4R)-4-[4-[3-Chloro-4-[1-(5-fluoro-2-pyridyl)-2-hydroxy-ethoxy]pyrazolo[1,5-a]pyridin-6-yl]-5-methyl-triazol-1-yl]-3-fluoro-piperidine-1-carbonitrile, Isomer 2 | 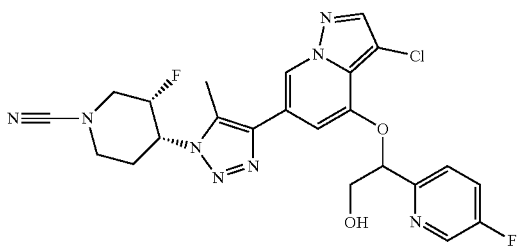 [SMILES: Cc1c(-c2cc(OC(CO)c3ccc(F)cn3)c3c(Cl)cnn3c2)nnn1[C@@H]1CCN(C#N)C[C@@H]1F] | 515.2 | 40-50% |
| 279 | (3R,4R)-4-[4-[3-Chloro-4-[1-(5-fluoro-2-pyridyl)-2-hydroxy-ethoxy]pyrazolo[1,5-a]pyridin-6-yl]-5-methyl-triazol-1-yl]-3-fluoro-piperidine-1-carbonitrile, Isomer 2 | 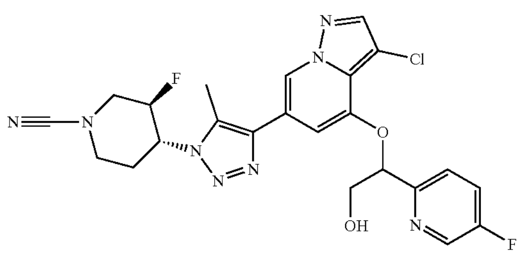 [SMILES: Cc1c(-c2cc(OC(CO)c3ccc(F)cn3)c3c(Cl)cnn3c2)nnn1[C@@H]1CCN(C#N)C[C@H]1F] | 515.20 | 40-60% |
| 280[18,19] | 7-((1s,3s)-3-(4-(3-Chloro-4-((S)-1-(5-fluoropyridin-2-yl)-2-hydroxyethoxy)pyrazolo[1,5-a]pyridin-6-yl)-5-methyl-1H-1,2,3-triazol-1-yl)cyclobutyl)-3-oxa-7,9-diazabicyclo[3.3.1]nonane-9-carbonitrile, Isomer 2 | 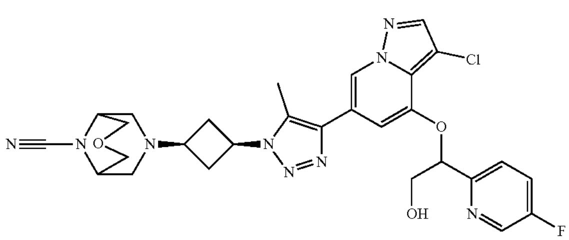 [SMILES: Cc1c(-c2cc(OC(CO)c3ccc(F)cn3)c3c(Cl)cnn3c2)nnn1[C@H]1C[C@@H](N2CC3COCC(C2)N3C#N)C1] | 594.4 | 10-95% |
| 281[20,21] | 7-[1-[(2SR,4RS)-1-cyano-2-cyclopropyl-4-piperidyl]-5-methyl-triazol-4-yl]-5-[(1R)-1-(2-pyridyl)ethoxy]imidazo[1,2-a]pyridine-3-carbonitrile, Isomer 1 | 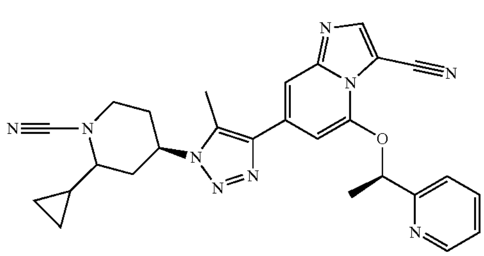 [SMILES: Cc1c(-c2cc(O[C@H](C)c3ccccn3)n3c(C#N)cnc3c2)nnn1[C@@H]1CCN(C#N)C(C2CC2)C1] | 494.4 | 30-52% |

TABLE 68-continued

| Ex. No. | Chemical name | Structure | ES/M m/z [M + H]+ | Elution Gradient |
|---|---|---|---|---|
| 282[23] | (3S,4S)-4-[4-[3-Chloro-4-[1-(5-fluoro-2-pyridyl)-2-hydroxy-ethoxy]pyrazolo[1,5-a]pyridin-6-yl]-5-methyl-triazol-1-yl]-3-hydroxy-piperidine-1-carbonitrile, Isomer 2 | 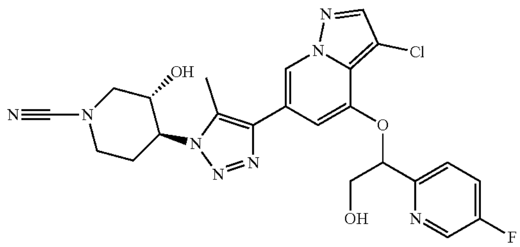 [SMILES: Cc1c(-c2cc(OC(CO)c3ccc(F)cn3)c3c(Cl)cnn3c2)nnn1[C@H]1CCN(C#N)C[C@@H]1O] | 513.1 | 30-45% |
| 283[22] | (3R,4S)-4-[4-[3-Chloro-4-[1-(5-fluoro-2-pyridyl)-2-hydroxy-ethoxy]pyrazolo[1,5-a]pyridin-6-yl]-5-methyl-triazol-1-yl]-3-hydroxy-piperidine-1-carbonitrile, Isomer 2 | 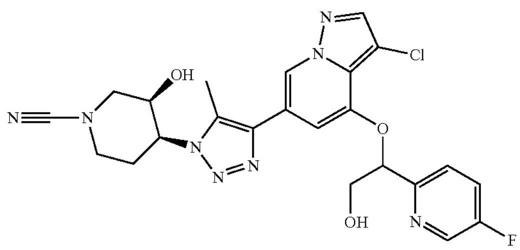 [SMILES: Cc1c(-c2cc(OC(CO)c3ccc(F)cn3)c3c(Cl)cnn3c2)nnn1[C@H]1CCN(C#N)C[C@H]1O] | 513.2 | |
| 284[22] | (3S,4R)-4-[4-[3-Chloro-4-[1-(5-fluoro-2-pyridyl)-2-hydroxy-ethoxy]pyrazolo[1,5-a]pyridin-6-yl]-5-methyl-triazol-1-yl]-3-hydroxy-piperidine-1-carbonitrile, Isomer 2 | 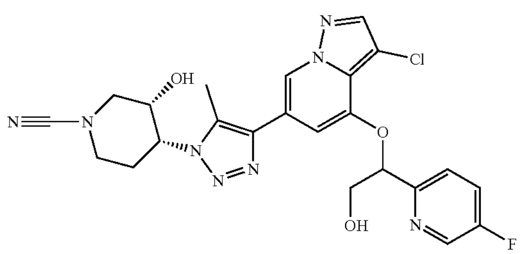 | 513.1 | |
| 285[9] | (3R,4R)-4-[4-[3-Chloro-4-[1-(5-fluoro-2-pyridyl)-2-hydroxy-ethoxy]pyrazolo[1,5-a]pyridin-6-yl]-5-methyl-triazol-1-yl]-3-hydroxy-piperidine-1-carbonitrile, Isomer 2 | 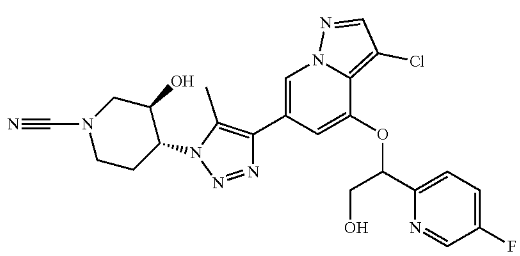 [SMILES: Cc1c(-c2cc(OC(CO)c3ccc(F)cn3)c3c(Cl)cnn3c2)nnn1[C@@H]1CCN(C#N)C[C@H]1O] | 513.2 | |

TABLE 68-continued

| Ex. No. | Chemical name | Structure | ES/M m/z [M + H]+ | Elution Gradient |
|---|---|---|---|---|
| 286 | 4-[4-[3-Fluoro-4-[1-(5-fluoro-2-pyridyl)-2-hydroxy-ethoxy]pyrazolo[1,5-a]pyridin-6-yl]-5-methyl-triazol-1-yl]-4-methyl-piperidine-1-carbonitrile, Isomer 2 | 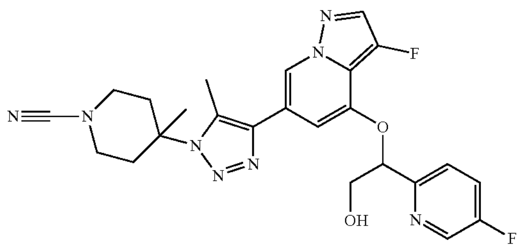 [SMILES: Cc1c(-c2cc(OC(CO)c3ccc(F)cn3)c3c(F)cnn3c2)nnn1C1(C)CCN(C#N)CC1] | 495.2 | 40-50% |

[1] XBridge30 Prep C18 OBD Column, 19*150 mm, 5 μm, mobile phase A: H₂O (10 mmol/L NH₄HCO₃), mobile phase B: ACN.
[2] Reverse flash chromatography: Column C18 silica gel, mobile phase A: H₂O (0.1% NH₃•H₂O), mobile phase B: ACN.
[3] XBridge Shield RP18 OBD Column, 19*150 mm, 5 μm, mobile phase A: H₂O (10 mmol/L NH₄HCO₃), mobile phase B: ACN.
[4] Prep-TLC (PE:EtOAc 1:2)
[5] Prep-TLC (DCM:MeOH 20:1).
[6] Reverse flash chromatography: column C18 silica gel, mobile phase A: H₂O (0.1% NH₄HCO₃), mobile phase B: ACN.
[7] XBridge Shield RP18 OBD Column, 19*150 mm, 5 μm, mobile phase A: H₂O (10 mmol/L NH₄HCO₃), mobile phase B: MeOH.
[8] Reverse Flash Chromatography: Column C18 silica gel, mobile phase A: H₂O (0.1% FA), mobile phase B: ACN.
[9] Prep-TLC (EtOAc:PE 1:1).
[10] Prep-TLC (EtOAc:PE 10:1).
[11] Reverse flash chromatography: Column C18 silica gel, mobile phase A: H₂O, mobile phase B: ACN.
[12] Reverse Flash Chromatography: Column C18 silica gel, mobile phase A: H₂O (0.1% NH₄HCO₃), mobile phase B: ACN.
[13] Reverse Flash Chromatography: Column C18 silica gel, mobile phase A: H₂O (0.1% FA), mobile phase B: ACN.
[14] Purification by trituration with iPrOH (5 mL).
[15] XBridge Shield RP18 OBD Column, 19*150 mm, 5 μm, mobile phase A: H₂O (0.05% NH₄OH), mobile phase B: ACN.
[16] Prep-TLC (DCM:MeOH 10:1).
[17] Reverse flash chromatography: Column C18 silica, gel eluting with a gradient of 50% to 60% ACN in H₂O.
[18] Reverse chromatography, Column C18 silica gel, eluting with ACN in H₂O (0.1% FA).
[19] After reverse phase purification fractions containing crude material are combined, pH adjusted to ~9.0 using sat. NaHCO₃. Material extracted with 3:1 CHCL₃:IPA. Organic phase is washed with H₂O, brine, dried over Na₂SO₄, filtered, and concentrated to a brown residue. Residue purified by reverse phase chromatography, eluting with 0% to 100% MeOH in DCM.
[20] Purified by reverse chromatography; Column: XSelect CSH Prep C18 OBD, eluting with ACN in H₂O (0.1% FA).
[21] ¹H NMR (400 MHz, DMSO-d6) δ 8.59 (dt, 1H), 8.48 (s, 1H), 7.86 (td, 1H), 7.64 (d, 1H), 7.57 (s, 1H), 7.37 (ddd, 1H), 6.82 (d, 1H), 6.02 (q, 1H), 4.67-4.43 (m, 1H), 3.66-3.51 (m, 1H), 3.29-3.11 (m, 1H), 2.47-2.36 (m, 4H), 2.22-1.91 (m, 4H), 1.80 (d, 3H), 1.05-0.86 (m, 1H), 0.70-0.61 (m, 1H), 0.59-0.51 (m, 1H), 0.49-0.42 (m, 1H), 0.35-0.22 (m, 1H).
[22] Purified by Prep-TLC (EA).
[23] Reverse chromatography, Column C18 silica gel, eluting with 30% to 45% ACN in H₂O (0.1% FA).

Example 287

(4R)-4-(4-[3-Cyano-4-methoxypyrazolo[1,5-a]pyridin-6-yl]-5-methylpyrazol-1-yl)azepane-1-carbonitrile

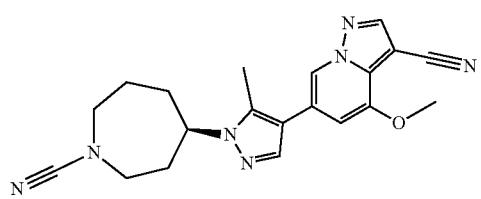 [SMILES: COc1cc(-c2cnn([C@@H]3CCCN(C#N)CC3)c2C)cn2ncc(C#N)c12]

BrCN (22.22 mg, 0.21 mmol) in DCM (1 mL) is added dropwise to a stirred solution of 6-[1-[(4R)-azepan-4-yl]-5-methylpyrazol-4-yl]-4-methoxypyrazolo[1,5-a]pyridine-3-carbonitrile (70 mg, 0.20 mmol) and DIEA (260 mg, 2.0 mmol) in DCM (6 mL). The mixture is stirred for 3 hrs at RT under N₂ and then diluted with DCM (50 mL). The organic layers are washed with sat. NaHCO₃ (aq.) (2×40 mL), dried over anhydrous Na₂SO₄, filtered, and the filtrate is concentrated under reduced pressure. The residue is purified by reverse Combi-flash chromatography with the following conditions: Column, C18; eluting with a gradient of 0% to 100% ACN in H₂O (0.1% NH₄HCO₃) to give the title compound as an off-white solid (25.6 mg, 38%). ES/MS m/z 376.2 [M+H]+.

The following compounds are prepared essentially as described for (4R)-4-(4-[3-cyano-4-methoxypyrazolo[1,5-a]pyridin-6-yl]-5-methylpyrazol-1-yl)azepane-1-carbonitrile using the appropriate reagents, adjusting the reaction time to determine completion of the reaction, and adjusting the purification system as appropriate.

TABLE 69

| Ex. No. | Chemical name | Structure | ES/MS m/z [M + H]+ |
|---|---|---|---|
| 288[1] | (4S)-4-(4-[3-Cyano-4-methoxypyrazolo[1,5-a]pyridin-6-yl]-5-methylpyrazol-1-yl)azepane-1-carbonitrile | 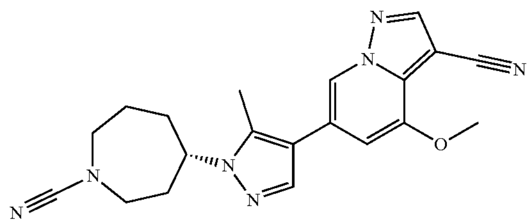 [SMILES: COc1cc(-c2cnn([C@H]3CCCN(C#N)CC3)c2C)cn2ncc(C#N)c12] | 376.1 |
| 289[2,3,11] | 6-[5-(4-cyanopiperazin-1-yl)-4-methyl-1,2,4-triazol-3-yl]-4-methoxy-pyrazolo[1,5-a]pyridine-3-carbonitrile | 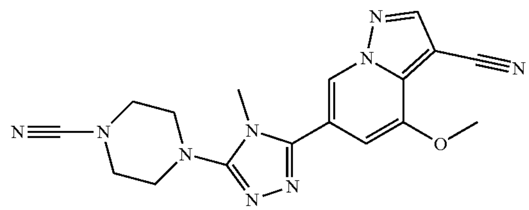 [SMILES: COc1cc(-c2nnc(N3CCN(C#N)CC3)n2C)cn2ncc(C#N)c12] | 363.1 |
| 290[4] | 7-[1-(1-cyano-4-piperidyl)-5-methyl-triazol-4-yl]-5-[(1R)-1-(3-pyridyl)ethoxy]imidazo[1,2-a]pyridine-3-carbonitrile | 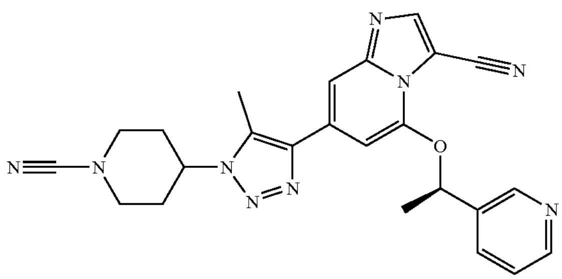 [SMILES: Cc1c(-c2cc(O[C@H](C)c3cccnc3)n3c(C#N)cnc3c2)nnn1C1CCN(C#N)CC1] | 454.1 |
| 291[5] | 6-[1-(1-Cyano-4-piperidyl)-5-methyl-triazol-4-yl]-4-[(1R)-1-(2-methylthiazol-4-yl)ethoxy]pyrazolo[1,5-a]pyridine-3-carbonitrile | 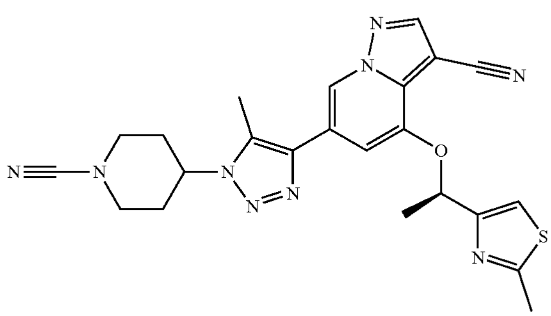 [SMILES: Cc1nc([C@@H](C)Oc2cc(-c3nnn(C4CCN(C#N)CC4)c3C)cn3ncc(C#N)c23)cs1] | 474.1 |
| 292[5] | 6-[1-(1-Cyano-4-piperidyl)-5-methyl-triazol-4-yl]-4-[(1R)-1-(1-methylpyrazol-3-yl)ethoxy]pyrazolo[1,5-a]pyridine-3-carbonitrile | 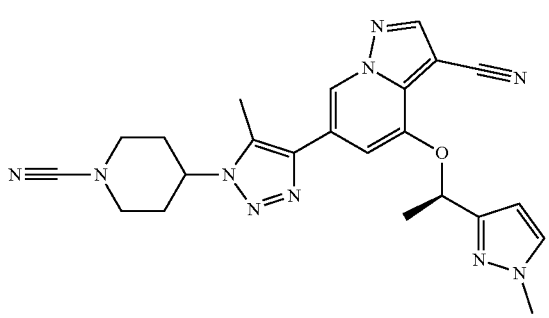 [SMILES: Cc1c(-c2cc(O[C@H](C)c3ccn(C)n3)c3c(C#N)cnn3c2)nnn1C1CCN(C#N)CC1] | 457.1 |

TABLE 69-continued

| Ex. No. | Chemical name | Structure | ES/MS m/z [M + H]+ |
|---|---|---|---|
| 293[6] | 7-[1-(1-Cyano-4-piperidyl)-5-methyl-triazol-4-yl]-5-[(1R)-1-(2,4-difluorophenyl)ethoxy]imidazo[1,2-a]pyridine-3-carbonitrile | 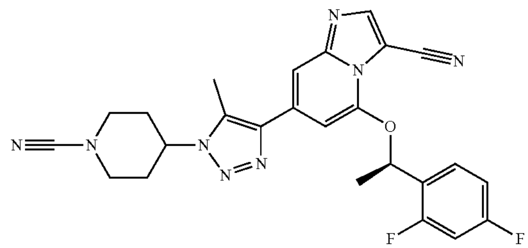 [SMILES: Cc1c(-c2cc(O[C@H](C)c3ccc(F)cc3F)n3c(C#N)cnc3c2)nnn1C1CCN(C#N)CC1] | 487.2 |
| 294[7] | 7-[1-(1-Cyano-4-piperidyl)-5-methyl-triazol-4-yl]-5-[(1R)-1-(4-fluorophenyl)ethoxy]imidazo[1,2-a]pyridine-3-carbonitrile | 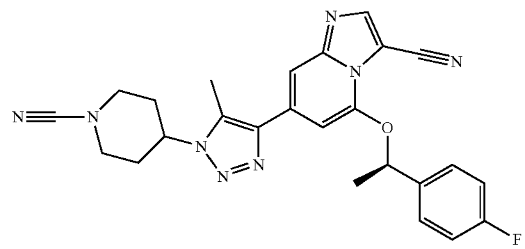 [SMILES: Cc1c(-c2cc(O[C@H](C)c3ccc(F)cc3)n3c(C#N)cnc3c2)nnn1C1CCN(C#N)CC1] | 471.2 |
| 295[8,10,9] | 7-[1-(1-Cyano-4-piperidyl)-5-methyl-pyrazol-4-yl]-5-[(1R)-1-(5-fluoro-2-pyridyl)ethoxy]imidazo[1,2-c]pyrimidine-3-carbonitrile | 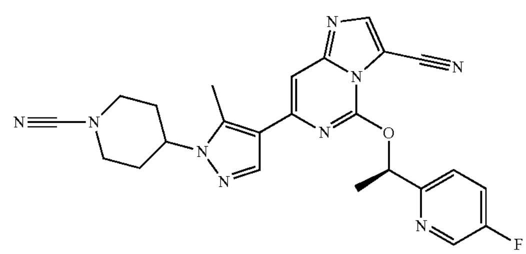 [SMILES: Cc1c(-c2cc3ncc(C#N)n3c(O[C@H](C)c3ccc(F)cn3)n2)cnn1C1CCN(C#N)CC1] | 472.2 |
| 296[8,9,3] | 4-[4-[3-Chloro-5-[(1R)-1-(5-fluoro-2-pyridyl)ethoxy]imidazo[1,2-c]pyrimidin-7-yl]-5-methyl-pyrazol-1-yl]piperidine-1-carbonitrile | 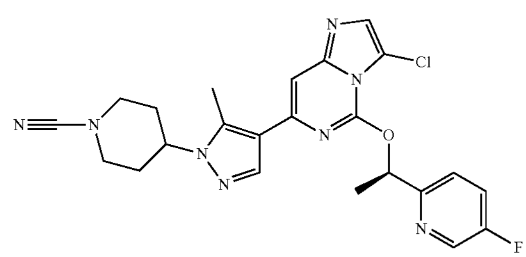 [SMILES: Cc1c(-c2cc3ncc(Cl)n3c(O[C@H](C)c3ccc(F)cn3)n2)cnn1C1CCN(C#N)CC1] | 481.2 |

[1] Prep-TLC (PE:EtOAc 1:1), aqueous phase is quenched with NaClO solution at RT.
[2] Purified by reverse phase chromatography eluting with 10% to 95% ACN in H$_2$O (0.1% FA).
[3] Purified by reverse phase chromatography eluting with 0% to 10% MeOH in DCM.
[4] Purified by reverse flash phase chromatography eluting with 10% to 50% ACN in H$_2$O.
[5] Purified by reverse phase chromatography eluting with 0% to 100% ACN in H$_2$O (0.1% FA).
[6] Purified by reverse phase chromatography eluting with ACN in H$_2$O (0.1% FA).
[7] Purified by reverse phase chromatography eluting with 60% to 70% ACN in H$_2$O (0.1% NH$_4$HCO$_3$).
[8] Reaction is diluted with diluted with 3:1 CHCl$_3$:IPA, washed with water, brine, dried over Na$_2$SO$_4$, filtered and concentrated in vacuo.
[9] Purified by reverse phase chromatography eluting with 10% to 95% ACN in H$_2$O (0.1% FA). Fractions containing title compound are combined and pH adjusted to ~9.0 with aq. NaHCO$_3$. Mixture extracted with 3:1 CHCl$_3$:IPA. Organic phase washed with water, brine, dried over Na$_2$SO$_4$, filtered and concentrated in vacuo.
[10] Purified by reverse phase chromatography eluting with 10% to 100% ACN in H2O.

Example 297

4-[4-[3-Chloro-4-[(1R)-1-(2-cyanophenyl)ethoxy]pyrazolo[1,5-a]pyridin-6-yl]-5-methyl-pyrazol-1-yl]piperidine-1-carbonitrile

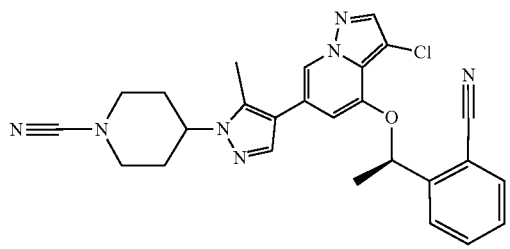 [SMILES: Cc1c(-c2cc(O[C@H](C)c3ccccc3C#N)c3c(Cl)cnn3c2)cnn1C1CCN(C#N)CC1]

A solution of 4-(4-[4-[(1R)-1-(2-cyanophenyl)ethoxy]pyrazolo[1,5-a]pyridin-6-yl]-5-methylpyrazol-1-yl)piperidine-1-carbonitrile (73 mg, 0.162 mmol) and 1,3-dichloro-5,5-dimethylimidazolidine-2,4-dione (16 mg, 0.081 mmol) in DCM (5 mL) is stirred for 1 hr at RT under $N_2$. The reaction is quenched with sat. aq. $NaHCO_3$. The mixture is extracted with DCM (100 mL). The combined organic layers are washed with brine (10 mL) then concentrated in vacuo. The residue is purified by reverse flash chromatography: Column, C18; mobile phase, eluting with 10% to 70% ACN in $H_2O$ (0.1% $NH_4HCO_3$), 254 nm to afford the title compound (60 mg, 76.37%) as a white solid (60 mg, 76%). ES/MS m/z 486.0 [M+H]+.

Example 298

4-[4-[3-Chloro-4-[2-(2,2-difluoroethylamino)-1-(5-fluoro-2-pyridyl)ethoxy]pyrazolo[1,5-a]pyridin-6-yl]-5-methyl-triazol-1-yl]piperidine-1-carbonitrile, Isomer 2

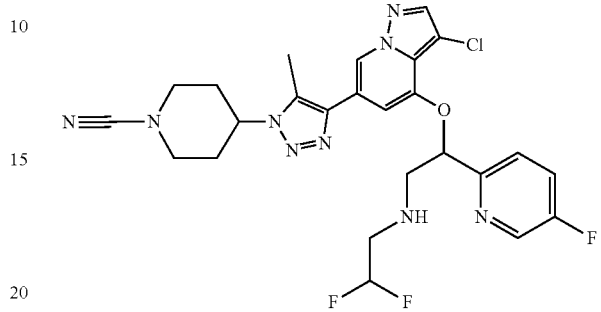

To a solution of 4-(4-(3-chloro-4-(1-(5-fluoropyridin-2-yl)-2-hydroxyethoxy) pyrazolo[1,5-a]pyridin-6-yl)-5-methyl-1H-1,2,3-triazol-1-yl)piperidine-1-carbonitrile (150 mg, 0.302 mmol) and DIPEA (117 mg, 0.906 mmol) in DCM (1.5 mL) at −78 C is added $Tf_2O$ (111 mg, 0.392 mmol). The cooling bath is then switched to a brine/ice bath and the reaction is stirred 1 hr at −20° C. Next, a solution of 2,2-difluoroethan-1-amine (24.5 mg, 0.302 mmol) in DCM (0.5 mL) is slowly added to the reaction and the cooling bath is allowed to expire overnight. The reaction mixture is diluted with DCM (10 mL) and washed with $NaHCO_3$ (10 mL), brine (10 mL), and the layers are separated. The organic layer is concentrated in vacuo. The residue is purified by reverse phase chromatography eluting with a gradient of 0% to 100% ACN in $H_2O$ to afford the title compound (110 mg, 65%). ES/MS m/z 560.4 [M+H]+.

The following compounds can be prepared essentially as described in the methods above.

TABLE 70

| Ex. No. | Chemical name | Structure |
| --- | --- | --- |
| 299 | (3S,4S)-4-[4-[3-Chloro-4-[(1S)-1-(5-fluoro-2-pyridyl)-2-hydroxy-ethoxy]pyrazolo[1,5-a]pyridin-6-yl]-5-methyl-pyrazol-1-yl]-3-hydroxy-piperidine-1-carbonitrile | 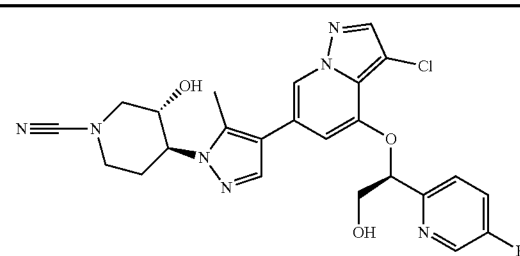 |
| 300 | (3S,4S)-4-[4-[3-Chloro-4-[(1R)-1-(5-fluoro-2-pyridyl)ethoxy]pyrazolo[1,5-a]pyridin-6-yl]-5-methyl-triazol-1-yl]-3-hydroxy-piperidine-1-carbonitrile | 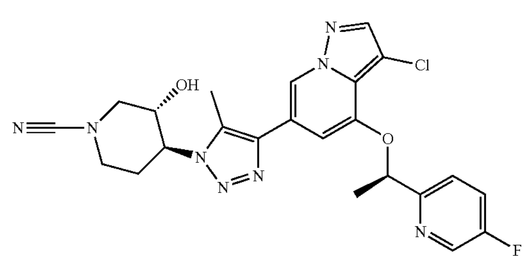 [SMILES: Cc1c(-c2cc(O[C@H](C)c3ccc(F)cn3)c3c(Cl)cnn3c2)nnn1[C@H]1CCN(C#N)C[C@@H]1O] |

TABLE 70-continued

| Ex. No. | Chemical name | Structure |
|---|---|---|
| 301 | (3S,4S)-4-[4-[3-Chloro-4-[(1S)-2,2,2-trifluoro-1-(5-fluoro-2-pyridyl)ethoxy]pyrazolo[1,5-a]pyridin-6-yl]-5-methyl-triazol-1-yl]-3-hydroxy-piperidine-1-carbonitrile | 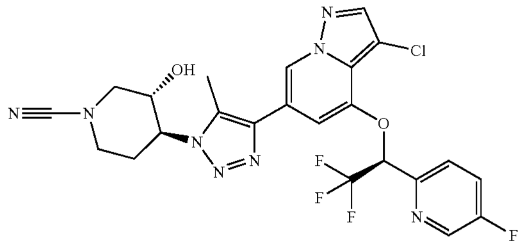 [SMILES: Cc1c(-c2cc(O[C@@H](c3ccc(F)cn3)C(F)(F)F)c3c(Cl)cnn3c2)nnn1[C@H]1CCN(C#N)C[C@@H]1O] |
| 302 | (3S,4S)-4-[4-[3-Chloro-4-[(1S)-2-fluoro-1-(5-fluoro-2-pyridyl)ethoxy]pyrazolo[1,5-a]pyridin-6-yl]-5-methyl-triazol-1-yl]-3-hydroxy-piperidine-1-carbonitrile | 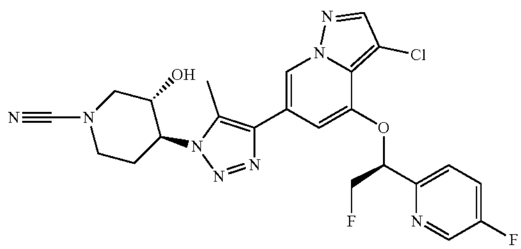 [SMILES: Cc1c(-c2cc(O[C@H](CF)c3ccc(F)cn3)c3c(Cl)cnn3c2)nnn1[C@H]1CCN(C#N)C[C@@H]1O] |
| 303 | (3S,4S)-4-[4-[3-Chloro-4-[2-(5-fluoro-2-pyridyl)-2-hydroxy-propoxy]pyrazolo[1,5-a]pyridin-6-yl]-5-methyl-triazol-1-yl]-3-hydroxy-piperidine-1-carbonitrile | 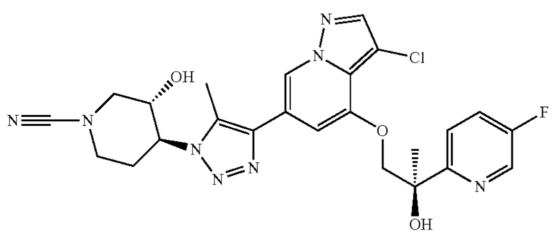 |
| 304 | (3S,4S)-4-[4-[3Chloro-4-[2-(5-fluoro-2-pyridyl)-2-hydroxy-propoxy]pyrazolo[1,5-a]pyridin-6-yl]-5-methyl-triazol-1-yl]-3-hydroxy-piperidine-1-carbonitrile | 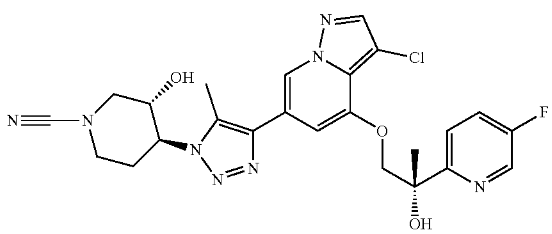 |
| 305 | (3R,4R)-4-[4-[3-Fluoro-4-[(1S)-1-(5-fluoro-2-pyridyl)-2-hydroxy-ethoxy]pyrazolo[1,5-a]pyridin-6-yl]-5-methyl-triazol-1-yl]-3-methyl-piperidine-1-carbonitrile | 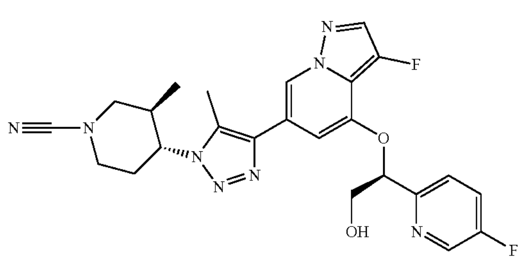 [SMILES: Cc1c(-c2cc(O[C@H](CO)c3ccc(F)cn3)c3c(F)cnn3c2)nnn1[C@@H]1CCN(C#N)C[C@H]1C] |
| 306 | (3R,4S)-4-[4-[3-Fluoro-4-[(1S)-1-(5-fluoro-2-pyridyl)-2-hydroxy-ethoxy]pyrazolo[1,5-a]pyridin-6-yl]-5-methyl-triazol-1-yl]-3-methyl-piperidine-1-carbonitrile | 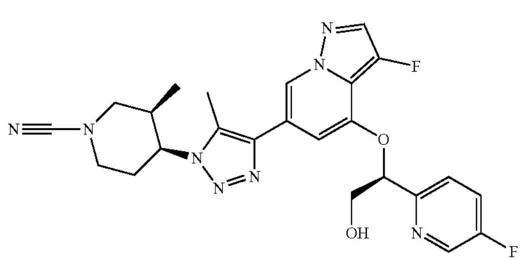 [SMILES: Cc1c(-c2cc(O[C@H](CO)c3ccc(F)cn3)c3c(F)cnn3c2)nnn1[C@H]1CCN(C#N)C[C@H]1C] |

TABLE 70-continued

| Ex. No. | Chemical name | Structure |
|---|---|---|
| 307 | (3S,4S)-4-[4-[3-Fluoro-4-[(1S)-1-(5-fluoro-2-pyridyl)-2-hydroxy-ethoxy]pyrazolo[1,5-a]pyridin-6-yl]-5-methyl-triazol-1-yl]-3-methyl-piperidine-1-carbonitrile | 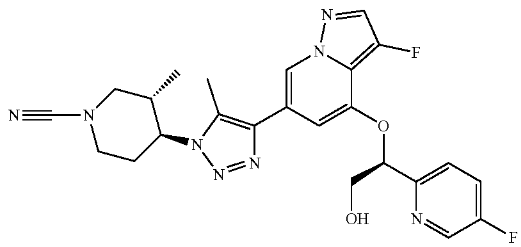 |
| 308 | (3S,4R)-4-[4-[3-Fluoro-4-[(1S)-1-(5-fluoro-2-pyridyl)-2-hydroxy-ethoxy]pyrazolo[1,5-a]pyridin-6-yl]-5-methyl-triazol-1-yl]-3-methyl-piperidine-1-carbonitrile | 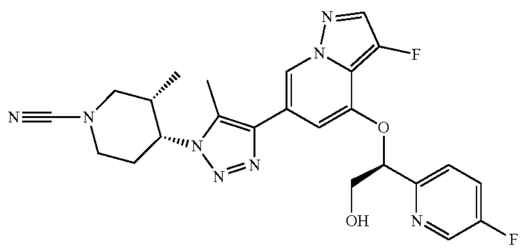 |
| 309 | (3R,4S)-3-Fluoro-4-[4-[3-fluoro-4-[(2S)-2-(5-fluoro-2-pyridyl)-2-hydroxy-ethoxy]pyrazolo[1,5-a]pyridin-6-yl]-5-methyl-triazol-1-yl]piperidine-1-carbonitrile | 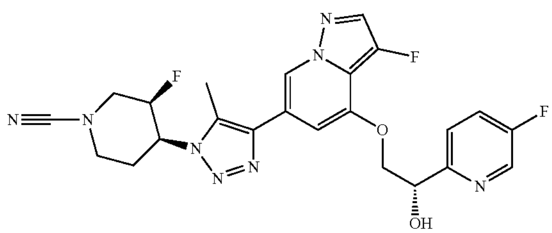 [SMILES: Cc1c(-c2cc(OC[C@@H](O)c3ccc(F)cn3)c3c(F)cnn3c2)nnn1[C@H]1CCN(C#N)C[C@H]1F] |
| 310 | (3R,4S)-3-Fluoro-4-[4-[3-fluoro-4-[(2R)-2-(5-fluoro-2-pyridyl)-2-hydroxy-ethoxy]pyrazolo[1,5-a]pyridin-6-yl]-5-methyl-triazol-1-yl]piperidine-1-carbonitrile | 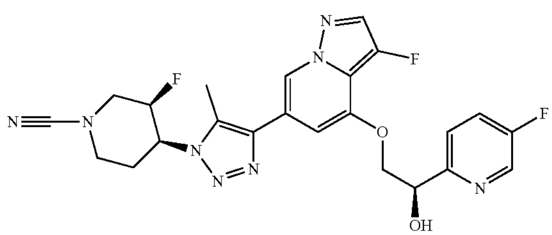 [SMILES: Cc1c(-c2cc(OC[C@H](O)c3ccc(F)cn3)c3c(F)cnn3c2)nnn1[C@H]1CCN(C#N)C[C@H]1F] |
| 311 | (3R,4S)-3-Fluoro-4-[4-[3-fluoro-4-[2-(5-fluoro-2-pyridyl)-2-hydroxy-propoxy]pyrazolo[1,5-a]pyridin-6-yl]-5-methyl-triazol-1-yl]piperidine-1-carbonitrile | 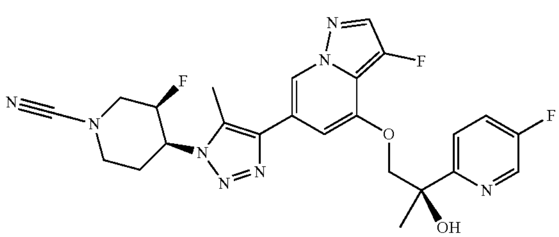 [SMILES: Cc1c(-c2cc(OC[C@](C)(O)c3ccc(F)cn3)c3c(F)cnn3c2)nnn1[C@H]1CCN(C#N)C[C@H]1F] |
| 312 | (3R,4S)-3-fluoro-4-[4-[3-fluoro-4-[2-(5-fluoro-2-pyridyl)-2-hydroxy-propoxy]pyrazolo[1,5-a]pyridin-6-yl]-5-methyl-triazol-1-yl]piperidine-1-carbonitrile | 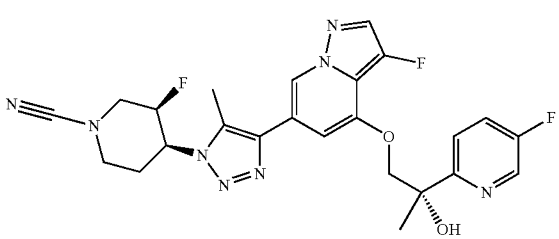 [SMILES: Cc1c(-c2cc(OC[C@@](C)(O)c3ccc(F)cn3)c3c(F)cnn3c2)nnn1[C@H]1CCN(C#N)C[C@H]1F] |

TABLE 70-continued

| Ex. No. | Chemical name | Structure |
|---|---|---|
| 313 | (3R,4R)-3-fluoro-4-[4-[3-fluoro-4-[(1S)-1-(5-fluoro-2-pyridyl)-2-hydroxy-ethoxy]pyrazolo[1,5-a]pyridin-6-yl]-5-methyl-triazol-1-yl]piperidine-1-carbonitrile | 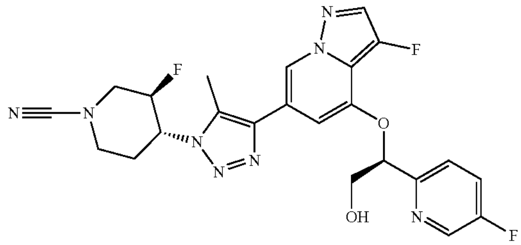 [SMILES: Cc1c(-c2cc(O[C@H](CO)c3ccc(F)cn3)c3c(F)cnn3c2)nnn1[C@@H]1CCN(C#N)C[C@H]1F] |
| 314 | (3R,4S)-3-fluoro-4-[4-[3-fluoro-4-[(1S)-1-(5-fluoro-2-pyridyl)-2-hydroxy-ethoxy]pyrazolo[1,5-a]pyridin-6-yl]-5-methyl-triazol-1-yl]piperidine-1-carbonitrile | 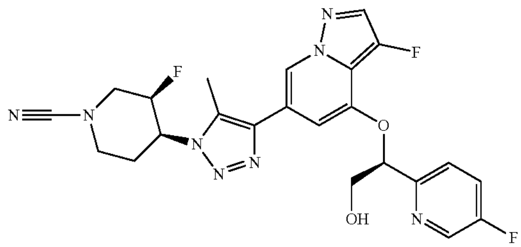 [SMILES: Cc1c(-c2cc(O[C@H](CO)c3ccc(F)cn3)c3c(F)cnn3c2)nnn1[C@H]1CCN(C#N)C[C@H]1F] |
| 315 | (3S,4S)-3-fluoro-4-[4-[3-fluoro-4-[(1S)-1-(5-fluoro-2-pyridyl)-2-hydroxy-ethoxy]pyrazolo[1,5-a]pyridin-6-yl]-5-methyl-triazol-1-yl]piperidine-1-carbonitrile | 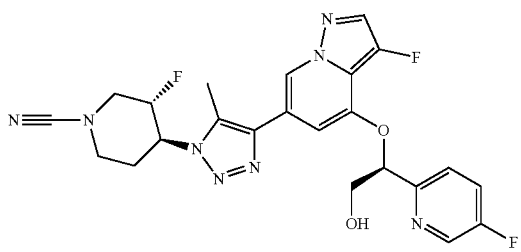 [SMILES: Cc1c(-c2cc(O[C@H](CO)c3ccc(F)cn3)c3c(F)cnn3c2)nnn1[C@H]1CCN(C#N)C[C@@H]1F] |
| 316 | (3S,4R)-3-fluoro-4-[4-[3-fluoro-4-[(1S)-1-(5-fluoro-2-pyridyl)-2-hydroxy-ethoxy]pyrazolo[1,5-a]pyridin-6-yl]-5-methyl-triazol-1-yl]piperidine-1-carbonitrile | 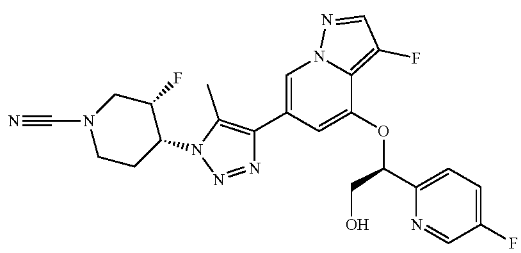 [SMILES: Cc1c(-c2cc(O[C@H](CO)c3ccc(F)cn3)c3c(F)cnn3c2)nnn1[C@@H]1CCN(C#N)C[C@@H]1F] |

Biological Assays

The following assays demonstrate that compounds provided herein are FGFR3 inhibitors The following assays demonstrate that certain compounds provided herein selectively target FGFR3.

FGFR3 and FGFR1 Enzyme Assay

FGFR3 protein was purchased from Reaction Biology (Cat. No. 1068), and FGFR1 protein was purchased from ThermoFisher Scientific (Cat. No. PV4105). Enzyme activity was monitored using the KinEASE™-TK Assay Kit (Cisflio, Cat. No. 62TK0PEC) according to the manufacturer's instructions. All assays were performed at the respective KmATP for each kinase in KinEASE™ Kinase Buffer. Reactions were performed in a white, small volume polystyrene 384 well plate (Greiner, Cat. No. 784075-25).

An incubation was conducted with FGFR3 protein or FGFR1 protein, 125.0 nM TK-Biotin Substrate (CisBio), 7.81 nM Streptavidin-XL665 (CisBio), 0.25× Anti-Phosphorylate TK-Biotin-Cryptate (CisBio). Final enzyme concentrations were 0.25 nM in 10 uL reactions. Titration of compounds were performed in a half-log manner in 100% dimethyl sulfoxide (DMSO) starting at 1 uM. Prior to the initiation of the reaction by adenosine triphosphate (ATP), FGFR1 protein and compounds were pre-incubated for 15 minutes at room temperature, and FGFR3 protein and compounds were pre-incubated on ice for 15 minutes. Reactions proceeded for 30 min at 30° C. Plates were quenched by the addition of the Anti-TK cryptate antibody/Streptavidin-XL665 mixture. After 1 hour. in the stopping solution, the plates were read on the Envision plate reader ((Perkin Elmer) (Ex. Filter. 320 nm and Em1 665 nm/Em2 615 nm)).

Ratios were converted to a percent of control (POC) using a ratiometric emission factor. One hundred POC was determined using no test compound, and 0 POC was determined in the presence of 1 uM of an appropriate control inhibitor. A 4-parameter logistic curve was fit to the POC values as a function of the concentration of compound, and the $IC_{50}$ value was the point where the best fit curve crossed 50 POC.

In the above assays the compounds of Examples 1-160, 165-275, 280, 281 and 287-298 all exhibited $IC_{50}$ values of less than 350 nM for FGFR3.

In the above assays the compounds of Examples 13, 21, 22, 24, 26, 41, 43, 45, 47, 48, 49, 51, 53, 61, 63, 68, 75, 77, 79, 94, 99, 142, 152, 154, 155, 156, 157, 169, 170, 171, 173, 179, 183, 189, 195, 201, 208, 209, 212, 215, 222, 225, 226, 228, 233, 245, 257, 264, 274, 280, 281, 291, 292 and 297 all exhibited $IC_{50}$ values of less than 100 nM for FGFR3 and are at least 3 fold more selective for FGFR3 than for FGFR1.

In the above assays the compounds of Examples 21, 22, 24, 26, 41, 43, 45, 47, 48, 49, 51, 53, 61, 63, 68, 79, 94, 99, 152, 154, 155, 156, 157, 169, 170, 171, 173, 179, 183, 189, 195, 201, 208, 209, 212, 215, 222, 226, 228, 245, 257, 280, 281, 291, 292 and 297 all exhibited $IC_{50}$ values of less than 50 nM for FGFR3 and are at least 10 fold more selective for FGFR3 than for FGFR1.

The invention claimed is:

1. A compound of the formula:

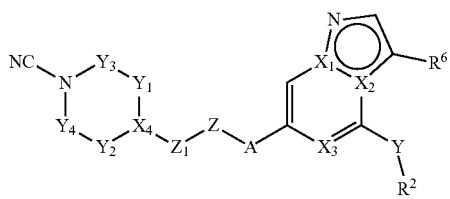

wherein

A is pyrazole, triazole, thiadiazole or oxadiazole, substituted with $R^1$ and $R^{1A}$;

$R^1$ is hydrogen or $C_1$-$C_3$ alkyl;

$R^{1A}$ is hydrogen, halo, CN, or $C_1$-$C_3$ alkyl optionally substituted with one or more substituents independently selected from halo, OH, and $OCH_3$;

$X_1$ and $X_2$ are independently selected from N and C, wherein when one of $X_1$ or $X_2$ is N the other is C;

$X_3$ is N or CH;

$X_4$ is N or C—$R^9$;

Y is NH, O, S or a bond;

$Y_1$ is a bond, $CHR^7$, $CH_2$—$CHR^7$, $CHR^7$—$CH_2$, $CF_2$, $CH_2$—$CF_2$ or $CF_2$—$CH_2$;

$Y_2$ is a bond, $CHR^3$, $CH_2$—$CHR^3$, $CHR^3$—$CH_2$, $CF_2$, $CH_2$—$CF_2$ or $CF_2$—$CH_2$;

$Y_3$ is $CR^4R^5$ or $CF_2$;

$Y_4$ is $CR^3R^4$, or $CF_2$;

Z is a bond, $CHR^{9A}$, $CR^4R^{4A}$, $CR^4R^{4A}$—$CH_2$, $CH_2$—$CR^4R^{4A}$, cyclobutyl, cyclopentyl, cyclohexyl, bicyclo(1.1.1)pentane, bicyclo(2.1.1)hexane, azetidine, pyrrolidine or piperidine;

$Z_1$ is a bond when Z is a bond, $CR^4R^{4A}$, $CR^4R^{4A}$—$CH_2$, $CH_2$—$CR^4R^{4A}$, cyclobutyl, cyclopentyl, cyclohexyl, bicyclo(1.1.1)pentane, bicyclo(2.1.1)hexane, azetidine, pyrrolidine or piperidine, or $Z_1$ is $CH_2$ or $CH_2$—$CH_2$ when Z is $CHR^{9A}$;

$Z_2$ is a bond, C(O), $SO_2$ or —$NR_4C(O)$;

$Z_3$ is a bond, C(O), $SO_2$ or —$NR_4C(O)$;

$R^2$ is $C_1$-$C_5$ alkyl or $R^8$, wherein $C_1$-$C_5$ alkyl is optionally substituted with one or more substituents independently selected from halo, OH, CN, oxo, —$OC_1$—$C_4$ alkyl, —$OC_3$—$C_5$ cycloalkyl, —$Z_2$—$R^{11}$ and $R^{10}$, wherein $C_1$-$C_4$ alky and $C_3$-$C_5$ cycloalkyl are optionally substituted with one or more substituents independently selected from halo, OH, $OCH_3$, methylamine, N,N-dimethylamine and CN;

$R^3$ is hydrogen, F, OH, $OCH_3$, $C_1$-$C_3$ alkyl, cyclopropyl, or one $R^3$ is fused with $R^5$ or $R^7$ to form $CH_2$, $CH_2$—$CH_2$ or $CH_2OCH_2$;

$R^4$ is hydrogen or $C_1$-$C_3$ alkyl;

$R^{4A}$ is hydrogen, halo, OH, or $C_1$-$C_3$ alkyl;

$R^5$ is hydrogen, F, OH, $OCH_3$, $C_1$-$C_3$ alkyl, cyclopropyl, or is fused with one $R^3$ to form $CH_2$, $CH_2$—$CH_2$ or $CH_2OCH_2$;

$R^6$ is hydrogen, halo, $C_1$-$C_5$ alkyl, CN, 3-6 membered cycloalkyl, 4-6 membered heterocycloalkyl, 5-6 membered aryl or 5-6 membered heteroaryl, wherein 3-6 membered cycloalkyl, 4-6 membered heterocycloalkyl, 5-6 membered aryl and 5-6 membered heteroaryl are optionally substituted with one or more substituents independently selected from halo, methyl, halomethyl, OH or $OCH_3$ and wherein $C_1$-$C_5$ alkyl is optionally substituted with one or more substituents independently selected from halo, OH and $OCH_3$;

$R^7$ is hydrogen, F, OH, $OCH_3$, $C_1$-$C_3$ alkyl or is fused with one $R^3$ to form $CH_2$, $CH_2$—$CH_2$ or $CH_2OCH_2$;

$R^8$ is 3-6 membered cycloalkyl, 4-6 membered heterocycloalkyl, 5-6 membered aryl or 5-6 membered heteroaryl, optionally fused or substituted with $R^{8A}$;

$R^{8A}$ is 3-6 membered cycloalkyl, 4-6 membered heterocycloalkyl, 5-6 membered aryl or 5-6 membered heteroaryl;

$R^9$ is hydrogen, $C_1$-$C_3$ alkyl, or is fused with $R^{9A}$ to form $CH_2$ or $CH_2$—$CH_2$;

$R^{10}$ is 3-6 membered cycloalkyl, 4-6 membered heterocycloalkyl, 5-6 membered aryl or 5-6 membered heteroaryl, optionally fused or substituted with $R^{8A}$;

$R^{11}$ is $C_1$-$C_4$ alkyl, $NH_2$, $NHC_1$—$C_3$ alkyl, $NHC_3$-$C_5$ cycloalkyl or $N(C_1$-$C_3$ alkyl$)_2$, wherein $C_1$-$C_4$ alkyl, $C_1$-$C_3$ alkyl and $C_3$-$C_5$ cycloalkyl are optionally substituted with one or more substituents independently selected from halo, OH, $OCH_3$, methylamine, N,N-dimethylamine and CN;

$R^{12}$ is $C_1$-$C_4$ alkyl, $C_3$-$C_5$ cycloalkyl, $NH_2$, $NHC_1$—$C_3$ alkyl, $NHC_3$-$C_5$ cycloalkyl or $N(C_1$-$C_3$ alkyl$)_2$, wherein $C_1$-$C_4$ alky, $C_1$-$C_3$ alkyl and $C_3$-$C_5$ cycloalkyl are optionally substituted with one or more substituents independently selected from halo, OH, $OCH_3$, methylamine, N,N-dimethylamine and CN; and $R^8$, $R^{10}$ and $R^{8A}$ are optionally substituted with one or more substituents independently selected from halo, OH, CN, —$OC_1$—$C_4$ alkyl, —$OC_3$—$C_5$ cycloalkyl and —$Z_3$—$R^{12}$ wherein $C_1$-$C_4$ alky and $C_3$-$C_5$ cycloalkyl are optionally substituted with one or more substituents independently selected from halo, OH, $OCH_3$, methylamine, N,N-dimethylamine and CN;

or a pharmaceutically acceptable salt thereof.

2. The compound according to claim 1 wherein $X_1$ is C, and $X_2$ is N; or $X_1$ is N, and $X_2$ is C.

3. The compound according to claim 1 of the formula:

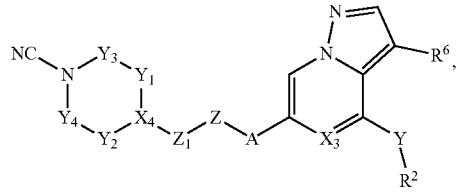

or a pharmaceutically acceptable salt thereof.

4. The compound according to claim 1 of the formula:

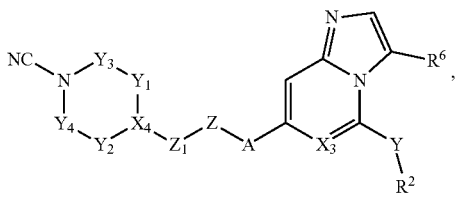

or a pharmaceutically acceptable salt thereof.

5. The compound according to claim 1, wherein $X_3$ is CH, or a pharmaceutically acceptable salt thereof.

6. The compound according to claim 1, wherein $R^1$ is methyl, or a pharmaceutically acceptable salt thereof.

7. The compound according to claim 1, wherein $R^{1A}$ is hydrogen or $C_1$-$C_3$ alkyl optionally substituted with one or more substituents independently selected from halo, OH, and $OCH_3$, or a pharmaceutically acceptable salt thereof.

8. The compound according to claim 1, wherein $R^{1A}$ is hydrogen, or a pharmaceutically acceptable salt thereof.

9. The compound according to claim 1, wherein $R^9$ is hydrogen or is fused with $R^{9A}$ to form $CH_2$ or $CH_2$—$CH_2$, or a pharmaceutically acceptable salt thereof.

10. The compound according to claim 1, wherein $R^6$ is CN, F, Cl, $CH_3$, $CF_3$ or cyclopropyl, or a pharmaceutically acceptable salt thereof.

11. The compound according to claim 1, wherein $R^6$ is CN, F or C, or a pharmaceutically acceptable salt thereof.

12. The compound according to claim 1, wherein $R^6$ is CN or C, or a pharmaceutically acceptable salt thereof.

13. The compound according to claim 1 wherein A is pyrazole or triazole, substituted with $R^1$ and $R^{1A}$, or a pharmaceutically acceptable salt thereof.

14. The compound according to claim 1, wherein Z is a bond, cyclobutyl, bicyclo(1.1.1)pentane, bicyclo(2.1.1)hexane, azetidine or piperidine, or a pharmaceutically acceptable salt thereof.

15. The compound according to claim 1, wherein Z is a bond, cyclobutyl, azetidine or piperidine, or a pharmaceutically acceptable salt thereof.

16. The compound according to claim 1, wherein $R^2$ is $C_1$-$C_3$ alkyl optionally substituted with one, two, three or four substituents independently selected from halo, OH, CN, oxo, —$OC_1$—$C_4$ alkyl, —$OC_3$—$C_5$ cycloalkyl, —$Z_2$—$R^{11}$ and $R^{10}$, wherein $C_1$-$C_4$ alkyl and $C_3$-$C_5$ cycloalkyl are optionally substituted with one or more substituents independently selected from halo, OH, $OCH_3$, methylamine, N,N-dimethylamine and CN, or a pharmaceutically acceptable salt thereof.

17. The compound according to claim 1, wherein $R^2$ is selected from:

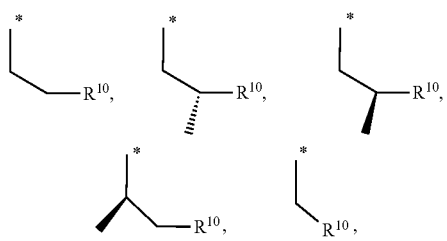

optionally substituted with one, two, three or four substituents independently selected from halo, OH, CN, oxo, —$OC_1$—$C_4$ alkyl, —$OC_3$—$C_5$ cycloalkyl, —$Z_2$—$R^{11}$ and $R^{10}$, wherein $C_1$-$C_4$ alkyl and $C_3$-$C_5$ cycloalkyl are optionally substituted with one or more substituents independently selected from halo, OH, $OCH_3$, methylamine, N,N-dimethylamine and CN, wherein * indicates the connection point to Y, or a pharmaceutically acceptable salt thereof.

18. The compound according to claim 17, wherein $R^2$ is optionally substituted with one, two, three or four substituents independently selected from F, OH, CN, oxo, —$OCH_3$ and —$OC_3$ cycloalkyl, or a pharmaceutically acceptable salt thereof.

19. The compound according to claim 1, wherein $R^{10}$ is 4-6 membered heterocycloalkyl or 5-6 membered heteroaryl, optionally fused with $R^{8A}$, or a pharmaceutically acceptable salt thereof.

20. The compound according to claim 1, wherein $R^{10}$ is 5-6 membered heteroaryl, optionally fused with $R^{8A}$, or a pharmaceutically acceptable salt thereof.

21. The compound according to claim 19, wherein $R^{10}$ and $R^{8A}$ are optionally substituted with one, two or three substituents independently selected from halo, OH, CN, —$OC_1$—$C_4$ alkyl, —$OC_3$—$C_5$ cycloalkyl and —$Z_3$—$R^{12}$ wherein $C_1$-$C_4$ alkyl and $C_3$-$C_5$ cycloalkyl are optionally substituted with one, two or three substituents independently selected from halo, OH, $OCH_3$, methylamine, N,N-dimethylamine and CN, or a pharmaceutically acceptable salt thereof.

22. The compound according to claim 1, wherein $Y_1$ is a bond, $CHR^7$, $CH_2$—$CHR^7$ or $CHR^7$—$CH_2$, wherein $R^7$ is selected from hydrogen, F, OH and $CH_3$, or a pharmaceutically acceptable salt thereof.

23. The compound according to claim 1, wherein $Y_2$ is a bond, $CHR^3$, $CH_2$—$CHR^3$ or $CHR^3$—$CH_2$, wherein $R^3$ is selected from hydrogen, F, OH and $CH_3$, or a pharmaceutically acceptable salt thereof.

24. The compound according to claim 1, wherein $Y_3$ is $CR^4R^5$ or $CF_2$ wherein $R^4$ is hydrogen or $CH_3$ and $R^5$ is hydrogen, F, OH or $CH_3$, or a pharmaceutically acceptable salt thereof.

25. The compound according to claim 1, wherein $Y_3$ is $CR^4R^5$ wherein $R^4$ is hydrogen and $R^5$ is fused with one $R^3$ to form $CH_2$, $CH_2$—$CH_2$ or $CH_2OCH_2$, or a pharmaceutically acceptable salt thereof.

26. The compound according to claim 1, wherein $Y_4$ is $CR^3R^4$ or $CF_2$ wherein $R^4$ is hydrogen or $CH_3$ and $R^3$ is hydrogen, F, OH or $CH_3$, or a pharmaceutically acceptable salt thereof.

27. The compound according to claim 1, wherein Y is NH or O, or a pharmaceutically acceptable salt thereof.

28. The compound according to claim 27, wherein Y is O, or a pharmaceutically acceptable salt thereof.

29. The compound according to claim 1, wherein Z is a bond, azetidine or piperidine, or a pharmaceutically acceptable salt thereof.

30. The compound according to claim 1, wherein $Z_1$ is a bond, or a pharmaceutically acceptable salt thereof.

31. The compound according to claim 1, wherein Z is CHR$^{9A}$, Z$_1$ is CH$_2$ and R$^9$ is fused with R$^{9A}$ to form CH$_2$, or a pharmaceutically acceptable salt thereof.
32. The compound according to claim 1, selected from the group consisting of:
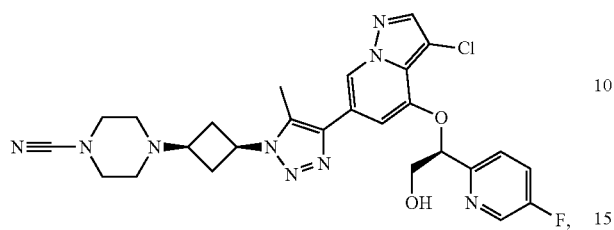
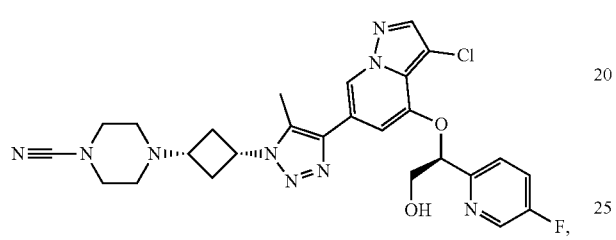
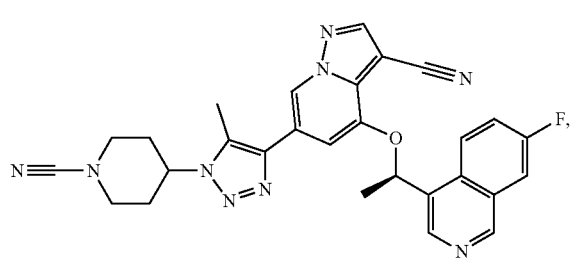
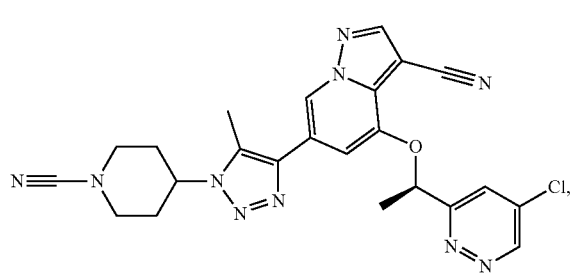
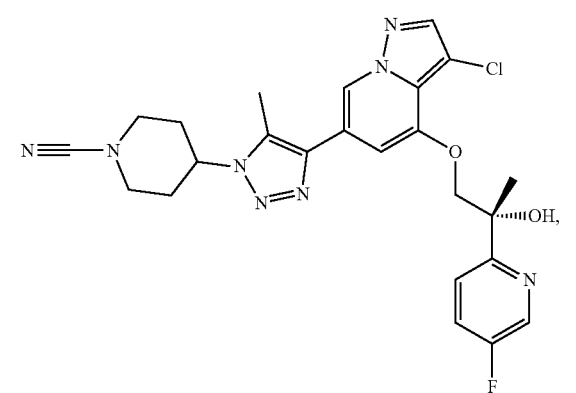
-continued
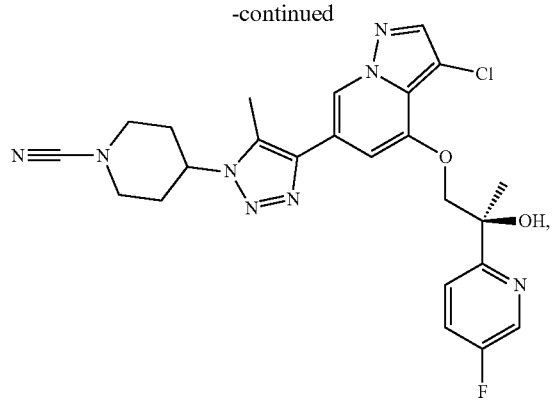
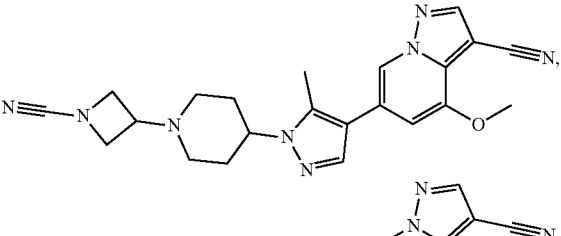
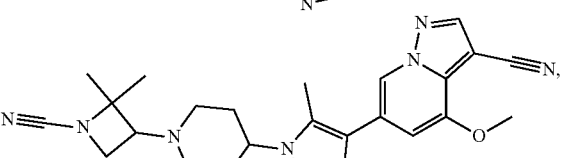
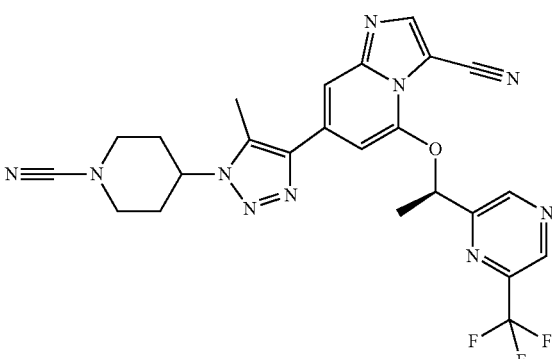
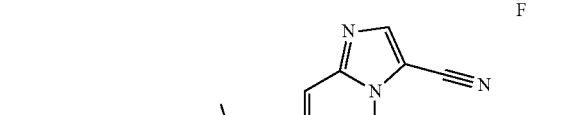
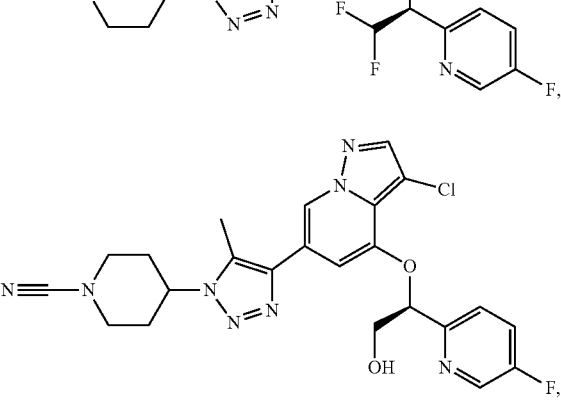

589
-continued
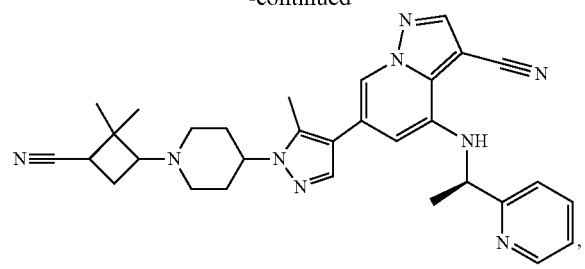
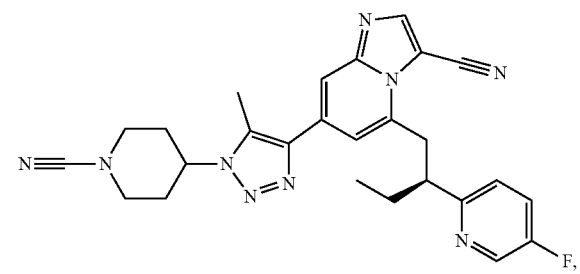
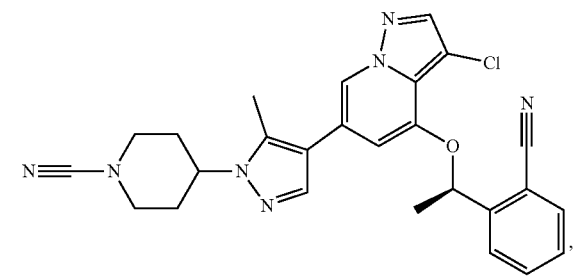
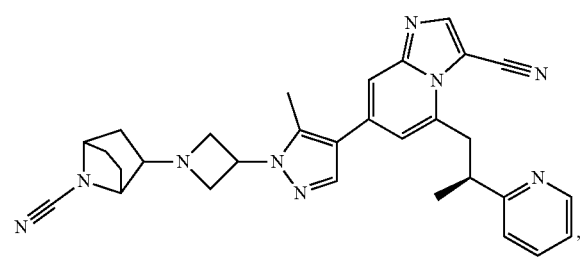
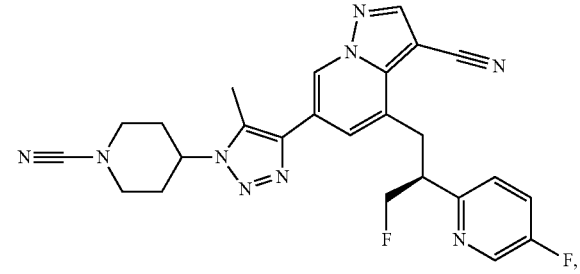
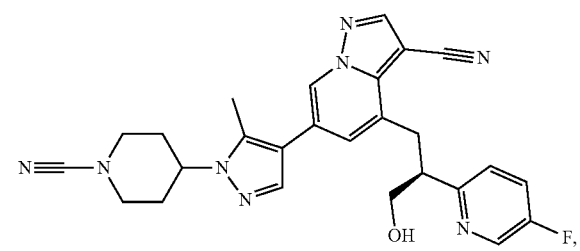
590
-continued
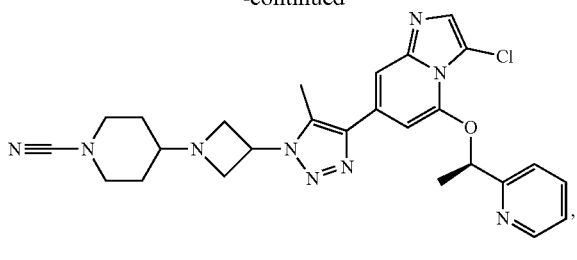
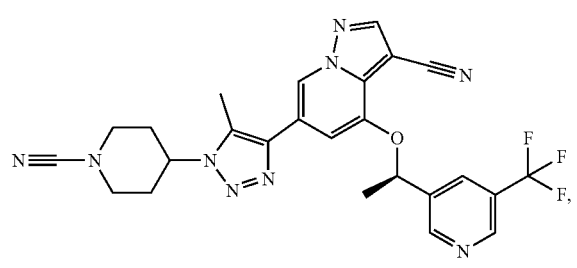
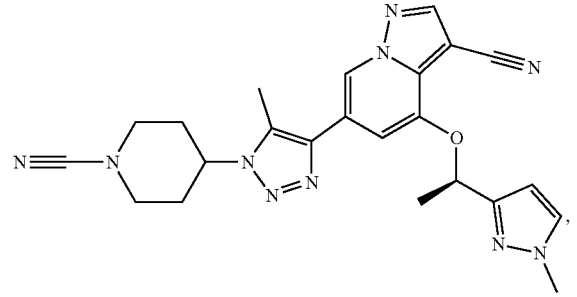
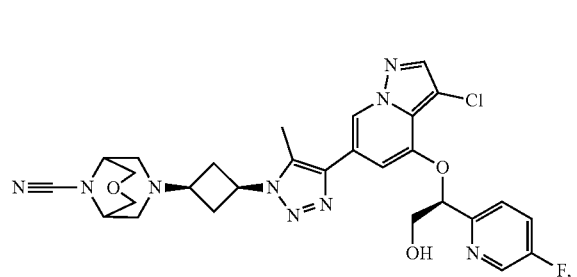
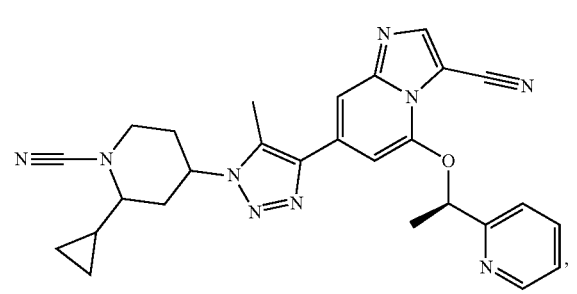
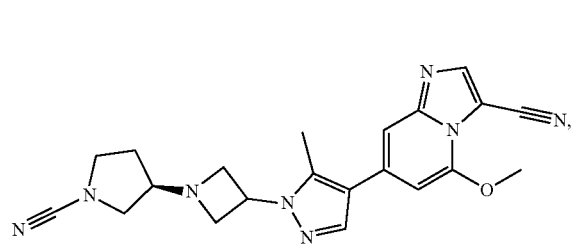

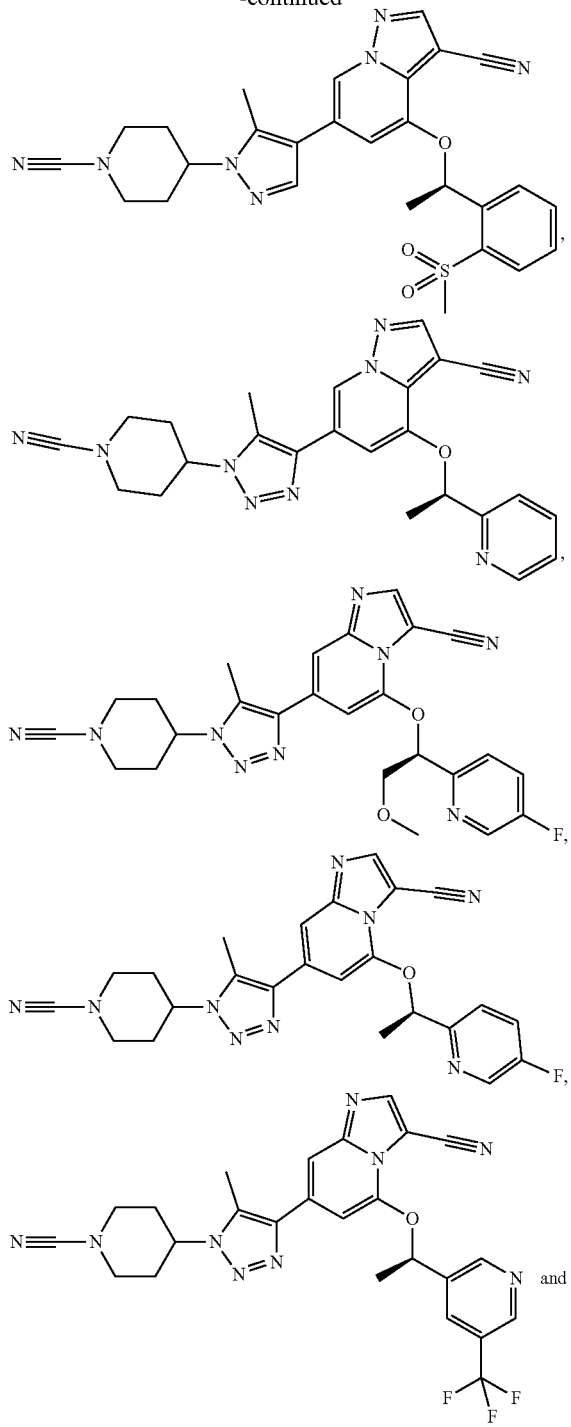

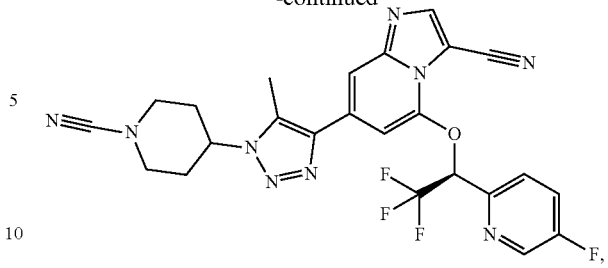

or a pharmaceutically acceptable salt thereof.

33. A pharmaceutical composition comprising a compound, or a pharmaceutically acceptable salt thereof, according to claim 1, and a pharmaceutically acceptable carrier, diluent or excipient.

34. A method of treating cancer, comprising administering to a patient in need of such treatment an effective amount of a compound of claim 1, or a pharmaceutically acceptable salt thereof, wherein the cancer is selected from the group consisting of breast cancer, invasive ductal breast cancer, invasive lobular breast cancer, lung cancer, non-small-cell lung cancer, lung adenocarcinoma, squamous cell lung cancer, small-cell lung cancer, urothelial cancer, bladder cancer, urothelial bladder cancer, non-muscle invasive bladder cancer, muscle invasive bladder cancer, upper tract cancer, urothelial upper tract cancer, urethral cancer, gastric cancer, pancreatic cancer, prostate cancer, colorectal cancer, multiple myeloma, liver cancer, melanoma, cutaneous melanoma, head and neck cancer, oral cancer, thyroid cancer, renal cancer, renal pelvis cancer, glioblastoma, endometrial cancer, cervical cancer, ovarian cancer, and testicular cancer.

35. The method of claim 34 wherein the treatment is cancer and the cancer is selected from the group consisting of breast cancer, invasive ductal breast cancer, invasive lobular breast cancer, lung cancer, non-small-cell lung cancer, lung adenocarcinoma, squamous cell lung cancer, small-cell lung cancer, urothelial cancer, bladder cancer, urothelial bladder cancer, non-muscle invasive bladder cancer, muscle invasive bladder cancer upper tract cancer, urothelial upper tract cancer, and glioblastoma.

36. The method of claim 35, wherein the cancer is selected from the group consisting of bladder cancer, urothelial bladder cancer, non-muscle invasive bladder cancer and muscle invasive bladder cancer.

37. The method of claim 34, wherein the cancer is FGFR3-associated cancer.

* * * * *

UNITED STATES PATENT AND TRADEMARK OFFICE
CERTIFICATE OF CORRECTION

Page 1 of 3

PATENT NO. : 11,878,976 B2
APPLICATION NO. : 17/685753
DATED : January 23, 2024
INVENTOR(S) : Adedoyin David Abraham et al.

It is certified that error appears in the above-identified patent and that said Letters Patent is hereby corrected as shown below:

In the Claims

Column 583, Line 60, In Claim 1, delete "—NR₄C(O);" and insert -- —NR$^4$C(O); --.

Column 583, Line 61, In Claim 1, delete "—NR₄C(O);" and insert -- — NR$^4$C(O); --.

Column 583, Line 66, In Claim 1, delete "alky" and insert -- alkyl --.

Column 584, Line 42, In Claim 1, delete "alky" and insert -- alkyl --.

Column 584, Line 49, In Claim 1, delete "alky" and insert -- alkyl --.

Column 585, Line 28, In Claim 10, delete "CI," and insert -- Cl, --.

Column 585, Line 31 (approx.), In Claim 11, delete "C," and insert -- Cl, --.

Column 585, Line 33 (approx.), In Claim 12, delete "C," and insert -- Cl, --.

Column 589, Lines 2-11, In Claim 32, delete

"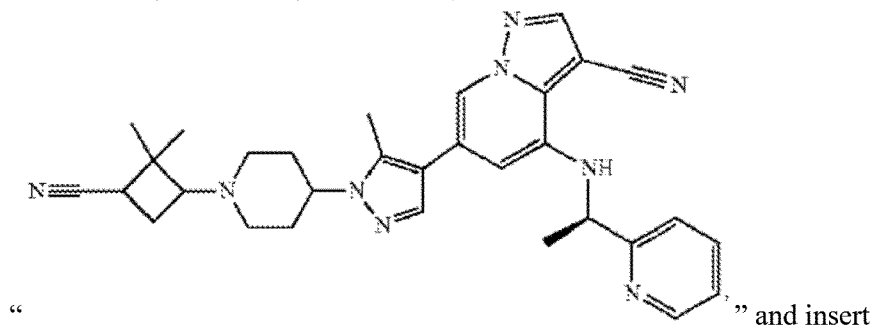" and insert

Signed and Sealed this
Sixteenth Day of July, 2024

Katherine Kelly Vidal
*Director of the United States Patent and Trademark Office*

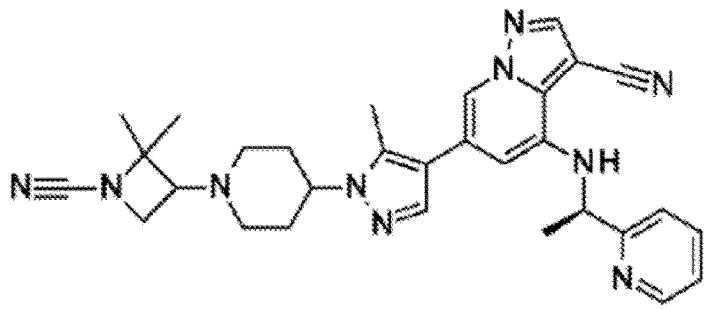
-- , --.
Column 589, Lines 13-23, In Claim 32, delete "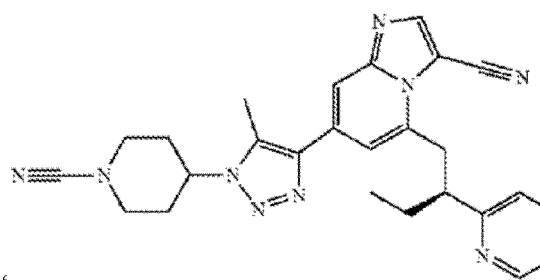"
and insert --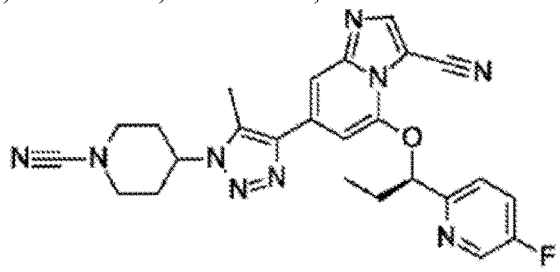 , --.
Column 589, Lines 35-45, In Claim 32, delete "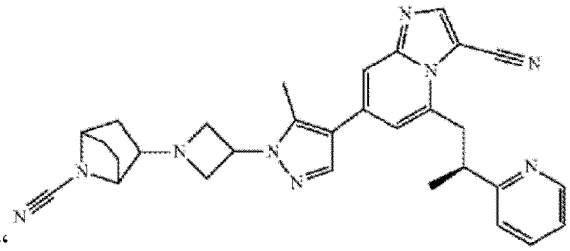" and
insert --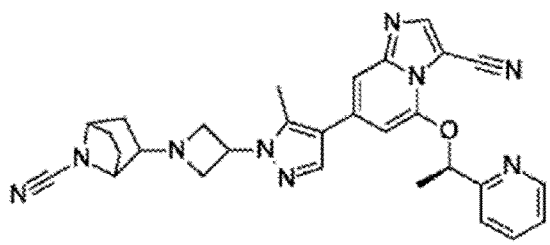 , --.

CERTIFICATE OF CORRECTION (continued)
U.S. Pat. No. 11,878,976 B2

Column 590, Lines 59-66, In Claim 32, delete " 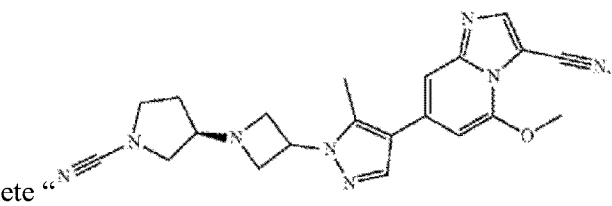 " and insert -- 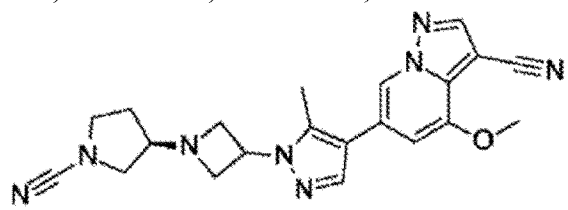 --.

Column 592, Line 45 (approx.), In Claim 36, delete "cancer" and insert --cancer,--.